(12) United States Patent
Hopkins et al.

(10) Patent No.: US 9,933,412 B2
(45) Date of Patent: *Apr. 3, 2018

(54) TRANSGENIC BIOSENSOR

(71) Applicant: KDT, INC., Murray, UT (US)

(72) Inventors: Christopher E. Hopkins, Salt Lake City, UT (US); Miluka Gunaratna, Salt Lake City, UT (US)

(73) Assignee: KDT, Inc., Murray, UT (US)

( * ) Notice: Subject to any disclaimer, the term of this patent is extended or adjusted under 35 U.S.C. 154(b) by 153 days.

This patent is subject to a terminal disclaimer.

(21) Appl. No.: 14/564,144

(22) Filed: Dec. 9, 2014

(65) Prior Publication Data

US 2015/0204849 A1 Jul. 23, 2015

Related U.S. Application Data

(63) Continuation of application No. 13/476,790, filed on May 21, 2012, now Pat. No. 8,937,213.

(60) Provisional application No. 61/488,720, filed on May 21, 2011.

(51) Int. Cl.
| | |
|---|---|
| *A01K 67/00* | (2006.01) |
| *G01N 33/50* | (2006.01) |
| *A01K 67/033* | (2006.01) |
| *C12N 15/85* | (2006.01) |

(52) U.S. Cl.
CPC ..... *G01N 33/5014* (2013.01); *A01K 67/0336* (2013.01); *C12N 15/8509* (2013.01); *G01N 33/5085* (2013.01); *A01K 2217/15* (2013.01); *A01K 2217/203* (2013.01); *A01K 2267/03* (2013.01); *A01K 2267/0393* (2013.01); *G01N 2520/00* (2013.01)

(58) Field of Classification Search
CPC .................. A01K 67/0336; C12N 15/8509
See application file for complete search history.

*Primary Examiner* — Marcia S Noble

(57) ABSTRACT

Systems and methods relate to transgenic organisms and their use as biosensors are described. In some embodiments, the systems and methods include a first population of transgenic organisms that includes a first constitutively expressed reporter gene, and a first transgene that includes a first inducible promoter from a response pathway gene, wherein the first inducible promoter is coupled to a first reporter gene. Other embodiments are described.

8 Claims, 7 Drawing Sheets biosensor profiling plate concept

A    8-well plate

B    cytoplasmic oxidative stress

Sensitivity and selectivity of hsp-16.41 biosensor

Chronic exposure reveals need for normalization to population change

Dual color worm normalization

Copas biosort

Specific and selective biosensor response to two types of oxidative stressors

Digitized readout toxicity pathway activation

Sets of Biosensor Panels detect Different Types of Toxicity

Genotoxicity

BER ① ② ③ ④
NER ⑤ ⑥ ⑦ ⑧
MMR ⑨ ⑩ ⑪ ⑫
RCR ⑬ ⑭ ⑮ ⑯

Oxidative Stress

Cytoplasmic ① ② ③ ④
Mitochondrial ⑤ ⑥ ⑦ ⑧
Endoplasmic reticulum ⑨ ⑩ ⑪ ⑫
Peroxisome ⑬ ⑭ ⑮ ⑯

Xenobiotic Activation

Cyp450s ① ② ③ ④
GSTs ⑤ ⑥ ⑦ ⑧
UGTs ⑨ ⑩ ⑪ ⑫
ABC transporter ⑬ ⑭ ⑮ ⑯

Endocrine Activity

NHRs ① ② ③ ④
Insulin pathway ⑤ ⑥ ⑦ ⑧
sterol receptors ⑨ ⑩ ⑪ ⑫
MAP kinases ⑬ ⑭ ⑮ ⑯

FIGURE 10

SEQUENCE LISTING

```
<160> NUMBER OF SEQ ID NOS: 162

<210> SEQ ID NO 1
<211> LENGTH: 346
<212> TYPE: DNA
<213> ORGANISM: Caenorhabditis elegans

<400> SEQUENCE: 1
gattatagtt tgaagatttc taatttcaca attagagcaa atgttgttcg gtatttattt      60
tcaacggtat ttatactatt ttccaccttt ttctagaaca ttcgagctgc ttgttgcaaa     120
aggagggcga ctcacattcg gtacatggaa aagtagtgta cacaataaag agacccagat     180
acattttccg tctgcgtctc tttgcaccca ccgggagtat tttcaaacga atgcatctag     240
gaccttctag aacattctgt aaggctgcag aatgcgggta tataaggaaa gcgggctcag     300
aggaagccaa cacgctttgt tctagtgcat ctaaaaaact tcgaaa                    346

<210> SEQ ID NO 2
<211> LENGTH: 346
<212> TYPE: DNA
<213> ORGANISM: Caenorhabditis elegans

<400> SEQUENCE: 2
tttcgaagtt ttttagatgc actagaacaa agcgtgttgg cttcctctga gcccgctttc      60
cttatatacc cgcattctgc agccttacag aatgttctag aaggtcctag atgcattcgt     120
ttgaaaatac tcccggtggg tgcaaagaga cgcagacgga aaatgtatct gggtctcttt     180
attgtgtaca ctactttttcc atgtaccgaa tgtgagtcgc cctcctttttg caacaagcag   240 ctcgaatgtt ctagaaaaag gtggaaaata gtataaatac cgttgaaaat aaataccgaa     300
caacatttgc tctaattgtg aaattagaaa tcttcaaact ataatc                    346

<210> SEQ ID NO 3
<211> LENGTH: 348
<212> TYPE: DNA
<213> ORGANISM: Caenorhabditis elegans

<400> SEQUENCE: 3
tcttgaagtt tagagaatga acagtaagca cttgaacaaa gtgtattggt ttcctctgaa      60
cacgattggc ttatataccc gtatcctgca gccgtttaga atgttctaga aggtcctaga    120
tgcattcatt tcaaaataca ccccataggt gcaaagagac gcagattgaa aaagtatctg    180
ggtttcttca gtacgcacac tatttctcaa tgttctgaat gtgagtcgcc ctccttttgc    240
aagaagcagc tcgaatgttc tagaaaaagg tggaaatgag tataaataca gtgacaaaac    300
cgaaccaaac aacattcact ctaattgtga aatcttcaaa ctacaatc                 348

<210> SEQ ID NO 4
<211> LENGTH: 348
<212> TYPE: DNA
<213> ORGANISM: Caenorhabditis elegans
```

-continued

<400> SEQUENCE: 4

```
tcttgaagtt tagagaatga acagtaagca cttgaacaaa gtgtattggt ttcctctgaa        60
cacgattggc ttatataccc gtatcctgca gccgtttaga atgttctaga aggtcctaga       120
tgcattcatt tcaaaataca ccccataggt gcaaagagac gcagattgaa aaagtatctg       180
ggtttcttca gtacgcacac tatttctcaa tgttctgaat gtgagtcgcc ctccttttgc       240
aagaagcagc tcgaatgttc tagaaaaagg tggaaatgag tataaataca gtgacaaaac       300
cgaaccaaac aacattcact ctaattgtga atcttcaaa ctacaatc                     348
```

<210> SEQ ID NO 5
<211> LENGTH: 348
<212> TYPE: DNA
<213> ORGANISM: Caenorhabditis elegans

<400> SEQUENCE: 5

```
gattgtagtt tgaagatttc acaattagag tgaatgttgt ttggttcggt tttgtcactg        60
tatttatact catttccacc ttttttctaga acattcgagc tgcttcttgc aaaaggaggg       120
cgactcacat tcagaacatt gagaaatagt gtgcgtactg aagaaaccca gatactttt        180
caatctgcgt ctctttgcac ctatggggtg tattttgaaa tgaatgcatc taggaccttc       240
tagaacattc taaacggctg caggatacgg gtatataagc caatcgtgtt cagaggaaac       300
caatacactt tgttcaagtg cttactgttc attctctaaa cttcaaga                    348
```

<210> SEQ ID NO 6
<211> LENGTH: 348
<212> TYPE: DNA
<213> ORGANISM: Caenorhabditis elegans

<400> SEQUENCE: 6

```
gattgtagtt tgaagatttc acaattagag tgaatgttgt ttggttcggt tttgtcactg        60
tatttatact catttccacc ttttttctaga acattcgagc tgcttcttgc aaaaggaggg       120
cgactcacat tcagaacatt gagaaatagt gtgcgtactg aagaaaccca gatactttt        180
caatctgcgt ctctttgcac ctatggggtg tattttgaaa tgaatgcatc taggaccttc       240
tagaacattc taaacggctg caggatacgg gtatataagc caatcgtgtt cagaggaaac       300
caatacactt tgttcaagtg cttactgttc attctctaaa cttcaaga                    348
```

<210> SEQ ID NO 7
<211> LENGTH: 1716
<212> TYPE: DNA
<213> ORGANISM: Caenorhabditis elegans

<400> SEQUENCE: 7

```
acaattcaga aggagcaata attctgtgat atttaaacta atttctcttt gtttctttgt        60
tatgagtatt tattttttagt tcttgttcat catgcttttt ttgtcacttt tccctcccca       120
atcccatatt cctctgcttt tctctcattt tcggttacgt gtattaattg aatgtatacg       180
acgacgacag tcactagttt cgaaataact attttacgag gatgaataaa cacactgatc       240
gctgagcgac gctccgagca cttttcgaga agtttctaag aagccacttg accgagagag       300
agggagaaag aaaagcttgg catagaaatg tgcttgtgtt tatttgaact gttaaaagtg       360
tttgacgggg gcgaagtcac tggggaaacc tcgagatcaa taggacacgt ggcaatttga       420
attttttggat aattggaaaa gcagtacccg actaaagatc cgaatttgat tttcagacat      480
```

```
tttactgcaa acttgattac acacggtaat tttccaaaag ttttgtgcat tgaatcccga      540
aaaacttcac aaacgcataa tattacaacc cgatctatga gcaaagtaaa tagagagaat      600
caggctgaaa gcttattgtg attaatgaac attaggaaca atgctgattt caatttgaaa      660
catttttttt tcagatcgaa aatcagtttt tcagatcga aaatcacatt ggatcttgac       720
attttcaaga gaattattaa aatttaaatg gctatttgaa aagtattgat tttctgaaag      780
ataataacta cttaccatct atgtcgtacc tgactatgcc aattattttc aacaattgtt      840
tattttaaaa aattttttgaa gtaagcttaa aacaaaccca ggacctctga aatgtaccaa     900
gtttggaaac taattccaag tactggtaat aacaaaaatt ttgaattcga ggcggataag      960
cgccagttgg gagttttctg attataatta tattaataga attgccaaaa atcatgataa     1020
acccctccaa tcattttttg attttcgaaa agtttcaat gtaggttttg gtgagctgcg      1080
aagttttcca aaaatgtcta aaaactaaat tcatatggtt caattttttgt caaaaacgtt    1140 cagctcatga ggagcttgaa actaaccaat aaatttggt cattaaattg gtcagttaaa      1200
ttgataattg aaattaaccg gatatgtttg gaaaaataaa tgcaaaagtt catgatcatc      1260
agatcaaaaa ccaaaaactt cccctacatt tctatttcca aattgaagat ttcttgaagc     1320
ctacaaatag tacagtttac aaatatctct ccttctttct ctcgtccctt cttgcgcatc     1380
ctcagagctc ggagctccta tccgtcaata taaacaatca ttgtttcttt tcttctcctc     1440
gtaccttttt tcttcttcaa atccattttt cctccgcccc cttatcctac agtccaattc     1500
ctttcactct ccactttctg agcttcttct ccaactcgca aaagcttcaa agctcacaga     1560 gcatttacg atagtgcatt gtaatgttct ccaccctaga gtgcatctcc aacctgcgca     1620
tatgttttcg ctctttgaca ttacattttc ttccgattca catttttattc atccacccga    1680 taaatatatt ttcacacttt taattttcta gagaaa                               1716

<210> SEQ ID NO 8
<211> LENGTH: 1859
<212> TYPE: DNA
<213> ORGANISM: Caenorhabditis elegans

<400> SEQUENCE: 8
tattctacgt caataggaat tgtcagaatt atcagttttg atatcaaaaa ttgccagctt       60
tagtacagta gaataactat gcgattcatg ctgcttatta tttattcaaa atttaaattt      120
taaccaactg tgagtttatt ttatagaaca ttttttcgaaa taaaattcaa aaaaataaaa    180
attgttattt ttcaaaatct taatcttaat ttagcaccat taccgacagg caatgataga    240
acaccaaacc ggactgacca agtgtcgtac cagtttcgag caatcaagta ttgagagact     300
gatattcttg ctgatactat actcttaaga tatgaaacga tatctacccc tctagccccc    360
tactcgtgcg ccctcagtta cctacctacc ccgttaccta ccctacccta cctacctact    420
cagtctccta cctaccccga ccgtatcata tctttagaat atagtatcaa caagaatacc    480
aatcacccaa ccccaatcac tcgaaaccgt taggcaccag gttagccagt ctggattaat    540
cgagagtaaa ccacttgact ccagacaact acatcttata cttacttacg tctggggac     600 aatcttggga ttctcaagat gacttccatt acgaagtctc ttgcaataac caattaccac    660
aattttggag cagaattaaa ctcacccacc agtacaggat caaagatgaa taatgaatga   720
gaggccctcc tctcattgtt gtgggcgggg tcaagggtc aaagttttt gaatttcgaa     780 attttgaaat tttggaattg ttaaattttt ggaaatctaa ttttttgaaag aaccacattt   840 tccgtttaca atttgagttc aattccgcaa ccccgtcaaa tttaagaaga gaaagaaaaa    900
```

```
aaacacaacg tgtttgcacc tgtaaggtag ttttttttg ttgccttcgg cgttttgatt        960
cacatgaaag tttctacgga aaaactttca ttgcataacg atcttcatat cttgtttctg       1020
gaaacgaaaa tttccaacat gaaagaaacc cgacgctatt tattctcgca acacaaaaat       1080
ttcacattta aataaccgcg gttttctcg aacagcatat ttgacgcgca ttgctcgtca        1140
agtttgatgc gtgcacacta ttttgctgtt gttttttct ttttctcta aattttcttt        1200 acgctttcgt agtttctata gaaacgattc tccactcccg gttttcttcc gattctcaaa      1260
attaattaaa atttagttat taaaaatcct ttttcttgaa ataatcgttc aatttcgagt      1320
tttcaagagt gggagacgttg aatttgtgag ccgcttattt tttctgtgtt tttgttttgt     1380
ggtttttaat cagtgtcata atcatacttt ccattgtttc tttattattc aaagttgtag      1440
attcagtatt ttagatcggt gatgtttatg aatcttctca ctcaggtctc caacgcgatt      1500
tttccgcagg tcagtgctta tccgaaacat tcgtcattcg caacttgggc ctatttgatc      1560
tatggcgttg tgttgttgcc tttaccttaa ttatcatcat tttcatcaga aacccacaaa      1620
aactagagac atagctacaa aattctgcga ccgagaggcg ggtacacaca caatgttgtc      1680
tatttcatct cgctccacct tctctctctc tctctcgtgt ttaccatttc tttttttaatt     1740 ttgcatctat cgactgtgat ctgcctgttt ttttctaatt ctaaactttt tgccgtgata      1800
ttccttagag tgttccctag aaaattcgtt gaatttacag gtcgaagccg ctcaaaaag      1859

<210> SEQ ID NO 9
<211> LENGTH: 1703
<212> TYPE: DNA
<213> ORGANISM: Caenorhabditis elegans

<400> SEQUENCE: 9
aaaaacttga tccgatcgaa gaaaaaaccg aaaaaaaatt cgaattgttg tgttgttcgt        60
cagttggatg gaatgatgat gaaggaagtt gattaatgga tatgactgat gattagtggt       120
ggaatatgga ataattattt atttgattta ttctgattat tctgaattag aatgtatttt       180
catatttcag gaaaaatgat tttatttcga acgaacttg ttctagatta aaaaaattga        240
aatttaatat ttagtgctat acaattacag tacccatgg aaatacacaa atatcataaa        300
tacaagaatt atcttcctgg aagttaaaact tatatttcg atgtaagtga aaaagtttaa       360
aagagaaatg atgtttgttg atcttcctgt aagtggaaac tggagaattc ataagcttaa      420
aaattccaaa atattaaaac ttgcgtgttt tttctgaaaa tcgattaaaa cagcaatatt       480
cagcatgttt ccagagccaa aaaaacctgc aagcatggga tacttttgca gttaaaaaat      540
gtttcaggaa cttgaatgaa gttaggatgc atttgaacag agtaatgaaa ttatatgaaa      600
ttcatatgta gactctccta ctcagttgtt tgtatgtgag ttttgtatat taaacttat        660 tttgaaatta tctttaatta cttgtaatgt tttttgtatg agttaaataa taatcttttg      720
aaaattcttt tcaaataac catttctgt ttaaaaaaac agtgagccca atataaactt         780
gttttccatc aaaccgagct tctaccaaag ttaacttaaa ttccataatt ttcacaaacc      840
attcatagtt tgtctacgta gccttatcct tttttgaaca ttgaaaaagt gagggagaaag    900 tgcgaaaaac gagtttttttt cttctcttc ttcttggtcg tcacgtcaag acactctgaa     960
cgttggaatg ggaaaagcat cgaagatcga aaaattctga ttttttctaa agtacacaac    1020
ttatattgat attgcattgg gatttaaaaaa agctctactc gaacattttg attaattta     1080 atatctcatt tattcatctt tcgataacag atatatcaca ttgttcggta ggataaaagg     1140
```

```
gctaaaatca agttttgagg aatgttcatt tgtttggaag gtgatattat agtctgcgat    1200
aactacataa gtttggaaac cgaacacatg ttttttttggc actttgctaa aaagttgtct    1260
gaaaacgttg gaaatcaata tttggtcatt tatttaggtc attttcggac cattataagt    1320
gttttctaat acaaaactgg cgctgctccg ctatttaaaa gactgaaagt gacataaatg    1380
atctaatttc cagatctctt ataacttttt ttatagcggt tccactccta atttgatgtg    1440
tttacttgtt gcatcagatc attttttcact tcttgtaatt cttatcagtt ttctatattt    1500
tctttcttat caattttttca gcttttcaac attttccagt tagttattca attttattc    1560 cgcacgatca ctgctgtttg aattcaaata ttggagtatt aaaattatac atttataacc    1620
attctaatgt ctaccttcta cacaaattac ccttcctagt agaaaatata ttttttggctt    1680 gaaatttgtt ctgtactgtc caa                                             1703

<210> SEQ ID NO 10
<211> LENGTH: 1851
<212> TYPE: DNA
<213> ORGANISM: Caenorhabditis elegans

<400> SEQUENCE: 10
tttctaagtt cgcacattcc tcgatttcca cttgccgtta cctttcatta tctccttta     60 ctttaatcta tcacagtttc atagatatca aacgttaatt ttttgttgcg agctagtttg    120
ttttttttcc tcttgttcgg tccattcgct ttaacttgtc acctattttt tgttttctct    180
acagtcctct tggttcatga tcctgttaat tatcaatgct cttttctgtg atattcgata    240
ttcgaatcaa caatgtgtat gattagtgtc aaagtaactt atcggatttt gaatataatt    300
caattattcg tgtaataaat aactattttt tagtttactc atgtttgcca caaactagaa    360
ggtttattta ttcataacta cttgcaattt cacatttgaa ttctaactgt atgattgctt    420
caactctctg cgatttttg cgctaaaata cggtacccgg tctcggcgcg acaaaaaatt    480
tctagatttt tagaaaattt tacagattta ttgcaacagc tgttacctt ttcacaaaaa      540 aatcgactga atttcgcgaa gttatgatat ctcaagcggc cgcttgcggg aaaagccata    600
ttttttttca aattttcgta gctgcacaat ttttcataat ttttttcatt gttaaaaata    660
aatgtatttt aaataattgt cctatttcag tttttcaata aatttttta acgaaaaact    720 ataaaaatag atgaattcta gagccacgta atttcagaat tacagtactc tttcaaggcg    780
catacccttt taacataaat tttcgcgtcg agaccgggta ccgtactttg acgcaaattt    840
tgcatctggg taattcttgt ttttgggttc ttcactttcc accactttttt tttcgaaagc    900 atcaaatttc acatattcac gtcacaatcc tagcaaagcc caatagctca ttcaagtcat    960
atttgtctct ttctttctca ttctcctgat tagcaacact gtcttatcaa ccactaggtt    1020
ccgtcttaat cgtccaaata ttgatccgct cgctcgtgtt ttctcaactt ctttatttgc    1080 tgtgttttc tgtttctata gttctccatt ttccatctcc tcttcgcttg ttgaatggac    1140 tttatttga taagttcatt ttaattttc taacaatctc atcactagct catgatgaca    1200
attgcaaaga aattcgtcat atagagggga aaaatgctga caaatattga aaagccttca    1260
ggagagatgt agagacgtag gagtagagac agaaacataaa tttgagaagc ttgtagggag    1320
aatagacata gagttaccat gggaaaaacg ctcgcatttt ccatttaacg agatttcta    1380 gatcacaaca ttttgtgatc cgttgtgcga aaatcaagct ttttatcaaa cttttatcgt    1440
ctgttcattc tttctgacaa tctttattat cttattaaac ttgactaatt gtattgaaag    1500 tatttttta gatgcgaacg aagttccatt tttcatgact taacatctct taacgttagt    1560
```

```
gaaattttg aattccaatt aggactacgg taggagttct gtagttgatt tcctgaacac   1620
ttgttttgta acctttctga acggatttta atatttctaa aattttaaat tgcaaatctg   1680
agtcctatta aaagatgttt catccgtaaa accaacaaac aaaatatcac tttatcatca   1740 tgagattta tgtttccttt tgattttctg aattgttgta ctttccttca aacgacttat   1800
tgaactgatg taactttcct tctaatgtta tcatttgtat tttttgcag a             1851
```

<210> SEQ ID NO 11
<211> LENGTH: 1614
<212> TYPE: DNA
<213> ORGANISM: Caenorhabditis elegans

<400> SEQUENCE: 11

```
aaaccaaatt tactactttt actatatttt tagttgaaaa taaaagaga aaacatta     60 ttttctaaaa acagtaattt tcctttagtc agtttatttc tcattgagat attgtgaact   120
cctgttttaa aatcaaatga gaaaaattga acacaaattt taaatttaca taaatcccca   180
aaaactatca atatttccaa cctagacaca ctataattga ataagattct cgtgaccttc   240
ggacatacag tttgtcaaag acaagcactc ccacatttgc cggttaattg tgataaccct   300
atcaacttgg ctccgtcttc actctcactt gcaattgcac aacttctttc ttttggatg    360 taagtagcaa cattttatca tcactctatt gggaaatttt taaaacaaaa tttcttcaat   420
acgattgccg gtctcgccac gataaattgt aggtacatgc gaaaaaataa tgcccattta   480
aagagtactg taatttccat ctctctttgt tgcaggattt tttgtcgatt tttttagttg    540
ttcaatacaa ataaattcat tcgaaaactg tcatgtcacg ataaacaaac aaattttggt    600
atttaacaaa aatttgtcgt gtcgagacct aagctagaat agtactataa ttttgagct    660 ttaattttt caagttttt acaaaatttt ttttctgtt gattaattga tgtatttta      720 tcggagatct ataaaaaaat caatgaaatt ttcgaagaag ccaaaaaagt actgttgata    780
ctacagtaat cttcaaaggc gcacaccttt cggcatttaa caaaaatttg tcgtgttaag    840
accgggtaat ttgttaggca aatatttgaa aaaaaactgc ttaaatattt catgaaaatt    900
ctgttatctt taatcagatt tttaaaaaat tattatcaaa tttcaaaaaa ttacctaaaa   960
taatgtctga aattcttctt tactcacgcg aactgcaact tccagacatt aattgaggaa   1020
atttcaaatt aatcaataac aatgaatacg attttcagat taaacgagta ttttcctaca   1080
tttttattaa ttttttgat taatattaat ttttaaaatg aaattttgg ataatcctac    1140 taaaataagc atgtcccgca aggccctatt tcaaagtttt agtgcctgaa aaatcaatat   1200
ttcgcaagaa cagtctacca atttttccaa tttatacttc cggcaattgc caccaattcg   1260
gtgatctaga aaatacccat ataggctcta cagtaccttc ccttatcacc cacatccaat   1320
tttgctatca gttagtcttc aatcacactt agtctttgaa caaatgaact cataactctc   1380
acaagatgtt tgcaactatc atattgatgt cattcagttc tcatatgaga aggcgggcac   1440
attgttgtat attgataaac caccccatt ttcctcttct tccagcaaaa aaaaataaaa    1500
ttaatattgt ctcagacgct tgtgaaactg gtgctctcaa ttgaaaagca ccattgactt   1560
cgcagaaact ggcagttcat ttggctttcg gatacttaca accatacgct caca          1614
```

<210> SEQ ID NO 12
<211> LENGTH: 388
<212> TYPE: DNA
<213> ORGANISM: Caenorhabditis elegans

<400> SEQUENCE: 12

```
tctgtatata tgcaaaagga aaattaaata ttatctatcg atggaaatgt tagaaaagcg    60
aattacttgg cacggcagca ggtgccacaa agcctgcagc tgaataaagt taagatacga   120
ttgcttgctg acaaatagga cactaaattg gaaaatacac accacatttt gattttaat    180
cagatctttt ttaattttaa ttttagtcac atctagacta ctctgactac tattctcaca   240
cgtgtggcca acaatcattc ggactacgct gtaggcagtc aggagttttc aaatgataag   300
gtgttcaaca gtgtagtctt atttgtatca ttttcacata aaacgcaatt tcaaaaactc   360
ccaattttct tcagactgcg gtaaaata                                      388
```

<210> SEQ ID NO 13
<211> LENGTH: 681
<212> TYPE: DNA
<213> ORGANISM: Caenorhabditis elegans

<400> SEQUENCE: 13

```
ccagttaccg agatctaatt tttttctatt ttcttttct actttcatg aaatacgcat     60
ttttgaaaac gaataataaa gtatgatatg ctgtcaaaaa atttcctgca ttcttgcaaa   120
accggacgtc gaacaccaat ttgccacttt gatctacgta gatctacaaa aaatgcggga   180
gaagatcttc tcgagacgca gaattctcaa ctgatttcaa atcgttaaga acgtgctgac   240
gtcacatatt tttgggcaaa aaattcccgc atttttgta gatcaaaccc tattgggaca    300
tcctggcatc acgtgatttg cctaaaacca aaaataatgc gcattcagag aacatgccta   360
ttgtgcctac ctatttatta actttgacag tagataggca ggcggctgct tagagcctat   420
aagctagcct acctaggcaa cccacatagc ctacctttca acttttcaaa agatcattgg   480
atcactaaca caatgtgact agttgtggtt tgttacaaat tgcctcattg tcaccctaaa   540
ctccctatta tttcccgtaa atgatgacga ttttgatctt ttgtagggtt atcttgaagt   600
gaaagatcac taagtaccca gactgcactc tagtcttttt ccccttaaaa tagtctcgag   660
aatgagtttg agaaactaaa a                                             681
```

<210> SEQ ID NO 14
<211> LENGTH: 1390
<212> TYPE: DNA
<213> ORGANISM: Caenorhabditis elegans

<400> SEQUENCE: 14

```
tataattttt tttcttaatt ttcatatgtt tacattaaaa atttgagaaa ataaagtagt    60
tcaagacaaa atcaaatatg gtagagactg tggtttaagt ttgggtttac tagggaatgg   120
tcagcttagg ggtgaggtac ctagagacgc cacatatgcc aaacggaagc tgagatcatt   180
ggctacaaga atatgctttc aaattctgca acggacctct gggagtctgg aaattcttgt   240
ctgaaattat gcttttgaat gctcgaaagt ggtaagaatt tagaatttat tacagaaaaa   300
cgtttaatta ataaaattag ttttatactt gaaacaagta ttgtatgcac tgtatcaaaa   360
cacatttca tctttctagg tattcaactt cacgttttc tgtaataaat tctaaattct     420
taccactttc gagcattcaa aagcataatt tcagacaaga atttccagac tcccagaggt   480
ccgttgcaga atttgaacgc atattcttgt agccaatgat ctcagcttcc gtttggcata   540
tgtggcgtct ctaggtacct cacccctaag ctgaccattc cctagttagg cttaggcttc   600
ggcttaggct tacgattaag cttaggatta agcctaggct taggctttgt ctgagttcaa   660
ctctccacca cgggaaaatt tttttgcaaa ttttttcgtc ccaaaaaaaa aaggaaaaaa   720
```

```
aaactttatt ttttacttgat ttttttcact ttttttttcga gttcaactct ccaccacggg    780
aaaatttttt tgcaaatttt ttcgtcccaa aaaaaaaagg aaaaaaaaac tttatttta      840 cttgattttt tcactttttt ttcgagctca gctcgaccgt ccctcaatga aaacaagcaa     900
cctgatgtat tccagatact cccgtaccaa aggtcatttc tcgttagtca caaaatattc     960
tgattgaaaa tggtgaaaaa taacgagaga gttgaaaatt ctacagacta tggcctaaac    1020
gcagcaggtg agacacagta gagaacaaga ggcagaagag agagcagaag gcagaggaag    1080
aactaaaggg tatataaaaa gtgttttgtt gatcagtggg atcaaatagt gtgcttttta    1140 aaagttttttt tttccataaa tgtattgata tctagaattt ttttcgagtt cactgttgtt    1200
taacagtgtc acatggtgtc aggctgtctc aatacagttt gatctacaaa aaatgcggaa    1260
atcttaacca tgcaaaatca gttgaaaact cttcgtattt tctcccgcat tttttataga    1320
tctacgtaga tcaaaccgaa atgagatact ttgatacacc gtgcagtgtt aaaaaaaata    1380
cagttacagc                                                           1390

<210> SEQ ID NO 15
<211> LENGTH: 395
<212> TYPE: DNA
<213> ORGANISM: Caenorhabditis elegans

<400> SEQUENCE: 15
tctcattctc ttcaagacat aacacaacgg gctgacgacc atatcatcaa cgacgatttt     60
ttaggaactg tactttatct gtgtctgacc aacacgtgtg aatgaagttt caactggaaa    120
atttgtttga aacactgcaa agaatttcga attttgatga taattttaaa tgccattatc    180
agttttaata cgccactcta gtctttgatt ctttgcacac acacacacac acacacacac    240
acacacactc acaaacacgc ctgaaatttc gcaatatgct gatttaacga gaaaacattt    300
gatgacaata aacttggcgt attaatataa aagggaaaat tcaattcaga ttctcaacgg    360 tttatttttct gtcacaactc ttcctaatat tcacc                              395

<210> SEQ ID NO 16
<211> LENGTH: 741
<212> TYPE: DNA
<213> ORGANISM: Caenorhabditis elegans

<400> SEQUENCE: 16
tacacagcca agtctcataa ccaaaataat attgatagta aaaacatgag tgaacacgtt     60
tcaaaacaac atgtcattga aaatcaattt taatgttcac gggaattttt ttccaaaaca    120
gttttactca aacatatttt ccatttgaaa gtttgggaaa ctatccctgg cacgttttca    180
ctgcattggt ctttccagtt gattcagcca gagttggaaa gcctgtactt ttttcccaac    240
aaccgtttct actgctcaac ttgtaacctc aaatttgcct aattgactcc gaagcttcaa    300
aacttgcttt aaagaacttt gatgaaaatc gctgcggcga aagaatcatt gcggaatttt    360
tgccccaggg atctaaattt ccaacctact ccactgaacc aaatttttc aaacttcacc    420 aattttttta ttttattttc acatgtcatt aaaacactaa gaattcaata catgtatgaa    480
aactgcaaac accaaagtac ggtttggact tgtaagcaaa acaccggtag tctctttgac    540
ttatcatgta ttgtcatcct atttcgtcag acggtcttgt aagttcacat tgacttactc    600
tgcgtctctc ataggacaca tactccgcat ctttctcaat agatcaaata tattttgtca    660
tcacctatta tttaaactgg ttggttttc acaatgtcac aactaattga actctccact    720
```

```
tattgaactt gacttgaaat c                                              741
```

```
<210> SEQ ID NO 17
<211> LENGTH: 330
<212> TYPE: DNA
<213> ORGANISM: Caenorhabditis elegans

<400> SEQUENCE: 17
accgccgagt tacgacatca gattcaagcc tttgaaagtt tgaatcttta ataattaaat     60
gaataattaa ttgggagaaa catgtacata aataaaattt ccattaaaca atgttcattt    120
gtttaagctg gcacagacca caaaagctga aaccacaaag ttttttaaac cttgttcttt    180
tcttaaattt tgtagtttct tatcttatca ctcgtgtttc ttgtcctcca aataattgtg    240
aaaattgtag ttaatgtgtc aaaaaagtca catataagaa gacgaacaac ttgattttt     300 gttgacttca tttgaaaaaa aatagaaaac                                     330
```

```
<210> SEQ ID NO 18
<211> LENGTH: 953
<212> TYPE: DNA
<213> ORGANISM: Caenorhabditis elegans

<400> SEQUENCE: 18
agaacccatt tttacaaatt gtgttcttgt ggtgttcgcg tattaacttt ttatagctgt     60
tttttactta taggatgatt aagaaaaaag ttccggcttt ctcaaagtaa ggtaaatatt    120
ttgaaaataa agaacttgta aaaggataca gctaactgat taaaaacaaa agacccatgt    180
tagttcacgc tcggatttgg agttcagctg gaggggaaag aattcagcgt tgaaatattt    240
cagttggaat ttcacctgat attatttaaa aaatgttata cgaaaattga aaaagcgcct    300 cttacccct cttcgcccgc tttcctcttg cctactgtgc agttttttgt ctttacggag      360
ttaacaagtt gataacctgt ttaaggacaa cagataaaaa cagagaaaat taaaaaccac    420
tattggcgat ttgaaatttc cgttcccatt tttcactttt caatttcaaa tatgtactta    480
acggtttccg atcattaaca cgtaatccat catttctaga caacaagtca caccaatgcc    540
aatcaaaagt gcaaacatgc tataacgaat cttttttttc aattaaactg tttacgatgg    600
aaattaggat agtgtcatag cattaatttt cattgttcaa aaacagaaag aagtcacaaa    660
atcttcacgt gaacatgttt cgtttccata aacaaattgt attttcaaag acagccggga    720
attttcagac caattcaggt gacaactatg gctaccacc cacctaactg tttgttcgcg     780
attattctga ctcacatcat gttttcaaaa gtgactgtat aattggagtg tagcataatc    840
aacacaaact acagaatggg aaatttgtga cagtatcaat cacattaaca gatctataaa    900
agagactggg aaagttgttc agagacacaa attcgttgtc tacttatcaa atc           953
```

```
<210> SEQ ID NO 19
<211> LENGTH: 607
<212> TYPE: DNA
<213> ORGANISM: Caenorhabditis elegans

<400> SEQUENCE: 19
aattttaaag tttatggatt atttagaatt tatgaatatt ttaaatatag cttgtaatag     60
tagcattggc tttttttatta gttagaatgc agtatttata tagattgtag ttgtgtgcgt    120
gctaagatta ttggagtatt ggtgttgtca cgtcttcagt ctctctgccg tgcgctcacg    180
agaatggggc aagcgaagtt gcggctgacg cgttattgga tgctggcgcg tttcgcgacc    240
agcgttggtt ttatcgagaa ttttctctgc agtacaaagt cccaaattcg gtggttttt     300
```

```
atcgatttga cgcgcgtttg ctcaatttct cgattttccg cgttttttat tcagttctca      360
ttaattaacg ttcgatgctt gttcacaaaa ttcagttttt gttttcactt gctcgttggt      420
gtcgttcgtt gtgtaagaaa attgattcct aaatattttg tttaaattgc taaaaaataa      480
ttcaataatt tacattattg aattattaaa agttgtattt ttcaaacatc tcgcgcattc      540
tccgtccgtt tctctcaatt tttcactgtc atgtccgcat tttaatattc atttttttc      600 aggtaat                                                                607

<210> SEQ ID NO 20
<211> LENGTH: 1723
<212> TYPE: DNA
<213> ORGANISM: Caenorhabditis elegans

<400> SEQUENCE: 20
ttggttatag gaatatcctc ctaggataga cgttttttc tagtaatttt tgttgttttt       60
gttcgttaca ataaatctca ttttatttt ctggattaat ttgattacca atcgtttcca      120
gcgattttca catattttc cagaatttaa tacagattaa tattttcgaa aaatttaaac      180
attttctttt cacattttaa ttcatctcta ttcattatgc aatactcttt tggttttcaa      240
gcatccgaca ttcctccgtt tcatttatgt ttgcattcct gctggcatga atgcatttca      300 tgtgtctcg atgagaaaaa ggacaatttc atgagcttat cagttacttc gttttcaaaa      360
ttttaatgtt gaccagccat tgatgtcata ttttgtctaa gaagctcaag aactattatt      420
ttttgaagct taatttcgaa gagcaacatt ttttttcatt aaaattcagc agtcattgtt      480
ctttaaaaag ttttgattct cgttttttaa cgattttaaa ttcagtcgag aattgaataa      540
cttcccgatt tcccggccac catcgtttaa tacctttcct ttatgagact aacttccaag      600
tatgcaaatt gcaaatcgac gcaaggggaa tacactcgct cacttctcat cgaaattcga      660
aaccttttcc cattttcttt catgtctttt tcgcttttct cctctctgcc catttccatt      720
tatttctcaa acaccgttca gtgaacacga aaacccttac ggaaattgtg ttgtaagaat      780
acaaaaactt ccgtagcata gcgagaaaga gtcaccattt tgtagtgttt gcccccggtg      840
gtatagtttg cacaagtttc tgaaagaaga agaagacaca tttgaggtct tatgcacata      900
aaaatcaatg ttagactatc ttttcacgt agttttcttt tgcaaagtgg aaacttctca      960
ttaaacactt tttgcttttc aattgtctga acaagttttc gattaaacag ctgtaaagct     1020
tttgcaagtt tcatggttta tgaactattt cgaatcggtt acattgctga agttttagtg     1080
tttcttgaat atgtcgtcac taccaggact ggaccaaaaa tcaaaagaa tttaaagtga      1140 ataccaaaa aaaaatcgt cgatttgcga ttttgaagg actgtaagtg acttttttgg        1200
cttcatttag gtcccaaaaa accttttttt tctcaaaaaa tgtgactcaa ataccaaaa      1260 aagtcttaac ctgatcactt cgccttctca actcaagcca tttttgctgt ttagttcgaa     1320
tatggaacaa atcataagaa tcttgagtac ctatatgcga tacccgattc atttttcctct    1380 cttctaaata acatcatttc ctctctttt ccctctctct ctctctctgt ttttgtttgt     1440
gactcacttt gtccacaacg cgcgcggaac cggcttgttg ccacacacac actgtgatga     1500
aatatgcggg aggaaagctt ttcgcctaat agttgactta cttttcatct atattcctca     1560 atttttgcaac taatagattg atttgtcatg gttttgattt cagggttttg aatattcttt    1620
gaaattggaa tttttaacaa aaatgcaaat tatgtgccaa gtcatatctc ctcctcacac     1680
tttttctatc acatgccccc aaaaaaatta attttttca gga                         1723
```

<210> SEQ ID NO 21
<211> LENGTH: 2546
<212> TYPE: DNA
<213> ORGANISM: Caenorhabditis elegans

<400> SEQUENCE: 21

```
gaatgcagga tataaatcac gattttcgtt ttcgaacaca actttaaact tcaattttc      60
ctttgtttct ctgaaaactt tgcagtcatt ttcaagcttc cacagaactt tacaaaaaaa    120
ctagattttc tccaacgtgg cgatattccc gagtttcgag aagaatccag cttgtcaatg    180
ctgtataaaa cctttacttt tctatcgttt ccattatttc tttcactgca cctgttactg    240
ccaggtgctt tatttcgcct atcgtctatt ttgttttcct cctaccaaat ttgacaaccc    300
tccgcaaaca ctcattccta ttttagcccg gtgaaatttc gatatggaga aaaacaaaaa    360
caagtgtgag cttccacttc ggaataattt ccggagaatg agaattgtac aattttctcc    420
tataagacca tacaataaaa ttttatcaga aacatgaagc tttggtcatt atcattttt     480
gttacccttg aaatttgatc acaaggcttt aattttcat gagacgtcaa ttttttctga     540
tgataaataa catagttcaa agtattgcgt aatgtttcaa ttttaacatg acacataata    600
aatcagaaac tcgaaaaacg tatttaaata tagatttgt cgggaagttt aatgtgcaac     660
tgtctcgata tctttctttg aaaacattta attttatta tattttccaa actggattcg    720
agaattctcg tattcttaaa caaatttaca atgaaaatat aaataattaa tttaaaggaa    780
catgttctgc aatcctccct gggtcccgcc acgaaaccgc cacgcactac catgaaaggc    840
gcgttcgcat tcgttctgcc gctcgtttct gttttccaga tctttccatc attttcttca    900
ttcattcgcg ctctctcatt atcttgagtt gccggctatt ttcgctgctc tctgcttttt    960
cgtatcgctt tttcactctt tccagcattc agaaaattgc attatttcgg ttttcattta   1020
aaaaactcat agcaaagtat tttgttattg atttcgcaat actttcgaaa agtatcggaa   1080
aattttaatg tttagtctgt gcgttcctca ttccctgttc tcgttgtact cttaactgat   1140
gttttttaaat ttagttttcc ggggctctct tgaaaagacc caatagtcgt attgaacctt   1200
cgcctgatcg ccactagctc atcttttagt cttatgacgg gctcacatga ttctccccag   1260
tgtcctcccg ttttctcact gcacttgttt tgtcgttcgt tcatcagtac aaagtacaag   1320
cactttcgcg tctgtctgaa aattggttcg ggtgccgtta ggacattatt catactttcc   1380
tgctagtcgc agattataaa aaaatgtcct tgaccgtctg ctctttctta tgttctccct   1440
atatatgcgt caaacgaaca actgaccctg ttcacttttc ctattcttcg tttcatcatt   1500
ttctgtaaca aaaatggaaa caatacttta cacagacgtc actattattc aggcctatga   1560
tttctctatc gttagttaa agatgaaaag aaactggtcg acccagttgc atgacgagaa    1620
aaaagaacac cccgttcgat tttcgttgta ttccctctgc acacattgtc cccttcttcc   1680
tcatcatttc tttccctaca cagcactcta gaatgttctt cttgtgcaga aagagtgccg   1740
tttgagtcag cgacccccc ccccccctc ctttctcttg ctcttcctca ctggttctcg    1800
taataggcga cttcttgcta acagaaagtg agcatagcaa cattttttac tttgtggcct   1860
tcaataatac gtgcgtcgtt taattagaat gtttgagtaa agttcaacgt gtagattcaa    1920
tattcacgtt ttgggcgctc tttaatttat tactgtcaag aatcagttta ccaaacggtg   1980
agtttctttt tttttgtcta attgtaagat ttagcggggt aaaaccaaca gaaatgtcat   2040
gcttttttga ataatctcaa tcagttgtta tatgaattat tttcccattt tagcaatact   2100
gcttggtagt tattttcggt cagagaaacg aggacatcag ctgaacatct gcgtctctaa   2160
```

| | |
|---|---|
| caacactcgg ggaaggcgga gtcagtgtgc gcgtgcgttg ggggttttat cgatcgttga | 2220 |
| ggcgggcata cagcagtcat acaccccatt cgaccagaac gctccgctcg cgtgccacct | 2280 |
| tgtctccatt ctcatttcac ttgtctctac tcggacatta ctcctcatcg attagctctt | 2340 |
| tactaccatt ttacttttat gcctttcttt tttcgtttga cttgcctatg acgagtgggg | 2400 |
| atgaagtttg ctttgttagt cttactagtg tatcgatttt ttgggtaata tttcgcaact | 2460 |
| ttctaggact ttctttcata atcacctctt ctctcgcctc ctcattccag ttttattcgc | 2520 |
| actcattttc tattttttca gcaatc | 2546 |

<210> SEQ ID NO 22
<211> LENGTH: 580
<212> TYPE: DNA
<213> ORGANISM: Caenorhabditis elegans

<400> SEQUENCE: 22

| | |
|---|---|
| aatcaataaa aaaacgttcg aaaaacgttt gaaacaaaaa aataatattc gaattcttct | 60 |
| ccccccttccc gtaaatcctg cagctctcta ccgtactttc gccgtctctc aatttcgcgg | 120 |
| cgagacccat caccacggca atcctccatt tgtgtcgctg ggcctaaatt ttttccgttt | 180 |
| ttttgctcga ttttcgccgt ttctctgcga aattttccca aatttctgtt caatttaatc | 240 |
| aaaatattgt tctggacgct tgttcagcat agaaagtgga gattctgttg tattttaagc | 300 |
| ttggaaaacg aatttattat gaatttcat ttttttgcta ataatttct ctattcttga | 360 |
| atttttacag cttttaacg caaaatattc tttcctcttt gttctaaatg ggtagttaca | 420 |
| cacattatgc ggtctataac gtcttttgtc acctttgaaa ctagtctcta aagaaaaatc | 480 |
| aataattttt gccctacgc tctcctccaa atgtttcgct ctcgccgtca ttttctgaca | 540 |
| attttactcg gtttctttc aaattatata atttcagtcg | 580 |

<210> SEQ ID NO 23
<211> LENGTH: 1037
<212> TYPE: DNA
<213> ORGANISM: Caenorhabditis elegans

<400> SEQUENCE: 23

| | |
|---|---|
| tgtaaacatt tgttattata tttttaaact ttgtgttgtg gatgtgaata tgtggaattt | 60 |
| aataaaacat ttctcgatat aataatgatt ttgttgaatt agaaaaatta gaaaagtgga | 120 |
| cgattctaaa aacaaaagtt acaacgaaaa tcatcgaagg aaaaaacaac tgaattccaa | 180 |
| aatagttttc agaggtgatc acaaaatgtt ctcaaacgat atatattcta ccatcaataa | 240 |
| ttttattggc actatatcac agtccataat tcctgtgctt taattatact ttcagtata | 300 |
| gaacaatatg ctatattatc aagttatgcg tccaataaac acaatttatt tttcagactg | 360 |
| aatttaagcc atattgagaa tagcgaaata aaaacgtaga ggaaatttgt gatcgccatt | 420 |
| cacaattaat tcttagatcg caatgataac aaacttcgat tcaaaagtca tcatgcaaat | 480 |
| tcaccgttct cgtgtgtgtg tgttttttgga ggaaataaca caattttgtg actgattttt | 540 |
| ttacaacatg tggtttgtag catagttcaa agtcattcta gaggggggctc agagggagtt | 600 |
| ctttcgctat gtcatcgttt gttttgcac accaagaaaa atgaaaataa atgctctagg | 660 |
| atgtcatgga tcgtttccat tcttaataag tagaagctag gatttcctat acaaaaataa | 720 |
| gtaatcttcg tttctacgtc tatcaactta aattttgta tacaatccac tttggtaata | 780 |
| ttcaaggcct tcctgtaaaa tgttttatga tcaatccgtt acaccaagaa aacaagtgca | 840 |

```
atttgtcatc atgtaggctt ccgcctgtgt ttacttcctt cccccagcac aacactgact    900
atttatacca aattaataat gcagcattcc tcatgtgata actcgtttga ctttttatatc   960 tttctacgtg catctttcaa gctcgaaaat taatttttaaa aatttacatt gcagaacaat  1020
tgcggaacga agaagcg                                                   1037
```

<210> SEQ ID NO 24
<211> LENGTH: 2502
<212> TYPE: DNA
<213> ORGANISM: Caenorhabditis elegans

<400> SEQUENCE: 24

```
attaatgaag aatccgaggt tcctcactaa agattctcgc tttatgatag agtcctcaag     60
cttgtatatt agagttttgg ggtgtttacc taaacttatg caaacggttt tatcatggtt    120
taactaaagt agtgaattgt tggaccaatt taaaataaca tcgatcgctt cctgcagatc    180
atttgtggaa ttagtttttt caaaagagca atatagtttg aggtcatcag cgtactgcat    240
atatttaaca gttttttggaa tgtttgcacc aagatcattt gcaaatatgc cgaaaagtat    300
aggtgaaagt acgctccctt gggggacacc acatggggcg ttcctaacag aagatagaga    360
attgttcact tttactttga acgtacggtt ggagaggaat gagtccaccc agcctatgag    420
catagaattg aacccggcct ttattaattt ttgcattaag agtgaatggt ttactttgtc    480
aaatgcctta ctgtaatcaa aaatacaac atctacttga ttattgaaat taaaattttc    540 tataggaa cttgatatac ccaatttcta ttaaaaaatt gaattcgcgc cgagcaaaat    600
gtgatgtcaa tttcagtttt ccaatttttct caatttttttt gaccactaac taaaattttg    660
ataccaaagg atttttgctc aaatttcgaa ataattgcgg taaaattggc tctaaacact    720 agttttgac ctagcgaatt ttgatgtcaa tttcaattta tttacatttt atttggaaat    780
tttcttcact gcggatccct agcaaaattt gttaaacatc acttttccga gcaatttgtg    840
atgtcgattt ccgtgtcttt acacggtttt tgccttttttg cttaaatttt tcaaaaattt    900
cagtaaaccc caaccaaaat gaatttact cacaaatttc gctcttcaat tattttttta    960
gtgaaattca caaatctga cctcacccta aattcccact gagcacattt ggatgtcgat   1020
gtttgttcaa gttttttggcc aagttttaaa caattgcagt caaattcaac caaatcacgt   1080
ggtgtcagtt tgtcccatta cggtttgatc tacaatgcgg gcatttttttg cccaatcaat   1140 tgagaactct gcatcacagc taccacattt tttgtagata tacgtagatc aaacggaaat   1200
tagacactct ggcaccactt gccaaatcat atgcaaaact gctcaatggt agaatttgac   1260
aacccaaatt gctcatcaag ttttttgtgtc attttccgcg caaacaggga ttcaaatttc   1320
tgccatcaaa aactcatttt ctacaaaaga actacaaata ttatttcaaa aaggcggcag   1380
tggtggtcaa agaacaaaca tctgaacata ttgaagaagg tgtctctctc tctctctctg   1440
tctttccctg ctcacacaaa tctgtgtgtc tctctccaga aaataacaac acttgaggtt   1500
cacgggagga cgggggggagc tcccgcctgt gctccaactc tcttgtcatg ccactttatg   1560
ttgctccagt gttttttgtct ctctaaatct ccagctagct gttctttcat gttccccttag   1620 ccccaatacc gccgccttttc gatcttttgg ctgtttttttg ggggatataa gaagtttcga   1680
ggaggaagac tagatctatt catcctaaaa taaatttttt ttctttttttt ttaggcttta   1740 tcagactcta aaatgctcgt acgacaccaa attccagatt tcagttttct atattttcgg   1800
tcctataata ctatattcaa aaaattagcg tcttcgaagg aatctgacat ctaaaagttc   1860
tattggtctt ttttccggca aatcggcaga ttgccgaaat caaaaatttc cggcaaattg   1920
```

```
gcaaaacggc aaattgagag attgccggaa ttgaaaattt ccggcacaga ggcaaaccgg    1980
caaattgctg atttctcaga aaaactgcaa ttgccgaaaa ttttcggcta attgaggttt    2040
tgcattttat ttttggcaaa ttgcctgaat tggaaatttc tggcaaacca gcaatttgcc    2100
aaaaatgaaa atttccggca aattgccgat ttgccgaatt tgctagaaaa aaaattaatc    2160
ggcaaaattt tacgcatcta ttttgaaaag aaagcaaatt ctatgaaaat atctaaagaa    2220
aatcttttaa aaaatgcac agttttaaat gtttcattcc tttcaaaaat ccctctaacc    2280
gcttccggca aattaatatc cggcaaaggg caaatcacca aaccggcaaa ttgccaattt    2340
gccgaacaaa aacaactgaa ttatgctatt aataattcct ggttcctgat ttccaatttt    2400
tgattatttc ttactcactt cagtatcgga aaacgttcac aactttggaa agaatttgat    2460
gcccgtaatt tgctgaataa atttaatttt ttcaatgtcc ag                      2502

<210> SEQ ID NO 25
<211> LENGTH: 609
<212> TYPE: DNA
<213> ORGANISM: Caenorhabditis elegans

<400> SEQUENCE: 25
gttttctgca aaataatcat tgattttaac acctcgtaaa ataattttaa aaaagaagt      60 taaaatttta attgcaaccc tatttgtaaa agaaaactc attttcgcca aaataaagc     120 aaaaataatt caagagaaaa acgcgccgcg tgttgcgatt ggggcgtaac tgcaatgtgt    180
gcgcacacaa tctcaacaag cgctgcgaga cccgccgcct gaccgtaatg tgaaatgggc    240
ggagacgaga agtttttttc tgtttgaaag ttgatgcaaa agcccgtgat tcttttttc     300 gagaaatttc tcgagttttt tccaacgaaa aattcattaa atttaaacct tttagctctc    360 cttttccaata ttttgcatca ttattctcct aaaacttggc atattcagtg gaaatgatgc   420
aaaatgccct gacttttgtt atcaaaaata caagaaattg tcccgtttaa cggttgaaaa    480
gcaaattttg tgtcatttg tttaggaaat gtcaaaataa gctcaaaaac cgattacaaa    540
ttatatttta ctgcttttta tcctattttc tcgcgttttc gttcatgatg caattttctt    600
tcaggcact                                                            609

<210> SEQ ID NO 26
<211> LENGTH: 836
<212> TYPE: DNA
<213> ORGANISM: Caenorhabditis elegans

<400> SEQUENCE: 26
ttttcggctg aaaaattggt ttttgagtt ttaaaattta ttttttagcgg gaaattacat      60 gaaaacaacg aaaaaacccg aagaaacccg cgaaaattca gaaaatgatc aaaaaaccaa    120
aagaagcttc gagaaaaaaa gcagaaaata aatgtgcggc gcgaaaaatc tcgtgcggca    180
aacttgcaaa tctaggcgtg tcgggccaat ggcagacacc gcgccgcaaa ttcagccaat    240
cagcgcgctc agctccacct agaaaagtgt gcgcaccttg caaaactggg cggagcgagt    300
gaaatgatgc aaaagtctat tctgatgtaa attagccatt ttacatcaaa atttgcgtca    360
ttttcgttat ttttctctca ttttcatat tttgaacgaa aaattgaggt ttttgcttc       420 tattttcatc agaaaccatt gaaaatgct tattttgg ccattttcg tcgaaattag        480 gggaaaaaac tattctacag ttttcccagc tattttctca tttattcctg tattttcag     540 tcattacctg cttcccagac gataatgcaa ggcttctcgc ttcattttca taaaaaacga    600
```

```
ttgaaaaatg cttatttata ggccatttat cgtctaaatt aggggaaata tctgttttac      660
cgttttccca gccgattcct catccattct cgttattttt cactccttt ctgcttctca      720
```
(Note: line at 720 as printed.)

```
ttgaaaaatg cttatttata ggccatttat cgtctaaatt aggggaaata tctgttttac      660
cgttttccca gccgattcct catccattct cgttattttt cactccttt  ctgcttctca     720
gacgataatg caaggcttct cgcttcattt tcgatgagaa actctgattt tgctcgcatt     780
ttcgcctttc cgctgcagat tttcacacaa ttttcgtagt ttttcagaca caaaag         836
```

<210> SEQ ID NO 27
<211> LENGTH: 580
<212> TYPE: DNA
<213> ORGANISM: Caenorhabditis elegans

<400> SEQUENCE: 27

```
agagaataca aaagagacg  aaatggttc  agtggaacga acaaacgtg  ggatgtaacc      60
atggaagtga gaataattga tggaatagct aatgagctga agctgagtag atcagagact    120
actttattct aaaaagtaca gtagttggaa aattacatgt ttcatttcta attttcaagg    180
aaaagctagt aattaccgta atcttgtttg tacctgaaat tttatgtact gcaggtgacc    240
aagtatgttt gaggcatgac ttcacacacc taactgataa aggcctctat cacaaactag    300
agttgtgacg aaaattcaa  cttctcagaa tatagctcaa aatctatcaa atttatttt     360
caaaatcca  aataattgtg cacgcaatgt acttactgct tcataaagtt cagaagaatt    420
ggataaattt gaatgaagtt ttcaaagctt ttatcagtga ctgtacattg tgataggctt    480
gtgctgttat cagctgcctc aaataggttg tcgcttgaaa atttatataa aaggcctacc    540
agcagacatg agaatcaagc ttcaaaggct ctactcaaaa                          580
```

<210> SEQ ID NO 28
<211> LENGTH: 584
<212> TYPE: DNA
<213> ORGANISM: Caenorhabditis elegans

<400> SEQUENCE: 28

```
ctgcgaggaa gagaaaaaat cgtgctgtga aggaaaaacc gagaagactg agcaaaagaa     60
ataaccaatg agcaagtgaa cttttcccac gtctactact aaattattgt cgatctataa    120
ttctttcgct tatcaatctt gtcaattgaa ataaaacaat atttttctaa ttctttttgg    180
aacgaacaca cgtgttaaa tgaatgttgt gctaaaaacg tcacatcaat ggtacgtgaa    240
tgttgcaaac accttgtcaa taactgataa aatcagaaac tagagctgtg actgaatcgt    300
atactagaac ggagtctctc taaaaacgtt ctaaaaacaa acaaaaaatt gtgcaaagga    360
ttagagtgct caagatcaat gagcaaactc acaatcaact atctgttatt gttttgggtc    420
tcttctatat ctctattctt ttagtatcat aagtttgtac attgtgacag gccaccctc     480
ttttatcaca tatttgaagt ggtaaacagc cagcaaaaac caaataaaaa ggcagtgaga    540
aaagaagaa  ggcagctcaa tttgactgct gaaattaaga aatc                     584
```

<210> SEQ ID NO 29
<211> LENGTH: 1031
<212> TYPE: DNA
<213> ORGANISM: Caenorhabditis elegans

<400> SEQUENCE: 29

```
tctgctgatt tatttgagct ctctgtgtg  accaagacga gagccgaaga gtgaagtttc      60
cactgtcaca ccatgtattt tatactagtt cagagtatct ttgaacaccct gttttaaaaa    120
ggtacaatac caaaggcgc  tcttaatgca cccggttaca tttgtatttg tttgatcaga    180
tggatgtctg tctgacaaac gtcggccaaa gaatgcactt gcagacttta ctttaatttt    240
```

```
ttgtctagtt tgaaaattct tcggatttgt tagtttcaag aactttcaat gaaaccgaaa      300
gtttgttgag ttagcgagaa ttacttctga ttacctgaaa attaatttga ctcaatcttt      360
tacctactta gaaagactaa agtttctgca caaatttgtt tgaacaggtg cttcaaaatg      420
ttacagaatt ttcatttca tccacataaa aagttgattg acaaatagtg tgggcgacat       480
gatttcttga caatttgtt tcgcttttca atttggactc agttcttcga aatttagtta       540
ttatccatat tattactgtt ttgagtttta tcgcagtagg aaatactggt gtatatacat      600
attatatttt tccgttttgt ttacccagaa agcttaaaat tcaagttggt cagaaaaata      660
aaaaaacaac ttttgcaaga aataccattt tttcatcgtg cggaaagaac aattgaaaac      720
taagtatttt ttgctaaact gcagtactgc tacaatacta atactgtacc acgatagtca      780
cccaacagta cgaactccta ctaaaaattt attaaaaaaa gttttattat tcaaattttg      840
aaaatccata agttctaaat actttgttca gtatgctata cttaacacaa atggtattct      900
gcaattgaaa cagaaactac aataatttta tcacaaaaca cagttctccc tactttctta      960
tcacattatg tcatcggggt ggcaagtata taaaggaatg ctgtaaaaag atatgtacta     1020
ctgtctcaag t                                                          1031

<210> SEQ ID NO 30
<211> LENGTH: 1084
<212> TYPE: DNA
<213> ORGANISM: Caenorhabditis elegans

<400> SEQUENCE: 30
agaatttgca aaacgagcag gaaagtcata ttcgcagaaa aaagtcgttg caaacattcg       60
tttttatatg tttttctttg agaaagcgtg gttcattttt gaaagtgaaa atatttgct      120 taaaacttcc aaatttaaat ctgcagtgat tcagagaggt tgagaattat tttcaaaaac      180
attcaatgtt ttcccttgga gtgactatgc aaatatgaaa atgttttcca aaaatatttg      240
gatgccctga taaaagtag gtgaaatttc gcaggggaac atcatattaa aatgttgaat      300
ttttagaaga aatggaaatg tttgtcggtg gtatgctcga atatttgaga tattatatat      360
ttactgttaa atccgaaatt tttgacaaac ggaaaaaatt tgtgtcgaaa tactacattt      420
tcgataacac aaaggtactt ccataacact tataaaaact gtttgactat cttatttcag      480
gaaaaaaaaa tccaagaata aacatttttc agaatttgaa ctttctaatg ctgattaat       540 aaaacaaagt tatacaacta ttcaaagcag ttgctcaatc tggcattttc ttgtgttttt      600
ttttgaatat ttcatcagca agatgttgat aattttgtgt taattctaat tgttttctac      660 aattttcaa ccgaaaatt gacctttgac tttgttact tgttctcgt gggttaactg         720 ttcactgatt tctattgctg ttgatgaggt ctttgatcaa atttgtattg tttttatact      780
gcatattgct tcaattctaa atcatctaat atattgtcaa acaacttctt gtttttttt      840 tcattcaaaa cttctgcaaa aacgttctct taacaaaggt tcacacaaca actctcctct      900
ccatctcttt ctctcaacaa caatgtgctg gccttgcatg tttgccagtg cgggttgttt      960 acgcgtttc aagattttg gtctcctatc taacgtcccg aaatgcattt tttcctttca      1020
tttggttttt ttctgttcga gaaagtgac cgtttgtcaa atcttctaat tttcagtgaa     1080
taaa                                                                  1084

<210> SEQ ID NO 31
<211> LENGTH: 1929
<212> TYPE: DNA
```

<213> ORGANISM: Caenorhabditis elegans

<400> SEQUENCE: 31

```
caattattat aagaaaataa atttaaagtt atccgagcaa caattatcaa taaatattac    60
ttttttaaat gaaacccttt ttaatttcag cagaaatctt agaaatcaga tgatcaataa   120
ataaaaacgg ctgactttt aaaggcgcat agaattttct tggtggcggg tcccgcaccg   180
aagagccgtt ttctaaataa tatacactaa tgattatttt tattaaattt tttcacggtt   240
ttcgagagta ttctttatat aaattcaatt ttaaagcatt ctcgtcgagt ttgaatccga   300
aattatcgat tttcgttttt ctctgctttc tctaccgctg ttttctctcc tccgctgtct   360
tcgcaagatt atagagctct tttgaatcaa tttgtttcat gtttccgctt ttgacgttat   420
tttaaacata tactgatata aataaattaa gaatagagta gaaaatctag ttcaagtaaa   480
gatgcaacat ttctttctgc aaaatttctc gaaaacacct gttttccaaa acttttcaat   540
tacacaatta gaatttcgga aaagttaaca tatataagaa catattatat atatatatat   600
atatatatat atatagatta actctcacag ttaaagaaat ctgaatagta atattgcgaa   660
atagttttgc ataagtttgt ttgattaaat taaatgtgaa gcactaacgc tattgaatcc   720
aggaaaaact cgaattattt gtttgatttt tattaaacac actttgtgaa caattttcgg   780
ttaagaggct tgttgtagt aaaaatccta aatctacgat tatcttctta aaatttgaca   840
tacttcttac gtatgttaca ggataaatcg agttttgatg tatttcgtaa atagttttta   900
atcatgttat cttttatt cccatctcta tgttttaatg ttgtctttac actaattcac   960
ccgtaatgtc cgtgcacaaa agaatttaac attcagatat tatggaaaca aaatcatccc  1020
aaacttcaca tccgtggctt gttctactca ttttcgccac ttttgcggtc tcaattttg   1080
ctgtatacag caattttcct gaagtctcgg cagatgagaa ggttcatttg aaatatccca  1140
ggaatctgga agacgctaag cagctgggca gagttctctc gaagtacaag gagaacaact  1200
attcagtagt tctgtgcggt gtaattgtcg tctacgtatt tctacagtcc ttcgctatcc  1260
ctggatctat ttttctaaca attctatcag gatacctgtt tccattctat gtggcaattg  1320
tgttggtgtg ctcctgctct gcaactggag ccgccatctg ctacaccatt tctaaacttt  1380
ttggacgatc atttgttttg caaaagtttc ccgaaagaat cgcaaaatgg caggatgatc  1440
tgagcaagca tcgtgatgac tttctgaact atatgatttt ccttcgagta actccaattg  1500
ttccaaattg gctaatcaac attgccagtc ctgttctaga tgttccactg gctccattct  1560
tctggggaac atttctaggc gttgctccac caagttcct gtatattcaa gctggctcaa  1620
cactggaaca attgagccat accagtgtag catggagttg gagttctatc gttttactta  1680
cgggttcggc gattttgtcg ctggctccta ttttgctcaa gaagaagctc aaatcggatt  1740
aattttctct cttatttcct ctttcgatct catttttttt ccattgcttt ctgtgcaaaa  1800
cttgtgatat ttagagaata tagccgataa ctcatttcta tactattttt attattttt  1860
cgcctccttt tttgtcataa taatcatatt ttcttcacta ataacaatt tttaggtgat  1920
gaaacaatg                                                          1929
```

<210> SEQ ID NO 32
<211> LENGTH: 1091
<212> TYPE: DNA
<213> ORGANISM: Caenorhabditis elegans

<400> SEQUENCE: 32

```
gaaactctcc tggatttttc tagattcttt tccagttaca tttcacatag aatctctaac    60
```

```
taccggtgca tttgccaatc ttcttactga aattctgtgc cttgttttgt cattaaaatt      120
ttacaccgaa taaattattt gtctttgtaa tagcttatga ctttaacaag gtcattttt       180 ctaactggct cattcgcgct gaagtttaaa agaagtttgc ttttttgtcg gttaagccgt      240
tcatacattt tttggcaatc ttggtacaac catctactac atttatatca aaacgaaaaa      300
atgtataaat tttccctcgt cttcatctac ccgcaatcat aaaggaatct cattccgtcc      360
cactcgccct ttctttcttc aaccgaaatt ttttttcccg cggcgcaaac cctcatgtgc      420
cgtcgatagc tcagttggta gagcggagga ctgtagagtc agcaggtatc cttaggtcac      480
tggttcgaat ccggttggac ggatttcttt tttattttct gtatcaagtg taactcttca      540
gaaaatcatc gggagcagtc gtacgaaatt ttaattataa aaattaaaca ttccagcatt      600
tttctttggg aggtgaagta gagtcagcgc ggatttaccg gatttacagt tagtttgata      660
cacattcaac attcaatatt accgaatttc aaaacaaaac attttttacct aagtctttta     720 gattattgga aaattacagg taaagttttg gtgaaatgcc aaagtcataa tgcgagatgg      780 ttttttttttt tgaaaaattc agatcaaaac tacgtgtttg gtttgtgata aatatattatg    840 atgaaaaaaa ctcgaagaaa tcataaccca aatgatattc agttcacaaa cataagtatc     900
atgatgcaaa atacaaagct gaatgtattt tttcaagacc gcagatcaca attaagacat     960
ggtaaacaca aactctactg cgtaccgcag tgaaatgtgg tttgtagtat gactggtaga     1020
gacacatcga cctatataaa catcaaaaaa ttgtttaaaa aaatattcca tcgagaattg     1080
cttcatttca a                                                          1091

<210> SEQ ID NO 33
<211> LENGTH: 1769
<212> TYPE: DNA
<213> ORGANISM: Caenorhabditis elegans

<400> SEQUENCE: 33
atattggaag tcaatgagaa ggaggaattc tggattgcaa acgagaattt ggaagtgagt       60
ttggagatag tagcaagcct aagcctgggc ctgagctgag tcaaagccaa agccgaagcc      120
taagcctaaa tctaagcctg agcctaagca taagcctcag tctaagatta agcctaagcc      180
tgagcctgag cctgagcctg agcctaagcc taagcctaag ccaaagccaa aacctaagct      240
taaacctaag cctgagaata agcctaagtc tatgccaaag ccaaagccaa agcctaaagc      300
taagcctatg cataaaccta agcataagcc ttaacctaag ccttaaccta aacctataag      360
cctaagccta aattttcagg cactcactac cgaaaatttt ccattaatgt tcaactcaat      420
gctgtcgacc gtcctgaaac caattgacac cctcattgaa tgtttcaaaa aagaaggacc      480
ctacggcctg gattactcgg cctattcgga ttttgaagaa atgcagcaaa aattcactaa      540
aatcgttcac gagaagcata tcattccgga tttggttcca gccattggaa acgggatcaa      600
ggagaagctg gaagctggtg ggatccgagt gttggatgtc gggtgtgggg gtggattcca      660
ttcgggcttg ctcgcggagc actatccgaa atctcagttt gttggattag atatcaccga      720
gaaagctatc aaagcagcga ggctcaagaa gaaatctgat ggcactgatt ttgaaaactt      780
ggaatttgta gtagctgacg ctgcaataat gccaagttca tggaccgact cattcgattt      840
agtcatcctg tttgggtctt gccacgatca aatgagacct gacttggtaa ttttttgtatt    900 cagtttcaga gaggtatccc aatcatttac agtgccttct cgaagttcac cgtgtggtga      960
agccagatgg tttagtcgcg gtcaccgacg ttgatggatc tagcaatgtg ttcaccgatc     1020
```

-continued

| | | |
|---|---|---|
| gtgagaccta cgggaagatg gctgcgatga agtatggtgg atcgatgctt cattgtcttc | 1080 | |
| cggttgggag caataggcca gatgcactat gttgcggctc aatgtgggga aggaagagag | 1140 | |
| cagttgagat aatgaataag tgtggttttg ataatatcga cattattccg actgactact | 1200 | |
| tccctggaac tgtttgtat ttgatgaaaa aataaataaa ctgtagctag tgttttttta | 1260 | |
| taattgtaat acttttttct atttattcaa tctttttcc cgattttcac tgctttgttg | 1320 | |
| tgactgtatc attatgatcc tgatgaataa atatcaataa acaaatacag ttttttttt | 1380 | |
| atttgacatt gattttgat tctgagaata taatacatat ctatgagaaa ttaattaatt | 1440 | |
| aataattaat aagaattaat aaatttaata agaattaaag taaatatag tgggaatata | 1500 | |
| gtggaaaaat tgttttgtaa ttgtatgcaa tatgtttata atttcaaaa tcaaagagca | 1560 | |
| gcacgacgga gcccaatatc aaagttcaa gcgacacact caaatacga ctcatacctg | 1620 | |
| cgtctcctcc ctctcccaat ttcgcaacat attttcgtat tttgtggttt cttcagtcgt | 1680 | |
| ctatttctcg cacatacttc cacctgatgc aatttcgagt cctcaccaaa taaatagccg | 1740 | |
| gcaatgtttg ccattctca gttttcatc | 1769 | |

<210> SEQ ID NO 34
<211> LENGTH: 1406
<212> TYPE: DNA
<213> ORGANISM: Caenorhabditis elegans

<400> SEQUENCE: 34

| | |
|---|---|
| tttttttt ttttggattt tcgactttaa aattagccta aatttatcct aaaattatcc | 60 |
| taaaaattaa aatttcacat ggttgacaaa tttgcagtgg agcgcatttg cagaattttt | 120 |
| tttttgaatt tttttttcat aaaaagcgta acattttcca aattaatggg atttttaaag | 180 |
| gaaaaaatta tcccaaaaat tttaattttc taattgaaaa aagtgttatt agcccaattt | 240 |
| ttaaaggttt tttttgcaat tttcatcaga aaaagcgtta aaaatatcaa ttttcgtga | 300 |
| aaagttgatg aattctctca aaaactcggc aaaagtacc gccaaaaatt caaattctcc | 360 |
| aattttcat ctctaccagc aaattcgcga tggagcgcat ttgcagagtt ttttcagaaa | 420 |
| aatcgtaaaa ttttccgaat taacgagttt tttttaagt aaaagtgatc ccaaaaattc | 480 |
| aaaatttcc gatttttgaa atttttttgg tgcaaaaaaa ctaatttca aattaaaaaa | 540 |
| aagtgatttg tctaaaataa aaagcgttta aaaaaaacctt ttaaaatttt tttttcccaa | 600 |
| aattcacgtg gtgccagggg ctgtcccatc gacggtttga tctacaaaaa atgcgggagt | 660 |
| ttttcgccca aaaatgttgt gacgtcagcg ctttcttaac catgcgaaat cagtccccgc | 720 |
| gcatttttg tagatcaaag tagatcaaat cgaaatgagg cattctgaca ccacgtgaaa | 780 |
| atttcaaatt ctccaatttt tcatctctac catcaaattt gcgatgaagc gcatttgcaa | 840 |
| ggcctttttt taattttttt aaaaactcct taaagttaaa aaaaatcatt tagctttaga | 900 |
| aagcccaaaa attaaaaaaa aattttttt taatcgaata tcaaaaatgc atttgtgctc | 960 |
| caccgcacgg cggtaattc gaatttcttt taaaattttt tttataaatt tctgtatttc | 1020 |
| acaactgtat tttttcccga attttcctcg cctaataaca ctatttgtca tgattcttac | 1080 |
| gtcattgtcg ccgccgtttc tctttttctc tcgccactct ctcatttcca tacactattt | 1140 |
| ccactctcat ttttatcatc atttttcttca gttttgctg cttttaaagc ctatgttttc | 1200 |
| cctttttata taatatcgca gaattttgtt tttgtaaatt taatatatat atatatatat | 1260 |
| tatttatttg atgataatgt gatttctaat ttttttttcc ccaatttttt tcaaattcaa | 1320 |
| attgtctcta cgcttttctt atacttcatt gccttttttt ttcaacaaaa atttgagaaa | 1380 | aaacaccaaa aaatttcaga aaaacc                                          1406

<210> SEQ ID NO 35
<211> LENGTH: 1051
<212> TYPE: DNA
<213> ORGANISM: Caenorhabditis elegans

<400> SEQUENCE: 35
gcacgtgtat ttttttcggc acgtgaaaat ttttttttcaa catgtatata tatattttt      60
caaatttgga atgtcttatg aaaaacgtcg aaaggagga actcatttag attaattgtt     120
atgcaaagtg cagatttta acaacgaatt tttgagatca aattgtcaca gttagctgat     180
gttttcgaac tctacacatg tgtgaaggtt cactcagtct gattggttca aaagtggcgg     240
tacgagtcgc tgatcggtct tgcagttctc aatttcgagg aaaatcaaac aagaagatta     300
gccaaaatta aaaatttacg ttttgaaca gtgttttcat tgttattctc atttatgtta     360
tgaaaacatt ttcaaacgtt ttttcctgga tggtaccatt cattcatca agaacttcct     420
gtcactttaa tgatcttttg tttttttgta gtttgaatta aatgatgat atccattgaa     480
attgagtgta ggcgtatcat gatgacaatt aattaattt gatcttttgc tacagggttt     540
tccataggtc agttagtaag tgaaatctat aaatttggat tgtaaacgtt ttttcaacct     600
tgattttgtg tttttttca gttttttatt tattttagat atttaacatt taaactattg     660
aagcttttaa aaatcatagt tttatgtaaa attgaaaatt gtggtaaatg acgttttagg     720
ccgaattagt ttttcattta agactacatt ttatttcaac atctaagaac ttttttgacat    780
ttttcgagcc attgttcaaa aaacatcatt gaacactaca cggttcaaaa tgtttacact     840
agatacacaa accaatagag acactctttt aagaggcaaa tggtcagaga attagacaat     900
gagacattct tttcttctgt gaatttgtat gttatagtga ttagacagtt aggatgacat     960
atatttgtca gcacaatttc tcttataaat acaagaaaat tttcagagat tctcatatcc    1020
atttctattt cattgaaaag ttttttcaaa c                                   1051

<210> SEQ ID NO 36
<211> LENGTH: 1121
<212> TYPE: DNA
<213> ORGANISM: Caenorhabditis elegans

<400> SEQUENCE: 36
tgactaacaa tatgaaatgt gtataaagct tcatgatttc acaaaattga agtctaaaaa      60
atataagctt taatttttttg ctgtatgagc ccctcaaatt ctcttatata cttttttcctg   120
ctaatggcta cttcttttgat cgaagatttg gccaaccggt taagtttgcc gacaccagca    180
taaagaaatt ccgttcatcg cattcaattg agttatagga gcaaacatta aaaattgatg    240
gtataacttc ttacaataac atgtgaacaa acagcacgtg ggcataatca agaaaagaag    300
cttttgattt tgaagttgat aagggaaacg atcaaggtgt tcaagaccga aataatatt     360
ttcagtttga gtaagttgaa aattatatta ttttttgaata ctttttaaac agctaacaga   420
tattgcaata gagtgcttga agttgtatgt caatatagtt ttcgtgaata gacattaatt    480
acagtgcggc tcataataaa ttttattgtt tttttagta ttctacaatt ccatcgagta     540
gctcctgaaa atgtgaatag cctagatagt aaccgattga gaaagtaaac gtgcgcttat    600
gagttacgtt tcgtattttc acaaaatcgc agtataattt ttagtcattt ttcaaaaaac   660
caaaaatcta ctgtaccctt attgtaatca aaaatgtgac ggaatctcgc atgaaaccaa    720

```
agattgttta caatcccaaa aataatccaa aaattgccct gtttctctca attcactgta    780
cattttcaaa gttttccaca gatacatttt cattcatctg tgaaatcgaa tcttttagac    840
tatgtatttg tcataaaatt ttgtgattct tttttgttct gttcactctc tgtcccttat    900
cgttcgtatc tctatttctc tattctctcg ttaccatctt atctattgtt attccatttt    960
tttggtcatt tgtttattga actcccttta ctcaactgca cacaaacatt tcttttttatt   1020 ttcttttgaa tatatgctcc atgctaacca gaactgacct gttgattctt ttttttttccc   1080 aatatactag tccttttctt aagttttacc aatgttttta g                        1121

<210> SEQ ID NO 37
<211> LENGTH: 854
<212> TYPE: DNA
<213> ORGANISM: Caenorhabditis elegans

<400> SEQUENCE: 37
tcagcgatga gcacaccgtt caaagatttt ctgaagcatt gggcttacat gtgaaacaag     60
cagcactcga tattagtgaa ggaaaaatac cgaaagcaat aattgcattc aactaaatac    120
tgtatttgca cttggtatta cagaaacgca agttctgag aatgcgtact gggtaacata    180
tttgacgcgc aaaatatctc gtagcgaaaa ctaaataat ttaaaaaata attcgctttc    240
gattagaaat tcatttcgaa attcgagtat gtaaatcgac tacagtagtc aataaaagta    300
ttactgtagt tttcgttacg aaatattttg cgcgtcaaat atgttgccca atacgcattc    360
tcagcatgtt gtgttcccgt aacatttaac ctattttaca taatctaggt gttttaaact    420
ttttataaaa ctttctcgta atgctatctt tgcctcttag aaaacttatt cagcgacgtg    480
tatcataacc aattctaatc ggcttgttag aaagaagaaa tataatactt cggcgtctcc    540
actttgtgac tgggcacaaa atgcaattca gattctactt tcgaaatagc cataaaatca    600
taagatcaca gatctttctt cgtttctcag gcaaccaggt gcacaattgt catcactcga    660
ccagtgagac cacaatagaa cagcaaacgt tgtcatcttt ttggttagac actttctttc    720
tgcctctgcg tcttttcata aggtgtgcat actcttgttt gcccaacaac ctagccgatc    780
agaaaacgca ctatatttga cctgcgtgta cactgctata aaagtaacat tttgttcttt    840
catttcttcg aaaa                                                      854

<210> SEQ ID NO 38
<211> LENGTH: 1616
<212> TYPE: DNA
<213> ORGANISM: Caenorhabditis elegans

<400> SEQUENCE: 38
aatgcaaaaa aataagcctt tccgaaaaaa cgggcccttg ggcctttaaa ggacacaaaa     60
acaggaaagc ataagacacc aaagagtaat tggatttcta cactttggtt cctagaatta    120
tttataaggt gttattgcgt ttttgtgaga ttgttctatt tatccagtca aaaattgcat    180
tttctttgtt tttgcttcaa aaaaatacat tttcagtgga aatttcagct gaaaagcaga    240 atttgaggt tttcgagtaa ataacgtaaa acactaaatt acaaatattg attttgatg    300 tcttagacca aattttcgta aacatgtttg tattttggga aaaaataggt ttttgtcga    360 ttttaactta atttttcgaa caaaaaatga tttttttctcc gatttaccaa agtttgact    420 taaaattccg atttttctggg tcattttttcc cctaaaaata cgattttaat tcaaaaaatc    480
tatattttca aagaccaaag taccataacc ttcaaaaaac aaccactttc tctattgcat    540
cagcgaattg tcatcaccccc tctcaaaata tacaaaacgt catcattttt ctgtgttttc    600
```

```
tctaattctc ctgaaaaatt ctataaaacc aacagttttt atcatcaaaa atgcctttg      660
accgactttt tttaaagttg aaaatcgtac agttttagca gaaattccag agtttcattt      720
tgaagtatgc tggaaataat aaaattattc taacatttat taatattttg taaaactaat      780
tctatacaat aaaaagtaa aatttaatat taaaaaaacc ggttttctc aaatttccat       840
tccccaatgt cctgttctat tatttgttcc gattcggcca cagaacgcgc acacacacac      900
ttttgctga ttctctgcct cctttctttg atttgaccgc attttatatt gattttcggc       960
cacaattcca ctatttgttc agtttgtcga tttgttggaa atttcaattc cggcaattcg     1020
ccgatttgcc ggaaatttaa attcagacaa tttgccggtt tgccgaaaat tttcagttcc     1080
ggcaatttt taatttgccg gaagtttcca tttcggcaac ttgccaattt gccggaaatt      1140
cgccgttttg ccggaaattt tcaattccga caacttgcct atttcccgga aattacaatt     1200
ccgccgattt accaatttgc cagaaatttt taattccggc aatttgccga tttgtcggag     1260
atttcaatcc ggcattttgc cgaaaatttc aatttcggca gttcgccgat tgtggaaaa    1320
taacaattct ggtcattcgc caatttgccg aaaatttcaa ttccggcaat tcgccgattt     1380
gccgaaaatt ttcaattccg gcgattttcc tatttggcga atattttaa ttccgccggt     1440
ttgccgcttt gccggaaatt tcaattccgg aactttgccg atttgccgat tgccggaaa     1500
aaatctttg ccgcccaccc ctaataaaga cttcaaaata tgcgttttt tttgcttta       1560
acacgctaaa actctctaaa atccccaat tttcagctt aaaaaacccc aaaaaa          1616

<210> SEQ ID NO 39
<211> LENGTH: 726
<212> TYPE: DNA
<213> ORGANISM: Caenorhabditis elegans

<400> SEQUENCE: 39
ttttgcagac taaaataac tactctgcca gtgtttaatt tatagatgca atttgtcact       60
attttcattt tatatcgacc aacccattca cacttcacta atcgtgttaa aactcaatta     120
gtggaaaatt tgaaattcta tgaaactttc atttgcgaca aaagattgtt gttttcttca     180
aaccaaaaat ttatcaatgg gaaaatgaga tagacaagaa ctgggaaaaa agtcgaggtt     240
aataatttaa agaatattg aatattcggc gccataatat taacgaaaat aaccaaaata    300
tgcccaatta ttatccaaaa agattagaag ttggcaaacc ttgggcaaga atttccagag     360
attgcactaa agttgtagcc aagtttgatc caactttatc caatctttta ctaaaattat     420
ccttaagact atttaaattt tagatagaga attggcgaga gttagatccc acttggatat     480
gacttatagt tagcctaacc tgaagctatt gcttgcttga tcatttggtt tatcgctttg     540
ctacttggat aaccagctcc aatagttgtt attttgctt ttgtcatcat ttttccacga     600
tttacactct caagtgaaac caactgttct tgatgccag acgatgacat tacacttgat     660
aagaaaatat atataaactg gaattaaaaa caattgatac atcgattcaa ttactgaatt     720
ctaatt                                                                726

<210> SEQ ID NO 40
<211> LENGTH: 1283
<212> TYPE: DNA
<213> ORGANISM: Caenorhabditis elegans

<400> SEQUENCE: 40
atttcatttc ttttttataa atacttcggc tctattactg aatgaataaa tgtataatga       60
```

-continued

```
tgctctccaa atcctcttat tattcgctcg aaccgcccgt tcccatagat accgtctagt      120
tttgacaggt gttcaaccat ctgccgggaa ttacgagaag agtcgaatta attgagatcc      180
tcgtctaaat aaatctgaag tttaaaataa agccagaaat acctgaaaag agagaaaaag      240
tgtgtccacg atgtctttgt ttatgaccag tggtgtgtta tcgagaaaaa ctccaatgaa      300
tcacacacca gagaagaatc gagaaaggtc gggaaattag gaatgagaaa taataaatgt      360
gaggaagtaa taaagaatc ttcgagaact cattccactt ttagatataa acaagcagc       420 aaacgggttt gtaggtatta tatttatcta ttttaagttt aataaactat ttttgctaaa     480
cttaaacggt tcaggtgttg aaaaagtcct aaaattttg atattatcaa attcttttag      540
cgtggcggtt ttctttttt tcgaaatatt gagttttca tctgaaaaat gcactattcg       600
tgtccttcaa aagttcatgt gtcatcagta gccactcgaa agatcgatca gtccattttg     660
atttcgaaag taagaagaga tcattactat tcaagagacg caggcacgga gcctgttgcg     720
ccgcgaatct tccaggcatt cttggcgctc cgcccaaaaa attgcaaaaa taaaagttgc     780
ttgaatcatg ttgaatgtca cttaatcgtg tggctttcaa tgttctcttt cagaaaatgt     840
attttttatt tgataatgtt aagaattcgc cgagttattc ttcctcaaaa tgtggtgcgc     900
gctctctctc cccttttcg tcgcgaacat tctctgcgga ggcatctctt cttttaattc      960
acaattctca acactttct gtaggcaaaa ctctctaata ttgctccttt ttcagatttt      1020
tgttcaaact tttttttgtat ttatcttgtt caagtgtttt ccattcagca gttacagact   1080
atttaaggaa attttaggtt tttagcacat ttttctaatt ttttgacgaa attcgaattt    1140
tctagaatcc cgccacgccc agtcatctag taaatttgtt gaacttcatt tctctatttt     1200
taatcattgt tctcgacgtc ctaatttttt atctccattt gagtgactat ttcttgattt     1260
ttaaattatt ttttacagta aaa                                              1283
```

<210> SEQ ID NO 41
<211> LENGTH: 1622
<212> TYPE: DNA
<213> ORGANISM: Caenorhabditis elegans

<400> SEQUENCE: 41

```
gctctgccag aagaagcatt aaattgtttg atattcaaac ttttgtatat agaatctcgt      60
tatttataaa ctcttttttt tgtatttctt ctggttttg atgataagaa attttatgtg      120
cacataaatc aaaaaagccg gaaattaaat agcgtttat caggcagaaa attggccacg      180
tgacgtcatc attttcctgt ttgaagaaaa tctggaaaat tttttgtttc agtcaatttt     240
taaagatgaa aacttaagtt agactgtaaa agcaattttc gcgccaaaat tacggtatcg     300
ggtctcgaaa cgacagtttt ttatctattg cgaaaatatg tgcgccttta agagtactg      360 tagttgcaaa cttttgtcgc tgtggagttt ttatcgattt tttatatttt ttcgatgaaa     420
acaactcaaa tataacaata aaaacacaaa attaaaaaa aaatcgataa aaaatccgcg      480
tcaacgaaag tttaaagtta cagtatttgt cgtttcgaga ccgggtaccg tagttttgg      540 tgaaaacatt gcaaaatttg gtcaacaatt tcatcgctgc gagaccgaca caacacttta    600 ttttatttt gggtttccct tatcgcttat cataaacatg tgacgtcatc atctcttgta     660
cagagcaccg cgactgggag tataagaatc gccggaaaac atcaataatc agttcggtag    720
aagtgaaaat tgagcgtaaa atatgatcat ttttcgatgc accatatttg acgcgcaata    780
cttctacaag ccgctgtgta ctgctcgtgg acaactttgg attattttt gttttaaaa      840 ttcaaaatag tcaatatatt gcttatttat agcgcgcctt tttgacagta agtttgtcaa    900
```

```
atttgcgcgt aagttatggt gtttgcacat atgcaccata cagcaacacc ccgcggcccg     960
gctagtggta catccatgca aatgcgctct actgataatt tgagtttaac caggtttagg    1020
cgcaagataa gaaaaaagct ttggaccaaa aaatttagag tttattttt tcggacattt     1080 tttatataca tcacaaaaat attgggccac tcgttttga taaaaacgac aagcccaaaa     1140
gttcaggtat acgtagaca aattgcgtac aggtaccact tttccacgta gtgccaggtt     1200
gtcccattac gctttgatct atgaaaaatg cgggaatttt tcgtccagaa aaatgtgacg    1260
tcagcacgtt ctcaaccatg cgaaatcagt tgaaaactct gcgtctattc tcccgcattt    1320
tttgtagatc tgtagatttg tagatcaatc cattccccgt atacctgac ccataatcaa     1380 tacctaccta attttgtct ttccccctac tttttgcct gtccaaaata agcgagacta      1440
tgccgtagtc tggtgtccaa caacatgttc cttatcagtg ataacgctac aatcttcttt    1500
cttttttctc tgtttctctt gtctctccca acccatattc cgtattacac ctcgtcgtgg    1560 tcatttttt gttcagagtt ttatttaatt ctaaatttcc taactaaaat ttcagaacca     1620
aa                                                                    1622

<210> SEQ ID NO 42
<211> LENGTH: 1555
<212> TYPE: DNA
<213> ORGANISM: Caenorhabditis elegans

<400> SEQUENCE: 42
aaactctttt ttttgtattt cttctggttt tgatgataa gaaattttat gtgcacataa      60
atcaaaaaag ccggaaatta aatagcgttt tatcaggcag aaaattggcc acgtgacgtc    120
atcattttcc tgttgaaga aaatctggaa aattttttgt ttcagtcaat ttttaaagat     180
gaaaacttaa gttagactgt aaaagcaatt ttcgcgccaa aattacggta tcgggtctcg    240
aaacgacagt ttttatcta ttgcgaaaat atgtgcgcct ttaaagagta ctgtagttgc     300
aaacttttgt cgctgtggag tttttatcga ttttttatat ttttcgatg aaaacaactc     360 aaatataaca ataaaacac aaaattaaaa aaaaaatcga taaaaaatcc gcgtcaacga     420
aagtttaaag ttacagtatt tgtcgtttcg agaccgggta ccgtagtttt tggtgaaaac    480
attgcaaaat ttggtcaaca atttcatcgc tgcgagaccg acacaacact ttatttatt     540 tttgggtttc ccttatcgct tatcataaac atgtgacgtc atcatctctt gtacagagca    600
ccgcgactgg gagtataaga atcgccggaa aacatcaata atcagttcgg tagaagtgaa    660
aattgagcgt aaaatatgat catttttcga tgcaccatat ttgacgcgca atacttctac    720
aagccgctgt gtactgctcg tggacaactt tggattattt tttgttttta aaattcaaaa    780
tagtcaatat attgcttatt tatagcgcgc ctttttgaca gtaagtttgt caaatttgcg    840
cgtaagttat ggtgtttgca catatgcacc atacagcaac ccccgcggc cggctagtg      900 gtacatccat gcaaatgcgc tctactgata atttgagttt aaccaggttt aggcgcaaga    960
taagaaaaaa gctttggacc aaaaaattta gagttttattt ttttcggaca tttttttatat  1020 acatcacaaa aatattgggc cactcgtttt tgataaaaac gacaagccca aaagttcagg    1080
tatacggtag acaaattgcg tacaggtacc acttttccac gtagtgccag ttgtcccat     1140 tacgctttga tctatgaaaa atgcgggaat ttttcgtcca gaaaaatgtg acgtcagcac    1200
gttctcaacc atgcgaaatc agttgaaaac tctgcgtcta ttctcccgca ttttttgtag    1260
atctgtagat ttgtagatca atccattccc cgtatacct gacccataat caataccta c    1320
```

```
ctaattttg tctttcccc tactttttg cctgtccaaa ataagcgaga ctatgccgta      1380
gtctggtgtc caacaacatg ttccttatca gtgataacgc tacaatcttc tttcttttt       1440 ctctgtttct cttgtctctc ccaacccata ttccgtatta cacctcgtcg tggtcatttt      1500
tttgttcaga gttttattta attctaaatt tcctaactaa aatttcagaa ccaaa          1555

<210> SEQ ID NO 43
<211> LENGTH: 2432
<212> TYPE: DNA
<213> ORGANISM: Caenorhabditis elegans

<400> SEQUENCE: 43
ttttattctg aactatatac aaaatgtgct caatataacg agttttgtaa ttttgtgaga      60
aagtcgtatt gaaaattagt ttaaatgtga tttaatattt cgaaaaagta gtctaatttt     120
agctaaattc tacaattttg acaacttttc cgtgtcgcaa aacgaatttt tgtagaggag     180
tgtacctaag cgagtcggag aaacgtgcat tcttccattt ttttcccccg gggagcccat     240
agccagtttc cggacgggcg gtcttgttcc aaacgttttt aaaatttaat attgcaattt     300
aattatctat tcagcatccg tagcccagcc gcattgtgga tctcagattg gcgaatgctt     360
gtgcgctcca ttggactccg gagccattcc gtctgttgat ttcctgattt ctgcggaatt     420
gtccggatcg acgagctctg taaaaaatta atttaggaaa aatcaacatt ttttcgataa     480
gcaaccctta ttccttcgt cacacttcta tggaatccag ctgacggcgg cggctgaaat     540 attttttgcaa aaaaactcac ttttcgactt ttcctctttc tgcgatcggt tttcgcctcg     600
atttgcgttg attagcttaa aatagttttt atattttaac taataataaa gaaaaacaaa     660
aaaaaatgag aaaaaacaat caaaaactcg aaaaaaacat tacgaaatca gcaagaaaa      720 tgaagaaaaa atatatacag taattttaaa ggcgcacaca caaagttttc ggtacgcgtg     780
ccgagaccac tcagcagaag tgtgctcctt tgaatctgga gtacggtcaa tggggattta     840
tttttgaaaa tgcaaatgcc aaaatacaag aaaaataaca aattgcatta attttagtga     900 atttttctgaa aatgagattt tttgtgctt ttttggaatt gtgcaacttt tagtgcattt      960
tcatcgtcct tttttctgaa ttcttgaagt ttctggaatt tttgttcccc ccccccccc    1020 aatctaagac taaacctaag gctgagtcta ggcctacgcc taagcctaag cctaagacta    1080
agcctattgg tgtatgtgca cataaatcaa ttttttttaa aattattatt attttttgca    1140
aaacacaaac gtttttttc agatttttta ttttcaccc tttcaacctg caaaacccat      1200
ttttcttcca ccaaaacaca gctgttcttg ccaccatttg cctgatggaa aatttatata    1260
aattggctgt cctttgtgag aaaactagaa caataatgat gacattaagt actagagtat    1320
aaatatattt ttttttgctg acaattcctg gcgtcccccg ttgacattga aaatgtataa    1380
aagaggcggc cagacaccat ccccgcaaat gtgttttgt tgttcacttt tcttttttt      1440 tccactctct ctctctcagc tgtttgcatg ttgttttat ggtgatctat ggtctctaag    1500 aatttgtta taagctaaga actgctcgct gagaaggttt ttttggttc gtagctagtt     1560 tttttacgt ttatcgaaaa aaaattgaaa aaagtcgaaa tttccatctt aaaaaattag   1620
tgaattttaa tattttttgtt aaataatcgc cattgtttcg tgcttttctc gctctgtaaa   1680
attgaaaatc tataaatttt gggtaatttc gagtattacg ggagcacaaa attttgagaa   1740
tgcgttttgc acaacctatt tgacgcgcaa aatatctcgt agcgaaagct acagtaattc   1800
tgtagcgctg gtgtcgattt acgggctcaa gtttcgaat taattttttt tcgaaaagtt   1860
acatcgatat ttcattttcc ttcgtgctat tttcaaaaat cgagcccgta aatcgacaca   1920
```

-continued

```
agcggtacag taatcattta aaggattact gtagttttcg ctatgagata ttttgcgcgt    1980
caaatatgtt ttgtgtcccc gtaatatttt tttaaatcaa atttcacatt ttaaccataa    2040
aaaactcttt caaagtgta attttctacg caaaaatgcc gttcggatga aaaattactt    2100
ttgaaaaaca aactcgaaac tacggtacgc aaaaaagtac atcggtgttt gcacataagt    2160
gaaaacaatg ttgttttttt gtaattaaaa tcgattaatt tttttttccg gaaaacaaaa    2220
acgttttcag cgtggatttc tattgttcct tgcgtaaaaa aaaattattt accaatttta    2280
aacgataatt tccacgaatt ttcgccatta atctctcgat tttgttgatt cttgactccg    2340
agcaatctct ccgtttttcg caaacgatta tattatttat ttgttttcct tttcagtgcc    2400
gattctcgga aattcaacag taaatcttca aa                                  2432
```

<210> SEQ ID NO 44
<211> LENGTH: 2150
<212> TYPE: DNA
<213> ORGANISM: Caenorhabditis elegans

<400> SEQUENCE: 44

```
tttgagaatt ttctcgggaa attaaacctg tgttttcat  taaatttgat gcaagcaaca     60
agtcattata caataaaatt ggtgaaaata tgatttttt  gaaatatttg gggcgaggct    120
tttagttttt tgaagagctt acaaaaatta gaatttaaga aatttcgaa cacaaatttg     180 agagaacttt tgactttttt caaaaaattg ttttcaaaaa ttttaatatt tcaaagacg     240 aaagaatttg ttttttgtc taaatttacc taatcattat ttttcaatca ataattgca     300 tctctgaaaa cctgggaact tgaaaatga cgtcattctt ttttccctcc ttttcttttc    360
catttggtta ttgacgtttt ccacccctc ttgcaaaaaa aactaaacaa aaagaaacc    420 attggcaact actaacgcca attttgtgtt gcttcatcgg gtttctttta gttttttc     480 tgagagcgct gagattattt ggaaatttgc atttctcac gttctagctc agaaagagat    540
cagctttctg aaattgaaat ttaaaaaatc gctctaaatt gaaacagctg tttttatgt    600 cgattgtctc tgcaaatata tttttttcag aatatataag tatgtgtttg tttaagtttt    660
attttaaatt ttcttgaatt ttatgaacga cattagagct tatgttagtc caaatatttc    720
aaaatttatt aacttgaatc ttgcgcaaaa ttatttgaaa aatcaatttc cagccaaaat    780 cttcttaaa attttatttg aattgtcaaa aacaaatgcc tcattattaa ttttatgcca    840
atattaaaaa aaaattaatt ctcgataatc ttaaaataag attttagaa  aaacaacttt    900 caaaagcttc tatgcgaaaa aaattgtttt tattcgaatt aaaaaaaatg ttttcttcaa    960
aaaaaacaaa tttcttaaat catagatccg tgttgctcaa ctgctcaatg tttcccatga   1020
caaaaagtcc atgtctctct ctatcatttc tcatctctct tttttctcta gccatcataa   1080
aaataaacac atgtttcaac aatcattcct tggtttttta tctctcgatt gctatatcat   1140 ttttatttttt tttactattg ggtaaatttt gaagaggggta ctgatttttt ttcaaaattt   1200
ttccaatcca aaagtctttt gaattgcgtt aaatcatgtc tattgtacca caatgaccaa   1260
atgccatagt aaaactttc  aaaaaaatgt ttgaattttt ttttgagcgt cagaaagtgg   1320
caattacaga gttttttta  gcactatgaa aattgaaaat tttcggagtt tttcaaaatg   1380
attttttgaa attggaaaaa ttacagaaaa caattttttg ccatttttt  ggaagttgcc   1440 gataaaaaaa aatttctttg gattttatgg ttttatttg  ttgaaaatat taatattcaa   1500
accaggggtg tgcggcaaat ctcaaaactt gccgagctcg gcaaattcgg caaatctctt   1560
```

-continued

```
ttttcaatat ttgccgagca cggcaaattc ggcaaatttg cctagctagg caaattcggc      1620
aaattcggca aatttgccgt gcttaacaaa ctcggaaaaa tttgatactt tttgatgttt      1680
tttggagcac caaaactact gaaatcttaa cactcatctg gtttctgaat aagttccgtg      1740
tagtatgtct gcttaagcat caaaataacg caattttgtg tcattttact aaattttttgg     1800 cgaaaaaatc aatggtttta gtcaaaattg cattgtcaaa tttatgacgt gtgcggcaaa      1860
tttcgaaatt tgccgagctc ggcaaattcc gcaaatctac tgttttgaaa tttgccgtgc      1920
tcggcaaatt cggcaaattt gccgcacacc cctgattcaa acattgtaag ggtttgaaca      1980
tgttcttaaa atgtgacaaa aactcagtaa taaaacattt aaattttttg aacactttta      2040
ccatgatatt tggtcatttt ggcacagcct taaggttaaa gctttaacaa tttccccact      2100
gacgctactc caccataatt ttgaaaatct aaaatattca gaaattcgaa                 2150
```

<210> SEQ ID NO 45
<211> LENGTH: 1845
<212> TYPE: DNA
<213> ORGANISM: Caenorhabditis elegans

<400> SEQUENCE: 45

```
tttttaagaa aatgaccaaa agaatattaa aattttgaat tatggtaaag aatacaagcc       60
agcaaagaat ctagttattg ttggaaaact atgaacatca tgtcctcagt tttcaagaaa      120
acattaagat ttcaaaacta tgtattctgc atggcaatgt tgcaacaaac catttcctca      180
taaaactagc caactaacac agttattcct aataaccaca atgttctctt ttcatatgtt      240
gcctatgtaa ttctttctca gaaacattat catgaccata aaatagacaa tgtattggtt      300
tctatgtttc ttcttcctgc cagtgtcctc tcgcgttgtt tgagtactat tgttccccac      360
tctccccccc cggcgtgcgt attatcgctg aaaatgtcat attatctaat cgaacaatgc      420 ccatttttg ggatgtttaa tagcaaacat attccgattg gaattgcaaa attgagttat        480
catcttttta ttgttggtct tgtgactgtg agtttatgtt tggaatatag ttttgataag      540
tttgaaacta ttgtgaactt ggaattttg attctccaag tttttaaaac gctatgcacc       600
taaacttggt atttttttc aatttaacaa aattctactt tcaaaaaaca ctactcttat       660
ttgcatgttc catagtatgt atttcttggc agtgttttc aaaaatagaa ctccttccga       720
tttaaacaca taatgttgtg ctttttaagc ctagacacga cttccgatgt gattttctt       780 cgaattctcc ctgtctgtaa gaaactcaca tgctgactgc aaagaatgtg cctattgcgg      840
acctcaatca gtgtcggcta cactttttta gtgtcgtccc gaaagttgtg gtgttctgag      900
aaaacataat ttttattgat ttttaatgca gcaaaatttc aaataactga tacccggttc      960
accctaattt tcccatggat actccaaata tgttcagaaa tgcatatttt tgtacaaaat     1020
ataacgtttt ctaaagtgtt tgctaaaatg ttattgttct aaaatctttt gaaagaacca    1080
gaaaatctca aattcttaaa acattttca tcgaaatgtg atatttgacc agccagtggc      1140
gcctaacttc tgaactttgc ttcacgcaat ctctgctttg atttctgtcg tttctctact    1200 gattttgtt cactttcacg taagcgttca actcgcggaa ccaaagcctc cgttcatatc     1260
atattaggct ttcatatcta ccatttttct actaatcatt ttgttacaa tcgtttttc      1320 tctgtttcga agaggcactc tacttatgac tacaacataa aagtagtatg gaattcgcgt    1380
ccttggtgac cagaggcgtt cctatttcga atctctattc gggtggaggc attatccgaa    1440
tcccgagaaa cattcttgtt tgtgtaatct gtctaatcaa tccccttcc tatttttctc     1500 tgttcccttc cttgtcttca acatcgccct tcgatcatct gaattcagtt cgttttcgct    1560
```

```
ccgcccatga agttgggcta cataaaaaga ggaactgaaa tgacatcagg ggaagttgga    1620
tatatatttc attaagttgt actatcattt ttttcttttt tctctttttt tcggtttgat    1680
tctatctttt caagatggcc tcgcttattt ctacgattgt caagtcaacg gtcaaagttt    1740
ttgaattgtt gcattttctc ggttctttga ttttgttcct ttttaattcc agttgtagtt    1800
taaattattt tcaggaaaga aaaccgagaa aaaagatatt acaaa                    1845
```

<210> SEQ ID NO 46
<211> LENGTH: 2272
<212> TYPE: DNA
<213> ORGANISM: Caenorhabditis elegans

<400> SEQUENCE: 46

```
agtttggcca atacctgtga ataaaaaata atttattatt ttaggaagtt ttataaatgc      60
aaaaaaagga gtagaggaat tgtattagaa tattattaaa tggaaatatg aaatagcaat     120
tggttgatat tatacttcga atctcagaat cactaaaatg aaaaccagaa ctgcttctgc     180 ttgatttttta acatactttt atgttatttg caatgattaa aaaatatata taatacgcga    240
gaaatttgaa actggtttgg ctcgataaaa aattggtgag aaacccaaaa tatcgtgaaa     300
gaagcggtgg aattaaaatg atttgagaaa gtaaattttg ataatacgaa ttataattcg     360
aaaaaatggt ggtacttaaa atatagcaaa taaaacaggt gagaaaaagt tttgaggttt     420
ttactatatt ttaatcaaac cgtttgtttt atttattttc aggcatcgaa attttatgta     480
ctcaagctta tagtaaaaat acaaatattt gatatattaa acagagataa aacataaata     540
acgagctcta aaaaattagc atattttggg aattaagaaa accagtgaaa gccgtaaaaa     600
tgatctgaag ctatgaataa gtttggttag agactctatt tctagtagat tactttatta     660
taataatgag cagaaacaga tattttttta gcattttttc acttcatcat taaattaaaa     720
tcattacaaa aaatcgatag tccttgagaa gagagacacc aatttacaag caggcaacaa     780
acgagagaga gcgtattatc gtgtaaacgg tatatacggg agaagagtac gggagaccga     840
cggaagaaaa gcaatgggag gtgtataggg tggtggctgt gttgtgccta ggaggcagga     900
aaatataacg ttaaaaagtg cagacgcaga cacaccaatt gcccctcaga ctccaattca     960
gctgtctccg tctcttcctc gtcctcatcg cacacccttta daccggttgc ttaaaaggag    1020
```

| | |
|---|---:|
| acatagcttc atctgctgta cattatgaaa attttattga agaggagtta atgaagtggt | 1860 |
| acaaaacacg atgaaatgat aaaacatgaa caaaatcgag ttggtcacta tacactaaac | 1920 |
| aggacacgta ataagaaaag tcataggca cggagagaca aaaaggtcat cctacaattg | 1980 |
| cggtggctaa ctgcatctta actacgtcgt agcattaaaa aagattgata agacagtgcg | 2040 |
| tgtatgaacg cacaaaaaga aaaacctagc aggacatcat gaggttttat tttagcgttt | 2100 |
| ttttgcatat cattttttat tcattttgtt tcagtaaaat aagtttagat tcattttta | 2160 |
| aagcgaaagt taatagaata atttgatctt gaagttgaaa attgttgtta attttttaaaa | 2220 |
| actttgtttt caaattgcct aatatttttt tgaaaacaga acataaaata ac | 2272 |

<210> SEQ ID NO 47
<211> LENGTH: 1075
<212> TYPE: DNA
<213> ORGANISM: Caenorhabditis elegans

<400> SEQUENCE: 47

| | |
|---|---:|
| cttctacgtg gaattctgga ggttgaagct tctggtctaa ccatcatcag taagaatgta | 60 |
| aagaccattt cgtgtttcat atttatgccg tcaattgtca gtacaagggg ccgcccgttt | 120 |
| tcgtttcgtt tcgtttaaat tatagggaat acattataaa atcacacctt ttgtgtatat | 180 |
| cttcgtagtt ttattggaca ttttaatagg ccttgtttat aaaagaaaat ataataatga | 240 |
| tgacattata caaaaaagta ttcaaggaat gttttatagt tacaaaacct ataggtatac | 300 |
| agaatatgtc aaaataggg aaaaaactga atgtatgcag tcgacgaata aggttgtctt | 360 |
| gacattttt tggttaataa tgttttttcct gccagtttcg atatctttga aattttgatc | 420 |
| cagatgacat caatcctagc tatggaataa tgggggaact ctctttaaat tcacaacttc | 480 |
| attcgagcaa aatttgtctt ttgcacacga aaaattatta ttattattgc acaatcaaat | 540 |
| attttttcccc cgtgcaagtg tgcaatgggg cgacgggtcg agccagaaac ccgtgttgtt | 600 |
| gaaaatcaaa ccaagtgcaa aatatccatt ttgcttaatt taaaacgatc taggataact | 660 |
| ccactagcaa ctagaatatc taattgaagg attgaaattt ggaaacttac aataaggtat | 720 |
| tctattttat tacgttttca atcttgctag gaaaacttgg aaaaaaaatc cataaacgtt | 780 |
| tcccggttat ttcagaaatc gatagtcgac ctccgttgtt ccttatctaa atttcatcaa | 840 |
| ttgtatcctt tttgataaga caatactatc ttttatcac tacgtctcct tcactctaaa | 900 |
| tcctaatgta gtatcaatca atttgatgaa aagactacac tggggcccac ttattttctt | 960 |
| tttcaatcaa aattcacact ttattttata tatttcttgt aaattgtatt tttcttcatt | 1020 |
| tttaattcta ctttttttca acaattaact ctcgaattct tcaattttt acaga | 1075 |

<210> SEQ ID NO 48
<211> LENGTH: 645
<212> TYPE: DNA
<213> ORGANISM: Caenorhabditis elegans

<400> SEQUENCE: 48

| | |
|---|---:|
| aattttcagg agaatcaatc gacgagcttg aagatttcga caccggtcta ctatcttccg | 60 |
| gaggatccga ttattctttt taaaattttc ttctttaaa aaatttcttt tgaaataaat | 120 |
| aaattctcac ctaggaattt caacaattca acttgaaaaa agttcgcgca aactacgaac | 180 |
| aaatgtgtgt cgagcgggcg gagccactga gaaagaggag caaaatgtac acaaaaccat | 240 |
| atttgagtgt aattttttcaa agtttggcgc cgattttctg tgagagatga gttttctcaa | 300 |
| tttatatttg gttatttta ttttagttct tactggtaaa tttctgggta agtcctgatg | 360 |

```
actttgaaaa cgaaaaaaac tctttcattg atgctagtgc gattgctagg aaagcaactt    420
ttcagttacc aagaaaaagt ccaaggccat agggattagc tgcgtggcat aacaactcat    480
ccatcctcgc agatgcaaat ccgctctatt ggcaaataac atggaagagt ataaacattt    540
tctcttccac acggaaacct agtccccttg gggagcggta gtgcccacaa ccccgcatgt    600
ttaccaaact acacagacag cgctattgtc tgcaagtggc aaaaa                    645
```

<210> SEQ ID NO 49
<211> LENGTH: 1825
<212> TYPE: DNA
<213> ORGANISM: Caenorhabditis elegans

<400> SEQUENCE: 49

```
agcgtttcgt tttagaatcg ccagtgtatt ttttgtgata gtcctatgtg ctttaaatta     60
tttattttga aaggttcaat aaattatatt ttatgaccga acacattata ttctcagttg    120
ttatcttata tatccacacc ggaatgttga atatctgacc atatatattt agaatgttgc    180
ggtaattttt ttgttgctgt ggaattttat tttattttta tttttcatag tttcaacatt    240
ttacaattta ttgaaatttta tgggttttaa ttgttatatt tggcgttttt cgtttacttt    300
ttcgataaaa ataaattcag ttaaaaacta agttataaca atgaaaacac ataaatttga    360
acaaatcgta gaaaaatcac tacaaatttg acagattttta tgggttctat cgcgatttat    420
tgaaattaac gtcttttaat tgttttattt tagttttta gataaatact gttttcaaac    480
gaaaaacttt gaaaaatcga taaatctcgc agtactcctg aaaggcacac actcgtttgt    540
acttaagaaa aattgtcgcg acgagaccaa ctgtccaact acggtagttt tcaaaatacg    600
cggttcaccg caaagtcaaa ttgcggacct gaacatttt ttatttttcc cgcaaacttt    660 tttttttcaat tttgcctaaa gcgctcgaat aaacatgaaa gtctcgtgtt tccttccatc    720
cagacctctc atttttcaat tttaaaacta aaagcacttt ttgacctact ttttgtcgca    780
accgccaaaa ctcgcttcca gaattattcc cttttttagga ttttcgacgc aacatctcca    840
accggttagt ttttcgcag attttctcgc attcgcgtag tttcacttgt ttacttcgtg    900
gcgcctcgtt ttttccgct ctctcgtctg accaccttca tatttattga tctgcgccta    960
gcggcgcccg ttgaaatact ccacatttt ttgcaatctt gtctgcgagt tcaggttatt   1020
ttcgactttt atgaaagctt gctaggaagc catagcaacc ggggaagaat acgctagcca   1080
aatgagagat agaatcgatc agctaaattt aagataaata gtgaattcga attctaagac   1140
ctgctcgacc agctgaaatt ctaaaactct gcgccaagat gtatagacag gtaataatat   1200
ttgaattttc tttaaaagtg accttgaacc ctaagatttt cgctcctcct aaacgttgta   1260
gtctgttact ccctgccgcg acaattgtca gcaaaaatcg cgtcacatga tgatgaaagt   1320
ttgtggcaat gttataaaaa gactgacctt atttcgtttc ttggaagatg caaagaaatg   1380
tttattaaaa attgcagtgt gaaatcatgt ctctcgctcc aaaggtgcat ttcttatttg   1440
ttttttaaaa atatatttgg ttacttagat attaatttaa atcacggaaa agtttaaacc   1500
cctcgatttc tgttatttaa catgatcact cacttttata acaattaatt tggttttca    1560 aagatgttcc cagaatgttt tattagttct catttcgtcc tccgatttt tttctttcgt    1620 cgctctccaa ttttgccaat gtatttcatt cccattagat aagcaccgcc cgtcaccta    1680 ttctccttct tttcacattg caaacaaatt cgttgccgtt gggttcaat atccttttca    1740 tttttttgtcg tattgttgtt cttgtgattg tggttgttat tttatcgcgg tattattttt   1800
```
ttttgttaaa ctaattaatt tttag 1825

<210> SEQ ID NO 50
<211> LENGTH: 2300
<212> TYPE: DNA
<213> ORGANISM: Caenorhabditis elegans

<400> SEQUENCE: 50

| | | | | |
|---|---|---|---|---|
| tatcaaagtt | tgttgttac | ccacccaaac | tttgttttag | ttgcaacaag | ctcacttaga | 60 |
| aggaaattga | ttttcagtat | ttattgaaca | cagcaagaaa | aatcagcaaa | cgtggtactt | 120 |
| gtgtgttgca | tgcgctcatt | ttaataataa | tgttgttgaa | ttataacaaa | taaaaacatg | 180 |
| tagcatattt | ttgtattttc | aggcttaaat | aaccatttct | aagcctaaag | agaaaaaaaa | 240 |
| atgtacaaca | cgttaaattt | aaatggagaa | agaaattaac | aacatttgat | tggatttaga | 300 |
| aataagggca | cgtaatacac | aagtaccaaa | cgtgaacttt | aaaaatttgc | gtacctacca | 360 |
| tataatacaa | aaccgtgaaa | ggtggaatag | ttttgaatgg | caaattgttt | gaattcattt | 420 |
| ctatagtgct | aaactgaaca | atattagtt | tcagttttaa | aaaaagtgtt | tgaaattctt | 480 |
| catttgcagt | caagcagtgg | caattactca | gcttttgaca | ttcaagacaa | ccaagaaata | 540 |
| tgttttcaaa | agttttttcc | gtattcagtc | aagttctatt | ttcctctgaa | ctatagctaa | 600 |
| taatttataa | ttgtacatat | caggaaaaat | tatgtggttt | aagaatctct | gaaattttt | 660 |
| ggaaattggg | aggtgaaaga | atacagtaca | cttttgtaat | tttagctaat | acgttcgaga | 720 |
| gttattatca | ttatggcagc | acacttgttg | gtgatttcta | ttttttgaca | tgatatgttt | 780 |
| gaatatgatt | ttcctcgtta | tgtggaaaat | tttgtagagg | cagatgctaa | acgacaagct | 840 |
| agactttta | gtgaattttt | gaatcaatta | tttataatgg | catcaaacaa | atcgaaagga | 900 |
| tctgtgcctt | ttgatatttt | tggttttgca | acaattgtc | tttgttgttc | aaacacgtat | 960 |
| acatcaaaaa | ctattgttta | tttcaacatt | ttcagtgtat | cttttaaaga | tcacatcagg | 1020 |
| ttgttactaa | aattagtttt | gaattcaaaa | ataaccaatt | aaatgttcca | acatataaaa | 1080 |
| aaatatttca | aatatgtatc | agcttcatga | gtagtccata | acaaaaccca | gaagttcatc | 1140 |
| ggaggttgta | tatctctgag | agtgtcaacc | cacttcttat | ttttgcgata | aaactaatta | 1200 |
| aaaactaaaa | taggaacaaa | acattaattt | tatgcttcga | gtgaaaattc | gtatttattc | 1260 |
| acttttagg | gagtttctca | attattttaa | tacatagata | catagatatt | acttttaaa | 1320 |
| taatatttac | gttcaatcca | aataagattt | taaaacgatt | cagtaaaagt | tcttgcaaaa | 1380 |
| caatcaatta | gcaactgagt | ttggttttta | aactgtttaa | atctgaaaac | atttttaaga | 1440 |
| aaatgaaatc | cgtctaaatt | cattatattt | agcaggaaca | tgttaaaatt | tagtttctga | 1500 |
| aatttaccaa | ttatttggaa | ctaatgtgaa | ataataagaa | tattattatt | caatcatttt | 1560 |
| cttgcagaca | aagggaatta | gaggcgtctg | gtcagcattt | gtcgtggctc | aactgttccg | 1620 |
| caagatacat | tcgtcgagtt | gcgggtctcg | tttgatattc | acaaaaggag | gggttcatct | 1680 |
| gcgaagttac | acacttcttc | tatcaaacca | cattgcctca | ttttcccaat | aactgtctca | 1740 |
| ttttgaaga | agatgcgatc | aatcaccgtc | taaaactgat | tgcgttgcaa | caaatctgtg | 1800 |
| atgatatgat | atgatggaac | ggacggaaag | gttaaatttc | gagtgaagaa | aaaatataga | 1860 |
| agtaatatga | atgagtagat | gaaagaaaaa | gacaaaagag | aaattgatat | gaccgcgcag | 1920 |
| cagacagggg | catctggtgt | gagcgtgcg | tttttctgt | tacctctaac | gcagtccgta | 1980 |
| cacttgtcgg | cgtttatttg | tggctgtggg | cccattgcgt | tgatgacggt | ccctctagct | 2040 |
| ggctttcatt | gtgatccaat | tgcaccatttt | ggttttgag | ttttattcta | tttctatcgt | 2100 |

| cttttgtgat aaattaattg agtgaatgaa taatgtataa gagcctcatt atattctatt | 2160 |
| tactaaacaa aactcaatta tttcttttga aaagataatg aaatttccag tcatcattcc | 2220 |
| ataaatataa ttattatttt gccttcgcaa taatcctaaa gattttttat atccttcaag | 2280 |
| tttatcaaaa ttgtttaggt | 2300 |

<210> SEQ ID NO 51
<211> LENGTH: 2931
<212> TYPE: DNA
<213> ORGANISM: Caenorhabditis elegans

<400> SEQUENCE: 51

| attccaattt cccagccatc cggaaattcg ctgtaaaaat tggaaagtag acaaatagaa | 60 |
| gaatataata caaagattaa acacttttta cgacaatgtt gacttcgtca tggtacattc | 120 |
| agaagtgtct gggaaatgtt cagcaggaaa acattgcaga agagaaaaac aactcggaat | 180 |
| gtttgctgaa aagttctgct tggaggtatt tttaaacttg agaagatat cattgctcta | 240 |
| ctttggcggc ttctatcgcg gtagtcttta gtttgatcaa aaatttatca actggcaaaa | 300 |
| tacgtacaaa atagttatat acattttgct agttgacaaa tttctgataa agttgaaggg | 360 |
| aactgagagg ttataacctg tcaatcaagg agcattatgt ttttaggcgc acctacttac | 420 |
| ttcatgcctg cttggctact tacctgccta ttacctgcag tttatatgta ggcactgatg | 480 |
| taggcacgta gccatcaagt aggccgcctt tgaggctca tttgacccat agaccttaaa | 540 |
| ataggccgtt ctagaaccct tcttatctga acaacaatc tttcagacat tttcgaatgg | 600 |
| tcaacaactt aagtttttat tttgcaaaaa caaaaaacaa caagttttca atgtttttt | 660 |
| gccagtggaa attattgttg ttggataggt acagatgcta ccgggttacc gagatcgtgc | 720 |
| ctaccaggcc tacctattgc ctgcctgcca tgtgcctacc tacacttcat ttcggcaaaa | 780 |
| ggtcaggggc caatgaaaaa ggagcatgaa tagattcgca tcagaaattg atgtcggtgt | 840 |
| aaggcaggtg caggtaaaat gaaggcaggc ctgtggcagg caaggtcag catggcaagc | 900 |
| attttgggaa taccaaccag tagttttcat cagagcacga ttgcatcgac gaaaaatttg | 960 |
| aattttgtg tattttgaag agtgccgtga aaagtctaaa tcttttgcta ttgcctctga | 1020 |
| ttccttctcg aacctgaact ataaaactga tgtaaagaaa aaagtttcc aacttaagag | 1080 |
| atatcttatc aatttaaact ttaccgagtg attctgtgat atctcaaatt tcagtcgaaa | 1140 |
| atcacatgtg gtttcctt ttaattccga gagagagaga gagagaaagg aatttcacct | 1200 |
| ccacaacaac ccataatcat tcaattaggt tctaaacaca tacaagaaga agacaggaaa | 1260 |
| atgttagcct tttagtcata ggtgctgctc gatcatgatg ttgatgaacc aaacatcgca | 1320 |
| ttttgtagga ggggaagagg acaggagact gtccatttga aagtgactac tttgtcggat | 1380 |
| atttagagag tgacttactt acgaaagtta taagtttgg ttagcaggaa atctggtttt | 1440 |
| tactgagaaa actctctgag ggaaaagctc ggggtgggtc atatacccgc gagatatctg | 1500 |
| ccggtcatta tttaagaatg tacagctcta ctttggcaga tcatatctcg gttattccag | 1560 |
| tacatatcaa aaattgactg aatatgaaaa taaggaaaa tgttcaacct gtattttacc | 1620 |
| agttgaacat ttttgataa aaccaaaaat aatcgaaatt gtgcttaacg gaaagaagt | 1680 |
| tagattaaga ttccaggctg ggtcccgcca cgataagctg caaaattatt ttttggagct | 1740 |
| gtctgttcag aatcgtcgtt attagaaggt ggaagtgctg aaatctgaaa aaaagaactc | 1800 |
| aagaatctat agaatctctc atatatgaga gatcggctcc gtgaaaggca ctaatctgga | 1860 |

| | |
|---|---:|
| atacttcaga aattcggcga aatcttggaa attgaaaact ttgagatttt tttcttgtag | 1920 |
| atcgaaaccc gcgagatgtc agatgcttct gaattcagat ttacaaaatg agctcttcag | 1980 |
| acactcctga aagatcagct gaccagaata tgcccaccta aggcaggcgt gacttacctg | 2040 |
| aaaggtgacc tacgcctatt ctcttgccag aactcgaaac tattttctag gaaaaacttt | 2100 |
| tttgtagatc gcattccatg ggagctatac cttccctgta ggcacgcagg cactagtttc | 2160 |
| cgtgcctacc tggaatccac ataaccggag cacggagcag caacttcacc ttcagaaatg | 2220 |
| attcagagct ttacatatag tttcctgttc ctgaaaagca tgttctacga tgccatgatt | 2280 |
| ctcatttcga tgccacttct caaccaactt ttgccgagct tctgaacttg tcgagggagt | 2340 |
| ctgaataccc cccaccgccc acactaaact tttttcctct gatccgtgag aatatcctca | 2400 |
| ttatctcaca atcagtaatg tccaaatcag gcggggagg aggggtaaaa aaacacggaa | 2460 |
| acgaggaggc gaaaagcgtc tctgggttcc cgcccttcct cccacacgtc ttctctatgc | 2520 |
| gtctctctga caatctctcg ttaaagttgc ctttttttggg aaaagcttct gtctctgttt | 2580 |
| ctctctgtca acgtgtttct cagcttgcgg gcgccaaacc accaccacca tcactgactg | 2640 |
| tcgattcgcg gtgtgttgtg tttcaattgc gtaaagagtg agagagagga aaagatagag | 2700 |
| agagagagag accccaaggt tatacgtctg ttatacttgt tacccatata ctcttctaca | 2760 |
| cctttacctt caacctttcc ccacattgac tccgcctctc tctctcttac ttcttggaag | 2820 |
| acactcccca ccccctctta tctattttt cgaaattctc gacccttcac cctccccct | 2880 |
| tacccgcacc ggtcatcatt ctgactctgc gaactactgg agaggaacac c | 2931 |

<210> SEQ ID NO 52
<211> LENGTH: 1860
<212> TYPE: DNA
<213> ORGANISM: Caenorhabditis elegans

<400> SEQUENCE: 52

| | |
|---|---:|
| catgaaggcg accgaaaagt gtccagtgaa gattttctaa aaatctcgaa tctggaatca | 60 |
| tgatgtgaaa tatatgaata aagaatcttt ttaaaatatt ttgaaaattc tatacatctc | 120 |
| taaaaaaatg caatctcgtt attacaaaaa gcaaatcttt tcaccttaag cctagatgta | 180 |
| ggtaatgttt gatgaacagt aaattttgaa acagtaaatt tttgaattac aaattgaaat | 240 |
| ttttttaaaa tctattcaga atccctatat ccgcatgcat cagggaacgt gccaaatttg | 300 |
| aaaaatgtgt gtttctcaat ctctaatcat ttatcatatg gtcatgacaa caactggtgt | 360 |
| caaggtgtac gataacggta cactgtggca attgacactc ttttttttctt tatttctcta | 420 |
| ttcaacaaga cttgtattta ttaagaaaat gcaatgagag agcgtggtga taagacgggt | 480 |
| aattccctcg ctttttctcat tttttgcggt gttgtgttcg tgtcatttga gataatccat | 540 |
| gttgattcca cttttattgt tgatttgata gatgttccaa gttttactg cttcctgaaa | 600 |
| gcataattct taaaaataat gcttcatagc agttgtggct tcatacaatt ttcaaaaaaa | 660 |
| aattcactgt ttcaaaaaaa ttgaattcaa tttcctgcat tatgacgtac gtgttaaaaa | 720 |
| aatatgttca cctaaaaatt ccgctcgaac tgtcgcgaaa tctgtgtttc agtgaaataa | 780 |
| aataaaaaca tctagacaaa atacagttcc cctcaaaaat tgctgtttca aaataataat | 840 |
| ttaaaaaaaa acaccaaagt gtcgtattta aatttaaaaa aaactatcg tttcaacaaa | 900 |
| acaggttcaa atctatttta gtattaaaat ctataacttt ataaaatttg ctatttaggt | 960 |
| tttacgaatt gttgtttttt actctgaatt gtaaaattac cgtttcaaat atattcttct | 1020 |
| aaattcaaaa atttagtata caattttct agaaacattg aagtattacc aggaattttt | 1080 |

```
ggatatttcc tataaattct attttgatca atttgtagtt gtcttatcat atattgcatt    1140
ggatgataat aggaaatgat ccgattctct ttcctgttcc aaaactaggt aaatgtacct    1200
catatatttt gttaattttg tagtcacaat aacatgttat gataataata tcgataaaaa    1260
atatcgtgat gtttaaacat taagtttcat ttttttcggt actgttctaa ttgttcaaaa    1320
caatttaaaa aatttcggtc aatttataga caataccgat tttaataatg aatgtaaaat    1380
tttcactgtt tcactaattt tataacaatt ttcattcctt ccaattcaca ttgtgttagt    1440
gtagtgatca ttacttatat attttaaaaa aatagggtgt tagttttttc cgtttgtctg    1500
tttgtttccg tgacgtcaca acgcatgaga cccatttttgg cgcaaattca aatttcttca    1560
gaaaaatttt ggtgcaaact caaatttctt cagaaaaatt ttagcgggaa ttcaaatttc    1620
ttctgaaaat tttggtggga tttcaaattt gttcagaaaa attttggtgc aaattcaaat    1680
ttcttcagaa atattttggt ggttttttct tccgcgccgg aggcgcgatc agcagctagt    1740
tttcaaataa atttactgtt tcaaaaatac gatatttttt gcctaatttt tgagaatatc    1800
actatgacgt ctaaacgtaa agcgattcca taatctactt caaaattcca ggctccccaa    1860

<210> SEQ ID NO 53
<211> LENGTH: 2793
<212> TYPE: DNA
<213> ORGANISM: Caenorhabditis elegans

<400> SEQUENCE: 53
cagtgtaggc cgtcttgctc atagagacaa ataaactttt tgagatggtt ttttaataga      60
aaatacattt tatagaaatg agaaaaataa agttttacta ttagaaaagc gtaacaaaaa     120
gcttccgtaa ttatttatat gaatgttccg atattttttag cgatgtgtgc atcgtgcact     180
cacaatacta atgttatgag cttccttgca ataaacggtg gggctggaaa ctgacaggaa     240
gtgggtttat tcgatgatta caataccaca ggactgatga cacgcgtaat caaaagttga     300
aactagaaaa cataaacacg cggctttcat ctgaatcaga gacgaatatc cataaatcac     360
ggcccccaaa tagaaaccag tttatttat gtcacttctt ttccccatta actttcctgt     420
cacaatcata aacagagtt cgatcataca ggtccaaagg ttttgggtat atcttgtgga     480
catgtatgct gtgaaatgtt gaacatttca tataaaattt taaaatcaga ctattagatc     540
gaatagttct acgaaatttg taaacagttt ccatcgaaat acctattttt tgtaacacga     600
agtcgacctc tctcccggag acgctgctac agaaaggttt gaattttgag caaagttacg     660
gtattaggtc tcgaatgaaa agtttcgaaa gtacgcaaaa ctctacaata gggttaagaa     720
tcgataattt tctagattgt ccaaaaaagt agactaattt tgccattccg ttcagtgcct     780
tcaagaagta cttgaagtct atacctcacc tacttgtctg atatggtaat ttactatcga     840
gcttattagc aatttttcttc acgggaaagg agttgtaggt taacttcaag tcgcgaggta     900
ggcatatttg tgcctggcga taacaagaga cgttccacaa acatcttact cagtttctat     960
ttgaaacttg gcgaagtaga catgaagttg aaccttcgga acgtcagtcc aaaggtttga    1020 aggagggggtt ccccgaactg tcatacactt catttcatcg tcagctgtct gagatcaaac    1080
attcaataag catgaagatc tctgaacgac cgaaaagata tcgataaagt gatgataaag    1140
gtctgcagca gaatggtttt gcagacattt cttcagaagt taaaacaacg ttgtcgtacc    1200
caagtatctt atcaagggag aaaaagagtc aaaagataaa ttccgccatt tgcccctccg    1260
gtccgtaata acgagtattt cttatcacgt gtgctgatct ttttttcttaa cacacataca    1320
```

-continued

```
atcaatcgat tgtcagaca tgggaaagaa taagacgtga tggatgaatg gaataatgtg      1380
aacgatgaac gagatacgtg acagtcagaa agttcactgt gaatagagta tggtataaat      1440
ggttgagaga cgacggatta cggaaagatc gaattatcac aacgttttg atgtatctgg      1500 accgttcaca tggaatttag taattgttac ttcttgggcg acagagaaaa ttcggccagt      1560
ctcatcaaat agagagtttt tttgaaaatc tgcattgcag ggcgaacaaa atcaatttcc      1620
acattatttt aggccggttt taagagaaa tggagagatt ttgagaactg tgaaataagg      1680
ctggttaata aattgtgcat aaaaaatcta gagagattgg aaagccatgc ctatttcact      1740
gcagcttcac caacaatcta atcataattt tgaaaatgaa aattacatta gcatggtcct      1800
ttactcacat ttttttagga tgtcgacact ttttcatt gaggtcgcta caactgttgc      1860
tcaaagttgg agcatgtgcg acctatttcc actcctcctc cacagacccc gtttgattgg      1920
tgcaaaagtg ggcagagcga aaagctgatt ggtcttgcag ttttcatttt gaagggaatt      1980
aaaaaacgga gttagtaaca attgagaatt accgttttta aatgtataac ttttcaaatc      2040
ttccgtttct gaatttatta tatacatata ttatatagac tcaattacaa attatataaa      2100
tttaatttat atattatata gccttaatta ttaaactttt tattttgaga tatttttaaa      2160
tttcaaactt ttttttcagta tttaagtaag cttcctattc acgctactcc acttttagtg      2220
tgtttcaaat gaatggacgt tataccaaaa ttcaattgaa atatccagct tcataaatat      2280
attggcatgg gaatgagcct cgtcacgaac atttagaaa aacatcagga caaacttata      2340
ttgtactata acttgcaaac ctgcagcagc agaactttga acacccaaat ccatttccga      2400
cggaagtatt ctacatcttg tggccgcgta tacccatgac tactgtaccc aaactgggga      2460
aaacccaaat tgctagtaaa cgcccactaa ataaactgtt agcattgaaa gtgtgaacac      2520
gtgaatcgta tgtcaagtga taggaagtgt gacgttttgt aattaatctt aacttccaag      2580 tgtttgttc cttgaaataa gatgcctaca cacggcggcg aaatggatac ttttatgtc      2640 tgcgcttatt ctctttgtcc cccatcatca tacaatcttc aacgccttca catatcagac      2700
agtccgtcgg gcactgacca accattcagg ctgcctgtct gtcatttata ggctgtctag      2760
ttatcttcaa ttaatgtttg aaaattcaga agc                                   2793
```

<210> SEQ ID NO 54
<211> LENGTH: 2016
<212> TYPE: DNA
<213> ORGANISM: Caenorhabditis elegans

<400> SEQUENCE: 54

```
aattaattat tttcacattt tttcgaattt tgtcgattta taggcgaaat tttacgttaa        60
cctaacggaa atatgagttt ataatgcatt tttaatcgaa aattcggttt tttcaataaa       120
atttgctatg aaatccgcaa aaacgcctgg aaattgtctg aaaacgaaga aaaataaaaa       180 taaaatccg aattctgtgc attgtgacgt ggcggtgttt gcgtacccga catttaattt       240
cacgacactt gttttatgt ttttattgtt ttctcgattt ctgcaagttt tccacttaaa       300
acgtgcggaa aaatccaga aactgtaaat aatactaaaa aatataaat tttccacaaa       360 aaaggcatga aaactaacaa ttacctcaaa tatcgtgaaa aatgcaaaaa ataagccctt       420
tccgaaaaaa cgggccctg ggcctttaaa ggacacaaaa acaggaaagc ataagacacc       480
aaagagtaat tggatttcta cacttttggtt cctagaatta tttataaggt gttattgcgt       540
ttttgtgaga ttgttctatt tatccagtca aaaattgcat tttctttgtt tttgcttcaa       600
aaaaatacat tttcagtgga aatttcagct gaaaagcaga attttgaggt tttcgagtaa       660
```

```
ataacgtaaa acactaaatt acaaatattg attttttgatg tcttagacca aattttcgta      720
aacatgtttg tatttttgga aaaaataggt ttttttgtcga ttttaactta attttcgaa      780 caaaaaatga tttttctcc gatttaccaa agttttgact taaaattccg attttctggg      840
tcatttttcc cctaaaaata cgattttaat tcaaaaaatc tatattttca aagaccaaag      900
taccataacc ttcaaaaaac aaccactttc tctattgcat cagcgaattg tcatcacccc      960
tctcaaaata tacaaaacgt catcattttt ctgtgttttc tctaattctc ctgaaaaatt     1020
ctataaaacc aacagttttt atcatcaaaa atgcctttg accgactttt tttaaagttg     1080
aaaatcgtac agttttagca gaaattccag agtttcattt tgaagtatgc tggaaataat     1140
aaaattattc taacatttat taatatttg taaaactaat tctatacaat aaaaaagtaa     1200
aatttaatat taaaaaaacc ggtttttctc aaatttccat tccccaatgt cctgttctat     1260
tatttgttcc gattcggcca cagaacgcgc acacacacac ttttgctga ttctctgcct     1320 cctttctttg atttgaccgc atttatatt gattttcggc cacaattcca ctatttgttc     1380
agtttgtcga tttgttggaa atttcaattc cggcaattcg ccgatttgcc ggaaatttaa     1440
attcagacaa tttgccggtt tgccggaaat tttcagttcc ggcaattttt taatttgccg     1500
gaagtttcca tttcggcaac ttgccaattt gccggaaatt cgccgttttg ccggaaattt     1560
tcaattccga caacttgcct atttcccgga aattacaatt ccgccgattt accaatttgc     1620
cagaaatttt taattccggc aatttgccga tttgtcggag atttcaatcc ggcattttgc     1680
cgaaaatttc aatttcggca gttcgccgat tgtggaaaa taacaattct ggtcattcgc     1740
caatttgccg aaaatttcaa ttccggcaat tcgccgattt gccggaaatt ttcaattccg     1800
gcgattttcc tatttggcga atatttttaa ttccgccggt ttgccgcttt gccgaaaatt     1860
tcaattccgg aactttgccg atttgccgat tgccggaaa aaatcttttg ccgcccaccc     1920
ctaataaaga cttcaaaata tgcgtttttt tttgcttta acacgctaaa actctctaaa     1980
aatccccaat ttttcagctt aaaaaacccc aaaaaa                              2016
```

<210> SEQ ID NO 55  
<211> LENGTH: 1336  
<212> TYPE: DNA  
<213> ORGANISM: Caenorhabditis elegans

<400> SEQUENCE: 55

```
atccatttat ttatgtccag tacaagacga ccgttcatat cttcttagtc attttctttc       60
agccggtgta ctctttgttc aatttctct ttcttggtgc aacctttatt cacgtgtatc      120
ttctccgagc ttgtttgcat attttttttt tgaaatttca tgtgctaatt tattcatgtc      180
atttttgaag ttaaactctt cacatttcat aataaatatt tattgaaccc gtttgactac      240
tccaaattca cgaagttacc aaaataaaag tgatatttga ctttcagaaa taccatttca      300
aattccctaa gacgctcggg aaatattaat tactgcaatt tatattctgc ttgtattttt      360
cgaagttggg tccaactgtg tgaagtattg taagaatcat atccttctcc ttcacattct      420
acataaacaa ttcatttcta ttctgtaaat ttttctgat gatttacggt aaaaacgagc      480
gaaattcggt ccgggacaag ggtttctacg acgagtccat cgtggtgccg ctcgcttgtt      540
tgaattcccg cgtgccgcat tcctcgtgtc gagacccgat gtccaactgg ggggattacc      600
aactcggggg attggccccg cccacagaac cgtggcttgc aattttttct tgttaattct      660
cgctctattg agaaaaaata attttaaaac cgtgcggcag tttcaaaaat gggcgtattg      720
```

| | |
|---|---:|
| caagccacgg ttctgtgggc ggggccaatc ccccgagttc ttcgggtctc taaggaaagg | 780 |
| attcgtacat tctggtcctt tttatttatt tttaacctct tttattttt ttaaaccgca | 840 |
| atccattacc agttccattt tctccgtact cgtcagtgta gcgagtgacg agtgaaattg | 900 |
| accccatttc ttatcttatc gaaaacaatc taaatagttt ccgcattcgc ataaccagaa | 960 |
| aattcttcgg tagtcgttct catttgtttt tatttcatga acataaagta acgccatagt | 1020 |
| cttttatga aacgtggcgt taagaaagct ctcgaaaagt ctcgattct ccagcactaa | 1080 |
| tacacgtcat ctccgataag tacacgttgc ataggcggtc ctaataaaag cgaccgcgga | 1140 |
| cgttcacatt cagttctttg ttttcttttt gtcgtctgca ctccttcttt gcgacgtgta | 1200 |
| ttttgtgttc ttctctgtgt ttccacttct cgttagtatt ctcgcgcttc tactctgaaa | 1260 |
| ggtttttctt cttaaatgtt ctcattttc agccactcag cgaacagttg aactgaccgc | 1320 |
| tcatcaagag aaaaat | 1336 |

<210> SEQ ID NO 56
<211> LENGTH: 2797
<212> TYPE: DNA
<213> ORGANISM: Caenorhabditis elegans

<400> SEQUENCE: 56

| | |
|---|---:|
| aaatttcaac ttccggagcc cgatacctat aggccacgtg agaactttct caggagagac | 60 |
| gcagagagac acaaattgac tgacgaggag ccaggagaaa tgagcagaaa taatcaaat | 120 |
| tgaagagttt ctgaggagtt ctttttctc tcttccactt catcctaccc gcctgagcca | 180 |
| ccggggaac tgacaaaaga gagctgtcac gtggttccag actgtcccat tacggtttga | 240 |
| tctacaaaaa atgcgggaat ttttttccca aaaaaaatgt gacgttagca cctatcggtt | 300 |
| agccatacga aatcagttga gaagtctgcc gcatttttg tagatctacg tagatcaagc | 360 |
| cgaaatgaga cactctgaca ccacgtgaga tgtgctcatt gtggccgcga gagtggtgtc | 420 |
| aaggaatatg agagtacata tggtaattgg tgtataccat aattagatgg gaatttgaga | 480 |
| gcttttggag gaaggagagg gttttcggc gaaaattag tgtccgaaat gagaaaaatt | 540 |
| gaaaaaaaat gcaagttttc actaaaaaac tacacttttt ggagaaaat tggaaaatct | 600 |
| gccagttttc agtgaaatcg agtttgaaaa aataaaaaat tcgagaattt tttttttaa | 660 |
| tgaaagattt gtgctcgaaa tagctgtaaa atcagcttaa tttccgaaaa aaagatcgtg | 720 |
| attttctcga aattcattt ttttaatttg taattttgat ttttccacac aatttcaagc | 780 |
| tttaaaaatg ttaaaagtca cctaaaaagt cgattttcat aacaaaatac ctagaaaatt | 840 |
| gtcgaaaacc ggcaaatttc ggcctaaatc tacttttagg cagattttaa gttgaaaaat | 900 |
| gcacaaatat ttctaaaacc tgacaattca acgattttt cctagaaaaa atcgtcgaaa | 960 |
| tcgacttttt cgacttttca gtattttttc agtagaaaag ttcacaaaaa tgtccgaatt | 1020 |
| cgacggaaaa ttcaaatttt tttttccag aaaaagtgct gattttagcc gaaattgggt | 1080 |
| ggaaaaatcg aaatttcgac gaaaaaaatc caattgcaat tgaaaaacat tgattttcgt | 1140 |
| tcatcgaagt atcctctttt gttatttcc actttttcc cgcaggtatt ctctcgccat | 1200 |
| tcaccaagac atcacacgaa tcccggagac gcagacaact gaagagaccc acttttgtg | 1260 |
| tgattcaaag gggtcaacgc atatagccgg ccgattcgtg atgactcatc tctgtgttat | 1320 |
| tctataaatc tcttgatttt tttgaggatt taactcttt ttttcgaaaa aaacgtgttt | 1380 |
| ttccgaattt tgtatggtta aaagtatcgg aatcaccgtt ttttgttgat ttttttctca | 1440 |
| atttttctttt ttgtttgagt aatgattaag aaataagaac ggaaagaaga gaagaaactg | 1500 |

```
tgaaaaatga gagaaaatat ttcaaaatca ggaaaaaaaa tcattttcca aattttcagg    1560
atattatgcg gattattagg gttagaacac atttttaaatt ataattttaa ttattttttaa  1620 cattgaaaaa acaaaaaatc atccgaaaac tactcttctt tcacaaaaat cggtcaaaaa   1680
taaaaaattg cgaaaaaaaa acaaaacaaa ttaaatgtag caagcgcgct ccattgacaa   1740
aatgccgaaa tttttgcgag cgaagtttga atttcgttgc aacatggggc attttttcgtg  1800 aaaaacaaga tttaaaagaa tttatacttt attcttgctc aagaaaatta attttttccat  1860 aaattctatt aaaagtggca gttaaaacaa caatttctaa gatttttttca cttttttttt   1920 ggcgtttgct tgttttttcag agtttggaat agttttatgt caaattttga tttcttctca   1980
ttactttctt cataaaaaaa aatgcaaaaa agcaaatttt atcactaaat cgttcaattt    2040
ccacctagaa aagacgaatt taacgcaatt ttccgattag agcgcatttg cattgtgcgg   2100
gaaattcaaa ttattcaaaa attctcctct agtttccagt tctagtacaa tcggtggccg   2160 agttttttttc ttttttttttc cagcggccac atagcaagag ccaacctgta tactttttgca  2220 gttcttgtgc aaatctgagc tccgccgagc acaaacaagt ttggacagtc cacttctctg   2280
cgtctctcgt gatgagtgtg ctctctcgtc taacctctaa tccttcccag atatttgcac   2340
atctacccca gttccacata gccataaaga cttgggtcat ttttatcgat ttttttcggtt   2400 tgctcacaat attgtgagtt tcttaattag gtcttggtag cttttttggag cattttgtga   2460 cttttttatgc ctaaaaacca gtttaaatat acttttttttaa tgcttaacta gatccaaaca  2520
cctttgaaaa ttgtccaaaa aaattatttt ttggccgaaa atttcagtcg aaaaaagcat   2580
tttttcggcc taaaaaaaat tccaaaaaaa tccctaattt tttctgtatc tccagagcca   2640
ctttttaagg tataaatcag caaaattttc cgatcaaaat tccatttccc tatatctttt   2700
ccctctctct atctcaccct atctcgtgcg ttagccgacg tttactaagt cccagtcagt   2760
ttaattctat caaattcttc acttttactt acagaaa                             2797
```

<210> SEQ ID NO 57
<211> LENGTH: 2737
<212> TYPE: DNA
<213> ORGANISM: Caenorhabditis elegans

<400> SEQUENCE: 57

```
atcacacggt tgaaaaaagt cgaaatgaat gaaaacaagg gcattttgga attttttttaa    60 aagaagaagt aaggtgagtt aaaagaatga aaagcggcgt gcttgagatc taatgaaaca   120
agggaccgcc cttgtttgtg atttgctaac aaccgctatc gttgaaaata ttccgggcgg   180
agttctagct gatttctact tggagtatca tagaattgga aacggaacga aattgccata   240
gtatgaaact tttaatttgt atatacaaat ataatcgacc catttaatag gcctactgcg   300
gattaatttc agtgctcctt ctaaaggcag acaatgaaac agttgtgtag taaaaacaat   360
gttcacaaga cctgaaacaa ttttctgaaa attgtttgat aatattgttc aataaacata   420
aaagatggtt cacaaaatta aaactaaatt aaaaattaat aagaaaacca gttgtcacaa   480
acgcattcgc aaccaaaacc gctaaacgct attccaacta aagttataat tgcattttttt  540 gcaattaact gttttaccac aaaacaaaac aaaattccag tttaacaaat tatcaaaatt   600
ccaataagat cctttttttaa attaaaaagg tgagattttt ctagagagtc cgaatagaaa   660
atggtaacca aaccgatgac gatgacaatg gtaatcggat caatgcagaa gttgttttga   720
aattattttc aaagtcgtta attttgagaa tatttgattt ttttttagagt atgtactaga   780
```

| | |
|---|---|
| tttgttctct acctcaaatg atcaaattct tgactgcat taaaacaaaa ttttggcaaa | 840 |
| attatcgaaa atctcagaga aaataaacaa acagtctatc acatttcaaa tgaagaggaa | 900 |
| gccaaatttg aatatagacg gtccgatgaa gaattttttg acaatttatt ttaactcgga | 960 |
| atggttatta aatttgattt ttttaaattt atatttccca ttattttaat tttttaattt | 1020 |
| atgaaacttt ttatgtgaaa aaaaaattta tgtgttttg attataacag attttacgtc | 1080 |
| agaagccgaa ccatctttaa taaaaaattt gaaaaaaaaa atcacttcta caattttcat | 1140 |
| ttttcaaatt tgagccatca aagtcaatta ggaaaattaa ttctttcaat cgttgcagtt | 1200 |
| acagtgctat ttcaggatct ttgagagctc gccgtgagct tggttctgga gattcgcaga | 1260 |
| taaaaattca tgagtaaccg tttcaagaca tgggctatca aatggcatag gtctcatatg | 1320 |
| caagtccgat tggcatcttc tgatggttcc ctagtgagtt tattaattca caagagcatt | 1380 |
| gtatcggaat tttggcaaac tgttaaaacg gaattatatg ctttgttcag ttttgtttca | 1440 |
| gtgtgttaca cagttaattg ttttagaaac cattgcaagc aattataact ttggtgttga | 1500 |
| agtttagttg tgaatgagtt cgtgacaact ggttttctta ttagtgtgta tattaatctt | 1560 |
| gtagatcatc tcacatgctt attaggcagt ggtcatttct atttaatttt gtttgaaagg | 1620 |
| gttttaattt tttgatttt tttgttttgt tttagcgaac tcaaattgaa actaatcgcc | 1680 |
| aaatttata ataaggcctt ttcaaaacat ttgatcaaac ggaaaagttt tttcaaaaaa | 1740 |
| taaaattttg cagcggctta ggcacacgaa catccgacag gcgattcaat tgtatcaaat | 1800 |
| acttagtgct tctaggcaaa atgtagattt tagatataaa ttaagcccct tttcacagtt | 1860 |
| tgtaacgcca gggaaaacat ttttgagcaa attttgaaaa atcttatcag aaaaatgttt | 1920 |
| tgattgggtt aaaaaaacac ctagaaactc tactcctctt taatgaaagc ttgtgtttca | 1980 |
| aactctttt gtgcttaaat aaattttat gcaaattcat aatttaccaa acttttttcc | 2040 |
| cactgaaaca tttcaaacat aatgtcaagt cgtacaaaat cttataacta acgattttct | 2100 |
| aatcgtatct cctgttatcg ttatctttac aatcgaagat aaacggctga gaaatttag | 2160 |
| gtccgaggta caccactacg cacaattgcg gattttgcac tatttggaga gttgagccaa | 2220 |
| aactgtctta cttttttatga aactgtggaa tgttgtaaac aattggtgaa tatatttatt | 2280 |
| gtaaaatttt tatttgaaaa tcatattctt ttgtatcgaa ttttggaatt ccacgtttga | 2340 |
| aaactgcaag agcgccttat gctgacgtgt gttagttaga ttgagagact cgcacggagt | 2400 |
| agacgcagac acaccacaca gcacaaacag acgtcgacgt ccgcaattct cgttggttat | 2460 |
| cgactctttt gtcccattcc accaccaaaa cttgccacga tttgatgttg ctaggacata | 2520 |
| aaggtccagt gggaaactgc aaattctttg ttttcactgg ttttttttcca tttgttagtt | 2580 |
| actagcttga taatttaaaa atgaaacgtc tcaaaactag ttcacttgac ctacttcgaa | 2640 |
| caccaatttg tatcgtgcgt catattcctt gccgttgcaa tttcacgtgc acttttatga | 2700 |
| atttcataga ttttttttca gataattaac cgacaaa | 2737 |

<210> SEQ ID NO 58
<211> LENGTH: 500
<212> TYPE: DNA
<213> ORGANISM: Caenorhabditis elegans

<400> SEQUENCE: 58

| | |
|---|---|
| ctgttgcggc gcacctcgaa gaatagctcc tgttgggaca ttttgtgatg gctgaagtag | 60 |
| gaaattatat taaatttaca ttaaaactaa agaaaaaata cgaaaaatta tgggaaatca | 120 |
| gtggtaaatg cgaaaaaatg atttaaaaaa ccgataaacg ttgaaaacgc gacggtctcc | 180 |

```
aaaataatgc aagcgtgctc cactgcgaat cccctgctca tttgcgcgcg cattcaaatt      240
tagatttccc cgatttatcg tgaaaatcgc tgccatctga caccgcattg caccgaagat      300
ggccaaagat aaccaaaaaa ccaatgaatc attggtctat cgaaaataca ttatattttg      360
ttgggagcag ccccacgaaa gccacgagag cccgcaaaaa ggtaaatatt gacttaatat      420
ttgtggcggt ctcttacttg gttccactta cttttaccaa taggcagtta ttttgcgtt       480 ttgtcgaaaa aatcgatata                                                  500

<210> SEQ ID NO 59
<211> LENGTH: 502
<212> TYPE: DNA
<213> ORGANISM: Caenorhabditis elegans

<400> SEQUENCE: 59
atcgccaacc aaggaaagta gtgatctaca agttttctct gcaaaaaaaa caatcgtaat       60
tgcataacat ctatcgaact cgagagtctc ccaaaaaatc cctccaaatc tttactgcat      120
ttgcatgtaa agatttacc tatttttcta aactgctgtg ttcctgtatt ttcactctac       180
ctgtttcgtt tatttattta tttaagcatc aagtttattg aactctaata aattctcggg      240
aaattcgtgt cttaattatt cttgccaggg aaagttacgt ttccttatcg aacacctgtt      300
gcgaaaccag aaaagggcgg gtctgactaa gtgaacaaat atttcgtaat aactttcttc      360
caacagaaat taaaacacgc aaaaaacggc caactcacta gctggaacgt ggagccatgg      420
agatggataa aataactctg attgtcgaca tagcttcaag aatatcgtat tctgcatttt      480
caaaaagtct ttttcgttca aa                                              502

<210> SEQ ID NO 60
<211> LENGTH: 1200
<212> TYPE: DNA
<213> ORGANISM: Caenorhabditis elegans

<400> SEQUENCE: 60
gcataaaatg tttgaacttg gcatattata atacaaaaac aaaaattgaa agagccaaga       60
aatgggcgga gcctattatt gattatcctt gtattttgca aaaattgttg acagatgatt      120 tttttttccac actaactcta ttgggagttt ttcaacaatt tgatatccaa aaaaaagagg     180
aaaatccgct aacaatgtga aaaactagca tcataatttg aattgccgcg cagtttcctg      240
gcgttccaga atgatctatt tgtatttgaa agaagacctt tgaaataggc atctcaaaat      300
ttgccgagct tggcaaattc ggcaaatttc tgtttccaat aattgccgag cacggcaaac      360
tcggcataat cggcaaattt gcctggcttc gcaaactcgg aaaaatctaa gaattttgat      420 atttttgga gcacaaaaat tactgttaca ctaagaacac gtttgcttgg ttggaaatgt       480
ccgtgtggtt caatttcatg ccagtttact agattttgg agccgaatca agagttttag      540
taattgtttt tctgttcaac ttttggtgta cgcggcaaat cccgaaattt gccgaactcg      600
gcaaacagca aaatatgaaa cgtttatcac agaacttgtt aggggatttt tcaaatatat      660 atatatttt ttaattcttg gaaaagcttt gtctacctcg aaatacccta aaatcattca      720
aaaattttaa atattaccat tgagagcaaa tttacgggcc tctgaaatag tggaaaaatg      780
aaaaattaac tgaaagttaa tacgaaaatt ttcaagcttg taaagatttt tggttgttc      840 cggaaatcgg ataatcggaa aacagccacc cttgttcctg actaatgagc taagaaattg      900
attggtactt ccatagttga tgaatgttat cagtaaaatg ggtttggcaa tgcttttgtt      960
```

```
attccaccgt gatataaact gaaaagcaca actgataaga tgaggcacct gagtgtctag    1020
acatggcaac ggaagtgggc gggattggaa tttttgagac gtggcttaag ttgtataaaa    1080
ctgaccggct aaattttaat ttcagtgagt ttttgagttt tccaattctc acccaaattc    1140
cacattttat gcatcgccta agttttttt ttaattttaa ttttttttc cagatcccga      1200
```

<210> SEQ ID NO 61
<211> LENGTH: 1994
<212> TYPE: DNA
<213> ORGANISM: Caenorhabditis elegans

<400> SEQUENCE: 61

```
gcttggagag catctatggc gtcttttcgg aatatcaagt cagtcacgaa gtcttgtgcc      60
aattccttta ccaatcgttc gaatctggat cgaggaatga gcagttcagt agactgttgt     120
tgttttcgga tttctcgcag agcaactgta ccagaatgaa aggatatga tcgtactggc      180 tgagtgcacg atttgcggca tactcccgaa aggttctttt tgccagccat tgtttggtag    240
atgtggtgtg aaatgagag attgtaaacc cttctatagg tgccaaggt gagtgggcgt      300 agcttcgaag tcaactgcgg tgaaggggc gtggtttctt actattagag aaactgtatc     360
agactaactc cgataaagcc atagtcagtg aactctcaac atagttagga agagttactc    420
agattaaata aaatcgtcaa agaacaatca ggccaattct gggctaggca tagttcatag    480
gcagaacttg gtagaggaaa tcagagtaaa gtaacgatga ttttaatttt tccgtctgaa    540
aaaagatatt gaaagcattt tgccgatcga acaagacacc caaagtctca tgacgacatc    600 ccagaaaagag tttcagccaa attcccaaca acagcctaaa ggaaaatctg aaaagaacaa   660
aacatttgaa cgtgctagag cgtacttgca catacttgca catactgtaa gtcaacatag    720
aactctactc ataagtgtga caaatttgtt acaccaacag tacgaagcca agatttgatt    780
aaagacaatt gttgtttaaa ctgcttgata aaaggtcaca tggttgcaaa gattgccaga    840
gcgaacgcaa aaattgctct cgctgtgaag gtggtgaaca ctgactcagc aaagtcggaa    900
aacatgatat gatttgtctt agtttattgg ttacctttat ccgaaggtgc atcaagttgc    960
ctattggcgt tatgttgaag atgactgata taatacattg taacgatttc gggaaaaata   1020
catatttaac aagataatta tttttttcga ttttccgaaa aaatggaata aagaaaaac     1080 ggacattttc gatatttttc aaaatccaat aaagatcagc attttttgt atttcaattt    1140 caaaaaaaaa atcgaaatta attttttaaa attggaactc gagttcctgc tcaatcctgg   1200
tcaatgatta aattaaatta tgctcgtaca gtaacttgtt atttctgtgt ttaattaaag   1260
gcgcattact gatgcgattt gggtctctcc acgattgcac tctgttgtgt tatttacttt   1320
tatttttaaa tattttattt gttattttaa ttcatttttcc gcatcatttt ttcaaggaat  1380
ttcattgata tttatgccat tcgatttaaa tttaattttt tgtcgttatt ttacgtcgaa   1440
caatgagtca acaccctaat tctggttatg caacgtgggg ttacacccct actatagtat   1500
atatatgaaa tacttgcaaa aattgttata tttacacttc gaaaatcagt ccgaaaaga    1560 cgtaaagcaa cttgtcctaa tgaacttttt taattaata atttcacaaa aattgtgaaa    1620
cttgttattt ctcttgtttt ttgccttga attttaaata tgtcgaattt ttccaactat    1680
tcagctgttc ttgtcgattt ttgttaattt cgaaactagt tcagtaagaa gtgcgaattc    1740
agaaagaaaa acaaatcaag agtatttttt atttcgtttt tctctcaatt tctcttcact    1800
tctctcccat tttagtgcat gtattttcct cttctctctt cttgttgtct agtttagaca    1860
acgcggtcac tgttagagag tgcagacggt tagcgtaaca aacaaaaaag tagaattcat    1920
```

```
ttttggcgtt ggaaaccgca ttaaatactg tcctcacagt ttccgttcgt cttaatttca   1980
aatctttgct cttg                                                      1994

<210> SEQ ID NO 62
<211> LENGTH: 2995
<212> TYPE: DNA
<213> ORGANISM: Caenorhabditis elegans

<400> SEQUENCE: 62
ctcgttttca ttgttggctt cgattattgg attttataaa ttatggtgat gtagttttga     60
atgtagacaa taaattggaa atgaaatcga tgaaatgctc aagtttataa atagcaaaaa    120
aaaaaacatc ggtagacttt atttgatcta ctgtgaaaat gttttccggc aaatcggcaa    180
attgccagaa ttgaaaattt ccggcaaatc ggcaaaatgc cagaattgaa atttccggcg    240
aatcggcaaa atgccaaaat tgaaatttcc ggcgaatcgg caaaatgcca gatttgaaat    300
ttccgacaat tcggcaaatt accacaattg aaaattccg gcaaatcggc aaattgtcag     360
aattgaaaat ttcggcaaat cggcaaattg ccagaattga aaatttcggc aaatcggcga    420
attgccagaa ttgaattccc cggcaaaatg ctagaattta aattttcggc aaatcggcaa    480
attaccagaa ttgaaaattt cggcaaatcg gcgaattgcc agaattgaaa tttccggcaa    540
atcgcaaaat aagcaaattc tataaaaaat atatagcgaa aaaatttcaa aaaggcactg    600
ttttaagtgt ttccgtctta taaaaaatcc cttgaaacat tttcggcaaa tctgatggca    660
aaccggcaat ttgccgaaaa tgaaaatttc cggcaaatcg gcaacatgcc gaatttgtcg    720
acaaaaaatt tgccaaaagg caattgattt aactagtttt aactaaattt gagttttcca    780
tcgatttcat ctcatttccc atcttcctga gttgtattag gcttcacatt acccccttca    840
aagtacggta gctttgaaga ccattttcat tgacacatag ctccgggtcg aataatgtat    900
cgttttccac cacctttcgt caataaatca tttacgtcat atcgtttttt gcaagcttat    960
acatatttct gtgtaggcgg caactgagac tgataaaaaa cgcatttcct aaatggtttt   1020
ttgatgttgt tggactgtgg aatggacta tggaattata acaatctgga gagaaaagag    1080
tgcccgagag aagcagagaa acaagatgaa cgtggcatac gtacacttcc acaacagcag   1140
ccgtcttgtg gcctatataa atgaccagat tcaagcggcc atttatactt ttcgatcttc   1200
ttcttttttc ctttgtcttg agattgaaat ttgagagata acgaatccaa atagacaata   1260
tgcacttaat ttacttgaaa atgagcttaa aactcacaaa aaaaacaaat aatttggact   1320
tttttgcaca tttcctgcaa aatttgatgt ttatccagct tgtgatgaat aattttttgca   1380 cagcaaaatg aatttgtgg caatttaat ttcaatcttc catccattag ttttcctgga    1440 attttttgt tgaaaattct gatgacttgg agatttaata taagcttttt agtcgaattc   1500 ctccgttta gacgtctaac tagttaaaaa tcgttcaaat ccttttaaat taattagtga   1560 gtaaattca aaagttcca gaactttt atagttcatt aaaaatgtat tttttcacac      1620
ctagttttaa tttaaaactc acgtggtgtc aggatgtctc ataagggttt gatctacaaa   1680
aaaatgcggg aatttttttg gaatcagttg agatctgaac tcccgcattt tttgtagatc   1740
tacgtagata agccgatat agcacactct gacaccacgt gaaaacctat aaattctcct    1800
aattcatttt gttaatctga tcccagtgac ctctaatctt gatcatttta tcaccacgcg   1860
tacttctatt ttgcaaagac ctatgatatc agttgtctga cggtcagaaa gtctcggaaa   1920
aaggcgttga ccgagtaatt acaataaaaa aattaacgat ataaaacgtc gaatagccaa   1980
```

```
ataggtagat agcgtcagaa aaaccaatca gtgatttgct ccgcccactt ttcaaccaat    2040
cagaagggtt tactgggcgg agctatacgt tctcaatttg gaaaaagttc aaatagtgag    2100
attttatctt ttttttttg tagattcatg aataaatttc agactaattc gtgttttcat     2160
tctcgctaat ttagctttat tacgcgaaca ctaggttctg agaatgcgta ttgcacaaca    2220
tatttgacgc gcataatatc tcgtagcgaa aactacagta ataattcgaa tgattactgt    2280
agcgtttgtc acgatttacg gggtcgatta tcgaaacgga ttaaaatcat ttagttatct    2340
ataaaattaa gcaagaaaat gaggaaataa aatggaaaat atattcattt aaataatcaa    2400
ccccgtaaat cgacacaaca gagctacagt agtcatttaa agggttactg tagttttcgc    2460
tatgagatat tttgcgcgtc aaatatgttg tgcaatactc aaaaattgtg tgactataat    2520
aattagctat acaattctgt ggttttttg agcaaaaccg aaaacgaaa aaatttcgtt      2580 tttggcaaaa cactccaaaa tcggtatttt tcattcaaaa aaccatattt tttacggttt    2640
acgccctatt tcctacaaac aacagaaatt gaacgtggtg tcagagtgtc tcattttggt    2700
ttgatctacg ttgatctaca aaaaatgcgg gagaagagac gcagagttct caactgattt    2760
agcatggtta agagtgtgct gacgtcacat ttttgagcaa aaaattcccg cattttttg     2820 tagatcaaac cgtaatggga gagcctggca tcacgtggca ttagacttt tgagcaagtt     2880 tgaccaaaat cttttttctt cgattttcg gttttccaaa aaaataacgc caggcttagc     2940
ctccacctca atattcttat gtgattgttt ccagaacctc ttccccacta aaaca         2995

<210> SEQ ID NO 63
<211> LENGTH: 648
<212> TYPE: DNA
<213> ORGANISM: Caenorhabditis elegans

<400> SEQUENCE: 63
ttactggcat ttaaaggaaa gaactcggaa aatttatgaa gatttgaaga aaggcacttg      60
ttaattgatg ggttttcatt gtgttttatt aaatatgaag ttgtgatagt tttaatgtga    120
ttaaaataaa atttaaatca actatcgtga aaagtttaac tacaaaactg tattaaatct    180
gagaacacat actttataag ttgggaaatt gttgatcaag tctaagttga actaatatat    240
tcttgatgga atcggaccga aaaaatcaat ttatcttatt cagaaaccat cttgagaatg    300
cctacatttt ggcgcgagaa tagcggcaga agagagagct agaacggtag gcattctcat    360
gatctcatgg ttttcttat acattttctt ttttctgcc gtttagttta ttgatctcaa      420
ttggtttgtt ggtctccccc tccccctgtc tgcggtcatt tagtccaata agtcaacgtg    480
tactaactgc acctggactt tgttcacttc ctctataaaa tgacttttg attgtcttct     540 ttcttattct atatctactt tttgaatttg taaattttat agctacaatt tcactttgaa    600
actgtttggt ttttttttca gaaaccatac aattttgttt ctccaaac                 648

<210> SEQ ID NO 64
<211> LENGTH: 1443
<212> TYPE: DNA
<213> ORGANISM: Caenorhabditis elegans

<400> SEQUENCE: 64
tggaatggga atgagaagat tcggatacgg gtacccaatg tggggataag ctgtgcaatc      60
actactgtgt agttatgtat aaactatgta aaattgaaga aaataaatat tttgactacc    120
tcaatccatg ttgtcacact gtaacaagaa aattaaaatc tgataagctt cagctaaaaa    180
ctcaaaacta agattctcag gaagatattt gggtatttga actaattttg accgcttttc    240
```

```
atgcacacgc aatggatttc taagtatcca agtatgatta tttcatattt cgccacttag    300
aatccagaaa tttcaggagc atattttgt gatacaaaat aacgtatttc tgttgcatta    360
aacttctgtc taaaactgtt cggatctgaa attgaaatta gcatttaact ttttgttcca    420
actgaaataa tgtattactg dacaaaaaaa tattaccatg acatcttgct tcttttggag    480
aataataaaa taccttcagt tatagatttt aggtaacaaa taccatattt attcacacaa    540
gttgatgaaa ctcgttcgat attttaaatt aaactgcctt taaatatcta ttagccagtt    600
gttgtatggt cctatgcaca cactatcttg tatctatagt ttaatatatg cggcctatat    660
tgtgacatat attcttcccg tttgctctgt tgttctcccc ttcctgtata atgggagatt    720
gtaaatgaga gttgttctgg tcccaatacc tagccactga gaaccctcct cttctatcta    780
ctactcattt atattatcgt cattattttt attttatt atacatatag tgggcttatc    840
aacatatatg agggtaaaat acttataatt aatcagcagt tcagaagaaa aaacaatgaa    900
tgataaggaa attttagag aacggataga aaagggatct tttgatttct tcagtgacac    960
tgttatcatt ttcgaaaatt gggtatgaca atggagacgc ccacaatgg aaataacttc    1020 aaggttatcc atatatactg catacatatc cacaatatta tgaggtttct ctaggaaact    1080
gaaagaatcc tagtgtttga atgtgttgag catattaatt ttaagaagcc aagaaaccat    1140
aacttctgat aatgactgat atctaggctg tcacgagggt tgcttaaagt gttacagttg    1200
tgccagtaat attaatagct caatttctac aacatacaaa ccattatggt accctacaaa    1260
cactacaaat ggtttgaaac cttgttgttt attgttttta ctgaactctt atccacctga    1320
tacctaaaaa acgtcatgtt aagagaacaa caccgcccat tttgaatcct ttataaccac    1380
tgggagatga ccggatttcc aagtactcgt agttctaaaa acctttaaaa acccaaaaaa    1440
aag                                                                  1443

<210> SEQ ID NO 65
<211> LENGTH: 494
<212> TYPE: DNA
<213> ORGANISM: Caenorhabditis elegans

<400> SEQUENCE: 65
catgttttct ctgcaaaaaa acaatcgtaa ttgcataaca tctttcgaac tcgatagtct     60
cccaaaaaat tcctccaaat ctttactgca tttgcttgta aagattttac ctattttct    120 aaactgctgt gttcctgtat tttcactcta cctgtttcgt ttatttattt atttaagcat    180
caagtttatt gatctctaat aaattctcgg gaaattcgtg tcttaattat taatattata    240
gttattcttg ccagggaaag ttacgtttcc ttatcaaaca cctgttgcga aaccagaaaa    300
gggcgggtct gactaagtga acaaatattt cgtaataact ttcttccaac agaaattaaa    360
acacgcaaaa aacggccaac tcactagctg gaacgtggag ccccatgata actccatgat    420
aaaataactc tgattgtcga catagcttca agaatatcgt attctgcatt ttcaaaaagt    480 attttttcgtt caaa                                                     494

<210> SEQ ID NO 66
<211> LENGTH: 1683
<212> TYPE: DNA
<213> ORGANISM: Caenorhabditis elegans

<400> SEQUENCE: 66
gcacaagccg ccgtgagact cgacgatacc acaaatttca acgatttctt cacaagcttc     60
```

-continued

| | |
|---|---|
| aataatgacc tcgggctcga tcaggaatgg atggttttca tcaaagcttt ctacgcagaa | 120 |
| ctcaatctca aagtcgaata atttttattt cattgttttt ttgtttgata cctgttttga | 180 |
| ttaccatttt ttatcactat atttctgact tctttctcat ttttttaaa tttccggtcg | 240 |
| atctttcaca gacacgattg tatccgtgca gtatttgaaa ataacaaatt tttctgattt | 300 |
| ctgtgggttt cacgtgaaga tcttcttcaa gaagaggtca tcagattgcg gaagatctat | 360 |
| attaccgatc tgacgcaaga ctaccatgta tatttggaaa ggaaaaattt tctgtgcaga | 420 |
| ggttgatggt ttaaattttg atttagatat tttcttcatt taatttgaaa atttccatgc | 480 |
| ctgaaaatat cctcagtgag gattctcacc taccgtatac ttaaaggcgc acacctgtct | 540 |
| caaccggagc gttgcgagac ccgcggcatc aaactacaca ctgtgttttg atgatctttc | 600 |
| gatcgttctc gaaaaagaa agagcagagt tcattaaaac aaatggcggc aaaatgtcta | 660 |
| taaaggcgag tcgttctctt cattatcttt tgattttcga tgtgttctcc ttattgtttt | 720 |
| gttcgttgac cccttatctg cattctcacc gctacgcaac gtatatttaa cgtcagcttt | 780 |
| ttcgcagaaa attttctat attctcatgc aaatttactg ttctcaatgc tggacgtgtc | 840 |
| gcttgtgctt tgatctcaaa tctaacattt tcccttcaaa tatttatat ctgcaacggt | 900 |
| ggggcagaaa tttaaaagtt gacctttgtc agccaactgc tatcagttat cagttggccg | 960 |
| gagatctttc tattttcact ttcttgcaac gtattcagac attttttgat gaatcggttc | 1020 |
| acagaattt cgtcctgatg ttggtcagtg atgcgccagc cggaaattag aaccgtatgc | 1080 |
| cgttatcaat ttttcaaagg ctaaaaagtt atgaggtgta tttattgttt taacacctga | 1140 |
| cctgctagta ggaaggaaat taattttatg tttaaattga aatgaaagag tcgagctcca | 1200 |
| cgtgtcgtct ccctagtttc tctattcctc ttcttctccg cctatctctc ggcttctctc | 1260 |
| cttcgcgct cctctcacaa ttcctcctaa tcgtgctgtt ttggggtgg tccaacacgg | 1320 |
| caaaaaggc agcaaaaagt gtctgccgtc tcgtgcctct ttcttattga aagggcacga | 1380 |
| gagaatagta tcaagaggct cctcgttcgg gccgttgaag atggtatctg gtgcttcggc | 1440 |
| ggagacggga ggagcggccg tttctcgggt catcacagcc cattccttct aatgtttaca | 1500 |
| ctgaacttgt cgcaatccct cctctaaatc tcattcatcc attcattcat attcgtgtta | 1560 |
| tgtgttcgct tttacataat ttccattttc accacgtttc tcctcaaatt tgcattattt | 1620 |
| aaatctctgc cttttcataa acatttataa ttttcagggt atcacctata ctaaccatcc | 1680 |
| aaa | 1683 |

<210> SEQ ID NO 67
<211> LENGTH: 2110
<212> TYPE: DNA
<213> ORGANISM: Caenorhabditis elegans

<400> SEQUENCE: 67

| | |
|---|---|
| aggcaaacat cacgtttccg atatcaaaag acattgaata aagaaaacc aatagaatgt | 60 |
| aaactattaa agtgacaatt tcagtgaaat ttatcaaaat acgaaaataa taaaattaaa | 120 |
| aattagcgcc agctaactat ttagcagagc aaatacgttt tgacccaata taaaaacaat | 180 |
| aatatgaaaa aaaaaattaa aataaagttt taccaaatcg atattggcaa aacatcttgt | 240 |
| ttttgaggct ccatatctct gcaggaaaaa atcgcactaa aaagtgatca actagaaact | 300 |
| tgttaaacac aatgtaatct aaaactttc agttgaacac tattttgtaa aaatttcgt | 360 |
| tgccaagata tagatcttta actatttaga atattcaaaa ataatgaagc tcaaatcaat | 420 |
| tggttccaac tcggcaacga aatttttac aaaaaagtgt tcaactgaaa tgttttagat | 480 |

```
cacattgtgt ttaacaagtt tctagttgat cacttttag tgcgatttt tcctgcagag    540 atatggagcc tcaaaaacaa gatgttttgc caatatcgat ttggtaaaac gtcttgataa    600
ggcatcagaa tcaatgattc ggtcattgaa ataatgaaa aataggttat ttgtgacact    660
ctaaaatatt tcatgcattt tttaaaaaat ttcaaaaaaa aattttcga tcaaatttc    720 tcatggtgga gaaaaagtg acaattttcg aaaaaaatta aaatttctga aaagttccaa    780
gggtaattat ggttcaatta aaaagcaaaa aaattatgta aaaccctcaa aaaaatgttc    840
taaatacttg tttcccgttc tgaaaatttt gtataaaaaa ggccaaaagt taaaccatgt    900
atgggaaccg aacccacaaa cttctgctca agaggcgaac gcgttcacca ctcgaccacc    960
gaaccgatgt tttcgcccctt ccaccattgt ggtgagactt ctgttggcgc cagagacaaa   1020
aatccactgt taaccatagg aaatgcactg atttcagtgt agaatttcag acgtaaaaat   1080
ttcagatttc cagcccgaac gggcaaaaat ttcagtcata ttcttatagt agagaatgtc   1140
agctttccga tacaatattt ttttttgaat atcgctccat ttattctggt cattccctag   1200
tcagttgcct gcccgtggcg gaggaagaac ataataggag gatacgcaga gatgcagaaa   1260
aaaaacttcc gtttgttggt aggtagtaat ttctccttt gatctccaaa gatgttggga   1320
aattcgcctt ttggaatgtt ttatggcgca ctttttaaca gttaaataca tagccacact   1380
ttctatagac taaacaagta ctcttgacat atgtcattca tcatgtactc tttagatttt   1440
ccagccttac caacctcctc cacagtttat ctcattgatt gtactctttg aaggaggacc   1500
attggttctg actttttga cctttatactg attcaaaatg tcatcaaaga cacgagcttc   1560
gtaatgagac ttcagaaaaa aatttctgaa catttttata gcggttcaaa aattctagga   1620
aatttagcaa attttagcta tagctatagg ctttacaaaa ccttcaattt attttttttg   1680
gtcagataca cgatctcatt tcattttgct gattaagatt catttgaagc tgagaggtaa   1740
acaaaaatcg ccggaaattg taaaaatgcc agaaccttta tacaacctgt atgaaggttc   1800
accttacaat tatatctgtg ttttttcactt gtttagagga gtggtaggtg gaagacatta   1860
aagtgtcgtt ctcgtagaac tgttgtttgg actgatagct tttaaatacg actttttaa   1920 aaacttttg agattataca actaattgca ccatcattta ttttttgccg atgtgcaact   1980
ttcatattgt ttttctcct cactttctcc gttgtccttg ttcataacac aatttgcaaa   2040
tcacattgaa atttcagatt tccgattctc gaagctttac taacatctcc accactaacc   2100
aagcctcaac                                                            2110
```

<210> SEQ ID NO 68
<211> LENGTH: 884
<212> TYPE: DNA
<213> ORGANISM: Caenorhabditis elegans

<400> SEQUENCE: 68

```
aacttttgc aattcctaaa tacttaccat tattttgcc caatcaggtt aatgatctct     60
atcgtgtagt tttccccttt tagttccagt tctgctgtga tatttattta tttttgcgaa    120
tacatttcaa ttcctaactt ttttcggaat acaaaccagt aactcataaa atgttcgatt    180
tatactcaca tccgcgcgaa cacttcagtg ccgggtgtta taacacgtca gcgtttcgcc    240
agatgatgca attggcgttt ttccttggag aacaaatagc ctcgtagaga cgcatttat    300 ttccacactg cattggactc aattggtggt gtatttgctt tgaaggtgaa tttaaattca    360 gactttttt tcgaaacttg cgcagaaaat tgtgaatttt tcgatttta tagtggaaaa    420
```

```
taggttttttt tcaaaatatt tttattgaaa attaaaatgt ttgctttcta tgctctatta      480
ttgccgaaga aatcaattttt aatgaaatat tcaaagaaat cgcggaaaat tttcaaaaaa      540
tttccacgat tttattttgt acgcaatcgc atctgcatac cgtacccggt ttcgaatttc      600
gaacttttcg aagcttttct tgaattttttt tctgctttcc aattagaatt aaaagtgtaa     660
tttaatcaaa ttctagtaaa tttcaaacaa atttgggatt aaatgttaaa ttttattaac     720
attttcaggc tttaaaaaaa tatttcaaag ttttgtgtca aagtctgcaa acactctcga     780
ataccgtaac cttgcatctt ttttaatttt ttgttttctt tattttttatc actcctatac    840 tttttctata atttaaagca attttataat atattttttac agaa                      884
```

<210> SEQ ID NO 69
<211> LENGTH: 1475
<212> TYPE: DNA
<213> ORGANISM: Caenorhabditis elegans

<400> SEQUENCE: 69

```
tgctagcggt caccactatc gactgagcta tctgcccta agaaagttta aaaaacttac       60
cgattttgag ttccaacatc attttctcgc tattttttgat aacgttttgg ttagcattgt    120
actccggcag tattggtagg tcattctcgt tgtttggagt ctttatttca gactccacga    180
cggctggagc aacattctga attatatttt ttaattattg ttatacttttt tagcaaaaaa  240 ctgacatttg aaatagatct actgttgcaa ataatgtctg gcaacggatc ccatctctca    300
cttggcctgc ctgagcctac atccaatctt gcaattgctt gctcacaatc tctcactaat    360
ttcaccaatc cgtaaaatct ggcttcccgg agcaactgat gtcgggttct gaaagttttta 420 tttaatttat aaaactttaa acttctagct taaaacatct accatttcct gaatttcagg    480
caaattcttg aagtatccat cgaactttgt tagagtcgct ttagaagtga caaattcctt    540
gccacctaca ttgagccgga gcatttactt tcagaaacaa taacagtttg agtttatctg    600
gaatttgtta gataacttta ggtagatttg aaattttttgg tagatcggtt tcatcaaatt    660
tatcaatgtc ataaataaac tttgtagcta taaatttttaa aatagctttt tttacacttt   720
attcaaggaa acactgagaa atagctgcga aaacaaaaaa aaacatttga ggggagaacc   780
tagacgcagg agagaaagaa cgtagaatct actagaaaaa gtgtctgcgt ctcttcaaaa    840
aacaaattta aacttagcaa gatgaccacc acagcaaaaa tgaaaagag gaacgcggag     900 ggacagggac agggttcagt gagaaaaaaa ttagaaattt tggaaaaatg agataatttt    960
taaacttttt gcagtattcc aaagttttttc ggaaaattga dcaaaaaatt ttaatcaaac  1020
ttcccatgaa aatgacagaa aatttttaaaa ttgaaattaa atgaaatttc tttattttct   1080
ggatttttag gagtttctgg aaatttctta gcataagcat aagcctaact acaaactaaa  1140
aacttcaaac taccaactga atacaattaa ttacctcatg attttgttcc cagcagccgt   1200
aacatgttaa aaactctatg ggtcctgtga gatgtcggcc gctctaactc tgcacattgc   1260
agagattttc agacagtgtg tgaccaatttt taggctgaaa atctgccgac tgtactcttt   1320
ttggaaatgt tttgttttcga aatttttttac tcactctcac tataactcca actcacctgg  1380
ttgcgaaatt cagcgcttttt caacgtaatc taaaatgaaa aatattcatt ccatcactcc   1440
tccaactccc cattttttgtt tgaaattctc tgaaa                               1475
```

<210> SEQ ID NO 70
<211> LENGTH: 2811
<212> TYPE: DNA
<213> ORGANISM: Caenorhabditis elegans

<400> SEQUENCE: 70

```
aagaacgccg acgacaacaa caaacatttt catcgggagc cctggaaaat gacgaatgta    60
tgcattacca ttgttgaaat ttggactgga agcgcaatgg atgaaaaaac cacgctattt   120
cgaagctcat ttctgatgct ggggcacaac acaaaattaa atgagacgag gaggggagga   180
agggatggag agcatgcatg ttttgttgtt cactttcgaa aaaatgtatc gattttttct   240
agcaaatgtt tgaagtaaat aacaactttc aaatgtgata attagttatc aattcagtca   300
gtttatcaaa aaaagtacg tcattagcat aactttgccg tatttgcatg tctaggaaat    360
tttagaaact agaattgcta aaaagtggtt taaaagttgc gggacgccga aaattggctg   420
agaaattgtc aaaaatttcc aagtgacgga aaaccgtatg ttattgtgat tagtaagacg   480
atttcgcaat tttatatata ttttgtcaca aatctgaaat cactcgtgct attttaggtg   540
taaaagtcac atgttattgc acaaacacga gcagaaaatg aattaaaatt accttctcgg   600
tttttcagac attgtcttca actttgtcta ggtatttcga aatttcaaaa aaactccacc   660
tgacccacaa atcaatacta gtaagttagt aaacacaaca gtatgggaat tggttgatat   720
gtacgttgcg agacttgttt gtgcttatct ttttcccctc tctacttaac aatcaaataa   780
cctgcaaaac actatggatt tttctcttca gtttgggca attcttccag aaaaccacca    840
aaaaagaccg caattttgct aacggtcttg ttcacactgg tagataagat aacattgcgt   900
aggtcgatcc taccgatcaa acgggagata tatgggggga gtaggagaga aattacggga   960
agaaggctat cgagcggcct tgacacggtg cttgactttt tggcgaaacg tatcagttga  1020
cctctattat ttgggctata cagagatgag gtatgatgga cagaaacaga aaaacacaca  1080
caaagggtat tgatgagaat catagacggt gacaacgcca attcaatgag cagtagatgt  1140
gcaggagacg tgtctcgttc agttggaaac gaaggcgaga cgtgaaaaga gtgcgtggtt  1200
gcgagagacg cagtgataga gacaaactgg ataggttatg agaacgagaa ccactcggac  1260
tgaggccatt cgtagaatga agaatggaag ttgtatctgt cttttaatag actcaaatga  1320
aactgaagaa aaaaagtaca aaacataaga cactatatat ttttttttcat attgaaaaag  1380
agtttgcaaa ttttcttgaa attcaaaaat tctgtttttc gtgacaacac tttttgctta  1440
ctcatttgt aaaatttaa cgtgggctat tgttttgtg tttaaatatt tatactacat     1500
ttttgaaaat tattattttc acattgccac gtgaactcaa aatttattca tgcaaattta  1560
gaataaaatc tgttcaacta agcctatacg cctcgtgcag aagtccaaat ttgaaggta    1620
aacctaaacc taaatttgat catgaacact gagcctgaaa gcctgtaaac cataggcaaa  1680
gcctaaaaac agcttacaaa cctttctctg aaattatgtc tgaatacgta agtttattat  1740
atgaactaag cttacagct aaatctatgt ttgcaggctc agttttgaac gttaataact    1800
ttcgaatcca catggaaatt tagatataat tgaataaaaa agtcctcgtt aatatttgaa  1860
aaaaaatgtt gtcaatttac gaatcctttt ttttcgccta aaaggagaa tgtcaaaagt    1920
actaaataaa aaaacaaaac attcaagagc aactaagcag ttttccgaa attttttcca    1980
aagttccaaa gtcaacctta accttaagct gcagaatttc tgatgtttac cagctactac  2040
gaaacaaaaa cgattctcat agatgatttc ccatttcgc acacaaaatg ttggcatcac    2100
aaacaaagtg agcacaagta tggagagaga tttgagagca cagacatcaa agaataaact  2160
atgttctttg ttcttttaa actactttga aaaaaacaa atgaattac atatttaaaa     2220
tgttgcaatt gcaatttcat gatggaaata ttggaaaatg tctataaaat aacgcagaca  2280
```

| | |
|---|---|
| gtgccaatca aaagctttc tcatctaccc agtcggttga gtgaatgaaa ggaaacatat | 2340 |
| aatatcaaag ctggcgtgcc aattccttt tgtgctcggc tgcattattt acactgccgg | 2400 |
| tgtttccgcg ctccttctca tcgacataat ttccctcatt tcctctcagt cttccgcgca | 2460 |
| gttccatcca tcgcaatccg ccttcttgcc taaatttgtc tgacccaata ctctaactaa | 2520 |
| ctttcattta tgtccaatgc attattctct ctgtaggtga cccagtgtcc ttccttttt | 2580 |
| ctctctcaag atgtgagacc cccccccct tttctcctca acggcgaggg gctacgtgag | 2640 |
| tttccgctgt gtgcgacgcg tccttgcccg ctcttcccaa actgcacggc caatggggtg | 2700 |
| ccgggaggcg gggtaggggc gggccaatcg acgcgttcca cgactaagta agcgtggaca | 2760 |
| ccccatcgtc tgcagaagag gacactctcg atccattcgc tattcatcgt g | 2811 |

<210> SEQ ID NO 71
<211> LENGTH: 1113
<212> TYPE: DNA
<213> ORGANISM: Caenorhabditis elegans

<400> SEQUENCE: 71

| | |
|---|---|
| gaacacgttg catcgataaa tcgagaatat tctcgaagcg caaaagaaa tttcgcaact | 60 |
| atttcagacc gaataatgta ataatgtaat gggtctcttc gatagaaaat aaacgaagat | 120 |
| aaacgaagac acaattcttc ctgacgcgcg agcttcaata tgcacgtgat gactaatttg | 180 |
| gtttccatgg tgatcttttt gttccttta tcgattcaaa tttacaataa aaataagaaa | 240 |
| ttaaagttct aaatggcgct ccaatcaatt tgccttccaa tttaacgtcg attccttcta | 300 |
| tatcaggtca taaatgaat aaaaacaat gatcaataaa atgatgcggt agttgcgtaa | 360 |
| atcgacacat gatggtcgcc tcttccgtgc gagacccatt gggcggagtt ctcacaagaa | 420 |
| tgaggccaat cggcacacaa cacgcgtgcg acaggcagtg aacgacgtgt ttttggctca | 480 |
| gttcctacca atccctggtg tacacacgag cgccacgtgg accttaacaa ttcgggtcta | 540 |
| ttttatgct tctgctctgc attttctgga ttattagtaa taatatcatt aaaagtgata | 600 |
| taacgctccc cgagtctata taaaatttct cctccataca acacatgttt tttggctttc | 660 |
| ttcttctaag cttaaaattt atagttattt actaactgta ttttccactt attaaagata | 720 |
| attttgaaa agtgtttgta aatacttaaa attgaacccg aaacaatctg tatttgtcca | 780 |
| ttcacatgtg attcacagaa aagaatgaaa ataaatgcga aaaaaaata aataaagtaa | 840 |
| aggcgcattg atttaccgc tcgcggtatc tcgccacgaa acacgtttc gcgtcaagcg | 900 |
| gctcacgttt tcgatgcgat cgcggtttgt taattgcgaa aacaccttcc cttctcttca | 960 |
| atcgttcgct caatttctag aaaatatttc tgaataatct gaaaacctct aatcttgttt | 1020 |
| cttagttttt aacttttgt cggtgttccc gataatctct cgccctctaa actcactcga | 1080 |
| tcgattgtcg tttataggta aagtttttag gta | 1113 |

<210> SEQ ID NO 72
<211> LENGTH: 2263
<212> TYPE: DNA
<213> ORGANISM: Caenorhabditis elegans

<400> SEQUENCE: 72

| | |
|---|---|
| aataaaagat gtgatggtca atttaggata gtaaagatg acaggtggat tgagggaaaa | 60 |
| gagacaggtt acttctgttg agtggacaca ttgcaacccc cggccaccac cgccacggac | 120 |
| acgccgccca cttttgcggt gtgaggtgcg aaactgtctt ccgacagatt tgtaaatatt | 180 |
| acgaggaagt tgatgtaata cggaagaggt ccactggatt tatgtgaatg aagaatcaaa | 240 |

```
agattgtaaa atgtttagat atgatgagct acagggtcaa aggtgatttg atacacgatt    300
ttcgagcaga aatgctgact tttcgaaatc tcattgttgt ttaatcaatc acggatgta     360
cgaaagggat cttggttttg gattttgaa atcaaaata ttacaggaaa atataatgca      420
aaactagtac agactgtgaa aatgtttcta accttgattt ctgctccgtc caactgtgaa    480
attacattgt gtgtcaattt caaaaacggt acgtgatttt ttagttctgg ttttaagtg     540
aactttatgt atatgagctc tgaaaacagg aaaataaggg aaaattaata aggtagtcag    600
aatgaaatat tgcaattcga acataagcat ttagtttgaa acaacccgta tttcccttat    660
tagttttgta gcttctagtt tgtcatgcac tgattttccg acagaccggc tatactctgt    720
gggaatttcc gcaaaaatta aatttaaaat taatagatga gatgtggtat gtagttttaa    780
aaaagtcgat ggattcagaa aatgctcaga aaaatccgcg cattaatttc caaaactatc    840
acatttcaga aaagtatcaa acatcatatt tttggagtcc aatactactt cttcatttct    900
tttttttttt tcttttccac tagttttaca ataaaatata ttgttttgtc ctaatgaagc    960
acatttcatt ttgtaatgtt ttttaacttt ctactgtagg atattctatt ccgtaatcgt   1020
acaaatcttc tttctctccc aaatttaggc tgcgccctgt ttcaaagctc tgctaatagt   1080
acgcaaaaca aatgtattcg ctaactcttt cgctcatttc ggtataagtg tcacttggag   1140
atctcttcgt ctctcgcaac ccgtatttgt attgtttatc ttccaaaatg gtagtcgact   1200
gctcatatga attgaattac tagcgggata tgaaagagac atgagattta taaaaagtaa   1260
ctgaatattt caacttttga aattgaactt gtatcatttt cgaaactaaa atggaaaaac   1320
aggaacgata ttacttcatt tttccactta agatggagt agcaaaattt gggtgattgt    1380
ttttagaatc aaaattgatc ctaaataccct attgagacaa cttgaaaatg tctcaaaaat   1440
tattgtatta ggttagtcat tctctaaaag aaaacgggca acccttcaag tattaaatca   1500
ttttgagctt gaaagagag acattgttc attaaaattc atgtttgggc tcctaaatct    1560
acaaaaaata tcacatttat attttcggca attctgattt cctgtaatcg acaatttcag   1620
cgattgccga aatcgtcgaa aagtcgatta ccgaacggca attgctgcat gctatgtatc   1680
acaccgtttc agcgttgtgt atcgtatttg ttcaaagata attttcttgt aaatctcgat   1740
gttattgact actgcagcta atacatttga attcccatta attcctttaa tttgataagt   1800
gtgacttggt tcccgttgcc caccatcttt tgttcctttc ctcctatctt caaatcaaac   1860
gcatctggaa tctatttttt tcattgttgt ctgtctaccg atgccaacga tctgaccttt   1920
cttaattggt attcgcgctc attttgacat tgtgtcaact tcaactattt gcgcgggttt   1980
acctgcaaaa aagtaaacaa gaaaaatgga gatgaaatga agaatttcc aatagaaatt    2040
tgttgttgaa aactctctga accatgagac cgtccaagac gttaacatca aatcttttca   2100
attcagaaac gtttcctctt tttctccttt tgtgacacgt ttcctccgtt cttttttgga   2160
gagtcactat attttaata cgattttgct ttacaatttc ttttttaaac ttttattgat    2220
tttgtgcttc ttatttttcca tttttcataa aaagtattcc aga                    2263
```

<210> SEQ ID NO 73
<211> LENGTH: 850
<212> TYPE: DNA
<213> ORGANISM: Caenorhabditis elegans

<400> SEQUENCE: 73

```
gtcgcgaaag gtttgaattc ccaactggaa aaactgagat taagaaatgg aggtatattg    60
```

```
cctgattgag atgagaaacc ggtttatgag acggataaac aagtaagttt gctgagtaac    120
gatcacaaat ttcacaaatt ctcaagacaa gtgagatgat taatttctat aaggattaat    180
ttagatgatc cgaacattac ttgagtgact gttataatag aaagactgaa aaatcgtctt    240
ttaaattaac atattccata ttgctggatc cggcaaacaa aaacaatgtt ccaggacact    300
cactccacgt gttctgagct gtcgtctcgg tcgttgattg gctgattccg cctctgtttg    360
caactagtaa cgcgccgcag tttgcagttt tcagtgaagg acaacgtgtt tgcaagagac    420
gcagacactg tgcggcactt gcaaattggg gcgggacttt tagggacacg tcgagaaggg    480
gtgagccccg gcgaaagaaa gcaaacaagc ggagagaaaa ggggagtaat tgaccgttgg    540
aaagacacct cattccattt attctcggtc gttaggaaga gacggcgatg agattccttt    600
tggtgggctt cgtcgccctt ctggctgttt caggtatgtc tttttattga ttttcagagc    660
ttagtgagct ttaaatagaa aaccgtagtt ttgaaattgt aaaaaaaatt tttaagctta    720
aatgtacgct gaaaatatta aaactgtgtt cacagaataa aaacattagg ctttattttt    780
tcattctgtg catacacgcc acgcagtttt tgaattcacg tttttattcc caacaatcat    840
cacttttcag                                                           850
```

```

<210> SEQ ID NO 74
<211> LENGTH: 2171
<212> TYPE: DNA
<213> ORGANISM: Caenorhabditis elegans

<400> SEQUENCE: 74
tctgcggttc tgaaaatatt aaaaccaatg atggaaaaga atttattcgg gataaggatt     60
tttgacaaac ggacatatgg catatcctaa tgtgagcaga ggagctgtgg tcggagcaac    120
cgaccgcacc ggctcacttc tgctgtgatt cggctcggcg ccacgaaaag agtaagagag    180
acgtgacgac ggcaatagat gaatcgaaat ctatggatgc aagaaacctc ttttcaaatc    240
attcgaacgg ttagaattgt gcaaacacgg cgacgcacaa acgcacatat cgtggggaca    300
cgtgaacgat ggccgacttg agaagaggaa gaataacaga cggcgggaga gacgaggaaa    360
gggcacaaaa ctgagatgat ggtggtcgca ggcgctgagc gtgatctctt ctgttctatt    420
tcagacacca cgggattgta ttcaacaaca ttttgttgtt tctactgatc ggatgggatg    480
attgtaatta accactattt atgtttctca cgaattgtga cactaaatgt gaaaaccaat    540
agaaaacata atcgtatttc ttcaaatctg atattaaacg ggtagttcta attatgaaaa    600
tattgcccca cgacgaagaa ttaatattaa taatatttct tatttttcac ctgcacagac    660
actatagtta tcgatgatcc cagttttatt tggtctaaaa ataaaatttg aacttctgag    720
ggattgttga gcgacattga tatggaagaa gcgctatcga taaaaatttc tatcgttcca    780
tgacaaccaa tcacatgttc aaatgactga atgccaaaga aaacctcgaa agcgaaccgg    840
tttttcttcc ggtgaccgtt tagattttta taaaatcttt tagttagctg aaaatgaaat    900
ttattgcagc tccgtgagaa aaataatcag atatacgcag aaatgactga gggacgatac    960
gaaaatgcga agaatctgcc ttgcaagagg acagatgtcg gtactcaaca cgtacccaac   1020
acagtctcct ataggattga caatttatct tcagagcaga ccggaataat attaacaaca   1080
aaaagctaaa cttaaaaacc gaaacgaaag caattcaaac ttaaaatgaa aactaaaata   1140
aaaagcaaaa accgaatgct gaaaaaaaaa ttgtctaccg tacacctaca gtaagattct   1200
gcatatttgc gtgacagtgt ttgcacatgt ttattcgaaa aatgtcattg ttttttttc    1260
gtttttactt ttttcgccaa tcatttagct ttaccctaga ttttcattct tattttgttt   1320
```

```
tccaaatcaa tcaataaaca ataaattttg tgaaaattta cctgcaaacc tccattaaaa    1380
tttgcaaacc cggcaaactg tcacagagag aatgaaaaat tgattgaaaa taataaaact    1440
gcttggccag tttgaaccga ttttaacaat taagcttaat ttttttgaag tatttgcata    1500
cacaccatgc agtttttttt taaagtttta ccgtaaatcc ctactgagct aataaattaa    1560
aaaatttcga ttaaaacaag catttatcac gagttctaaa ctgatatgag acatatttaa    1620
tttattccga ttcacttcaa ctgatgaaaa cttttgttca aattctcaaa tatatttcaa    1680
tcgtatcaca ttttttttcg gcagctgcag cgaattttc ctttcatgag ccatgggcaa    1740
cggcttaatt acaccaacag ccgttgtcgg tgtttggatg tattgcccta atgaccgcc     1800 cgtacgttgt cctctccatg caacgacgct gaatattctt ctgctctcac actcgtatac    1860
tagttgtggt tgaggcgcct cgatggacag catgagagag agtgtatcct ataataagac    1920
gtagacagac gcgctctagc aaattcttta ccgcagcact ccacagcgtt cgtcagtccg    1980
ccttgtttca cgttgtcgat tgcagacaca atgcccctca ttttctattc acttctcatt    2040
gtattctatc tgtatgtgca tagtaacttg ttttacagcg agtaatctca aaaatcgata    2100
tattttccct tttcataata ttgttctgtt accttggtac cctcattatt atttttgaa     2160 tttaggtaac c                                                         2171
```

<210> SEQ ID NO 75
<211> LENGTH: 4107
<212> TYPE: DNA
<213> ORGANISM: Caenorhabditis elegans

<400> SEQUENCE: 75

```
aagtgatgtt ttggcaattg gaaaagctag actaggaatg aggataaatt atgacatcat      60
taggacttgt aatttagaaa ttacacggag gcaaaccgta atgcgttttt ttaaaataat     120
attttcttaa tttttttcctt ttaatttctg ctcaagtttg tttgttggca aaataaatta    180
tttaaaactt ctcaaaacta tttaaatagg tttttttgaaa ggatgtgaaa ttccttatgg    240
aattttagat gatcttcaat ttgaaaactg ttggcagagt atcgccagtg aaaaatttt     300 ctaaacaaaa taactcaaaa aaaatcagat cttttcaaagt tgtcagtaga agtttttggt    360
aaattgccaa atgttccaaa atgtggacg ttttgaaaat gttgagcatt tcagatttaa     420
gctactgcaa tcttcaaata aaaatatttg aaacatagct agaatatatg aatcgcaaaa    480
agagttttgg taaattggta tattttttcac aactgtggta ttggtctcat tcagttatac    540
atctttattc ttaactttga tataccgtac tctaaataaa cttttcctatt acaaccacac    600 ttttaaattt catatgtttt cactcttcag aggtcaaaaa ttggaagaaa ttattaacga    660
aaaaaataaa aaattagaaa ttaattatta tgttttttatg ttcaatttac gtttcaattt    720
ttcgtatttg aaacttggca atttaccaaa gctttcacta taaattttt tactttttct    780 acaaaatttt agtgtgtttt actacgttat cctgtcattt tagactataa taagtgagta    840
cagtattgtt ttcatttagt tcatatttct atgttctatt ataattgtct gtatctgata    900
ttcgattttt ttgaatgaac atgagttta aagtatatca aagttaaaat acggatgtat     960
agctaaagga ggcagtaaca catatttgaa aactttgatt tcatgttctc ttccttcttt   1020
tcccacggcg ttatgtttga ccacagaagc atctattttt ggaatcaata tattttttt    1080 cggtgctttt agcaaataat ataaagtttg ggaactacct ctaatgttca ttttcatttt   1140
tgatattctc ccttgacata tcaaaatatt tcgagcagta tgcatttcct tatcattttt   1200
```

```
caactgtatt tcctgatttt agcttttcat attaatcaag taggttcatg gtttcaataa    1260
attgtgggtt aattatagat ctgcctaatc ttcaagccaa tgccttctac ggagtattgc    1320
cagtgtggat ttagtttgaa aagtattcta ataaaatact ccaaaatttt aagttagttt    1380
tggcaaattg ccaacatttg gacttttga gctatttcca gcattgccac aggaactgtc     1440
agaatgtttg aatacaaaca gttgaaaata taaaaattgt agaaaattgt tttaggtcta    1500
cttcaaaat tttataggt tttattataa ctaaaattat tatgactaat ttttcaccat      1560
aaaaaattaa ttgcaaataa aaaatttcaa aaatgttttg aaacgtttta ctattttatt   1620
tggacattta agcactaacg tgttcaaagc tgaaatttca aaacgtcata actttgctga    1680
aacttgactt gggcagctaa attttcgga gagatcataa ctaacagtct tctatcggat     1740
attcaacatg agaaccccaa acctacgggc cccttcaaag atttcccttg tgaatgggca    1800
atttaaata atctctccat ttacgatatt tcaccttcaa ataaacaatg aattattcta     1860
gattacttgt tgtcattcag tcaagatatt ctcaagtatt ccaagttctc cattgtttaa   1920
tgattttgct ccaattctat ccaatttccc tttgttcgct gctttagtcc cgccaccacc   1980
ccctgtgcaa agagataacg tgtgagtgaa tctaatagcc agaatctgga aatatatata   2040
tgtttagaat cacaaaagga aaatgtgcag gcggggagat caaaatcgaa actgtatttg   2100
tgtggaacaa tgcaactatt gagagaaaca tgaagcatat ggactacgag ttgagtaggc   2160
ttcaaaagta ttcaggaatc tcaaccaacg agttttgccc agaaattacc aagaaaccag   2220
tgtaagtttc atttatttt ttggatttag ttagattttt taaataatca aaaaccgatt    2280
tcttgccgat gtcatactgt agacactgtg agaagtagga ctacctcaat attgataagt   2340
gcctacctat gtgcctagaa ggcaggtgtg gcttgcattg aacttaacag tagacgtagg   2400
tctcttgaag ttttgcttcc aggcaggcag gtaggcattt gaataattta aagctatagt   2460
aaggagtacg gtaaattaca atatcatttc gtgataaatt tcaggcaaga tcgaaatcat   2520
tttgcaatgc tctacacctt tccttatatt acgtcaactt gtgatcgtgt cagacttttt   2580
gttcgaaatg cagtttcctg gagttcagag gtctaaaaat attcctgaaa aaattataat   2640
tctagatgtt caggtgaacc gagcccgagt agcatgcgaa tgtgaaaaaa ttgtggaaat   2700
gacgcgtggc taacgaggta cttctcgtcg ccgatctttc tcttgaccag gaccgaataa   2760
atatttgaaa atgcacttat tgtttgttct caatgccgaa ttgttacaa tgtacctttt    2820
ggtaaagagg aactcgtttg tactggccag ctaataaaat attcacatta ttcttcatac   2880
tatgttttca tatagaattt atcaatttta taatttagat gataacgagt gctgtactcc   2940
tggagtccac caggacttga taagagaatt gaagcaccac ttttataatg agcagtacta   3000
atttcgaatc tggaaatgat atttcagaaa caatccagga aacaccagaa aaatatcacc   3060
acttgaaaa atatgtgcat ttattcaatt atgctcaaat ttcagctttg gctcacgagt    3120
gatacggtca accacaattt tctccagagt acgcaattta cgcaaacacc aaacgatggc   3180
gccaaagcgc cattcaaatt ttattcatcc gtttcagcct ttttcagtct tcttgtctct   3240
catttttcgcc attttcattg ttttatttac acaaacggtc gtttaaaatg tagtttccat   3300
ctttttccga tggttcatca ttttttgtcat gcgtcttttg tgaaactggt tttgcaaaac   3360
gaagcaaaaa atggataact gtgtcaaggg cgattttcg attcgtcatg tccacataaa     3420
cgcgataatg tgttttatc gttggtttca ttcagaaatt ggttgataaa tacattctac    3480
tacattctgg ctgtgtgatc caattttaa atccgaaagt ctagaaattt agtgcaaaat    3540
aagcatggaa agttctaaac ccccttaaaga atactgatct cagctgtttc tgttcttttc   3600
```

```
aatcagattc ccaattgcga taatatcaaa agccctctg ctggactgct gtccacccgc    3660
aagggcatta tttccttatc ccaaaatgct ctccgtctgc atctcttcaa ctcactcact    3720
ctctcgctct cttcgcagtg cgaggccgac acgcaacgtg gcctctcatc agacacgctc    3780
cgcctattct caatgtgtgg cgaccgccga ttggccagtc gctgacgtgg accaatagat    3840
acgcggcacc tcgagccgtg tcagccacgc aagacacacg tcgacttact ccattgtcgt    3900
agcagacgag ctcagttcaa catcatcagt ttcagttttg ctcttgttcg gtttcatttc    3960
tagtctttct tctctgaaat tctcgaattt tattctttgg tatattctca ttcaatttat    4020
ctcttctttt tccgattcat atgtttaatt gttatattta ctttttaatt tcagattcaa    4080
cttggtgtcg ttttatcgaa aaacgaa                                        4107

<210> SEQ ID NO 76
<211> LENGTH: 1524
<212> TYPE: DNA
<213> ORGANISM: Caenorhabditis elegans

<400> SEQUENCE: 76
ttcactcctt gtctgcaaca acgaataat agaatcaata gatggcaaaa atttgaaaac       60
agcgtacagt caagataagg gtaatgtatg ttttttgtcgt caacctctaa acgtcaaact     120
gaaaacttaa agggcggcgg ttggttaaat ggcgggcgtg tagtactaaa aacaaaggtt     180
tgagtaagtg cgccccattg ataacaagga tctgaagaag tcttcttcgg ataatggagg     240
tcagttctga tgggaaaatc gagaaatcga gttttttta tttgattgca agctaatcac      300
atttaaaacg cttacatggg aaagttggcg tttgaaaatc gaatgtaata tacatttttt    360 tgatttctg attacttttg agctagcatt ttaccattta tatgaaaaat aaaaaactaa     420
gttgcgattt ggatgtggtc aattacccat ttataaaact gaaaagtatg tttatttcag    480
ttcaaaaaca ttagaatttt agaacccttc tagctaattc gacccttctc caagccatgc    540
aataaccttt gatgaatctt atctcaacca attcacattg cagagattct tatctccagc    600
ataacgtatc tccaatcgct ttctccccca tcgtccaaca cagccgctat tatcggccaa   660
agtactacgt gtctcgagtc cgatcctgac ctactttta tgtgtacttt agttcaattg     720
cgtctggttg gatttgaatt tgttgattcc caaataggag agattctgga taatttcttc    780
gaaagcgtta caaaatgcgc agaatttgt gtattttaa aacagttgat tttagttttt      840
tggtttaaat atctagtgta tctgctttta gcaacaaaaa atgattctaa aactcgtttc    900
tttctaaatc atgtcaccac ttatacactt ggccttttcc gattttctt tctctctttc     960 tatagctctt tcttactctc acctgccgtt tccataacag tgctctctaa atttggtata   1020
aaacacgcag cgcaaccgca acgcaaccta gtaactgacg tgtcccacgg acaccctcca   1080
ctcacgacac tctcgcacac aaacgcgcac acagggccac acgcggcgct cgccgattgg   1140
ccgaatgact ctgcgtctct gcgcgctgca cacggtgagc cttcgctgtg ctgacgttgc   1200
cttgtcctat cgtcctaggc cacgtcgacg attcggcagt tcgttccttc gctctctccc   1260
tctcgatgcg ctcgtcgatc cgtcagtttg ctctcccttc accactccca tcggttgacg   1320
gtaccatttc ggcctacagt cgaccttgag cattcgggcg gtctatcggg agagacgacc   1380
tacaaacaga agcagtccta ggttttcctg cattccattt ctctcaccga ctggccttgt   1440
ttcggttctt tctttatctc tttcttctca gcaattcaac aagtcgtttc atattttagg   1500
cctaataata attttatttt ttac                                           1524
```

<210> SEQ ID NO 77
<211> LENGTH: 1560
<212> TYPE: DNA
<213> ORGANISM: Caenorhabditis elegans

<400> SEQUENCE: 77

| | |
|---|---|
| gccatttggt ttgacaccac acttcacaaa accaaagtca caaatcatag aagttgaggg | 60 |
| aaatctttct attcgatggc tttcagatct agtcttaaat agcgacaata tttgttcaaa | 120 |
| aagaaacaga atcgttcgaa attctgatat ttatcttaaa tcaaagcgtt atttggcttt | 180 |
| ttttttaaaa gatctctatt aacagaaaca ccacgatgac gcgtgagttt ataacttaca | 240 |
| attggcaaca agaatagtga ataaaactga caaggctaca cttgacgggc agaccatctc | 300 |
| ggaagacgac gaaacggaca gaatgatcta gaagagtctc gtctgcggga tttcgactca | 360 |
| gcgtcgtcat cccttccgga acctccatat caaatagcac cgtttctcgc ttctccgcct | 420 |
| ccccaggcac tattatgagc tgttgtgtgt gtgcaagctc acatcataca agaaatctcg | 480 |
| aattcccact aataatagac aatgagactg atgtttgat tgagttgaga tcgtttgatt | 540 |
| agtcagaata gacggaaatt ggatggacca acagaaaaag agaggaacgc gaatcgaaaa | 600 |
| atataactgt ggaaatcggc aaaaaaaaag aatgataaca aagggaaaa gcgcgtggca | 660 |
| tattcttcca acaaaatatg tgttttttg gcgaccgact gtgcaactct ctcatcattt | 720 |
| atattctaca caaaaataat tcggaatatc caaaaacatg cataaagtcg cggaaatgtt | 780 |
| acgaatgtca atccgaaaac agaattgtga gtttacatga atatatactc aaatctactt | 840 |
| gaataatgct gaaatgtgta ttccaataca cttttttaat ctcacaaaat tcagtaaata | 900 |
| atctcacact ggagagtcaa agagttctac agctaaattt ctcatttacg aatcaaatta | 960 |
| gagttttaaa gcgttccttc gtattaatat cagtgtaaaa aataattaa gacaaaaaat | 1020 |
| atttcaaaaa accagaaaaa gcgaaaaaat gaaaaaaaa aagaatgac aaaaacaaag | 1080 |
| cgaaactttt ttctcagact acggtagatc ttgttgtgtg cagcgtgttt gcacagattg | 1140 |
| tcgaccgtac ccggaacttt tttatttgaa atattttcaa aaaatatat tttctctttc | 1200 |
| caaattattc acatttttcg atattttaat cgtttcttca tggttttgct gtttggaaaa | 1260 |
| agacgttcat cacagggtaa gatttataat tgtttaattc tcagcaatta atttccatga | 1320 |
| gcagcgaacg actaattgtc aaaattgagc gtgttttata ttgattctgt ctctgtgcta | 1380 |
| ttccatcttt cctgcctaaa atgtatggct tttctcgtta catttctcca atactttcca | 1440 |
| aagagacgca gacataaacg aatgtttgcc ctattgcgaa agaagtaaat gaatcaccct | 1500 |
| tccttttccc tttttttccac tatttttttat tttttatttt ttgaagcaac atcggcgacc | 1560 |

<210> SEQ ID NO 78
<211> LENGTH: 784
<212> TYPE: DNA
<213> ORGANISM: Caenorhabditis elegans

<400> SEQUENCE: 78

| | |
|---|---|
| tccattaatc tatttgttta atttattcta attctcgatc gggaataaat aatttggaaa | 60 |
| ttattcaact tattaaattc atagatctgg gaaactatca agaatcaaaa tcttaagact | 120 |
| attctcctct cgtctcgttt cacatctctt cgttctccgt ctatcgatcg ggtgatgctg | 180 |
| caaatcattt ttatcgatct acaaagtgct gcatttacta acggcatatc gtttcgagac | 240 |
| ccaaacgctg atgtgcgtta ttgcaaataa cagttatttt tccaaccag cattacatta | 300 |
| cagtccactt ttttttccttt tcatatttttc atcctggacc cagctacata cattaccgca | 360 |

```
aacgtgcaaa cggtagattt tatttactag ttccttttt ccgaaaaatt tcaaaaaatt    420
gtaaactgcg tttccgtttt caagaactt ttttgaagtt tcaacgcttt tcatcgcaaa    480
tatttacaaa tacgtctcgt tatttagaaa ttttaaaatt ttttgaacag tgaaaatcct    540
tttcaaactt cgcgctaaaa ttataaagca accgcgccct aacgtcagaa tcaccaaaca    600
ctttttgcgt acacttgttg aaaacacgct tctatatgcg tggatgatga caattttcaa    660
atctgtgtcg ttttttagaaa taatttcgtg aactttttta aaatctcaat tttcttttat    720
agtttcgttc ccactatcat tttggacact cattcttctt attttaggtc ttaaattgta    780
cata                                                                  784

<210> SEQ ID NO 79
<211> LENGTH: 1487
<212> TYPE: DNA
<213> ORGANISM: Caenorhabditis elegans

<400> SEQUENCE: 79
atattcaatt cattccaaaa acgatttttt taaagttttt ttcaccagac acactttatt      60
tctctcaatt ttcaacagac acgatagttc tgtccaacct ccattcgatt tgtgtagtcc    120
ttttccggca ttcgtacttc aagctcatac aacgtgtcgt ctgtttcatt tcgatgagcc    180
atcataaacg cacgtctgta aatgtgttca ttatttcatg tcataaatta tttgcaatat    240
ataccgttcg tttctttgtt gaaccgatcg tttgatatac tccaaatctt ctggagtcaa    300
ttgatgacga acatttggtc ctgaatggat tccaattctt atttctatta ttaatttatt    360
atctcaccat tgataactgg ctttttcattc tgatctttct ttctcttctt ttcatcagta    420
ttatcaactt ttcttgccgg ttttgctttt tctggtgatt tttgtttttc tccaattgtg    480
ggcattgggt agtaagtaga tgtggcgaac tgttttgtt ggtaagtagg tgcaatagct    540
gtatgaggat ctgatcccat tctttcaata ggaatttcag atgcttgtct gaaatattca    600
aataattatt ttgttagttc ggatgtttcg ataagatatt attcagatgc aaaattttta    660
ttctgcccga aaactacggt actgtactat aattttctcg cgaaaatcac aaaatattgc    720
atccaaataa catccaatac gccttcaaat ttatgaaaaa ttacggtagc ttatgagtag    780 gtttggcac atgtacattc gtgtgaacga ctgtggttgt tcatgctttt ttgacttctt    840
gcttgacttc tgaaataaaa aaaaactttc ataagatgct ttgttcattc aacaaaagcc    900
gtttaccttg cttcttgata cttttctctg gaacgtgtgc actagtcttc tgatgagttg    960
gctccacagt atcgttgagc aaagttttcg agtaatgctt cacatttagt tcttctgatt   1020
caacacttgt cgattgactt gttggctgac tgaatcatag aataattgat aatctgaata   1080
tattaaaaag ttaactcacg tttcgtcgaa atgtgcaact cgattgtgat gaatcgatcg   1140
ttccaatgga tgctctttct tcagtatcgc tgatttggac tttgagtttt tgtttttact   1200
atgactacag cccattcttg aatctttctc tcttattgca cacgatacga tttcctggta   1260
ttttgtcggc ggaagaatat atgagtaaaa tcagaaatga atcttttttt atctaaagtt   1320
ttttattcga agaaagaatc ttcgcgaaac atgtttctgt cacagtttat ctgaactaca   1380
aatcttaggt tcacgaactt acttacttgc ttcgttaatt aaaaaaaaat tatattcttt   1440
tgctttcgtt tgcatgcaat ttccaaaact ataactccta ttttcag                 1487

<210> SEQ ID NO 80
<211> LENGTH: 1659
<212> TYPE: DNA
```

<213> ORGANISM: Caenorhabditis elegans

<400> SEQUENCE: 80

| | |
|---|---|
| gcaaatgtga atggaaccaa gaagagaacg agcaaaaatg ccaccgggaa actcattata | 60 |
| tcattctgga aacaattata cttcaaaaaa tggaagcaaa atataaaaca ggagttgtga | 120 |
| atagagaaaa cgacgcttta tatcatcagt tttggcattg aaatgaatca ataacataaa | 180 |
| ttgagcgaga aaaagagaaa cagcaaaata gtgaaaaacg aatgattgac cgagagaacg | 240 |
| ggggaaggtt ggaattttg taaacaaacg agggaaacat catgttgaaa acatatatat | 300 |
| acacattttt tatttaatgc gtcggaatat tcagaaaatc gttcagatca tcgataattt | 360 |
| ttattgataa aagaccaaaa atccagttta catgaggaaa acaatacact gtgaattta | 420 |
| aagaaaatta atattccaa aaaaatttaa tttaatttgt aatttgggaa actgaaacaa | 480 |
| taaacacta tcgaaaactt aaaaaaaaac atggattgaa gctcaaaaaa actgttttaa | 540 |
| tgtttcgttt tgtagaactt tagattttg taaagcggga gacaccacga atccgcaaga | 600 |
| agtttcttcc agaagcagat tcgctgaaaa aaatgaagt tgtcttaaac ctgatgcttt | 660 |
| ttttgataa tttttataca ttatgtggtt cctggttgg ccattttgtt aaaatcatta | 720 |
| tttcctgtaa taaaagtcag gcgttctcag ttatttccag atatcggatt cctaaaatag | 780 |
| ctgaactcca aaaacggtc aagtctctga acaccaaacg cgctccttcg aacaaaaaaa | 840 |
| gcagcgcgta cgtttaacga acagttttt cttctagaaa ttgttttctc attgcgcaat | 900 |
| gcattgctca ttataaataa ttatgtttta aacagttgct gggaggtttt cgctatctca | 960 |
| gtcgttgtta aacaattacc agagtgtgtt atcgtattta tctttgccgt ataatatctt | 1020 |
| ttccatatt atgcgattgc ggaaattac cactgactct gcggaaactg cggaaattta | 1080 |
| ccactgaaat atcactcata tcgtacgttt ctttgaattc gtctccttgt tattcaaatt | 1140 |
| atgtcttcgt ttttgaacga gatatttacc tctagctttc tagatcgtca catcacttag | 1200 |
| gttcgccttg aacttctgtt ccgctaaaga cggctggttc acatatattt ttaacaatgt | 1260 |
| aattattact tatgacccga ataaaacggt agaacgcttt gtgaaattat tcgaaagcaa | 1320 |
| atgcgcccca aggagagagt gtgaatgaga ggctgcgttt tgtcatcatg tagaggcagc | 1380 |
| attggggtgt tctgtagaga acttagtcta cgtgtctcat cttccatatt tcttaatttt | 1440 |
| gttctattgg ctctttttgc atctcttctt tgattcgatt cttaactga attagatcag | 1500 |
| aaattatact tgaagtttta tcttgaaaac ctactgtaga aaagtttgtc cgtgttctac | 1560 |
| tttcttatta gactttcgcg tttcggcctt tcctatgttc tacccccatc ttccgttctt | 1620 |
| ttttattatt ccaagatttt acagagaagt cgtttaacc | 1659 |

<210> SEQ ID NO 81
<211> LENGTH: 747
<212> TYPE: DNA
<213> ORGANISM: Caenorhabditis elegans

<400> SEQUENCE: 81

| | |
|---|---|
| ccgggctcga acaagacatg gacgagccat tcgatatgtg atcatctgtt atcacaaaaa | 60 |
| tgatcaattt tcttcataat ttatcaaagt ttctgttttc cttccatttc atctgatgaa | 120 |
| ttcctacttt cttgttcctt tcactaact ttattattat aattataatt attcataatg | 180 |
| ttctttcttt cccatcatca tatccatcct tctatacatt ttgtttccat ttgttgttga | 240 |
| aattttatat gctatttcat ttttttgtcgt cctttttttc cgttcttcat tttattgact | 300 |
| tctcttcatg atttctggca ttcagctcga taattcattt ataccctgtt ctttctagtg | 360 |

```
tttttcgcg ttgtttgtga cggttaaatt cttccctcta catctttgcg cgtttccaca    420
caaaatctg tacacgacat tcggttttct cgttgttcca tttctttttt gttcaacgga    480
gcgcgtttgt cgttgcagga atcggtttta atatcatcat ccattcacgc attctctttt    540
tcatgttgtt cattgtgttt ttcttcaatt tttgtcaagt ttccttcaca cgtgcatttt    600
agtaatttct ttctataata aattgcagtt tgttaaatat ttaaatgatc aatgagctct    660
cttttcttgg ttggctcatc ctctttgtat ttttgaattt atagttgaag aaaacgttaa    720
taacttttca gaaaaccaaa aataaaa                                       747
```

<210> SEQ ID NO 82
<211> LENGTH: 2141
<212> TYPE: DNA
<213> ORGANISM: Caenorhabditis elegans

<400> SEQUENCE: 82

```
atatagaaaa acggtctctt aatttcaaaa aaactaaatc aaataatgtg atagactctc     60
tcaattgaaa tagataaaat tgagagagac cgtggctatt acatttgtaa attaattttc    120
ttaaactcta cttctatctc cagtgagcca tactcgtgaa ttgatcgcat tgaattcttc    180
tcttcaatat caccttgtcc aataattaca tcgtctcgtg agcacatctt ctattaaaca    240
aaattagcac taggctagtt ctcttctaaa gtgagaaatg agaagaaatg tgagttgtag    300
agacgtgtat aataaaatcc ataaaaatta aaatattgt gagttcttct gagattacgt     360
gaaggccgaa taagaggtga cggtgataat cacaagaatt taaaaataat ttttccatag    420
aacgaatata taattgcgta aatggtcgtg gttgctcaga atctcgagag actgtggcaa    480
attgtcgaag ttttggcatt ttgccaaaat ttggtaaatt gccaaatcat cgaaaatgta    540
tattttcaaa gtgatttcga gcagttttgg aaacttttac tataatattt gagcacttga    600
gaaaccgatt tcaactattt ccataccgtg gaaaaattat gttttaagtt ttggcattct    660
gccaaagttt tgacattttg ccaaaatttg gtaaattgcc aattagttca aggtgtgtac    720
ttttaaagtg attttgaaca gttttggaaa ctattactgt gatatttag cactttagga     780
actgatttta actatttcaa tactgtataa taattctttc gacaacattc tcatcgggcc    840
acatgcgatc acggaagaat ctgaaattaa aagataaata gaaacaatt tgagattatt     900
aaatattacc tctcggtgag atctggaaaa gcttgatcgt agagagtcaa aatttccggc    960
acattttgtt cgtcaaccat gcgggaaaag tagaccaggt agtcggcgac ctcatttgga   1020
actccatcct catcggctga agctgttaaa aattaagaaa tgagataagt ttgtgttgtt   1080
aacaagcacc taaataacta ccataaatat gtttatagaa ttactctatt gattgattat   1140
caattttct tttgaaaaga tttcacaatg cacgatcatt gatcctctga tactcaactt    1200
ctctctcggg cttttaaatg attaacttct tatgaactct tatgaacacc ttttcattta   1260
ttatttcttt caaatgaata aagctgtgat tcatttaatc tgagatttga ggatattcga   1320
caccgaaaaa cactgaaaat gacaaaagta gtcatttca tatacaatga gggagttctg    1380
agaattggca ttgattcttc actgtaacag tatttggaaa atttggtttt tctgaatttt   1440
atgtattttg ctcatggaat gttaatctgc agttttatg caaaattatt tcagaccaaa    1500
ttctccaaat gtctgtttgc cgaattaaaa taaatcggtt aatcaaaaaa ggaccgagtc   1560
ttcagtcttt tcgaactgtt tcaaatttta acatttttca actcatttta ctcttattca   1620
tcaattctga aaaatagcat tctgtgaact tacaagaaaa ggtgttggtg cgacgacgat   1680
```

| | |
|---|---|
| cagagtgatc ttcagtggat aaatcgaatt ccacgcgtcg agacattact gaaagaaggt | 1740 |
| ttttatattg atattattta aatgtcaaac taaattcgaa aaggtacgct aaaattaaga | 1800 |
| gaaacattt ttttaattgt aaaatttgat gaaaggaatt ggaaaatgtg atggaaaaaa | 1860 |
| gaaaattgca agcgttgcat gggatttcgc aagagtgccg cacggttttt tgtgtacgca | 1920 |
| tttgctcgtc attcatgttg tctaggcagt tttgatgaca ttttttattc taaaaacaaa | 1980 |
| atgttttatt tcatttgctg tttaatgttt gaatatgtat ggaaactaat ttgatacect | 2040 |
| ttccgctgca ttattttgc aaaatctcaa aattatatat cttcaattca ctacctagaa | 2100 |
| ggcatatctt cctgcattta aaaatctatt ttatttcaga t | 2141 |

<210> SEQ ID NO 83
<211> LENGTH: 1463
<212> TYPE: DNA
<213> ORGANISM: Caenorhabditis elegans

<400> SEQUENCE: 83

| | |
|---|---|
| agatcaatgg cactgaaaac gctcatttaa atgcaaaaga tcgtgtcccg taaaaatttt | 60 |
| ctgtataatt ccgtgattat tttcactcgg gaatcgctcg cccactatgg gggagtctac | 120 |
| gcaaggacaa cgcaaggaca aggacaacat tctaatggaa tggaaacgat tgcccgactg | 180 |
| caccaattct agttcaagtg aacaatgata acttttgtat tctgtattcc ttcacgtctc | 240 |
| ccagcgagcg taataaatta ttattattat tataaaagga gagttttgat cagataaatt | 300 |
| tattatcgtt gaatatccac tttctctgtt tctcgtttca ttctctaaac gacgtatgga | 360 |
| taatacatat gatgaaggtc taaaaacttc aaagaaatgt ctcctagttt tgcaaatttc | 420 |
| caccgaaaaa aaatttggtc ggttctcgga ccatttatgt attgtatttt atttggctta | 480 |
| tgttttactc aggaaagtaa ataacttttg ctaaatgtac ataaaatcag caatgttttc | 540 |
| aaaaatgttt tgaggtaatc cggcttctat gtgatatatt aattcaatcc taactgataa | 600 |
| gataattata aatttaaaac ttactgctac ctccaacttc tggaacagca taagaattgg | 660 |
| ttggtggaat ggtaacatat cttggctgcc catatccatg acgtggtggt aatttgattc | 720 |
| tatagactgc ccgttttct ctaattgatt cagttatcaa attccacgca tcatcggaat | 780 |
| atttctacaa acattgaat taaaaacttg aaaaattaat tatggaccaa cttcaaatgt | 840 |
| tttcagatct tcaagggaag taatttcaaa gttttcaatt tcattaaaaa ccgaaaaaat | 900 |
| tgaagcgaga atcgtaagaa ctgcaaaaac aatgagcaga atagtagcga atagaaaatt | 960 |
| tgtgtgcttc atttttgttt tcagtttcag acaggtgtct atattttata cttttcaaca | 1020 |
| caatagatat taattatttt agagagaaaa aaacaggaaa cagctacata gtgtgaagtg | 1080 |
| aaaatagaaa tatgaaaaat gaaataacaa tgactttgac gaatttatcc ctcttaccct | 1140 |
| aaatttcaa taaaatcaaa atacaacaaa agctccaaac tctaaaatta ctaaattgta | 1200 |
| tttttgtacc aaaactagct tcccgacatt gataagtaac gcactggcac aaactctaat | 1260 |
| tttttagtga acacaaaaac agtaatctgc aaaactttct ttctcgtatt ctctgtttct | 1320 |
| ctacataccg tacttaatat ttcactatct tatctctctg tgtctcttgc cgaccaaaaa | 1380 |
| actaatggtg gatcgctata taagaaatg ttaggtaagg agttgaatgt cagttatttc | 1440 |
| tgtaaaaact agaagtttct aaa | 1463 |

<210> SEQ ID NO 84
<211> LENGTH: 628
<212> TYPE: DNA
<213> ORGANISM: Caenorhabditis elegans

<400> SEQUENCE: 84

```
attattatgt tcctatttct tttatcaaat aaatgcagtt ttaaaatttt ggactttttct      60
gagaacgtac agcaataaat aaaaatctaa aaccaatcac attcaaaagg tcggagcaag     120
ttcggagctc cgggattcaa ggtcacaata atgaaattgt ttttttattg cttgacattg     180
atcgaaatta atttgttatt ttttgcaaaa tcgaaaatga atattttttga attagaaatg     240
ttttttacaaa attttgaacc gccataaaaa atgttgaaaa gttaaagttt tattacgaaa     300
ttcgtacatt tgaaaacctt tgggtctac atgttcaaaa tcgcccgaac cgttagtctt     360
cctttaaagt cagttatgac tgtgttctgt gtctcctcga ctctgttttc tgaattgtca     420
tcacaccaaa agaccaatct ttagatcttt gtatttcttt tcattacttg ctatcaaatt     480
agccatgaaa aacatatgtc atcatattac tcactcaaaa tactacaaac tacactgacg     540
aggttaccgt ttgatcttat catctcttaa attagtcggg gtatataaga agaacaaatc     600
gagtacattg tttcaagaaa aattccca                                         628
```

<210> SEQ ID NO 85
<211> LENGTH: 1441
<212> TYPE: DNA
<213> ORGANISM: Caenorhabditis elegans

<400> SEQUENCE: 85

```
gattattttc ttatgctaaa ctggcagaca gcagatcttt ttatatctgc acaaggggcg      60
gtgggattta tagaaactta agttactac gcctgccgcc taatccgtga aaccttattt     120
ttatattttt ccgcctcccg aaacagttga tacgtgaaaa agcacggaag agaaaaaagc     180
ttctttttgga cttgattaat ctgttggtca tgagaaagcg tgacacaagg taggttacgg     240
tagcaattgc gtaattaatc ggatcagtct atgcgcattt ctgaaacatt ggggatttca     300
aatctagttt atcaaacaga tacaaatcac attgacatct cgtggaaaca gtctgtaaag     360
taccgcaaat tttacaattt tgatattat tgtcgttaaa caagttccat ttcaaatttt     420
ttattgaata cggtaaaaaa acaagagagg cagctggttg aagtgagtca ctcttgttga     480
gttttcgtta ctggaaaacct gaatgaagat agttttttaac tttagcatta cgcctcatta     540
ttttcctatt tcctttttac tattttactt gtattttttaa actttgttta gcacattgag     600
cacataaaac caaatgttat aaatatcctt atcatcaacc catcggtttc ttttaacctt      660
ttttctttct cgaatttcaa tgacccggaa aaccaccaca tcatatgaaa atcgaatcta     720
aaaatttgca gatacgcatc tgtcctgctg cgctctttt ttattttga atgttttttt     780
ttctgcaaac gttgggaaca gtcatccaat ccttcaaccg ttcgtctcgt tttgaatgac     840
aaacgttctc tttccgtcct ctgtttgagt atatttacat tgctaattca aaaaaaaata     900
gtatagaata taatgatact tagagatagt tctggcataa agtttaaact tgaatgaaat     960
catcaatgcc attaataact gtgtcactgc attagtttat cagcaagtgt gccagcaaaa    1020
aaacgtttc gagacgattc gatacattcc tgaaaaactt cgataaaagg gaagtatcca    1080
aacaaccaca cccaactttc atcattgact cgctgttttg cttttttattt ttgttaatct    1140
tccttacaat tagttttaaa gtttaaaaca aatattcat gttagaaaga actgtattt     1200
ggtcagtttg ttcgaataat ttcgaaatct aaaacctttt cttttgatg attcgtcgga    1260
gtagatgttt ctcgaaggag gtaaaaaaaa ccgtgggcga ttcttgtttg cattgaggat    1320
aatagagcag tagtagaaaa gcagggagtg tcaactcagt tttgtcttct tcttccccta    1380
```

```
tttctgtctt actttcgttt tgtttctttg aaataattag attttcagaa actattataa     1440
a                                                                     1441
```

<210> SEQ ID NO 86
<211> LENGTH: 537
<212> TYPE: DNA
<213> ORGANISM: Caenorhabditis elegans

<400> SEQUENCE: 86

```
aggaaattta tccaaatgat tttactattt gagaatgtat tatgcggtaa cttttttgaa       60
ataaactaat cgtgacactc aaaaacttag aatctatttt aaaagaatag ataattccag      120
tttttgatat ccgggaattt atgatttttt ggaagaacgc aagaaatcga tacatttggg      180
tacgcataat aggtactctt gcacttggat caaattccta gagaacgatt agatgcttta      240
gacgcagaaa caaaaaaatg tgaccgatac aaaatcgacc acaatctcaa gaaaaataag      300
tgcgcaacac aatccgaggt caatctagac atttatgctc ttcctgcgag acaaaaatgc      360
attgtatttt ttcattcaga ttcattcagg tgtcttgaag agatatcaaa tcacatgtga      420
caaaattttg atcgaaaaat aagttgcatc ataataaaat catcttatga tcttcctata      480
taatctttct tcaatttcgg aaactacgat tcgaatatat gttttatttt aggcgaa        537
```

<210> SEQ ID NO 87
<211> LENGTH: 2201
<212> TYPE: DNA
<213> ORGANISM: Caenorhabditis elegans

<400> SEQUENCE: 87

```
aaccttaggg taaagtttat tttattttttt tttctttacg atagggttat ccaggctttc       60
taagccgtaa ataaacttcc attttaaatt ttaaatatatt ttaaagctca agcttatagt      120
atagggaaca aagctttctg atagtttaga actaacaaag agcttatgtt ctacaaaaac      180
agggacgttt ttatttatag gggggggaggt gtaaggattc taaccgtctc tacacttctc      240
ccacttccct tttccccagt gatagaaggc taagagtgta tagggattaa tgcttttatt      300
tacaggatca ccggccagaa agtcagtcac gccatggatc aacccttcgc tcttctccga      360
atacagctct gcaattgatc catccgtgca cagtgccaaa cgctccttac gcgttcgatc      420
cctgagataa ttgcaataat tcccacacac tcgatttatt ccaagcctct aaacttcctg      480
gctaccgtaa ccctgtgtgt gtgtgcgcac acttgtgtgc gcgcaccttg tttacgtctt      540
ctggaccttt ctgcggagga atccagggct ccgccctgcc accgcagagg ggtatataag      600
acgtggattc tatcactcca gatcttctct tacttttctg ttccccttta cttgttccct      660
ttgtctcatt tcttacttgt acccattcca ttggggttat taattcataa taaatctatt      720
ccttagcaca taccttgttc tgttgtagta tgggatgcaa caacttcggt tgtcataatg      780
ataattgagg ggaacactta acaattacc ggtatacgct taaacattta ctatatgttc      840
attcaatcaa tcacatatcg acacaacaat taacacaatc cacaagtttt tgcgcaatac      900
tccttcttct gttcctttgt gattcgtgga tccgcacaga agccacgtcc tgcccagaga      960
tggcagctga aatttttatg aatttttatt atcaaattcg aattcccgt cattttttgt     1020
tcataatcct atattttcaa agatctagct caaaattgcg tgaaattcca tgtttgcgga     1080
cttttggcgc tacagtaacc cggattattt ttgaaaatcg agatggagct ctgaaaatat     1140
gggagaaaag gtgaaaaatc atggaaaact cgaatttggc attgaatttt ttaaagaaaa     1200
aataaaatct gaaatttaaa aaattgaaaa tttcacccaa agtttcaagc aaaattatcg     1260
```

```
aacaaaaata tcgattttta tccgttttgt aatatcaaat tcgaattccc cttcattttt    1320
tgcccccaac cagagatcta gctaaaaatc gcgtgagatt cggtgtttgc gtacttttgg    1380
cgctacagta atccggtaat tttctgaaaa ttaagctatt tagagctcta aaattttcgg    1440
tttcgggcaa aaaatggcag ggaactcgaa aattttaat aaattttaa aataaagtgc      1500 aggaaaaaag ttacgaacgc cccaaaactt actcaatatt atcgtgacat gacggagtgg    1560
tctgagcact ttcaaattca ttcgggtgga aatttggaat actcatggca aaattggtgc    1620
cgaagagcac ataaagagca gtaataatca gaaagaatcg cattctggaa gcttctgacc    1680
tgaaaatgct ccagtgggga gattttatac tggaaaattt ttaagtattt agataattaa    1740
ttgttcgtat ttcggaactg tgttttatca aaaagcactg tgttttgtgc tcttaattct    1800
gtaatagtag atttttttcc ctaaaaatta gagttttttca ttatcaaact ttgattttttt   1860 catgattttt ttctaaacat gcggttcaac aattccatga actcaaaaca agccgaaatt   1920
tgaagtaaat tctgtgaaaa atgatatttt ttctaatatt attcaataaa tctattttct    1980
tgtcctatat ttggagcatt tcaattgaag tttgctccat tttctgcccg cggcctagaa    2040
acctccgtgg ccgaacaaca agcgcgctct actgcactct ttttattttc gtattttcaa    2100
tttaatttca ataatttta tcggttttct tcgatttttt cgcacttccc cccagtattt     2160
tttcaatttt tccgataaaa atacaaattt tccagctaac a                        2201
```

<210> SEQ ID NO 88
<211> LENGTH: 942
<212> TYPE: DNA
<213> ORGANISM: Caenorhabditis elegans

<400> SEQUENCE: 88

```
ttttatacga aaaatacttt aaaatcagag gaaaatactt tgggaccggt gaaaaagcat     60
ggaggttcgc acaaacttgt ttaggaaaac agaaatatgt ctccgtggca ggaccatact    120
gtgcgccgtt gatgtcccctt tgatacagta ctcttcgcat tatttattttt ttttcggcgc  180 gcctaggggt tttcgagcgc agagttcagg aggccttctg gattatggat agaggcttga    240
tttttaaaat tgtttaattc aatacagttt tattaaagtt ttttctaaaa atcttttcta    300
aaaataatat ctgattgctg tttatacacg agaacaaaac taatttcatg gaaacaattt    360 tttctctttta ttttctcttc gaataattta aattttaaca attcaggttt taaataatca   420 attttttaaat aagcaagtga attttaagca taactttttct tcctagtgta cgtaaatcat   480
tctttccaac aaacatatttt tttcgtgacg aaacttcgcc ttccagaata ttctttttttc   540 agaaaataaa taccaaaaag cacaatttct tatctcttgc tcattctttt ctttgtatcg    600
tgctcatgct tttattcatt cctcattttt atcttgcgaa accaatgtat tttcaataaa    660
aaaaacgagt gatgcatgtg cgctccaccg gccgacggaa gatcgaacat gcactgcgct    720
tcgcgagtaa atagaacgct ctggaaagtt ccgcactctt ctctctcatg attcggcgca    780
ctctctcttc catttctccg tgtttcctct tctgatgttg acccatatttt attctgccgg    840 gtgtattctt tttatctatc tgttgcttca tttattccgt taacctgtta ctggttaata    900
tttcaaaaat tcatatgatt tcttttcaga ttactttcca ca                       942
```

<210> SEQ ID NO 89
<211> LENGTH: 1311
<212> TYPE: DNA
<213> ORGANISM: Caenorhabditis elegans

<400> SEQUENCE: 89

```
aactaaacat tgaaatttct gcacttcttt attgtaatga tgcttctgtg tctgacttgg      60
cattttcaaa aataatggaa tggtggagaa ttgacagcgc agaccattgt taagactatg     120
actgtgcagt ttatttgcac agcactgtct ggcacactct cttcatatca catggactct     180
ctcttgctca ccctttgaca cggattaggt tagaggcata ccagtgggag tcagagtgct     240
cagaaaagta gttgccatcg tggtaagagt tctgaaaagc atcgaaggtt ttttagggac     300
caaggaaata tgaatggagc atgtaaaaat acttgtaaaa ctgtaaaaaa taactcagcc     360
caaaactgag ggaaccgtac tttctgaaag aaatatgtat gaataccgat gttttttaggt    420
tcaatcaaac aatttattcg gattttttcac gaaatattac agagagtgtg acgttacata    480
ataatgttca ctgtttgacg cagtcacgag cttccaaaca attttatatt atcgagacgc     540
aaagattcac aattttcgcg ccagaatagc acaacctggt ctcgacatga caagttttag    600
ttaaatgcga aaagatgtgc gcctttaaag agtactgtaa cttcgaattt ttcttgttgc     660
ggaatttgtg aattttcatc gctttctcat tgtatttcga atgaaaaatt ggcttttttg     720
acaaacttag acacaaaaat aatgctcatt aaattttaac aaatcgagga aaaaaaatat     780
tgtgaaatgt gaaaaattcc gcagaaatga acgctttcc ggtggcaact ttcccacaat     840
ttttcactga tagaatgtaa attttgaat taatatcact ttcagaagtt tttatacatt     900
attttctcct tataaagttt gtgtgaatca cattttcggc cgaaaaaacc ggttttccat     960
ggaatgcatg cttccgatgc ttttcgcttt tattggcgga tggttacgca acctcaccga    1020
ttttatctct attttccgca ctttctttct ctatttccaa aattttcagc ctagtttatt    1080
tttgaaattt cagcaaaata attaatttcc tcacaaaact ggcgaaaggg cttttcgttt    1140
ctctgccgtc tctctttttcg cacgctctat aagcaagtgt ccgtgaagcg cacttgcacc    1200
cgtttatttt cacaacacgt tttcagataa ttttagctat ttttcattga ttttcagtag    1260
tttttacagc tattataatg gtattttttta gtaatttcca gtataaatcc g             1311
```

<210> SEQ ID NO 90
<211> LENGTH: 550
<212> TYPE: DNA
<213> ORGANISM: Caenorhabditis elegans

<400> SEQUENCE: 90

```
tttctctgca aaaaattgga gattttttca gtctctttca actaatgtaa atacgctctc     60
ttgtgactaa gcgcgcgcgt ttgaaccaga ggacaatttt ttttcctcagc gctagtagcc    120
cctgaaagag ttattcatac ttgaaaaaag aaactttttct atagatttct gcatgaaaaa    180
tcaatcctca gcgcttcttc tcttgctttt cctgattgta atgaaatttt agagttttta    240
aattgtaaaa aaaaaactaa acaagttctt tttgaaggga aaattcgttt ttaaatgctt    300
aaaatgcttc aaaaaaaaa caaataaaaa aaattgtttc tgtgcataca ccgtcacgac     360
aaaatgcaga cttgccattg gtctcgccgc gaaaaaacat gtttctttttg aaagattgtc    420
ttaatttttt gatttcaatc atgatttcaa tcagaatttt gcgatctttc agcattttta    480
tctatttttaa agcttataa attaaaaatt aaattttttaa aaatcttcca gattgtcata    540
cgggtcccgg                                                            550
```

<210> SEQ ID NO 91
<211> LENGTH: 836
<212> TYPE: DNA
<213> ORGANISM: Caenorhabditis elegans

<400> SEQUENCE: 91

```
aaattattat ataattttca aaattactgg ttgatgaggt tagattagtg ataccttgga      60
agtggtctat gtaataacaa ttttgcaca aaaggagatg agatttgata tggaagattg     120
gcaacacaaa cgtcaaagaa tggccattcc attttcatta catctcctcc attaacttgt    180
aatttgtttt gtagaggtct gaaatatatt tattttaaat tcgaaaatat ttttcaaaaa    240
atacgtacgt tcccataact cttttcttga cttcagcaat cattctagga tcgatttcac    300
atgcaattac agttttgcc acctccagca ttttaaccgt caagtttcct gttcctggtc    360
cgacttcaag cactgtatcg gtggcttaa gagctgattc tcaacgatt gcattcacaa     420
ctccaggatt tttgagaata tgttgtcctt tgtcggtgtt aaatggaagt gctataaaat    480
caatgttatg aatagaaatt tgcaaaaat aacatacatt gaacatttcc agttgatgat    540
cctgctttcg tcttttaac tttactcgtt tttcccattt tgagtttttt taaatctgaa    600
aatgaacgaa aaataatagt atttctgaaa ataggaaaat aatgaaaaga ataaaggta    660
gaatgatttg tccacgtgaa gtacaaaacg tgggactaaa aaacaattct agtccgcgcg    720
tcgtgtactc ctctcagaca aacagaagtt gcacaatttt ttgaaatcga tcccttttaa    780
tcacttttc ctattcttct agcgtttaat tattttctat tgattttatt tacaca        836
```

<210> SEQ ID NO 92
<211> LENGTH: 2115
<212> TYPE: DNA
<213> ORGANISM: Caenorhabditis elegans

<400> SEQUENCE: 92

```
aaaaaaaccg gctggtttgc tgaacggcaa ttgctgttca tccctatacc tgcctaccta     60
ccgccaattc agataatgtg gtgaaaaatt tcacgaaaaa aagagcaaaa agaaactata    120
atttttaaaac cggagtttga aaccgtcatc gtcgttgtca ttaataccat tatcattatt    180
gacatcagga atcacgccat tttgctccgt tatcatacac atcgtcatca tcatcatcgt    240
cgtcaacacc catcaaaaaa aatgtataaa aggtttcact caaaagagg gttttatcat     300
tttatcaaga cttaaaaatg tcctcgtagt ttgactatga tatcattttt ccattatcac    360
catgtttgcg ttttccttt tccaaacatt tcttttgcac ggcgatgatg cttggcatt     420
tgcactcgtg aaagtttcag cttgccagtg cgccgccgcg ttgtccatgg caatgcggca    480
tttgtattca acggcagaaa attgagagat tgtttctct cgcgtacctc gcatgttttg     540
attttcgac ctcggtttgt ccctcaaaca aagagaatcg tttgtcgccc tcaccgcgca     600
cgcatatacg gaaaaatgct acaatttcaa ggcgtgatag agatcagctc tcccgctgat    660
ttctatcgat tccaatagag atttattcac ctcatacggc ggcattagtt tgggcggtgt    720
tttttggtgt tgttgtgtc caaaatacga aaacggaaaa ccttcatttc agcttagttt    780
ctaaaattga ttttctttta tataattttt ttcaataatg ctgaatgcac gtgctcgccg    840
gctgccctt tgcaatgaga ctatgcaaac gcgcccgaat gcaaacgctg ctggtggacc    900
cctctcggac ataaaattat atttcttatt ttttcgaatc tgttttttctt tcatattttc    960
gaaaaaaat gacaatatta tttgatgaaa aaactacgaa aattggcaaa accaaaaaca   1020
aaccaagga aggatttctg gcttccctca taaattgaaa taaaagagtt taccgaacta   1080
ggccattttg gctcggccat atctggggta gattacggc gcgttgcttg tcgcgtcgcg   1140
gctcgagttt agttgtaaaa ctaaatgtat ttgtccgtgt ggagtataca actttgccac   1200
```

| | |
|---|---|
| gcgttgtcca gcaggagatt tgcaatagag caagaaaaat tcaatgagga aggccggacc | 1260 |
| ccgtgaaaat tcgcagaaaa gtaatgaaat cgaaacagaa aactccgaga ggactacacg | 1320 |
| gccgaggatt tttcctcgtc cgctcttttg ttaggccatt ttttgaattg gtaaacggag | 1380 |
| ttttctagtc cccgaaaata taatttagac caaccagcga gcacgtgctg ccattgtcgg | 1440 |
| accaaaaaaa aaacgccaaa aaaccgtgta ttttttttc gttttttgat ccaaatgctc | 1500 |
| atttcgtcaa aactgatgcc tactttggct gcctacctac gcctacctac ctacgtgcct | 1560 |
| acatatcgcc tattctttgc attttggcgt ccagtacttc actttccaca gaatagataa | 1620 |
| aaaagtgtat tttgacaaaa aaatttattt gacctcggcg catttgatct cgagaaaacg | 1680 |
| tggcgatttt tgtttttacc agttccaaac tacatgtaac tttgccacgt ctgccagatt | 1740 |
| tgcgttccaa catgtcaaaa tttggaaaaa aaaccgttg tttaccgaat gacacacaaa | 1800 |
| cactttccc catctcattg ccctcttaat ctttgcaagg tttcacaaca ttttgagaat | 1860 |
| tctgctaaac cgtctgcgtc tctcattcct ccaccctatt gtcacggttt tgctatctgt | 1920 |
| ttctctcgtt ttttcgtggt ttttctctt tttatgacct tgcgtgtatt tgccaactat | 1980 |
| tttttgtttg tgggcatttt ttttggggaa aaagtttgat ttctggatga tttgaatatt | 2040 |
| cgtgtatttt ataagctttt tcctaacttt tctactttcg ttcatttctg ttgtttcagc | 2100 |
| cgtaatccga acagc | 2115 |

<210> SEQ ID NO 93
<211> LENGTH: 1106
<212> TYPE: DNA
<213> ORGANISM: Caenorhabditis elegans

<400> SEQUENCE: 93

| | |
|---|---|
| tatttcttgt gattcgcttc gattttctga aaaagatt aattgaatat taaaactaca | 60 |
| aagaggttaa aaatgatttc cgattttctc gattcaaatt tagagaattc cagatttag | 120 |
| ctcaattgtt gtgaaaacaa ttttagctt ttgagaatta actttttctg ccaaaaaaat | 180 |
| tacctggagg agccaattac aattagctcc aagtgtttca atacagtatt tgagagctcc | 240 |
| atttggtcca gtccaagtc gatccattac atcattcaca gtgatcattt cctaaacttt | 300 |
| agtatttaa atgaaaata tgaccttaag tattaaaata acattgatag atgatctgta | 360 |
| ccacgtttca taattattgt cctatattca ttggaataaa atacttacag tgatatttac | 420 |
| atcaggtgcg tatgccattg tgtcattagc aggatcaaga ttgatagtga gaaatggtcg | 480 |
| tttggtttgt gagaaaatgt ccgttaatcc tgcacaaaat gtagattttc cagctccagg | 540 |
| agctccaatt acaagaactc cgtacatagt ccaatgagta ctgaaatttt ctagttgaat | 600 |
| cttaattttc tacggattgt tttgatagga aaacatttaa gaagaacaaa atatataaa | 660 |
| tacaattaa tttaattaa aacaaacaaa aaagcaggat aaacgggcct ggcacagggc | 720 |
| caagtacgca tttacaccgt acatgacgac atattgcgga ccattgcatt ttgccgcgtt | 780 |
| aattttttat ttaaacggct tgcatttctc cttactatcc agctgacaat ttttagtttc | 840 |
| tttagaatta tttgcaatca aaactcgttt tttgtaaaca tatttactca ggtaatgtgt | 900 |
| tgatttctca cttttttg aaatcaaagc agaattagtc ctattttat tctacataaa | 960 |
| tatctaaatg tattcaatta aaaattgggc cattgaactt ctaattaatt caatttataa | 1020 |
| atttatcgtg atgttttctt ttagttaatt tgtccttaat cgtgccgtct attttatttc | 1080 |
| ttcataaaaa acttttcagt tccgac | 1106 |

<210> SEQ ID NO 94
<211> LENGTH: 2241
<212> TYPE: DNA
<213> ORGANISM: Caenorhabditis elegans

<400> SEQUENCE: 94

```
caccagcatc aggagccaac atcagtgccg acaccatcgt cgcgaaacat gcaaagctgt      60
ggagtcgaaa gcactcaaca gccggaccgt aaacaggtga gcatacagta ctcggaggaa     120
gaaggctccg aatattttac cgatgagctt gacgatgttg atgatgagat tgatgatgct     180
gctgctgcag cccgtgcggc tgagaatatt cgtattccgg cgtgtctatt acagacggct     240
gctcaaaaat ctgaggaaga ggatgagtac gatgtaagac actcattggg ttacccattt     300
ttctttggtt ggccggagaa aaattattta ctatgctccg atatttgttg atcgaaattt     360
tccaaaaaaa gagctgtagg aaattgagat tgataaaatt aatttttatg cattttttcgc    420
caccacctga tgtcatggtt tacaaaaaac caaacagtta aaatttaatt agatacaatt     480
tttgaaaaaa aaagtgtttt tgtacattta gaactaatcc ataagcgacg tgcatttcaa     540
tgaaattgtt tatttttatt tggcgtattt ctacgatttt ggacaaactt gtttgaaaca     600
agacaacaat tttcgaaata tcgtagcatc gtttgaactt atcatattta tttttaaaaa     660
atttcttttcc gccaagaaaa atgggtaacc agcgtcgtcg aaaggctatg atcattaatt     720
tttataggtc atggagacgt atctttaatt aatactctat atactggtac gacgggtaag     780
atacattaag ttgtacaaaa attacagttt tcctcctttta ttttctccaa aaaacctttt    840
gtctagaaac atctcaacat tatttagtta attttttttt agttttcaa agtttataat      900
ttcaaaaaat tattttttctg cttttcggt tttttcttcat gttcaaaact tcttcctctc    960
tcgtcatttt tgtataatgc atcgcggcga tataaatttg catttatct ggttatggct     1020
tcatcattt tttttcaaac gaattttggg aaaaagaat gctatagtca ttttaattac      1080
atccctcata tttgtggcgt actgttttcct ttccctgcta tcccgattga tgtttttaaa    1140
ggcacaccga cgagaatttt cgattaaaat tgtaaattag agtaaaatct atgacttgtc    1200
aatcgaaaat cttgtcggcg ctcttttagga actccataaa aattgaaaca aaaattattt    1260
taaaaattac caattttttc caggtggccg ctgcgtggtc gacaaaaatc gacgtggaca    1320
cgcgcctcga acaagatcaa atggagggtg tcgatgaggc ggaatgggac aaataggcgc    1380
tactggacca tttcatatta ttttcagtca agtagtgtac aatgaacaca attttctcac    1440
ggttctgtaa aaatgttttt tctattgaaa tgtttgattt ttcgccccca tcaccaatcc    1500
atcaccacct ctccctctct cgcttttat ttgtctcatg ctttattcat catttttat     1560
gattattatt atgagtatta ttactattgt atagtctcca atttcgtgat ttttggtttt    1620
ctagaaaatt gcgcccgctc gcccgccccc acgacttacc acctcccct gaattttttt     1680
gtgctcccat cgcctagtcg aatttattct tttgtatttt tgtgtgtcca ctttctctct    1740
cggtcgatgt gttttaacat ccatatttc tgccccgcct cgtcccccct ctcaatcgcc    1800
cgctccccgc ccgcctttta cactgtgttt cgatgaaata aacagtagag aattgtaaaa    1860
ctatgtgcgt gagaatttgg aaaatttag ttttttgtga tatcggaagc ttttttaggg     1920
gaatttgaat ttatttttaa aaattgttca aagataaatt agctccgaaa ttggaaatcg    1980
tagtggaaca tttgaatttc cgccagccag acatgtggca ttgcggttac cgtacccgca    2040
attgtgatga attttcaaaa atcggtgatc ttctggattt tcgctgtcaa gcttgagttt    2100
aagggtctcc tcactgatct atgtccattt tgcggcagga attctttttt ttttagtttc    2160
```

```
attcggatat ctctaaaata tcaagaaaaa tcgataattt cacttttcct gaaaactttc    2220
atattttcag aattttcact a                                              2241

<210> SEQ ID NO 95
<211> LENGTH: 661
<212> TYPE: DNA
<213> ORGANISM: Caenorhabditis elegans

<400> SEQUENCE: 95
tttcatagat ttttaataa tcagtctgct cactgataaa cacgtcgatt gccgcagtat       60
cttggagaag agaactgaac ttcattgttt gaaacctaga aatagtgaa aattagttag      120 aaagagaagg agacggagaa tgaaaaaggg aaaatcgcgc gcgatggaag aaatttgaaa     180
aaagacttta cttttgatat ttttcgaaat ttttaaaat aattatgttt agagttaaaa      240
ttgcaaggaa aaatgaaaca aaaattagtt taaaaataaa aaccaccgta tctctttccc     300
tgcgaaacca attcaccgta ttattgtatg tgcctttaat ctttaacagt aagcataaca     360
tgtgattttc gccttctttt tattaaaatc taaattatta cagaacttt aaataatttg      420 attatattct ttgtttaatt tttaatcatt taaattcaat ttagaaatgc taaaaatccc     480
aaaacaatga gacactattt ccctgcagga ccatttaca gaaatactgt atgcacctt      540 aatttctttt caaagtaag cggccttct gtcgaatcat ttttcgttga tgaactcttt      600
tttcttcact tttactctat attatcacaa aaattcgaat ttttcagcga aaaatcgaa     660 a                                                                    661

<210> SEQ ID NO 96
<211> LENGTH: 1207
<212> TYPE: DNA
<213> ORGANISM: Caenorhabditis elegans

<400> SEQUENCE: 96
agaatgtctg gtctccgaat cgtcaactcc cttgcatatt ctttagctcc aggacagctc       60
ggtgtagctg caatttgcaa cggaggagga gaagccacag cagtgctcat caaaaaactg     120
taatatgaac ctcttgccta atgttttct ggtcttctat tcatcattcc ttgattcact      180
tttacaacaa atttcgatta cgtatttata aatagttaag gttcttgtca cataaatgtt     240
tattctcaaa tggtgcatac gtgttattga ttgggaaatg aattaaggtt aatatgtaca     300
ttatcaggaa tggttttgag ccatctcaaa agagatatac tggaaaaatc ggaaaagcat     360
ttttcttttg agatatatca ttcattcacg tcttcaaggc aaaacatata aggggagatc     420
gtatacaaat aatcacaggg aagaattggt ggatgataaa atgatcccat aaaccattat     480
tagtttgaga gatcaagttg ggggaatgag aatattaagg ggggaagaat ttaaccggga     540
agcaaacata gagcgattta attttccgg gatttgcttt gctaggcggt tccaggtggc     600
gaggttggct ctgaggaatc ctttgtttgt ttcgccaaca gatctgagca tgtaggggta     660
tcttggagtt acagctttct tcaccgacga tgacacattt gggtagtgga agtttccagt     720
tatgatgttg tggtaggtgc gaaggatctg caagacccgc ctatattgca ctgacttcaa     780
attggcttgg gccaaacgat cctcgtatga agaatacttt atgttgcagc gttggaagac     840
gagcctggtg aagaaatgag atgaatcaat aaaggctatg aacgggtaac tcaataaagt     900
atcttcctgg actgggatga ttccgagaaa acaatcacaa acgatacggt aatgaatagg     960
aatccattga tttcatttta tctgtaattt cagtgtctga caagagatcg tcgtttcgga    1020
attattacag gcccaaatat ggctggaaag tcaacatatc tgaaacaagc tgcccaacta    1080
```

```
gcaatcatgg cataggtagg atgcttcatt ccagcaaact atgcttcgtt gccaagtaac   1140
ctaaaagttt tgatttgcta ttttctatcg tcgaattaat ttcagttttt aatcgtatct   1200
tctccag                                                              1207

<210> SEQ ID NO 97
<211> LENGTH: 475
<212> TYPE: DNA
<213> ORGANISM: Caenorhabditis elegans

<400> SEQUENCE: 97
gatggtactg agaagaagac cgatttcgat gctccaacaa cacttgctta attattcacg     60
gagatgtcat aattacagct ttggttttca ttatttgttt ggttattatt tatatcacaa    120
atttcgctaa tcggcgagac ccctctattg cttttctctc ctatctcgtt tttgttaacc    180
cagtttcttt tgaatgaacc cttgttatga cgattttatg gttttccaac ggtaattcaa    240
taaatgatat tatatgtgga aatcttgaat ctgatttgat cgatttagtc tcgaaacgtt    300
catgaaggca acaaacaaac aaccgttgat taaattagtt ttttgaattt cgcgcaccta    360
atattccaga ggagcgggct tgcattatct tttttacacg aatttcttat ttacagtatg    420
cactattctt tctcctctcc cattaatttc ttgtcaatcc catcccttt tgtag          475

<210> SEQ ID NO 98
<211> LENGTH: 1109
<212> TYPE: DNA
<213> ORGANISM: Caenorhabditis elegans

<400> SEQUENCE: 98
gcgagccgtt ttttgagac cctgaaattc ggaatttctt tttattttat attttttaaat     60 tcatttaaat ataaaaatag agcacaaacc tcatcaaatg tgctcactag aaaattacac    120
gtcctgcatt tttcgttttt gatggtgact tcttttttgtg acgtggcacc aattaataca    180
gcaagcagga gcagtatccg gctcattttc accctgaaaa atggaaaaaa ttggattttt    240
atgtagcttt aagacacgac aaaccgttat tttagagaaa ttacacgcag aataagcgaa    300
tgagcgcggc cgaatgcact gcaaattgtc tacgttgtcc agtttctcgg ccctgtgagc    360
ggagaaaaga gagggagaaa agaaaaatga acaaatattg gctttgaccg ggattactag    420
caaaagaggt gactgatgga gagggaaca attaaatatt agaaaattc gaaaagtta      480 attattttcg ctggaaatca ccttaatttg gggagtttcg aaagaaattt tgataaaaat    540
agaattatcc acttttttatt tcgtgaaaaa acaacaatt tcgactgaaa atccagcttt    600
aattcgagaa ataacaaata tttatttatt taattaaatt aaattaaatt aagaaaata    660 attgaattac tgtagtgatc gttgcgggac ccgatgaacc gaaatcggta tgcgccttgt    720
agttacggta agaaaaacgg gcggtgtcga gaatttaatt taaattgcat ttccaaaaca    780
attttcctcg tttgaaaata aatttacga gttttggtt agtttaaatg ctaaaaactt    840
gatttaattt aataaaacgt acctaaaaat tcagtttcgt agcagaaaac acgaaaattt    900 cagttttag taaaatttc ggaatttcta ttttcaagtc ttgtttatag ttacttttta    960
tggtgttcaa tcaactttt gaagtttaaa atgttaaaaa cgttaaaat tacttacaa   1020 gaaccgaaaa aaaccgaaaa tatttcaatt tttagttttt cagcaacctt tcttaaatc   1080 agaaataatt ttatgaaatt ttggttcaa                                    1109

<210> SEQ ID NO 99
```

```
<211> LENGTH: 1049
<212> TYPE: DNA
<213> ORGANISM: Caenorhabditis elegans

<400> SEQUENCE: 99
cgagaaacat caaccatcga agagcagctt ccttggccag agtgtcgtct gataggtcga      60
tgtagtcgag caggcacacg actgctctgc acagttctcc gttgtaaaag tagaaaaagc     120
agagtttcgc gggaatactc gcgaaaatct ctcgatcttt gctccgacac tccatcgcct     180
cctttcgtag agtttgccac gtgatgaaca ttttgcatgc ggttcgttga tacttcgcaa     240
gtccttgaaa gtattcggac gaggcgtagt atgaggtgat tcgagccaat ttgctcagcg     300
agttcatgtc aatcggtcca ttgacgccga attcggcgat aaaaagctcg gaaatctcct     360
gttgcaactc ggcagtttgt tcggcaaacc cgatcaccgt gcagctcaca tttttgcgta     420
gctcatctag ttttcgatg tgctgcttgt caactgactt gtttgtgatc ttcatgaaag      480
tttatctaga aaaattaaaa ttaaactgtt ttaatggaat taacattatt acatacataa     540
aaagcaagtt ttttgattga ttttcattaa aaatcgagga aaaattgaaa atgaaagggt     600
ttcaacgcac gttatcttct aaaaaattta aaaaatttc ttctagatga tacgcttcac      660
atacgcgacg cgtaacattg gagcaacgtt gtcactttt cttaaaaatc tcttataaga      720
gttggcacgg tgccagatcc ggaattccac cagatcttga attaaaataa gttttttgc      780
aagttttagc aagttgaagc aagtttttt attgattttc accggaaatc gaggaaaatt      840
gaaatgaaa cgattttcga ggcaaaaata aaaaatttcc ctccgatttt gaagtccgtg      900
aatgcgcgtg cggtgcaact gcgtacaaaa caccaaaactt tacgcagtg cggtaaattc      960
tacttttcaa agtttgagcc ccaaaattcg tttaatttt gtttaaaact ttccttgttt     1020
attgaattat ttacatttt tcagtcgac                                       1049

<210> SEQ ID NO 100
<211> LENGTH: 282
<212> TYPE: DNA
<213> ORGANISM: Caenorhabditis elegans

<400> SEQUENCE: 100
ttgaccaaga tactttgaaa tcatccgcgg atcatacaca attagtacaa cgtttgacat      60
ttctcctgaa aaatggaatt tcagttctaa aaacacaaaa ataaagttag aaattgttaa     120
aaacaaaaaa gtttatttga attcgccgaa gagcgcgcca aaacatgtga catttctcgg     180
ccgtgaaaac taggccaccg cggccacaaa caaatttag ttttcttcgc tgaaaaaaac      240
atgttttca gtctgaaatc agagttttta gtatgaaaca ag                        282

<210> SEQ ID NO 101
<211> LENGTH: 1275
<212> TYPE: DNA
<213> ORGANISM: Caenorhabditis elegans

<400> SEQUENCE: 101
ccctaaatat attcacaata tctcatattt ctagatatgc agtttcttct tctggaacta      60
cacatcgttg gccattatgc ttcgcccatt tggtaatgat ttggatactt gcgttgcacc     120
ttgggtcttc tatctaactc atccggtttt tcggaagaaa gttgttcaga gaatatttat     180
ttttaggcct gactcatgat aataaagttt cgatttattt tctataagtc cgcagagatt     240
gaaaagtggc aaatttgatt ttgcttattc cataaaagtt atctctactt aattaatttt     300
atcatgtttt atgcaatttt caaagtaatg ttggtgcgcc aaaaaattct acttaagctt     360
```

-continued

```
gaaaatttga gatgaaactc taaattgtat gcagttattt tggtaataca gctttcaaaa    420
cacagaactt gcatcttttg atcatttcta acaatgtagc cttcacctaa ttttagttcc    480
cagaagttaa ctcagacgga taatgagcgt tttaaatttt tgaatttctg gttttgccgc    540
caatacttaa caagagcaca cgctatcttg aggaaaacaa ctacctgaaa aggggcgtag    600
tcatttagtt cacacttctc tgtgcgtttt tttaaataat gttagtttcc aaaaattttt    660
agagacccga agaactcggg ggatgtccaa ttgggggggat taccaactcg ggggacacgg    720
ttttaaaatt attttttctt gttaattctc gctctattga gaaaaataca gttttaaaac    780
cgtgcggcag ttgcagaaat gggcgtattg caagccacgg ttctgtgggc ggggccaatc    840
ccccgagttg gtaatccccc caattgggca tcccccgagt tcttcgggtc tcaattttta    900
gaattgttta aaaataataa tgccaaccca aagcacaaaa tccctgcctc ttaagtgaca    960
gtcttcattc tccgagtttt gaattccagg cgtgtgtgac gactcattca aattattgtt   1020
tttgtttttt tttcagattc tcactcaatt ttgaaatttt ctgcgtttca aaaggttttt   1080
tcggaatatt ttttaattct aaagcttcaa aaactgaatt aaaagaattt tctcctaaaa   1140
agtcgccgaa gaaacgcaga gaaaatcggc aaaaggcggc aaacatttta ttttcaaatt   1200
ttatccgctt tcccttgtgt ttatctttat tttccctcaa tttgcttaac cgaaacgtct   1260
gttttcagaa tataa                                                    1275
```

<210> SEQ ID NO 102
<211> LENGTH: 1549
<212> TYPE: DNA
<213> ORGANISM: Caenorhabditis elegans

<400> SEQUENCE: 102

```
ggacgtgcgg cgaattgcac caattggtgc atgttcaaaa aggaacggag aagagccacc     60
ctgtgaccac tcgagcacta atttgaatga atcaacctcc ccaagtagta acatactaac    120
cgagaatagt ttgaagttct gggggtataa acaagaatgg agatagcaaa actaacgccc    180
gagagtaagt aaatacttat atggtgagcc taagtctcgc gtcgatttat tgttttctgt    240
tcagaacaca acgtgcatat ctagaaattt tcgatgattc atgcaaaaat gttttcaaat    300 aattttctcaa aaactgaaga aagtttgaga ataatataaa atttaggctt tccttcagat    360
aaatttaaat ataaaaaatc atatatattt tcaagatgcg agaaaaatat ggaagcggcc    420
agcagagata cgctatagcg ctaaacaatg tgtgcgattc acaagagctt ctgaaagata    480
aaaattgtga ctacgattca ataattgatt caaagtttga taagtcaatc gatttcaagt    540
gaaaagaaag agcttgagaa catgatgagt agcaggtgta gaaaacgcat cgacgcgatt    600
ttttgttttg tttggcgcca ctaaacacac agacattcgg tcatacactc ttccaaatat    660
agtcaatata cagtgtgttc gagtgagaga gaatggaaca tgtcgaaata tagtgtctga    720
agacgagaca ctggattatt ttgacgggaa agcgtgttcc ttccggttgc aggatgctgg    780
tgcagcaaag tgtcaaaatc gatgggaaca gggaaggacc ccaaggataa ttgaaagatg    840
agcgaggaga aagagagcga ctgaatgagt tattacgagc ggcagatagc cggaatagct    900
ggcctatttt acattgcggt cgtcgctttt tgcggaacgg gtcgaacggt tttcaatgca    960
attagacgat tcgtcatctt tttgacattt tttagataca aaaatactt atcaataaaa    1020 aagtttttta gaaaaactta aaatatcgaa tttatcttta gaaatgaatt aaagaagat    1080 gaaaaataaa atgaaaatct aaaacagatt ccataccgta gtttcacaca aagggacatt   1140
```

| | | | | |
|---|---|---|---|---|
| tatagttctc | aaatttgtgt | cccgccgcga | aatcaaaaca | aaagaaagtt agtccgtgta | 1200 |
| ctccactcgg | acaacattgt | ttcgcaacac | ttttttctgc | gaacattaaa aaatataaat | 1260 |
| ttgttcaact | tccattttt | aatgttatca | aatgtttcaa | ttttcttaa tttttatgat | 1320 |
| attttcagct | gaaattttg | tttcgattag | atcacaaact | ttttttgat gtttaattga | 1380 |
| aattttagag | atgtattaga | aagttttta | atcttcaaac | aaaaacatt tttgtcaaat | 1440 |
| cgagacctca | aaataattta | tcttttcaat | acaatttagt | ttccttgctt ttaacgttca | 1500 |
| aatcttgatc | atttctttt | ttttgttat | aaacgattgt | ttcagataa | 1549 |

<210> SEQ ID NO 103
<211> LENGTH: 2228
<212> TYPE: DNA
<213> ORGANISM: Caenorhabditis elegans

<400> SEQUENCE: 103

| | | | | |
|---|---|---|---|---|
| actgggtcga | cgagaagttt | tggaagtgag | aatttactaa | aaaaaagaat taaaattaga | 60 |
| ataattctgt | agacatccac | aaatcacctg | ttttcagtc | gatgaaaact tgaaagttta | 120 |
| taatcgtcta | ctttatcctc | cttcttttca | aagtcaatta | gaacaccatc agctcctgaa | 180 |
| catcgatttt | ttatatatcg | atcactggga | aagaatctga | aatcactgat ataatagaga | 240 |
| cattgcattg | ttgacatacc | ttgtcagtcg | aactcgaatc | aacgatctga tcttcatttt | 300 |
| ttgtgttagt | tggttagtcg | ttagtagatt | ataaaattcgg | taataaattt atagtggtag | 360 |
| aaattaatga | gaattatatc | cacgaatccg | cgtgtactgc | ggaaatattc attttatatt | 420 |
| tataaaaaat | gttacaagtg | agatcaaatt | tttttttaat | gtatcataga agagaagcgc | 480 |
| caaatcaata | gaatgctgca | cattttaccg | catccaatcg | ttccattttc tgaatttgaa | 540 |
| ataattattc | atagctccat | aacggttgag | taacgtgaat | gataattctg ttttaaatta | 600 |
| ttaagactaa | ttcccctatt | tgaattccct | ccaaaataag | aactgcaaga ctagcgattt | 660 |
| gatttgagca | atttgcatcg | cctactttcc | aaccaatcaa | attaagtgtg cgaagttcga | 720 |
| agtcgcctac | ctaccatata | cttcccatcg | ggtctcttaa | caatcattgg cttgaacgaa | 780 |
| acttctctac | aaactctcgt | tggtggcgac | agaaaccgtc | ttgtcatttt gccacgtagc | 840 |
| aatagatccg | ccaatgcttc | aggaatctga | tttgatttca | gtgcttctga tggaatactt | 900 |
| ccaaagcatc | gatgaaatgc | ctgtgggact | ccatcaatgt | cttcgaattg gaacttccat | 960 |
| agacaacatg | gttgttctct | gaattttaaa | aaaatgatta | tgattaatga ttgagtataa | 1020 |
| gttcctgagc | cagttgggca | acctacattc | caagagaagg | atcgcactcc tttccaaatg | 1080 |
| tgatccttgg | aagtatggac | tttgtgtcaa | ggattgctcg | agcatccaga ttccgtggta | 1140 |
| gaagatatcg | attgttccaa | aaatcatcga | gaaccactag | aatctctctg atcctagacc | 1200 |
| tctcattata | tgaatttacg | atagaagttg | tccgaaatct | ggcattttct ccccaatcca | 1260 |
| tcggttttgt | ttcaattggg | tgaatttta | gaaacgtctc | acctgaatca agaggatgtg | 1320 |
| atgaagatct | taaatctctg | cagttcacct | tcataacata | cgtacatcag tggagaccta | 1380 |
| cttccagggt | ctctgaacca | tcgatcagga | atatgaattg | ttaaactgaa cacgtgggtt | 1440 |
| actgtagtta | tatttatatt | tctcacttaa | caacaggaat | cggtatctgt ttgataggt | 1500 |
| tgaagtgtat | tccatctcga | aaatgaatcg | gaacatggaa | gaattgtttc ctggctagag | 1560 |
| atccacaaaa | gttcgagacg | ttgtcaccgg | taatccgatc | tccgagaaga acaatctgta | 1620 |
| agaggtctca | tctgggagaa | gcttattca | gtagttacct | tctgttcaga ctctgcgatt | 1680 |
| ccttgactat | aatagtcgat | cccttcaaga | ttctgatgaa | ttgcatccga aatgcttct | 1740 |

```
ttaacaactt cgtgcaaatg aaaacgtaat tcgttttgat catcatactg aaacttcgga      1800
aagattttaa gtattacccc gatccaaatg tttcgaatta agttataaa tacggtaccc       1860 ggtttcgaca cgattttgt caaactcgag gaaactacag tagtccttaa aggcgcatac      1920
taatagcgca aaatctcaac cttcgcttac caacttaccc gcacaccttc ctttctctgc      1980
gaatcaataa taaaattcga atcggcgtc atcattctat aaccagtaca atgaataatc       2040
aaactaaata gaaaggcagc ttgaaacatt tctttaatct tctcgcaacg aaatgtgctc      2100
cggctctcca ggcttatcag tgttagaaga gaagagaagg ataaaacaac aataaaaaca      2160
gttttcattt gtctcgtttc ttgcttcttc ccccacgatc tgctgatctg aaaatgcatt      2220
ctttcagt                                                              2228

<210> SEQ ID NO 104
<211> LENGTH: 1895
<212> TYPE: DNA
<213> ORGANISM: Caenorhabditis elegans

<400> SEQUENCE: 104
caagtggtat gccaactcat ttgagagatc taaacatcga agcccatcct ctacttcgac        60
agcccgtaga agttgtgtag cacattttga acatgtgagc ctgtacaaaa gccataatac       120
ttctcaacta ctatcatcgt catctctccg tcaccaatga tctctactca aaacggttat       180
ggacggtttt tttgcataag gattcaacta gccctacacg attgctttga tctctgtaca       240 ttttgcgtt taatatggat atttgctttt taatggattt tcgatcttct acttttattg        300 ttgattttc tggttttgtg ggggttgtgt acaaattttg tttatttgtt gtcggtaacc        360
acgggtacca tattatgtga atcgtttatc atcgtattaa atcatgtata catgcattgt       420
acagagtttt tgaatataat aaatgaacat gacgtcattt gcacctactt tgtgcttttg       480
aactttcact gtttcagata tttttttatt atgaaaaaag gtatctatga acaagctttt       540
caatacatta taactttgtt gtatctggtc tgatcctcaa tattttgag tcttcaaaag        600 aaacaattat aaattgcaat acatctcaac actgttttat ggcgtctcaa attttgaaaa       660
aaaaaattat tttataaaaa ttgatttgca gcagacatgt tgaaaacggt gcttttcttt       720
taaattattt ttgttgtgat aatgtaatta actacaactt tacataaatt gaactgaata       780
tacgggtcat tcattttac aaaccttatc tattctatca ataccatgac ttttttcgcg        840
aaaagtcagc cgacatgaca tgactcttat ctctttttttt tttgttaatt ctttttttgt      900
tgcgacaaat tagtgtcaaa aaacgtgaac ccattcgatc acataacatt ttgaacttca      960
agaaaatcac acaatcgata aatgatgaag tatggtaagt caaaattttc taatattcca     1020
actgattaat agttagtgtg tttgagtttt acttttcaa attaatgttt acattaaaac      1080
aactataaca atcctcaatt gaaatattgt acacgaaata aaaatcaaaa catatgtatg     1140
aacatatttc tcttatcttt ttgtattctg tcaaagggt ctaattttttt tgaccatttt     1200 tttgtcagtt agaaccaaat aaaatcatgc cgcatgtctg tgaaaaatca ccttattctt     1260
tctctttgag attgataaaa acgttctgta ggttttccaa aatgttaact aaaaaatcaa     1320
atttaagccg tcggtatagt attacaggct aggtatagga tgctcggata atattaattt    1380
taaaaattcg aaaatgcatc atacataaaa cttttaata caaaatatag atgttttctt     1440
tttatttatt tattaatata acgtatctat ataattttca attaagcaat aaatattttt    1500
gaagatttga ggataaaact aagcaaattc taaaactgca atgttcaatg aaattgcgtt    1560
```

| attcagtgtt acctataaag attttcaaa acgttactct cttattcttc tcccattcac | 1620 |
| gtgttgcact ttctgccagc cgccttctcg gagaaactag gaaatatctg tgactttctc | 1680 |
| tagccactct ctactctctc gtcagtgcaa atagagcgcg aatgctttaa aatgacgcat | 1740 |
| caatcactct gtcggtcatt tgattttaca cttttcactg atagcttaaa gctcggaagc | 1800 |
| ggaactatag tgaaacattt tataaattac gatttagatt ttttgaatt ctgtatcatg | 1860 |
| ctgcctaatt tttaataatt tgaatatttt taggc | 1895 |

<210> SEQ ID NO 105
<211> LENGTH: 1302
<212> TYPE: DNA
<213> ORGANISM: Caenorhabditis elegans

<400> SEQUENCE: 105

| tgcccagaga gccgtcgacc aattcaacgg agtcgatttc aacggaagag ctctacgcgt | 60 |
| caacttggct caaaacagaa acaactaatt ttcatatcgg tactttgtta cttgtttgat | 120 |
| ctttaatgat ctcaataata ataaacccat gaaatcgtta tcataaatat atatgctcta | 180 |
| tttttttatt tcgaatcttc atttggggtc aatctgatgg caagcgttga ggctagaagc | 240 |
| ttgaaggaac ggcttcggtt cgagcaagtt ttgaatcctg gctatgcgc agcccaatgt | 300 |
| gagcttacaa ctgaaaattc aagtttcaac actcttcgcg gtcttatttt ggactaattc | 360 |
| ctcatatttt cagcttgaaa tggaaaaaat ctgtcgaaat cgatgctatt cgaggggcgg | 420 |
| ggccaaaacg caaccctggc acggttttta cgcaactgcc gcacgttttc tccaaggcag | 480 |
| ggtgagcgga aaaattaaac cgtcataaat tttctgctac ggcctaaaat cgtcatgtct | 540 |
| ggaatcttct ctgtttacgg ttagtttttt aataatttat tttaagtatt aaacaatcgg | 600 |
| aaactggtta aaatagccaa taaaactcga tattgtcctg aaattttggg attttcgga | 660 |
| aaaatcgaat tcgcgaagtt ttccctaata tttcatttg aaaaggcaat tttaagtgtt | 720 |
| tagattcaaa tttggttgcg aaatatttaa atcaattaaa attttccttt tttttagttg | 780 |
| gaaacgctcc attccagacc accgaggagg agcttggaaa cttcttcagc agcatcggac | 840 |
| aaatcaacaa cgtcaggtaa ctctcccagc cagcccgagc ttcatgattt ctaacgcaat | 900 |
| atctctttca gaatcgtctg tgatcgcgaa accggacgtc cacgtggatt cgccttcatc | 960 |
| gagttcgccg aggaaggatc cgcacagaga gccgtcgagc agatgaatgg agccgagttc | 1020 |
| aatggaagac cactccgcgt caacctcgcc aacaaataag ttgatcttca tatcgggttt | 1080 |
| ttgttacttt tttgctcttc actgatctca ttattaataa caatccaatg aaactatcga | 1140 |
| tttaattatt taattcaatt tcaactattc tctaactaat ctgttcaaca ttcggggaag | 1200 |
| tttctctatt tgtcatcctt ccatccgccg acctgattca actttcttct tccccagctg | 1260 |
| ctccgttcaa gagcctactc gactactaac ctgttgctga aa | 1302 |

<210> SEQ ID NO 106
<211> LENGTH: 2410
<212> TYPE: DNA
<213> ORGANISM: Caenorhabditis elegans

<400> SEQUENCE: 106

| tccggcaaat cggcacattt ccggaattga aaatttccgg cgaatcggca aattgccgga | 60 |
| attgaaaatt ttctgcgaat cggaaaatag tgggaaattg aaaatttccg gcgaatcggc | 120 |
| aagtttgccg gagtcgtaaa tttctggcaa ctcagcaaat tggaggaata aaacatttgc | 180 |
| agaccggaaa ttgtcgccca cccctgtttt gcactacgct ttgacaagtg tgaatttatt | 240 |

```
cgcttttttt atttgcctga attttgccga taaagaagat ttccggcaaa gtggaaaatt    300
gccggaattt aaaaatttcc ggcaaatcgg caaaatgccc aatttgccgc ccacgcctgc    360
ttcacaaatt gattaattgc agcctcttcc gtagctgaac ctctggaaga agccactaca    420
acgagtgtgc cagagccaac agagtttcaa ttgtcacggg acatttatag cactgtaaag    480
ccgactgatg aggctcatag cccgccgatt caagcccaac cgaagaaaaa agccacgcca    540
agacggaaga aagcagatga cgtggaaact gtagtagctg acggaacagc gacgatcccg    600
aagccgaaga gaaaaggcc gccgaggaag aagcctgagc cgaagccgaa tatcgttttt    660
gaaacaacgc cgaatcctcc gacagaaagc ttcgcagcca acaacaattt ccagcagttc    720
cagtttcaaa atcagcctgg tagttggacc tacaacaatg gattcggcaa tggatatggg    780
tacggcggtg gaaccactgg atacatggat aatcttgttg gcagagggtt tgacacggtt    840
tctcagcagc ctggatttca gaatcaaggt acattttta aaaggaattg agaaaaatgt    900
gccaaaaaat tttaaaggtg gactacgctt tgtggggaaa ttgctttaaa atacgcctat    960
ggtaccacaa tgaccgaata tcatgattaa aaaattcaaa aatttttct aaatttata   1020
tgattttttg aaaattggaa aaatcacagt ttttcccctaa ttcctatttg aattaccgcc   1080
aattgaattt gttcgatggg gcgcgcttgc acgtttttaa atttatttat tttattttt   1140
gttattttcc accgatttt aatgttttcg gtgtatttt gctcgaattt tagagaaaaa   1200
gtcaaaataa atgcaaattt tcgattaaaa agtgcgctta caggcgtaaa tcagtgaaat   1260
taattaattc aggttcgaaa tcgtttaaaa gcgttacttt ttcattttta cgcctgtaag   1320
cgtgcttttt aatcgaaaat ttgcatttat gttgattttt tctctaaaat tcgagcaaaa   1380
atacaccgaa aacattaaaa atcggtggaa ataacaaaa aataaaataa ataaatttaa   1440
aaacgtgcaa gcgcgcccca tcgaacaaat tcaattggcg gtaattcaaa taggaattag   1500
gggaaaactg tgattttttc aattttcaaa aaatcatata aaatttataa attttttttt   1560
gaatttttta tcatgaaatt cggtcattgt ggtaccatag gcatgtttta aagcaatttc   1620
cccactagcg ctaccccacc tttaaaggaa ttgtgaaaat tgtgaaaaaa aaaatcaaaa   1680
tttcgaaaaa aaagcgcta attttaacta aaatctctaa ttttggccac ttttccgtgc   1740
tgcagcgtcc gaaagtgcac ttttttttgaa ttattattct tattattata cattaaaaac   1800
ccccgtactc ctccaataac gccaatatta tcgaccatct ggacgtgacc gcgtgcaacc   1860
acggcctagc tgccgccacc ccattcaaac gagacatttc ggcgggagag tcctttttt   1920
cgataattcg gattttttg tctgtttcaa gtaattttcg ccataaaaat taccattttc   1980
ttcttcggtg ccatttctaa tgattttcca gtgcgtttg agtctgaaag tttgaaaata   2040
agagttttg cacaaaaatg tgtgagaaaa gttcaagaaa atcgtcgaaa aattcaataa   2100
attaattta aaatttaaaa aaaattaat ttttttaaa aatcaattct gtgcatacac   2160
cgccacgcaa aagtgcacac aattacctac cgtagtcaat gcgaaattaa atgatttta   2220
tcgattttct tcatttcag gttacgaatt caccggtttg cctgcaaata actcgaataa   2280
tttcccattt ttgtgattta atttttcaaa tatccttatc tatgccctca ggtttatttt   2340
atctcatttc cactcgtgtt ttttgaataa aaattctttt tttttcttct agatttccgt   2400
ttatttcaga                                                          2410
```

<210> SEQ ID NO 107
<211> LENGTH: 2249
<212> TYPE: DNA

<213> ORGANISM: Caenorhabditis elegans

<400> SEQUENCE: 107

```
attttcgaa tattttgtct gaaagtttca cgtgatgtca gagtgtctca tttcggcttg     60
atctacgtag atctacgaaa atgcgggagt tgagacgcag agttttcaac tgatttcgca    120
tggttaagaa cgtgctgacg tcacattttg ttgggcaaaa aatgcccgcg tttttgtaga   180
tcaaaccgta atgggacagc ctggcaccac gtgaaattcc agaaaaaatg tctgaaccta   240
ctgtagttca caatttaaag gcgcatacca aaaattata gcgggaatta aattttatt    300
taataatttt ttcagttaca gagcaattaa aaaattcaat ttcatcaaaa ttttatagac   360
caattttctc gctttatagc tgagctccgc gagccaaaat aggaagggga gcacgaaaaa   420
aaaacagaaa aatgagctcg acagagccca tagcctcaag cgctaacgaa ccaaaaaatg   480
cacacacaca caggaggcgg agtcgtggaa atttcgaaaa aaaaaacaag attttcttct   540
ctctcggctc aaatttgaat gcggagcaag aatattacgg gaacaaaaaa ttctgagaat   600
gcgtactgca caacatattt gacgcgcaaa atatctcgtt gcgaaaagca aactacagtg   660
attcttaaa tgacatttgt agtgtcgatt tacgggatct cgattttcga atgaattca     720
tttatcattg atcgagcccg taaatcgaca cacgcactac agtagtaatt taagggtta    780
ctgtagtttt gttttcgcta cgagatattt tgtgcgtcaa atatgttgcc caatacgcat   840
tctcaggatt ttttgttagc gtaataaaat aacagaaaac acagaaaaag gcatgaaatt   900
taatttgaaa taccgcgctg agttttctag gccacgtgtc gtgtactccc cgtggacaag   960
cggttttgc cttattttc tgaagtacaa attctcaagt acaagtaaaa aagtacaaat    1020
tttaccaaat ttgaggaaaa gaactagcat gacaaaaata gaattagaaa aattctagag  1080
aaaaactacg gatttctggc ttccctcata aaatgaaatg gaagagtttg ccgaactagg   1140
ccatttggc tcagccatat ctggagtaga tttacggcgc gttccgtgtc gcggctcgat   1200
tttagttgta aaactaaatg aatttgtccg tgtggagtac acgactttac cacgcgttgt   1260
ccggcaggcg attgtcaatg gagcgcgaaa aattcaatgc accagatttg acgcgcaaaa   1320
tttgaatttt caagttgtaa atcccttttt tcttcccatt gtcccatcaa atatccttct   1380
tcaaaaaaac ccctgcgtct ctcaggccat atctgcggta gatttacggc gcgttgcgtg   1440
tcgcgtcgcg gctcgatttt agttgtctgg cgggcgatta tcaatgaagc gcgaataaat   1500
caatgaggaa ggccagaacc ccgtgaagat ccaagaaaag ttttctaggc cacgttccgt   1560
gtactccacg tggaaaatgt cctttccggc aggagattgt caatggagcg cgaaaaattc   1620
aatgcaccag atttgaccac gcgtcgtgta ctccacgtgg aaaatgtgga cactagggat   1680
ctactaaatg cctggaaaat cgtaaaaatc tcgaaacttc ctaaagaaaa aaaaagcaaa   1740
tacacaaaaa cgcattgatg tatgaacaaa ttgccctccc cgtctcccac caaaaactcc   1800
caaaaattgc tctttttca tgtttatatg ggggaccgcg ggattcata atagctccgt     1860
ggtccgctca gctcatccgg agccaaaaag agcacacaca cacacgcaca cataaaagtt   1920
gtaaactagt ttcgagcaaa aatgatacga cggatgagtg tgtcacgcaa tcagtgagct   1980
tctctcgctt tcgaaagaaa aatctttttc gcaaaaagaa aaagtacttt acactggcca   2040
cagtgtaaaa taagggtgaa aagatcgaaa atcggaggtt tcaaatttga atttccgcgc   2100
aaatgagagg gacgaggtgc gatggcctac aaaactccgc aggtgtactc ctctcggaaa   2160
acggtgcgag aattaatttt ttaatttata tttaattttc agcgatttt ctcagttttc    2220
cggttaaaat ttaaattttt tcaggaaaa                                    2249
```

<210> SEQ ID NO 108
<211> LENGTH: 1234
<212> TYPE: DNA
<213> ORGANISM: Caenorhabditis elegans

<400> SEQUENCE: 108

| | | | | | |
|---|---|---|---|---|---|
| aaactgcaat | ttcgtaaacg | attgaaaatt | gagaaagatc | aggtatctga | acaaaaactt | 60 |
| gtacatttga | atctcaact | tcatttattc | caggatacct | acaaatatga | atcctatgtg | 120 |
| cttcaatgaa | ttctacagga | aaatattcaa | taaatgacca | aatcgaaaaa | ctttatttat | 180 |
| gatcccaatt | atgttttctt | tgattatgct | acaaattcaa | gaatcggcaa | ataatgggaa | 240 |
| aatacgattt | ttttttcaca | atcaatatat | actgcttgat | ctctctgtta | gaatttcctc | 300 |
| caaaatctga | actgtatgac | caaaaatcaa | ttttttttgaa | aatgcatttg | tcccaatatt | 360 |
| tccttctac | cattctgctt | tgatcttttt | taacctttt | attcgaataa | aaatatattc | 420 |
| cgaattaaat | acaattaatg | tgtttccacc | aactttacac | ataaaaattc | attttctgat | 480 |
| gtaaagattt | tttctaacat | acatgcatta | acttatttct | ggagaaatat | ttctctggtt | 540 |
| taaaaaaaaa | aacttctatt | tagttatgat | ttttccttt | cacaacgtga | aaagttgcaa | 600 |
| aacttctgcg | aacgacgcca | cttctccacg | gtgttgtttc | tccggaacat | ttttccccag | 660 |
| tgggacgcca | cgcgcaactg | cgctctactg | ccaattttca | aaaacggaat | tctttcgctg | 720 |
| aaattttctt | taattttctt | tcgttttttca | acgttttca | ttctctaaac | ttaaataatc | 780 |
| gaaatatttc | gaaatgatta | atgaagaaag | gtaggcgtta | taatatttat | aatcaaaatt | 840 |
| tctcaatatc | atgttagata | ttcattttg | gcgaatattc | aacaattgaa | aatcaaaata | 900 |
| ccattattta | tcgactggcg | ttattttat | tgtttcagaa | aagctgaaat | aaagcgaatg | 960 |
| ttggaaaaat | gccgtaaaac | ggaaaaccga | cagaaatttt | ggcgatggtt | gcccaatttt | 1020 |
| cagttgaaca | gctggcagac | tcctgttgtc | attggtgttg | cagctgtttc | tgctgcaatt | 1080 |
| atctatcact | attttcccta | attaccctta | ttcctattgt | tcaattttc | ttcatcctga | 1140 |
| ttttgtgatc | tacctcatgt | aataattttc | tcttcttctt | tattattttc | tgcgctctgt | 1200 |
| actttcttaa | aactgtataa | attaaaattg | caga | | | 1234 |

<210> SEQ ID NO 109
<211> LENGTH: 435
<212> TYPE: DNA
<213> ORGANISM: Caenorhabditis elegans

<400> SEQUENCE: 109

| | | | | | |
|---|---|---|---|---|---|
| cccacacagc | cagaagattt | ttatgggcgg | cagacatttt | cttaaatcca | ataatgtttt | 60 |
| aatttgataa | aatcgaagat | aaagttcac | gataaacaca | agtgaagtta | aaaaataaaa | 120 |
| ataaaacatt | caaaaagaa | ataaacgcat | tctccgtaaa | tcgacacaat | gacaattctg | 180 |
| gcaggtctcg | ccacgaagag | tgttcaaatc | atgtgcgcct | ttaagacgcc | aagccatttt | 240 |
| ctcttctgtt | ttttaccact | tattttgttc | ttcaaaatgg | ttttttttgtt | ttgttcttt | 300 |
| attaataatc | aaatgtttgt | ttattttata | catatatact | gcttgttttg | cattaatatc | 360 |
| aatctgttat | cgatatttat | ttcttttttct | ttcaatacat | gactctattc | gtaacatttc | 420 |
| acaattttttt | gcagg | | | | | 435 |

<210> SEQ ID NO 110
<211> LENGTH: 1559
<212> TYPE: DNA

<213> ORGANISM: Caenorhabditis elegans

<400> SEQUENCE: 110

```
gaacgtccga catgatgaga tgcaataacc tgaaaatgag gcactttatg ataagaaaat      60
gcggtaaaac atgcgaaata tggcaccata aaccgtgagc aggacaaaga acaaacactt     120
ggaaaagaaa agaaaataga aagaaaaaaa ggaaaactgg agaaaacaaa ctcaataaca     180
caacgcgaga aatacaattt cgtttcgttt tttcttctat ttattagatt tctcacaatt     240
tgttaccagt aaagtcacgt tctatatttc aaactactcc taaaattcgg tttgaacagt     300
tctctgataa acgaatttcg aagaacgatc agaaaacaaa tctacggttg tgtgtgatca     360
atggggtcaa acggtggacg aaaggggacg gcggagagag gaaaaagtga gagaaaataa     420
ataaaattga ccttcgagtg cagagttttg ctggtatttt ggtcagaatt gattatgaaa     480
atctgaaaat taccgccggg aaagttgaaa atttgacgtg gaaacgttta aaaaaataag     540
atgagaaagt tagtactgta gatgtcgtcg gatcaagtgc acagtacgca agcaccgtta     600
cgaaaaattg cactaattgc tcaattaaat tttttttaaaa aattaatttt tatagtgtgt     660
tttgtgtttt ttttctgctt ttttaatgat ttttaaaggc ttgattatgt ttttttctca     720
aaatttgaat aatcaataac attaattaat tactttatta aaaaaccaca tttggcattt     780
taataaagca agttatcgcg acaaacggca aaaatgtctc ttttttataaa aattgttttt     840
ttttgagtta agagaagatg tggagttttt tgaactacat tagttttcta aaaattttat     900
catctagatt ttgaggaaaa aagcagatta tatatctttaa atcttggttt taaaattttt     960
ttaaaaagca gaatattaaa gtaaatatt ataaaaagaa aaattcgtgt ttgcaaaatt    1020
tgtttgaacg gaaccttgca aaaatgatat ttagcagcta aactaactga aaactactgc    1080
ataaagcttt cccaaaaaga gctaccatcc agaaaatgtt tttttttttca aagccgaaaa    1140
agaagaaaaa aagatagaaa accgaaaaag cagcatcgtt ttcgcgcact cttttcttctt   1200
tttttctttc tttttctaaa aaaaaatatt ctccgtagct tgaagtctca ggatttccaa    1260
agggaatttc cttgatagaa tatggaaaaa caagagagtc atcagagaag ggagaggaaa    1320
agcggggatg ctggcgaaga ccgggggcac cgactgaaat ataggcaccg gcggggaggc    1380
ggggcgctct ctcctctccg ctttactccg ccccgattgt cagtggagca ggtttgcaat    1440
gagtgttctc tgatgccccc tcagcgcggg agttttgaaa tcaaatatttt tgtattttaa    1500
cctactttat tgattttca attaaaatga aatgttattt gtttaaaatt taatttcag     1559
```

<210> SEQ ID NO 111
<211> LENGTH: 1476
<212> TYPE: DNA
<213> ORGANISM: Caenorhabditis elegans

<400> SEQUENCE: 111

```
tgtaggtcta aaatatttg tttgagaata aatattcgaa atcaatctaa cgttttttcca      60
atctacaggt ggcacgacac gctcacaacc aataagtttc ttgccacgct cgtcgatttt     120
ttgtagaatt cccatttctg agagtgtttc ttcgctttct gcttgctctg aacttctga     180
aataactttc ccgcgattat ttggatttct atatatttc aaactactta cctattttcg     240
ttttccaaag tctcgaattg tgtacttgtc gacgttggtt ccagatttga gcattatgaa     300
gaattccaat tttaaaatca caaactggct caaaatctat acgctcgaat agagaattgt     360
gtgatgtaag agcctgaaaa ttatatttga ttttctttcc atcttttttt attttcggga     420
ataataaaac attcaaaaag ggctgagatc tatctatttt tcacatgcga cccatttcta     480
```

```
tttcacgtga agcacatgat tctgaagggc aatggaaatg aaacccgga aaacaaaat      540 ctttcagttt aaattgtatc aaaacaagtt tttctagatt acaaatgtac ctgaatagtg    600
atccatgaat tgggacagac cacatcgaaa taacatttca cacgtggcaa tggagccatt   660
ttgaagtttg gctgaaatta aatttatgtc gagaaattaa aaaaaatcag agcgtcatca   720
tgagaaaata ggaaaggttt agactgtaaa atcaggtttt catggcggga atgacattaa   780
aatggtgata aggtgattat tttatcaaaa gaatttttg aatgattgca cctaaaatcg    840
agtgcttttt ctttaatttg attatcaaaa gaaaatacc aagaaatgga aatgaaaat    900 ttaagagatg aaaggaaaaa gcgacccgga aaaacatcaa gctgggaaga aatctcaact  960
agttagacca aagcttcgaa ctctgcgagc atgtattttt tttcctcact ttctcctttt  1020
cttctctatt tctctagatc tttattactg cggggcaaa aagagtaaga gatagaaag   1080 aatgacgcaa aaaatacacg gatttaatat ttgctttgct tttttattca gagaggaaag  1140
gtcaattggg ggtttcccct cgttttatga atgaaaaccg cacataaata taattatttc   1200
cacagtttta aacggcagaa acggttcgtg ttataatttg tgagataatt gattttgcat   1260
tacgaaatta aagaaaagg cggaaataaa taaattagtg tcgcaatttt tttctcaaaa   1320
aggaaataat gcaattacgc tccaccggac agtaaaattc tcagtttatt tgaaaaacaa   1380
aaatttaatt ttttccctt ttttcaattg aaatctcaaa tttctgaact caaaatgaaa   1440
ttttcagact ttaccagaat attgtgacat cgaccg                             1476

<210> SEQ ID NO 112
<211> LENGTH: 1697
<212> TYPE: DNA
<213> ORGANISM: Caenorhabditis elegans

<400> SEQUENCE: 112
atcgcagaaa tgtgaaatca taaaatccat agtgagattg agttgtttat tattttatga   60
aatgagataa tcagttggat aactactgct cacgccgtat tcgatctatc attcgattct  120
ccgattctgg aacatcaaat tttaatcata gggagagagg ttcgggtact tgagaaaaaa  180
atgtcgtgtt tcgagaggtt ttgaaaagtc agttgttaac tggttcggtc aacatgtaga  240
gattgtagag aaatatgaga acttagaaa ttgacgtatg aagagaaaaa agtgggaaag   300
gggagccgct gttgttttcg aaagaagaaa ataagacaga aaaatcgga gaggaacata    360 acaacaagtt aagttgactt tgaactgga aatttgtcaa tattgaaaaa aggaacagtg   420
agaaatatcg atttccacgt cgctcgattc tatgaaaaga aattatgcac acacaagctt   480
cacagtgagc atgctgaatg attgagcaaa tacatgagag aataagagag gaatgagatg   540
aaaagaagcg ttcaaatcaa aagaaaccag acaaatggc gatttttac gggaatatga     600 acctactgat tggcagtgga cagctggaag aataagaaga tactgaagga aggttgaagt   660
tgaagcttgg aagacagatg atgagagaga ggaaaacctg tttcttttg attacgatcg    720 gacggaaatg agaaggaagt aagtgttttc acacgtaggt gggcattgag atctttgaag   780
gtgcattcga caggttaata atcattctaa ataccaggtg acaatggagg atacttttaa   840
acagtaaata tattggaata aaacataaaa gttagtctta ctcagaattt ctaaaatttc   900
agccttctgg aacgaaaggt aaaatcataa taataataca gtggggctg ttagtagccc    960 taaatacaag taaatgacc gaacacagcc gttaaagaat gttgcagaaa attgcgaaat   1020
atttccttac tcttaagaac aacattcgat gtgacgcaat atgatgcatt tccttagaca   1080
```

```
aaaacgttca gttcaaaata acaacaata  aaaccgtttg tacgatttct agaatacgag   1140
tttatcagtt gttcggaaaa tatcttatca atcgtttgac tgatgttttt taaccatgtg   1200
agaatttgaa aaaaaatttc atgattgcca aaaattaaaa taaacaggaa gcttttaccg   1260
agttttcgtg atttcagaa tgaagaaatt aatatgaagc tcaaaatcaa agcagaggg    1320 aaaagaaaaa atcgaaatct tctttcggtt aaacaacacg cgcttgcgga acttcggagc   1380
atcgtatttt gttttgcgc tctattttg aatcggaaac tgttttttg tcagttttcg     1440 aaattgtttt ttttctgttt ttttacttca tgcaagagtt taactttacg caaaaattaa   1500
ttaaaaatac gcagaaggcc cactttacac aggaattaat tgaaaatact caggaatttc   1560
actttactta gtccttttc cagagtttcc aacggaatca atatattaat ttaatttcgc    1620 aacattttc tttgaataaa cctatttgca atgagaatg tttcagatat ttgcttatcg      1680
aagcctggga attgctt                                                   1697

<210> SEQ ID NO 113
<211> LENGTH: 849
<212> TYPE: DNA
<213> ORGANISM: Caenorhabditis elegans

<400> SEQUENCE: 113
gcgtaaattg gtttctataa attcttgaca aactcattcc gaacggctga aaatattgat      60
tgaactgaat tcacattatt cattaaaaaa ataggttag cctgttatgt agagaaattt     120
agtgaataaa aaactgaata tgtatttatt taatagattt ctcggcacac aggaattagg    180
aataactccc aaaaaataga tatttggcag gagggccgaa cagctgtgtt ttccgtgacg    240
tcatacaggt caatggacac aggatgtagt catattacgg gaacacacaa ttctgagaat    300
gcgcactggg gcatttgatt tgacgcgcaa tatctcttag cgaaaactat ttacagtaag    360
aatttaaatt ctaccgtagc gggctcaatt ttcgaaaata tattttctta tcgaattttg    420
agagcagttt ttcagttttc catgcttgat tttattattt tatctttaaa taaatttttt    480
tcattgaaaa acgggaaaa acaccgggag aaattgatct ggtgagaaaa ttataatatt     540
tctgctgttt tcctgttgac aactttagaa atgtcaatta aacaactata ttttaaaata    600
atcatttatt ttttaatta cgtcaactag aaaacattaa cttttgcga aaattcactt     660 ctaccacact catcatcccg aaaacagcga ggtctcatga aattgcaagc gcgctctact    720
gcaaggaaag gcagcgcgcg aagcaaattt tcaaacaatt ttttgaacgt tttaccgcat    780
tttctcactt tctcgcttaa ttttgctatg tttttttgcga tttttttgta attttcttc    840 gttttcag                                                             849

<210> SEQ ID NO 114
<211> LENGTH: 828
<212> TYPE: DNA
<213> ORGANISM: Caenorhabditis elegans

<400> SEQUENCE: 114
tcactaaaca aaaacatat atttgtaaaa taccattttt cttttcatca acagcttcaa       60
aactatctga agtgctggat tttcgttcag ctccgtcgat cagctcgaag tcttgctcct     120
gttctggagt atcgctcatt ctggaaagat ttaaatacaa ccgaggaacc agaagagcgc     180
atgaaaatat agagcgtgta atttaacgtc agttattgac agagaaaata gaattacgaa     240
agaccaaatc gggcaacgag gaaacgtttt aacacaaaca caacactgaa ataagcaag     300 aaaaggagga agttatcgga aaaccgaaga acttcaact tcggaagaa ccgtttaatt       360
```

```
tatgtttaaa atcaaacaaa aaattcccga aacatcccrr ttaaactttg attttcacga    420
aaaacaacga atgaccgaaa aatgtgatca atctctgaga gtgtgcactt ttgcgtgacg    480
gtgaactgtc cgcgtgcacc agattcgacg cgcaaaataa tcggcgcgag gttcgaacga    540
acgttcgtga atttgtggga gcggttttta atgtttaaaa atcagttttg gtttattta     600 tttgaaaaaa aaaacgataa aagctatatt ccagcagtat ctaaaatgat cttcttttaa    660
tattctaatt ttaatgtttt aaaattcatt tttcgctgca gcaaaaagtt ggtgtttgcg    720
tacaaaaccc gcgccagtct tgaaaaacgc acgcattatt tattcacatg tttcgcaata    780
tttccatatg aacttctcaa catcaccaat ttaaattaag ttacagga                 828
```

`<210> SEQ ID NO 115`
`<211> LENGTH: 222`
`<212> TYPE: DNA`
`<213> ORGANISM: Caenorhabditis elegans`

`<400> SEQUENCE: 115`

```
cttgtttcat actaaaaact ctgatttcag actgaaaaac atgttttttt cagcgaagaa     60
aactaaaatt tgtttgtggc cgcggtggcc tagttttcac ggccgagaaa tgtcacatgt    120
tttggcgcgc tcttcggcga attcaaataa acttttttgt ttttaacaat ttctaacttt    180 attttttgtgt ttttagaact gaaattccat ttttcaggag aa                      222
```

`<210> SEQ ID NO 116`
`<211> LENGTH: 222`
`<212> TYPE: DNA`
`<213> ORGANISM: Caenorhabditis elegans`

`<400> SEQUENCE: 116`

```
ttctcctgaa aaatggaatt tcagttctaa aaacacaaaa ataaagttag aaattgttaa     60
aaacaaaaaa gtttatttga attcgccgaa gagcgcgcca aaacatgtga catttctcgg    120
ccgtgaaaac taggccaccg cggccacaaa caaatttttag ttttcttcgc tgaaaaaaac   180 atgttttttca gtctgaaatc agagttttta gtatgaaaca ag                      222
```

`<210> SEQ ID NO 117`
`<211> LENGTH: 633`
`<212> TYPE: DNA`
`<213> ORGANISM: Caenorhabditis elegans`

`<400> SEQUENCE: 117`

```
ctcttctttt actaatccat caagcgactt ttcacggagt aatctgaatt aataatattt     60
atcagtgcat atctctgaaa actaacttga cgacaaatgc ttcgacatca aaatccggct    120
ttgtgacgtc caaacactca gacatttac attcaatact gaaaaattaa agaaaattca    180
ggaaaactcg agaatgaaaa aaaacagatt tgagacacca tcaatacaaa gggaacgaaa   240
tttgggggaa atgctggttg ccgaaaaaat aagtagaagg taagatgtgt tcaactggaa    300
catacatttt ctgaattgca aactcgattt ctctcacatt cacaattttt aatcacattt    360
aatgcttcag ttttagaaag ttctgaagta tcctcttctt cctattcagt ttctcaaaat    420
cgatggtgtc tccaggacgt gcacaaatgc gctctattgc gaattgtgga acatcattgc    480
gcgcgcgact agaaaaaaat gagcgcgttc ttgaaaatta ttttgctttc tctaatttta    540
aacgatttcg attacatttt atctgaactt tcttgggttt aatcgaataa aaacacaaa    600 aatattcttc agactggtaa aaacttcttc aat                                 633
```

<210> SEQ ID NO 118
<211> LENGTH: 898
<212> TYPE: DNA
<213> ORGANISM: Caenorhabditis elegans

<400> SEQUENCE: 118

| | | | | | |
|---|---|---|---|---|---|
| gtctagtttc | aaaaaaaatt | aaattaaatt | aaattgtgta | atatgtggca | ttatttatat | 60 |
| acttttttgt | cgatcatctg | ttaagttagt | ttttagtctt | atcttcttgt | cgcacaaaac | 120 |
| attatggttt | gtgtttaata | gaacaagaaa | gtgggtgaca | agaatcgtat | gatttggaga | 180 |
| aacccagcaa | tcaagaagat | tttgtttcaa | aattcgtagt | ctggatactt | tagaatgtat | 240 |
| tctcaatttt | cgaataaagt | ttagaggatg | ttttttcaaa | cttttatcaa | ttttttgaaaa | 300 |
| ctatctgatg | gtttataat | tattacagtc | acatatttgt | agcttgtgaa | tctaaaccta | 360 |
| ttatgtatat | tctcgtttta | aaaaaattaa | ttgccgaaaa | aaagcaaaaa | attttaatct | 420 |
| tacgaaaaaa | agtttttttt | ttggatttat | cagcttcagt | gctcattttc | atccctaact | 480 |
| ttctttcaag | aaatttaga | tatgaagaac | aattttaaaa | ttctagatca | accaaatctc | 540 |
| tgaaacaaaa | ctagttttct | attgtttcta | catattgata | ttttttttaa | actccattat | 600 |
| cattttttaat | ttttttaaaaa | gttttctaac | taccatctgc | tctccatcac | ctctttatgt | 660 |
| tttttgcatt | tgagcagtga | aaagtttgaa | gaatattggt | acaactttta | taccttccaa | 720 |
| aaagtgcttg | ccccattctc | tatgttctct | tatcagtaca | ctatatctca | acagtcgaca | 780 |
| catttgtgtg | gaaagtgtt | gtttgtgtct | gactgttgtt | tctaccaccg | atactattta | 840 |
| taaggtggtc | taccgaaaaa | catcaatacg | tttctttttt | attcctgaaa | ataaaaac | 898 |

<210> SEQ ID NO 119
<211> LENGTH: 898
<212> TYPE: DNA
<213> ORGANISM: Caenorhabditis elegans

<400> SEQUENCE: 119

| | | | | | |
|---|---|---|---|---|---|
| gtttttatttt | tcaggaataa | aaaagaaacg | tattgatgtt | tttcggtaga | ccaccttata | 60 |
| aatagtatcg | gtggtagaaa | caacagtcag | acacaaacaa | cacttttcca | cacaaatgtg | 120 |
| tcgactgttg | agatatagtg | tactgataag | agaacataga | gaatggggca | agcacttttt | 180 |
| ggaaggtata | aaagttgtac | caatattctt | caaacttttc | actgctcaaa | tgcaaaaaac | 240 |
| ataaagaggt | gatggagagc | agatggtagt | tagaaaactt | tttaaaaaat | taaaaatgat | 300 |
| aatggagttt | aaaaaaaata | tcaatatgta | gaaacaatag | aaaactagtt | ttgtttcaga | 360 |
| gatttggttg | atctagaatt | ttaaaattgt | tcttcatatc | taaaatttct | tgaaagaaag | 420 |
| ttagggatga | aaatgagcac | tgaagctgat | aaatccaaaa | aaaaaacttt | ttttcgtaag | 480 |
| attaaaatttt | tttgcttttt | ttcggcaatt | aattttttta | aaacgagaat | atacataata | 540 |
| ggtttagatt | cacaagctac | aaatatgtga | ctgtaataat | tataaaacca | tcagatagtt | 600 |
| ttcaaaaatt | gataaaagtt | tgaaaaaaca | tcctctaaac | tttattcgaa | aattgagaat | 660 |
| acattctaaa | gtatccagac | tacgaatttt | gaaacaaaat | cttcttgatt | gctgggtttc | 720 |
| tccaaatcat | acgattcttg | tcacccactt | tcttgttcta | ttaaacacaa | accataatgt | 780 |
| tttgtgcgac | aagaagataa | gactaaaaac | taacttaaca | gatgatcgac | aaaaaagtat | 840 |
| ataaataatg | ccacatatta | cacaatttaa | tttaatttaa | ttttttttga | aactagac | 898 |

<210> SEQ ID NO 120
<211> LENGTH: 890

```
<212> TYPE: DNA
<213> ORGANISM: Caenorhabditis elegans

<400> SEQUENCE: 120
gaatcttcga tgttcattgt gaattttgta tcactgcctt gcctttattc acttcaggaa      60
ttttatgttt tacttgtaat ctcaataaaa atgaactttc aaattaataa taacaaacta     120
attttctagt tttacatcag atatctgctg agcttctgct cctcttccgt caaaattaaa     180
tcaaattggc tgagcagcgg cccagtcaac tagcgaagtt aggacatagg ttttcttttt     240
ttttttgtt gaaatgggca aattgccgga attgaaattt ctggcaaatt ggcaaattgc      300
cggaattgaa catttgccca atctgcaaa ttgccggaat tgaaatttct ggcaaatggg      360
caaatcgcca gaattgaaat tccgccaaa ttgtgatttt gcactttttt ctggaaattt      420
cagaatttca atttcaatcg gcaaatttgt acgcatccta ttttgaaaag taagcaaatt      480
ctatgaaaat atctaaagaa aacgggaaaa aaactcaaaa agacactgtt tttagtgttt     540
ccgttttata aaaaatgcct ctaaacattt ccgacaaatt tgatgatccg gcaaacgaca     600
caccggcaat ttgccgacga aaaaagttgc caaacggcaa ttgttactgg atcttatagt     660
gatcaaattt tggaaaactc aagtacagtc agaaaagcag tcagaaccca gggtctatta      720
aaacatcttt tacacattga aaagttacat atacttgaaa aaggagaca tagagaaaaa      780
ctcagatact gtctctgaca atttttctgc tttgtgccac tgaatggtaa acaagctgaa      840
aggtataaaa actattgcaa tttttgacag aatggtattt gaaatcaagg                 890

<210> SEQ ID NO 121
<211> LENGTH: 1116
<212> TYPE: DNA
<213> ORGANISM: Caenorhabditis elegans

<400> SEQUENCE: 121
atgtaacccc aataattttt ttttgttgca tttactact tatatccgtt tccatttttt      60
aattttatgt tgtcacgttt tgtctaaata gtgtaatctt cttgtactaa ttattccaat    120
tattttaacc cgtaagcgat aaatgaaaca acacttttg gttttatttt gctaattta     180
aataaattgt catcaattct gaaaataat aaattttaaa aaataccga agaggcaaac      240
aagacatttt ggaaattctg atccggataa atattccgtt agattttat tagactcgaa      300
attgcctgaa acccccgatt ttataacgaa acctcttgaa aacttctcaa aaagagaag      360
ttaccaaact ttaccaaatt tggtctccca tcgaccttca atgtacctaa ctctagttga      420
atacgcaaga taattaattg ctacaaccaa aattaaacgg cggtttcaaa aaatatttgt      480
tttcagccgc tgcaacattg acaagtggga aaaatttcaa attttaacta attttaggtc      540
attttttgag ccgccataac ttttttttgag aagttttcaa gatatttat tttgaagttc      600
ggagttttca gacaacttcg agtcaaataa aaatattttt taagtcgacg acaccacctc      660
ggagataatc tttaaaaaaa tcttttcaga atgcaaaaa ttccaataag tgtcaaaact      720
cccgagtagc gcttaagcag tggcacgtct gtatttatgt attttgttt ttttttttta      780
ctttattatt ttgtgctttta ttactgtttt ttttttaaat ttattttgtt tcatgaaatt      840
ttaggactaa cgtgaaactc aacataaaaa agctagaaaa gttcgcgta ctgtattcta       900
tttttctttg attttattaa tgtaatacat cacttttata tcttgagtga ctaaactctt      960
gttaagtgtg tttcaataat gttttgattt tttgactta cttatacgtg ctttgtagtt     1020
ttagtgacat tagtgaccga aagtgagacg ataacaaatt gggagcggta tataagtgaa     1080
```

```
ctacgaaact tctaaaaaaa caaaggctgt ttcaca                               1116
```

<210> SEQ ID NO 122
<211> LENGTH: 1807
<212> TYPE: DNA
<213> ORGANISM: Caenorhabditis elegans

<400> SEQUENCE: 122

```
tgtgggaaaa gttggaggtt tttgcacatt ttaggtgagc gaatatcccg ttgaaattat     60
agaaattacc gattgccgga cagttttgga aattgtcaaa tccatctatt tttcgaaaaa    120
ttaatagaaa actacattgg ttttcagtat ttgataagtc tacgagacaa aaatgtctac    180
gagacaaatg tacacaaatt atcaaattta cacttccggc aattctgatt ttcggaaatt    240
gtccattccg gcaattttgc aaaatttgaa attttataaa ataattctc tacctgcctg     300
cctacaggca tgccgcaact aaccttgaaa actttaaaag aaactccgaa tttcttaaaa    360
ttttaagtcg gctggaaact tagaaatctc ttgccaagat aaaaaacatc gagaacatcg    420
taatcaattt tatttgattt gatacgttca caaagtgaaa ttccaatatt gaaaatcaaa    480
ttcaattaat caattaagag ttcagtgagt cgtccttgaa atgtaccaat ttcacttgag    540
cgctcagaat ttcgttcaaa atcatcaatt tctcgtccaa aaatcgatga aattttgcga    600
gtaggtacaa gtttgtgctg gaattaatt tattggttgt atggatattt tttttttaatt    660
taagaattaa aaatttacca tgaaaataaa gtatgaaata ttacaactat cagggtaaac    720
caagcaacgc gagatccagt caaactgtac acgactaaac tttaaatagc aatactaatc    780
taaaagcaa atattttct ttaagtagaa gcaaggcaga agtttgacat ttttccgac       840
cagttgaatt gtgattctat atacatctgg ttcactcgaa tttcagacaa acaactccac    900
attcctcaat ttctgtgata gaacaataac ttatttcctt cacatttctc tttcaattat    960
gcattttcat tctttaagtg tcttttttta aaatttgaca ccatttgccc gcgactcgtt   1020
gtccggaggt ttcctcttac ctcggagaaa ttccgctaaa tctaccatgc atgagtctca   1080
ccacgtggac aacgagttac tgtaacttgt gtcaatttac gggccgctat cctttttta    1140
aatgatatgt accaattgat acaaagaaat acttgttttg ttatcaaaat agagtataaa   1200
atataaatga ataattcaa aaattattct caattgggcc agatacaata ggatagtggg    1260
gaagttcaag gatgatattg tgtcagacaa ggagcaaaaa tgcattaggc cagttttac    1320
agaattcatt ccaagtacag aattttttcaa acattccatt aggaaatggt gaagaaaacc   1380
aatacatttc aacttccaaa tttttgaaat ggatttaaag cttccctata aaatttgttt   1440
atgaaaataa ttttaacgat ttcatttaca atcaccacat ttttttagaat tctcagcaca   1500
ggttgaattg ttcagtacct tttttcaaca tctagttcac ctacatatga gttcttaatt   1560
taattacgtt ttttgaaaag taaatatgtt atttggcaag tccattcaaa caaaagacgt   1620
cgaccactta taatcaaaaa gtacacttgc ggcagacatc tcgatacttg ttttctctgc   1680
ctgttgtcac tgatcttatc gatatgtaat attgtgaaat gttgcgcagt gttgaaaaat   1740
aagatataaa attaggaaag aattgtataa aaatcagaca aaactattct gtccaacaaa   1800
gatcatt                                                              1807
```

<210> SEQ ID NO 123
<211> LENGTH: 1546
<212> TYPE: DNA
<213> ORGANISM: Caenorhabditis elegans

<400> SEQUENCE: 123

```
gatgagatgc aataacctga aaatgaggca ctttatgata agaaaatgcg gtaaaacatg      60
cgaaatatgg caccataaac cgtgagcagg acaaagaaca acacttgga aaagaaaaga     120 aaatagaaag aaaaaaagga aaactggaga aacaaactc aataacacaa cgcgagaaat     180
acaatttcgt ttcgttttttt cttctattta ttagatttct cacaatttgt taccagtaaa     240
gtcacgttct atatttcaaa ctactcctaa aattcggttt gaacagttct ctgataaacg     300
aatttcgaag aacgatcaga aaacaaatct acggttgtgt gtgatcaatg gggtcaaacg     360
gtggacgaaa ggggacggcg gagagaggaa aaagtgagag aaaataaata aaattgacct     420
tcgagtgcag agttttgctg gtattttggt cagaattgat tatgaaaatc tgaaaattac     480
cgccgggaaa gttgaaaatt tgacgtggaa acgtttaaaa aataagatg agaaagttag     540 tactgtagat gtcgtcggat caagtgcaca gtacgcaagc accgttacga aaaattgcac     600
taattgctca attaaatttt tttaaaaaat taatttttat agtgtgtttt gtgttttttt     660
tctgcttttt taatgatttt taaaggcttg attatgtttt tttctcaaaa tttgaataat     720
caataacatt aattaattac tttattaaaa aaccacattt ggcattttaa taaagcaagt     780
tatcgcgaca aacggcaaaa atgtctcttt ttataaaaat tgttttttttt tgagttaaga     840 gaagatgtgg agttttttga actacattag ttttctaaaa attttatcat ctagattttg     900
aggaaaaaag cagattatat atctttaatc ttggttttaa aattttttta aaaagcagaa     960
tattaaagta aatattata aaaagaaaaa ttcgtgtttg caaaatttgt ttgaacggaa    1020
ccttgcaaaa atgatattta gcagctaaac taactgaaaa ctactgcata aagctttccc    1080
aaaaagagct accatccaga aaatgttttt tttttcaaag ccgaaaaaga agaaaaaaag    1140
atagaaaacc gaaaaagcag catcgttttc gcgcactctt tcttctttttt ttctttcttt    1200 ttctaaaaaa aaatattctc cgtagcttga agtctcagga tttccaaagg gaatttcctt    1260
gatagaatat ggaaaaacaa gagagtcatc agagaaggga gaggaaaagc ggggatgctg    1320
gcgaagaccg ggggcaccga ctgaaatata ggcaccggcg gggaggcggg gcgctctctc    1380
ctctccgctt tactccgccc cgattgtcag tggagcaggt ttgcaatgag tgttctctga    1440 tgcccctca gcgcgggagt tttgaaatca aatattttgt attttaacct actttattga    1500
tttttcaatt aaaatgaaat gttatttgtt taaaatttaa tttcag                  1546
```

<210> SEQ ID NO 124
<211> LENGTH: 1375
<212> TYPE: DNA
<213> ORGANISM: Caenorhabditis elegans

<400> SEQUENCE: 124

```
accatgtacc caatttctcc agatgtctca aaaagtcctt cttcttgtta atatagctcg      60
cctcctcaaa ttttgatctt ccaattcctc tccgcccaat atattctagt ccgtgtctta     120 cccttgaca aaaatgagct tttctcagat tccgactaat tccaaaaaaa ttccctacgt     180
tttgaataat tgtcgctttg tatttttttt tctcgttttc atacgggtgt tcatcattca     240
ttttactttt ttaaaaattt tcctctcgtt tcttttgaac gtcccatttt tattgcaatc     300
gttcattgtc tagggtctat ccttctaatc attcttcttc tcagaaatat cacaaaccgt     360
ctgtgttgca ttcaaatttt taagtaaaaa taataaacta agaaccaca atgaaggtct     420 aagttggcaa aattgaaaag ccgaaagctt ttcccggaat aatagtaatt actggagtgc     480
atcccgaact gtctaaaagt agagaaaaga ttaagtggat atatatttttt tatatttttt     540
```

| | |
|---|---|
| aatatagtaa tctgtttgaa ctgttataca aaccgaaatc gtgttagttt ggacaaagtt | 600 |
| ttgcatcaaa ttttttttga gttttagatc gaactattgt gttttttaatg taccagtcaa | 660 |
| tatttggcat tcacaagcgg tatagccaaa tgtacccaga gttgatcaga tagcgttttt | 720 |
| cttcactgtg ttccgttgtt atcaaataaa ttatgcaaaa actgcgaaaa tttgagttca | 780 |
| aacattaaaa aaaatcatat ttttctaggt tattgcgagt ttttagcaag aacaactaat | 840 |
| gttttcatgt ttaaacaaaa aaactgagtg agtgagaaaa aatctcatgt atgccatggg | 900 |
| atcaagccat atattttcca tagactaaaa ttatttagag atggaaaatt gaaaacagga | 960 |
| gacgggttac tgtaggaaga ttttttttaag actattgcaa atacataaat cttttgaata | 1020 |
| tattttactt cttcgaccgc cgctttgaaa cagtgcgtta ctgtgaacgt tgaaaaccaa | 1080 |
| acatttgaac tcttcacctc acttgtccat tttgttaatt gtctagccaa ctgtagccac | 1140 |
| ctttgatcag gtagaccttt tccaatctgc gtctctcatt ctctcaaatt cacttagcca | 1200 |
| tgttttgtac ggacatcatt tctgatacat taactacgat aatagttgtg cacgctgtgg | 1260 |
| tcatttgatt aactttttt cctgttgcag cagttcgcga gtatataacc tgtctttaac | 1320 |
| tgataaatcg tttgcattgg tcgtttgaag gaaacaacaa tacgctttcc aaaaa | 1375 |

<210> SEQ ID NO 125
<211> LENGTH: 1350
<212> TYPE: DNA
<213> ORGANISM: Caenorhabditis elegans

<400> SEQUENCE: 125

| | |
|---|---|
| tacagttaca attgaaataa atggaaatct ctcttatttt tacattgaaa tttcttgctg | 60 |
| gtcacttctt ccaatccacc gtagttaacc gactgggtgg tctactaccc gtttctggtt | 120 |
| ttctctgcac tctcttcgga gagagtgcag acaaaattct ccgcgttcgc agtcctggtt | 180 |
| ctgtttcgag acgttgacgt cgcccgacac cactcctaca actgttcgga cagcgtctgc | 240 |
| aattttcgat tagtaatata gttttggttg tgaatataat ataaattgtg aaaaattgca | 300 |
| ttgagaatta ggaaaagagc atgtgagaag aggaggggaa ttttagaat aactgagaat | 360 |
| ataatttaga gaaacacgat tacttcgcat caattcagaa tatcttttaa aatctgagaa | 420 |
| attttggtta aaaaataaca cagggcgctt agtttgtggt tttctcaatt ctgtttaatt | 480 |
| tttaaaacag taattcttat ttcgataaac taaaatgaat atgaaatttt cttacgatta | 540 |
| aaaaatgcat gaaaccagat ataacaaatt gaaggaaaac tgaaaaactt cagaaagtgt | 600 |
| ttttttctga aaataaaagc agaaaaattc gaagctcgcg caaagaacgt aaacgcgctc | 660 |
| cattgctaac tcatttgaac attagttttt ttcattgggc tttcaatctt gtaagtgatg | 720 |
| tttaggcatc taaaagtttt ataaattgac aaaatccagc ttaaagatg ctatcaaaaa | 780 |
| ctaactttc agaatattta tttggctaat gtttgaccca tacgtttttt gccgaaaaga | 840 |
| atttcaaaaa tgaaagtat cttgaaatgc atcaaaatcc gggaatattg ccgatggtca | 900 |
| gttttcagc atttctaaat tgagagactg aaatgggaat ttatttattt ttattcatct | 960 |
| gcttttttat ttcatgaata tccgcatctg aaatcagctt ttttttcag gaaaattgat | 1020 |
| tgaaagaaga caataacagc tcgttgttca acatctcgat tcttccatat gaatcgatga | 1080 |
| atggaaaaac cgtggcattt ggtaaagttt tggctggaac cgaagttgtc tcccgcatcg | 1140 |
| ccttcaataa atcaaacacg aagggttcca aggcttgcgt catcaccgac tgtggagaag | 1200 |
| ttatctgaaa ggttttatca tagattttca aattttttgg tttattatta tttctttctt | 1260 |
| tttgttccga taagtccata tatgaaattt gtccagtttt tatgaaaata aacatttatt | 1320 |

```
ttatttaata ttttttatt catcatatgc                                  1350
```

<210> SEQ ID NO 126
<211> LENGTH: 632
<212> TYPE: DNA
<213> ORGANISM: Caenorhabditis elegans

<400> SEQUENCE: 126

```
tctgaaaaac gttgatttaa aattttataa aaaatttgaa gcaaaaatga agagaaaac    60
taaaaaaaaa gtaaatgtac tgaagtgatt ggcagattaa taataattta tcgataaaac   120
cattttttaa aaaacttcat cagtttttgt gagtgtcagc aaagaagaag aagattcacg   180
atcaaaaatt cgttgagcct atatgaaata gttgcgctgg ttttcgacg ggggatcaa    240
atacgtcaaa taggtcaaat agacgaagca ttcataaaaa gtacaatatt cattgaaaaa   300
tagttttgga tttgtttttt tgttttcttc attttttgt tgaaaaaata atggtaatta   360
aaagttttta ataattattt aaatcaagat tgaaatatca gaaaacgaca aaaattcgtt   420
cgagaacttt ctcaagacta ccgtactctt taaagacgca tgacgatttt cacatgggtc   480
tcaccacgac ttgtctgaaa tttgaatgtt cgttcaaaaa cttttttttt tgcgattttc   540
aaaaccaaag cttaacaaac aattttcctc aagttttcaa cgcttttgc tcgttttttt    600
cgctcaaata aattatttca gaaggttttg ca                                 632
```

<210> SEQ ID NO 127
<211> LENGTH: 1057
<212> TYPE: DNA
<213> ORGANISM: Caenorhabditis elegans

<400> SEQUENCE: 127

```
tatattcaaa aaatatatt ttttgtaaat gttcttgaca aggtgtcagg aaatcagaat    60
aaacattcaa caggtgttta tgttttttt gtatcattct aaaaatccta acccgtgcct   120
gattttcata aaactaaaac actaaatgtt gtcaatctgt gaccctggag cctagaataa   180
gttttccaaa atctgattat taaaaacaca caacagatt ttaaatagat ttgagcacaa    240
gtcatgcatt gagcataagc cacaaatgaa ataacgagag tgaattttta gagtctaatt   300
gaattgcatt agcttttcta aaacttttt ttcggctcaa atcatttcc acaaaaaaaa    360
cagttttaaa ataataagag ttggccttca gagcggtttt tgtttaaca aattataatt   420
cttattgtca gctcgattac gtttttttt cagtatcttt cgttttgctt tttgtttta    480
gttactcgcc acgagagagg gtttccctcc aaatttcgca aaaactagca caattatat    540
gtatgtaccg gaactaacct ataatacttc cgggttcatg ccaaattcta atttctaaat   600
ccccagacag cacgctctc aacttcctcc ctctttttgt ttatgaatga atttagtttg    660
tgacaatcag ctaaaagtcg tgatttgaaa agttcaagaa atcgtcaagc tcgtgaccac   720
gaaaaagttc tagtcacaat acatcataga ctagaaagca tttctcgatc aactagttga   780
cagcttttg tgaataaaga ttgagaattc gagttgtttt cgaaccatga ttacatggct    840
taacaataat acatgcagct cattgagtct atacaaacac aaaatacggg tctgcgtcta   900
attatttcct acaatatttt tgttattatt cacaaaaaac gggagatagt cgacagctct   960
caaccggttg aagagttgtg tcgtgaagaa acaatataaa acattgaaa agtaataact   1020
gataacaaca gttctcaaac aatattatag tgatcaa                           1057
```

<210> SEQ ID NO 128

<211> LENGTH: 509
<212> TYPE: DNA
<213> ORGANISM: Caenorhabditis elegans

<400> SEQUENCE: 128

```
agcaaataaa ataattttat ggttttttcat ttgaaaaaaa agttattaac cttccggcgc    60
aaatgaataa aataataaaa atgattaagt tattgcacgg cccaattcat cgttgctata   120
cttattgact acagaatatt tttacttcta tcaacaatgc aagtttgaaa atttccataa   180
ataagatttt tcttatcact accttttttgc ttattttcat tttaatttcg tggtctctgc   240
tctcccttttt ctgacctgct gacagtttga atcgtcttca aactaaatac tcggtatgtt   300
tgcctaaatc tcttgtaaga gagtagtctc tcattcagag aatttcactc ttgttgttag   360
aacaaacttc actggcgtgt attttgggaa aatagattat atatatttaa gagattaata   420
cgatttctaa ttttagttgt ccatcaaatt gaatttttttt gtgtcgtttt tctgaataaa   480
catctgaaat tgattcacca tttttcaga                                     509
```

<210> SEQ ID NO 129
<211> LENGTH: 570
<212> TYPE: DNA
<213> ORGANISM: Caenorhabditis elegans

<400> SEQUENCE: 129

```
ttattaatat tattgtatttt ctgaatgtac cgtattgtat ttctacatat tgaatcaata    60
aattgttttg tacaataatt ctttggctga gactggtcgg acaaattcaa tgcaagcctg   120
caaacttatt agactctaat agaaaatttt ctcaaattgg aacaattatt ctataattcc   180
ttgccggttt tgcagaaaaa atgttttttt aagaattaaa aattttaatt atgttccaat   240
taaacctaca tcaatgctct agaattctcc aaaacatcaa aaaaatttgt tgacaagatt   300
ggaaaatctg aaatatttttt aatttttttaa tatcaaaccc ccttcaaatg ctacacaact   360
taaaaataaa aacaaaaagt gtggtcaaca actttcaaag cgtagaacac gcattttgtg   420
ttgtgtgtct tatttcttttt ctacctctta tctatcgtct cattcgcgcg cttttcaatt   480
ttgggggtag gctgagttag tataagaaaa gttaataaaa aatattagtt tctaattttc   540
gagtttctaa tctagcagta ttttaaaata                                    570
```

<210> SEQ ID NO 130
<211> LENGTH: 287
<212> TYPE: DNA
<213> ORGANISM: Caenorhabditis elegans

<400> SEQUENCE: 130

```
atctttaata attaaatgaa taattaattg ggagaaacat gtacataaat aaaatttcca    60
ttaaacaatg ttcatttgtt taagctggca cagaccacaa aagctgaaac cacaaagttt   120
tttaaacctt gttcttttct taaattttgt agtttcttat cttatcactc gtgtttcttg   180
tcctccaaat aattgtgaaa attgtagtta atgtgtcaaa aaagtcacat ataagaagac   240
gaacaacttg attttttgtt gacttcattt gaaaaaaaat agaaaac                 287
```

<210> SEQ ID NO 131
<211> LENGTH: 1670
<212> TYPE: DNA
<213> ORGANISM: Caenorhabditis elegans

<400> SEQUENCE: 131

```
tactgaattt tgcaaaaatg aggagtatag gaaaactcgc tcagaaaatc gaaaaaaaat    60
```

```
tagttccgtt ttgtaacact cagactttac aactaccaat tagaaaaaat aataatacac      120
taaaagagaa gaatagaaat cagaagaagt cagtatcatg ggagctcatg agttaattgc      180
ctgaaatgcg tattcccaga aataaaaatg cggtttctta gctctgagat ctgaagtgta      240
agactgccaa tagattccat gagattcgtt gtgacaaggg gttctgaaaa aaggaatcgc      300
gcaaatttat ttattgcaca gttgtagatg ataaagtttc tttcagattt gaataatttt      360
taaaagcttc taaaaattat cttgcagcta attgtccaaa aattattaaa catttgaata      420
tttttctttg cttccaacag gttttatgga aattattaac aactgtaaaa cgttaacgta      480
gaataaagta aatcgatctt gaaacccaa agaaccggc cctatatttt tggcaggtgg        540
aaattttgaa tgaaatttaa taatatagct cctgaacttt taaacgatga tattagatgt      600
tgaatgatca atttccttgt agtcataacc atacggtttt tgaaacatca taattttatc      660
gaaatcactt gtaaatcccc cgggtacagc tataaccaac cctattcgac aatttcaatt      720
tcggatattg taaaaaaaaa ttttaaaggt ggtgtagtcg aattttttt attgctttat        780 taggttcaaa attgtctgaa aaaaaccgaa tttcataatg aaacttcttg aaaacttctc      840
aaaaaaagtt atgacggctc aaaaaatgac ctaaaattag ttaaaatttg aaatttgacc      900
gacttgtcaa tgacgcagct gctggaaaca atttttttt gaattaccg tccaatttgg        960 gtatttaagt taattatctc gcgttttcaa cttcattata aagcttataa acagcgagaa      1020
ttttaaattt tttttaccaa atctcgccgt ccatcgaatt caaaatacat aaatggtgtt      1080
gaaaacgcaa aatacataat tacatgctat actcacaatt tgacggtgat ttcaaaaaaa      1140
aattgtttcc agccgctgcg acattgacaa gtcggtcaaa tttcaaattt aaacgaattt      1200
tagaccattt tttgagccgt cataacttt tttgttgag aagttttcaa gaaatttcat        1260
tatgaaattc ggcttttca gacactttt agtctaataa agcaatcaaa aaattcgact        1320
tcaccacctt taacttagca attgccaaaa ttttttattg cagtacatat aaaattagaa      1380
acacacaatg tctcaaacct ggaattacta ggaattttta agaaaatgac tgaaaaaaca      1440
aactatgcca aggacaaatt taatgttttt ttcaaagtat agcatgtcga aaatactgtt      1500
tttgataatt aaactgttta atactactaa ttttcacat tctcatacga ctatgaaaat       1560
aagtgtagga aatgtaacct gtgtgatgaa cattctactt tgccttatca aattggaaaa      1620
acctcgtata aatggtcaa caaaaatga aactgattta acttctgatc                    1670

<210> SEQ ID NO 132
<211> LENGTH: 648
<212> TYPE: DNA
<213> ORGANISM: Caenorhabditis elegans

<400> SEQUENCE: 132
aagttcacaa tttattcatt catccatgta aactgtatat tttgaatttg tgttgtaaag       60
aatttatctt cgaataaaat gttttaaag gttttaaat tgtattctgg tgagattgct         120
taaatagagt ccttcggcga taaaaatgct aaaaattata tgaaaaaaac tatacaaaga      180
atatgtctcg aagtgtttca ttccagatca aagtcgaaaa ttagcttaga aaaaggatct      240
tcgtcaaaac ccctgattta acaccaagac gaataggaaa aataaagtaa tttaaaataa      300
ataaaattac aagtgcgctc cattgtaaaa acgctagaat ttgcaaaaac tgaacaatat      360
ttgattttcg actggaaaaa aaacttgttg gtaaattgca tgaacagttt taaaatgtca      420
ttaagaaaac tgatgccaat ttttggttgt tttctctcgt ttaggaaatt aaaattccct      480
```

```
cttatttttt tagcatgaac cgtcaacgat ttctggtcag ataaattatg gttattatag      540
tgtgtagttt tttgagttta aaccaatgtt tcgaaatttt tatcagtaaa cagaaactac      600
ggtttgctgt atataagtta attccgatag caaaagtaga aatccaaa                   648
```

<210> SEQ ID NO 133
<211> LENGTH: 1081
<212> TYPE: DNA
<213> ORGANISM: Caenorhabditis elegans

<400> SEQUENCE: 133

```
cttctgtaat aaaaaaaaat tgaaatgttt agtgaggaga gtgatagaaa ataaaaaaag       60
ccgagactaa acattttccc tgtgctgccc tgtttataaa cgtttcaaag gaaaattctg      120
aaccctgtaa caactgtcgt cgaccttcga atagctcaaa acatttggt ctgcttgtgg       180 atcgcacgtt tgtttcacaa aattcattgt gatttgtcgt ttgagatata tcccttctat     240
caatcaacat gttgatgccg gaacttttaa tcccaagaaa tctgttacac aaagatcgga     300 aaatacctt aattgcttac aacttttatt aatagtcgat agatacactt gcttttgact      360
tgccagaaat ttaagtatga tgcttatcaa ataattacat tgattacaat tattaaataa    420
ttgaataatt gctaactaca actaaaaaat tattcgaaac tttttttgtaa aactaagaat    480 cagtccgcgg atgaatggta atattgttca aattcgtcta gaaaaaaaac caaaaaaata    540
attaaaaaat gagaaactgc gcaaaatata tatatttaaa atgaaacaca acgaggcggc    600
tctcgttaac cagcattgtg caaataaccc aaaaactctg ttcacgccaa agtgctgaaa    660
agagaaaaga ggctggcgtg aagccgacag gtataggtcc tgaaaccgcg ccccactggt    720
tactcgaatt tgcgaatcat tcttcttttt tttttttcaa agcaacttcc ctttattaat    780
ttcagattat tgaacattca atttttttt gttgtaaaaa tcaattgttt ttctccgaat     840
agttaagaaa aatgtatgtt ttgaaaatta tctgttcttg ggaataata gagttctgca    900 aacaaactta ctatcagtcg attcgcctaa ttcgacccctt ctatcaaaaa cgttgtgctg    960
aatgtataaa ttgtgaattt ttgagtgaaa ataactgata agagcttttt tatcagtcaa    1020
ctgacagtgt gcatgttttg tataaaaaca gtccactgat ttcgaaaaat caaatcagaa    1080
t                                                                    1081
```

<210> SEQ ID NO 134
<211> LENGTH: 2047
<212> TYPE: DNA
<213> ORGANISM: Caenorhabditis elegans

<400> SEQUENCE: 134

```
ctttgtaaat tattttcaat taatttattt gcacatgtga actattagaa aagaaaaagt       60
ttacttttat atttggtgct atattggtga taaatctatg caattggtaa taaatcggaa      120
atacgtttat tttctgcaat tgaatataat aaaaggtaaa taaatgatga gtgcgagaaa     180
tttgagttcc ataattgtac aagccaggga gttttgaaaa ataacagaac cggtacctat     240
ttctcttttt ataacatata acatctgaaa ccgacatgtt aaataaaaaa ttttgagaaa     300
gaaagttgtt aattctcgtt aatttgcgat atgtctataa taaacctcgt agcatttcta     360
tcgactaaaa atttgttata atcagaaaaa accatcgaag ttttcaagtc aaatttcaaa    420
atactcttca catcaaaact tgcaaaatta aactcacaga ctggaaaagg aaattcgaaa    480
atgtctgaag aataacggtt ttggaaaccg agctgtactt ttttccagga agatcgttca    540
caaacaaaat caaatagcca taaattgaaa tacttgcaca acttaaaaaa tacgagaaca    600
```

```
ttgaagaaat atcgatgttc ttcaatacac ataaaatgtt gttgtcatat tgtttccatg      660
agcaaatggc tgaaatctgg gcaataataa tatttgataa atgtccatta ctcacttggt      720
atagcaactt tatgaactaa agaaattata aagaattga taattataaa tgcaagacat       780
cggggtcgaa acctaacgaa tgatcgaaaa tttggaaatt tcaatgatat gacttttgt       840 attgctagta gaaacatgga aacagcgaaa atattcggga aaacggtatt ttgagaatgt      900
gctattagag ccataatgga ctgaacgata gcccaatttg taattagaat cttacgattt      960
acatttctga aaatttatag atattaactt taaacatat atgaatggat cttacaatcc      1020
attaattaca atcaatacaa taacattgtt catattaatt aaaaataaag taatgctcat     1080
taataaagac atcaaatgat taattttta aatgtgacat gatttatgtc tcaaataatg      1140
tgtcttgttg tgattccatg aacggcagta aaatataaaa acgatactat ttgtagaagc     1200 aaaaccatc aataaagtta tttcaaagtc aatatgactt gttgctaagt tctgaaaagt      1260
ctgaaatact tgcatagctt aaaagcgtaa aagtgaatta ctatgcataa gtctgtgggc     1320
gaaatgcatg tgacaacatt tgcacctgtt tggttttaa tagcctccaa atttaagact      1380
atgaaaattc attctgcggt ccttcctgaa caatggcacg tccaaacgtc tacaacattt     1440
gaatatttat atttaataca aaagtagacc ataaaatag aattaacatt tttttgatcg      1500
acaatttcca aaaaataac aaaaactgag attgttccaa attttttttc caaaagttat      1560 ataaatttt aaaaaaattt caaaactttt actatgatat atttacagcc cccccccc       1620 acaaaaataa cggatttcat cgctttgaat ttttaataaa ttttcaatga aaatttatgg     1680
aatagacacg ggaccaggcg gaagtcttga tacttttttgg tactgtgtac caaccaaaaa   1740
ttgcagatac aaaaagaata aaaacattt ttttaaattt ttttattcaa tttttccgtat    1800 ttttgaacca cacttaaata aactctattt gaagcacagt cttatttccg tgttttcatc    1860
agagaccaca gttccttatc cttgcgttat caattttcat tacatcttta catcaaatct    1920
tttgtggcaa atgtacaaaa tgtacatttt gaagtaaata tacccgataa gaattagtta   1980
tcggtcaaga gactgtttga ttgctttata taaaatcaga tatttcaatt ttaattctca    2040
aatcgaa                                                              2047

<210> SEQ ID NO 135
<211> LENGTH: 2212
<212> TYPE: DNA
<213> ORGANISM: Caenorhabditis elegans

<400> SEQUENCE: 135
ttgtcttata ttttattaaa atcggggcga agccctgatt ttaaatccat attgttttt      60 ttgtcttcca ctatccctac aaataggaaa gagaatgtgt tctttctgat gaagtaaaaa    120
cggcgcagcc agccgacagc cgaaattttc acgattttcg gctggtagcg ccagccgaaa    180
aattaaaaga agtcggctgg cggcgccagc cgacagccga accagctttt tgtcggctgg    240
tagctttaaa tttttttcca gtttttaca gaaaattcgt ccagttctta cagaaaattc     300
gcgtttctat gttttaaatt tgataacatt tgcagtaacg gagactgctg acccggcgtt    360
tcccatgaga aagagagag agagagagag ggggagacag tgagatatac ggcagagaca    420
tagacagggg agacaccatt agagatcgtc tcctatagag tgctgccggc agggggcgtt   480
gtggaccgtg gggaagaagg ggggagacaa ccgcacactg tgcggttgta aatgcggaat   540
aatccattta aaactaagga aaatagtggt ctaatgctta acagtgagcc gcctagataa    600
```

| | |
|---|---|
| aacaaaaaaa agtcggctgg ctgcgccagc cgacagccga aatttt cact attttcggct | 660 |
| ggtgccacca gccgcagcc gaaaaattga agtcaatcgg ctgtcggcgc cagccgacag | 720 |
| ccgaaaaaat cagccagccg ctcagccctg gtggggtggc gatgtgttgg cagccaaccc | 780 |
| ttcaacgaac tgtatctccc gcctgtatct cccttcaaag tgagatcctg taacagtaat | 840 |
| tagagaccat atttacagcc agcctacatg catcactgga gactctgtgg agagggagga | 900 |
| ggcaagagaa aggggaggca agaggggggcg ggcgggcact gctgaacctt gaaagcgccg | 960 |
| tagctccgct cacaattgga attgaaaaat gaaaagtata tatttgaagt caacgttaaa | 1020 |
| aggagaatat gatagcattt gaaattttgg aaattggtga agaatgaaaa aaaaagcctc | 1080 |
| tggagcaagg cttgaagctc acaacttcag gaacggggct cgaggaactc atggccaaaa | 1140 |
| acttttatt tgtctcgctt ctcatagcaa aataataag atttaaaaca taaaattgat | 1200 |
| tatccaacaa aaaactggtc caggaaaaga gggaaactga aaattcgagg tcaaaaatta | 1260 |
| aataaactaa aattgtgaaa aatggtcgta gagagctgtg ctttcagctg gcattcggaa | 1320 |
| tttatgcact tattacgaat ttaacataaa atcccatttg atagtggaaa aattttcatt | 1380 |
| tttccagcaa aaacgtcatt ttttttgagaa aatgcagcaa tttgcgattt ctgaagttat | 1440 |
| ttttaacttt tttgaaaaaa aaaaatattt ttgaagagaa aatttcctga aaaatacgtt | 1500 |
| tttcaaaaaa tttacctcaa aaagtgccaa actgaccgac ttatggacga aaaccatca | 1560 |
| aaaatcgcta atttgcacac caaaaaaaag gggggggggg ggaaatgcaa ttttcgattt | 1620 |
| cacactaaag agcccacttc tatagcaatt tttgagtttc actcaaaata tctcggctca | 1680 |
| atgagctcca atctttctga aaacaagaat acagaggtgg ggcaagcttt ttgaagagac | 1740 |
| agcaaaaaac tgcatcaaaa tccatccacc caccgtcaag ttacacgcgc gttttcattt | 1800 |
| accactttg tcggattttg aagcttaata tctcggctcc tgtaaatcga atcggctga | 1860 |
| aaattcacaa gaaaacttac ttcactacga tcctcctgtc attaaatttt cgtgagctta | 1920 |
| gaccgaaaac tgacaaaacg ccaaactttg ctaacgctcg ccactgacgc caagccttca | 1980 |
| gacacgcttt cactaaatac agtctatttt tccgtgtttt catcagagac cacagtttta | 2040 |
| aaataatgcg ttttcaattt atttgatgtg atttatacat tttcccatca gaaatgctgt | 2100 |
| gctaaatgta ttcaatgtgt cttttttgagt gaaaccactc ttaatttatc agtcaacaga | 2160 |
| taatgttgct ttgtataaaa aggattcatc gaatttgaaa ttttcaatca aa | 2212 |

<210> SEQ ID NO 136
<211> LENGTH: 1481
<212> TYPE: DNA
<213> ORGANISM: Caenorhabditis elegans

<400> SEQUENCE: 136

| | |
|---|---|
| ggccaaaaat agtaaaactt gatcgttttc tgccattgaa aactgcgtta ctatcatgct | 60 |
| tggttttttgg gggcgctggt atagaatatg tgctcaagga agtgccggat atcagaaaac | 120 |
| tgatagtttt gatcaaaaag ttgtgtatgc ctgtctttct gtctgtctgt tgacactccc | 180 |
| tccgagaggc agccagagcc tcagagtgac aaaatgcgaac ggcagacgga atggaggaaa | 240 |
| aggatgagcg gtgctaataa cagtacacag tttgacgaaa atccaagttt attgagcagg | 300 |
| gcagctttaa gctgggaata acaaggcaa aaacgtagag aatatttagg gaattgggca | 360 |
| cgaagatcag caacgagcag ccatggcgtt gggagaacga agaaaagaag tgaagaatgg | 420 |
| ctacatttta ggccagaatt aatatgagca agggaataaa cagcgcgcgc tacgacactc | 480 |
| cgatgtgtac aatggcgcgc gcttgcatcc ttggcggcaa attcaaatga gaattattta | 540 |

```
atttaattaa tttaaatggt ggaatgatta ttaaagaacg aacaaacgga attgtgtgag      600
taaattaccg gcggatgatt atcgctggat tgtgggcaat tcttgccgat aattataatc      660
cgcaaagttg gggcggagga cctctactga ggccaagtca caacactgtc taccgtctgt      720
ctattctata tctagaagat gtcaacattc agtggttatt ttttagtaat aaaagtgtaa      780
aacaaaacaa ttcagatctg caaagctgaa aagtgatgaa aattgatatc ttcaattata      840
atttatagta ctttttttaat aattactcta attacacccc actgctttac tttgaaatct      900
catatctcgc tccattctga agtagtcaac tagaaacggt aaaaaatcca tagaaaattg      960
tttttccagg tgacaatttt taaataaaaa tggggtgcaa tagtaataga gcaattatgc     1020
taattttgtg aaactgtagt ttcaatactt taaactctat ctgtacgttg ttctctattg     1080
aaaaatacat accagatcag ttatcaattt catttctcat atgtcaatcg ctattaattt     1140
tactgataag aacacgctgt gtcagttgtg tcagttgtag ttgcaacgag aaatacaatt     1200 tcttttggg tttcttctta agtttctcgg cttgaataat gggaaaacta attaacagtt     1260
gactaaatta tttaatttta ttatcccgcc cttaaaaagt tacccaaaaa gatttagtga     1320
agttatgtcg ttctaatata atacttcgaa caacttgtgt cagttgtagt cagttgttaa     1380
aatctaaatt tggtgataag atagtcgtat cactagttct gcaacgttat tatttaaata     1440
gccggagatt gacaaaaata ttcattcata attttttaaaa a                        1481

<210> SEQ ID NO 137
<211> LENGTH: 895
<212> TYPE: DNA
<213> ORGANISM: Caenorhabditis elegans

<400> SEQUENCE: 137
tctttaatga taatttatgg gatctgtatt tctctttctg tcaataaaaa ttgaaaatga       60 ttttttacatt ctcaatatt tctaaatcat gtttcgtgaa gctgaagagt aaaattcgac      120
atttagaagg tttcgttaga aaaatgaaaa gtgtagtgcc agaggggact ttatctaaaa      180
caggcctgaa ggttcgaccc gcgttacagt tccagtctaa agtaataaca ctaattcaaa      240
ataatatata cgaaaaaaaa acacttgaat attatttgat ttttaaagat tttcaatttt      300
gaaattatca aatttccttg aatttgggaa tttttgaaga agtttcagat gcaggtttga      360
aatcctagaa tgtgcaagta tgaaaactga acaaaatgt atttatacga ctttttttggt     420 cactgccaaa cttataatcg gtcaaaacta tgtttgcaca aatttctaac attaaaaata      480
aacgatttta atttttttt gaaaattatg cctgtataca tttcagcatt ataagagcgt      540
ttttaagcga ttccctactg atgatactgt agcattctaa aattattgta gcttaatagc      600
tatcaatttt gtaaaattaa atttaaaaaa ataaatttga agtggatcta ttagaacctt      660
catacaatat ttcctactct tttaaatttg aaattttcg agtcagtgct agtgatagat      720
agaatacatc cattccgtag ttatctacgc tttcctcttg gaatcaacac atcaaaactc      780
aaagtacgcc tttattaaag aaccgtgctt tgtagtttta aattacttgc ttccattgtt      840
tgtagccttt ccttataaaa gatagcaggt tctgtttaac tatctcaatt tcaaa           895

<210> SEQ ID NO 138
<211> LENGTH: 1036
<212> TYPE: DNA
<213> ORGANISM: Caenorhabditis elegans

<400> SEQUENCE: 138
```

| | |
|---|---:|
| atttttgaac taaataatat ttcaaattgc acccgcaaat atcgtcactt ttataccgat | 60 |
| aaacaaataa agtttagtga tgacttatga taagaacctc tttgagtcta tatgtacgtg | 120 |
| aaacaaacgt taaagaataa cggctttacg tgttagtcat tcataaaatt tcataagttg | 180 |
| atctggaaat ttgtgttatg gacgttacgc cattatttct cgtcactcaa cgtctcgtca | 240 |
| atggtaattg ttttttcagag acggtgaatc atgtttcagt tgatgatttt aggaaacgca | 300 |
| tgccatgttg agacaccata ataatttaaa ttttttgtggg tacctttat tgggattttc | 360 |
| taacatttca gtcagaactt ttagtagaat ttttttatag atctttttttt ttcagcttaa | 420 |
| aattagtgtt ctaattactg tttaaaaaat gaaaactgaa acgtttgatg attttgtttt | 480 |
| taaaaatttt tcaatttttt tcgatatgtt tttattgatt gtaagatcaa ctcttttaaa | 540 |
| gtttactttt catttttgt taataaataa gaaaattttta ccgactttt agaaatttaa | 600 |
| tttattgaaa aactgataaa cgtcttgttt tgatcaattt tccaataaag aatacttttta | 660 |
| gcgttagtca caacatatac tcaaaatgtg tcaaaaaaca atgtttcgaa cagttttatt | 720 |
| gttttttta gcttcatccc gaacaactaa aaattgactt tcccgataac ttaagacgaa | 780 |
| taagtttaaa atttgaaatc tagttatttt tcacgatttt gacttttgtt ctgtccgcgc | 840 |
| cgaatctgaa acttgaacac taattcaatg tacacataag aatagacaag tagtgaatat | 900 |
| gcccattatc acacagacta catactttga ctgttccaag cgtcgcaagc gtcgcaagtg | 960 |
| tagcattttg agtcagtgat aacaatgtaa gaaagtatat aagaacatg catttgttca | 1020 |
| tttctattgc aaaaca | 1036 |

<210> SEQ ID NO 139
<211> LENGTH: 1435
<212> TYPE: DNA
<213> ORGANISM: Caenorhabditis elegans

<400> SEQUENCE: 139

| | |
|---|---:|
| tgattccaaa tgataattgg ctagtcttaa aacatttttat attttaggga attcgaaatc | 60 |
| aaaactatgc acgtcatatc aaaatcaatt tttgttcaat attaatgtta tttattcatt | 120 |
| tgacagctat caataattat atttattaaa atagctgata gaactatttta gggcattcac | 180 |
| aaacatttca gaatgtttcc gaaagttcgc aacagcggat tcgccacaat gcttcctcat | 240 |
| aacccatttg taacaccatt tttcaattgt aaacatgctt gtcaaaaatg cagtatcatt | 300 |
| gggttgcaaa acataactcg ggcatttgta tttaaatata ttgaagttag aagaacggag | 360 |
| ctttgacaaa caggcaatga atggagtttg tttcaaataa atgaaatcac atccaacaaa | 420 |
| aaccaactct gtgtatcaat cgcctcttgg caaacatttta tcggagaaac tctgaaacgg | 480 |
| gtactatttc tagtttagtt ttggtatatt tcacaactga acaccttcac actgtttact | 540 |
| tatttccact atatcagcat tatttctcga gttccgataa tcgtccaaca ttctatgagc | 600 |
| tttatctcca aactggctat atcgtaaatg cttgaaaaaa taaaaaggat catagcaatc | 660 |
| cgactcatta gcaggtgttg tgggaatatt atcaagaaat gcgttgtaat tctccgtagt | 720 |
| attttctgtt tttagctttt cacaaatgtt tcttatagta tccgaaaagc atgtctttcc | 780 |
| atcttctaat tgatcactga tatcatcaat ctgaaaatat tagattgatt ttttgctgag | 840 |
| aagaacctca aaaccaacta tgaaaaaatc atttagtttg atgcagccgt cacggtagtt | 900 |
| taacaaatgt gtacaagcaa cttggacaca aggacgaggg tcattgatgt agtaagattg | 960 |
| caaaaaagga actcagaaca gtaagaaagc caagtttaaa agcattgttg tcctgaaaaa | 1020 |
| tccttattag tgtgtgataa aaataaattt cacaagttgg acagttatta tttcacaaaa | 1080 |

```
taaaatatta ttttgttgtg tgtactttac aattgacgaa aagatcaaac cgacgcaaaa    1140
atgatcaata taatccgttc atatttgttt ggtaaagcat ttttctgcta atcaaaaact    1200
gttggtgcaa aataatcgca cgttttttcg tttttttttt aatttttttgg tctcaaaatt   1260 acataaattt tcggaaacat ttctaacgct gaaaaaaaca tttaattgtg tgaagtgtag    1320
ccgtgaaaat gtgttaggtg ttgctaccct cttatcttca atcttatcat gtttttgtct    1380
cctttataaa gaattgccgg tgaacttgaa gttcagatgt ataactgttt ctatc         1435
```

<210> SEQ ID NO 140
<211> LENGTH: 1043
<212> TYPE: DNA
<213> ORGANISM: Caenorhabditis elegans

<400> SEQUENCE: 140

```
tcccttgtta tttgattttt aagatttgcc cttatgtcag tgtcttctgc atgagtacat     60
gcatatttgc atattattag aatgttatgt ataaaaagaa aaagagagcc acctcttaac    120
gataatccaa tttcttgtta cgcagaaacg cctcgttttc ctgtggactt tcgatatctt    180
caacatgctg ctattatcac tcccatgacc cgtttcctat ctgtttttat ttcgattact    240
acacatctgc tagaaacaca cgtcacgtgt gatttgtact caccgttttc tcctttcata    300 cttttttagcc tacaaaccac gaattgcttt gtgacttgac tcaattttct cccgaaactt    360
tttttcgtcc tcaattccca ctacccattt tcttgcttct ccctgttgca atattttcaa    420
tttcccatcc aaaaacggcc cgagcacggg ttttctttttc cttttttgtag gttcacttct    480 tcttttttctt cttcgtttct atttttttac acaatcattg ttcacctttg ggcaccccag    540
tgaaacattt gtttgataaa aattgtgtgt tccacggcac taaccacaaa atctttgcta    600
caaatactac tcgtattgtt tgtgatgact gtggtgaaag taagaagaat cgagagacat    660
taggggacaa atataaaata gaaacgataa ggcgacgaaa acgcacattc ttctcgattt    720
ccgaccgtca atcgctgagt gaataattgt tgacggcaac tgggaaaatc tgtgagaaaa    780
taatgtacca tgttttcgaa tttctaaaat tagagataat ttcttccgtt ttctctttta    840
catcttgttt tcttcatttt acaacaaatc cttcttcttt ctcttaccgc tttgtgcact    900
tgcactgtaa atgacggcaa cttacggacc tagcgttcga cgaacacagt caaggacgct    960
cacacatcgt cgacgggttc acctgctctg ttgcagtgat ttttgatgtt tttattggtg   1020
actagttttt gactttttac aaa                                            1043
```

<210> SEQ ID NO 141
<211> LENGTH: 1364
<212> TYPE: DNA
<213> ORGANISM: Caenorhabditis elegans

<400> SEQUENCE: 141

```
atttgaggac tgggatgtca ttaggactga aattattcta aattagataa tatattttaa     60
ggtaaaacgt ctgtttaaat tatttgtata agcaacaaaa aataaacgaa aactaaaatt    120
ctacctgaag ttcaggtcct gaacaataac ataaaaaatt tgggaaaaca cgaaaaaata    180
aacttaaaaa attaattaaa aaattaaaga ttaaattaa agattaaata atctctagaa     240
catagatctc taaaacactt cccgtagcgg ttcattttttg ttcgagtctg actggcgttt    300
tctatgggaa acagaaaaca acacgctgtt tgctcagttt cgagaatttt ggaattcaca    360
gacttatttt gttttgccgt atatgatctt aatcatagac atataatatt tatgacaatg    420
```

| | |
|---|---|
| ctttgctata attctgtgtg gtgagcgttc gcagaaggtt ctgcacaatt ctttcaatga | 480 |
| aaaaaaaaag aaaattataa gaacttatta gaaaattata agatgtagaa agttattcat | 540 |
| aaaagttagt attcccaaga aaaatcataa agaaaggttt ttttcaagg ttttttcag | 600 |
| attttttggcg ttgttcaact tgtattgcaa tcattattat tgcgatcatt agtaatttaa | 660 |
| tataatttgc tccagagcat tgtaagcaa tgaaatccaa ttttccctct gtggtgtttg | 720 |
| gtttagaaac ttttgcaatt tcgtcttgat gtgccgcggc atgccgcaaa aatcatagg | 780 |
| gatttgattt cccagtagtt gaagttggca gagttaacta taaggatgac ctaaaacaag | 840 |
| ttttaggcta cttgttatag acatggactt cgatttctaa tttggacagc atccgctaca | 900 |
| gtgaaagtct gcggattgat ttcaaactct ctaaaatcga acgagttttc aattttttt | 960 |
| tcaattttga tgcctaattt agtgaacacg gtaattatag tttcttgtat ataaaacccg | 1020 |
| tttaactcct taaattactg tttacgtttc gtgttgtaat aaacgatctc ttgatcttca | 1080 |
| ttcaactatg ctggcacaaa aatagacaca attcgaagag gcgcagaggg agtaacagac | 1140 |
| acaaaaaatg ttaggacgtc tgcgatctcg ccggtaagaa acactgaaaa tactctctgc | 1200 |
| gtagtcacga aagctacaaa cttaatgta ttcaaccaaa taatgttaac tgtataaaaa | 1260 |
| gaaacaaga aaaaaagta taaaagaaa ctttaaacca aaactaatca tcagattcaa | 1320 |
| tatcttctat ctgtttgaca ttctatttct gtaagctcga aaat | 1364 |

<210> SEQ ID NO 142
<211> LENGTH: 625
<212> TYPE: DNA
<213> ORGANISM: Caenorhabditis elegans

<400> SEQUENCE: 142

| | |
|---|---|
| agtagagtca atatcttgaa atgtttagaa ttctcgcgta tctcacatgt tgaggtgaga | 60 |
| tatttgtaat gaatagtttc atagtctttg gccaaaatat gattatacgt taaagcaaat | 120 |
| tttgatgtta cgccgtttga agaaatgttt ttagcatgtt taacagagat tcagactaaa | 180 |
| tttattctac acagtttctg aagggatatt ttttgccaga gtcaatttc ttgtaaacca | 240 |
| gtgagcctta ggtacataga aaattttgaa aaatatccaa gaataaaatt ttttctgcat | 300 |
| gccttattct gggcttattt tttgcggttt tcaattcaat tttatcgtat ttcaaaaaat | 360 |
| taaattagaa caaatgcata ttcattttta catccttttc taattggtaa ttataatttc | 420 |
| aaaaatcttc tttgcttatc atttgtaaca acaactacaa aaactgtact cgtagtttta | 480 |
| tctaaccgta ttctttgacc gcatcctccc ttttgaccat tcaagtaaaa agatgacaat | 540 |
| cgccgtctac atattgccac gtgacgcaaa ttacttataa aaccattcgt ataaatattt | 600 |
| cattgatttc ttgaattcaa aaagc | 625 |

<210> SEQ ID NO 143
<211> LENGTH: 2328
<212> TYPE: DNA
<213> ORGANISM: Caenorhabditis elegans

<400> SEQUENCE: 143

| | |
|---|---|
| cccgaatttt tttatcgcag aaaaccaaga tggaataaat aaatggataa tctaattaaa | 60 |
| aattgtaatt tactatttgg aatcaaaaat aaataaacaa atcttataat atgtcagcaa | 120 |
| taaaaataat aaaagaacaa ttgaaagttc aatgtgttgt caagaaatcc attaaagtat | 180 |
| cgtcatcaac ggggtcatca atttccatgt tgttgttatt gtcttccata acatctattt | 240 |
| ccatgaagtc ttagagtact gacaatagtt tatttagtaa attaattttt gagaaagttt | 300 |

```
cttgacacat tgctttgaga ctttgattaa atcacaaatg actcactatt atcataattt    360
tctatccaaa atgttgattt catttcaatt tccattgaat cagctattcc attacatcca    420
tcagttggtt tacaaaatgg gaccagtggc ctcaatatct gtattttctt cctttttgt     480
gaaaatcgta cttttgaaaa tactaatgga ttctcgttct gatcgaaatg aggaaactgt    540
gctgttttct aagaacactt gagacgtgga ttttctttgt tgttcttaaa tacgaaaatc    600
aaatttactg acaaaatatc taaaacttac aatcacttcg ttgctgtagg gataatcaca    660
aaaatttgac atgatttct ggttttcatt ctgaaaaact gggagcattt taatttgaaa     720
aaaacgaacc gtagtctgcc ccaattgatt tgttggtaaa ggaagtgaat taaagcgaca    780
aggaatacat ttatctgttg aaagtgaatg cattttctg gaaagacgga ataaattgaa     840
attaaaacaa tattcagtta aagggaaact gaattatccc aaacccgggt tatttcaaaa    900
cggaatctac atcttacttt aattctgatt gtcagcccta taacaactat ttcatctatt    960
caaaagata caaaaataaa ccaattaaca ttacttcgta gatacctcat cacatgacca    1020
ccctctcaag ttgatataat taactttcta aattgaccaa aagtgtttgc taatgtgtat    1080
agggtatagt aaataggaag gagttcggaa gttcgatgag agtaaatatc ttttgtgaaa    1140
tatctattgg aaattagcgg aaaaaagata aattttctcc tgaagtgcac aactaataac    1200
gaatatctta atgtggaaat aaatcaaatc aaatcaatat acatcccaat catgacatcc    1260
aagaacccca caaaaatatg ttcctaaaaa ctaactgata attaatttga atgtttccaa    1320
cagaaccttg ctcgcttttt gcacattttt ccactttgtt tcgctctaca cgcttgtatt    1380
tttttaatta attatatttt ttcggcctca ataaaaatta aaattccaga ttgaacacat    1440
ttaatgtcag aatataatta cagtaccttt ttatgacaaa acatatttcg gtataatctc    1500
agatttccac ttcttgtttc atggcccaag ttttttctcaa tgctcacttg taacggaaaa    1560
tggagtcagt gaagctgttc aattctagat aatatgatgc tatcaaaggt cttaaaattt    1620
agataaaatg atgaaaatga cgacattaaa gtgtagcctt actgaaaaaa ccaattattg    1680
aactttaaga aaaaaaacat tttgaaaat aaaggtaatt catttttcgt acacctaaaa     1740
tttgaaaaac cgaaatttca gtgagaacgt cttcaactgc atcaaaaaaa ttgtgaagaa    1800
aatcgaattg aaaagagagg ctaaattggc ttcatatctt taatttagcc gattatacac    1860
gtcgggccag tctttttttaa atgactgtca tggaggactt gatttcaaga ttggaagtga    1920
tgaactacaa aaaatatcaa acaatttta actgcataaa aacggttttt ctccgggatc     1980
aaagatgttt tcggtatcaa gtcacattca tggttcatta aaacatacta ttttctagt     2040
cttaaaatgt aatctgtata atttatgtt gttgattgaa ctcataatat gacaggattt     2100
tttttgtgat ttctgtaatg aagtacagtc ttacacgaaa actagagtaa tacaagtcat    2160
aaatttatt cgtcttttt cccgtagtcc tttcaataat gtatgaaaag catttacaaa      2220
ctacaactct ttcaaaaact agagttctta tcatacaaac cacacatttt ttgcagctct    2280
atataaacca actgataatg aggttttgtc tactctcatt actcaatt                 2328
```

<210> SEQ ID NO 144
<211> LENGTH: 948
<212> TYPE: DNA
<213> ORGANISM: Caenorhabditis elegans

<400> SEQUENCE: 144

```
gtgaatacca caactgaatg tctcgaatat ggagccaatg attcggaaat ctatgaggaa     60
```

```
atggcatcga tttgcaagta tattgtacgg gattcgagag ctcacgggga ctcggttcca    120
gagtgatttt tgttgttcgc caattttatg attgtttctt gttgttaagt tttctaaaaa    180
ataaattctt tgattttaat aaatttcgaa aattcaaata ttatggggac gccgagggaa    240
tcagggtgca aaggcgctct aacgccaaat gacaaccgag cattgggtct cgttaggaaa    300
tggcggcaaa cgagacattt aaattttta ttacgggaac acaaaattct aataatgcgt    360
attgcacaat atatcttacg cgctaagtat ctcgtagcga aaactacagt aattttttaa    420
tgactacgct tgtgtcgatt tacgagctcg attttagaga tgaatttatt ttcgaatagt    480
gtcagcgata tttcgcttta atttcgaatc gagcccgtaa atcgacacaa acgctacagt    540
agtcatttaa agaaattact gtagttttcg ctacgagata ttttgtgcgt caaatatgat    600
gcgcaatacg cagtctcaga actttgtgtt cccataataa aaagtgagag ttttcatgcg    660
cccttggagc gctactgcac ctcaatttca aaaaacgcat ttttctgcgt ccccataata    720
caccgggatt ttcttttctc ttcgtctgaa aacaatcaa tcatcattaa aatcatcatc    780
tatcaccaat acagaatcca tagatcaaac agatcaaaaa accaacttga acgcttgcag    840
gcaactacga taaaaatata ttttgtagtg tagtcatcat atcaatcatc tagctataat    900
aatgcctgcc gtataaatac aaaacacgat gatgatcttt ttgcgaaa              948

<210> SEQ ID NO 145
<211> LENGTH: 1233
<212> TYPE: DNA
<213> ORGANISM: Caenorhabditis elegans

<400> SEQUENCE: 145
attagagaac ttttcgagaa gtctaccgtt gtagttttcg aaatagtaat ttatttagtg     60
acgtttataa aggtttacat gatttggttt ggaaattttt taggagttta ttcataaaaa    120
caaagtaacc atggacattc agaagtctta tagtacacgc gatcctaccg tacccttcag    180
tatttctatc agattgatag ctttcggtag tcaggtacag cctaaaaaat tcctgcttgc    240 cttttttgcct acatgtctgc ctaccttcag tcataatgcc tacataatga tttttttccaa    300 ttgaaacttg cagacagaaa ttcaaatggc aaaaagaaac aaaacaccgaa acattaatca    360 catttctttt catatcagtt ttcctgtcaa agcacatttc tggagtctgt gtgtattttt    420
ttgtgtcttt atgtgatcgg tgttgtgaaa tttgtagttg atgttgataa catacttttt    480
tttgaaacaa aaagtgattg attaggcttg aattcagaga tatgttcgtg atactttgcg    540
attctcgagc caaaaacacg gtatccggtc tcgacacgac aacttttcg caaaatacaa    600 gctgatgtgc gccttgaaag agtactgtaa tttcaacctt tcgttgttgc ggaatttca    660 tagtttctcg ttcaaaatat atgtatttat taaacaaaaa actaaaacaa acaattgag    720 aacacataaa ttgtgaaaaa tcaatgagac cacagcaaaa aattttgtat ctacagtact    780
ctttaaaggc gcacatccgt tcttatttc agcaaaaatg tcgcttcgag accgggtacc    840 gtatttttt ttgtgcaaaa ctttaggtct aggtaatatt aaaaaaaaat tccacaaaac    900
tagaatctag agcttttccat taaattttt gatgacattt gaaaattcat gatgatttt    960 ttccaacaat ttcgaaatat ccctcttttc acctggtcca ctgaattctc tttccgaaag   1020
accaccacaa tttcagggct ccgcccattt cgtggtttgt agccttcccg accctacgtt   1080
tttgatgaca attgtgagag aagtgagagg ttcagacaca aaaagcgacg tggtcgaatg   1140
agtataaata gagagtgaag tttccaattt ccctcacaat tgtttgtttg caatccactt   1200
tccaaaaaaa cacaacttca atcaaaaatc att                               1233
```

<210> SEQ ID NO 146
<211> LENGTH: 656
<212> TYPE: DNA
<213> ORGANISM: Caenorhabditis elegans

<400> SEQUENCE: 146

| | | |
|---|---|---|
| gctaaacttt cgtattcgac tgataatgag aacgtggagg agtatcgtga ggttctcact | 60 |
| gaaaaagctg aacgtctcat ggaagactta aagcgatggc acttgtacag taaagatgtg | 120 |
| acaaaggatt tagaaacggc ggaaaagttg actttatgat aagaataccg ataaaattat | 180 |
| gaaatttctc gaaactttg aattgtgaag caacttctta ataaagtaac tcattgactt | 240 |
| taatttttaa accacggctt agagaaaatt aaaaatcaaa cactgcagct tttttgatgc | 300 |
| gaaaattcat tgatatggaa caaacctcaa atttgataaa taatacaata atttgtcaag | 360 |
| aaatcacaaa aacgttcttt tgaaatgcaa gttataagac atacgcaaga tgttatgtcg | 420 |
| gtggctggtt ttaactataa aatacgaaac aattgacctc ctgacacaaa atttccgagc | 480 |
| ttgatttgtc tgatatcatt tgtgctttgg aattattgtt tcatgtgcat aaaatctaca | 540 |
| ctgtgttcat tcacgataag aagaatttca gacagaaacc acaggaggtt catcgatata | 600 |
| aaatgctaat catttgattt aaagaaccat actctttta ctctcgtcgt taagaa | 656 |

<210> SEQ ID NO 147
<211> LENGTH: 1275
<212> TYPE: DNA
<213> ORGANISM: Caenorhabditis elegans

<400> SEQUENCE: 147

| | | |
|---|---|---|
| cagctatccc gaattctcga gcgacatccg tcatctgaaa gagatactaa tgtcatgtga | 60 |
| agtggtatta aaaatatagt aagcacggta gaaacattaa cttataaaat tgagatttct | 120 |
| gataaataaa attttccgg gagttctgta aaacttctta cggttttaac ttgataattc | 180 |
| catagggttt aaaattcct tttgtttctt gagtttcttc tcggaatttg aacaaaaata | 240 |
| acgcgtttaa tctcgaatca gtacaatgat ggactacacg gcagttttaa aaaaccaatt | 300 |
| aataataata atcctaaaaa atgagaagaa tatttaagaa aatgtaaaag ttttccgcgg | 360 |
| aattccgcta aaattcgaaa attgaaagtg ttcaaattgc aagcgattgt gcattcagac | 420 |
| gtgacagtgt ctggggtgta ttgcgtactc gacattttaa ctgacgacac ttgtactttt | 480 |
| gcgccatact tccggagctc cagctccgcg gagccctgag caattatttt tttacttttt | 540 |
| atgaaaagct ttctatagat atcttttaag aagttacact ataattgtgc aaatcaaact | 600 |
| ggctccggac aacacaaatt tcgtctatac ctttatgatc ttttttgtt aaacaagtga | 660 |
| aacaattatt tccttttcaa actgctcttg tttcttctct ttattaatca atttttttt | 720 |
| ttttgctttg tgtaaattaa ttgtttgtcg cggatgagct aattctgagg tttgaccagc | 780 |
| agaaatctgt tttctgaaaa atcaataact cgccgcttaa ttttggtttt attcaagtga | 840 |
| tatgcaatta gaaggttcta atcatttata tctcgctgaa agatctcaga tttcaagcct | 900 |
| tttgctaagg attttaattcc taaaactttt tttgacctat cattttttgt gtgatctacc | 960 |
| gctgtaaata cttgttgttt tgcggctaaa ctctttcaat gttccaaca agtgagccaa | 1020 |
| tatcaagtaa aaaagaaaa atcgttttct attcaaccat tttattctgt aaataatatt | 1080 |
| aaattcatct tcacggtaca atcttcttct cccatctaat aaagtccacg cacactccgt | 1140 |
| tccgtcgttt ccctattcgt tatcattcat catcttgcca ttttcttctc cgccaaatcc | 1200 |

```
cattgtctta tactaaattt catcctctcg tctgtagaag tgtatattat tgaaaaatta    1260
aagtatattt tcagg                                                     1275

<210> SEQ ID NO 148
<211> LENGTH: 358
<212> TYPE: DNA
<213> ORGANISM: Caenorhabditis elegans

<400> SEQUENCE: 148
cgcttcattt tccaacaaac caagtactgg agccatttac tataagaact aaattaaata     60
ttaaatatat cgtttcaaga attcattgga atgaggcaaa agtaaatact taggattaaa    120
aaatccagct ttatattaaa aactttaaag gcgcatatga gatgttattc gggtcccgca    180
gcgctcatgc ggggtacgat agtacttcaa agaattcgc gggaatttct tttatgcggg     240
aaaacggttt tttcttgttt actagttcct ttctttcgtc taattttgat atcttgtgtt    300
tttttccaat tataaaatgt ttgtctcttc ttaaatttga aattttgaaa ttttttcag    358

<210> SEQ ID NO 149
<211> LENGTH: 2636
<212> TYPE: DNA
<213> ORGANISM: Caenorhabditis elegans

<400> SEQUENCE: 149
ctctccttct ttcatattct gtgtccactt ctcactcatt gaatcataca tctctatgtt     60
ttctcatagt catcatatat tgtcagctgc agaaatctca tcattttcc aaacgaaaag    120 ctcttaagag aaatgcttgt tttctgtggg gtacagcgaa tggcttctgt gggaatgcag    180
tttgtgaatg taaatagatt gttatgcagt cttgcaaatg tgtcggaggc caaaagtaga    240
gtagacatat ttgaaattta tagctttgag tgtccttagt ctattttgat atttcatttc    300
tgctttcctc agtctctcat tccagctgca aaaataaaa ataagaaaaa acacgaatcc    360
cgtccattcg ccattcaaca tagatcatat tcctcagatt ttttgcagaa tatgtaattt    420
ttgctgaatg ctcgctctat tgtccttcat tggttatcaa tcttttttgca ttaatagctt   480 taattttga tgttttcgaa agattaggga aaaattttt aatgtgtctt ttgtgacttg      540
agattatatg ctacactgaa aaaattggtc gcataacatt tcagagttca aagtgttttt    600
tctttcgatt gtgtaagcgg caaaattcta ctttatcatg cattttttgtt tcaatcaaaa   660 atttgatgtg atttgtacat ggcgtcggtt tggtactagt tgtccacttc ctcagccatg    720
aaaagtgtga gtaagtgata acgtttatta tcttttttga attcattcta tgtttaagct    780
acacgtattt aactagctga ctcatttcca ccaaatatgc caaagacct ccgagatttt     840 tttttgaaga taatttcgat ttcgcagaaa aaaaaacata taagtgatgt gggggtgtgt    900
cgccttcttc agctttccat agtgaaagtt tcgtaaaaac aagcttgcta tttcattttt    960
ccccgttcta ataccttgtc gcccagaaaa aatatttata tgatcttttt caactctttt   1020
tttgtaaaaa tggccaaaga ttagctaata tttgtatacc atcaaagttc tgccaaaatc   1080
tcgttgaaac atccatcgta gaacactcat tgggttccat caatacattt tttgtgtaac   1140
atcagtcgat tgttatcatt cgtatatgca tggtcatctc aaccgccctt acgacgtctt   1200
caaccatttt ctcttctaac tctctttctc tcaatttcac ttctcactac tctagtctat   1260
tcaattcttt gaaaggcaa aaaaaaatgc ataaaaagat gaagaagaca ttcaacagac    1320
gggtgtcttc cttattttta ttcaaatcaa acaaatggc gaccttctta ttcttctctt    1380
ttgcccgatg attcatttc ttttccatt aattttgtta tctattgctg aataacccgc     1440
```

```
tttactgaat gtgtggactg gcatttgcca cgttgcattt tggaaaagag ccgatgtagt    1500
tcttccgggt atatgtattc acagaacgat tcataagatc agacatatag acataaaatt    1560
cagcgcattc tgccttgtgg tttgtcaact acttccgtct ttttctgca tattcatttc     1620 ccgcttctgc tgtcttgttc atgaactctt gaactttgca ctttgccctc tttttaagtt    1680
tctctcgatt gatgcagcag cagcagactg tcattcatat ttgtctagtg atttcgtagg    1740
ttcaaacaac ttattaagcg gtttcaccta aaatttcgca tcccaaaata aaagttcaat    1800
tgcgaactag aagtacccag aagcgaaatt ttttttgcttc aaaaatacgg tacccggttt   1860
tcaacaaaat cgttttcaag tgacatgagc gattttcctt tttatggaaa atttctaatt    1920
caaaaataaa tatttgaaat acctttttta gattattata tttattcttg gtattttctc    1980
tattcccact aaaatagact gatacgagaa cagttcttgt ttgcgcaaac tcacattttc    2040
tctctctatc tctccgtctc ttcttccgta tctctctgac ggtcccatac tctctcactc    2100
atcgtcagac accaccactt atcgatctat tttcgacgag tgagcggctg ttcgtcgcat    2160 gttttttttat aacttgattc gatcaatttc atcatatctt cttcacttat ttgaatttcc   2220
gttttgaaca tcattttttcc gtcggaaagt tgaagcattt gtttgatttt ctcggtggaa   2280
gattagattt caaaactttc gaaatttaac aatagaaaaa gagaaaaaag tgtagttatt    2340
aggaaatatt ttagacaatt ttgttggcaa ttaattgaaa ttaatttctt ctttctacat    2400
attttaaaaa tgtatctttt tttctattta tatttccttt ccggggatga gcgacaatta    2460
ttttcggcag ctctacaaaa tgactgcttg agataaaatt tctacttaaa atttattgtc    2520
gaaagataga aaaatgttgc ctcaaactgt aatttttgtcg agttgcccaa ataattgtc    2580 gcacacctca gattttttttt tctattattt tttaaataat taaaattaca gtggaa       2636
```

<210> SEQ ID NO 150
<211> LENGTH: 2645
<212> TYPE: DNA
<213> ORGANISM: Caenorhabditis elegans

<400> SEQUENCE: 150

```
tattttgact tttgaatttt ggaggttttc aagaataggc aaacgttttg gcatcttttt     60
gaaaaaatct gattttttgg tagattctat ccactttcta aaaattctac atgctctgaa    120
caaagtggaa aatacactga aaatttcaga tcgaagtttc aggtgtttga atttgtgtaa   180
tagtctgaaa aatctgaata taagctttca aatgagacat ctcgaagaaa atgaatttgt   240
gaaaaaatcc aatttttttc taattcgagc acaaaatgat gtcggtctat cacacctcct   300
tgttgttagg tgaataattg ttaaattctt aatctttatg atataacaaa gataggcttc   360
taactacgtc acgcctacat attcaatgaa attttgtagt gctactacta tttgtgcaag   420
ccggaatatg aatgtccttt catttttttt cgtcccaaaa gtatataaaa tatctcacga   480
tatactcaga gattgggcaa caaagttcag gagaactttt gatgcacacc ggaaataaaa   540
gggcttcact gctttttttg ttgaattcat attggttttg gcgggaaata ttgaatcatt   600
attgatactt ttgaaacagg aatagacagt attttttcgta cggaaattcg ataatttccg   660
aaaatgttcg gttgcctccc tcgccccctt gaaattaca ggagactaaa attcgaagaa    720
tgcgtattac gaaacgtata cgcgcaaaat atctcatagc gaaaactaca gtaattttttt   780 aaattactac tgtagcgctt gtgtcgattt atgggctcga ttaaaattga gcaaaaaatt   840
tagaaaatac tatgcaggcg cggaggaaaa taaaatatcg atatcactat tcggaaacaa   900
```

| | |
|---|---:|
| attcatttca aaaatcgagc acgtaaatcg acacaagcgc tacagtagca attttttaaaa | 960 |
| aaattactgt agttttcgct acgagatatt ttgcgcgtca aatttgctgc gcaatacgca | 1020 |
| ttctcagaat tttgcgttac cgtaatatac acggtgaaga acacgagcca ccaggagtac | 1080 |
| ggtagccctg actttaattg caaaaaaaga gaaaacagtg aaaaaaatct gtatataatt | 1140 |
| gctattattt ttaaatttcg caaaaaaaat tagaaatgac cacattaatt ttgaattcct | 1200 |
| gcgcgaatga attctatttt ttgcgtattc ctgcaatatt tattggattt tctcttagcc | 1260 |
| taaagcctaa aacgcagaaa tttcgaaata ataaattgac catttttgaa ttattggtgc | 1320 |
| aaaattgaga aaaattgtga aaaattatac catttttttga acaattacgc tcagcttact | 1380 |
| aattgtaaga ttactcagat ttatggcaaa acacgatttt tacgccttca aaaaatccta | 1440 |
| gcttttggca aaacttacag gaaattaaaa aattcagaat aaaaagtaat aagatccagg | 1500 |
| aagccatgac tcgaatcatt gtagttgaac tgtatgaatg atttgatccc agcttcttcc | 1560 |
| gccaccctaa acaccccata atttccgttt tccgcttgaa taggaaatgt tgtatatttc | 1620 |
| tgtactcctt cctgaagtat taaaactcgt tttcgtttat taaactgttt ctttttttcag | 1680 |
| atcactcaac ttcctcttct caacgtcaac ttcgactcgg ctaattataa ttttatttat | 1740 |
| ttttctgatt ttttttaaaat tcttgttttt tctcaaattt ccaatttcaa catcatctta | 1800 |
| ttttcaaata aaaatattta ttttgcgact ttctattaat ttgaaacagc gaatattgtt | 1860 |
| aattattaa gtaaatttaa tcatttttaga tcgttttcaa ccgattttcg agggctttcc | 1920 |
| acaaattttg tacttttaaa taaatttaaa gtttattcta ccgaaaacac tatttatttt | 1980 |
| tccacgtgga caccgccaat tttctctgaa aattctaaaa ttctggttga aaattaattt | 2040 |
| ttaaagcttc ctcacgagaa aagcgccaac gcacgaggag cgcgccagca aacccgcatt | 2100 |
| gacgcagtct cggtgcactt ctgaactcca aaacacactg ttcccgttcg attttttctcg | 2160 |
| cattttttcat agttttttttc gaaattgaag cttttaaagg tgttttagac ttgattcgaa | 2220 |
| gtgaaatatt gattgattga gccggaaaat aggcaaaaag ttctggaaaa acgcgcgaaa | 2280 |
| ttaaaattcc agtgactttc gagataatga tattgatttt tccgagtaat taagttgata | 2340 |
| tccagctatt tattttttgcg tgacattcta attaccggat tttcaaagtt ttttcgaaaa | 2400 |
| aaaaacaaag caaaatcgat ttatttcgaa ttactcgcga cttctcaact ttgaagctga | 2460 |
| aaatagttag ttttgttttt tctgttatca gtgcgcgctt tttctgcaat aataacattc | 2520 |
| cgcagtacga ttttttcaaa tttttttgctt ttcgagaacg gaaaatcaag tttatttcag | 2580 |
| tgtgcacgaa aaacgagcga gattctgact tgaccagttc gttcggaatc gactcatttt | 2640 |
| tggag | 2645 |

<210> SEQ ID NO 151
<211> LENGTH: 1848
<212> TYPE: DNA
<213> ORGANISM: Caenorhabditis elegans

<400> SEQUENCE: 151

| | |
|---|---:|
| gatctgttct ttccgaaaag aagtagttaa caggtgcggc ttcactgggt ggtctcattt | 60 |
| ttcattttaa cctgttaatt tattccggct tcacctctaa tccttaatga cattaacatc | 120 |
| ttcctaatgt gtctaagctt ttcccacgga aagctaattt cctctctctt attttttctca | 180 |
| ttaccgttct ggttgagctt catcttatac cgtgaatggt ttcataatta cgtgctacat | 240 |
| aatttgttat gctggtcgag gctcaacgtt tcgaacatct ggctcttttc cttcagctaa | 300 |
| ccacaccact cttcgttaca atcccttctg cgcacacata tcctatctac cagccggaca | 360 |

```
gatgctcgtt tctcggtgca aaacgttgag agttgagatc gagcagccgg ttggtagttc      420
ttaatgacaa attgccaaga cttttttctga attattttag gatttaaaac ttttctaaag     480
tattacgata gttcataatt tcttttcttttt ttaaaaattg gctcttttttt gtaatgtatg   540 gtatctaact aaaactaggc ctcatttcca taactattct ttaaattgag ttgagctcaa      600
agagttagac agaactggtg tgaatcatag aacccacctg tgtttttact ttctttgaaa      660
aatgtcggtc acttagtcgt ctctctgtct gttccttttc ctaatcacaa gtaacaacac      720
acagtcttct ttcacatata ttatttgttg accaatcgta gggtcaacta tctagtactc      780
gagaccgcct atttgaacag agctcctcac tgtcaccaaa tgtaccgtat tgctttccgg      840
ctgttattgt tgttatcact gcttcttctt cctatcatgt tacccatcca actatacacc      900
ttagactagt catcttattg atatacattc ctcccatcca acacaacggt attctattta      960
tttatccaat tagtcatagt cgtaccacca tccagcacga aggtgcctct ttagtaaaga     1020
gtagaaagaa gaaccggatg ggaaatgttt ttgttacaaa aatgacacat attgtagtgg     1080
acagaaggag tgagacagac atgagcaagc caatttgttt ataattttctc ttctagaaaa    1140 aaatacattt ttccatactt cactagtcaa aacctttcac cttttctaata catctcgtaa     1200 accataatct tgatagttct gagcatttca atacgaaagc ttctcactgt ctagatctct      1260
gactgagtgc cctcatcaaa agtgcaatct gtcatctgtt tcctcataat cacggagcac     1320 taattttttct ctctgcgtct ctataatcag atatctctcg tcactaagaa ctttccgaaa    1380
tgtttatgct tctcatctga ccacttcggt tccgcacaaa aaagtacggc attccaaaag     1440
aaatctgatc cccctccgtt cattcgtggt ccgagtcggt gccaccagtc gttgcgcatt     1500
gaatatttgt ttggtccgtt cccctttcttc tccgactgct gacctcgggc actttgatga    1560
ccgggccacc acctcagtac ccctctatta caccctcttt gcctccgcgc atatgactcc     1620 acccccttctc gtggaaggcg tgtatctccc ctcttttccg ctattccctc gatggatata    1680
tattcaaatg tatgtgtgtt cctgacggga gggcgtctcg cttgagagca tcgtcacatc     1740
ttttacaatt ttacttatga ttttacttca tcttcttctt cttactgcga ttttgatatg     1800
cattcttatg taaactatta ttattccagg tttcctcact cttttcaa                  1848

<210> SEQ ID NO 152
<211> LENGTH: 1957
<212> TYPE: DNA
<213> ORGANISM: Caenorhabditis elegans

<400> SEQUENCE: 152
taggttaaca ctgataaatc ttgcagaact gttttatttt attaaatgag acattaccga      60
tctaaataaa tttacaatcc catcaaactt tctcctttat cctccagaat cccatcattt     120
tcatcggcac ttcttcaaaa gtttaaatgt gagtgaccgc ccgtctcgct ctactaatcg     180
tatatgcaaa ttttctttga tatcatagaa cctgtcatac ttctccaagt atatgaaaga    240
caattaaaac tactgagaga aagaagtagt tcgcgataaa aaagtacata taatacacct     300
tttcacctag aagagatgct ttcaacttct acttttctgg tcatatgtaa atagttgggt    360 ttttttgacag tttgacaggt ttacggcagt caagacgaca aaaatgggtta tcaaaaggag   420 ctggcataca gccaatacca ccagttctga tcttttttacg attatcaaat tgtacatggg   480
gggttaagtt gaattttagt ttcattttttt caaaagttta aactcgaaaa ataactgaat    540
tgaaatatag tgaagttggc aatataccaa gggtagaaaa tcagacgagt gattttattt     600
```

```
ctagacaatc ttaaattgct caaattgtgg tcttttctat atttgaactt ttaaatgcag      660
caatttgtga acatacaat tgaaacaaat ttcctcaaaa actgccacca gctgaggtat      720
catgaagcct tctgttcaca catgttgcca cctaatcggt cacttatcct aattaacatt      780
cttccactaa attgtcccct agtcacccCC acttgaacga tatacacacc aactgttctc      840
gttcactaat acacttcttc cggagggatt caactggtta tattctgcag ttgtcggcag      900
gtgtgtggta gacggtgacg taatattgca cagggtgtcg gggaatgatt atgaagtcga      960
gatgcgcaac agctggtaat tgaagccacg agagaaaatg gaaagacta tgatgagggc     1020 acaaggatag aaaaattgac tgggagtgac caaacaggcg aggtcacaat gaaattggtg     1080
aaaatggaaa ccctaaaagt aactttagat tttagaaaat agttggacga ttttttcgttt    1140 tcaaagttca agcatgcat tattatcatc tgaagatgca cgatttgact tgtgtgactg      1200
atatctcgtc gcgatcttac cgtaacctac agtacttcca tattaactaa agttggttcg     1260
cttcgagaca tcgggaacgt gagttatgta tttggcatta ttcgtcattt tatattctag     1320
aaagatttac attctgtcaa gttggaatat ttttcttag ccgtgcaata gaactttgt      1380 tgaatttctc agagtacaat ttttatgacc gccgatttcc tctcgataag cattacgtta     1440
tttacctatg gttttcaact atttaatgag atttatcagg acctcccgta gttttatctt     1500
ctatttttac tcaaatttg agctcaaaaa taacaggaaa gatttaatcg aaaaaaacat      1560
atttctgaaa tccaagagca atcgcgcgct attgataatc tggtttgccg catttctcgc     1620
ggcaacaaca aagagtttga atcgaaacgc cttttatttt gaaaaaaaac cttttttgtt     1680
ttaaaattta gtctatacgt gaatctaaca cacacaaact gttcactaat ttctctttgt     1740
tcgtcttttt accatttcat ttcgaaactc gctgtcgtct cgtttctctc accactcttc     1800 acactttgc cgcctaatcg atcgatcttg ccgcggcgca ctcacatttt tctcttattt      1860
tcttaccggc aaaaaatgta cgttttaccg cacttttcgc ttacattact atttcaaatt    1920
ctcttatcaa aattatttca gaaacgaagt aacacaa                              1957
```

<210> SEQ ID NO 153
<211> LENGTH: 791
<212> TYPE: DNA
<213> ORGANISM: Caenorhabditis elegans

<400> SEQUENCE: 153

```
catgaagaaa cagtggccgt attgggaaaa atgaacgatt tttcggcggg ataaatttat      60
ttttttatgt ttttctatgc gttttcgggt gttttcgggt tgctaagcga ttggttgcct     120
ttttgaatca ctagtcttgg ttttttgttgt ttctgtgaat gaataattgg ttttttcgagg    180 tttttttgtc aaacatgcct aaaaaataaa ttatgacgtt ttagttgatt tgtttgttct     240
ttaaacgtct gaaataagg tttaaatcta atttattaat tataaaattc gtcaaaataa     300
gttgcgcgtc aaattatatg tattgtacgc agtgtcaaac tccaggcctc agttttcatg     360
aatttaccag cgattttgt tataaatttt tttattgaaa tttaaaattt ttattttca     420 accaatttgc ctcgaaaatt cgttatttcc ccattaaaaa ccgctttct aaagtgttgc      480 gcgtcaaata aaatgcctgg tacgcaatgc acggagaatg cgcaaggac gactgctggc     540 gcacttttg aatgcggtaa attgaggcgc gaagtttcat tcgaaaacgc gcgcgaaact     600
tcattcatcg cactttctcc gttcatttcg tcctattttt ttgtggtttt tcgcgatttt     660
ttcgcttttc tgagtgaaaa aataattttc cttcgttttt tcaatgaaaa tccgcggaaa      720
acccattttt tcccgtgaaa atccgcattt ttcgctgtat ttcataattt ttattcagat     780
```
ctcccgtcaa a                                                                791

<210> SEQ ID NO 154
<211> LENGTH: 1005
<212> TYPE: DNA
<213> ORGANISM: Caenorhabditis elegans

<400> SEQUENCE: 154
ttgctgttct taattgattt cataaatatg tataaagcat taaatttgaa tatatttta     60 ataaagaaaa atcgatattc acattagagc gcgcttgcaa tttcacgatg agacctgacg    120
ataccgcgcg aattaaatcg atcgcttttt ggcctaaaat gctcattaac aattgttttt    180
gtagttttta gcttaaaatt atattttaaa atccagtttg ccttgttaca tattggaaaa    240
cggtattttt agagtttttc ctcaaaaacc aagcgaaaac cttgaatttt gttccgaaaa    300
cttgttcaaa acatttttt cgttgaaaac tcaaataatt caccaattta tctattttag     360
gccgaaatct cttattttt cagtccaaaa agcaccaaat ttggtcaaaa acctgtccaa     420
aatctaccgt accctcgtgt tgctcgtgaa atgcggtgca ttgtgtgcaa acaccgcggc    480
gtgaacatgc acactctgca acgcgggaaa tcatttcgaa aaggttttta ggcgcgtatt    540 gcccgattt tcggctcatt tcgtgtgttt tcatttattt ttgccttctt tctccggtcg     600
cgatgcgttt aattaagttt tgcttctaaa tttcgtcaat ttcgctgaaa aaccacgtag    660
aaaacttgat aggaactgga tatcctaaaa aaaggattt ccttgagaaa atgggtttt     720 ttttctgaat ttcgcagtga tattcttgaa attctcagcg cagcgctccc cagacaatcg    780
atattcctaa ttttcaagc atcttgtggc tcagccagct gttctgtaat tatcgatttt    840
atttgttaca gcgtctatat aaataccta gaaagtcatc attctgcact cttaatacct    900
ttcactcgtg tgagttgcat tctccatagc aactctacct ctctccttct atctcttttt    960
ctcttttcaa atctaatttc gtttcagaga ctcccgctat aaacg                   1005

<210> SEQ ID NO 155
<211> LENGTH: 727
<212> TYPE: DNA
<213> ORGANISM: Caenorhabditis elegans

<400> SEQUENCE: 155
ttcgctttaa ctcctccaga agttgacggt ccgccagtgc ctccactagt cgtcgggagt     60
ttatggttca gtttcgcctt tttcatgtcc tccggcttca taatcgtatc atttaggcgt    120
ttgtgttttt tacgttccat tatttataag attctaaacg agaaactctt aagattttcc    180 ggaaataat gataaaaacg gttgtgaaat tgaatgagaa taaaaaaacg aaacaagcac     240
gagtgaggca ggtgcgctcc aatgcgaatt tctttgcgcg gatgttaaaa tggttatttt    300
tttatgggaa tcgacaagtc acatgctacg ctagagagag ttttacattt tacagtcttt    360
ttggaattta ataatatata tattatcata aaatcgaata aaaattgttt cgaataatga    420
atagctttgt ttttcgtct tgacttctga ataattttta aatttgagaa aaatttgtgt     480
cgcaatatat aattattaat attattaata atgtaatttt tttataataa actgatttat    540
attttaaaaa caaaaaagga atgacaattc agtttagttt tatgaaaaac tttgaaagaa    600
caaaaataat tacagtaaaac gcgctccgct agactcccca aatttgtttt tgttttccag    660
gcttgtgtcc aggcaaattc cagctttctt tttgtttcag aatttctagg tatttatctc    720
cgtgaaa                                                              727

<210> SEQ ID NO 156
<211> LENGTH: 2600
<212> TYPE: DNA
<213> ORGANISM: Caenorhabditis elegans

<400> SEQUENCE: 156

```
gaaaacttcg attcttatgg ttaaaacgag ccttgttagt aaaaattatt gagtgaataa      60
ataaattaga tcaagtattt tcacttctgc caaaattcaa ctaaatagaa atggttggaa     120
ttaagttaca agctaccagt ttacaaaaca ataattgaca ggtaatcgga gtgaagacag     180
tttttttgcct tgataatttt tacattcaca tttaatttta cattcacata aaaaaagaat    240
cacacatttt tttcaattga caagttttttg ataaagtgga agacatcgga gatatgaccc    300
gtcaaagttg ctcagcaggg tgcaaaacta aagaggaaa tactgtgaaa cattttgaca     360
atttagagaa atacacagcg aaagaatgaa atctaaaaaa gcgtattaac tttaactaga    420
taaacatact aacttattga ggtaaatctg agcagatcct cttcctattc ccaatatttta    480
cccaattagt cttctgattg cgcacctgca tatcttaagt actcaaatac aacacacatc    540
ttgagaaatg atgactccac actcagaatg caattcacac tattagaagc catgtgcaat    600
atgaaaacaa gcttatcctg aagctgcaaa cccatttacc tcatcaatta tttgcgatgt    660
gccgacctgt tgcatggctt ccgacactgt aaggggataa tctgttttgtc ggcacgcttc    720
aaccgattaa ttggcgtgtg aaacgatact aatccagtcg attctcgact aactgtaaac    780
actttgatgc taaccgacgt gccggctaat atactctctg tgttacgtca gaatccttta    840
aatatgcaaa tatggataag gtggaatgat ctcaagaggt gtgattgggt caaattggat    900
tacgtaattc ttaagtgggc taaaggtata ctgtaactgg ggtgcaattt atgtgggaag    960
tgcggcgaag ttatattggg gttttataga ttctataact tgttacattg attttgaata   1020
gatttcaatt ttcagaaaag tgggaaaact gtatttacat tttgaaagaa atttaatgca   1080
acagaaaata gtgattggct ggaaaagtgc ccctatgtta taaactttttt gttgaagctt   1140
tgaaattttt cacaaattat tcaactgaag tctcacacgt cgaaaaatgg ccaaacaaat   1200
ttttaaaaaa tagaggcctg atcatagttt ctgccatttc atggccgtct gtgacgtcac   1260
atgaggtttt tcgactattt ggcttccagg gttttacctg tttttaattt caaaattata   1320
tattcttcag taaatctctg aaagtcacag tcgtttcagc gaactttcaa ggccgcgtgt   1380
gacgtcacac tcttgcaaag aaagctgcac gtggtgtcag gttgtcccat aacggtttgc   1440
tctacgaaaa atgcgggaat tttttcatca aaaaatgtga cgtcagcacg ttcttaacca   1500
tgcgaaatca gttgagaagt ctgcgtctaa gttcccgcgt ttttttgtaga tcacaacgga   1560
atgggacatt ctgacaccat gtgaagctgg ccttgagata gttttgtaga ttcaaaatat   1620
ttttaatgtc caatatttgt tttcaaaaca ttcgttaaaa tgtgcagaat atgttaaact   1680
gaaggttcct aggtttaaaa cttcaagcta aagctttccg gctcagttct caggttcagg   1740
tctgtaatct ttctgtaagc ttgtaatctt gttagttcct cagacagact tagctgctaa   1800
atttatttca tgtctaatat tacacttcaa gagctatgag tttgtcttca taaaagttttt   1860
ggctcccata taggaacttt ggaacatcat ttgatccccg tttcgaaaac gttcgaaaat   1920
tgttttgttt ctttattttaa acccgacagt tcaaattctt tatcttgatc aaacccttttt  1980
ttttcatctg tccattcctc ggccttaacc taatttatac agtttcgcaa taacctcccc   2040
cgtgcttgct ccagtaccag ctgttgcgtc acgacttctt attttcaaaa ctcaaatctt   2100
gcatcacacc tcatcaatta atcatcctca tcaagcctgc aaacttatac cccttctct    2160
```

```
agacccctct cctgacattt gacactcctg tggtagaggg gtgtggcctt gcctgggcgg    2220
ggcgtgcaat gagaagctgt gcacgcacac cattcattca cacccaaaac attcacaccg    2280
attagtcgta ttctaacttc tcttttcaat tcagttgata tgctggtaag tctagaaatt    2340 atttatttt gatctacata cctgtccaat attgttcgtc tcccctccc cctcctgaga    2400 aacaaatttt tgttttttgtc tgctcgcctc accctcaacc tctctctctc tggatgtgtt    2460
cgtggtgtag aaacaaaaac agattttgt tttttgttt tttgtttctt gttttagaac    2520
ttgtatccta gtaattgtta gacatctccc tactatcttt ccctatata aaccccttc    2580 aaaaccttac taatttccag                                                2600

<210> SEQ ID NO 157
<211> LENGTH: 394
<212> TYPE: DNA
<213> ORGANISM: Caenorhabditis elegans

<400> SEQUENCE: 157
aacagaactc acccgtttct agaacaacgt ttgctatcaa ctccaccccg aaagaatcca      60
ggtggttcgt ctgacattat gctgcaattt tatgagaata ttcagacgca acaacaacgt     120
gacaaacgac gagataaaaa tctatcaagg ctgaaacaat gacaaaaaag aaatcccgac     180
aaatgaaaat ggcgcctaaa acaaactttt ttaaaggacg tcgggtttca ttcacagatg     240
ggtctcggaa cgaaatcatg gagtacggta tcacacactt gaatttgaaa gtgaacttct     300
ttatttgttt ctcttgcaag tttaaactta agttttaat tttttctgct tgtttctcaa      360
taaaataaaa atattacttg atttgtagcg caga                                 394

<210> SEQ ID NO 158
<211> LENGTH: 2557
<212> TYPE: DNA
<213> ORGANISM: Caenorhabditis elegans

<400> SEQUENCE: 158
ttctgcgtga aatgtgatgt ttctacagta acccgtacaa ccaaggcatc gaacttcacg      60
acatttacga attcaaattt gaattgcaaa cttttttaatt ttatcgattt tctttctttt    120
tgagctttat caatagctct aagcgattat tcaacagaat ttcactttt tacgcctaaa     180 tgattgaaaa tttgataaaa tatcaataat ttacggttat cctcttcgta atcttcgctt    240
tcttcccaga gtagtgaaaa tatcgacttt ttgatagaaa ctggattttt taacttccct    300
gttcgaaaaa ctattttcc ttaaatgaga tctgaaataa ggtgataaat taataaatta    360
agtgtatttc tgaggaaatt tgactgtttt agcacaatta atcttgtttc agaaaaaag    420 tccagttttc tagatttttc cgtcttattg tcgaattaat atccctatta tcactttttc    480
atgctcatcc tcgagcggca gcgtctcaaa gaattgtgag agcaaacgcg ctccattgac    540
ctccacactc agccgccaaa aacaaacgtt cgaacattcg tgtgttgtgc ctccttttcc    600
gttatcttgc agtcatcttt tgtcgttttt tctttgttc ttttgttga acgtgttgct    660 aagcaattat tacatcaatt gaagaaaagg ctcgccgatt tattgttgcc agaaagattc    720
tgagattctc gaagtcgatt ttataatatt taaccttggt tttgcattg tttcgtttaa    780 aaaaaccact gtttatgtga aaacgatta gtttactaat aaaactactt ttaaacctt    840 acctttacct caccgctccg tgttcatggc tcatagattt tcgatactca aatccaaaa    900 taaatttacg agggcaatta atgtgaaaca aaaacaatcc taagatttcc acatgtttga   960
```

```
cctctccggc accttcttcc ttagccccac cactccatca cctctttggc ggtgttcttc    1020
gaaacccact taggaaagca gtgtgtatct catttggtat gctcttttcg attttatagc    1080
tctttgtcgc aatttcaatg ctttaaacaa tccaaatcgc attatatttg tgcatggagg    1140
caaatgacgg ggttggaatc ttagatgaga tcaggagctt tcagggtaaa cgcccggttc    1200
attttgtacc acatttcatc attttcctgt cgtccttggt atcctcaact tgtcccggtt    1260
ttgttttcgg tacactcttc cgtgatgcca cctgctccgt ctcaattatc gtttagaaat    1320
gtgaactgtc cagatgggtg actcatattg ctgctgctac aatccacttt cttttctcat    1380
cggcatgctt acgagcccat cataaacttt tttttccgcg aaatttgcaa taaaccggcc    1440
aaaaactttc tccaaattgt tacgcaatat atacaatcca taagaatatc ttctcaatgt    1500
ttatgatttc ttcgcagcac tttctcttcg tgtgctaaca tcttattttt ataatatttc    1560
cgctaaaatt ccgattttttg agtattaatt tatcgtaaaa ttatcataat agcaccgaaa    1620
actacaaaaa atggtaaagt cttttaaatc ggctcgacat tatcgtatta aggaatcaca    1680
aaattctgag aatgcgtact gcgcaacata tttgacgcgc aaaatatctc gtagcgaaaa    1740
ctacagtaat tctttaaatg actactgtag cgcttgtgtc gatttacggg ctcaattttt    1800 gaaataatt tttttttttcg aatttgtgaca acccgtaaat cgtcacaagc gctacggtag    1860
tcatttaaag gattactgta gttctagcta cgagatattt tgcgcgccaa atatgatgcg    1920
taatacgcat tctctgaatt ttgtgtttcc gtaataattt cacaagattt tggcattcct    1980 cttttaaaggc gcacggattt attccaatgg gtctcggcac gcaaaaagtt tgatagactt    2040
ttaaattctc cttgcatttt taattcaatt actaaaattt tcgtgaattt ttctgttaaa    2100 attttaaaa tcagttttct aatattttcc aggctgacaa acagaaacaa aaacacaaca    2160 aacatttaa aaatcagttt tcaaattaaa ataacgatt tctcattgaa aattgtgttt    2220
tatgtttgcg aaaataaaag agaactgatt caaacaatt ttaacaaaaa aaacccccaa    2280
aattcgccag aaatcaagat aaaaaattca agagggtcaa aattttccga ttttactgac    2340 tttcacctttt ttttttcgtag ttcagtgcag ttgttggagt ttttgacgaa aactaggaaa    2400
aaaatcgata aaaattactc aaatcgagct gaatttttgag gacaatgttt aaaaaaaaac    2460 actattttttc caataatttc actcattttc agactaaatc gaaaatcaaa tcgtactctg    2520
actacgggtc agtagagagg tcaaccatca gccgaag                             2557
```

<210> SEQ ID NO 159
<211> LENGTH: 284
<212> TYPE: DNA
<213> ORGANISM: Caenorhabditis elegans

<400> SEQUENCE: 159

```
aaattcgagg aatttttagat tcatcttga aatttgcaat ggaaaaaata attattcaaa     60
gaaaatcaca gaaaatgcaa caaaaaaac aaaaaaagaa caaaaaacaa gtcgaaaagt    120
gcgcccgggt cgtttgctga cgcatctctt caaacgagac gcgctgctgg cgcacttctc    180
gtgccctgtg cgtgcatttc cgcaacaaaa ttcaacactt gttttgaaac gcaccgccct    240
gtttcttttt tcaattttga taagaaaatc agcattgttt cagg                    284
```

<210> SEQ ID NO 160
<211> LENGTH: 405
<212> TYPE: DNA
<213> ORGANISM: Caenorhabditis elegans

<400> SEQUENCE: 160

```
tagaaacatg tttcccgtaa gtgacctatc cagtgaaaca aaaacatgtt tctgtccgcc    60
ttccttccat cggtggaggt gcatgctaga ttgcctccta aactctaata cctaaaattt   120
taataattta ttgacaacat acagtttcac cgataaccga cactcttatt ttttctgatc   180
ctgactattc tgttcattat ttcagctcct atcatagaac gatctttcca gatcttggac   240
aagtcacagt tacaggtaat tttttcaaca ggtgtttgta taatgtctta gtttctgtaa   300
aattgtttta tcatgtaaaa tatttcagat tattcgaggg cagaaaaacg tgatattact   360
attggagagg aattgacaaa gttgtgtgat aaatttaatt ttgag               405
```

<210> SEQ ID NO 161
<211> LENGTH: 899
<212> TYPE: DNA
<213> ORGANISM: Caenorhabditis elegans

<400> SEQUENCE: 161

```
cgagtttctt gtgagaacca aaaactattc ctctgcaaga aaaaatttat taatccggca    60
taaaatactt tttattacaa taggaacttc acagtcgctt cctccgacgc tttgagcggt   120
acatcgatgc ttatcaccat gctgattgtt acctttctta cccgtttgac tttctgcaat   180
ttttaactgc aaagatgttt aatgcagata ctcgaaagaa acgaaaaaat gataaaaaag   240
tgaaaacccc caaaaataaa tttgaaaact ccgcgtaagc ttgctcgatc gctgcgagac   300
cattgcatac cgtactactt cttttaaaggc gcacacatca aatctagctg tttcgtgaca   360
ggacccagca atgttcagcc gcgaagtttt gaatcgccat ttttttttaa tttctagaat   420
gtttatagtt ttgctttcga tgagattttt aagcattatg aggaacaaat ttttttaaaa   480
actttagaag ttttaaaatt taattttgcg attatgcttt gctttcgcgt gtcctttccg   540
ttgttcctcg ctccaaatat atcacagtaa ttaaccacta cttatgtagt tatcacgttt   600
ctaaaaatat aaattcattt ttatttctct attgattcgg tttgttgctc ttcttgtctc   660
aatcttgtgc tactgccgaa taccctgcta attttcgtt ttcagtcatt cgattcactt   720
gggttgttgt ttaaaatggt aagattttg caggttactt tctttcccat gaggtaaatg   780
catttattgc gggtgcgctc tatcgcacga cgccgcgaat cattgtattt caaattgatt   840
ttcctgttgc acttttatta gttacaattt ttattagtta ttttttagttg gattcgaca    899
```

<210> SEQ ID NO 162
<211> LENGTH: 1290
<212> TYPE: DNA
<213> ORGANISM: Caenorhabditis elegans

<400> SEQUENCE: 162

```
gaaaacctaa aatgaacaaa attttttgtc attaaataac aacgcttcgg ttaacgcttg    60
aaattgatat tcggaaaata aaaagcctga ttttgttcg atttctgaaa tatatttcat   120
gctttacccg ttttaattg cgaacaattc taaatttgaa atataatttt caatcaacga   180
aaaacaattt tcaagataaa aaattattat ataaatttaa gctaagtatt aataaattaa   240
taagtaatag tattcaaaaa tcatagaatc ttgcaagaaa aaatgttta aagatttaat   300 agttcgagtg attgaaaaac gaatagtact ttaaaaata tgctttaag gcagaaaagt   360 gatataaaaa ttaagctcaa aagggcaaaa gataaggtta atgtccagtt ttggttttaa   420
aatggttcgg acacaatgta catagtagac atttgggtgt cctcttcctt ctcttttccc   480
cattgcgtcc actgaccctc cttgctgtat gtctgcgcat cgtcttttc tacactttt   540
```

-continued

```
ccttttccct ggcccgttcc tatcggtgcc tttcacacac gcgagcggca gtggacgaga    600
cgggagggcg aggtgttgaa caagagtaca gcaagtgcgc gccatcgaaa aagcggaaaa    660
aaaaatttca aatggcgcta ctttgaaaat tgagaattct gtatttactg ccagttttac    720
ttgcatttaa atttccatgt tttctattct aaaacgaaaa tctatctaag aaaaccctta    780
ataaaaacct ataaatcata aattgtgatt cttaaattcg aaaatatgtt cgttcaacgt    840
gacgcctaga aatatgtgga cttaatcctg ttataaatca gtagttgacg acaaaaatag    900
tagagcagca aaagcagttc taacttgtga aaaacatgaa agttcttgtt ttcgtcaagc    960
gaacgggggc tcgaggaagg acttggcacg tgtctctagg ccatgttttt ctcaattttt   1020
gttgctctag agaaagcttt tgctattgat tatgggacaa tcttggggat atgaaggtaa   1080
cattttaaaa ataagtttag gtaaatgtgt agcataattt ttgaaaaaaa aagctccact   1140
gttaaaaatg ccgattttag ggattgcgaa acgttcacta tgtacacata aatggctata   1200
taatttgaat ttgcattcaa taaatctttt ccttccaatt gtatgtttta acttaaaaat   1260
aattaattaa aattatctca ggagtcaaaa                                    1290
```

TRANSGENIC BIOSENSOR

CROSS-REFERENCE TO RELATED APPLICATIONS

The application claims priority to U.S. provisional patent application No. 61/488,720, filed May 21, 2011 which is hereby incorporated by reference in its entirely.

BACKGROUND

One of the most difficult problems in drug discovery and toxicology is the ability to extrapolate results from early studies at the biochemical and cell-based level to effects in humans. The resulting inefficiencies in this extrapolation result in a high attrition rate in drug development and are an enormous drain of resources, effectively passing the buck on to consumers in one manner or another.

From the pollutants in the air we breathe to side-effects from drugs necessary for our health, we are surrounded by chemicals in our environment. It is important to determine which of these chemicals pose health risks and which are relatively harmless. Over 50,000 chemicals are in need of accurate toxicology assessment (Whittenberger J. Toxicity testing: strategies to determine needs and priorities. Washington D.C.: National Academy Press; 1984; and Kreweski D. Toxicity Testing in the 21st Century: A Vision and a Strategy. 500 Fifth Street, NW Washington, D.C. 20001: National Academy Press; 2007). Understanding the mechanism of action is becoming recognized as a critical parameter for accurate toxicology assessment (Lock et al. Toxicol. Lett. 2003 April; 140-141:317-322.). However, there are limited choices in the marketplace for comprehensive tests to report toxicology pathway activation. The currently available methods are tedious in application or removed from a whole-organism format. As a result, toxicology researchers are in need of fast and efficient high-throughput methods to detect toxicology pathway activation.

Methods using intact cells or whole organisms are challenging to apply in high-throughput formats. Whole organism approaches are the most reliable in capturing accurate correlative toxicity data because the tests are performed in a native-context platform. Yet these approaches are costly for high-throughput implementation with classical models such as the mouse. Tissue must be harvested and either RNA extracted for transcription analysis (microarrays (Shioda J. Environ. Pathol. Toxicol. Oncol 2004; 23(1):13-31), RNA-seq (Kamb Res. Toxicol. 2011 August; 24(8):1163-1168.), rtPCR (Walker J. Biochem. Mol. Toxicol. 2001; 15(3):121-127.)) or metabolic analysis by specific biochemical assay (P450 (Guengerich Chem. Res. Toxicol. 2008 January; 21(1):70-83) and MDR (Sarkadi Physiol. Rev. 2006 October; 86(4):1179-1236.) transporter activity). Furthermore, tissue specific toxicity mandates careful dissection to allow accurate capture of toxicology data (such as sedimented-tissue lysates of liver, brain, and other tissues). As a result, intact organism toxicity approaches are difficult to implement in cost effective high-throughput strategies. In vitro analysis on cell culture systems is a method more amenable to high-throughput analysis. The common approach is to transfect primary cultures with reporter plasmids and detect gene activation as increased expression of reporter genes. These platforms are expensive, time consuming to maintain, and can be plagued with reproducibility problems. An additional drawback of cell culture transfection methods is the lack of native context. Frequently cell culture responses can give hypersensitive results and these results disappear upon whole organism analysis. Creation of transgenic immortalized lines can solve some reproducibility issues (Youdim et al. Drug Metab. Dispos. 2007 February; 35(2):275-282), but these lines are even further removed from native context and can give misleading results. Better methods are needed both in the research setting and in the market place.

Other public health related areas are also in need of improved methods for predicting effects in humans and animals including air quality, cosmetics, apparel, infant food, drinking water, environmental toxicology, food additives, nutraceuticals, manufacturing, organic foods, plastics, pesticides, industrial toxicity, toys, and waste water. Just about any area where exposure of potential toxins to humans or animals occurs is an area where improved method for detecting toxicological liabilities would be a benefit.

BRIEF SUMMARY

The described systems and methods relate to transgenic organisms and their use as biosensors. In some implementations, the described systems and methods include a first population of transgenic organisms that includes a first constitutively expressed reporter gene, and a first transgene that includes a first inducible promoter from a response pathway gene, wherein the first inducible promoter is operably coupled to a first reporter gene.

In other implementations, the population of transgenic organisms further includes a second population of transgenic organisms having a second transgene that includes a second inducible promoter that is operably coupled to a second reporter gene, wherein the second population of transgenic organisms further includes a second constitutively expressed reporter gene, and wherein the first inducible promoter and the second inducible promoter each include a promoter that is derived from a different gene.

In still other implementations, the described systems and methods comprise an object that includes a transgene, a transgenic organism, or a construct, wherein the object includes a promoter region having a promoter, a fragment of the promoter, or a homolog of either the promoter or the fragment of the promoter, wherein the homolog includes at least about a 95% identity to the promoter or the fragment of the promoter, wherein the promoter region is operably coupled to a reporter gene, wherein the reporter gene encodes a protein selected from a fluorescent protein and a luminescent protein, and wherein the promoter region includes a promoter region for a gene selected from: *C. elegans* genes cdr-1, gcs-1, ugt-1, gst-38, hsp-60, hsp-16.41, mtl-2, hsp-16.2, gst-4, ugt-13, hsp-3, hsp-6, hsp-4, hsp-1, skn-1, dnj-13, daf-21, Hsp-17, cyp-13A7, cyp-14A3, cyp-35A2, zyg-12, ZK742.4, ZK742.3, fkb-1, fkb-2, fkb-3, fkb-4, fkb-5, fkb-6, fkb-7, fkb-8, fmo-1, fmo-2, fmo-3, fmo-4, fmo-5, ftn-1, ftn-2, fzy-1, gen-1, glp-1, gsr-1, gst-1, gst-23, gst-25, gst-41, H01G02.2, haf-6, syp-2, T05A12.4, T05G5.3, T06E6.2, T07F12.4, Hsp-12.2, T05E11.3, Cnx-1, Crt-1, cyp-35A1, cyp-35C1, cyp-35A3, pqe-1, cyp-37B1, cyp-35B2, cyp-35B1, cyp-22A1 (daf-9), cyp-14A5, cyp-35B3, cyp-34A6, daf-16, exo-3, nth-1, pme-1, ung-1, xpa-1, mrt-2, ercc-1, ZK697.8, ZK287.5, haf-7, hda-1, hda-10, hda-11, hda-2, hda-3, hda-4, hda-5, hda-6, hdac-1, hif-1, him-1, him-14, him-3, him-4, him-6, hmg-3, hmg-4, hmg-5, hpr-17, hpr-9, hrdl-1, hsf-1, hsp-1, hsp-16.48, tbb-4, tnc-2, top-3, tor-2, trx-2, xpf-1, xpg-1, rad-23, mlh-1, msh-2, msh-4, msh-5, msh-6, brc-1, brc-2, rad-50, cku-70, lin-35, mei-1, cki-1, cki-2, cep-1, ced-3, ced-9, ced-13, vem-1, dhs-23, sodh-2, dnj-19, Xbp-1, hsp-16.49, hsp-2, htp-1, htp-3, hus-1, imb-3, ire-1, irk-1, K07C5.2, K07C5.4, K08F4.1, K11G12.5, kin-18, lagr-1, let-2, let-92, fig-1, lig-4, lim-4, lin-12, lin-44, lin-49, lrk-1, lst-3, M18.5, vps-41, W01A11.1, W02C12.1, W03G1.5, W06H8.2, Hipr-1, cdc-48.1, cdc-48.3, Ubq-1, Ubq-2, Gst-10, Gst-13, f25d1.5, fil-1, k10h10.6, hsp-70, f44e5.4, f44e5.5, hsp-16.11, hsp-16.1, nurf-1, aip-1, y43f8b.2, Dod-17, Dod-24, C55A6.7, F56D5.3, cyp-13A11, cyp-13A6, cyp-25A4, mac-1, mboa-2, mdf-1, mdf-2, mec-14, med-1, mel-28, misc-1, mnat-1, mre-11, mrp-1, mrp-2, mrp-3, mrp-4, mrp-5, mrp-6, mrp-7, mrp-8, mspn-1, mus-1, mut-2, mxl-1, mxl-2, mxl-3, ndx-1, Y55B1AL.2, Y56A3A.33, Y66D12A.15, Y66D12A.15, Y73C8C.10, cyp-29A2, cyp-31A1, cyp-31A3, cyp-33B1, cyp-33E1, cyp-34A10, cyp-34A9, cyp-35A4, cyp-35D1, abl-1, abu-1, acr-14, acr-22, agt-1, ahr-1, air-2, ama-1, apa-2, apn-1, apn-1, aps-2, arf-1, asp-5, atf-5, atgr-7, ndx-4, nft-1, nhr-6, nol-5, npl-4.2, nuc-1, odc-1, paa-1, pas-4, pat-10, pcn-1, pdi-1, pdi-2, pdi-3, pdr-1, pek-1, pgp-1, pgp-10, pgp-2, phi-37, phi-44, phi-9, pink-1, pme-2, pme-3, T08D2.4, T08D2.7, T08H10.1, T10B5.8, T13A10.2, atl-1, atm-1, B0222.9, B0432.2, B0495.2, B0563.7, brd-1, C01G5.5, C06A1.6, C06H2.3, C07D8.6, C08H9.3, C09D4.3, C11E4.2, C25A1.5, C30G7.5, C35C5.2, C35D10.2, C35D10.6, C37A2.4, C37C3.6a, C44H4.4, C56G3.2, catp-6, cbn-1, F17A9.5, F18A1.5, F19G12.2, F23C8.9, F36A4.15, F43D2.1, F43G6.5, F44B9.8, F45E12.3, F49E12.6, F52B5.2, F52C12.1, F53C11.5, F53F1.2, F53F1.3, F53F10.2, F55B11.1, F57B10.5, F57B10.6, F58F9.1, F59A2.3, F59F4.1, fan-1, fdps-1, figl-1, trxr-1, tut-1, uba-1, ubc-1, ubc-20, ccch-1, cct-1, cct-2, cct-3, cct-4, cct-5, cct-6, cct-7, cct-8, cdc-14, cdc-48.2, cdk-7, ced-4, cel-1, cft-1, chk-1, chk-2, chn-1, cku-80, cle-1, clk-2, clpp-1, cmd-1, cnb-1, col-135, pme-4, pme-5, pmrt-5, pms-2, png-1, polh-1, polk-1, prx-6, ptl-1, R02D3.3, R03D7.2, R05D11.6, R05F9.10, R09H10.3, R10E4.9, R13D11.4, R151.6, rab-1, rab-7, srp-2, ssc-1, sti-1, sulp-7, sut-1, sut-2, wrn-1, xpc-1, Y110A7A.4, Y38F1A.5, Y38H8A.3, cps-6, crb-1, crn-1, crn-2, crn-3, crn-4, crn-5, crn-6, crp-1, csb-1, ctl-2, ctl-3, cul-1, cul-2, cul-4, cul-5, cyh-1, cyn-1, cyn-10, cyn-11, cyn-12, cyn-13, cyn-14, cyn-15, cyn-16, rad-51, rad-54, rbx-1, rbx-2, rcf-3, rcq-5, rec-8, rev-1, rfc-1, rfc-4, rfl-1, rme-8, rnf-121, rnh-1.0, rpa-1, rpa-2, rpn-10, rps-19, rps-26, T23G5.6, T26A5.5, T27E9.1, tag-353, tars-1, tbb-2, Y73F8A.24, ymel-1, ZC168.4, ZC395.10, ZC443.1, cyn-17, cyn-2, cyn-3, cyn-4, cyn-5, cyn-6, cyn-7, cyn-8, cyn-9, cyp-13A2, cyp-13A4, cyp-14A2, cyp-33C1, cyp-33C2, cyp-33C9, cyp-33E2, cyp-42A1, cyp14A2, cyp33C9, cyp34A6, D1081.8, D2023.4, daf-1, daf-14, daf-3, rpt-3, rpt-4, rpt-5, rpt-6, rtel-1, san-1, scav-1, scav-2, scav-3, scav-4, scav-5, scc-3, sdz-8, sec-22, sep-1, set-25, set-26, set-8, set-9, unc-11, unc-26, unc-57, uri-1, usp-14, vps-4, T15B7.2, T16H12.4, ugt-62, Y39G8B.1, Y39G8B.2, daf-5, daf-7, daf-8, dbl-1, ddb-1, dhs-22, djr-1.1, dna-2, dog-1, drh-3, drp-1, dut-1, E01A2.1, eft-2, egl-1, eif-2, emb-9, epg-2, eps-8, exo-1, F09E5.2, F14F9.5, F15E6.6, F16A11.2, F17A9.4, sft-4, sgg-1, sin-3, sir-2.1, sir-2.2, sir-2.3, sir-2.4, skr-15, slt-1, slx-1, smf-1, smk-1, sod-1, sod-2, sod-3, sod-4, sod-5, spas-1, ugt-61, Y43E12A.1, Y43F8C.13, Y48G1BL.2, Y50D7A.1, Y50D7A.2, Y54E10A.3, ufd-1, ugt-22, ugt-52, ZK1128.4, ZK1290.5, and Y39H10A.7; ABCE-1, ABCF-1, ABCF-2, ABCF-3, ABT-1, ABT-2, ABT-4, ABT-5, ABTM-1, acr-14, acr-22, ahr-1, akt-1, akt-2, apa-2, ape-1, apn-1, aps-2, ard-1, arf-1, arf-1.1, arl-7, asp-5, atf-5, atgr-7, B0222.9, B0432.2, B0495.2, B0563.7, bec-1, bmk-1, C01B10.7, C01G12.5, C01G5.5, C01H6.4, C03A7.12, C03A7.13, C04F12.1, C05C9.1, C06A1.6, C06E4.3, C06E4.4, C06E4.6, C06G1.1, C06H2.3, C07A9.13, C07D8.6, C08H9.3, C09D4.3, C11E4.2, C16C8.14, C23G10.6, C25A1.5, C25A1.6, C27D8.4, C28H8.11, C30G12.2, C30G7.5, C31H1.1, C32D5.12, C33E10.10, C35B1.5, C35C5.2, C35D10.2, C35D10.6, C37A2.4, C37C3.6a, C41A3.1, C44H4.4, C46H11.2, C55A6.3, C55A6.4, C55A6.6, C55C3.1, C55H1.1, C56G3.2, cah-5, car-1, catp-6, cbn-1, ccch-1, cct-2, cct-3, cct-4, cct-5, cct-6, cct-7, cct-8, cdc-14, cdr-5, ced-1, ced-10, ced-12, ced-13, ced-2, ced-5, ced-6, CED-7, ceh-20, ceh-30, ces-1, ces-2, cgh-1, chn-1, cit-1.2, ckb-2, cle-1, clec-149, clpp-1, cmd-1, cnb-1, Cnx-1, cnx-1, col-135, coq-6, cpb-3, crb-1, crp-1, Crt-1, crt-1, csp-1, csp-2, csp-3, ctl-1, cul-1, cul-2, cul-3, cul-5, cyn-1, cyn-10, cyn-11, cyn-12, cyn-14, cyn-15, cyn-16, cyn-17, cyn-2, cyn-3, cyn-4, cyn-5, cyn-6, cyn-7, cyn-8, cyn-9, CYP-13A1, CYP-13A10, CYP-13A2, CYP-13A3, CYP-13A5, CYP-13A8, CYP-13B1, CYP-13B2, CYP-14A1, CYP-14A4, CYP-23A1, CYP-25A1, CYP-25A2, CYP-25A3, CYP-25A5, CYP-25A6, CYP-29A3, CYP-29A4, CYP-31A2, CYP-32A1, CYP-32B1, CYP-33A1, CYP-33C11, CYP-33C3, CYP-33C4, CYP-33C5, CYP-33C6, CYP-33C7, CYP-33C8, CYP-33D1, CYP-33D3, CYP-33E3, CYP-34A1, CYP-34A2, CYP-34A4, CYP-34A5, CYP-34A7, CYP-34A8, CYP-35A5, CYP-36A1, CYP-37A1, CYP-43A1, CYP-44A1, cyp14A2, cyp14A5, cyp33C9, D1007.16, D1054.8, D1081.8, D2023.4, dad-1, daf-1, daf-14, daf-21, daf-3, daf-5, daf-7, daf-8, DAF-9, dbl-1, DC2.5, dhs-1, dhs-10, dhs-11, dhs-12, dhs-13, dhs-14, dhs-15, dhs-16, dhs-18, dhs-19, dhs-2, dhs-20, dhs-21, dhs-24, dhs-25, dhs-26, dhs-28, dhs-29, dhs-3, dhs-30, dhs-31, dhs-4, dhs-5, dhs-6, dhs-8, dhs-9, djr-1.1, dnj-11, dnj-25, dnj-27, dnj-7, Dod-17, Dod-24, dop-1, dop-1, dop-3, dop-3, dpl-1, dpr-1, drh-3, duox-2, dut-1, E01A2.1, E04F6.15, eat-3, efl-1, efl-2, eft-2, egg-1, egg-2, egl-38, emb-9, eor-1, eor-2, epg-2, eps-8, exos-3, F02C12.2, F07A11.2, F09E5.2, F10D11.6, F10D2.12, F10D2.8, F10D7.3, F12E12.11, F14D12.1b, F14F9.5, F15E6.6, F16A11.2, F17A9.5, F18A1.5, F19G12.2, F20G2.1, F20G2.2, F22D6.15, F22E5.6, F23C8.9, F26D2.15, F28A10.1, F28H7.2, F30B5.4, F32A5.8, F36A4.15, F43G6.5, F44B9.8, f44e5.4, f44e5.5, F45E12.3, F46H5.2a, F49E12.6, F52B5.2, F52C12.1, F53C11.5, F53F1.2, F53F1.3, F53F10.2, F54C1.1, F54F3.4, F55A11.6, F55B11.1, F55E10.6, F56A4.4, F57B10.5, F57B10.6, F58F9.1, F59A2.3, F59E11.2, F59F4.1, fan-1, fasn-1, fdps-1, fil-1, fipr-24, fis-1, fkb-1, fkb-2, fkb-3, fkb-4, fkb-5, fkb-6, fkb-7, fkb-8, fnta-1, ftn-1, ftn-2, gab-1, gad-3, gale-1, gdi-1, ggtb-1, gla-3, gld-1, glp-1, glrx-10, gsr-1, gst-11, gst-12, gst-14, gst-15, gst-16, gst-18, gst-19, gst-2, gst-20, gst-21, gst-22, gst-24, gst-26, gst-28, gst-29, gst-3, gst-30, gst-31, gst-32, gst-33, gst-34, gst-35, gst-36, gst-39, gst-40, gst-42, gst-43, gst-44, gst-5, gst-6, gst-8, gst-9, gstk-1, gstk-2, gsto-1, gsto-2, gsto-3, H01G02.2, H04M03.3, H06H21.9, H10D18.6, H23N18.4, HAF-1, HAF-2, HAF-3, HAF-4, HAF-8, HAF-9, hda-10, hda-11, hda-5, hi-14, hif-1, him-10, him-4, hke-4.1, hlh-2, hlh-3, HMT-1, hpo-15, hps-1, hps-60, hsd-1, hsd-2, hsd-3, hsf-1, hsp-1, hsp-16.1, hsp-16.1, hsp-2, hsp-60, icd-1, ikb-1, imb-3, ing-3, irk-1, irp-1, irp-2, itr-1, jkk-1, jnk-1, K02E11.3, K02E11.4, K02E11.5, K02E11.6, K02E11.7, K02E11.9, K04A8.10, K07C5.2, K07C5.4, K08F4.1, K10F12.4, K11D12.6, K11G12.5, kin-18, kin-4, lagr-1, lbp-1, lbp-2, lbp-3, lbp-4, lbp-5, lbp-6, lbp-7, lbp-8, lbp-9, let-2, let-23, let-60, let-92, lim-4, fin-1, lin-12, lin-3, lin-31, lin-44, lin-49, lip-1, lips-11, lrk-1, lst-3, M18.5, M57.2, mab-5, maoc-1, mca-2, mec-14, med-1, mei-2, mek-1, mek-2, mel-26, mev-1, misc-1, mlt-7, mpk-1, mtl-1, mus-1, mut-2, mxl-1, mxl-2, mxl-3, nas-39, ncs-3, ndx-4, nhr-181, nhr-6, nhr-64, nol-5, npl-4, npl-4.2, nrf-5, nsy-1, nurf-1, odc-1, paa-1, pag-3, pah-1, pas-4, pat-10, pax-2, pdi-1, pdr-1, pek-1, PGP-11, PGP-12, PGP-13, PGP-14, PGP-15, PGP-3, PGP-4, PGP-5, PGP-6, PGP-7, PGP-8, PGP-9, phi-37, phi-44, phi-9, pink-1, pkc-2, pmk-1, pmk-2, pmk-3, PMP-1, PMP-2, PMP-3, PMP-4, PMP-5, pmrt-5, png-1, polq-1, pqe-1, pqn-60, prdx-2, prx-1, prx-5, psr-1, ptl-1, ptp-3, ptp-3, pxn-2, qdpr-1, R03D7.2, R05D11.6, R05D8.7, R05D8.9, R05F9.10, R07B7.4, R07B7.5, R09H10.3, R10E4.9, R119.3, R11A8.5, R13D11.4, R151.6, rab-1, rab-5, rae-1, rcf-3, rcq-5, rfc-1, rfl-1, rfp-1, rgef-1, rgs-2, rgs-2, rme-8, rnf-1, rnf-121, rnh-1.0, rnp-2, rpa-2, rps-19, rps-26, rtel-1, scav-1, scav-2, scav-3, scav-4, scav-5, sdz-8, sdz-8, sec-22, sek-1, sel-10, sel-8, sem-5, ser-3, set-25, set-26, set-8, set-9, sex-1, sft-4, sgg-1, skr-15, slt-1, smf-1, smk-1, smo-1, sod-2, sod-4, sod-5, srp-2, srp-7, sti-1, sulp-7, sup-9, sup-9, sut-1, sut-2, syp-2, T01G6.1, T01G6.10, T05A12.4, T05G5.3, T06E6.2, T07F12.4, T08D2.4, T08D2.7, T08H10.1, T10B5.10, T10B5.8, T13A10.2, T15B7.2, T16G1.6, T19B4.1, T19C3.5, T19H12.3, T21B4.4, T23G5.6, T25G12.2, T26A5.5, T27E9.1, tag-124, tag-353, tag-63, tars-1, tbb-2, tbb-4, tbh-1, tnc-2, tor-2, tra-1, trx-2, trxr-1, tut-1, uba-1, ubc-14, ubc-20, ubxn-4, ugt-10, ugt-11, ugt-12, ugt-14, ugt-15, ugt-16, ugt-17, ugt-18, ugt-19, ugt-2, ugt-20, ugt-21, ugt-23, ugt-24, ugt-25, ugt-26, ugt-27, ugt-28, ugt-29, ugt-3, ugt-30, ugt-31, ugt-32, ugt-33, ugt-34, ugt-35, ugt-36, ugt-37, ugt-38, ugt-39, ugt-4, ugt-40, ugt-41, ugt-42, ugt-43, ugt-44, ugt-45, ugt-46, ugt-47, ugt-48, ugt-49, ugt-5, ugt-50, ugt-51, ugt-53, ugt-54, ugt-55, ugt-56, ugt-57, ugt-58, ugt-59, ugt-6, ugt-60, ugt-63, ugt-64, ugt-65, ugt-7, ugt-8, ugt-9, unc-11, unc-2, unc-26, unc-36, unc-36, unc-43, unc-43, unc-57, unc-73, uri-1, usp-14, vit-1, vit-2, vit-3, vit-4, vit-5, vit-6, vps-11, vps-16, vps-18, vps-33, vps-39, W01A11.1, W01B11.6, W02C12.1, W03F9.9, W03G1.5, W1008.4, wah-1, WHT-1, WHT-2, WHT-3, WHT-4, WHT-5, WHT-6, WHT-7, WHT-8, WHT-9, Y110A7A.4, Y23H5A.2, Y38F1A.5, Y38H6C.17, Y38H8A.3, Y39G8B.1, Y39G8B.2, Y39H10A.7, Y41C4A.11, Y43D4A.2, Y43E12A.1, y43f8b.2, Y43F8C.13, Y45G12C.3, Y47D3A.22, Y47D3A.29, Y47G6A.21, Y47G6A.22, Y48G1BL.2, Y50D7A.1, Y53G8B.1, Y54E10A.3, Y56A3A.33, Y66D12A.15, Y71G12B.4, Y73B6A.3, Y73C8C.10, ymel-1, ZC168.4, ZC395.10, ZC443.1, ZC513.1, ZC513.2, ZK1290.5, ZK287.5, ZK550.6, ZK616.8, ZK697.14, ZK697.8, ZK742.3, ZK742.4, ZK829.1, and zyg-12; and homologous genes from an organism selected from *Danio rerio* (zebrafish), *Drosophila melanogaster*, *Daphnia* spp., and *Xenopus laevis*.

In yet other implementations, the described systems and methods include an object selected from a transgene, a transgenic organism, and a construct, wherein the object comprises a promoter region that includes a promoter, a fragment of the promoter, or a homolog of either the promoter or the fragment of the promoter, wherein the homolog has at least about a 95% identity to the promoter or the fragment of the promoter, wherein the promoter region is operably coupled to a reporter gene of an inducible reporter, wherein the reporter gene encodes a protein selected from a fluorescent protein and a luminescent protein, and wherein the promoter region includes a sequence selected from those found in SEQ ID NO:1 to SEQ ID NO:162.

BRIEF DESCRIPTION OF THE DRAWINGS

FIG. 2A shows the initial plate layout before addition of a selected agent. FIG. 2B shows wells highlighted in grey when the selected agent is one that selective induces cytoplasmic oxidative stress (e.g., induces promoter driven expression of reporter gene).

FIG. 10 shows sets/formats of arrays or panels for different types of stress response biosensors and specific subgroups.

DETAILED DESCRIPTION

Figure 1:
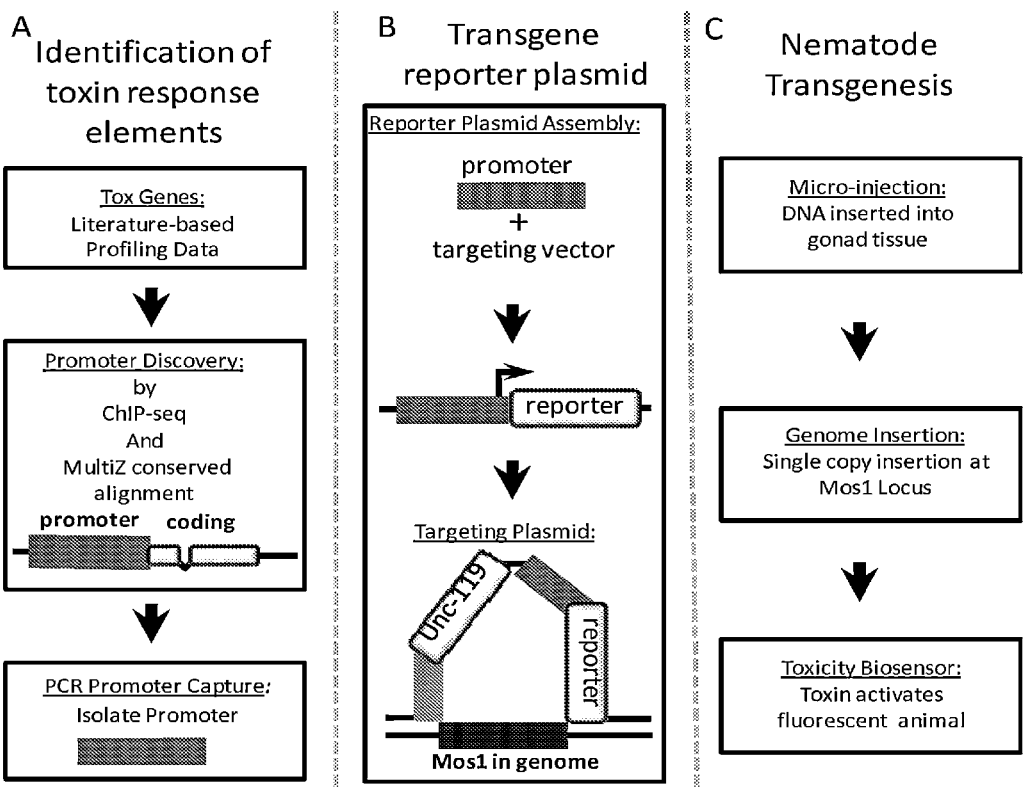
FIG. 1 shows a schematic representation of a transgenesis algorithm for generating transgenic organisms for use in the invention. The transgenesis algorithm involves (A) identifying a promoter response element, (B) operably linking or fusing the promoter response element to a reporter gene to create a functional transgene and (C) inserting the functional transgene into the host organism's genome (e.g., *C. elegans*). Step (A) comprises (1) toxicity profiling data analyzed for genes involved in response pathways (e.g., qPCR, microarray, RNA seq, and/or RNAi screens from literature), (2) promoter discovery (e.g., bioinformatic scan using ModENCODE ChIP-seq data and bioinformatics scan with MultiZ alignment for 5' conserved elements), and (3) promoter isolation (e.g., design primers for region of interest and amplify from wild-type DNA). Step (B) comprises (1) reporter plasmid assembly (e.g., insert promoter into targeting vector/construct by standard molecular biology techniques) and (2) targeting plasmid assembly (e.g, having a positive selection marker (e.g., unc-119 rescue) and a homology arm for transposition (e.g., sequence flanking Mos1 site to yield transgene of interest—toxin sensitive promoter driving reporter gene). Step (C) comprises (1) microinjection of targeting plasmid into worm (e.g., insert targeting plasmid mix into gonad tissue of selectable background animals (e.g., unc-119 mutants)) and (2) genome insertion (e.g., array formation, Mos1 transposon insertion, homologous gene repair, transgene insertion, and array loss) to give the desired transgenic worm.

The invention described herein is a remarkable new paradigm useful for probing the effects of exposure to a stimuli (e.g., a chemical agent or heat shock), on gene expression at the organismal level in a rapid and efficient manner. The inventors have created biosensor organisms that are easily useable and provide robust reproducible results in an out-of-the-box format for testing the effects of exposure to various stimuli on gene expression levels as measured by reporter genes. Importantly, the compositions and methods described herein are unexpectedly useful for identifying gene expression responses to stimuli at the whole organism level.

In a specific implementation of the invention, the inventors have used nematodes (e.g., C. elegans) as model organisms. Other organisms can be used as model systems, especially those that are translucent or partially translucent. A panel for oxidative stress response transgenic biosensor organisms was created based on the promoters of 7 genes induced by oxidative stress. Seven unique nematodes lines each corresponding to a different oxidative stress gene were created by genetic engineering technology (each line "representative" of a particular oxidative stress gene). More specifically, promoter regions for each oxidative stress response gene were identified and fused, or operably linked, to the coding region of a fluorescent protein gene to create a transgene promoter reporter construct using standard molecular biology methodology. Importantly, the promoter regions were identified/chosen to contain transcription factor response elements (e.g., transcription factor binding elements) that recruit transcription factors to help modulate transcription of genes under control of the promoter. Each transgene then was inserted into the nematode genome as a single copy (e.g., using single copy transgenesis procedures) to yield seven unique lines (also referred to as representative transgenic organisms e.g., seven representative transgenic organisms). Each line also has a constitutively expressed transgene encoding another fluorescent protein for normalization purposes which was introduced using standard techniques.

The seven different promoters used to create the lines were obtained from genes involved in oxidative stress response. Two genes used were alpha cystallins which respond to cytoplasmic heat shock (hsp-16.2 and hsp-16.41) (David et al. Environ. Toxicol. Chem 2003 January; 22(1): 111-118; Hong et al. J. Mol. Biol 2004 November; 344(2): 369-381; Candido EPM. Prog. Mol. Subcell. Biol 2002; 28:61-78; Dengg et al. J Pharmacol Toxicol Methods 2004 December; 50(3):209-214; and Strayer et al. FASEB J 2003 December; 17(15):2305-2307). A metallothionein gene was used to detect oxidative metal toxicity (mtl-2) (Sukaina Zeitoun-Ghandour et al. Aquatic Toxicology 2010 October; 100(2):140-150; Cui et al. Genome Biol 2007; 8(6):R122; Roh et al. Environ. Toxicol. Chem 2006 November; 25(11): 2946-2956; Liao et al. J. Biol. Chem 2002 November; 277(44):42049-42059; and Dong et al. J. Mol. Biol 2008 February; 376(3):621-633) as well as a uridine diphosphate-glucuronosyl/glucosyl transferases gene (ugt-1) (Cui et al. Genome Biol 2007; 8(6):R122). The remaining 3 genes were chosen for unfolded protein response (UPR) oxidative stress in the mitochondria (hsp-6 and hsp-60) (Yoneda et al. J. Cell. Sci 2004 August; 117(Pt 18):4055-4066.) and endoplasmic reticulum (hsp-4) (Vadim Kapulkin et al. FEBS Letters 2005 June; 579(14):3063-3068; and Urano et al. J. Cell Biol 2002). Promoters for these genes were selected to contain all clearly identified transcription factor binding sites and were cloned into expression vectors containing hsRFP, which is mCherry red fluorescent protein fused to the his-57 histone gene. The resulting hsRFP reporter construct expresses red fluorescence in cell nuclei. The reporter is injected into GFP expressing nematodes (unc-47::GFP) using the MosSCI method (Frokjaer-Jensen et al. Nat Genet 2008; 40(11): 1375-83), which creates single copy insertions of the transcriptional reporter genes at Mos1 loci. The result is a two-color fluorescent nematode (FIG. 5), where each strain contains both a ubiquitously-expressed GFP and hsRFP whose expression is driven by an oxidative-stress gene promoter.

Figure 7:
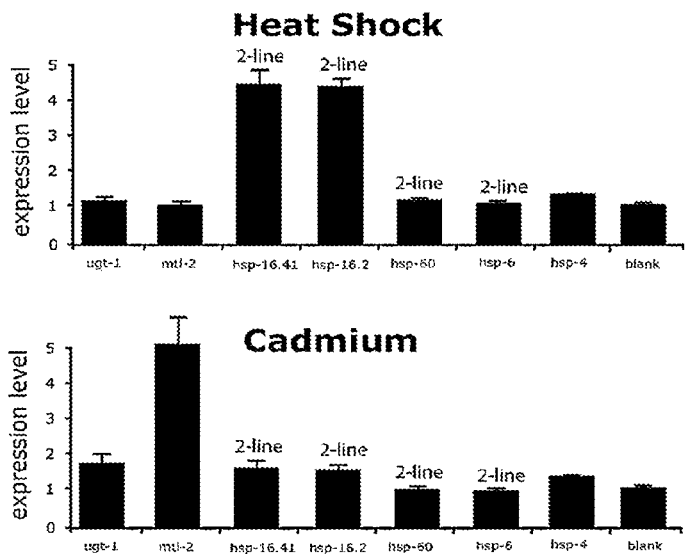
FIG. 7 shows expression response profiles using two-color nematode biosensors. A) Biosensors exposed to 34° C. for 1.5 hrs on seeded NGM plates followed by 4 hrs recovery at 20° C. B) Biosensors exposed to cadmium (1 mM, NGM plates) for 15 hrs. Responses are population-normalized changes relative to unexposed control. Error bars indicate average of 2 to 6 independent measurements. The label "2 line" indicates data derived from combining responses of two independently-derived MosSCI lines for the same reporter.

Changes in expression were quantified with a plate reader assay. The 7-member oxidative stress response biosensor panel was heat shock exposed. Significant increased expression was observed in the hsp-16.41 and hsp-16.2 reporters (FIG. 7A), in contrast to the low to non-existent expression induction of the remaining genes. Exposure to metal toxicity elicited a different response in the panel. Cadmium primarily induced metallothionein gene expression (FIG. 7B) and only mildly induced expression from ugt-1, hsp-16's, and hsp-4. Thus, the simple 7-promoter panel was capable of distinguishing different types of responses. In particular, the panel differentiated between two types of oxidative stress responses: heavy metal ion induced oxidative stress and heat shock induced oxidative stress.

In addition, these results show the inventive methods and composition have 4 remarkable features. First, the system shows induction at significant levels over background. For example, the oxidative stress response panel has strong responses occurring at greater than 4-fold over background. Second, the system shows important levels of fidelity. The panel responses are highly reproducible, where less than 10% error occurs in the assays of 2 to 6 measures done on different days and/or different populations. Third, the method of MosSCI transgenesis creates independently derived strains with similar responses as indicated. Fourth, the arrangement of reports in a plate-reader panel provides an easy-to-use format that quickly reveals which genes are important for toxicity pathway response and can identify different types of response like one response pathway versus another response pathway.

In conclusion, the oxidative response panel demonstrated the system is feasible for sensitive and selective detection of changes in gene expression at the whole organism level when the organism is exposed to external stimuli. This system has advantages over cell culture methods because it is easier to use and amazingly less costly to implement. The inventive system is a whole organism approach, which detects cellular response in a native context. The ease of assay implementation makes the system ideal for high-throughput applications. In general, application of this technology in toxicogenomics is expected to be extremely valuable in the drug discovery sector (Yang et al. Chem Biol Interact 2004 November; 150(1):71-85). With this inventive system, pharmaceutical companies will decrease their financial exposure because better toxicology capture at the front end of drug development translates to lower frequency of drugs failing in clinical trials due to unwanted side-effect toxicity. Additionally, this technology has clear utility in a variety of other sectors, including screening potential pharmaceutical effects for wanted or on-target effects, or differentiating between types of on-target effects.

Definitions

As used herein, "operably linked" and "operably fused" may refer to the association of two or more nucleic acid elements in a recombinant DNA construct, e.g. as when a promoter is operably linked with DNA that is transcribed to RNA for expressing a protein. Additionally, the term "operably coupled" may be used herein to comprise the terms "operably linked" and "operably fused."

As used herein, "percent identity" means the extent to which two optimally aligned DNA or protein segments are invariant throughout a window of alignment of components, for example nucleotide sequence or amino acid sequence. An "identity fraction" for aligned segments of a test sequence and a reference sequence is the number of identical components that are shared by sequences of the two aligned segments divided by the total number of sequence components in the reference segment over a window of alignment which is the smaller of the full test sequence or the full reference sequence. "Percent identity" ("% identity") is the identity fraction times 100. Such optimal alignment is understood to be deemed as local alignment of DNA sequences. For protein alignment, a local alignment of protein sequences should allow introduction of gaps to achieve optimal alignment. Percent identity is calculated over the aligned length not including the gaps introduced by the alignment per se.

As used herein, the term "promoter" refers to a region of DNA which lies upstream of the transcriptional initiation site of a gene to which RNA polymerase binds to initiate transcription of RNA. An "inducible promoter" is a promoter that increases expression of its cognate gene or reporter when exposed to an inducing agent.

As used herein, the term "fluorescent protein" refers to proteins that fluoresce in response to excitation at a particular wavelength or range of wavelengths of light. As used herein, "RFP" refers to a class of proteins called red fluorescent proteins which are fluorescent proteins that fluoresce in the red region of the spectrum, generally in emitting light having a wavelength in the range of 600 to 650 nanometers. As used herein, "GFP" refers to a class of proteins called green fluorescent proteins which are fluorescent proteins that fluoresce in the green region of the spectrum, generally in emitting light having a wavelength in the range of 500 to 50 nanometers. The terms "RFP" and "GFP" are not intended to be construed based on the amino acid sequence of the underlying protein but are intended to be construed based on the wavelength of light they emit. For example, a RFP has been constructed by site-directed mutagenesis of a protein that was originally a GFP. As the term is used herein, this new protein is a RFP.

As used herein "detectably different" refers to measurements or observations that can be meaningfully distinguished from one another. In the context of "detectably different fluorescent proteins" this refers to proteins that fluorescent at different wavelengths of light such that they level of amount of the two proteins can be meaningfully determined. Detectably different can refer to no greater than 50%, 40%, 30%, 20%, or 10% of emissions.

As used herein, the term "transgene" refers to a gene in an organism that has been introduced, or is to be introduced, that is non-native. Typically transgenes according to the invention are created by genetic engineering technology and inserted into an organism to create a transgenic organism.

Figure 2:
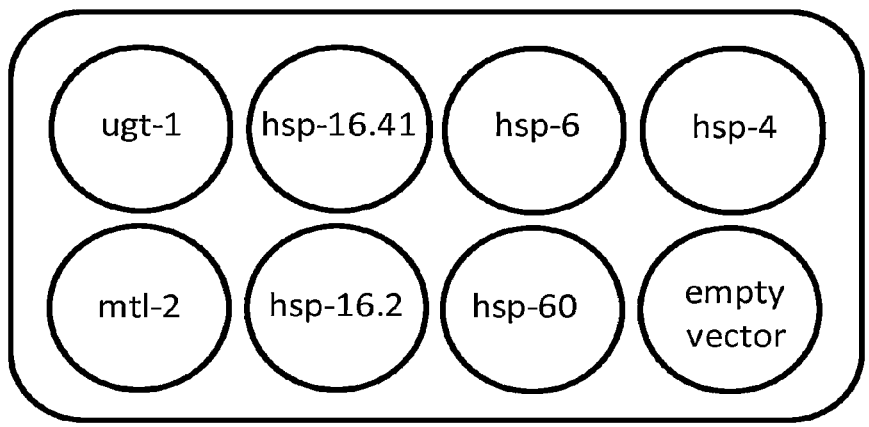
FIG. 2 shows a schematic representation of a plurality of representative populations of transgenic organism within the context of a multiwell plate. Each well has a population of worms from the indicated strain (as indicated by the abbreviation in the well which signifies the promoter region of the indicated gene that is fused, or operably linked, to a reporter gene).
Figure 2:
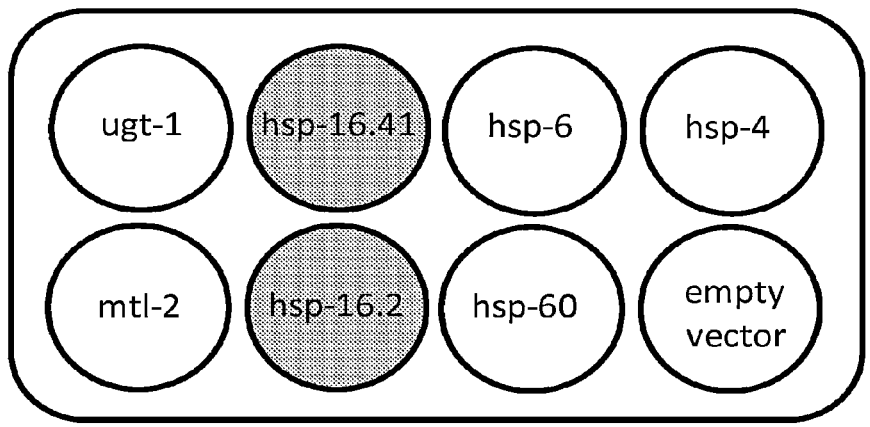

Thus, in one embodiment, the invention is one or more (a) representative transgenic organisms or (b) populations of representative transgenic organisms as biosensors for detecting an alteration in gene expression in response to exposure to a selected agent. Each representative transgenic organism or population of representative transgenic organisms has a transgene which is an inducible promoter of a gene operably linked, or fused, to a reporter gene. Thus, a representative transgenic organism is a biosensor having a transgene which is an inducible promoter of a gene of interest operably linked, or fused, to a reporter gene. In a specific aspect, the transgenic organisms have a second reporter transgene that is a constitutive reporter that is used to normalize the expression level of the reporter driven by the inducible promoter. A population of transgenic organisms is 1 or more transgenic organisms each organism having as a transgene the same inducible promoter operably linked or fused to a reporter gene. In one aspect, the invention is a plurality of representative transgenic organisms or population of representative transgenic organisms where each representative transgenic organism or population of representative transgenic organisms has a distinct transgene that is a distinct inducible promoter of a gene operably linked, or fused, to a reporter gene. In a specific aspect, each population of representative transgenic organisms has 10 or more, 30 or more, 50 or more, 100 or more, 150 or more, 200 or more, or 300 or more transgenic organisms. A plurality of representative populations of transgenic organisms can be envisaged in the format of e.g., microwell plate with (a) each individual well having 2 or more transgenic organisms having as a transgene the same inducible promoter operably linked or fused to a reporter gene and (b) at least 2 wells differing from one another in the identity of the inducible promoter of the transgene (e.g., the inducible promoters in the transgenic organism in the first well and the inducible promoter for the transgenic organism in the second well are different i.e., from different genes). This concept is exemplified in FIG. 2. According to a method of this embodiment, the plurality of representative transgenic organisms or population of representative transgenic organisms is contacted with or exposed to a selected agent, incubated for a time sufficient for induction of the gene driven by the inducible promoter, and expression of reporter gene is determined. In a specific aspect, the reporter gene driven by the inducible promoter encodes a fluorescent or luminescent protein. In a specific aspect, the constitutive reporter encodes a fluorescent or luminescent protein. In a specific aspect, each transgenic organism has an inducible promoter operably linked or fused to a reporter gene encoding a first fluorescent protein and a constitutive reporter encoding a second fluorescent protein wherein the first and second fluorescent protein fluoresce at detectably different wavelengths. Non-limiting examples of fluorescent proteins that fluoresce at detectably different wavelengths are GFP and RFP. Preferably, the inducible reporter expresses at least 2-fold greater, 3-fold great, or 4-fold greater than background levels (e.g., untreated organisms).

In a specific aspect of the embodiment described in the paragraph above, the invention is two or more (a) representative transgenic organisms or (b) populations of representative transgenic organisms as biosensors for detecting an alteration in gene expression as a response to exposure to a selected agent. In another specific aspect, the invention is three or more (a) representative transgenic organisms or (b) populations of representative transgenic organisms as biosensors for detecting an alteration in gene expression as a response to exposure to a selected agent. In yet another specific aspect, the invention is four or more (a) representative transgenic organisms or (b) populations of representative transgenic organisms as biosensors for detecting an alteration in gene expression as a response to exposure to a selected agent. In another specific aspect, the invention is five or more (a) representative transgenic organisms or (b) populations of representative transgenic organisms as biosensors for detecting an alteration in gene expression as a response to exposure to a selected agent. In another specific aspect, the invention is seven or more (a) representative transgenic organisms or (b) populations of representative transgenic organisms as biosensors for detecting an alteration in gene expression as a response to exposure to a selected agent. In another specific aspect, the invention is ten or more (a) representative transgenic organisms or (b) populations of representative transgenic organisms as biosensors for detecting an alteration in gene expression as a response to exposure to a selected agent. In another specific aspect, the invention is fifteen or more (a) representative transgenic organisms or (b) populations of representative transgenic organisms as biosensors for detecting an alteration in gene expression as a response to exposure to a selected agent. In another specific aspect, the invention is twenty or more (a) representative transgenic organisms or (b) populations of representative transgenic organisms as biosensors for detecting an alteration in gene expression as a response to exposure to a selected agent. Preferably, the inducible reporter is capable of expressing at least 2-fold greater, 3-fold greater, or 4-fold greater than its background expression level (e.g., untreated organisms).

The invention is a plurality of transgenic organisms for use as biosensors. The plurality of transgenic organisms includes at least two (a) representative transgenic organisms or (b) populations of representative transgenic organisms wherein the representative transgenic organisms or populations of representative transgenic organisms are distinct from one another in having transgenes comprising different inducible promoters operably linked or fused to a reporter gene (e.g., different strains) wherein the inducible promoter or promoters are chosen from SEQ ID NO:1 through SEQ ID NO:162, or a fragment thereof having 50, 100, 200, 300, 400, or 500 or more nucleotides of said promoter. For example, transgenic organism (1) has a transgene which is the inducible promoter of gene (1) operably linked or fused to a reporter gene and transgenic organism (2) has a transgene which is the inducible promoter region of gene (2) operably linked or fused to a reporter gene. The reporter genes used in the transgenic organism can be the same or different reporter genes. In a specific aspect, the reporter gene is the same gene in each transgenic organism. Typically, the inducible promoter is selected from a response pathway gene. Response pathway genes are genes from pathways that modulate an organism's response to an agent or stimuli at the gene expression level. In one specific aspect, the response pathway gene is a toxicity response pathway gene. In another specific aspect, the toxicity pathway response gene is a heavy metal, oxidative stress, endocrine disruption, xenobiotic, carcinogenic, genotoxic, neurotoxic, hepatatoxic, nephratoxic, or immunotoxic response pathway gene. In another aspect, the response pathway gene is an oxidative stress response gene, a carcinogen response pathway gene, an apoptosis pathway gene, an endocrine pathway gene, a genotoxin pathway gene, or a xenobiotic metabolism pathway. In one aspect, the response pathway gene is an oxidative stress response gene. In one aspect, the response pathway gene is a genotoxin response gene. In one aspect, the response pathway gene is a xenobiotic metabolism pathway gene. In one aspect, the plurality of (a) representative transgenic organisms or (b) populations of representative transgenic organisms comprise 2 or more, 3 or more, 4 or more, or 5 or more (a) representative transgenic organisms or (b) population of representative transgenic organisms having transgenes whose promoters are chosen from distinct oxidative stress response genes. In one aspect, the plurality of (a) representative transgenic organisms or (b) populations of representative transgenic organisms comprise 2 or more, 3 or more, 4 or more, or 5 or more (a) representative transgenic organisms or (b) population of representative transgenic organisms having representative transgenes whose promoters are chosen from distinct genotoxin stress response genes. In one aspect, the plurality of representative transgenic organisms or populations of representative transgenic organisms comprise 2 or more, 3 or more, 4 or more, or 5 or more (a) representative transgenic organisms or (b) population of representative transgenic organisms having representative transgenes whose promoters are chosen from distinct xenobiotic metabolism pathway genes. Preferably, the inducible reporter is capable of expressing at least 2-fold greater, 3-fold greater, or 4-fold greater than its background expression level (e.g., untreated transgenic organism or identical transgenic organism except for not having the inducible promoter reporter construct).

The invention is a transgenic organism, or a transgene, nucleic acid, or construct, comprising an inducible promoter operably linked, or fused, to a reporter gene to provide a biosensor functionality. In one specific aspect, the transgenic organism has the inducible promoter reporter transgene inserted into its genome by a single copy site specific insertion technology. In another specific aspect, the transgenic organism has a second reporter in its genome wherein said second reporter is expressed at a constitutive level. In one aspect, the constitutive reporter is inserted into the organism's genome as a single copy or using a single site insertion technology. The second reporter (constitutive) is used e.g., for normalization of the signal generated from the first reporter (inducible reporter). In one specific aspect, the transgene comprising the inducible promoter operably linked, or fused, to the reporter gene is inserted into the organism's genome in multiple copies, for example, 2 or more copies, 3 or more copies, 5 or more copies, 7 or more copies, or 10 or more copies. In one aspect, the reporter gene driven by the inducible promoter encodes a fluorescent or luminescent protein. In one aspect, the second reporter gene expressed at a constitutive level encodes a fluorescent protein or luminescent protein. In one aspect, the reporter gene driven by the inducible promoter encodes a fluorescent protein. In one aspect, the second reporter gene expressed at a constitutive level encodes a fluorescent protein. In one aspect, the reporter gene driven by the inducible promoter encodes a fluorescent protein which fluoresces at a wavelength that is detectably different than the wavelength that the fluorescent protein encoded by the constitutive reporter fluoresces. In one specific aspect, the reporter driven by the inducible promoter encodes a protein comprising a RFP and the reporter driven by the constitutive reporter encodes a protein comprising a GFP. Preferably, the inducible reporter is capable of expressing at least 2-fold greater, 3-fold greater, or 4-fold greater than its background expression level (e.g., untreated transgenic organism or identical transgenic organism except for not having the inducible promoter reporter construct).

In one embodiment, the invention is a method for detecting expression of a reporter gene operably linked, or fused, to an inducible promoter in a transgenic organism. According to this method, a plurality or array of representative transgenic organisms, or populations thereof, is provided wherein each representative transgenic organism, or population thereof, has an inducible promoter reporter construct integrated into its genome. A representative transgenic organism is one that has one type of inducible promoter reporter construct as a transgene e.g., a promoter from a specific gene. For example, a plurality of representative transgenic organisms can refer to e.g., a representative transgenic organism or population thereof (a) which has a transgene which is inducible promoter (a) operably linked or fused to a reporter; and representative transgenic organism or a population thereof (b) which has a transgene which is inducible promoter (b) operably linked or fused to a reporter. According to the method, each representative organism, or population thereof, is characterized by the identity of its inducible promoter (the organism "represents" a specific type of response characterized by the identity inducible promoter). Thus, each representative organism, or population thereof, has a distinct inducible promoter which is derived or obtained from a distinct gene. Each different representative transgenic organism can be present as multiple organisms to give a population of representative transgenic organisms (e.g., 3, 5, 10, 50, 100, 200 or 300 or more organisms) or as a single organism. The representative transgenic organism or population of transgenic organisms are exposed to or contacted with a selected agent and incubated with reagent and time sufficient to allow expression of the reporter gene. The reporter gene is detected or quantified. Optionally, the quantity of reporter can be normalized against the value for a second reporter gene, e.g., the constitutive reporter gene. Preferably, the reporter or reporters are fluorescents proteins. In one aspect, the inducible reporter encodes a protein comprising a RFP. In one aspect, the constitutive reporter encodes a protein comprising a GFP. Preferably, the inducible reporter is capable of expressing at least 2-fold greater, 3-fold greater, or 4-fold greater than its background expression level (e.g., untreated transgenic organism or identical transgenic organism except for not having the inducible promoter reporter construct).

In one embodiment, the invention is a method for detecting expression in a transgenic organism a first reporter gene operably linked or fused to an inducible promoter and a second reporter expressed at constitutive levels. According to this method, a plurality or array of representative transgenic organisms, or populations thereof, is provided wherein each representative transgenic organism, or population thereof, has an inducible promoter reporter construct and a constitutively expressed reporter integrated into its genome wherein the inducible promoter or promoters are chosen from SEQ ID NO:1 through SEQ ID NO:162, or a fragment thereof having 50, 100, 200, 300, 400, or 500 or more nucleotides of said promoter. A representative transgenic organism is one that has one type of inducible promoter reporter construct as a transgene. For example, a plurality of representative transgenic organisms can refer to e.g., a representative transgenic organism (a) which has a transgene which is inducible promoter (a) operably linked or fused to a reporter; and representative transgenic organism (b) which has a transgene which is inducible promoter (b) operably linked or fused to a reporter. According to the method, each representative organism, or population thereof, is characterized by the identity of its inducible promoter (the organism "represents" a specific type of response characterized by the identity inducible promoter). Thus, each representative organism, or population thereof, has a distinct inducible promoter which is derived or obtained from a distinct gene. The representative transgenic organism or population of transgenic organisms are exposed to or contacted with a selected agent and incubated with reagents and time sufficient to allow expression of the reporter genes. The level of the reporter gene is then detected or quantified. The quantity or level of the inducible reporter can be normalized against the quantity or level of a second reporter gene, e.g., the constitutive reporter gene. Preferably, the reporter or reporters encode a fluorescent proteins or proteins. In one aspect, the inducible reporter encodes a protein comprising a RFP. In one aspect, the constitutive reporter encodes a protein comprising a GFP. Preferably, the inducible reporter is capable of expressing at least 2-fold greater, 3-fold greater, or 4-fold greater than background its level (e.g., untreated transgenic organism or identical transgenic organism except for not having the inducible promoter reporter construct).

The combination of use of single site insertion technology for the inducible promoter reporter transgene and the use of second constitutive reporter for normalization in the invention has produced remarkable unprecedented results for whole organism biosensors. In one aspect, the transgene is inserted into a single site of the host organisms's genome using single site insertion technology and is present as one copy. In one aspect, the transgene is inserted into multiple sites in the host organism's genome using a site-specific insertion technology and is present in from 2 to 50 copies, more preferably 2 to 20 copies and even more preferably from 2 to 10 copies.

In an alternative aspect, the transgene is inserted into the organism's genome as multiple copies. For example, ballistic genes guns can be used to insert the transgene into the organism's genome in the range of 1 copy to about 50 copies. In another aspect, the transgene is inserted into the extra-chromosomal array of a *C. elegans* host organism. In this aspect, the host organism typically has from about 100 to about 1000 copies of the transgene.

According to one aspect of the invention, the transgenic organism is translucent or at least partially translucent. More specifically, the transgenic organism of this aspect is translucent or at least partially translucent to allow for spectrophotometric detection of one or more reporter genes in a medium or high-throughput fashion. In one specific aspect, medium or high throughput format refers to the ability detect the expression level of the reporter gene in a multi-well plate format using a plate reader that is capable of detecting and quantitating the level of fluorescence or bioluminescence of the respective reporter. In another specific aspect, the transgenic organism is a nematode, *Danio rerio* (zebrafish), *Drosophila melanogaster, Daphnia* spp., or *Xenopus laevis*. In one specific aspect, the organism is a nematode. In another specific aspect, the organism is *C. elegans*. The ordinary skilled artisan is capable of identify promoters in organisms such *Danio rerio, Drosophila melanogaster, Daphnia* spp., or *Xenopus laevis* to create the transgenic organisms in a manner similar to that described herein for *C. elegans*.

In one embodiment, the invention involves transgenesis of DNA into the worm genome (e.g., *C. elegans*). This DNA is a transgene that contains an inducible promoter operably linked or fused to a gene encoding a reporter protein. The inserted DNA then allows reporter protein expression in the transgenic organism upon exposure to a selected agent or toxin that activates or induces its expression. The genetically engineered animal serves as a biosensor (e.g., for toxicity). According to one aspect of this embodiment, the transgene is inserted into the genome using MosSCI technology. The method involves (a) providing a strain of an organism having an insertion element site and a marker for positive selection (b) injecting the organisms with a vector having a transgene comprising (1) an inducible promoter reporter construct, (2) a marker for selection, and (3) sequence elements (e.g., homology arms) sufficient for effectuating insertion into the insertion element site or sites of the strain, a vector for producing a transposase compatible with the transposon and insertion element site, and one or more plasmids acting as markers for tracking the presence of extrachromosal arrays. Injected animals are transferred to plates, allowed to grow or incubate for a time sufficient to allow for transformation and recovery, and are then screened for insertion events by use of the selection markers in the strain, the transgene, and the markers for tracking the presence of extrachromosomal markers.

Inducible Promoters

Figure 8:
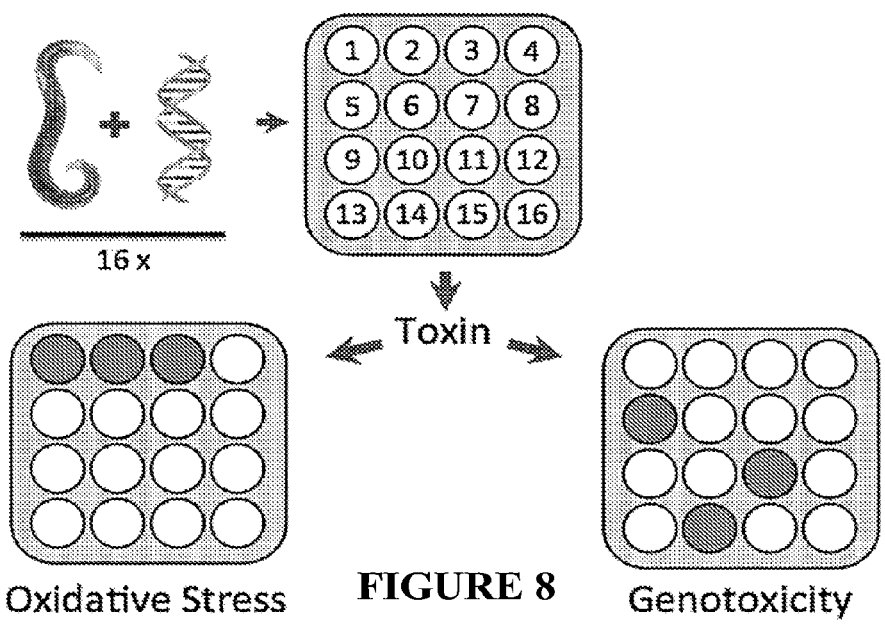
FIG. 8 shows a predicted set of results related to a panel or array of biosensors involved in oxidative stress and genotoxic stress. A 16 well microwell plate having populations of representative transgenic organisms for both oxidative stress and genotoxin stress are seeded into the wells of the plates. Exposure of organisms in the wells of the plates to a selected agent that induces oxidative stress or genotoxic stress gives digitized read-outs indicative of which toxicity pathway is being activated by the selected agent. The lower left plate shows activation of an oxidative stress pathway whereas the lower right plate shows activation of a genotoxin pathway.
Figure 9:
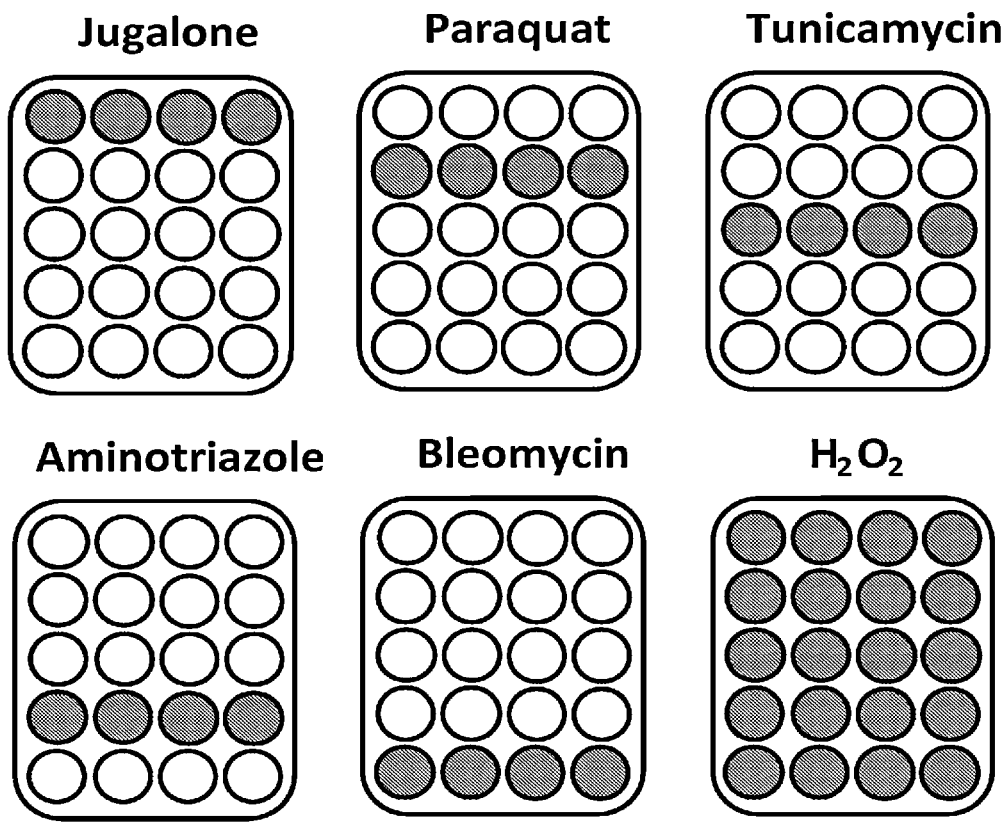
FIG. 9 shows a predicted set of results related to a panel or array of biosensors involved in oxidative stress. A 16 well microwell plate having populations of representative transgenic organisms for both oxidative stress are seeded into the wells of the plates. Exposure of the wells in the plate with a selected agent that induces oxidative stress give digitized read-outs indicative of which oxidative stress toxicity pathway is being activated by the selected agent. The plates show activation of the indicated oxidative stress pathway by induction of the reporters in the highlighted rows.

A variety of inducible promoters are used to make different transgenic biosensors organisms of the invention. Inducible promoters are chosen from different genes that are selected for being activated or modulated in response to stimuli or conditions, e.g., like toxins or a drug or drug candidate. The promoters are chosen to include transcription factor response elements which are DNA sequences that enhance or drive transcription of a gene involved in a response pathway by serving as a template for the transcriptional machinery (transcription factors) associated with the response pathway. In one embodiment of the invention, the resulting transgenic biosensor organisms are arranged into a panel. A test compound (selected agent) is exposed to members of the panel and specific types of response (e.g., toxicities) are detected (see e.g., FIG. 8 or FIG. 9). In an alternative embodiment, the same representative transgenic strain, or population thereof, is duplicated in all wells of the panel and a population of molecules, like a library, are screened for one type of toxicity. In one specific example, a library of molecules designed to inhibit or modulate a specific target or that inhibited or modulated a specific target are counter-screened against one or more representative transgenic organisms, or populations thereof, to identify a molecule or molecules that have the least toxicology liabilities or have a desirable toxicity profile.

The inducible promoters used in the invention can be any promoter element or region that is involved in regulating gene expression. Promoter regions typically lie upstream of a gene, anywhere from about 1 to 10,000 or more base pairs (bp) upstream of the start site. In general, regions ranging from 1 to 4,000 bp upstream of start codon are chosen for promoter selection. In one aspect, the region ranges from about 1 to 2500 bp upstream from the start site. In one aspect, the region ranges from about 1 to 2000 bp upstream from the start site. In one aspect, the region ranges from about 1 to 1000 bp upstream from the start site. In one aspect, the promoter is within about 500 bp upstream of the transcription start site. See e.g., Gerstein et al. Science. 2010 Dec. 24; 330(6012):1775-87.

The genes chosen for the exemplary oxidative stress response panel are the following oxidative response genes (hsp-16.41, hsp16.2, hsp-6 and hsp-60, hsp-4, mlt-2, and ugt-1). To choose the oxidative-response gene promoters and any other promoters for use in the invention, a combination of modENCODE's TF-GFP ChIP-seq data (Niu et al. Genome Res. 2011 February; 21(2):245-254) and multi-z 6-species alignment (Niu et al. Genome Research 2004; 14(4):708-715.) can be used to find the extent of conserved genomic regions containing TF (transcription factor) sites in front of the oxidative-response gene's start codon (or other response pathway genes). Promoter-reporter fusion constructs can be designed for Gibson (Gibson et al. Nat. Methods 2009 May; 6(5):343-345) reaction cloning using APE plasmid editor (biologylabs.utah.edu/jorgensen/wayned/ape). In general, regions ranging from 300 to 4,000 bp upstream of start codon were chosen for promoter selection. Other techniques for identifying, selecting and cloning inducible promoter regions for use in the compositions and methods of the invention are known to the skilled artisan.

Reporter Genes

Reporter genes for use in the invention include any reporter that can be expressed and quantified. Preferably, the reporter gene encodes a protein that can be detected spectrophotometrically. Some examples include fluorescent proteins (e.g., green fluorescent protein (GFP), cyan fluorescent protein (CFP), red fluorescent protein (RFP), mCherry, Tag-RFP, etc.), luciferase which is a luminescent reporter (Ranella, Firefly, etc.), chomogenic (beta-Gal, etc.), etc. See e.g., Pollock et al., Trends in Cell Biology 9:57 (1999). Useful fluorescent proteins also include mutants and spectral variants of these proteins which retain the ability to fluoresce. See e.g., Shaner et al., Nat. Biotech. 22:1567 (2004), Tag-RFP (Shaner, N. C. et al., 2008 Nature Methods, 5(6), 545-551), fluorescent proteins fused to e.g., his-GFP or his-RFP which is histone H2B fused to the indicated fluorescent protein Essex et al. Mol. Biol. Cell 2009 February;

20(4):1252-1267). Other fluorescent proteins that can be used in the invention include, but are not limited to, AcGFP, AcGFP1, AmCyan, AmCyan1, AQ143, AsRed2, Azami Green, Azurite, BFP, Cerulean, CFP, CGFP, Citrine, copGFP, CyPet, dKeima-Tandem, DsRed, dsRed-Express, DsRed-Monomer, DsRed2, dTomato, dTomato-Tandem, EBFP, EBFP2, ECFP, EGFP, Emerald, EosFP, EYFP, GFP, HcRed-Tandem, HcRedl, JRed, Katuska, Kusabira Orange, Kusabira Orange2, mApple, mBanana, mCerulean, mCFP, mCherry, mCitrine, mECFP, mEmerald, mGrape1, mGrape2, mHoneydew, Midori-Ishi Cyan, mKeima, mKO, mOrange, mOrange2, mPlum, mRaspberry, mRFP1, mRuby, mStrawberry, mTagBFP, mTangerine, mTeal, mTomato, mTurquoise, mWasabi, PhiYFP, ReAsH, Sapphire, Superfolder GFP, T-Sapphire, TagCFP, TagGFP, TagRFP, TagRFP-T, TagYFP, tdTomato, Topaz, TurboGFP, Venus, YFP, YPet, ZsGreen, and ZsYellow1 which are described in the literature or otherwise commercially available. hRFP and hsRFP are RFP's fused to e.g., a histone protein like H2B from *C. elegans*.

Isolated Nucleic Acids, Transgenes, Constructs, Transgenic Organisms and Transgenic *C. elegans* Organisms The invention is nucleic acids and constructs and transgenic organisms comprising those nucleic acids as described herein.

In one embodiment, the invention provides a transgene, a transgenic organism, or a construct which comprises a promoter, a fragment of a promoter having 50, 100, 200, 300, 400, or 500 or more nucleotides of the promoter, or a homolog thereof having at least 95%, 96%, 97%, 98%, or 99% identity thereto operably linked, or fused, to a reporter gene wherein said reporter gene encodes a fluorescent or luminescent protein and wherein the promoter is for the *C. elegans* gene cdr-1, gcs-1, ugt-1, gst-38, hsp-60, hsp-16.41, mtl-2, hsp-16.2, gst-4, ugt-13, hsp-3, hsp-6, hsp-4, hsp-1, skn-1, dnj-13, daf-21, Hsp-17, cyp-13A7, cyp-14A3, cyp-35A2, zyg-12, ZK742.4, ZK742.3, fkb-1, fkb-2, fkb-3, fkb-4, fkb-5, fkb-6, fkb-7, fkb-8, fmo-1, fmo-2, fmo-3, fmo-4, fmo-5, ftn-1, ftn-2, fzy-1, gen-1, glp-1, gsr-1, gst-1, gst-23, gst-25, gst-41, H01G02.2, haf-6, syp-2, T05A12.4, T05G5.3, T06E6.2, T07F12.4, Hsp-12.2, T05E11.3, Cnx-1, Crt-1, cyp-35A1, cyp-35C1, cyp-35A3, pqe-1, cyp-37B1, cyp-35B2, cyp-35B1, cyp-22A1 (daf-9), cyp-14A5, cyp-35B3, cyp-34A6, daf-16, exo-3, nth-1, pme-1, ung-1, xpa-1, mrt-2, ercc-1, ZK697.8, ZK287.5, haf-7, hda-1, hda-10, hda-11, hda-2, hda-3, hda-4, hda-5, hda-6, hdac-1, hif-1, him-1, him-14, him-3, him-4, him-6, hmg-3, hmg-4, hmg-5, hpr-17, hpr-9, hrdl-1, hsf-1, hsp-1, hsp-16.48, tbb-4, tnc-2, top-3, tor-2, trx-1, xpf-1, xpg-1, rad-23, mlh-1, msh-2, msh-4, msh-5, msh-6, brc-1, brc-2, rad-50, cku-70, lin-35, mei-1, cki-1, cki-2, cep-1, ced-3, ced-9, ced-13, vem-1, dhs-23, sodh-2, dnj-19, Xbp-1, hsp-16.49, hsp-2, htp-1, htp-3, hus-1, imb-3, ire-1, irk-1, K07C5.2, K07C5.4, K08F4.1, K11G12.5, kin-18, lagr-1, let-2, let-92, lig-1, lig-4, lim-4, lin-12, lin-44, lin-49, lrk-1, lst-3, M18.5, vps-41, W01A11.1, W02C12.1, W03G1.5, W06H8.2, Hipr-1, cdc-48.1, cdc-48.3, Ubq-1, Ubq-2, Gst-10, Gst-13, f25d1.5, fil-1, k10h10.6, hsp-70, f44e5.4, f44e5.5, hsp-16.11, hsp-16.1, nurf-1, aip-1, y43f8b.2, Dod-17, Dod-24, C55A6.7, F56D5.3, cyp-13A11, cyp-13A6, cyp-25A4, mac-1, mboa-2, mdf-1, mdf-2, mec-14, med-1, mel-28, misc-1, mnat-1, mre-11, mrp-1, mrp-2, mrp-3, mrp-4, mrp-5, mrp-6, mrp-7, mrp-8, mspn-1, mus-1, mut-2, mxl-1, mxl-2, mxl-3, ndx-1, Y55B1AL.2, Y56A3A.33, Y66D12A.15, Y66D12A.5, Y73C8C.10, cyp-29A2, cyp-31A1, cyp-31A3, cyp-33B1, cyp-33E1, cyp-34A10, cyp-34A9, cyp-35A4, cyp-35D1, abl-1, abu-1, acr-14, acr-22, agt-1, ahr-1, air-2, ama-1, apa-2, apn-1, apn-1, aps-2, arf-1, asp-5, atf-5, atgr-7, ndx-4, nft-1, nhr-6, nol-5, npl-4.2, nuc-1, odc-1, paa-1, pas-4, pat-10, pcn-1, pdi-1, pdi-2, pdi-3, pdr-1, pek-1, pgp-1, pgp-10, pgp-2, phi-37, phi-44, phi-9, pink-1, pme-2, pme-3, T08D2.4, T08D2.7, T08H10.1, T10B5.8, T13A10.2, atl-1, atm-1, B0222.9, B0432.2, B0495.2, B0563.7, brd-1, C01G5.5, C06A1.6, C06H2.3, C07D8.6, C08H9.3, C09D4.3, C11E4.2, C25A1.5, C30G7.5, C35C5.2, C35D10.2, C35D10.6, C37A2.4, C37C3.6a, C44H4.4, C56G3.2, catp-6, cbn-1, F17A9.5, F18A1.5, F19G12.2, F23C8.9, F36A4.15, F43D2.1, F43G6.5, F44B9.8, F45E12.3, F49E12.6, F52B5.2, F52C12.1, F53C11.5, F53F1.2, F53F1.3, F53F10.2, F55B11.1, F57B10.5, F57B10.6, F58F9.1, F59A2.3, F59F4.1, fan-1, fdps-1, figl-1, trxr-1, tut-1, uba-1, ubc-1, ubc-20, ccch-1, cct-1, cct-2, cct-3, cct-4, cct-5, cct-6, cct-7, cct-8, cdc-14, cdc-48.2, cdk-7, ced-4, cel-1, cft-1, chk-1, chk-2, chn-1, cku-80, cle-1, clk-2, clpp-1, cmd-1, cnb-1, col-135, pme-4, pme-5, pmrt-5, pms-2, png-1, polh-1, polk-1, prx-6, ptl-1, R02D3.3, R03D7.2, R05D11.6, R05F9.10, R09H10.3, R10E4.9, R13D11.4, R151.6, rab-1, rab-7, srp-2, ssc-1, sti-1, sulp-7, sut-1, sut-2, wrn-1, xpc-1, Y110A7A.4, Y38F1A.5, Y38H8A.3, cps-6, crb-1, crn-1, crn-2, crn-3, crn-4, crn-5, crn-6, crp-1, csb-1, ctl-2, ctl-3, cul-1, cul-2, cul-4, cul-5, cyh-1, cyn-1, cyn-10, cyn-11, cyn-12, cyn-13, cyn-14, cyn-15, cyn-16, rad-51, rad-54, rbx-1, rbx-2, rcf-3, rcq-5, rec-8, rev-1, rfc-1, rfc-4, rfl-1, rme-8, rnf-121, rnh-1.0, rpa-1, rpa-2, rpn-10, rps-19, rps-26, T23G5.6, T26A5.5, T27E9.1, tag-353, tars-1, tbb-2, Y73F8A.24, ymel-1, ZC168.4, ZC395.10, ZC443.1, cyn-17, cyn-2, cyn-3, cyn-4, cyn-5, cyn-6, cyn-7, cyn-8, cyn-9, cyp-13A12, cyp-13A4, cyp-14A2, cyp-33C1, cyp-33C2, cyp-33C9, cyp-33E2, cyp-42A1, cyp14A2, cyp33C9, cyp34A6, D1081.8, D2023.4, daf-1, daf-14, daf-3, rpt-3, rpt-4, rpt-5, rpt-6, rtel-1, san-1, scav-1, scav-2, scav-3, scav-4, scav-5, scc-3, sdz-8, sec-22, sep-t, set-25, set-26, set-8, set-9, unc-11, unc-26, unc-57, uri-1, usp-14, vps-4, T15B7.2, T16H12.4, ugt-62, Y39G8B.1, Y39G8B.2, daf-5, daf-7, daf-8, dbl-1, ddb-1, dhs-22, djr-1.1, dna-2, dog-1, drh-3, drp-1, dut-1, E01A2.1, eft-2, egl-1, eif-2, emb-9, epg-2, eps-8, exo-1, F09E5.2, F14F9.5, F15E6.6, F16A11.2, F17A9.4, sft-4, sgg-1, sin-3, sir-2.1, sir-2.2, sir-2.3, sir-2.4, skr-15, slt-1, slx-1, smf-1, smk-1, sod-1, sod-2, sod-3, sod-4, sod-5, spas-1, ugt-61, Y43E12A.1, Y43F8C.13, Y48G1BL.2, Y50D7A.1, Y50D7A.2, Y54E10A.3, ufd-1, ugt-22, ugt-52, ZK1128.4, ZK1290.5, or Y39H10A.7. The transgene, transgenic organism, or construct is used for the gene expression biosensors as described herein. According to the invention, an inducible promoter or fragment thereof, or a homolog having at least 95%, 96%, 97%, 98%, or 99% identity thereto, of one or more of the genes listed above and is operably linked, or fused, to a reporter gene using standard molecular biology techniques as described herein and elsewhere. The resulting construct can be transformed into an organism to a yield a transgenic biosensor organism as described herein. In a specific aspect, the construct further comprises one or more of the following: a selectable marker, sequence elements sufficient for site-specific integration into the host organism's genome. In one aspect, the transgene is introduced into the organism with a technique that yields a site specific single copy stable insertion. In a specific aspect, the transgenic biosensor organisms are arranged into an array or panel. The panels can be arranged into kits useful for detecting a wide variety of toxicities or gene expression responses. In one specific aspect, the transgenic organism is a nematode. In another specific aspect, the transgenic organism is *C. elegans*.

In one embodiment, the invention provides a transgene, a transgenic organism, or a construct comprising a promoter, a fragment of a promoter having 50, 100, 200, 300, 400, or 500 or more nucleotides of the promoter, or a homolog thereof having at least 95%, 96%, 97%, 98%, or 99% identity thereto, operably linked, or fused, to a reporter gene wherein said reporter gene encodes a fluorescent or luminescent protein and wherein the promoter is from an organism chosen from *Danio rerio* (zebrafish), *Drosophila melanogaster*, *Daphnia* spp., or *Xenopus laevis* and the promoter is for gene that organism that is homologous to the gene in *C. elegans* corresponding to cdr-1, gcs-1, ugt-1, gst-38, hsp-60, hsp-16.41, mtl-2, hsp-16.2, gst-4, ugt-13, hsp-3, hsp-6, hsp-4, hsp-1, skn-1, dnj-13, daf-21, Hsp-17, cyp-13A7, cyp-14A3, cyp-35A2, zyg-12, ZK742.4, ZK742.3, fkb-1, fkb-2, fkb-3, fkb-4, fkb-5, fkb-6, fkb-7, fkb-8, fmo-1, fmo-2, fmo-3, fmo-4, fmo-5, ftn-1, ftn-2, fzy-1, gen-1, glp-1, gsr-1, gst-1, gst-23, gst-25, gst-41, H01G02.2, haf-6, syp-2, T05A12.4, T05G5.3, T06E6.2, T07F12.4, Hsp-12.2, T05E11.3, Cnx-1, Crt-1, cyp-35A1, cyp-35C1, cyp-35A3, pqe-1, cyp-37B1, cyp-35B2, cyp-35B1, cyp-22A1 (daf-9), cyp-14A5, cyp-35B3, cyp-34A6, daf-16, exo-3, nth-1, pme-1, ung-1, xpa-1, mrt-2, ercc-1, ZK697.8, ZK287.5, haf-7, hda-1, hda-10, hda-11, hda-2, hda-3, hda-4, hda-5, hda-6, hdac-1, hif-1, him-1, him-14, him-3, him-4, him-6, hmg-3, hmg-4, hmg-5, hpr-17, hpr-9, hrdl-1, hsf-1, hsp-1, hsp-16.48, tbb-4, tnc-2, top-3, tor-2, trx-2, xpf-1, xpg-1, rad-23, mlh-1, msh-2, msh-4, msh-5, msh-6, brc-1, brc-2, rad-50, cku-70, lin-35, mei-1, cki-1, cki-2, cep-1, ced-3, ced-9, ced-13, vem-1, dhs-23, sodh-2, dnj-19, Xbp-1, hsp-16.49, hsp-2, htp-1, htp-3, hus-1, imb-3, ire-1, irk-1, K07C5.2, K07C5.4, K08F4.1, K11G12.5, kin-18, lagr-1, let-2, let-92, lig-1, lig-4, lim-4, lin-12, lin-44, lin-49, lrk-1, lst-3, M18.5, vps-41, W01A11.1, W02C12.1, W03G1.5, W06H8.2, Hipr-1, cdc-48.1, cdc-48.3, Ubq-1, Ubq-2, Gst-10, Gst-13, f25d1.5, fil-1, k10h10.6, hsp-70, f44e5.4, f44e5.5, hsp-16.11, hsp-16.1, nurf-1, aip-1, y43f8b.2, Dod-17, Dod-24, C55A6.7, F56D5.3, cyp-13A11, cyp-13A6, cyp-25A4, mac-1, mboa-2, mdf-1, mdf-2, mec-14, med-1, mel-28, misc-1, mnat-1, mre-11, mrp-1, mrp-2, mrp-3, mrp-4, mrp-5, mrp-6, mrp-7, mrp-8, mspn-1, mus-1, mut-2, mxl-1, mxl-2, mxl-3, ndx-1, Y55B1AL.2, Y56A3A.33, Y66D12A.15, Y66D12A.15, Y73C8C.10, cyp-29A2, cyp-31A1, cyp-31A3, cyp-33B1, cyp-33E1, cyp-34A10, cyp-34A9, cyp-35A4, cyp-35D1, abl-1, abu-1, acr-14, acr-22, agt-1, ahr-1, air-2, ama-1, apa-2, apn-1, apn-1, aps-2, arf-1, asp-5, atf-5, atgr-7, ndx-4, nft-1, nhr-6, nol-5, npl-4.2, nuc-1, odc-1, paa-1, pas-4, pat-10, pcn-1, pdi-1, pdi-2, pdi-3, pdr-1, pek-1, pgp-1, pgp-10, pgp-2, phi-37, phi-44, phi-9, pink-1, pme-2, pme-3, T08D2.4, T08D2.7, T08H10.1, T10B5.8, T13A10.2, atl-1, atm-1, B0222.9, B0432.2, B0495.2, B0563.7, brd-1, C01G5.5, C06A1.6, C06H2.3, C07D8.6, C08H9.3, C09D4.3, C11E4.2, C25A1.5, C30G7.5, C35C5.2, C35D10.2, C35D10.6, C37A2.4, C37C3.6a, C44H4.4, C56G3.2, catp-6, cbn-1, F17A9.5, F18A1.5, F19G12.2, F23C8.9, F36A4.15, F43D2.1, F43G6.5, F44B9.8, F45E12.3, F49E12.6, F52B5.2, F52C12.1, F53C11.5, F53F1.2, F53F1.3, F53F10.2, F55B11.1, F57B10.5, F57B10.6, F58F9.1, F59A2.3, F59F4.1, fan-1, fdps-1, figl-1, trxr-1, tut-1, uba-1, ubc-1, ubc-20, ccch-1, cct-1, cct-2, cct-3, cct-4, cct-5, cct-6, cct-7, cct-8, cdc-14, cdc-48.2, cdk-7, ced-4, cel-1, cft-1, chk-1, chk-2, chn-1, cku-80, cle-1, clk-2, clpp-1, cmd-1, cnb-1, col-135, pme-4, pme-5, pmrt-5, pms-2, png-1, polh-1, polk-1, prx-6, ptl-1, R02D3.3, R03D7.2, R05D11.6, R05F9.10, R09H10.3, R10E4.9, R13D11.4, R151.6, rab-1, rab-7, srp-2, ssc-1, sti-1, sulp-7, sut-1, sut-2, wrn-1, xpc-1, Y110A7A.4, Y38F1A.5, Y38H8A.3, cps-6, crb-1, crn-1, crn-2, crn-3, crn-4, crn-5, crn-6, crp-1, csb-1, ctl-2, ctl-3, cul-1, cul-2, cul-4, cul-5, cyh-1, cyn-1, cyn-10, cyn-11, cyn-12, cyn-13, cyn-14, cyn-15, cyn-16, rad-51, rad-54, rbx-1, rbx-2, rcf-3, rcq-5, rec-8, rev-1, rfc-1, rfc-4, rfl-1, rme-8, rnf-121, rnh-1.0, rpa-1, rpa-2, rpn-10, rps-19, rps-26, T23G5.6, T26A5.5, T27E9.1, tag-353, tars-1, tbb-2, Y73F8A.24, ymel-1, ZC168.4, ZC395.10, ZC443.1, cyn-17, cyn-2, cyn-3, cyn-4, cyn-5, cyn-6, cyn-7, cyn-8, cyn-9, cyp-13A12, cyp-13A4, cyp-14A2, cyp-33C1, cyp-33C2, cyp-33C9, cyp-33E2, cyp-42A1, cyp14A2, cyp33C9, cyp34A6, D1081.8, D2023.4, daf-1, daf-14, daf-3, rpt-3, rpt-4, rpt-5, rpt-6, rtel-1, san-1, scav-1, scav-2, scav-3, scav-4, scav-5, scc-3, sdz-8, sec-22, sep-1, set-25, set-26, set-8, set-9, unc-11, unc-26, unc-57, uri-1, usp-14, vps-4, T15B7.2, T16H12.4, ugt-62, Y39G8B.1, Y39G8B.2, daf-5, daf-7, daf-8, dbl-1, ddb-1, dhs-22, djr-1.1, dna-2, dog-1, drh-3, drp-1, dut-1, E01A2.1, eft-2, egl-1, eif-2, emb-9, epg-2, eps-8, exo-1, F09E5.2, F14F9.5, F15E6.6, F16A11.2, F17A9.4, sft-4, sgg-1, sin-3, sir-2.1, sir-2.2, sir-2.3, sir-2.4, skr-15, slt-1, slx-1, smf-1, smk-1, sod-1, sod-2, sod-3, sod-4, sod-5, spas-1, ugt-61, Y43E12A.1, Y43F8C.13, Y48G1BL.2, Y50D7A.1, Y50D7A.2, Y54E10A.3, ufd-1, ugt-22, ugt-52, ZK1128.4, ZK1290.5, or Y39H10A.7. The transgene, transgenic organism, or construct is used for the gene expression biosensors as described herein. According to the invention, an inducible promoter or fragment thereof, or a homolog having at least 95%, 96%, 97%, 98%, or 99% identity thereto, of one or more of the genes listed above and is operably linked, or fused, to a reporter gene using standard molecular biology techniques as described herein and elsewhere. The resulting construct can be transformed into an organism to a yield a transgenic biosensor organism as described herein. In one aspect, the transgene is introduced into the organism with a technique that yields a site specific single copy stable insertion. In a specific aspect, the transgenic biosensor organisms are arranged into an array or panel. The panels can be arranged into kits useful for detecting a wide variety of toxicities or gene expression responses. In one specific aspect, the transgenic organism is a nematode. In another specific aspect, the transgenic organism is *C. elegans*.

In one embodiment, the invention provides a transgene, a transgenic organism, or a construct which comprises a promoter, a fragment of a promoter having 50, 100, 200, 300, 400, or 500 or more nucleotides of the promoter, or a homolog thereof having at least 95%, 96%, 97%, 98%, or 99% identity thereto operably linked, or fused, to a reporter gene wherein said reporter gene encodes a fluorescent or luminescent protein and wherein the promoter is for the *C. elegans* gene ABCE-1, ABCF-1, ABCF-2, ABCF-3, ABT-1, ABT-2, ABT-4, ABT-5, ABTM-1, acr-14, acr-22, ahr-1, akt-1, akt-2, apa-2, ape-1, apn-1, aps-2, ard-1, arf-1, arf-1.1, arl-7, asp-5, atf-5, atgr-7, B0222.9, B0432.2, B0495.2, B0563.7, bec-1, bmk-1, C01B10.7, C01G12.5, C01G5.5, C01H6.4, C03A7.12, C03A7.13, C04F12.1, C05C9.1, C06A1.6, C06E4.3, C06E4.4, C06E4.6, C06G1.1, C06H2.3, C07A9.13, C07D8.6, C08H9.3, C09D4.3, C11E4.2, C16C8.14, C23G10.6, C25A1.5, C25A1.6, C27D8.4, C28H8.11, C30G12.2, C30G7.5, C31H1.1, C32D5.12, C33E10.10, C35B1.5, C35C5.2, C35D10.2, C35D10.6, C37A2.4, C37C3.6a, C41A3.1, C44H4.4, C46H11.2, C55A6.3, C55A6.4, C55A6.6, C55C3.1, C55H1.1, C56G3.2, cah-5, car-1, catp-6, cbn-1, ccch-1, cct-2, cct-3, cct-4, cct-5, cct-6, cct-7, cct-8, cdc-14, cdr-5, ced-1, ced-10, ced-12, ced-13, ced-2, ced-5, ced-6, CED-7, ceh-20, ceh-30, ces-1, ces-2, cgh-1, chn-1, cit-1.2, ckb-2, cle-1, clec-149, clpp-1, cmd-1, cnb-1, Cnx-1, cnx-1, col-135, coq-6, cpb-3, crb-1, crp-1, Crt-1, crt-1, csp-1, csp-2, csp-3, ctl-1, cul-1, cul-2, cul-3, cul-5, cyn-1, cyn-10, cyn-11, cyn-12, cyn-14, cyn-15, cyn-16, cyn-17, cyn-2, cyn-3, cyn-4, cyn-5, cyn-6, cyn-7, cyn-8, cyn-9, CYP-13A1, CYP-13A10, CYP-13A2, CYP-13A3, CYP-13A5, CYP-13A8, CYP-13B1, CYP-13B2, CYP-14A1, CYP-14A4, CYP-23A1, CYP-25A1, CYP-25A2, CYP-25A3, CYP-25A5, CYP-25A6, CYP-29A3, CYP-29A4, CYP-31A2, CYP-32A1, CYP-32B1, CYP-33A1, CYP-33C11, CYP-33C3, CYP-33C4, CYP-33C5, CYP-33C6, CYP-33C7, CYP-33C8, CYP-33D1, CYP-33D3, CYP-33E3, CYP-34A1, CYP-34A2, CYP-34A4, CYP-34A5, CYP-34A7, CYP-34A8, CYP-35A5, CYP-36A1, CYP-37A1, CYP-43A1, CYP-44A1, cyp14A2, cyp14A5, cyp33C9, D1007.16, D1054.8, D1081.8, D2023.4, dad-1, daf-1, daf-14, daf-21, daf-3, daf-5, daf-7, daf-8, DAF-9, dbl-1, DC2.5, dhs-1, dhs-10, dhs-11, dhs-12, dhs-13, dhs-14, dhs-15, dhs-16, dhs-18, dhs-19, dhs-2, dhs-20, dhs-21, dhs-24, dhs-25, dhs-26, dhs-28, dhs-29, dhs-3, dhs-30, dhs-31, dhs-4, dhs-5, dhs-6, dhs-8, dhs-9, djr-1.1, dnj-11, dnj-25, dnj-27, dnj-7, Dod-17, Dod-24, dop-1, dop-1, dop-3, dop-3, dpl-1, dpr-1, drh-3, duox-2, dut-1, E01A2.1, E04F6.15, eat-3, efl-1, efl-2, eft-2, egg-1, egg-2, egl-38, emb-9, eor-1, eor-2, epg-2, eps-8, exos-3, F02C12.2, F07A11.2, F09E5.2, F10D11.6, F10D2.12, F10D2.8, F10D7.3, F12E12.11, F14D12.1b, F14F9.5, F15E6.6, F16A11.2, F17A9.5, F18A1.5, F19G12.2, F20G2.1, F20G2.2, F22D6.15, F22E5.6, F23C8.9, F26D2.15, F28A10.1, F28H7.2, F30B5.4, F32A5.8, F36A4.15, F43G6.5, F44B9.8, f44e5.4, f44e5.5, F45E12.3, F46H5.2a, F49E12.6, F52B5.2, F52C12.1, F53C11.5, F53F1.2, F53F1.3, F53F10.2, F54C1.1, F54F3.4, F55A11.6, F55B11.1, F55E10.6, F56A4.4, F57B10.5, F57B10.6, F58F9.1, F59A2.3, F59E11.2, F59F4.1, fan-1, fasn-1, fdps-1, fil-1, fipr-24, fis-1, fkb-1, fkb-2, fkb-3, fkb-4, fkb-5, fkb-6, fkb-7, fkb-8, fnta-1, ftn-1, ftn-2, gab-1, gad-3, gale-1, gdi-1, ggtb-1, gla-3, gld-1, glp-1, glrx-10, gsr-1, gst-11, gst-12, gst-14, gst-15, gst-16, gst-18, gst-19, gst-2, gst-20, gst-21, gst-22, gst-24, gst-26, gst-28, gst-29, gst-3, gst-30, gst-31, gst-32, gst-33, gst-34, gst-35, gst-36, gst-39, gst-40, gst-42, gst-43, gst-44, gst-5, gst-6, gst-8, gst-9, gstk-1, gstk-2, gsto-1, gsto-2, gsto-3, H01G02.2, H04M03.3, H06H21.9, H10D18.6, H23N18.4, HAF-1, HAF-2, HAF-3, HAF-4, HAF-8, HAF-9, hda-10, hda-11, hda-5, hi-14, hif-1, him-10, him-4, hke-4.1, hlh-2, hlh-3, HMT-1, hpo-15, hps-1, hps-60, hsd-1, hsd-2, hsd-3, hsf-1, hsp-1, hsp-16.1, hsp-16.1, hsp-2, hsp-60, icd-1, ikb-1, imb-3, ing-3, irk-1, irp-1, irp-2, itr-1, jkk-1, jnk-1, K02E11.3, K02E11.4, K02E11.5, K02E11.6, K02E11.7, K02E11.9, K04A8.10, K07C5.2, K07C5.4, K08F4.1, K10F12.4, K11D12.6, K11G12.5, kin-18, kin-4, lagr-1, lbp-1, lbp-2, lbp-3, lbp-4, lbp-5, lbp-6, lbp-7, lbp-8, lbp-9, let-2, let-23, let-60, let-92, lim-4, fin-1, lin-12, lin-3, lin-31, lin-44, lin-49, lip-1, lips-11, lrk-1, lst-3, M18.5, M57.2, mab-5, maoc-1, mca-2, mec-14, med-1, mei-2, mek-1, mek-2, mel-26, mev-1, misc-1, mlt-7, mpk-1, mtl-1, mus-1, mut-2, mxl-1, mxl-2, mxl-3, nas-39, ncs-3, ndx-4, nhr-181, nhr-6, nhr-64, nol-5, npl-4, npl-4.2, nrf-5, nsy-1, nurf-1, odc-1, paa-1, pag-3, pah-1, pas-4, pat-10, pax-2, pdi-1, pdr-1, pek-1, PGP-11, PGP-12, PGP-13, PGP-14, PGP-15, PGP-3, PGP-4, PGP-5, PGP-6, PGP-7, PGP-8, PGP-9, phi-37, phi-44, phi-9, pink-1, pkc-2, pmk-1, pmk-2, pmk-3, PMP-1, PMP-2, PMP-3, PMP-4, PMP-5, pmrt-5, png-1, polq-1, pqe-1, pqn-60, prdx-2, prx-1, prx-5, psr-1, ptl-1, ptp-3, ptp-3, pxn-2, qdpr-1, R03D7.2, R05D11.6, R05D8.7, R05D8.9, R05F9.10, R07B7.4, R07B7.5, R09H10.3, R10E4.9, R119.3, R11A8.5, R13D11.4, R151.6, rab-1, rab-5, rae-1, rcf-3, rcq-5, rfc-1, rfl-1, rfp-1, rgef-1, rgs-2, rgs-2, rme-8, rnf-1, rnf-121, rnh-1.0, rnp-2, rpa-2, rps-19, rps-26, rtel-1, scav-1, scav-2, scav-3, scav-4, scav-5, sdz-8, sdz-8, sec-22, sek-1, sel-10, sel-8, sem-5, ser-3, set-25, set-26, set-8, set-9, sex-1, sft-4, sgg-1, skr-15, slt-1, smf-1, smk-1, smo-1, sod-2, sod-4, sod-5, srp-2, srp-7, sti-1, sulp-7, sup-9, sup-9, sut-1, sut-2, syp-2, T01G6.1, T01G6.10, T05A12.4, T05G5.3, T06E6.2, T07F12.4, T08D2.4, T08D2.7, T08H10.1, T10B5.10, T10B5.8, T13A10.2, T15B7.2, T16G1.6, T19B4.1, T19C3.5, T19H12.3, T21B4.4, T23G5.6, T25G12.2, T26A5.5, T27E9.1, tag-124, tag-353, tag-63, tars-1, tbb-2, tbb-4, tbh-1, tnc-2, tor-2, tra-1, trx-2, trxr-1, tut-1, uba-1, ubc-14, ubc-20, ubxn-4, ugt-10, ugt-11, ugt-12, ugt-14, ugt-15, ugt-16, ugt-17, ugt-18, ugt-19, ugt-2, ugt-20, ugt-21, ugt-23, ugt-24, ugt-25, ugt-26, ugt-27, ugt-28, ugt-29, ugt-3, ugt-30, ugt-31, ugt-32, ugt-33, ugt-34, ugt-35, ugt-36, ugt-37, ugt-38, ugt-39, ugt-4, ugt-40, ugt-41, ugt-42, ugt-43, ugt-44, ugt-45, ugt-46, ugt-47, ugt-48, ugt-49, ugt-5, ugt-50, ugt-51, ugt-53, ugt-54, ugt-55, ugt-56, ugt-57, ugt-58, ugt-59, ugt-6, ugt-60, ugt-63, ugt-64, ugt-65, ugt-7, ugt-8, ugt-9, unc-11, unc-2, unc-26, unc-36, unc-36, unc-43, unc-43, unc-57, unc-73, uri-1, usp-14, vit-1, vit-2, vit-3, vit-4, vit-5, vit-6, vps-11, vps-16, vps-18, vps-33, vps-39, W01A11.1, W01B11.6, W02C12.1, W03F9.9, W03G1.5, W1008.4, wah-1, WHT-1, WHT-2, WHT-3, WHT-4, WHT-5, WHT-6, WHT-7, WHT-8, WHT-9, Y110A7A.4, Y23H5A.2, Y38F1A.5, Y38H6C.17, Y38H8A.3, Y39G8B.1, Y39G8B.2, Y39H10A.7, Y41C4A.11, Y43D4A.2, Y43E12A.1, y43f8b.2, Y43F8C.13, Y45G12C.3, Y47D3A.22, Y47D3A.29, Y47G6A.21, Y47G6A.22, Y48G1BL.2, Y50D7A.1, Y53G8B.1, Y54E10A.3, Y56A3A.33, Y66D12A.15, Y71G12B.4, Y73B6A.3, Y73C8C.10, ymel-1, ZC168.4, ZC395.10, ZC443.1, ZC513.1, ZC513.2, ZK1290.5, ZK287.5, ZK550.6, ZK616.8, ZK697.14, ZK697.8, ZK742.3, ZK742.4, ZK829.1, or zyg-12. The transgene, transgenic organism, or construct is used for the gene expression biosensors as described herein. According to the invention, an inducible promoter or fragment thereof, or a homolog having at least 95%, 96%, 97%, 98%, or 99% identity thereto, of one or more of the genes listed above and is operably linked, or fused, to a reporter gene using standard molecular biology techniques as described herein and elsewhere. The resulting construct can be transformed into an organism to a yield a transgenic biosensor organism as described herein. In a specific aspect, the construct further comprises one or more of the following: a selectable marker, sequence elements sufficient for site-specific integration into the host organism's genome. In one aspect, the transgene is introduced into the organism with a technique that yields a site specific single copy stable insertion. In a specific aspect, the transgenic biosensor organisms are arranged into an array or panel. The panels can be arranged into kits useful for detecting a wide variety of toxicities or gene expression responses. In one specific aspect, the transgenic organism is a nematode. In another specific aspect, the transgenic organism is *C. elegans*.

In one embodiment, the invention provides a transgene, a transgenic organism, or a construct comprising a promoter, a fragment of a promoter having 50, 100, 200, 300, 400, or 500 or more nucleotides of the promoter, or a homolog thereof having at least 95%, 96%, 97%, 98%, or 99% identity thereto, operably linked, or fused, to a reporter gene wherein said reporter gene encodes a fluorescent or luminescent protein and wherein the promoter is from an organism chosen from *Danio rerio*, *Drosophila melanogaster*, *Daphnia* spp., or *Xenopus laevis* and the promoter is for gene that organism that is homologous to the gene in *C.*

*elegans* corresponding to ABCE-1, ABCF-1, ABCF-2, ABCF-3, ABT-1, ABT-2, ABT-4, ABT-5, ABTM-1, acr-14, acr-22, ahr-1, akt-1, akt-2, apa-2, ape-1, apn-1, aps-2, ard-1, arf-1, arf-1.1, arl-7, asp-5, atf-5, atgr-7, B0222.9, B0432.2, B0495.2, B0563.7, bec-1, bmk-1, C01B10.7, C01G12.5, C01G5.5, C01H6.4, C03A7.12, C03A7.13, C04F12.1, C05C9.1, C06A1.6, C06E4.3, C06E4.4, C06E4.6, C06G1.1, C06H2.3, C07A9.13, C07D8.6, C08H9.3, C09D4.3, C11E4.2, C16C8.14, C23G10.6, C25A1.5, C25A1.6, C27D8.4, C28H8.11, C30G12.2, C30G7.5, C31H1.1, C32D5.12, C33E10.10, C35B1.5, C35C5.2, C35D10.2, C35D10.6, C37A2.4, C37C3.6a, C41A3.1, C44H4.4, C46H11.2, C55A6.3, C55A6.4, C55A6.6, C55C3.1, C55H1.1, C56G3.2, cah-5, car-1, catp-6, cbn-1, ccch-1, cct-2, cct-3, cct-4, cct-5, cct-6, cct-7, cct-8, cdc-14, cdr-5, ced-1, ced-10, ced-12, ced-13, ced-2, ced-5, ced-6, CED-7, ceh-20, ceh-30, ces-1, ces-2, cgh-1, chn-1, cit-1.2, ckb-2, cle-1, clec-149, clpp-1, cmd-1, cnb-1, Cnx-1, cnx-1, col-135, coq-6, cpb-3, crb-1, crp-1, Crt-1, crt-1, csp-1, csp-2, csp-3, ctl-1, cul-1, cul-2, cul-3, cul-5, cyn-1, cyn-10, cyn-11, cyn-12, cyn-14, cyn-15, cyn-16, cyn-17, cyn-2, cyn-3, cyn-4, cyn-5, cyn-6, cyn-7, cyn-8, cyn-9, CYP-13A1, CYP-13A10, CYP-13A2, CYP-13A3, CYP-13A5, CYP-13A8, CYP-13B1, CYP-13B2, CYP-14A1, CYP-14A4, CYP-23A1, CYP-25A1, CYP-25A2, CYP-25A3, CYP-25A5, CYP-25A6, CYP-29A3, CYP-29A4, CYP-31A2, CYP-32A1, CYP-32B1, CYP-33A1, CYP-33C11, CYP-33C3, CYP-33C4, CYP-33C5, CYP-33C6, CYP-33C7, CYP-33C8, CYP-33D1, CYP-33D3, CYP-33E3, CYP-34A1, CYP-34A2, CYP-34A4, CYP-34A5, CYP-34A7, CYP-34A8, CYP-35A5, CYP-36A1, CYP-37A1, CYP-43A1, CYP-44A1, cyp14A2, cyp14A5, cyp33C9, D1007.16, D1054.8, D1081.8, D2023.4, dad-1, daf-1, daf-14, daf-21, daf-3, daf-5, daf-7, daf-8, DAF-9, dbl-1, DC2.5, dhs-1, dhs-10, dhs-11, dhs-12, dhs-13, dhs-14, dhs-15, dhs-16, dhs-18, dhs-19, dhs-2, dhs-20, dhs-21, dhs-24, dhs-25, dhs-26, dhs-28, dhs-29, dhs-3, dhs-30, dhs-31, dhs-4, dhs-5, dhs-6, dhs-8, dhs-9, djr-1.1, dnj-11, dnj-25, dnj-27, dnj-7, Dod-17, Dod-24, dop-1, dop-1, dop-3, dop-3, dpl-1, dpr-1, drh-3, duox-2, dut-1, E01A2.1, E04F6.15, eat-3, efl-1, efl-2, eft-2, egg-1, egg-2, egl-38, emb-9, eor-1, eor-2, epg-2, eps-8, exos-3, F02C12.2, F07A11.2, F09E5.2, F10D11.6, F10D2.12, F10D2.8, F10D7.3, F12E12.11, F14D12.1b, F14F9.5, F15E6.6, F16A11.2, F17A9.5, F18A1.5, F19G12.2, F20G2.1, F20G2.2, F22D6.15, F22E5.6, F23C8.9, F26D2.15, F28A10.1, F28H7.2, F30B5.4, F32A5.8, F36A4.15, F43G6.5, F44B9.8, f44e5.4, f44e5.5, F45E12.3, F46H5.2a, F49E12.6, F52B5.2, F52C12.1, F53C11.5, F53F1.2, F53F1.3, F53F10.2, F54C1.1, F54F3.4, F55A11.6, F55B11.1, F55E10.6, F56A4.4, F57B10.5, F57B10.6, F58F9.1, F59A2.3, F59E11.2, F59F4.1, fan-1, fasn-1, fdps-1, fil-1, fipr-24, fis-1, fkb-1, fkb-2, fkb-3, fkb-4, fkb-5, fkb-6, fkb-7, fkb-8, fnta-1, ftn-1, ftn-2, gab-1, gad-3, gale-1, gdi-1, ggtb-1, gla-3, gld-1, glp-1, glrx-10, gsr-1, gst-11, gst-12, gst-14, gst-15, gst-16, gst-18, gst-19, gst-2, gst-20, gst-21, gst-22, gst-24, gst-26, gst-28, gst-29, gst-3, gst-30, gst-31, gst-32, gst-33, gst-34, gst-35, gst-36, gst-39, gst-40, gst-42, gst-43, gst-44, gst-5, gst-6, gst-8, gst-9, gstk-1, gstk-2, gsto-1, gsto-2, gsto-3, H01G02.2, H04M03.3, H06H21.9, H10D18.6, H23N18.4, HAF-1, HAF-2, HAF-3, HAF-4, HAF-8, HAF-9, hda-10, hda-11, hda-5, hi-14, hif-1, him-10, him-4, hke-4.1, hlh-2, hlh-3, HMT-1, hpo-15, hps-1, hps-60, hsd-1, hsd-2, hsd-3, hsf-1, hsp-1, hsp-16.1, hsp-16.1, hsp-2, hsp-60, icd-1, ikb-1, imb-3, ing-3, irk-1, irp-1, irp-2, itr-1, jkk-1, jnk-1, K02E11.3, K02E11.4, K02E11.5, K02E11.6, K02E11.7, K02E11.9, K04A8.10, K07C5.2, K07C5.4, K08F4.1, K10F12.4, K11D12.6, K11G12.5, kin-18, kin-4, lagr-1, lbp-1, lbp-2, lbp-3, lbp-4, lbp-5, lbp-6, lbp-7, lbp-8, lbp-9, let-2, let-23, let-60, let-92, lim-4, fin-1, lin-12, lin-3, lin-31, lin-44, lin-49, lip-1, lips-11, lrk-1, lst-3, M18.5, M57.2, mab-5, maoc-1, mca-2, mec-14, med-1, mei-2, mek-1, mek-2, mel-26, mev-1, misc-1, mlt-7, mpk-1, mtl-1, mus-1, mut-2, mxl-1, mxl-2, mxl-3, nas-39, ncs-3, ndx-4, nhr-181, nhr-6, nhr-64, nol-5, npl-4, npl-4.2, nrf-5, nsy-1, nurf-1, odc-1, paa-1, pag-3, pah-1, pas-4, pat-10, pax-2, pdi-1, pdr-1, pek-1, PGP-11, PGP-12, PGP-13, PGP-14, PGP-15, PGP-3, PGP-4, PGP-5, PGP-6, PGP-7, PGP-8, PGP-9, phi-37, phi-44, phi-9, pink-1, pkc-2, pmk-1, pmk-2, pmk-3, PMP-1, PMP-2, PMP-3, PMP-4, PMP-5, pmrt-5, png-1, polq-1, pqe-1, pqn-60, prdx-2, prx-1, prx-5, psr-1, ptl-1, ptp-3, ptp-3, pxn-2, qdpr-1, R03D7.2, R05D11.6, R05D8.7, R05D8.9, R05F9.10, R07B7.4, R07B7.5, R09H10.3, R10E4.9, R119.3, R11A8.5, R13D11.4, R151.6, rab-1, rab-5, rae-1, rcf-3, rcq-5, rfc-1, rfl-1, rfp-1, rgef-1, rgs-2, rgs-2, rme-8, rnf-1, rnf-121, rnh-1.0, rnp-2, rpa-2, rps-19, rps-26, rtel-1, scav-1, scav-2, scav-3, scav-4, scav-5, sdz-8, sdz-8, sec-22, sek-1, sel-10, sel-8, sem-5, ser-3, set-25, set-26, set-8, set-9, sex-1, sft-4, sgg-1, skr-15, slt-1, smf-1, smk-1, smo-1, sod-2, sod-4, sod-5, srp-2, srp-7, sti-1, sulp-7, sup-9, sup-9, sut-1, sut-2, syp-2, T01G6.1, T01G6.10, T05A12.4, T05G5.3, T06E6.2, T07F12.4, T08D2.4, T08D2.7, T08H10.1, T10B5.10, T10B5.8, T13A10.2, T15B7.2, T16G1.6, T19B4.1, T19C3.5, T19H12.3, T21B4.4, T23G5.6, T25G12.2, T26A5.5, T27E9.1, tag-124, tag-353, tag-63, tars-1, tbb-2, tbb-4, tbh-1, tnc-2, tor-2, tra-1, trx-2, trxr-1, tut-1, uba-1, ubc-14, ubc-20, ubxn-4, ugt-10, ugt-11, ugt-12, ugt-14, ugt-15, ugt-16, ugt-17, ugt-18, ugt-19, ugt-2, ugt-20, ugt-21, ugt-23, ugt-24, ugt-25, ugt-26, ugt-27, ugt-28, ugt-29, ugt-3, ugt-30, ugt-31, ugt-32, ugt-33, ugt-34, ugt-35, ugt-36, ugt-37, ugt-38, ugt-39, ugt-4, ugt-40, ugt-41, ugt-42, ugt-43, ugt-44, ugt-45, ugt-46, ugt-47, ugt-48, ugt-49, ugt-5, ugt-50, ugt-51, ugt-53, ugt-54, ugt-55, ugt-56, ugt-57, ugt-58, ugt-59, ugt-6, ugt-60, ugt-63, ugt-64, ugt-65, ugt-7, ugt-8, ugt-9, unc-11, unc-2, unc-26, unc-36, unc-36, unc-43, unc-43, unc-57, unc-73, uri-1, usp-14, vit-1, vit-2, vit-3, vit-4, vit-5, vit-6, vps-11, vps-16, vps-18, vps-33, vps-39, W01A11.1, W01B11.6, W02C12.1, W03F9.9, W03G1.5, W1008.4, wah-1, WHT-1, WHT-2, WHT-3, WHT-4, WHT-5, WHT-6, WHT-7, WHT-8, WHT-9, Y110A7A.4, Y23H5A.2, Y38F1A.5, Y38H6C.17, Y38H8A.3, Y39G8B.1, Y39G8B.2, Y39H10A.7, Y41C4A.11, Y43D4A.2, Y43E12A.1, y43f8b.2, Y43F8C.13, Y45G12C.3, Y47D3A.22, Y47D3A.29, Y47G6A.21, Y47G6A.22, Y48G1BL.2, Y50D7A.1, Y53G8B.1, Y54E10A.3, Y56A3A.33, Y66D12A.15, Y71G12B.4, Y73B6A.3, Y73C8C.10, ymel-1, ZC168.4, ZC395.10, ZC443.1, ZC513.1, ZC513.2, ZK1290.5, ZK287.5, ZK550.6, ZK616.8, ZK697.14, ZK697.8, ZK742.3, ZK742.4, ZK829.1, or zyg-12. The transgene, transgenic organism, or construct is used for the gene expression biosensors as described herein. According to the invention, an inducible promoter or fragment thereof, or a homolog having at least 95%, 96%, 97%, 98%, or 99% identity thereto, of one or more of the genes listed above and is operably linked, or fused, to a reporter gene using standard molecular biology techniques as described herein and elsewhere. The resulting construct can be transformed into an organism to a yield a transgenic biosensor organism as described herein. In one aspect, the transgene is introduced into the organism with a technique that yields a site specific single copy stable insertion. In a specific aspect, the transgenic biosensor organisms are arranged into an array or panel. The panels can be arranged into kits useful for detecting a wide variety of toxicities or gene expression responses. In one specific aspect, the transgenic organism is a nematode. In another specific aspect, the transgenic organism is *C. elegans*.

Examples of preferred nucleic acids corresponding to promoters that are used in the compositions and methods of the invention are given below in reference to the pathways and gene abbreviations in SEQ ID NO:1 through SEQ ID NO:XX.

Cytoplasmic Oxidative Stress Toxicity

```
hsp-16.41
                                                               SEQ ID NO: 1
gattatagtttgaagatttctaatttcacaattagagcaaatgttgttcggtatttattttcaacggtatttatactattttccacctttttc tagaacattcgagctgcttgttgcaaaaggagggcgactcacattcggtacatggaaaagtagtgtacacaataaagagacccagatacattt tccgtctgcgtctctttgcacccaccgggagtattttcaaacgaatgcatctaggaccttctagaacattctgtaaggctgcagaatgcgggt atataaggaaagcgggctcagaggaagccaacacgctttgttctagtgcatctaaaaaacttcgaaa hsp-16.2
                                                               SEQ ID NO: 2
tttcgaagttttttagatgcactagaacaaagcgtgttggcttcctctgagcccgctttccttatatacccgcattctgcagccttacagaat gttctagaaggtcctagatgcattcgtttgaaaatactcccggtgggtgcaaagagacgcagacggaaaatgtatctgggtctctttattgtg tacactacttttccatgtaccgaatgtgagtcgccctccttttgcaacaagcagctcgaatgttctagaaaaaggtggaaaatagtataaata ccgttgaaaataaataccgaacaacatttgctctaattgtgaaattagaaatcttcaaactataatc hsp-16.1
                                                               SEQ ID NO: 3
tcttgaagtttagagaatgaacagtaagcacttgaacaaagtgtattggtttcctctgaacacgattggcttatatacccgtatcctgcagccg tttagaatgttctagaaggtcctagatgcattcatttcaaaatacaccccataggtgcaaagagacgcagattgaaaaagtatctgggtttctt cagtacgcacactatttctcaatgttctgaatgtgagtcgccctccttttgcaagaagcagctcgaatgttctagaaaaaggtggaaatgagta taaatacagtgacaaaaccgaaccaaacaacattcactctaattgtgaaatcttcaaactacaatc hsp-16.11
                                                               SEQ ID NO: 4
tcttgaagtttagagaatgaacagtaagcacttgaacaaagtgtattggtttcctctgaacacgattggcttatatacccgtatcctgcagccg tttagaatgttctagaaggtcctagatgcattcatttcaaaatacaccccataggtgcaaagagacgcagattgaaaaagtatctgggtttctt cagtacgcacactatttctcaatgttctgaatgtgagtcgccctccttttgcaagaagcagctcgaatgttctagaaaaaggtggaaatgagta taaatacagtgacaaaaccgaaccaaacaacattcactctaattgtgaaatcttcaaactacaatc hsp-16.48
                                                               SEQ ID NO: 5
gattgtagtttgaagatttcacaattagagtgaatgttgtttggttcggttttgtcactgtatttatactcatttccacctttttctagaacat tcgagctgcttcttgcaaaaggagggcgactcacattcagaacattgagaaatagtgtgcgtactgaagaaacccagatacttttcaatctgc gtctctttgcacctatggggtgtattttgaaatgaatgcatctaggaccttctagaacattctaaacggctgcaggatacgggtatataagcca atcgtgttcagaggaaaccaatacactttgttcaagtgcttactgttcattctctaaacttcaaga hsp-16.49
                                                               SEQ ID NO: 6
gattgtagtttgaagatttcacaattagagtgaatgttgtttggttcggttttgtcactgtatttatactcatttccacctttttctagaacat tcgagctgcttcttgcaaaaggagggcgactcacattcagaacattgagaaatagtgtgcgtactgaagaaacccagatacttttcaatctgc gtctctttgcacctatggggtgtattttgaaatgaatgcatctaggaccttctagaacattctaaacggctgcaggatacgggtatataagcca atcgtgttcagaggaaaccaatacactttgttcaagtgcttactgttcattctctaaacttcaaga hsp-12.2
                                                               SEQ ID NO: 7
acaattcagaaggagcaataattctgtgatatttaaactaatttctctttgtttctttgttatgagtatttattttagttcttgttcatcatg cttttttgtcacttttccctccccaatcccatattcctctgcttttctctcattttcggttacgtgtattaattgaatgtatacgacgacgac agtcactagtttcgaaataactattttacgaggatgaataaacacactgatcgctgagcgacgctccgagcacttttcgagaagtttctaagaa gccacttgaccgagagagagggagaaagaaaagcttggcatagaaatgtgcttgtgtttatttgaactgttaaagtgtttgacgggggcgaag tcactggggaaacctcgagatcaataggacacgtggcaatttgaattttttggataattggaaaagcagtacccgactaaagatccgaatttgat tttcagacattttactgcaaacttgattacacacggtaattttccaaaagttttgtgcattgaatcccgaaaaacttcacaaacgcataatatt
```

-continued acaacccgatctatgagcaaagtaaatagagagaatcaggctgaaagcttattgtgattaatgaacattaggaacaatgctgatttcaatttga aacatttttttttcagatcgaaaatcagttttttcagatcgaaaatcacattggatcttgacattttcaagagaattattaaaatttaaatggc tatttgaaaagtattgattttctgaaagataataactacttaccatctatgtcgtacctgactatgccaattattttcaacaattgtttattt aaaaaattttgaagtaagcttaaaacaaacccaggacctctgaaatgtaccaagtttggaaactaattccaagtactggtaataacaaaaatt ttgaattcgaggcggataagcgccagttgggagttttctgattataattatattaatagaattgccaaaaatcatgataaacccctccaatcat tttttgattttcgaaaaagtttcaatgtaggttttggtgagctgcgaagttttccaaaaatgtctaaaaactaaattcatatggttcaattttt gtcaaaaacgttcagctcatgaggagcttgaaactaaccaataaattttggtcattaaattggtcagttaaattgataattgaaattaaccgga tatgtttggaaaaataaatgcaaaagttcatgatcatcagatcaaaaaccaaaaacttccctacatttctatttccaaattgaagatttcttg aagcctacaaatagtacagtttacaaatatctctccttctttctctcgtcccttcttgcgcatcctcagagctcggagctcctatccgtcaata taaacaatcattgtttcttttcttctcctcgtaccttttttcttcttcaaatccattttcctccgccccttatcctacagtccaattcctt cactctccactttctgagcttcttctccaactcgcaaaagcttcaaagctcacagagcattttacgatagtgcattgtaatgttctccaccta gagtgcatctccaacctgcgcatatgttttcgctctttgacattacattttcttccgattcacattttattcatccacccgataaatatatttt cacacttttaatttttctagagaaa sod-1

SEQ ID NO: 8 tattctacgtcaataggaattgtcagaattatcagttttgatatcaaaaattgccagctttagtacagtagaataactatgcgattcatgctgc ttattatttattcaaaattttaaattttaaccaactgtgagtttattttatagaacatttttcgaaataaaattcaaaaaaataaaaaattgttat ttttcaaaatcttaatcttaatttagcaccattaccgacaggcaatgatagaacaccaaaccggactgaccaagtgtcgtaccagtttcgagca atcaagtattgagagactgatattcttgctgatactatactcttaagatatgaaacgatatctaccccctctagcccctactcgtgcgccctca gttacctacctaccccgttacctaccctaccctacctacctactcagtctcctacctaccccgaccgtatcatatctttagaatatagtatcaa caagaataccaatcacccaaccccaatcactcgaaaccgttaggcaccaggttagccagtctggattaatcgagagtaaaccacttgactccag acaactacatcttatacttacttacgtctgggggacaatcttgggattctcaagatgacttccattacgaagtctcttgcaataaccaattacc acaattttggagcagaattaaaactcacccaccagtacaggatcaaagatgaataatgaatgagaggccctcctctcattgttgtgggcggggtc aagggggtcaaagttttttgaatttcgaaattttgaaattttggaattgttaaattttggaaatctaattttgaaagaaccacatttttccgtt tacaatttgagttcaattccgcaacccgtcaaatttaagaagagaaagaaaaaaaacacaacgtgtttgcacctgtaaggtagttttttttg ttgccttcggcgttttgattcacatgaaagttctacggaaaaactttcattgcataacgatcttcatatcttgtttctggaaacgaaaatttc caacatgaaagaaacccgacgctatttattctcgcaacacaaaaatttcacatttaaataaccgcggtttttctcgaacagcatatttgacgcg cattgctcgtcaagtttgatgcgtgcacactattttgctgttgttttttctttttctctaaattttctttacgctttcgtagtttctataga aacgattctccactcccggttttcttccgattctcaaaattaattaaaatttagttattaaaaatcctttttcttgaaataatcgttcaatttc gagttttcaagagtggagacgttgaatttgtgagccgcttatttttctgtgtttttgttttgtggttttaatcagtgtcataatcatactttt ccattgtttctttattattcaaagttgtagattcagtattttagatcggtgatgtttatgaatcttctcactcaggtctccaacgcgatttttc cgcaggtcagtgcttatccgaaacattcgtcattcgcaacttgggcctatttgatctatggcgttgtgttgttgcctttaccttaattatcatc attttcatcagaaacccacaaaaactagagacatagctacaaaattctgcgaccgagaggcgggtacacacacaatgttgtctatttcatctcg ctccaccttctctctctctctcgtgtttaccatttcttttttaattttgcatctatcgactgtgatctgcctgtttttttctaattctaaac tttttgccgtgatattccttagagtgttccctagaaaattcgttgaatttacaggtcgaagccgctcaaaaag sto-1

SEQ ID NO: 9 aaaaacttgatccgatcgaagaaaaaaccgaaaaaaaattcgaattgttgtgttgttcgtcagttggatggaatgatgatgaaggaagttgatt aatggatatgactgatgattagtggtggaatatgaataattatttatttgatttattctgattattctgaattagaatgtattttcatatttc aggaaaaatgatttatttcgaaacgaacttgttctagattaaaaaaaattgaaatttaatatttagtgctatacaattacagtaccccatggaa atacacaaatatcataaatacaagaattatcttcctggaagttaaacttatattttcgatgtaagtgaaaaagtttaaaagagaaatgatgttt gttgatcttcctgtaagtggaaactggagaattcataagcttaaaaattccaaaatattaaaacttgcgtgttttttctgaaaatcgattaaaa -continued cagcaatattcagcatgtttccagagccaaaaaaacctgcaagcatgggatacttttgcagttaaaaaatgtttcaggaacttgaatgaagtta
ggatgcatttgaacagagtaatgaaattatatgaaattcatatgtagactctcctactcagttgtttgtatgtgagttttgtatattataactt
attttgaaattatctttaattacttgtaatgttttttgtatgagttaaataataatcttttgaaaattcttttcaaataaccattttctgttt
aaaaaaacagtgagcccaatataaacttgttttccatcaaaccgagcttctaccaaagttaacttaaattccataattttcacaaaccattcat
agtttgtctacgtagccttatcctttttgaacattgaaaaagtgaggagaaagtgcgaaaaacgagttttttttctttctcttcttcttggtcg
tcacgtcaagacactctgaacgttggaatgggaaaagcatcgaagatcgaaaaattctgattttttctaaagtacacaacttatattgatattg
cattgggatttaaaaaagctctactcgaacattttgattaattttaatatctcatttattcatctttcgataacagatatatcacattgttcgg
taggataaaagggctaaaatcaagttttgaggaatgttcatttgtttggaaggtgatattatagtctgcgataactacataagtttggaaaccg
aacacatgtttttttggcactttgctaaaaagttgtctgaaaacgttggaaatcaatatttggtcatttatttaggtcattttcggaccattat
aagtgttttctaatacaaaactggcgctgctccgctatttaaaagactgaaagtgacataaatgatctaatttccagatctcttataactttt
ttatagcggttccactcctaatttgatgtgtttacttgttgcatcagatcattttcacttcttgtaattcttatcagttttctatattttctt
tgaattcaaatattggagtattaaaattatacatttataaccattctaatgtctaccttctacacaaattacccttcctagtagaaaatatatt
tcttatcaattttcagcttttcaacattttccagttagttattcaattttattccgcacgatcactgctgtttttggcttgaaatttgttct
gtactgtccaa gcs-1

SEQ ID NO: 10 tttctaagttcgcacattcctcgatttccacttgccgttacctttcattatctccttttactttaatctatcacagtttcatagatatcaaacg
ttaattttttgttgcgagctagtttgttttttttcctcttgttcggtccattcgctttaacttgtcacctatttttttgttttctctacagtcct
cttggttcatgatcctgttaattatcaatgctcttttctgtgatattcgatattcgaatcaacaatgtgtatgattagtgtcaaagtaacttat
cggattttgaatataattcaattattcgtgtaataaataactattttttagtttactcatgtttgccacaaactagaaggtttatttattcata
actacttgcaatttcacatttgaattctaactgtatgattgcttcaactctctgcgattttttgcgctaaaatacggtacccggtctcggcgcg
acaaaaaatttctagattttagaaaattttacagatttattgcaacagctgttacctttttcacaaaaaaatcgactgaatttcgcgaagtta
tgatatctcaagcggccgcttgcgggaaaagccatatttttttcaaattttcgtagctgcacaattttttcataatttttttcatttgttaaaaa
taaatgtattttaaataattgtcctatttcagttttttcaataaattttttttaacgaaaaactataaaaatagatgaattctagagccacgtaat
ttcagaattacagtactctttcaaggcgcataccttttaacataaattttcgcgtcgagaccgggtaccgtactttgacgcaaattttgcatc
tgggtaattcttgtttttgggttcttcacttttccaccactttttttttcgaaagcatcaaatttcacatattcacgtcacaatcctagcaaagcc
caatagctcattcaagtcatatttgtctctttctttctcattctcctgattagcaacactgtcttatcaaccactaggttccgtcttaatcgtc
caaatattgatccgctcgctcgtgtttttctcaacttctttatttgctgtgttttctgtttctatagttctccattttccatctcctcttcgct
tgttgaatggacttatttgataagttcatttttaattttttctaacaatctcatcactagctcatgatgacaattgcaaagaaattcgtcatat
agaggggaaaaatgctgacaaatattgaaaagccttcaggagagatgtgagagacgtaggagtagagacagaacataaatttgagaagcttgtag
ggagaatagacatagagttaccatgggaaaaacgctcgcattttccatttaacgagattttctagatcacaacattttgtgatccgttgtgcga
aaatcaagcttttttatcaaacttttatcgtctgttcattctttctgacaatctttattatcttattaaacttgactaattgtattgaaagtatt
ttttagatgcgaacgaagttccatttttcatgacttaacatctcttaacgttagtgaaattttttgaattccaattaggactacggtaggagtt
ctgtagttgattcctgaacacttgttttgtaaccttctgaacggattttaatatttctaaaattttaaattgcaaatctgagtcctattaaa
agatgtttcatccgtaaaaccaacaaacaaatatcacttttatcatcatgagatttaatgtttccttttgattttctgaattgttgtactttcc
ttcaaacgacttattgaactgatgtaactttccttctaatgttatcatttgtatttttttgcaga hpo-15

SEQ ID NO: 11 aaaccaaatttactacttttactatattttttagttgaaaataaaaagagaaaaacatttattttctaaaaacagtaattttcctttagtcagtt
tatttctcattgagatattgtgaactcctgttttaaaatcaaatgagaaaaattgaacacaaattttaaatttacataaatcccaaaaaactat
caatatttccaacctagacacactataattgaataagattctcgtgaccttcggacatacagtttgtcaaagacaagcactcccacatttgccg
gttaattgtgataacccctatcaacttggctccgtcttcactctcacttgcaattgcacaacttctttcttttggatgtaagtagcaacatttt
atcatcactctattgggaattttttaaaacaaaatttcttcaatacgattgccggtctcgccacgataaattgtaggtacatgcgaaaaaataa -continued tgcccatttaaagagtactgtaatttccatctctctttgttgcaggattttttgtcgatttttttagttgttcaatacaaataaattcattcga aaactgtcatgtcacgataaacaaacaaattttggtatttaacaaaaatttgtcgtgtcgagacctaagctagaatagtactataatttttgag ctttaattttttcaagttttttacaaaatttttttttctgttgattaattgatgtattttatcggagatctataaaaaaatcaatgaaatttt cgaagaagccaaaaaagtactgttgatactacagtaatcttcaaggcgcacacctttcggcatttaacaaaaatttgtcgtgttaagaccggg taatttgttaggcaaatatttgaaaaaaaactgcttaaatatttcatgaaaattctgttatctttaatcagatttttaaaaaattattatcaaa tttcaaaaaattacctaaaataatgtctgaaattcttctttactcacgcgaactgcaacttccagacattaattgaggaaatttcaaattaatc aataacaatgaatacgattttcagattaaacgagtattttcctacattttattaatttttttgattaatattaatttttaaaatgaaatttt ggataatcctactaaaataagcatgtcccgcaaggccctatttcaaaagtttagtgcctgaaaaatcaatatttcgcaagaacagtctaccaat ttttccaatttatacttccggcaattgccaccaattcggtgatctagaaaatacccatataggctctacagtaccttcccttatcacccacatc caatttttgctatcagttagtcttcaatcacacttagtctttgaacaaatgaactcataactctcacaagatgtttgcaactatcatattgatgt cattcagttctcatatgagaaggcgggcacattgttgtatattgataaaccaccccattttcctcttcttccagcaaaaaaaataaaattaa tattgtctcagacgcttgtgaaactggtgctctcaattgaaaagcaccattgacttcgcagaaactggcagttcatttggctttcggatactta caaccatacgctcaca dhs-18

SEQ ID NO: 12 tctgtatatatgcaaaaggaaaattaaatattatctatcgatggaaatgttagaaaagcgaattacttggcacggcagcaggtgccacaaagcc tgcagctgaataaagttaagatacgattgcttgctgacaaataggacactaaattggaaaatacacaccacattttgatttttaatcagatctt ttttaattttaattttagtcacatctagactactctgactactattctcacacgtgtggccaacaatcattcggactacgctgtaggcagtcag gagttttcaaatgataaggtgttcaacagtgtagtcttatttgtatcattttcacataaaacgcaatttcaaaaactcccaattttcttcagac tgcggtaaaata gst-14

SEQ ID NO: 13 ccagttaccgagatctaattttttttctattttcttttctacttttcatgaaatacgcatttttgaaaacgaataataaagtatgatatgctgt caaaaaatttcctgcattcttgcaaaaccggacgtcgaacaccaatttgccactttgatctacgtagatctacaaaaaatgcgggagaagatct tctcgagacgcagaattctcaactgatttcaaatcgttaagaacgtgctgacgtcacatatttttgggcaaaaaattcccgcatttttgtaga tcaaacccctattgggacatcctggcatcacgtgatttgcctaaaaccaaaaataatgcgcattcagagaacatgcctattgtgcctacctattt attaactttgacagtagataggcaggcggctgcttagagcctataagctagcctacctaggcaacccacatagcctacctttcaacttttcaaa agatcattggatcactaacacaatgtgactagttgtggtttgttacaaattgcctcattgtcaccctaaactccctattatttcccgtaaatga tgacgattttgatcttttgtagggttatcttgaagtgaaagatcactaagtacccagactgcactctagtctttttcccctttaaatagtctcg agaatgagtttgagaaactaaaa gst-32

SEQ ID NO: 14 tataatttttttttcttaattttcatatgtttacattaaaaatttgagaaaataaagtagttcaagacaaaatcaaatatggtagagactgtggt ttaagtttgggtttactagggaatggtcagcttaggggtgaggtacctagagacgccacatatgccaaacggaagctgagatcattggctacaa gaatatgctttcaaattctgcaacggacctctgggagtctggaaattcttgtctgaaattatgcttttgaatgctcgaaagtggtaagaattta gaatttattacagaaaaacgtttaattaataaaattagttttatacttgaaacaagtattgtatgcactgtatcaaaacacattttcatctttc taggtattcaacttcacgttttctgtaataaaattctaaattcttaccactttcgagcattcaaaagcataatttcagacaagaatttccagac tcccagaggtccgttgcagaatttgaacgcatattcttgtagccaatgatctcagcttccgtttggcatatgtggcgtctctaggtacctcacc cctaagctgaccattccctagttaggcttaggcttcggcttaggcttacgattaagcttaggattaagcctaggcttaggctttgtctgagttc aactctccaccacgggaaattttttttgcaaatttttttcgtcccaaaaaaaaaggaaaaaaaaactttatttttacttgatttttttcacttt ttttcgagttcaactctccaccacgggaaattttttttgcaaatttttttcgtcccaaaaaaaaaggaaaaaaaaactttattttttacttgat ttttcactttttttttcgagctcagctcgaccgtccctcaatgaaaacaagcaacctgatgtattccagatactcccgtaccaaaggtcatttc tcgttagtcacaaaatattctgattgaaaatggtgaaaaataacgagagagttgaaaattctacagactatggcctaaacgcagcaggtgagac -continued

```
acagtagagaacaagaggcagaagagagagcagaaggcagaggaagaactaaagggtatataaaaagtgttttgttgatcagtgggatcaaata
gtgtgctttttaaaagtttttttttccataaatgtattgatatctagaattttttttcgagttcactgttgtttaacagtgtcacatggtgtcag
gctgtctcaatacagtttgatctacaaaaaatgcggaaatcttaaccatgcaaaatcagttgaaaactcttcgtattttctcccgcattttttta
tagatctacgtagatcaaaccgaaatgagatactttgatacaccgtgcagtgttaaaaaaaatacagttacagc
``` gst-38

SEQ ID NO: 15

```
tctcattctcttcaagacataacacaacgggctgacgaccatatcatcaacgacgattttttaggaactgtactttatctgtgtctgaccaaca
cgtgtgaatgaagtttcaactggaaaatttgtttgaaacactgcaaagaatttcgaattttgatgataattttaaatgccattatcagttttaa
tacgccactctagtctcttgattctttgcacacacacacacacacacacacacacacactcacaaacacgcctgaaatttcgcaatatgctga
tttaacgagaaaacatttgatgacaataaacttggcgtattaatataaaagggaaaattcaattcagattctcaacggtttattttctgtcaca
actcttcctaatattcacc
```

W06H8.2

SEQ ID NO: 16

```
Tacacagccaagtctcataaccaaaataatattgatagtaaaaacatgagtgaacacgtttcaaaacaacatgtcattgaaaatcaattttaat
gttcacgggaattttttttccaaaacagttttactcaaacatattttccatttgaaagtttgggaaactatccctggcacgttttcactgcattg
gtctttccagttgattcagccagagttggaaagcctgtactttttccccaacaaccgtttctactgctcaacttgtaacctcaaatttgcctaa
ttgactccgaagcttcaaaacttgcttttaaagaactttgatgaaaatcgctgcggcgaaagaatcattgcggaattttttgccccagggatctaa
atttccaacctactccactgaaccaaatttttttcaaacttcaccaattttttttatttttatttttcacatgtcattaaaacactaagaattcaata
catgtatgaaaactgcaaacaccaaagtacggtttggacttgtaagcaaaacaccggtagtctctttgacttatcatgtattgtcatcctattt
cgtcagacggtcttgtaagttcacattgacttactctgcgtctctcataggacacatactccgcatcttttctcaatagatcaaatatattttgt
catcacctattatttaaactggttggttttttcacaatgtcacaactaattgaactctccacttattgaacttgacttgaaatc
``` cyp-34A9

SEQ ID NO: 17

```
accgccgagttacgacatcagattcaagcctttgaaagtttgaatctttaataattaaatgaataattaattgggagaaacatgtacataaata
aaatttccattaaacaatgttcatttgtttaagctggcacagaccacaaaagctgaaaccacaaagttttttaaaccttgttcttttcttaaat
tttgtagtttcttatcttatcactcgtgtttcttgtcctccaaataattgtgaaaattgtagttaatgtgtcaaaaaagtcacatataagaaga
cgaacaacttgattttttgttgacttcatttgaaaaaaaatagaaaac
``` ugt-41

SEQ ID NO: 18

```
agaacccatttttacaaattgtgttcttgtggtgttcgcgtattaactttttatagctgttttttacttataggatgattaagaaaaaagttcc
ggctttctcaaagtaaggtaaatattttgaaaataaagaacttgtaaaaggatacagctaactgattaaaaacaaaagacccatgttagttcac
gctcggatttggagttcagctggaggggaaagaattcagcgttgaaatatttcagttggaatttcacctgatattatttaaaaaaatgttatacg
aaaattgaaaaagcgcctcttaccccctcttcgcccgcttttcctcttgcctactgtgcagttttttgtctttacggagttaacaagttgataac
ctgtttaaggacaacagataaaaacagagaaaattaaaaaccactattggcgatttgaaatttccgttcccattttttcacttttcaatttcaaa
tatgtacttaacggtttccgatcattaacacgtaatccatcatttctagacaacaagtcacaccaatgccaatcaaaagtgcaaacatgctata
acgaatctttttttttcaattaaactgtttacgatggaaattaggatagtgtcatagcattaattttcattgttcaaaaacagaaagaagtcaca
aaatcttcacgtgaacatgtttcgtttccataaacaaattgtattttcaaagacagccgggaattttcagaccaattcaggtgacaactatggg
ctaccacccacctaactgtttgttcgcgattattctgactcacatcatgttttcaaaagtgactgtataattggagtgtagcataatcaacaca
aactacagaatgggaaatttgtgacagtatcaatcacattaacagatctataaaagagactgggaaagttgttcagagacacaaattcgttgtc
tacttatcaaatc
``` dnj-19

SEQ ID NO: 19

```
aattttaaagtttatggattatttagaatttatgaatattttaaatatagcttgtaatagtagcattggcttttttattagttagaatgcagta
tttatatagattgtagttgtgtgcgtgctaagattattggagtattggtgttgtcacgtcttcagtctctctgccgtgcgctcacgagaatggg
gcaagcgaagttgcggctgacgcgttattggatgctggcgcgtttcgcgaccagcgttggttttatcgagaattttctctgcagtacaaagtcc
caaattcggtggttttttatcgatttgacgcgcgtttgctcaatttctcgattttccgcgttttttattcagttctcattaattaacgttcgat
```

-continued gcttgttcacaaaattcagtttttgttttcacttgctcgttggtgtcgttcgttgtgtaagaaaattgatttctaaatattttgtttaaattgc taaaaataattcaataatttacattattgaattattaaaagttgtattttcaaacatctcgcgcattctccgtccgtttctctcaatttttc actgtcatgtccgcattttaatattcatttttttttcaggtaat hipr-1

SEQ ID NO: 20 ttggttataggaatatcctcctaggatagacgttttttctagtaattttgttgttttgttcgttacaataaatctcatttttattttctgg attaatttgattaccaatcgtttccagcgattttcacatatttttccagaatttaatacagattaatattttcgaaaaatttaaacattttctt ttcacattttaattcatctctattcattatgcaatactcttttggttttcaagcatccgacattcctccgtttcatttatgtttgcatttctgc tggcatgaatgcatttcattgtgtctcgatgagaaaaaggacaatttcatgagcttatcagttacttcgttttcaaaattttaatgttgaccag ccattgatgtcatattttgtctaagaagctcaagaactattatttttgaagcttaatttcgaagagcaacatttttttcattaaaattcagc agtcattgttctttaaaaagttttgattctcgttttaaacgattttaattcagtcgagaattgataacttcccgatttcccggccaccatc gtttaataccttttctttatgagactaacttccaagtatgcaaattgcaaatcgacgcaaggggaatacactcgctcacttctcatcgaaattc gaaacctttcccattttctttcatgtctttttcgcttttctcctctctgcccatttccatttatttctcaaacaccgttcagtgaacacgaaa acccttacggaaattgtgttgtaagaatacaaaaacttccgtagcatagcgagaaagagtcaccattttgtagtgtttgccccggtggtatag tttgcacaagtttctgaaagaagaagaagacacatttgaggtcttatgcacataaaaatcaatgttagactatcttttcacgtagttttctttt tgcaaagtggaaacttctcattaaacacttttgcttttcaattgtctgaacaagttttcgattaaacagctgtaaagcttttgcaagtttcat ggtttatgaactatttcgaatcggttacattgctgaagttttagtgtttcttgaatatgtcgtcactaccaggactggaccaaaaatcaaaag aatttaaagtgaaataccaaaaaaaaaatcgtcgatttgcgattttgaaggactgtaagtgactttttggcttcatttaggtcccaaaaac cttttttttctcaaaaaatgtgactcaaaataccaaaaaagtcttaacctgatcacttcgccttctcaactcaagccattttgtctgtttagtt cgaatatggaacaaatcataagaatcttgagtacctatatgcgatacccgattcatttcctctctcttctaaataacatcatttcctctcttttt ccctctctctctctctctgttttgtttgtgactcacttgtccacaacgcgcgcggaaccggcttgttgccacacacacactgtgatgaaata tgcgggaggaaagcttttcgcctaatagttgacttactttcatctatattcctcaattttgcaactaatagattgatttgtcatggttttgat ttcagggttttgaatattctttgaaattggaattttaacaaaaatgcaaattatgtgccaagtcatatctcctcctcacactttttctatcac atgcccccaaaaaaattaatttttttcagga Ubq-1

SEQ ID NO: 21 gaatgcaggatataaatcacgattttcgttttcgaacacaactttaaacttcaattttcctttgtttctctgaaaactttgcagtcattttca agcttccacagaactttacaaaaaaactagattttctccaacgtggcgatattcccgagtttcgagaagaatccagcttgtcaatgctgtataa aaccttttactttctatcgtttccattatttctttcactgcacctgttactgccaggtgcttatttcgcctatcgtctatttttgttttcctcc taccaaatttgacaaccctccgcaaacactcattcctattttagcccggtgaaatttcgatatggagaaaaacaaaaacaagtgtgagcttcca cttcggaataatttccggagaatgagaattgtacaattttctcctataagaccatacaataaaattttatcagaaacatgaagctttggtcatt atcattttttgttaccctt gaaatttgatcacaaggctttaattttttcatgagacgtcaatttttttctgatgataaataacatagttcaaagta ttgcgtaatgtttcaattttaacatgacacataataaatcagaaactcgaaaaacgtatttaaatatagattttgtcgggaagtttaatgtgca actgtctcgatatctttctttgaaaacatttaattttttattatattttccaaactggattcgagaattctcgtattcttaaacaaatttacaat gaaaatataaataattaatttaaaggaacatgttctgcaatcctccctgggtcccgccacgaaaccgccacgcactaccatgaaaggcgcgttc gcattcgttctgccgctcgtttctgttttccagatctttccatcattttcttcattcattcgcgctctctcattatcttgagttgccggctatt ttcgctgctctctgctttttcgtatcgcttttttcactcttttccagcattcagaaaattgcattatttcggttttcatttaaaaaactcatagca aagtattttgttattgatttcgcaatacttctgaaaagtatcggaaaattttaatgtttagtctgtgcgttcctcattccctgttctcgttgta ctcttaactgatgttttaaatttagttttccggggctctcttgaaaagacccaatagtcgtattgaaccttcgcctgatcgccactagctcat cttttagtcttatgacgggctcacatgattctccccagtgtcctcccgttttctcactgcacttgttttgtcgttcgttcatcagtacaaagta caagcacttcgcgtctgtctgaaaattggttcgggtgccgttaggacattattcatactttcctgctagtcgcagattataaaaaaatgtcct tgaccgtctgctctttcttatgttctccctatatatgcgtcaaacgaacaactgaccctgttcacttttcctattcttcgtttcatcattttct -continued

```
gtaacaaaaatggaaacaatactttacacagacgtcactattattcaggcctatgatttctctatcgtttagttaaagatgaaaagaaactggt cgacccagttgcatgacgagaaaaaagaacacccgttcgattttcgttgtattccctctgcacacattgtcccttcttcctcatcatttctt tccctacacagcactctagaatgttcttcttgtgcagaaagagtgccgtttgagtcagcgaccccccccccccctcctttctcttgctcttc ctcactggttctcgtaataggcgacttcttgctaacagaaagtgagcatagcaacatttttactttgtggccttcaataatacgtgcgtcgtt taattagaatgtttgagtaaagttcaacgtgtagattcaatattcacgttttgggcgctctttaatttattactgtcaagaatcagtttaccaa acggtgagtttcttttttttgtctaattgtaagattagcggggtaaaaccaacagaaatgtcatgctttttgaataatctcaatcagttgt tatatgaattatttcccatttagcaatactgcttggtagttattttcggtcagagaaacgaggacatcagctgaacatctgcgtctctaaca acactcggggaaggcggagtcagtgtgcgcgtgcgttgggggttttatcgatcgttgaggcgggcatacagcagtcatacaccccattcgacca gaacgctccgctcgcgtgccaccttgtctccattctcatttcacttgtctctactcggacattactcctcatcgattagctcttactaccatt ttacttttatgcctttcttttttcgtttgacttgcctatgacgagtggggatgaagtttgctttgttagtcttactagtgtatcgatttttgg gtaatatttcgcaacttctaggactttctttcataatcacctcttctctcgcctcctcattccagttttattcgcactcattttctattttt cagcaatc
```

Ubq-2

SEQ ID NO: 22
```
aatcaataaaaaaacgttcgaaaaacgtttgaaacaaaaaaataatattcgaattcttctcccccttcccgtaaatcctgcagctctctaccgt actttcgccgtctctcaatttcgcggcgagacccatcaccacggcaatcctccatttgtgtcgctgggcctaaattttttccgttttttgctc gattttcgccgtttctctgcgaaattttttccaaatttctgttcaatttaatcaaaatattgttctggacgcttgttcagcatagaaagtggaga ttctgttgtattttaagcttggaaaacgaattttattatgaaatttcatttttttgctaaataattctctattcttgaattttacagcttttt aacgcaaaatattctttcctctttgttctaaatgggtagttacacacattatgcggtctataacgtcttttgtcacctttgaaactagtctcta aagaaaaatcaataattttgcccctacgctctcctccaaatgtttcgctctcgccgtcattttctgacaattttactcggtttcttttcaaat tatataatttcagtcg
``` sto-2

SEQ ID NO: 23
```
tgtaaacatttgttattatatttttaaactttgtgttgtggatgtgaatatgtggaatttaataaaacatttctcgatataataatgattttgt tgaattagaaaaattagaaaagtggacgattctaaaacaaaagttacaacgaaaatcatcgaaggaaaaaacaactgaattccaaaatagttt tcagaggtgatcacaaaatgttctcaaacgatatatattctaccatcaataattttattggcactatatcacagtccataattcctgtgcttta attatacttttcagtatagaacaatatgctatattatcaagttatgcgtccaataaacacaatttattttttcagactgaatttaagccatattg agaatagcgaaataaaaacgtagaggaaatttgtgatcgccattcacaattaattcttagatcgcaatgataacaaacttcgattcaaaagtca tcatgcaaattcaccgttctcgtgtgtgtgtgttttttggaggaaataacacaatttttgtgactgattttttttacaacatgtggtttgtagcata gttcaaagtcattctagagggggctcagagggagttcttcgctatgtcatcgtttgttttttgcacaccaagaaaaatgaaaataaatgctcta ggatgtcatggatcgtttccattcttaataagtagaagctaggatttcctatacaaaaataagtaatcttcgtttctacgtctatcaacttaaa tttttgtatacaatccactttggtaatattcaaggccttcctgtaaaatgttttatgatcaatccgttacaccaagaaaacaagtgcaatttgt catcatgtaggcttccgcctgtgtttacttccttcccccagcacaacactgactatttataccaaattaataatgcagcattcctcatgtgata actcgtttgacttttatatctttctacgtgcatctttcaagctcgaaaattaattttaaaaatttacattgcagaacaattgcggaacgaagaa gcg
``` sto-3

SEQ ID NO: 24
```
attaatgaagaatccgaggttcctcactaaagattctcgctttatgatagagtcctcaagcttgtatattagagttttgggtgtttacctaaa cttatgcaaacggttttatcatggtttaactaaagtagtgaattgttggaccaatttaaaataacatcgatcgcttcctgcagatcatttgtgg aattagttttttcaaaagagcaatatagtttgaggtcatcagcgtactgcatatatttaacagtttttggaatgtttgcaccaagatcatttgc aaatatgccgaaaagtataggtgaaagtacgctcccttggggacaccacatggggcgttcctaacagaagatagagaattgttcactttact ttgaacgtacggttggagaggaatgagtccacccagcctatgagcatagaattgaacccggcctttattaattttttgcattaagagtgaatggt ttactttgtcaaatgccttactgtaatcaaaaaatacaacatctacttgattattgaaattaaaattttctatataggaacttgatataccaa tttctattaaaaaattgaattcgcgccgagcaaaatgtgatgtcaattcagttttccaattttctcaattttttgaccactaactaaaattt
```

-continued

```
tgataccaaaggattttttgctcaaatttcgaaataattgcggtaaaattggctctaaacactagttttttgacctagcgaattttgatgtcaatt
tcaatttatttacatttttatttggaaattttcttcactgcggatccctagcaaaatttgttaaacatcacttttccgagcaatttgtgatgtcg
atttccgtgtctttacacggttttttgcttttttgcttaaattttttcaaaaatttcagtaaaccccaaccaaaatgaattttactcacaaatttc
gctcttcaattattttttagtgaaattcacaaaatctgacctcaccctaaattcccactgagcacatttggatgtcgatgtttgttcaagttt
ttggccaagttttaaacaattgcagtcaaattcaaccaaatcacgtggtgtcagtttgtcccattacggtttgatctacaatgcgggcatttt
tgcccaatcaattgagaactctgcatcacagctaccacatttttgtagatatacgtagatcaaacggaaattagacactctggcaccacttgc
caaatcatatgcaaaactgctcaatggtagaatttgacaacccaaattgctcatcaagttttgtgtcattttccgcgcaaacagggattcaaa
tttctgccatcaaaaactcattttctacaaaagaactacaaatattatttcaaaaaggcggcagtggtggtcaaagaacaaacatctgaacata
ttgaagaaggtgtctctctctctctctgtctttccctgctcacacaaatctgtgtgtctctctccagaaaataacaacacttgaggttcacg
ggaggacggggggagctcccgcctgtgctccaactctcttgtcatgccactttatgttgctccagtgttttttgtctctctaaatctccagctag
ctgttctttcatgttcccttagccccaataccgccgcctttcgatcttttggctgttttttggggatataagaagtttcgaggaggaagacta
gatctattcatcctaaaataaattttttttcttttttttaggctttatcagactctaaaatgctcgtacgacaccaaattccagatttcagtt
ttctatattttcggtcctataatactatattcaaaaaattagcgtcttcgaaggaatctgacatctaaaagttctattggtctttttccggca
aatcggcagattgccgaaatcaaaaatttccggcaaattggcaaaacggcaaattgagagattgccggaattgaaaatttccggcacagaggca
aaccggcaaattgctgatttctcagaaaaactgcaattgccgaaaattttcggctaattgaggttttgcattttattttggcaaattgcctga
attggaaatttctggcaaaccagcaatttgccaaaaatgaaaatttccggcaaattgccgatttgccgaatttgctagaaaaaaaattaatcgg
caaaattttacgcatctattttgaaaagaaagcaaattctatgaaaatatctaaagaaaatcttttaaaaaaatgcacagttttaaatgtttca
ttccttttcaaaaatccctctaaccgcttccggcaaattaatatccggcaaagggcaaatcaccaaaccggcaaattgccaatttgccgaacaaa
aacaactgaattatgctattaataattcctggttcctgatttccaattttttgattatttcttactcacttcagtatcggaaaacgttcacaact
ttggaaagaatttgatgcccgtaatttgctgaataaatttaattttttcaatgtccag
```

Mitochondrial Oxidative Stress Toxicity hsp-6

SEQ ID NO: 25
```
gttttctgcaaaataatcattgattttaacacctcgtaaaataattttaaaaaagaagttaaaattttaattgcaaccctatttgtaaaaaga
aaactcattttcgccaaaaataaagcaaaataattcaagagaaaaacgcgccgcgtgttgcgattggggcgtaactgcaatgtgtgcgcacac
aatctcaacaagcgctgcgagacccgccgcctgaccgtaatgtgaaatgggcggagacgagaagttttttctgtttgaaagttgatgcaaaa
gcccgtgattctttttttcgagaaatttctcgagttttttccaacgaaaaattcattaaatttaaacctttagctctcctttccaatattttg
catcattattctcctaaaacttggcatattcagtggaaatgatgcaaaatgccctgacttttgttatcaaaaatacaagaaattgtcccgttta
acggttgaaaagcaaattttgtgtcattttgtttaggaaatgtcaaaataagctcaaaaaccgattacaaattatattttactgcttttatcc
tattttctcgcgttttcgttcatgatgcaattttctttcaggcact
``` hps-60

SEQ ID NO: 26
```
ttttcggctgaaaaattggtttttgagttttaaaatttattttagcgggaaattacatgaaaacaacgaaaaaacccgaagaaacccgcgaa
aattcagaaaatgatcaaaaaaccaaaagaagcttcgagaaaaaagcagaaaataaatgtgcggcgcgaaaaatctcgtgcggcaaacttgca
aatctaggcgtgtcgggccaatggcagacaccgcgccgcaaattcagccaatcagcgcgctcagctccacctagaaaagtgtgcgcaccttgca
aaactgggcggagcgagtgaaatgatgcaaaagtctattctgatgtaaattagccattttacatcaaaatttgcgtcattttcgttattttct
ctcattttcatattttgaacgaaaaattgaggttttttgcttctattttcatcagaaaccattgaaaaatgcttatttttgggccattttcg
tcgaaattaggggaaaaaactattctacagttttcccagctattttctcatttattcctgtattttcagtcattacctgcttcccagacgata
atgcaaggcttctcgcttcattttcataaaaaacgattgaaaaatgcttatttataggccatttatcgtctaaattaggggaaatatctgtttt
```

-continued accgttttcccagccgatttctcatccattctcgttattttttcactccttttctgcttctcagacgataatgcaaggcttctcgcttcatttc gatgagaaactctgattttgctcgcattttcgcctttccgctgcagattttcacacaattttcgtagttttttcagacacaaaag mtl-2

SEQ ID NO: 27 agagaatacaaaaagagacgaaaatggttcagtggaacgaaacaaacgtgggatgtaaccatggaagtgagaataattgatggaatagctaatg agctgaagctgagtagatcagagactactttattctaaaaagtacagtagttggaaaattacatgtttcatttctaattttcaaggaaaagcta gtaattaccgtaatcttgtttgtacctgaaatttatgtactgcaggtgaccaagtatgtttgaggcatgacttcacacacctaactgataaag gcctctatcacaaactagagttgtgacggaaaattcaacttctcagaatatagctcaaaatctatcaaattttattttcaaaaatccaataat tgtgcacgcaatgtacttactgcttcataaagttcagaagaattggataaatttgaatgaagttttcaaagcttttatcagtgactgtacattg tgataggcttgtgctgttatcagctgcctcaaataggttgtcgcttgaaaatttatataaaaggcctaccagcagacatgagaatcaagcttca aaggctctactcaaaa mtl-1

SEQ ID NO: 28 ctgcgaggaagagaaaaaatcgtgctgtgaaggaaaaaccgagaagactgagcaaaagaaataaccaatgagcaagtgaacttttcccacgtct actactaaattattgtcgatctataattcttcgcttatcaatcttgtcaattgaaataaaacaatattttctaattcttttggaacgaaca cacgtgtttaaatgaatgttgtgctaaaaacgtcacatcaatggtacgtgaatgttgcaaacaccttgtcaataactgataaaatcagaaacta gagctgtgactgaatcgtatactagaacggagtctctctaaaaacgttctaaaaacaaacaaaaaattgtgcaaggattagagtgctcaagat caatgagcaaactcacaatcaactatctgttattgttttgggtctcttctatatctctattcttttagtatcataagtttgtacattgtgacag ggccacccctcttttatcacatatttgaagtggtaaacagccagcaaaaaccaaataaaaaggcagtgagaaaagaagaaggcagctcaatttg actgctgaaattaagaaatc cdr-1

SEQ ID NO: 29 tctgctgatttatttgagcttctctgtgtgaccaagacgagagccgaagagtgaagtttccactgtcacaccatgtattttatactagttcaga gtatctttgaacacctgttttaaaaaggtacaataccaaaaggcgctcttaatgcacccggttacatttgtatttgtttgatcagatggatgtc tgtctgacaaacgtcggccaaagaatgcacttgcagactttactttaattttttgtctagttttgaaaattcttcggatttgttagtttcaagaa ctttcaatgaaaccgaaagtttgttgagttagcgagaattacttctgattacctgaaaattaatttgactcaatcttttacctacttagaaaga ctaaagtttctgcacaaatttgtttgaacaggtgcttcaaaatgttacagaattttcattttcatccacataaaaagttgattgacaaatagtg tgggcgacatgatttcttgaacaatttgtttcgcttttcaatttggactcagttcttcgaaatttagttattatccatattattactgttttga gttttatcgcagtaggaaatactggtgtatatacatattatattttccgttttgtttacccagaaagcttaaaattcaagttggtcagaaaaa taaaaaaacaacttttgcaagaaataccatttttttcatcgtgcggaaagaacaattgaaaactaagtatttttgctaaactgcagtactgcta caatactaatactgtaccacgatagtcacccaacagtacgaactcctactaaaaatttattaaaaaaagttttattattcaaattttgaaaatc cataagttctaaatactttgttcagtatgctatacttaacacaaatggtattctgcaattgaaacagaaactacaataattttatcacaaaaca cagttctccctactttcttatcacattatgtcatcggggtggcaagtatataaaggaatgctgtaaaaagatatgtactactgtctcaagt sod-3

SEQ ID NO: 30 agaatttgcaaaacgagcaggaaagtcatattcgcagaaaaaagtcgttgcaaacattcgttttatatgttttctttgagaaagcgtggttc attttttgaaagtgaaaaatatttgcttaaaacttccaaatttaaatctgcagtgattcagagaggttgagaattattttcaaaaacattcaatg ttttcccttggagtgactatgcaaatatgaaaatgttttccaaaaatatttggatgccctgataaaaagtaggtgaaatttcgcagggggaacat catattaaaatgttgaattttttagaagaaatggaaatgtttgtcggtggtatgctcgaatatttgagatattatatatttactgttaaatccga aattttttgacaaacggaaaaaatttgtgtcgaaatactacattttcgataacacaaaggtacttccataacacttataaaaactgtttgactat cttatttcaggaaaaaaaaatccaagaataaacattttttcagaatttgaactttctaatggctgattaataaaacaaagttatacaactattca aagcagttgctcaatctggcattttcttgtgttttttttttgaatatttcatcagcaagatgttgataattttgtgttaattctaattgttttct acaattttttcaaaccgaaaattgacctttgactttgtttactttgttctcgtgggttaactgttcactgatttctattgctgttgatgaggtct ttgatcaaatttgtattgtttttatactgcatattgcttcaattctaaatcatctaatatattgtcaaacaacttcttgtttttttttttcattc -continued

```
aaaacttctgcaaaaacgttctcttaacaaaggttcacacaacaactctcctctccatctctttctctcaacaacaatgtgctggccttgcatg
tttgccagtgcgggttgtttacgcgttttcaagattttggtctcctatctaacgtcccgaaatgcatttttccttcatttggtttttttct
gttcgagaaaagtgaccgtttgtcaaatcttctaattttcagtgaataaa
``` eat-3

SEQ ID NO: 31

```
caattattataagaaaataaatttaaagttatccgagcaacaattatcaataaatattactttttaaatgaaaacctttttaatttcagcaga
aatcttagaaatcagatgatcaataaataaaaacggctgactttttaaaggcgcatagaattttcttggtggcgggtcccgcaccgaagagccg
ttttctaaataatatacactaatgattattttattaaatttttcacggttttcgagagtattctttatataaattcaattttaaagcattct
cgtcgagtttgaatccgaaattatcgattttcgttttctctgctttctctaccgctgttttctctcctccgctgtcttcgcaagattatagag
ctcttttgaatcaatttgtttcatgtttccgcttttgacgttattttaaacatatactgatataaataaattaagaatagagtagaaaatctag
ttcaagtaaagatgcaacatttctttctgcaaaattctcgaaaacacctgttttccaaaacttttcaattacacaattagaatttcggaaaag
ttaacatatataagaacatattatatatatatatatatatatatatatatagattaactctcacagttaaagaaatctgaatagtaatattgcg
aaatagttttgcataagtttgtttgattaaattaaatgtgaagcactaacgctattgaatccaggaaaaactcgaatttatttgtttgattttta
ttaaacacactttgtgaacaattttcggttaagaggctttgttgtagtaaaaatcctaaatctacgattatcttcttaaaatttgacatacttc
ttacgtatgttacaggataaatcgagttttgatgtatttcgtaaatagttttaatcatgttatcttttatttcccatctctatgttttaatg
ttgtctttacactaattcacccgtaatgtccgtgcacaaaagaatttaacattcagatattatgaaacaaaatcatcccaaacttcacatccg
tggcttgttctactcattttcgccacttttgcggtctcaattttgctgtatacagcaattttcctgaagtctcggcagatgagaaggttcatt
tgaaatatcccaggaatctggaagacgctaagcagctgggcagagttctctcgaagtacaaggagaacaactattcagtagttctgtgcggtgt
aattgtcgtctacgtatttctacagtccttcgctatccctggatctatttttctaacaattctatcaggatacctgtttccattctatgtggca
attgtgttggtgtgctcctgctctgcaactggagccgccatctgctacaccatttctaaacttttggacgatcatttgttttgcaaagtttc
ccgaaagaatcgcaaaatggcaggatgatctgagcaagcatcgtgatgactttctgaactatatgattttccttcgagtaactccaattgttcc
aaattggctaatcaacattgccagtcctgttctagatgttccactggctccattcttctggggaacatttctaggcgttgctccaccaagtttc
ctgtatattcaagctggctcaacactggaacaattgagccataccagtgtagcatggagttggagttctatcgttttacttacgggttcggcga
ttttgtcgctggctcctatttgctcaagaagaagctcaaatcggattaatttctctcttatttcctctttcgatctcatttttttccattg
ctttctgtgcaaaacttgtgatatttagagaatatagccgataactcatttctatactatttttatttatttttcgcctccttttttgtcataa
taatcatattttcttcactaataaacaattttttaggtgatgaaacaatg
``` cyp-14A4

SEQ ID NO: 32

```
gaaactctcctggatttttctagattcttttccagttacatttcacatagaatctctaactaccggtgcatttgccaatcttcttactgaaatt
ctgtgccttgttttgtcattaaaattttacaccgaataaattatttgtctttgtaatagcttatgactttaacaaggtcatttttttctaactgg
ctcattcgcgctgaagtttaaaagaagtttgcttttttgtcggttaagccgttcatacattttttggcaatcttggtacaaccatctactacat
ttatatcaaaacgaaaaaatgtataaattttccctcgtcttcatctacccgcaatcataaaggaatctcattccgtcccactcgccctttcttt
cttcaaccgaaattttttttcccgcggcgcaaaccctcatgtgccgtcgatagctcagttggtagagcggaggactgtagagtcagcaggtatc
cttaggtcactggttcgaatccggttggacggatttcttttttattttctgtatcaagtgtaactcttcagaaaatcatcgggagcagtcgtac
gaaattttaattataaaaattaaacattccagcattttctttggggaggtgaagtagagtcagcgcggatttaccggatttacagttagtttga
tacacattcaacattcaatattaccgaatttcaaaacaaaacattttttacctaagtcttttagattattggaaaattacaggtaaagttttggt
gaaatgccaaagtcataatgcgagatggtttttttttttgaaaaattcagatcaaaactacgtgtttggtttgtgataaaatattatgatgaaa
aaaactcgaagaaatcataacccaaatgatattcagttcacaaacataagtatcatgatgcaaaatacaaagctgaatgtatttttttcaagacc
gcagatcacaattaagacatggtaaacacaaactctactgcgtaccgcagtgaaatgtggtttgtagtatgactggtagagacacatcgaccta
tataaacatcaaaaaattgttaaaaaaatattccatcgagaattgcttcatttcaa
``` cyp-33C8

SEQ ID NO: 33

```
atattggaagtcaatgagaaggaggaattctggattgcaaacgagaatttggaagtgagtttggagatagtagcaagcctaagcctgggcctga
gctgagtcaaagccaaagccgaagcctaagcctaaatctaagcctgagcctaagcataagcctcagtctaagattaagcctaagcctgagcctg
```

-continued agcctgagcctgagcctaagcctaagcctaagccaaagccaaaacctaagcttaaacctaagcctgagaataagcctaagtctatgccaaagcc aaagccaaagcctaaagctaagcctatgcataaacctaagcataagccttaacctaagccttaacctaaacctataagcctaagcctaaatttt caggcactcactaccgaaaattttccattaatgttcaactcaatgctgtcgaccgtcctgaaaccaattgacaccctcattgaatgtttcaaaa aagaaggaccctacggcctggattactcggcctattcggattttgaagaaatgcagcaaaaattcactaaaatcgttcacgagaagcatatcat tccggatttggttccagccattggaaacgggatcaaggagaagctggaagctggtgggatccgagtgttggatgtcgggtgtggggtggattc cattcgggcttgctcgcggagcactatccgaaatctcagtttgttggattagatatcaccgagaaagctatcaaagcagcgaggctcaagaaga aatctgatggcactgattttgaaaacttggaatttgtagtagctgacgctgcaataatgccaagttcatggaccgactcattcgatttagtcat cctgtttgggtcttgccacgatcaaatgagacctgacttggtaattttgtattcagtttcagagaggtatcccaatcatttacagtgccttct cgaagttcaccgtgtggtgaagccagatggtttagtcgcggtcaccgacgttgatggatctagcaatgtgttcaccgatcgtgagacctacggg aagatggctgcgatgaagtatggtggatcgatgcttcattgtcttccggttgggagcaataggccagatgcactatgttgcggctcaatgtggg gaaggaagagagcagttgagataatgaataagtgtggttttgataatatcgacattattccgactgactacttccctggaactgttttgtattt gatgaaaaataaataaactgtagctagtgttttttttataattgtaatacttttttctatttattcaatcttttttcccgattttcactgcttt gttgtgactgtatcattatgatcctgatgaataaatatcaataaacaaatacagttttttttttatttgacattgattttttgattctgagaata taatacatatctatgagaaattaattaattaataattaataagaattaataaatttaataagaatttaaagtaaaatatagtgggaatatagtgg aaaaattgttttgtaattgtatgcaatatgtttataattttcaaaatcaaagagcagcacgacggagcccaatatcaaaagttcaagcgacaca ctcaaaatacgactcatacctgcgtctcctccctctcccaattcgcaacatattttcgtattttgtggttcttcagtcgtctatttctcgca catacttccacctgatgcaatttcgagtcctcaccaaataaatagccggcaatgtttgccatttctcagttttcatc glrx-10

SEQ ID NO: 34 ttttttttttttttggattttcgactttaaaattagcctaaatttatcctaaaattatcctaaaaattaaaatttcacatggttgacaaatttg cagtggagcgcatttgcagaatttttttttgaattttttttcataaaaagcgtaacattttccaaattaatgggattttaaaggaaaaaat tatcccaaaaattttaattttctaattgaaaaaagtgttattagcccaattttaaggtttttttgcaattttcatcagaaaaagcgttaaa aatatcaattttcgtgaaaagttgatgaattctctcaaaaactcggcaaaaagtaccgccaaaaattcaaattctccaattttcatctctac cagcaaattcgcgatggagcgcatttgcagagtttttcagaaaaatcgtaaaattttccgaattaacgagtttttttttaagtaaaagtgatc ccaaaaattcaaaattttccgattttgaatttttttggtgcaaaaaactaatttcaaattaaaaaaagtgatttgtctaaaataaaag cgtttaaaaaaacctttaaaaattttttttcccaaaattcacgtggtgccaggggctgtcccatcgacggtttgatctacaaaaatgcggga gttttcgcccaaaaatgttgtgacgtcagcgcttcttaaccatgcgaaatcagtccccgcgcatttttgtagatcaaagtagatcaaatcg aaatgaggcattctgacaccacgtgaaaatttcaaattctccaattttcatctctaccatcaaatttgcgatgaagcgcatttgcaaggcctt ttttaaatttttaaaaactccttaaagttaaaaaaatcatttagctttagaaagcccaaaaattaaaaaaaatttttttttaatcgaata tcaaaaatgcatttgtgctccaccgcacggcggtaatttcgaaatttctttaaaatttttttataaatttctgtatttcacaactgtattttt tcccgaattttcctcgcctaataacactatttgtcatgattcttacgtcattgtcgccgccgtttctctttttctctcgccactctctcatttc catacactatttccactctcatttttatcatcattttcttcagtttttgctgcttttaaagcctatgttttcccttttatataatatcgcaga attttgttttgtaaatttaatatatatatatatattatttatttgatgataatgtgatttctaatttttttttccccaattttttttcaaat tcaaattgtctctacgcttttcttatacttcattgccttttttttcaacaaaaatttgagaaaaaacaccaaaaaatttcagaaaaacc

F56D5.3

SEQ ID NO: 35

Gcacgtgtatttttttcggcacgtgaaaatttttttttcaacatgtatatatatattttttcaaatttggaatgtcttatgaaaaacgtcgaaaa ggaggaactcatttagattaattgttatgcaaagtgcagattttttaacaacgaattttttgagatcaaattgtcacagttagctgatgttttcga actctacacatgtgtgaaggttcactcagtctgattggttcaaaagtggcggtacgagtcgctgatcggtcttgcagttctcaatttcgaggaa aatcaaacaagaagattagccaaaattaaaaatttacgttttgaacagtgttttcattgttattctcatttatgttatgaaaacattttcaaa cgttttttcctggatggtaccattcattacatcaagaacttcctgtcactttaatgatcttttgttttttttgtagtttgaattaaaatgatgat atccattgaaattgagtgtaggcgtatcatgatgacaattaattaattttgatcttttgctacagggttttccataggtcagttagtaagtgaa -continued atctataaatttggattgtaaacgttttttcaaccttgatttgtgttttttttcagttttttatttattttagatatttaacatttaaactat
tgaagcttttaaaaatcatagttttatgtaaaattgaaaattgtggtaaatgacgttttaggccgaattagttttttcatttaagactacatttt
atttcaacatctaagaactttttgacatttttcgagccattgttcaaaaaacatcattgaacactacacggttcaaaatgtttacactagatac
acaaaccaatagagacactcttttaagaggcaaatggtcagagaattagacaatgagacattcttttcttctgtgaatttgtatgttatagtga
ttagacagttaggatgacatatatttgtcagcacaatttctcttataaatacaagaaaattttcagagattctcatatccatttctatttcatt
gaaaagttttttcaaac gad-3

SEQ ID NO: 36 tgactaacaatatgaaatgtgtataaagcttcatgatttcacaaaattgaagtctaaaaaatataagctttaattttttgctgtatgagcccct
caaattctcttatatacttttttcctgctaatggctacttctttgatcgaagatttggccaaccggttaagtttgccgacaccagcataaagaaa
ttccgttcatcgcattcaattgagttataggagcaaacattaaaaattgatggtataacttcttacaataacatgtgaacaaacagcacgtggg
cataatcaagaaaagaagcttttgattttgaagttgataagggaaacgatcaaggtgttcaagaccgaaaataatatttttcagtttgagtaagt
tgaaaattatattattttttgaatacttttaaacagctaacagatattgcaatagagtgcttgaagttgtatgtcaatatagttttcgtgaata
gacattaattacagtgcggctcataataaaattttattgttttttttagtattctacaattccatcgagtagctcctgaaaatgtgaatagccta
gatagtaaccgattgagaaagtaaacgtgcgcttatgagttacgtttcgtattttcacaaaatcgcagtataattttagtcatttcttcaaaa
accaaaaatctactgtaccctattgtaatcaaaaatgtgacggaatctcgcatgaaaccaaagattgtttacaatcccaaaaataatccaaaa
attgccctgtttctctcaattcactgtacattttcaaagttttccacagatacattttcattcatctgtgaaatcgaatcttttagactatgta
tttgtcataaaattttgtgattcttttttgttctgttcactctctgtcccttatcgttcgtatctctatttctctattctctcgttaccatctt
atctattgttattccattttttttggtcatttgtttattgaactccctttactcaactgcacacaaacatttctttttattttcttttgaatata
tgctccatgctaaccagaactgacctgttgattctttttttttcccaatatactagtccttttcttaagttttaccaatgtttttag

F17A9.4

SEQ ID NO: 37

Tcagcgatgagcacaccgttcaaagattttctgaagcattgggcttacatgtgaaacaagcagcactcgatattagtgaaggaaaaataccgaa
agcaataattgcattcaactaaatactgtatttgcacttggtattacagaaacgcaaagttctgagaatgcgtactgggtaacatatttgacgc
gcaaaatatctcgtagcgaaaactaaaataatttaaaaaataattcgctttcgattagaaattcatttcgaaattcgagtatgtaaatcgacta
cagtagtcaataaaagtattactgtagttttcgttacgaaatattttgcgcgtcaaatatgttgcccaatacgcattctcagcatgttgtgttc
ccgtaacatttaacctattttacataatctaggtgttttaaacttttttataaaactttctcgtaatgctatctttgcctcttagaaaacttat
cagcgacgtgtatcataaccaattctaatcggcttgttagaaagaagaaatataatacttcggcgtctccactttgtgactgggcacaaaatgc
aattcagattctactttcgaaatagccataaaatcataagatcacagatctttcttcgtttctcaggcaaccaggtgcacaattgtcatcactc
gaccagtgagaccacaatagaacagcaaacgttgtcatctttttggttagacactttcttctgcctctgcgtcttttcataaggtgtgcatac
tcttgtttgcccaacaacctagccgatcagaaaacgcactatatttgacctgcgtgtacactgctataaaagtaacattttgttctttcatttc
ttcgaaaa

C35B1.5

SEQ ID NO: 38 aatgcaaaaaaataagcctttccgaaaaaacgggcccttgggcctttaaaggacacaaaaacaggaaagcataagacaccaaagagtaattgga
tttctacactttggttcctagaattatttataaggtgttattgcgttttttgtgagattgttctatttatccagtcaaaaattgcattttctttg
ttttgcttcaaaaaaatacattttcagtggaaatttcagctgaaaagcagaattttgaggttttcgagtaaataacgtaaaacactaaattac
aaatattgattttgatgtcttagaccaaattttcgtaaacatgtttgtattttggaaaaaataggttttttgtcgattttaacttaatttttt
cgaacaaaaaatgattttttctccgatttaccaaagttttgacttaaaaattccgattttctgggtcatttttccctaaaaatacgattttaat
tcaaaaaatctatattttcaaagaccaaagtaccataaccttcaaaaaacaaccactttctctattgcatcagcgaattgtcatcacccctctc
aaaatatacaaaacgtcatcatttttctgtgttttctctaattctcctgaaaaattctataaaaccaacagttttttatcatcaaaaatgccttt
tgaccgacttttttaaagttgaaaatcgtacagttttagcagaaattccagagtttcatttgaagtatgctgaaataataaaattattcta
acatttattaatattttgtaaaactaattctatacaataaaaaagtaaaatttaatattaaaaaaaccggttttttctcaaatttccattcccca
atgtcctgttctattatttgttccgattcggccacagaacgcgcacacacacacttttttgctgattctctgcctcctttctttgatttgaccgc
attttatattgattttcggccacaattccactatttgttcagtttgtcgatttgttggaaatttcaattccggcaattcgccgatttgccggaa -continued

```
atttaaattcagacaatttgccggtttgccggaaattttcagttccggcaattttttaatttgccggaagtttccatttcggcaacttgccaat
ttgccggaaattcgccgttttgccggaaattttcaattccgacaacttgcctatttcccggaaattacaattccgccgatttaccaatttgcca
gaaattttaattccggcaatttgccgatttgtcggagatttcaatccggcattttgccgaaaatttcaatttcggcagttcgccgatttgtgg
aaaataacaattctggtcattcgccaatttgccgaaaatttcaattccggcaattcgccgatttgccggaaattttcaattccggcgattttcc
tatttggcgaatattttaattccgccggtttgccgctttgccggaaatttcaattccggaactttgccgatttgccgatttgccggaaaaaat
cttttgccgcccaccccctaataaagacttcaaaatatgcgttttttttgcttttaacacgctaaaactctctaaaaatccccaattttcagc
ttaaaaaacccccaaaaaa
``` gst-4

SEQ ID NO: 39
```
ttttgcagactaaaaataactactctgccagtgtttaatttatagatgcaatttgtcactattttcattttatatcgaccaacccattcacact
tcactaatcgtgttaaaactcaattagtggaaaatttgaaattctatgaaactttcatttgcgacaaaagattgttgttttcttcaaaccaaaa
atttatcaatgggaaaatgagatagacaagaactgggaaaaaagtcgaggttaataatttaaagaaatattgaatattcggcgccataatatta
acgaaaataaccaaaatatgcccaattattatccaaaaagattagaagttggcaaaccttgggcaagaatttccagagattgcactaaagttgt
agccaagtttgatccaactttatccaatcttttactaaaattatccttaagactatttaaattttagatagagaattggcgagagttagatccc
acttggatatgacttatagttagcctaacctgaagctattgcttgcttgatcatttggtttatcgctttgctacttggataaccagctccaata
gttgttattttgcttttgtcatcattttccacgatttacactctcaagtgaaaccaactgttctttgatgccagacgatgacattacacttg
ataagaaatatatataaactggaattaaaaacaattgatacatcgattcaattactgaattctaatt
```

Peroxisomal Oxidative Stress Toxicity hps-1

SEQ ID NO: 40
```
atttcatttcttttttataaatacttcggctctattactgaatgaataaatgtataatgatgctctccaaatcctcttattattcgctcgaacc
gcccgttcccatagataccgtctagttttgacaggtgttcaaccatctgccgggaattacgagaagagtcgaattaattgagatcctcgtctaa
ataaatctgaagtttaaaataaagccagaaatacctgaaaagagagaaaaagtgtgtccacgatgtctttgtttatgaccagtggtgtgttatc
gagaaaaactccaatgaatcacacaccagagaagaatcgagaaaggtcgggaaattaggaatgagaaataataaatgtgaggaagtaataaaag
aatcttcgagaactcattccactttagatataaacaagcagcaaacgggtttgtaggtattatattatctatttaagtttaataaactat
ttttgctaaacttaaacggttcaggtgttgaaaaagtcctaaaattttgatattatcaaattctttagcgtggcggttttcttttttttcga
aatattgagttttcatctgaaaaatgcactattcgtgtccttcaaaagttcatgtgtcatcagtagccactcgaaagatcgatcagtccattt
tgatttcgaaagtaagaagagatcattactattcaagagacgcaggcacggagcctgttgccgccgcgaatcttccaggcattcttggcgctccg
cccaaaaaattgcaaaaataaaagttgcttgaatcatgttgaatgtcacttaatcgtgtggctttcaatgttctctttcagaaaatgtatttt
tatttgataatgttaagaattcgccgagttattcttcctcaaaatgtggtgcgcgctctctctcccctttcgtcgcgaacattctctgcgga
ggcatctcttctttttaattcacaattctcaacacttttctgtaggcaaaactctctaatattgctcctttttcagatttttgttcaaactttt
ttgtatttatcttgttcaagtgttttccattcagcagttacagactatttaaggaaattttaggttttttagcacattttttctaatttttttgacg
aaattcgaattttctagaatcccgccacgcccagtcatctagtaaatttgttgaacttcatttctctattttttaatcattgttctcgacgtcct
aatttttatctccatttgagtgactatttcttgattttttaaattattttttacagtaaaa
``` ctl-1

SEQ ID NO: 41
```
gctctgccagaagaagcattaaattgtttgatattcaaactttttgtatatagaatctcgttatttataaactcttttttttgtatttcttctgg
ttttttgatgataagaaattttatgtgcacataaatcaaaaagccggaaattaaatagcgttttatcaggcagaaaattggccacgtgacgtca
tcattttcctgtttgaagaaaatctggaaaatttttgtttcagtcaattttttaaagatgaaaacttaagttagactgtaaaagcaattttcgc
gccaaaattacggtatcggtctcgaaacgacagttttttatctattgcgaaaatatgtgcgcctttaaagagtactgtagttgcaaacttttg
tcgctgtggagtttttatcgatttttttatattttttcgatgaaaacaactcaaatataacaataaaaacacaaaattaaaaaaaaaatcgataa
```

-continued aaaatccgcgtcaacgaaagtttaaagttacagtatttgtcgtttcgagaccgggtaccgtagtttttggtgaaaacattgcaaaatttggtca acaatttcatcgctgcgagaccgacacaacactttatttttattttttgggtttcccttatcgcttatcataaacatgtgacgtcatcatctcttg tacagagcaccgcgactgggagtataagaatcgccggaaaacatcaataatcagttcggtagaagtgaaaattgagcgtaaaatatgatcattt ttcgatgcaccatatttgacgcgcaatacttctacaagccgctgtgtactgctcgtggacaactttggattattttttgtttttaaaattcaaa atagtcaatatattgcttatttatagcgcgcctttttgacagtaagtttgtcaaatttgcgcgtaagttatggtgtttgcacatatgcaccata cagcaacaccccgcggcccggctagtggtacatccatgcaaatgcgctctactgataatttgagtttaaccaggtttaggcgcaagataagaaa aaagctttggaccaaaaaatttagagtttatttttttcggacatttttatatacatcacaaaaatattgggccactcgttttttgataaaaacg acaagcccaaaagttcaggtatacggtagacaaattgcgtacaggtaccacttttccacgtagtgccaggttgtcccattacgctttgatctat gaaaaatgcgggaattttttcgtccagaaaaatgtgacgtcagcacgttctcaaccatgcgaaatcagttgaaaactctgcgtctattctcccgc atttttttgtagatctgtagatttgtagatcaatccattccccgtatacctgacccataatcaatacctacctaattttttgtctttcccccta cttttttgcctgtccaaaataagcgagactatgccgtagtctggtgtccaacaacatgttccttatcagtgataacgctacaatcttctttctt ttttctctgtttctcttgtctctcccaacccatattccgtattacacctcgtcgtggtcatttttttgttcagagttttatttaattctaaattt cctaactaaaatttcagaaccaaa ctl-2

SEQ ID NO: 42 aaactcttttttttgtatttcttctggttttttgatgataagaaatttttatgtgcacataaatcaaaaaagccggaaattaaatagcgttttatc aggcagaaaattggccacgtgacgtcatcattttcctgtttgaagaaaatctggaaattttttgtttcagtcaattttttaaagatgaaaactt aagttagactgtaaaagcaattttcgcgcaaaattacggtatcgggtctcgaaacgacagttttttatctattgcgaaaatatgtgcgccttt aaagagtactgtagttgcaaacttttgtcgctgtggagttttatcgatttttttatatttttcgatgaaaacaactcaaatataacaataaaa acacaaaattaaaaaaaaaatcgataaaaaatccgcgtcaacgaaagtttaaagttacagtatttgtcgtttcgagaccgggtaccgtagtttt tggtgaaaacattgcaaaatttggtcaacaatttcatcgctgcgagaccgacacaacactttatttttattttttgggtttcccttatcgcttatc ataaacatgtgacgtcatcatctcttgtacagagcaccgcgactgggagtataagaatcgccggaaaacatcaataatcagttcggtagaagtg aaaattgagcgtaaaatatgatcattttttcgatgcaccatatttgacgcgcaatacttctacaagccgctgtgtactgctcgtggacaactttg gattattttttgtttttaaaattcaaaatagtcaatatattgcttatttatagcgcgcctttttgacagtaagtttgtcaaatttgcgcgtaag ttatggtgtttgcacatatgcaccatacagcaacaccccgcggcccggctagtggtacatccatgcaaatgcgctctactgataatttgagttt aaccaggtttaggcgcaagataagaaaaaagctttggaccaaaaaatttagagtttatttttttcggacatttttatatacatcacaaaaaata ttgggccactcgttttttgataaaaacgacaagcccaaaagttcaggtatacggtagacaaattgcgtacaggtaccacttttccacgtagtgcc aggttgtcccattacgctttgatctatgaaaaatgcgggaattttttcgtccagaaaaatgtgacgtcagcacgttctcaaccatgcgaaatcag ttgaaaactctgcgtctattctcccgcatttttttgtagatctgtagatttgtagatcaatccattccccgtatacctgacccataatcaatac ctacctaattttttgtctttcccctacttttttgcctgtccaaaataagcgagactatgccgtagtctggtgtccaacaacatgttccttatca gtgataacgctacaatcttctttctttttctctgtttctcttgtctctcccaacccatattccgtattacacctcgtcgtggtcatttttttg ttcagagttttatttaattctaaatttcctaactaaaatttcagaaccaaa ctl-3

SEQ ID NO: 43 ttttattctgaactatatacaaaatgtgctcaatataacgagttttgtaattttgtgagaaagtcgtattgaaaattagtttaaatgtgattta atatttcgaaaagtagtctaattttagctaaattctacaattttgacaacttttccgtgtcgcaaaacgaattttttgtagaggagtgtaccta agcgagtcggagaaacgtgcattcttccattttttccccgggggagcccatagccagtttccggacgggcggtcttgttccaaacgttttttaa aatttaatattgcaatttaattatctattcagcatccgtagcccagccgcattgtggatctcagattggcgaatgcttgtgcgctccattggac tccggagccattccgtctgttgatttcctgatttctgcggaattgtccggatcgacgagctctgtaaaaaattaatttaggaaaaatcaacatt ttttcgataagcaaaccttaattccttcgtcacacttctatggaatccagctgacggcggcggctgaaatattttgtcaaaaaaactcacttttt cgacttttcctcttttctgcgatcggttttcgcctcgatttgcgttgattagcttaaaatagttttttatattttaactaataataagaaaaaca aaaaaaatgagaaaaaacaatcaaaaactcgaaaaaaacattacgaaatcagcaaagaaaatgaagaaaaaatatatacagtaattttaaagg cgcacacacaaaagtttcggtacgcgtgccgagaccactcagcagaagtgtgctcctttgaatctggagtacggtcaatgggggatttatttttg -continued aaaatgcaaatgccaaaatacaagaaaaaataacaaattgcattaattttagtgaattttctgaaaatgagatttttttgtgctttttttggaatt gtgcaacttttagtgcattttcatcgtcctttttctgaattcttgaagtttctggaattttttgttccccccccccccaatctaagactaaa cctaaggctgagtctaggcctacgcctaagcctaagcctaagactaagcctattggtgtatgtgcacataaatcaattttttttaaaaattatta ttatttttgcaaaacacaaacgtttttttttcagattttttatttttcaccctttcaacctgcaaaacccatttttcttccaccaaaacacagc tgttcttgccaccatttgcctgatggaaaatttatataaattggctgtcctttgtgagaaaactagaacaataatgatgacattaagtactaga gtataaatatttttttttgctgacaattcctggcgtccccgttgacattgaaaatgtataaaagaggcggccagacaccatcccgcaaat gtgttttttgttgttcacttttcttttttttccactctctctctcagctgtttgcatgttgtttttatggtgatctatggtctctaagaatt tgtttataagctaagaactgctcgctgagaaggttttttttggttcgtagctagttttttttacgttatcgaaaaaaaattgaaaaagtcga aatttccatcttaaaaaattagtgaattttaatattttgttaaataatcgccattgtttcgtgcttttctcgctctgtaaaattgaaaatcta taaattttgggtaatttcgagtattacgggagcacaaaattttgagaatgcgttttgcacaacctatttgacgcgcaaaatatctcgtagcgaa agctacagtaattctgtagcgctggtgtcgatttacgggctcaagttttcgaattaatttttttcgaaaagttacatcgatatttcattttcc ttcgtgctattttcaaaaatcgagcccgtaaatcgacacaagcggtacagtaatcatttaaaggattactgtagttttcgctatgagatatttt gcgcgtcaaatatgttttgtgtccccgtaatattttttaaatcaaatttcacattttaaccataaaaaactctttcaaaagtgtaatttcta cgcaaaaatgccgttcggatgaaaaattacttttgaaaaacaaactcgaaactacggtacgcaaaaaagtacatcggtgtttgcacataagtga aaacaatgttgtttttttgtaattaaaatcgattaattttttttcccggaaaacaaaaacgttttcagcgtggatttctattgtttcttgcgta aaaaaaaattatttaccaatttttaaacgataatttccacgaattttcgccattaatctctcgattttgttgattcttgactccgagcaatctct ccggttttcgcaaacgattatatttatttgttttccttttcagtgccgattctcggaaattcaacagtaaatcttcaaa

W01B11.6

SEQ ID NO: 44 tttgagaattttctcgggaaattaaacctgtgttttcattaaatttgatgcaagcaacaagtcattatacaataaaattggtgaaaatatgat tttttttgaaatatttggggcgaggcttttagttttttgaagagcttacaaaaattagaatttaagaaattttcgaacacaaatttgagagaact tttgacttttttcaaaaaattgttttcaaaaatttttaatattttcaaagacgaaagaatttgttttttttgtctaaatttacctaatcattattt ttcaatcaaataattgcatctctgaaaacctgggaactttgaaaatgacgtcattcttttttccctccttttcttttccatttggttattgacg ttttccacccctcttgcaaaaaaactaaacaaaaaagaaaccattggcaactactaacgccaatttttgtgttgcttcatcgggtttctttta gtttttttttctgagagcgctgagattatttggaaatttgcatttttctcacgttctagctcagaaagagatcagctttctgaaattgaaatttaa aaaatcgctctaaattgaaacagctgttttttatgtcgattgtctctgcaaatatatttttttcagaatatataagtatgtgtttgtttaagtt ttatttttaaattttcttgaattttatgaacgacattagagcttatgttagtccaaatatttcaaaatttattaacttgaatcttgcgcaaaatt atttgaaaaatcaatttccagccaaaatcttcttaaaattttatttgaattgtcaaaaacaaatgcctcattattaattttatgccaatatta aaaaaaattaattctcgataatcttaaaataagattttagaaaaacaactttcaaaagcttctatgcgaaaaaaattgttttattcgaatt aaaaaaaatgttttcttcaaaaaaaacaaatttcttaaatcatagatccgtgttgctcaactgctcaatgtttcccatgacaaaagtccatgt ctctctctatcattttctcatctctctttttctctagccatcataaaaataaacacatgtttcaacaatcattccttggtttttatctctcga ttgctatatcattttattttttttactattgggtaaattttgaagagggtactgattttttttcaaaatttttccaatccaaaagtcttttga attgcgttaaatcatgtctattgtaccacaatgaccaaatgccatagtaaaacttttcaaaaaaatgtttgaatttttttttgagcgtcagaaa gtggcaattacagagttttttttagcactatgaaaattgaaaattttcggagttttcaaaatgattttttgaaattggaaaaattacagaaaa caatttttttgccattttttggaagttgccgataaaaaaaatttctttggattttatggttttattttgttgaaaatattaatattcaaacca ggggtgtgcggcaaatctcaaaacttgccgagctcggcaaattcggcaaatctcttttttcaatatttgccgagcacggcaaattcggcaaatt tgcctagctaggcaaattcggcaaattcggcaaatttgccgtgcttaacaaactcggaaaaatttgatactttttgatgttttttggagcacca aaactactgaaatcttaacactcatctggtttctgaataagttccgtgtagtatgtctgcttaagcatcaaaataacgcaattttgtgtcatttt tactaaattttggcgaaaaaatcaatggttttagtcaaaattgcattgtcaaatttatgacgtgtgcggcaaatttcgaaatttgccgagctc ggcaaattccgcaaatctactgttttgaaatttgccgtgctcggcaaattcggcaaatttgccgcacacccctgattcaaacattgtaagggtt -continued tgaacatgttcttaaaatgtgacaaaaactcagtaataaaacatttaaattttttgaacacttttaccatgatatttggtcattttggcacagc
cttaaggttaaagctttaacaatttcccactgacgctactccaccataattttgaaaatctaaaatattcagaaattcgaa

F10D7.3

SEQ ID NO: 45 ttttggaaatggtatcagaattgtttaaatatcttatctgaagtttatttaagtttgttacttaaaagtttgtcggtttcgcacaaaactttat
ttaagttaggggcacgaaaaaagtaaaatcacaaattatcaataattttaaaatcaaaccatcaaccagaaaccagaaaactaaaccttgtatt
ttgaaatgtgcccgtttgaagatctatgcaataaaaaaattacattttgaactgctatcaattttttaaaaccggcaattttgacatttgccgg
tttagtacattttttgaccgatctagataaattaaaaagctgataaatttgttaagtattcaacttttgagattcaaaattttaagaagcttttc
ggcattttgaaaacatatgtgacgtatgtcaagtttgttttttgccgttcaaccgatgagcctgtatgaacatttgactaatgtttttttttcaa
tatcagatcattttaattgtttaaatttgataaacgaaattgaaaattttcgaaaatatatgtttcgaagttgtatacattttaagagttttc
actttgtggcagattttctcttttcaatttgaaagtgtcacgtaccttgaaatagtttgttttttttaagaaaatgaccaaaagaatattaaa
attttgaattatggtaaagaatacaagccagcaaagaatctagttattgttggaaaactatgaacatcatgtcctcagttttcaagaaaacatt
aagatttcaaaactatgtattctgcatggcaatgttgcaacaaaccatttcctcataaaactagccaactaacacagttattcctaataaccac
aatgttctcttttcatatgttgcctatgtaattctttctcagaaacattatcatgaccataaaatagacaatgtattggtttctatgtttcttc
ttcctgccagtgtcctctcgcgttgtttgagtactattgttcccactctccccccccggcgtgcgtattatcgctgaaaatgtcatattatct
aatcgaacaatgcccattttttgggatgtttaatagcaaacatattccgattggaattgcaaaattgagttatcatcttttttattgttggtctt
gtgactgtgagtttatgtttggaatatagttttgataagtttgaaactattgtgaacttggaattttttgattctccaagttttttaaaacgctat
gcacctaaacttggtattttttttcaatttaacaaaattctactttcaaaaaacactactcttatttgcatgttccatagtatgtatttcttgg
cagtgtttttcaaaaatagaactccttccgatttaaacacataatgttgtgcttttaagcctagacacgacttccgatgtgattttttcttcga
attctccctgtctgtaagaaactcacatgctgactgcaaagaatgtgcctattgcggacctcaatcagtgtcggctacacttttttagtgtcgt
cccgaaagttgtggtgttctgagaaaacataattttttattgattttaatgcagcaaaatttcaaataactgatacccggttcaccctaattt
cccatggatactccaaatatgttcagaaatgcatatttttgtacaaaatataacgttttctaaagtgtttgctaaaatgttattgttctaaaat
cttttgaaagaaccagaaaatctcaaattcttaaaacattttttcatcgaaatgtgatatttgaccagccagtggcgcctaacttctgaacttg
cttcacgcaatctctgctttgatttctgtcgtttctctactgattttgttcactttcacgtaagcgttcaactcgcggaaccaaagcctccgt
tcatatcatattaggctttcatatctaccattttctactaatcattgttgttacaatcgttttttctctgtttcgaagaggcactctacttat
gactacaacataaaagtagtatggaattcgcgtccttggtgaccagaggcgttcctatttcgaatctctattcgggtggaggcattatccgaat
cccgagaaacattcttgtttgtgtaatctgtctaatcaatccccttcctatttttctctgttcccttccttgtcttcaacatcgcccttcgat
catctgaattcagttcgttttcgctccgcccatgaagtgggctacataaaaagaggaactgaaatgacatcaggggaagttggatatatattt
cattaagttgtactatcattttttcttttttctcttttttcggtttgattctatcttttcaagatggcctcgcttatttctacgattgtcaa
gtcaacggtcaaagttttgaattgttgcattttctggttctttgattttgttccttttaattccagttgtagtttaaattattttcaggaa
agaaaaccgagaaaaagatattacaaa prx-1

SEQ ID NO: 46 agtttggccaatacctgtgaataaaaaataatttattattttaggaagttttataaatgcaaaaaaggagtagaggaattgtattagaatatt
attaaatggaaatatgaaatagcaattggttgatattatacttcgaatctcagaatcactaaaatgaaaaccagaactgcttctgcttgattt
taacatacttttatgttatttgcaatgattaaaaaatatatataatacgcgagaaatttgaaactggtttggctcgataaaaaattggtgagaa
acccaaaatatcgtgaaagaagcggtggaattaaaatgatttgagaaagtaaattttgataatacgaattataattcgaaaaaatggtggtact
taaaatatagcaaataaaacaggtgagaaaaagttttgaggttttactatattttaatcaaaccgtttgttttatttattttcaggcatcgaa
attttatgtactcaagcttatagtaaaaatacaaatatttgatatattaaacagagataaaacataaataacgagctctaaaaaattagcatat
tttgggaattaagaaaaccagtgaaagccgtaaaaatgatctgaagctatgaataagtttggttagagactctatttctagtagattactttat
tataataatgagcagaaacagatattttttttagcattttttcacttcatcattaaattaaaatcattacaaaaaatcgatagtccttgagaaga
gagacaccaatttacaagcaggcaacaaacgagagagagcgtattatcgtgtaaacggtatatacgggagaagagtacgggagaccgacggaag -continued aaaagcaatgggaggtgtataggggtggtggctgtgttgtgcctaggaggcaggaaaatataacgttaaaaagtgcagacgcagacacaccaatt gccctcagactccaattcagctgtctccgtctcttcctcgtcctcatcgcacacccttagaccggttgcttaaaaggaggagaagcaagtacg caagcattacaaacgacgacattactgacctcttataattaaagtaataaattgtgaaaatgtacaccgttttttatgaattgcataaagcgaa tttatttataaaaagttaatatatataaaagctacatgttcactgatctacaattttttggtttcagattttttttgaaatgttgttatcaacagt cgaactttaaatttttcttgaaaacttgatacataaattaaaaattgaacgataacatttggctaacttttttccatgtttgcctttgtgcaaag gttatcacttgattattttatttttttgaaatctggagcaataaaaaaaaatagtaaggatagagataaatacaaactgaagcccttatgtttat tacaagttatgacaatttcagtgtagttttgaaaatatcaagtattgcagttaaatttacaatgccaaaaaatctaagaaacattacgaagttt tcatgaaaatacctcgaaaactatgaaatagatcaaagaatatccttaaatatgaaagaattcagacttcattgggttttgaaaaaaaatgga agggaaaaggaatctgattaaaatcagttttttggcattgtagaagtatacttcaataagtttgttttcaatgatagagcttagtcagttaacat tcaagttaacttgtaattgtaacctggtaataaaaaatcaaaagataaacaaaaaatattgtggaattatcaaatacaactaatcggaaaagt tgattttgaggcaaacatagcttcatctgctgtacattatgaaaattttattgaagaggagttaatgaagtggtacaaaacacgatgaaatgat aaaacatgaacaaaatcgagttggtcactatacactaaacaggacacgtaataagaaaagtcaataggcacggagagacaaaaggtcatccta caattgcggtggctaactgcatcttaactacgtcgtagcattaaaaaagattgataagacagtgcgtgtatgaacgcacaaaaagaaaaaccta gcaggacatcatgaggttttattttagcgttttttttgcatatcatttttttattcattttgtttcagtaaaataagtttagattcattttttaaa gcgaaagttaatagaataatttgatcttgaagttgaaaattgttgttaattttttaaaaacttttgttttcaaattgcctaatatttttttgaaaa cagaacataaaataac prx-5
SEQ ID NO: 47 cttctacgtggaattctggaggttgaagcttctggtctaaccatcatcagtaagaatgtaaagaccatttcgtgtttcatatttatgccgtcaa ttgtcagtacaagggggcccgccgttttcgtttcgtttcgtttaaattatagggaatacattataaaatcacacctttttgtgtatatcttcgtag ttttattggacattttaataggccttgtttataaaagaaaatataataatgatgacattatacaaaaaagtattcaaggaatgttttatagtta caaaacctataggtatacagaatatgtcaaaatagggggaaaaaactgaatgtatgcagtcgacgaataaggttgtcttgacatttttttggtta ataatgttttttcctgccagtttcgatatctttgaaattttgatccagatgacatcaatcctagctatggaataatgggggaactctctttaaat tcacaacttcattcgagcaaaatttgtcttttgcacacgaaaaattattattattattgcacaatcaaatatttttcccccgtgcaagtgtgca atggggcgacgggtcgagccagaaacccgtgttgttgaaaatcaaaccaagtgcaaaatatccatttttgcttaatttaaaacgatctaggataa ctccactagcaactagaatatctaattgaaggattgaaatttggaaacttacaataaggtattctattttattacgttttcaatcttgctagga aaacttggaaaaaaaatccataaacgtttcccggttatttcagaaatcgatagtcgacctccgttgttccttatctaaatttcatcaattgtat ccttttttgataagacaatactatcttttttatcactacgtctccttcactctaaatcctaatgtagtatcaatcaatttgatgaaaagactacac tggggcccacttatttttcttttttcaatcaaaattcacactttattttatatatttcttgtaaattgtattttttcttcattttttaattctactttt ttttcaacaattaactctcgaattcttcaattttttttacaga duox-2
SEQ ID NO: 48 aattttcaggagaatcaatcgacgagcttgaagatttcgacaccggtctactatcttccggaggatccgattattctttttaaaattttcttct tttaaaaaattttcttttgaaataaataaattctcacctaggaatttcaacaattcaacttgaaaaaagttcgcgcaaactacgaacaaatgtgt gtcgagcgggcggagccactgagaagaggagcaaaatgtacacaaaaccatatttgagtgtaatttttcaaagtttggcgccgattttctgtg agagatgagttttctcaatttatatttggttattttttattttagttcttactggtaaatttctgggtaagtcctgatgactttgaaaacgaaaa aaactctttcattgatgctagtgcgattgctaggaaagcaacttttcagttaccaagaaaaagtccaaggccataggggattagctgcgtggcat aacaactcatccatcctcgcagatgcaaatccgctctattggcaaataacatggaagagtataaacattttctcttccacacggaaacctagtc cccttggggagcggtagtgcccacaaccccgcatgtttaccaaactacacagacagcgctattgtctgcaagtggcaaaaa prdx-2
SEQ ID NO: 49 agcgtttcgttttagaatcgccagtgtatttttttgtgatagtcctatgtgctttaaattatttattttgaaaggttcaataaattatatttttat gaccgaacacattatattctcagttgttatcttatatatccacaccggaatgttgaatatctgaccatatatatttagaatgttgcggtaattt aattttatttttattttattttttcatagtttcaacatttttacaatttattgaaatttatgggttttaattgttatatttggcgttttcgttta -continued ttttgttgctgtggctttttcgataaaaataaattcagttaaaaactaagttataacaatgaaaacacataaatttgaacaaatcgtagaaaaa
tcactacaaatttgacagattttatgggtctatcgcgatttattgaaattaacgtcttttaattgttttattttagttttttagataaatact
gttttcaaacgaaaaactttgaaaaatcgataaatctcgcagtactcctgaaaggcacacactcgtttgtacttaagaaaaattgtcgcgacga
gaccaactgtccaactacggtagttttcaaaatacgcggttcaccgcaaagtcaaattgcggacctgaacattttttttattttttcccgcaaact
ttttttttcaattttgcctaaagcgctcgaataaacatgaaagtctcgtgtttccttccatccagacctctcattttttcaattttaaaactaaa
agcacttttgacctacttttttgtcgcaaccgccaaaactcgcttccagaattattccctttttaggattttcgacgcaacatctccaaccggt
tagttttttcgcagattttctcgcattcgcgtagtttcacttgtttacttcgtggcgcctcgttttttttccgctctctcgtctgaccaccttca
tatttattgatctgcgcctagcggcgcccgttgaaatactccacattttttttgcaatcttgtctgcgagttcaggttattttcgacttttatga
aagcttgctaggaagccatagcaaccggggaagaatacgctagccaaatgagagatagaatcgatcagctaaatttaagataaatagtgaattc
gaattctaagacctgctcgaccagctgaaattctaaaactctgcgccaagatgtatagacaggtaataatatttgaattttcttttaaaagtgac
cttgaaccctaagattttcgctcctcctaaacgttgtagtctgttactccctgccgcgacaattgtcagcaaaaatcgcgtcacatgatgatga
aagtttgtggcaatgttataaaaagactgaccttatttcgtttcttggaagatgcaaagaaatgtttattaaaaattgcagtgtgaaatcatgt
ctctcgctccaaaggtgcatttcttatttgttttttaaaaatatatttggttacttagatattaatttaaatcacggaaaagtttaaaccctc
gatttctgttatttaacatgatcactcacttttataacaattaatttggttttttcaaagatgttcccagaatgttttattagttctcatttcgt
cctccgatttttttttcttttcgtcgctctccaattttgccaatgtatttcattcccattagataagcaccgcccgtcaccttattctccttcttt
tcacattgcaaacaaattcgttgccgttgggtttcaatatccttttcattttttgtcgtattgttgttcttgtgattgtggttgttattttatc
gcggtattattttttttttgttaaactaattaattttttag pxn-2

SEQ ID NO: 50
tatcaaagttttgttgttacccacccaaactttgttttagttgcaacaagctcacttagaaggaaattgattttcagtatttattgaacacagc
aagaaaaatcagcaaacgtggtacttgtgtgttgcatgcgctcatttttaataataatgttgttgaattataacaaataaaaaacatgtagcatat
ttttgtattttcaggcttaaataaccatttctaagcctaaagagaaaaaaaaatgtacaacacgttaaatttaaatggagaaagaaattaacaa
catttgattggatttagaaataagggcacgtaatacacaagtaccaaacgtgaactttaaaaatttgcgtacctaccatataatacaaaaccgt
gaaaggtggaatagttttgaatggcaaattgtttgaattcatttctatagtgctaaactgaacaaatattagtttcagtttaaaaaaagtgtt
tgaaattcttcatttgcagtcaagcagtggcaattactcagcttttgacattcaagacaaccaagaaatatgttttcaaaaagttttttccgtat
tcagtcaagttctattttcctctgaactatagctaataatttataattgtacatatcaggaaaaattatgtggtttaagaatctctgaaatttt
ttggaaattgggaggtgaaagaatacagtacacttttgtaattttagctaatacgttcgagagttattatcattatggcagcacacttgttggt
gatttctatttttttgacatgatatgtttgaatatgattttcctcgttatgtggaaattttgtagaggcagatgctaaacgacaagctagactt
tttagtgaattttttgaatcaattatttataatggcatcaaacaaatcgaaaggatctgtgccttttgatatttttggttttgcaacaatttgtc
tttgttgttcaaacacgtatacatcaaaaactattgtttatttcaacattttcagtgtatcttttaaagatcacatcaggttgttactaaaatt
agttttgaattcaaaaataaccaattaaatgttccaaacatataaaaaatatttcaaatatgtatcagcttcatgagtagtccataacaaaacc
cagaagttcatcggaggttgtatatctctgagagtgtcaacccacttcttattttttgcgataaaactaattaaaaactaaaataggaacaaaac
attaattttatgcttcgagtgaaaattcgtatttattcacttttttagggagtttctcaattattttaatacatagatacatagatattacttttt
taaataatatttacgttcaatccaaataagatttttaaaacgattcagtaaaagttcttgcaaaacaatcaattagcaactgagtttggtttta
aactgtttaaatctgaaaacattttttaagaaaatgaaatccgtctaaattcattatatttagcaggaacatgttaaaatttagtttctgaaatt
taccaattatttggaactaatgtgaaataataagaatattattattcaatcattttcttgcagacaaagggaattagaggcgtctggtcagcat
ttgtcgtggctcaactgttccgcaagatacattcgtcgagttgcgggtctcgtttgatattcacaaaaggaggggttcatctgcgaagttacac
acttcttctatcaaaccacattgcctcattttcccaataactgtctcattttttgaagaagatgcgatcaatcaccgtctaaaactgattgcgtt
gcaacaaatctgtgatgatatgatatgatggaacggacggaaaggttaaatttcgagtgaagaaaaaatatagaagtaatatgaatgagtagat
gaaagaaaaagacaaaagagaaattgatatgaccgcgcagcagacagggggcatctggtgtgagcgtgcggttttttctgttacctctaacgcag
tccgtacacttgtcggcgtttatttgtggctgtgggcccattgcgttgatgacggtccctctagctggctttcattgtgatccaattgcaccat ttggttttgagttttattctatttctatcgtcttttgtgataaattaattgagtgaatgaataatgtataagagcctcattatattctatttactaaacaaaactcaattatttcttttgaaaagataatgaaatttccagtcatcattccataaatataattattattttgccttcgcaataatcctaaagatttttttatatccttcaagtttatcaaaattgtttaggt mlt-7

SEQ ID NO: 51 attccaatttcccagccatccggaaattcgctgtaaaaattggaaagtaggacaaatagagaatataatacaaagattaaacacttttttacgacaatgttgacttcgtcatggtacattcagaagtgtctgggaaatgttcagcaggaaaacattgcagaagagaaaaacaactcggaatgtttgctgaaaagttctgcttggaggtatttttaaacttggagaagatatcattgctctactttggcggcttctatcgcggtagtctttagtttgatcaaaaatttatcaactggcaaaatacgtacaaaatagttatatacattttgctagttgacaaatttctgataaagttgaagggaactgagaggttataacctgtcaatcaaggagcattatgttttaggcgcacctacttacttcatgcctgcttggctacttacctgcctattacctgcagtttatatgtaggcactgatgtaggcacgtagccatcaagtaggccgcctttgaggctcatttgacccatagaccttaaaataggccgttctagaacccttcttatctgaaacaacaatctttcagacattttcgaatggtcaacaacttaagtttttattttgcaaaaacaaaaaacaacaagttttcaatgtttttttgccagtggaaattattgttgttggataggtacagatgctaccgggttaccgagatcgtgcctaccaggcctacctattgcctgcctgccatgtgcctacctacacttcatttcggcaaaaggtcaggggccaatgaaaaaggagcatgaatagattcgcatcagaaattgatgtcggtgtaaggcaggtgcaggtaaaatgaaggcaggcctgtggcaggcaaaggtcagcatggcaagcattttgggaataccaaccagtagttttcatcagagcacgattgcatcgacgaaaaatttgaattttttgtgtattttgaagagtgccgtgaaaagtctaaatcttttgctattgcctctgattccttctcgaacctgaactataaaactgatgtaaagaaaaaaagtttccaacttaagagatatcttatcaatttaaactttaccgagtgattctgtgatatctcaaatttcagtcgaaaatcacatgtggttttccttttaattccgagagagagagagagagaaaggaatttcacctccacaacaacccataatcattcaattaggttctaaacacatacaagaagaagacaggaaaatgttagccttttagtcataggtgctgctcgatcatgatgttgatgaaccaaacatcgcattttgtaggaggggaagaggacaggagactgtccatttgaaagtgactactttgtcggatatttagagagtgacttacttacgaaagttataaagtttggttagcaggaaatctggttttttactgagaaaactctctgagggaaaagctcggggtgggtcatatacccgcgagatatctgccggtcattatttaagaatgtacagctctactttggcagatcatatctcggttattccagtacatatcaaaaattgactgaatatgaaaataaaggaaaatgttcaacctgtatttaccagttgaacattttttgataaaaccaaaaataatcgaaattgtgcttaacggaaaagaagttagattaagattccaggctgggtcccgccacgataagctgcaaaattattttttggagctgtctgttcagaatcgtcgttattagaaggtggaagtgctgaaatctgaaaaaaagaactcaagaatctatagaatctctcatatatgagagatcggctccgtgaaaggcactaatctggaatacttcagaaattcggcgaatcttggaaattgaaaactttgagatttttttcttgtagatcgaaacccgcgagatgtcagatgcttctgaattcagatttacaaaatgagctcttcagacactcctgaaagatcagctgaccagaatatgcccacctaaggcaggcgtgacttacctgaaaggtgacctacgcctattctcttgccagaactcgaaactattttctaggaaaaacttttttgtagatcgcattccatgggagctataccttccctgtaggcacgcaggcactagtttccgtgcctacctggaatccacataaccggagcacggagcagcaacttcaccttcagaaatgattcagagctttacatatagtttcctgttcctgaaaagcatgttctacgatgccatgattctcatttcgatgccacttctcaaccaacttttgccgagcttctgaacttgtcgagggagtctgaataccccccaccgcccacactaaactttttttcctctgatccgtgagaatatcctcattatctcacaatcagtaatgtccaaatcaggcgggggaggagggtaaaaaacacggaaacgaggaggcgaaaagcgtctctgggttcccgcccttcctcccacacgtcttctctatgcgtctctctgacaatctctcgttaaagttgccttttttgggaaaagcttctgtctctgtttctctctgtcaacgtgtttctcagcttgcgggcgccaaaccaccaccaccatcactgactgtcgattcgcggtgtgttgtgtttcaattgcgtaaagagtgagagagaggaaaagatagagagagagagagaccccaaggttatacgtctgttatacttgttacccatatactcttctacacctttaccttcaacctttccccacattgactccgcctctctctctcttacttcttggaagacactcccaccccctcttatctattttttcgaaattctcgaccctt caccctccccccttacccgcaccggtcatcattctgactctgcgaactactggagaggaacacc

ZK550.6

SEQ ID NO: 52 catgaaggcgaccgaaaagtgtccagtgaagattttctaaaaatctcgaatctggaatcatgatgtgaaatatatgaataaagaatcttttttaaaatattttgaaaattctatacatctctaaaaaaatgcaatctcgttattacaaaaagcaaaatcttttcaccttaagcctagatgtaggtaatgtttgatgaacagtaaattttgaaacagtaaattttttgaattacaaattgaatttttttaaaatctattcagaatccctatatccgcatgcatcagggaacgtgccaaatttgaaaaatgtgtgtttctcaatctctaatcatttatcatatggtcatgacaacaactggtgtcaaggtgtacgataac -continued ggtacactgtggcaattgacactcttttttttctttattctctattcaacaagacttgtatttattaagaaaatgcaatgagagagcgtggtga
taagacgggtaattccctcgcttttctcatttttttgcggtgttgtgttcgtgtcatttgagataatccatgttgattccacttttattgttgat
ttgatagatgttccaagttttttactgcttcctgaaagcataattcttaaaaataatgcttcatagcagttgtggcttcatacaatttttcaaaaa
aaaattcactgttttcaaaaaaattgaattcaatttcctgcattatgacgtacgtgttaaaaaaatatgttcacctaaaaattccgctcgaactg
tcgcgaaatctgtgttttcagtgaaataaaataaaaacatctagacaaaatacagttctcctcaaaaattgctgtttcaaaataataatttaaaa
aaaaacaccaaagtgtcgtatttaaatttaaaaaaaaactatcgtttcaacaaaacaggttcaaatctattttagtattaaaatctataactttt
ataaaatttgctatttaggttttacgaattgttgtttttttactctgaattgtaaaattaccgtttcaaatatattcttctaaattcaaaaattt
agtatacaattttttctagaaacattgaagtattaccaggaattttttggatatttcctataaattctattttgatcaatttgtagttgtcttatc
atatattgcattggatgataataggaaatgatccgattctctttcctgttccaaaactaggtaaatgtacctcatatattttgttaattttgta
gtcacaataacatgttatgataataatatcgataaaaaatatcgtgatgtttaaacattaagtttcattttttcggtactgttctaattgttc
aaaacaatttaaaaaatttcggtcaatttatagacaataccgattttaataatgaatgtaaaattttcactgtttcactaattttataacaatt
ttcattccttccaattcacattgtgttagtgtagtgatcattacttatatattttaaaaaaatagggtgttagtttttccgtttgtctgtttg
tttccgtgacgtcacaacgcatgagacccatttggcgcaaattcaaatttcttcagaaaaattttggtgcaaactcaaatttcttcagaaaaa
ttttagcgggaattcaaatttcttctgaaaattttggtgggatttcaaatttgttcagaaaattttggtgcaaattcaaatttcttcagaaat
attttggtggttttttcttccgcgccggaggcgcgatcagcagctagttttcaaataaatttactgtttcaaaaatacgatattttttgcctaa
ttttgagaatatcactatgacgtctaaacgtaaagcgattccataatctacttcaaaattccaggctcccaa

C28H8.11
 SEQ ID NO: 53 cagtgtaggccgtcttgctcatagagacaaataaacttttttgagatggttttttaatagaaaatacattttatagaaatgagaaaaataaagtt
ttactattagaaaagcgtaacaaaaagcttccgtaattatttatatgaatgttccgatattttagcgatgtgtgcatcgtgcactcacaatac
taatgttatgagcttccttgcaataaacggtggggctggaaactgacaggaagtgggtttattcgatgattacaataccacaggactgatgaca
cgcgtaatcaaaagttgaaactagaaaacataaacacgcggctttcatctgaatcagagacgaatatccataaatcacggccccaaatagaaa
ccagtttattttatgtcacttcttttccccattaactttcctgtcacaatcatacaacagagttcgatcatacaggtccaaaggttttgggtat
atcttgtggacatgtatgctgtgaaatgttgaacatttcatataaaatttttaaaatcagactattagatcgaatagttctacgaaatttgtaaa
cagtttccatcgaaataccttattttttgtaacacgaagtcgacctctctcccggagacgctgctacagaaaggttttgaattttgagcaaagtta
cggtattaggtctcgaatgaaaagtttcgaaagtacgcaaaactctacaatagggttaagaatcgataattttctagattgtccaaaaaagtag
actaattttgccattccgttcagtgccttcaagaagtacttgaagtctataccctcacctacttgtctgatatggtaatttactatcgagcttat
tagcaattttcttcacgggaaaggagttgtaggttaacttcaagtcgcgaggtaggcatatttgtgcctggcgataacaagagacgttccacaa
acatcttactcagtttctatttgaaacttggcgaagtagacatgaagttgaaccttcggaacgtcagtccaaaggtttgaaggagggttcccc
gaactgtcatacacttcatttcatcgtcagctgtctgagatcaaacattcaataagcatgaagatctctgaacgaccgaaaagatatcgataaa
gtgatgataaaggtctgcagcagaatggttttgcagacatttcttcagaagttaaaacaacgttgtcgtacccaagtatcttatcaagggagaa
aaagagtcaaaagataaattccgccatttgcccctccggtccgtaataacgagtattttcttatcacgtgtgctgatcttttttcttaacacaca
tacaatcaatcgatttgtcagacatgggaaagaataagacgtgatggatgaatggaataatgtgaacgatgaacgagatacgtgacagtcagaa
agttcactgtgaatagagtatggtataaatggttgagagacgacggattacggaaagatcgaattatcacaacgttttgatgtatctggaccg
ttcacatggaatttagtaattgttacttcttgggcgacagagaaaattcggccagtctcatcaaatagagagttttttgaaaatctgcattgc
agggcgaacaaaatcaatttccacattatttaggccggttttaaagagaaatggagagattttgagaactgtgaaataaggctggttaataaa
ttgtgcataaaaaatctagagagattggaaagccatgcctatttcactgcagcttcaccaacaatctaatcataattttgaaaatgaaaattac
attagcatggtcctttactcacattttttttaggatgtcgacacttttttcatttgaggtcgctacaactgttgctcaaagttggagcatgtgcg
acctatttccactcctcctccacagacccgtttgattggtgcaaaagtgggcagagcgaaaagctgattggtcttgcagttttcattttgaag
ggaattaaaaaacggagttagtaacaattgagaattaccgttttttaaatgtataactttcaaatcttccgtttctgaatttattatatacata
tattatatagactcaattacaaattatataaatttaatttatatattatatagccttaattattaaacttttttattttgagatattttttaaatt -continued

```
tcaaacttttttttcagtatttaagtaagcttcctattcacgctactccacttttagtgtgtttcaaatgaatggacgttataccaaaattcaat
tgaaatatccagcttcataaatatattggcatgggaatgagcctcgtcacgaacattttagaaaaacatcaggacaaacttatattgtactata
acttgcaaacctgcagcagcagaactttgaacacccaaatccatttccgacggaagtattctacatcttgtggccgcgtatacccatgactact
gtacccaaactggggaaaacccaaattgctagtaaacgccactaaataaactgttagcattgaaagtgtgaacacgtaatcgtatgtcaagt
gataggaagtgtgacgttttgtaattaatcttaacttccaagtgtttgtttccttgaaataagatgcctacacacggcggcgaaatggatactt
tttatgtctgcgcttattctctttgtcccccatcatcatacaatcttcaacgccttcacatatcagacagtccgtcgggcactgaccaaccatt
caggctgcctgtctgtcatttataggctgtctagttatcttcaattaatgtttgaaaattcagaagc
```

C35B1.5

SEQ ID NO: 54
```
aattaattattttcacatttttcgaattttgtcgatttataggcgaaattttacgttaacctaacggaaatatgagtttataatgcattttta
atcgaaaattcggttttttcaataaaatttgctatgaaatccgcaaaaacgcctggaaattgtctgaaaacgaagaaaaataaaaataaaaatc
cgaattctgtgcattgtgacgtggcggtgtttgcgtacccgacatttaatttcacgacacttgttttatgttttattgttttctcgatttct
gcaagttttccacttaaaacgtgcggaaaaaatccagaaactgtaaataatactaaaaaaatataaattttccacaaaaaaggcatgaaaacta
acaattacctcaaatatcgtgaaaaatgcaaaaaaataagcctttccgaaaaaacgggccctgggcctttaaaggacaaaaacaggaaagc
ataagacaccaaagagtaattggatttctacacttggttcctagaattatttataaggtgttattgcgttttgtgagattgttctatttatc
cagtcaaaaattgcattttctttgttttgcttcaaaaaaatacattttcagtggaaatttcagctgaaaagcagaattttgaggttttcgagt
aaataacgtaaaacactaaattacaaatattgattttgatgtcttagaccaaattttcgtaaacatgtttgtattttggaaaaaataggttt
tttgtcgattttaacttaattttttcgaacaaaaaatgattttttctccgatttaccaagttttgacttaaaattccgatttctgggtcattt
ttccctaaaaatacgattttaattcaaaaatctatatttcaaagaccaaagtaccataaccttcaaaaaacaaccactttctctattgcat
cagcgaattgtcatcacccctctcaaaatatacaaaacgtcatcattttctgtgttttctctaattctcctgaaaaattctataaaaccaaca
gttttatcatcaaaaatgccttttgaccgactttttttaaagttgaaaatcgtacagttttagcagaaattccagagtttcattttgaagtat
gctggaaataataaaattattctaacatttattaatatttgtaaaactaattctatacaataaaaaagtaaaatttaatattaaaaaaaccgg
ttttttctcaaatttccattccccaatgtcctgttctattatttgttccgattcggccacagaacgcgcacacacactttttgctgattctct
gcctcctttctttgatttgaccgcattttatattgattttcggccacaattccactatttgttcagtttgtcgatttgttggaaatttcaattc
cggcaattcgccgatttgccggaaatttaaattcagacaatttgccggtttgccggaaattttcagttccggcaatttttaatttgccggaag
tttccatttcggcaacttgccaatttgccggaaattcgccgttttgccggaaatttcaattccgacaacttgcctatttcccggaaattacaa
ttccgccgatttaccaatttgccagaaattttaattccggcaatttgccgatttgtcggagatttcaatccggcattttgccgaaaatttcaa
tttcggcagttcgccgatttgtggaaaataacaattctggtcattcgccaatttgccgaaaatttcaattccggcaattcgccgatttgccgga
aattttcaattccggcgattttcctatttggcgaatattttaattccgccggtttgccgctttgccggaaatttcaattccggaactttgccg
atttgccgatttgccggaaaaatcttttgccgcccacccctaataaagacttcaaaatatgcgtttttttttgcttttaacacgctaaaactc
tctaaaaatccccaattttcagcttaaaaaacccccaaaaaa
```

Endoplasmic Reticulum Oxidative Stress Toxicity hsp-4

SEQ ID NO: 55
```
atccatttatttatgtccagtacaagacgaccgttcatatcttcttagtcattttctttcagccggtgtactctttgttcaattttctcttcttggtgcaa
cctttattcacgtgtatcttctccgagcttgtttgcatattttttttttgaaatttcatgtgctaatttattcatgtcattttgaagttaaactcttcaca
tttcataataaatatttattgaacccgtttgactactccaaattcacgaagttaccaaaataaaagtgatatttgactttcagaaataccatttcaaattc
cctaagacgctcgggaaatattaattactgcaatttatattctgcttgtattttcgaagttgggtccaactgtgtgaagtattgtaagaatcatatc
cttctccttcacattctacataaaacaattcatttctattctgtaaattttttctgatgatttacggtaaaaacgagcgaaattcggtccgggacaagg
gtttctacgacgagtccatcgtggtgccgctcgcttgtttgaattcccgcgtgccgcattcctcgtgtcgagacccgatgtccaactgggggg
attaccaactcgggggattggccccgcccacagaaccgtggcttgcaattttttcttgttaattctcgctctattgagaaaaaataattttaaaac
```

-continued cgtgcggcagtttcaaaaatgggcgtattgcaagccacggttctgtgggcggggccaatcccccgagttcttcgggtctctaaggaaagg attcgtacattctggtcctttttatttattttttaacctcttttttatttttttaaaccgcaatccattaccagttccattttctccgtactcgtcagtgtagc gagtgacgagtgaaattgaccccatttcttatcttatcgaaaacaatctaaatagtttccgcattcgcataaccagaaaattcttcggtagtcgttc tcatttgttttatttcatgaacataaagtaacgccatagtcttttatgaaacgtggcgttaagaaagctctcgaaaagtctcgatttctccagca ctaatacacgtcatctccgataagtacacgttgcataggcggtcctaataaaagcgaccgcggacgttcacattcagttctttgttttcttttgt cgtctgcactccttcttgcgacgtgtattttgtgttcttctctgtgtttccacttctcgttagtattctc aatgttctcattttcagccactcagcgaacagttgaactgaccgctcatcaagagaaaat dnj-27

SEQ ID NO: 56 aaatttcaacttccggagcccgatacctataggccacgtgagaactttctcaggagagacgcagagagacacaaattgactgacgaggag ccaggagaaatgagcagaaataaatcaaattgaagagtttctgaggagttctttttttctctcttccacttcatcctaccgcctgagccaccgg gggaactgacaaaagagagctgtcacgtggttccagactgtcccattacggtttgatctacaaaaaatgcgggaattttttttcccaaaaaaaa tgtgacgttagcacctatcggttagccatacgaaatcagttgagaagtctgccgcatttttttgtagatctacgtagatcaagccgaaatgagac actctgacaccacgtgagatgtgctcattgtggccgcgagagtggtgtcaaggaatatgagagtacatatggtaattggtgtataccataatt agatgggaatttgagagcttttggaggaaggagagggttttttcggcgaaaaattagtgtccgaaatgagaaaaattgaaaaaaaatgcaag ttttcactaaaaaactacactttttggagaaaaattggaaaatctgccagttttcagtgaaatcgagtttgaaaaaataaaaaattcgagaatttttt tttttttaatgaaagatttgtgctcgaaatagctgtaaaatcagcttaatttccgaaaaaaagatcgtgattttctcgaaattcattttttttttaatttgtaa ttttgattttttccacacaatttcaagctttaaaaatgttaaaagtcacctaaaaagtcgattttcataacaaaatacctagaaaattgtcgaaaacc ggcaaatttcggcctaaatctacttttaggcagattttaagttgaaaaatgcacaaatattctaaaacctgacaattcaacgattttttcctagaa aaaatcgtcgaaatcgacttttttcgacttttcagtatttttttcagtagaaaagttcacaaaaatgtccgaattcgacggaaaattcaaatttttttttt ccagaaaaagtgctgattttagccgaaatttgggtggaaaaatcgaaatttcgacgaaaaaaatccaattgcaattgaaaaacattgattttcgt tcatcgaagtatcctcttttgttatttttccacttttttcccgcaggtattctctcgccattcaccaagacatcacacgaatcccggagacgcagac aactgaagagacccacttttttgtgtgattcaaaggggtcaacgcatatagccggccgattcgtgatgactcatctctgtgttattctataaatct cttgatttttttgaggatttaactcttttttttcgaaaaaaacgtgttttttccgaattttgtatggttaaaagtatcggaatcaccgttttttgttgattttt tttctcaattttctttttgtttgagtaatgattaagaaataagaacggaaagaagagaagaaactgtgaaaaatgagagaaaatatttcaaaatca ggaaaaaaatcattttccaaattttcaggatattatgcggattattagggttagaacacattttaaattataatttttaattattttttaacattgaaaaa acaaaaaatcatccgaaaactactcttctttcacaaaaatcggtcaaaaataaaaaattgcgaaaaaaaacaaacaaattaaatgtagcaa gcgcgctccattgacaaaatgccgaaattttttgcgagcgaagtttgaatttcgttgcaacatggggcattttcgtgaaaaacaagatttaaaa gaatttatactttattcttgctcaagaaaattaattttttccataaattctattaaaagtggcagttaaaacaacaatttctaagatttttttcactttttttt tggcgtttgcttgttttcagagtttggaatagttttatgtcaaattttgatttcttctcattactttcttcataaaaaaaatgcaaaaaagcaaattttta tcactaaatcgttcaatttccacctagaaaagacgaatttaacgcaattttccgattagagcgcatttgcattgtgcgggaaattcaaattattca aaaattctcctctagtttccagttctagtacaatcggtggccgagttttttctttttttttccagcggccacatagcaagagccaacctgtatacttt tgcagttcttgtgcaaatctgagctccgccgagcacaaacaagtttggacagtccacttctctgcgtctctcgtgatgagtgtgctctctcgtct aacctctaatccttcccagatatttgcacatctaccccagttccacatagccataaagactgggtcattttatcgattttttcggtttgctcacaa tattgtgagtttcttaattaggtcttggtagcttttggagcattttgtgacttttatgcctaaaaaccagtttaaatatactttttaatgcttaactag atccaaacacctttgaaaattgtccaaaaaaattattttttggccgaaaatttcagtcgaaaaaagcattttttcggcctaaaaaaaattccaaaa aaatccctaatttttctgtatctccagagccacttttaaggtataaatcagcaaaattttccgatcaaaattccatttccctatatcttttccctctct ctatctcacctatctcgtgcgttagccgacgtttactaagtcccagtcagtttaattctatcaaattcttcacttttacttacagaaa dnj-7

SEQ ID NO: 57 atcacacggttgaaaaaagtcgaaatgaatgaaaacaagggcattttggaattttttttaaaagaagaagtaaggtgagttaaaagaatgaaa agcggcgtgcttgagatctaatgaaacaagggaccgcccttgtttgtgatttgctaacaaccgctatcgtttgaaatattccgggcggagttct -continued agctgatttctacttggagtatcatagaattggaaacggaacgaaattgccatagtatgaaacttttaatttgtatatacaaatataatcgaccca tttaataggcctactgcggattaatttcagtgctccttctaaaggcagacaatgaaacagttgtgtagtaaaaacaatgttcacaagacctgaa acaattttctgaaaattgtttgataatattgttcaataaacataaaagatggttcacaaaattaaaactaaattaaaaattaataagaaaaccagtt gtcacaaacgcattcgcaaccaaaaccgctaaacgctattccaactaaagttataattgcatttttttgcaattaactgttttaccacaaaacaaa acaaaattccagtttaacaaattatcaaaattccaataagatccttttttaaattaaaaaggtgagattttctagagagtccgaatagaaaatggt aaccaaaccgatgacgatgacaatggtaatcggatcaatgcagaagttgttttgaaattattttcaaagtcgttaattttgagaatatttgattttttt ttagagtatgtactagatttgttctctacctcaaatgatcaaattctttgactgcattaaaacaaaattttggcaaaattatcgaaaatctcagaga aaataaacaaacagtctatcacatttcaaatgaagaggaagccaaatttgaatatagacggtccgatgaagaattttttgacaatttatttttaact cggaatggttattaaatttgatttttttaaatttatatttcccattattttaattttttaatttatgaaacttttttatgtgaaaaaaaaatttatgtgttttt tgattataacagattttacgtcagaagccgaaccatcttttaataaaaaatttgaaaaaaaaaatcacttctacaattttcatttttcaaatttgagccatca aagtcaattaggaaaattaattctttcaatcgttgcagttacagtgctatttcaggatctttgagagctcgccgtgagcttggttctggagattcg cagataaaaattcatgagtaaccgtttcaagacatgggctatcaaatggcataggtctcatatgcaagtccgattggcatcttctgatggttcc ctagtgagtttattaattcacaagagcattgtatcggaattttggcaaactgttaaaacggaattatatgctttgttcagttttgtttcagtgtgttac acagttaattgttttagaaaccattgcaagcaattataactttggtgttgaagtttagttgtgaatgagttcgtgacaactggttttcttattagtgtg tatattaatcttgtagatcatctcacatgcttattaggcagtggtcatttctatttaattttgtttgaaagggttttaattttttgattttttttgttttgt tttagcgaactcaaattgaaactaatcgccaaattttataataaggccttttcaaaacatttgatcaaacggaaaagttttttcaaaaaataaaattttgc agcggcttaggcacacgaacatccgacaggcgattcaattgtatcaaatacttagtgcttctaggcaaaatgtgatttttagatataaattaag ccctttttcacagtttgtaacgccagggaaaacattttttgagcaaattttgaaaaatcttatcagaaaatgttttgattgggttaaaaaaacacct agaaactctactcctcttttaatgaaagcttgtgtttcaaactcttttttgtgcttaaataaattttttatgcaaattcataattttaccaactttttttcccact gaaacatttcaaacataatgtcaagtcgtacaaaatcttataactaacgattttctaatcgtatctcctgttatcgttatctttacaatcgaagataa acggctgagaaattttaggtccgaggtacaccactacgcacaattgcggattttgcactatttggagagttgagccaaaactgtcttacttttta tgaaactgtggaatgttgtaaacaattggtgaatatatttattgtaaaattttttatttgaaaatcatattcttttgtatcgaattttggaattccacgttt gaaaactgcaagagcgccttatgctgacgtgtgttagttagattgagagactcgcacggagtagacgcagacacaccacacagcacaaa cagacgtcgacgtccgcaattctcgttggttatcgactctttttgtcccattccaccaccaaaacttgccacgatttgatgttgctaggacataaa ggtccagtgggaaactgcaaattctttgttttcactggttttttttccatttgttagttactagcttgataatttaaaaatgaaacgtctcaaaactagtt cacttgacctacttcgaacaccaatttgtatcgtgcgtcatattccttgccgttgcaatttcacgtgcacttttatgaatttcatagatttttttttcaga taattaaccgacaaa

Y41C4A.11

SEQ ID NO: 58

Ctgttgcggcgcacctcgaagaatagctcctgttgggacattttgtgatggctgaagtaggaaattatattaaatttacattaaaactaaagaa aaaatacgaaaaattatgggaaatcagtggtaaatgcgaaaaaatgatttaaaaaaccgataaacgttgaaaacgcgacggtctccaaaat aatgcaagcgtgctccactgcgaatcccctgctcatttgcgcgcgcattcaaatttagatttccccgatttatcgtgaaaatcgctgccatctga caccgcattgcaccgaagatggccaaagataaccaaaaaaccaatgaatcattggtctatcgaaaatacattatattttgttgggagcagcc ccacgaaagccacgagagcccgcaaaaaggtaaatattgacttaatatttgtggcggtctcttacttggttccacttacttttaccaataggca gttattttgcgttttgtcgaaaaaatcgatata arf-1.1

SEQ ID NO: 59 atcgccaaccaaggaaagtagtgatctacaagttttctctgcaaaaaaaacaatcgtaattgcataacatctatcgaactcgagagtctccca aaaaatccctccaaatctttactgcatttgcatgtaaagatttttacctatttttctaaactgctgtgttcctgtattttcactctacctgtttcgtttattt atttatttaagcatcaagtttattgaactctaataaaattctcggaaattcgtgtcttaattattcttgccagggaaagttacgtttccttatcgaacac ctgttgcgaaaccagaaaagggcgggtctgactaagtgaacaaatatttcgtaataactttcttccaacagaaattaaaacacgcaaaaaac -continued ggccaactcactagctggaacgtggagccatggagatggataaaataactctgattgtcgacatagcttcaagaatatcgtattctgcattttc aaaaagtcttttttcgttcaaa lips-11

SEQ ID NO: 60 gcataaaatgtttgaacttggcatattataatacaaaaacaaaaattgaaagagccaagaaatgggcggagcctattattgattatccttgtatt ttgcaaaaattgttgacagatgattttttttccacactaactctattgggagttttcaacaatttgatatccaaaaaaagaggaaatccgctaa caatgtgaaaaactagcatcataatttgaattgccgcgcagtttcctggcgttccagaatgatctatttgtatttgaaagaagacctttgaaatag gcatctcaaaatttgccgagcttggcaaattcggcaaatttctgtttccaataattgccgagcacggcaaactcggcataatcggcaaatttgc ctggcttcgcaaactcggaaaaatctaagaattttgatattttttggagcacaaaaattactgttacactaagaacacgtttgcttggttggaaat gtccgtgtggttcaatttcatgccagtttactagattttttggagccgaatcaagagttttagtaattgtttttctgttcaacttttggtgtacgcggca aatcccgaaatttgccgaactcggcaaacagcaaaatatgaaacgtttatcacagaacttgttagggggattttttcaaatatatatatattttttttaa ttcttggaaaaagcttgtctacctcgaaataccctaaaatcattcaaaaatttaaatattaccattgagagcaaatttacgggcctctgaaatag tggaaaaatgaaaaattaactgaaagttaatacgaaaaattttcaagcttgtaaaagattttggttgttccggaaatcggataatcggaaaaca gccacccttgttctgactaatgagctaagaaattgattggtacttccatagttgatgaatgttatcagtaaaatgggtttggcaatgcttttgttat tccaccgtgatataaactgaaaagcacaactgataagatgaggcacctgagtgtctagacatggcaacggaagtgggcgggattggaattt ttgagacgtggcttaagttgtataaaactgaccggctaaattttaatttcagtgagttttgagttttccaattctcacccaaattccacattttatgc atcgcctaagtttttttttttaattttaattttttttttccagatcccga srp-7

SEQ ID NO: 61 gcttggagagcatctatggcgtcttttcggaatatcaagtcagtcacgaagtcttgtgccaattcctttaccaatcgttcgaatctggatcgagg aatgagcagttcagtagactgttgttgttttcggatttctcgcagagcaactgtaccagaatgaaaaggatatgatcgtactggctgagtgcac gatttgcggcatactcccgaaaggttcttttttgccagccattgtttggtagatgtggtgtgaaatggagagattgtaaacccttctataggtgcc aaaggtgagtgggcgtagcttcgaagtcaactgcggtgaaggggcgtggtttcttactattagagaaactgtatcagactaactccgataa agccatagtcagtgaactctcaacatagttaggaagagttactcagattaaataaaatcgtcaaagaacaatcaggccaattctgggctagg catagttcataggcagaacttggtagaggaaatcagagtaaagtaacgatgattttaattttccgtctgaaaaaagatattgaaagcattttgc cgatcgaacaagacacccaaagtctcatgacgacatcccagaaagagtttcagccaaattcccaacaacagcctaaaggaaaatctgaaa agaacaaaacatttgaacgtgctagagcgtacttgcacatacttgcacatactgtaagtcaacatagaactctactcataagtgtgacaaattt gttacaccaacagtacgaagccaagatttgattaaagacaattgttgtttaaactgcttgataaaaggtcacatggttgcaaagattgccagag cgaacgcaaaaattgctctcgctgtgaaggtggtgaacactgactcagcaaagtcggaaaacatgatatgatttgtcttagtttattggttacc tttatccgaaggtgcatcaagttgcctattggcgttatgttgaagatgactgatataatacattgtaacgatttcgggaaaaatacatatttaaca agataattatttttttcgattttccgaaaaaatggaataaaagaaaaacggacattttcgatattttcaaaatccaataaagatcagcattttttgt atttcaattcaaaaaaaaaatcgaaattaattttttaaaattggaactcgagttcctgctcaatcctggtcaatgattaaattaaattatgctcgta cagtaacttgttatttctgtgtttaattaaaggcgcattactgatgcgatttgggtctctccacgattgcactctgttgtgttatttacttttatttttaaa tattttatttgttattttaattcattttccgcatcatttttttcaaggaatttcattgatatttatgccattcgatttaaatttaattttttgtcgttatttt acgtcgaacaatgagtcaaacacctaattctggttatgcaacgtgggttacacccttactatagtatatatatagaatacttgcaaaaattgttatattta cacttcgaaaatcagtccgaaaagacgtaaagcaactttgcctaatgaactttttttaattaataatttcacaaaaattgtgaaacttgttatttct cttgttttttgcctttgaattttaaatatgtcgaattttttccaactattcagctgttcttgtcgattttttgttaatttcgaaactagttcagtaagaagtgc -continued gaattcagaaagaaaaacaaatcaagagtatttttttatttcgttttttctctcaatttctcttcacttctctcccatttttagtgcatgtatttttcctcttctc tcttcttgttgtctagtttagacaacgcggtcactgttagagagtgcagacggttagcgtaacaaacaaaaaagtagaattcatttttggcgttgg aaaccgcattaaatactgtcctcacagtttccgttcgtcttaatttcaaatctttgctcttg ale-1

SEQ ID NO: 62 ctcgttttcattgttggcttcgattattggatttttataaattatggtgatgtagttttgaatgtagacaataaattggaaatgaaatcgatgaaatgct caagtttataaatagcaaaaaaaaaaacatcggtagactttatttgatctactgtgaaaatgttttccggcaaatcggcaaattgccagaattga aaatttccggcaaatcggcaaaatgccagaattgaaatttccggcgaatcggcaaaatgccaaaattgaaatttccggcgaatcggcaaaa tgccagatttgaaatttccgacaattcggcaaattaccacaattgaaaatttccggcaaatcggcaaattgtcagaattgaaaatttcggcaaa tcggcaaattgccagaattgaaaatttcggcaaatcggcgaattgccagaattggaattcccggcaaaatgctagaatttaaattttcggcaa atcggcaaattaccagaattgaaaatttcggcaaatcggcgaattgccagaattgaaatttccggcaaatcgcaaaataagcaaattctataa aaaatatatagcgaaaaaatttcaaaaaggcactgttttaagtgtttccgtcttataaaaaatcccttgaaacattttcggcaaatctgatggcaa accggcaatttgccgaaaatgaaaatttccggcaaatcggcaacatgccgaatttgtcgacaaaaaatttgccaaaaggcaattgatttaact agtttttaactaaatttgagttttttcatcgatttcatctcatttcccatcttcctgagttgtattaggcttcacattaccccttcaaagtacggtagcttt gaagaccattttcattgacacatagctccgggtcgaataatgtatcgttttccaccacctttcgtcaataaatcatttacgtcatatcgttttttgca agcttatacatatttctgtgtaggcggcaactgagactgataaaaaacgcatttttctaaatggttttttgatgttgttggactgtgggaatggact atggaattataacaatctggagagaaaagagtgcccgagagaagcagagaaacaagatgaacgtggcatacgtacacttccacaacagc agccgtcttgtggcctatataaatgaccagattcaagcggccatttatacttttcgatcttcttctttttcctttgtcttgagattgaaatttgagag ataacgaatccaaatagacaatatgcacttaatttacttgaaaatgagcttaaaactcacaaaaaaaacaaataatttggacttttttgcacattt cctgcaaaatttgatgtttatccagcttgtgatgaataatttttgcacagcaaaatgaattttgtggcaattttaatttcaatcttccatccattagtttt cctggaattttttgttgaaaattctgatgacttggagatttaatataagcttttagtcgaattcctccgttttagacgtctaactagttaaaaatcgt tcaaatccttttaaattaattagtgagtaaaattcaaaaagttccagaaactttttatagttcattaaaaatgtatttttttcacacctagttttaattaa aactcacgtggtgtcaggatgtctcataagggtttgatctacaaaaaaatgcgggaattttttggaatcagttgagatctgaactcccgcatttt ttgtagatctacgtagataaagccgatatagcacactctgacaccacgtgaaaacctataaattctcctaattcattttgttaatctgatcccagt gacctctaatcttgatcattttatcaccacgcgtacttctattttgcaaagacctatgatatcagttgtctgacggtcagaaagtctcggaaaaag gcgttgaccgagtaattacaataaaaaaattaacgatataaaacgtcgaatagccaaataggtagatagcgtcagaaaaaccaatcagtgat ttgctccgcccacttttcaaccaatcagaagggtttactgggcggagctatacgttctcaatttggaaaaagttcaaatagtgagattttatcttt ttttttttgtagattcatgaataaatttcagactaattcgtgtttttcattctcgctaatttagctttattacgcgaacactaggttctgagaatgcgtattg cacaacatatttgacgcgcataatatctcgtagcgaaaactacagtaataattcgaatgattactgtagcgtttgtcacgatttacggggtcgat tatcgaaacggattaaaatcatttagttatctataaaattaagcaagaaaatgaggaaataaaatggaaatatattcatttaaataatcaaccc cgtaaatcgacacaacagagctacagtagtcatttaaagggttactgtagttttcgctatgagatattttgcgcgtcaaatatgttgtgcaatact caaaaattgtgtgactataataattagctatacaattctgtggttttttgagcaaaaccgaaaaacgaaaaatttcgttttttggcaaaacactcc aaaatcggtattttcattcaaaaaaccatattttttacggtttacgccctatttcctacaaacaacagaaattgaacgtggtgtcagagtgtctca ttttggtttgatctacgttgatctacaaaaaatgcgggagaagagacgcagagttctcaactgatttagcatggttaagagtgtgctgacgtca cattttgagcaaaaaattcccgcatttttttgtagatcaaaccgtaatgggagagcctggcatcacgtggcattagacttttttgagcaagtttga ccaaaatctttttttcttcgattttttcggttttccaaaaaaataacgccaggcttagcctccacctcaatattcttatgtgattgtttccagaacctcttc cccactaaaaca ckb-2

SEQ ID NO: 63 ttactggcatttaaaggaaagaactcggaaaatttatgaagatttgaagaaaggcacttgttaattgatgggttttcattgtgttttattaaatatga agttgtgatagttttaatgtgattaaaataaaatttaaatcaactatcgtgaaaagtttaactacaaaactgtattaaatctgagaacacatacttta taagttgggaaattgttgatcaagtctaagttgaactaatatattcttgatggaatcggaccgaaaaaatcaatttatcttattcagaaaccatctt -continued gagaatgcctacattttggcgcgagaatagcggcagaagagagagctagaacggtaggcattctcatgatctcatggttttcttatacatttt cttttttctgccgtttagtttattgatctcaattggtttgttggtctcccctcccctgtctgcggtcatttagtccaataagtcaacgtgtactaac tgcacctggactttgttcacttcctctataaaatgacttttgattgtcttctttcttattctatatctacttttgaatttgtaaattttatagctacaat ttcactttgaaactgtttggtttttttttcagaaaccatacaattttgtttctccaaac fipr-24

SEQ ID NO: 64 tggaatgggaatgagaagattcggatacgggtacccaatgtggggataagctgtgcaatcactactgtgtagttatgtataaactatgtaaaa ttgaagaaaataaatattttgactacctcaatccatgttgtcacactgtaacaagaaaattaaaatctgataagcttcagctaaaaactcaaaact aagattctcaggaagatatttgggtatttgaactaatttttgaccgcttttcatgcacacgcaatggatttctaagtatccaagtatgattatttcata tttcgccacttagaatccagaaatttcaggagcatattttttgtgatacaaaataacgtatttctgttgcattaaacttctgtctaaaactgttcggat ctgaaattgaaattagcatttaactttttgttccaactgaaataatgtattactggacaaaaaaatattaccatgacatcttgcttcttttggagaata ataaaataccttcagttatagattttaggtaacaaataccatatttattcacacaagttgatgaaactcgttcgatattttaaattaaactgcctttaa atatctattagccagttgttgtatggtcctatgcacacactatcttgtatctatagtttaatatatgcggcctatattgtgacatatattcttcccgttt gctctgttgttctccccttcctgtataatgggagattgtaaatgagagttgttctggtcccaatacctagccactgagaaccctcctcttctatcta ctactcatttatattatcgtcattattttttattttattttatacatatagtgggcttatcaacatatatgagggtaaaatacttataattaatcagcagttc agaagaaaaacaatgaatgataaggaaattttagagaacggatagaaaagggatctttgatttcttcagtgacactgttatcattttcgaaa attgggtatgacaatggagacgccccacaatggaaataacttcaaggttatccatatatactgcatacatatccacaatattatgaggtttctct aggaaactgaaagaatcctagtgtttgaatgtgttgagcatattaattttaagaagccaagaaaccataacttctgataatgactgatatctagg ctgtcacgagggttgcttaaagtgttacagttgtgccagtaatattaatagctcaatttctacaacatacaaaccattatggtaccctacaaaca ctacaaatggtttgaaaccttgttgtttattgttttactgaactcttatccacctgatacctaaaaaacgtcatgttaagagaacaacaccgccca ttttgaatcctttataaccactgggagatgaccggatttccaagtactcgtagttctaaaaacctttaaaaacccaaaaaaaag arl-7

SEQ ID NO: 65 catgttttctctgcaaaaaaacaatcgtaattgcataacatctttcgaactcgatagtctcccaaaaaattcctccaaatctttactgcatttgcttg taaagattttacctattttttctaaactgctgtgttcctgtattttcactctacctgtttcgtttatttatttaagcatcaagtttattgatctctaat aaattctcgggaaattcgtgtcttaattattaatattatagttattcttgccagggaaagttacgtttccttatcaaacacctgttgcgaaaccagaaaa gggcgggtctgactaagtgaacaaatatttcgtaataactttcttccaacagaaattaaaacacgcaaaaaacggccaactcactagctgga acgtggagccccatgataactccatgataaaaataactctgattgtcgacatagcttcaagaatatcgtattctgcattttcaaaaagtattttcgt tcaaa

F07A11.2

SEQ ID NO: 66 gcacaagccgccgtgagactcgacgataccacaaatttcaacgatttcttcacaagcttcaataatgacctcgggctcgatcaggaatggat ggttttcatcaaagcttctacgcagaactcaatctcaaagtcgaataattttttatttcattgtttttttgtttgatacctgttttgattaccatttttat cactatatttctgacttctttctcattttttttaaatttccggtcgatctttcacagacacgattgtatccgtgcagtatttgaaaataacaaattttctg atttctgtgggtttcacgtgaagatcttcttcaagaagaggtcatcagattgcggaagatctatattaccgatctgacgcaagactaccatgtatat ttggaaaggaaaaattttctgtgcagaggttgatggtttaaattttgatttagatattttcttcatttaatttgaaaatttccatgcctgaaaatatcct cagtgaggattctcacctaccgtatacttaaaggcgcacacctgtctcaaccggagcgttgcgagacccgcggcatcaaactacacactgt gtttgatgatcttcgatcgttctcgaaaaagaaagagcagagttcattaaaacaaatggcggcaaaatgtctataaaggcgagtcgttctc ttcattatcttttgattttcgatgtgttctccttattgttttgttcgttgaccccttatctgcattctcaccgctacgcaacgtatatttaacgtcagcttt ttcgcagaaaattttctatattctcatgcaaatttactgttctcaatgctggacgtgtcgcttgtgctttgatctcaaatctaacattttcccttcaaat attttatatctgcaacggtggggcagaaatttaaaagttgacctttgtcagccaactgctatcagttatcagttggccggagatctttctattttca ctttcttgcaacgtattcagacattttttgatgaatcggttcacagaattttcgtcctgatgttggtcagtgatgcgccagccggaaattagaacc gtatgccgttatcaattttcaaaggctaaaaagttatgaggtgtatttattgttttaacacctgacctgctagtaggaaggaaattaatttatgttt aaattgaaatgaaagagtcgagctccacgtgtcgtctcccctagtttctctattcctcttcttctccgcctatctctcggcttctctcctttcgcgctc

```
ctctcacaattcctcctaatcgtgctgtttttggggtggtccaacacggcaaaaaggcagcaaaaagtgtctgccgtctcgtgcctctttctta ttgaaagggcacgagagaatagtatcaagaggctcctcgttcgggccgttgaagatggtatctggtgcttcggcggagacgggaggagc ggccgtttctcgggtcatcacagcccattccttctaatgtttacactgaacttgtcgcaatccctcctctaaatctcattcatccattcattcatatt cgtgttatgtgttcgcttttacataatttccattttcaccacgtttctcctcaaatttgcattatttaaatctctgccttttcataaacatttataattttc agggtatcacctatactaaccatccaaa

C04F12.1

SEQ ID NO: 67 aggcaaacatcacgtttccgatatcaaaagacattgaataaaagaaaaccaatagaatgtaaactattaaagtgacaatttcagtgaaatttat caaaatacgaaaataataaaattaaaaattagcgccagctaactatttagcagagcaaatacgttttgacccaatataaaaacaataatatgaa aaaaaaattaaaataaagttttaccaaatcgatattggcaaaacatcttgttttttgaggctccatatctctgcaggaaaaaatcgcactaaaaa gtgatcaactagaaacttgttaaacacaatgtaatctaaaacttttcagttgaacactattttgtaaaaaatttcgttgccaagatatagatcttt aa ctatttagaatattcaaaataatgaagctcaaatcaattggttccaactcggcaacgaaatttttt acaaaaaagtgttcaactgaaatgttttag atcacattgtgtttaacaagtttctagttgatcacttttt agtgcgattttttcctgcagagatatggagcctcaaaaacaagatgttttgccaatat cgatttggtaaaacgtcttgataaggcatcagaatcaatgattcggtcattgaaaataatgaaaaataggttatttgtgacactctaaaatatttc atgcatttttaaaaaatttcaaaaaaaaattttt cgatcaaattttctcatggtggagaaaaagtgacaattttcgaaaaaaattaaaatttctga aaagtttccagggtaattatggttcaattaaaaagcaaaaaattatgtaaaaccctcaaaaaaatgttctaaatacttgtttcccgttctgaaaa ttttgtataaaaaggccaaaagttaaaccatgtatgggaaccgaacccacaaacttctgctcaagaggcgaacgcgttcaccactcgacc accgaaccgatgttttcgcccttccaccattgtggtgagacttctgttggcgccagagacaaaaatccactgttaaccataggaaatgcactg atttcagtgtagaatttcagacgtaaaaatttcagatttccagcccgaacgggcaaaaatttcagtcatattcttatagtagagaatgtcagcttt ccgatacaatatttttttttgaatatcgctccatttattctggtcattccctagtcagttgcctgcccgtggcggaggaagaacataataggagga tacgcagagatgcagaaaaaaaacttccgtttgttggtaggtagtaatttctccttttgatctccaaagatgtgggaaattcgccttttggaatg ttttatggcgcacttttt aacagttaaatacatagccacactttctatagactaaacaagtactcttgacatatgtcattcatcatgtactctttagatt ttccagccttaccaacctcctccacagtttatctcattgattgtactctttgaaggaggaccattggttctgactttttt gacct tatactgattcaaa atgtcatcaaagacacgagcttcgtaatgagacttcagaaaaaaattttctgaacattttt atagcggttcaaaaattctaggaaatttagcaaatt ttagctatagctataggcttt acaaaaccttcaatttattttttttggtcagatacacgatctcatttcattttgctgattaagattcatttgaagctgag aggtaaacaaaaatcgccggaaattgtaaaaatgccagaacctttatacaacctgtatgaaggttcaccttacaattatatctgtgttttt cactt gtttagaggagtggtaggtggaagacattaaagtgtcgttctcgtagaactgttgtttggactgatagcttttaaatacgactttttt aaaaacttt ttgagattatacaactaattgcaccatcatttatttttttgccgatgtgcaactttcatattgttttttctcctcactttctccgttgtccttgttcataaca caatttgcaaatcacattgaaatttcagatttccgattctcgaagctttactaacatctccaccactaaccaagcctcaac hke-4.1

SEQ ID NO: 68 aacttttttgcaattcctaaatacttaccattattttt gcccaatcaggttaatgatctctatcgtgtagttttcccctttt agttccagttctgctgtgata tttatttatttttt gcgaatacatttcaattcctaactttttt cggaatacaaaccagtaactcataaaatgttcgatttatactcacatccgcgcgaac acttcagtgccgggtgttataacacgtcagcgtttcgccagatgatgcaattggcgttttt ccttggagaacaaatagcctcgtagagacgca ttttatttccacactgcattggactcaattggtggtgtatttgctttgaaggtgaatttaaattcagactttttttt cgaaacttgcgcagaaaattgt gaattttt cgattttt atagtggaaataggttttttt caaaatatttttattgaaaattaaaatgtttgctttctatgctctattattgccgaagaaatca atttt aatgaaatattcaaagaaatcgcggaaaattttcaaaaaatttccacgattttattttt gtacgcaatcgcatctgcataccgtaccggttt cgaatttcgaacttttcgaagcttttcttgaattttttt tctgctttccaattagaattaaaagtgtaatttaatcaaattctagtaaatttcaaacaaattt
```

-continued gggattaaatgttaaattttattaacattttcaggctttaaaaaaatattcaaagttttgtgtcaaagtctgcaaacactctcgaataccgtaacctt gcatctttttaattttttgttttctttattttatcactcctatactttttctataatttaaagcaattttataatatattttacagaa

F22E5.6

SEQ ID NO: 69 tgctagcggtcaccactatcgactgagctatctgcccctaagaaagtttaaaaaacttaccgattttgagttccaacatcattttctcgctattttt gataacgttttggttagcattgtactccggcagtattggtaggtcattctcgttgtttggagtctttatttcagactccacgacggctggagcaac attctgaattatattttttaattattgttatacttttagcaaaaaactgacatttgaaatagatctactgttgcaaataatgtctggcaacggatccca tctctcacttggcctgcctgagcctacatccaatcttgcaattgcttgctcacaatctctcactaatttcaccaatccgtaaaatctggcttccg gagcaactgatgtcgggttctgaaagttttatttaatttataaaactttaaacttctagcttaaaacatctaccatttcctgaatttcaggcaaattct tgaagtatccatcgaactttgttagagtcgctttagaagtgacaaattccttgccacctacattgagccggagcatttactttcagaaacaataa cagtttgagtttatctggaatttgttagataactttaggtagatttgaaattttggtagatcggttcatcaaatttatcaatgtcataaataaacttt gtagctataaatttaaaatagctttttttacactttattcaaggaaacactgagaaatagctgcgaaaacaaaaaaaaacatttgagggggaga acctagacgcaggagagaaagaacgtagaatctactagaaaaagtgtctgcgtctcttcaaaaaacaaatttaaacttagcaagatgacca ccacagcaaaaatgaaaagaggaacgcggagggacagggacagggtcagtgagaaaaaaattagaaattttggaaaatgagataa ttttaaactttttgcagtattccaaagttttcggaaaattgagacaaaaattttaatcaaacttcccatgaaaatgacagaaaatttaaattga aattaaatgaaatttcttatttctggattttaggagtttctggaaatttcttagcataagcataagcctaactacaaactaaaaacttcaaactac caactgaatacaattaattacctcatgattttgttcccagcagccgtaacatgttaaaaactctatgggtcctgtgagatgtcggccgctctaac tctgcacattgcagagattttcagacagtgtgtgaccaattttaggctgaaaatctgccgactgtactcttttggaaatgttttgtttcgaaattttt tactcactctcactataactccaactcacctggttgcgaaattcagcgcttttcaacgtaatctaaaatgaaaaatattcattccatcactcctcca actcccattttgtttgaaattctctgaaa pdi-2

SEQ ID NO: 70 aagaacgccgacgacaacaacaaacattttcatcgggagccctggaaaatgacgaatgtatgcattaccattgttgaaatttggactggaag cgcaatggatgaaaaaaccacgctatttcgaagctcatttctgatgctggggcacaacacaaaattaaatgagacgaggagggggagaag ggatggagagcatgcatgtttgttgttcactttcgaaaaaaatgtatcgattttttctagcaaatgtttgaagtaaataacaactttcaaatgtgata attagttatcaattcagtcagtttatcaaaaaaaagtacgtcattagcataactttgccgtatttgcatgtctaggaaattttagaaactagaattgc taaaaagtggtttaaaagttgcgggacgccgaaaattggctgagaaattgtcaaaaatttccaagtgacggaaaaccgtatgttattgtgatta gtaagacgatttcgcaatttatatatattttgtcacaaatctgaaatcactcgtgctattttaggtgtaaaagtcacatgttattgcacaaacacga gcagaaaatgaattaaaattaccttctcggtttttcagacattgtcttcaactttgtctaggtatttcgaaatttcaaaaaaactccacctgaccca caaatcaatactagtaagttagtaaacacaacagtatgggaattggttgatatgtacgttgcgagacttgtttgtgcttatcttttttcccctctctac ttaacaatcaaataacctgcaaaacactatggattttctcttcagtttgggcaattcttccagaaaaccaccaaaaaagaccgcaattttgct aacggtcttgttcacactggtagataagataacattgcgtaggtcgatcctaccgatcaaacgggagatatatggggggagtaggagagaa attacgggaagaaggctatcgagcggccttgacacggtgcttgacttttggcgaaacgtatcagttgacctctattatttgggctatacagag atgaggtatgatggacagaaacagaaaaacacacacaaagggtattgatgagaatcatagacggtgacaacgccaattcaatgagcagta gatgtgcaggagacgtgtctcgttcagttggaaacgaaggcgagacgtgaaaagagtgcgtggttgcgagagacgcagtgatagagac aaactggataggttatgagaacgagaaccactcggactgaggccattcgtagaatgaagaatggaagttgtatctgtcttttaatagactcaa atgaaactgaagaaaaaagtacaaaacataagacactatatattttttttcatattgaaaagagtttgcaaattttcttgaaattcaaaaattct gttttttcgtgacaacacttttgcttactcattttgtaaaattttaacgtgggctattgttttgtgtttaaatatttatactacatttttgaaaattatta ttttcacattgccacgtgaactcaaaatttattcatgcaaatttagaataaaatctgttcaactaagcctatacgcctcgtgcagaagtccaaattga aaggtaaacctaaacctaaatttgatcatgaacactgagcctgaaagcctgtaaaccataggcaaagcctaaaaacagcttacaaacctttct ctgaaattatgtctgaatacgtaagtttattatatgaactaagctttacagctaaatctatgtttgcaggctcagttttgaacgttaataacttcgaa tccacatggaaatttagatataattgaataaaaaagtcctcgttaatatttgaaaaaaaatgttgtcaatttacgaatcctttttttttcgcctaaaaa -continued ggagaatgtcaaaagtactaaataaaaaaacaaaacattcaagagcaactaagcagttttttccgaaattttttccaaagttccaaagtcaacct taaccttaagctgcagaatttctgatgtttaccagctactacgaaacaaaaacgattctcatagatgatttcccattttcgcacacaaaatgttgg catcacaaacaaagtgagcacaagtatggagagagatttgagagcacagacatcaaagaataaactatgttctttgttcttttttaaactactttg aaaaaaaacaaatgaatttacatatttaaaatgttgcaattgcaatttcatgatggaaatattggaaatgtctataaaataacgcagacagtgc caatcaaaagcttttctcatctacccagtcggttgagtgaatgaaaggaaacatataatatcaaagctggcgtgccaattccttttttgtgctcgg ctgcattatttacactgccggtgtttccgcgctccttctcatcgacataatttccctcatttcctctcagtcttccgcgcagttccatccatcgcaat ccgccttcttgcctaaatttgtctgacccaatactctaactaactttcatttatgtccaatgcattattctctctgtaggtgacccagtgtccttcctttt tttctctctcaagatgtgagaccccccccccttttctcctcaacggcgaggggctacgtgagtttccgctgtgtgcgacgcgtccttgcccg ctcttcccaaactgcacggccaatggggtgccggaggcggggtaggggcgggccaatcgacgcgttccacgactaagtaagcgtgg acacccatcgtctgcagaagaggacactctcgatccattcgctattcatcgtg pdi-3

SEQ ID NO: 71 gaacacgttgcatcgataaatcgagaatattctcgaagcgcaaaaagaaatttcgcaactatttcagaccgaataatgtaataatgtaatggg tctcttcgatagaaaataaacgaagataaacgaagacacaattcttcctgacgcgcgagcttcaatatgcacgtgatgactaatttggtttcca tggtgatcttttttgttccttttatcgattcaaatttacaataaaaataagaaattaaagttctaaatggcgctccaatcaatttgccttccaatttaac gtcgattccttctatatcaggtcataaaatgaataaaaaacaatgatcaataaaatgatgcggtagttgcgtaaatcgacacatgatggtcgcc tcttccgtgcgagacccattgggcggagttctcacaagaatgaggccaatcggcacacaacacgcgtgcgacaggcagtgaacgacgtg ttttggctcagttcctaccaatccctggtgtacacacgagcgccacgtggaccttaacaattcgggtctatttttatgcttctgctctgcattttct ggattattagtaataatatcattaaaagtgatataacgctccccgagtctatataaaatttctcctccatacaacacatgttttttggctttcttcttct aagcttaaaatttatagttatttactaactgtattttccacttattaaagataatttttgaaaagtgtttgtaaatacttaaaattgaacccgaaacaat ctgtatttgtccattcacatgtgattcacagaaaagaatgaaaatgcgaaaaaaaataaataaagtaaaggcgcattgattttaccgct cgcggtatctcgccacgaaaacacgtttcgcgtcaagcggctcacgttttcgatgcgatcgcggtttgttaattgcgaaaacaccttcccttct cttcaatcgttcgctcaatttctagaaaatatttctgaataatctgaaaacctctaatcttgtttcttagttttttaacttttttgtcggtgttcccgataatc tctcgccctctaaactcactcgatcgattgtcgtttataggtaaagtttttaggta itr-1

SEQ ID NO: 72 aataaaagatgtgatggtcaatttaggatagtaaaagatgacaggtggattgagggaaaagagacaggttacttctgttgagtggacacatt gcaaccccggccaccaccgccacggacacgccgcccacttttgcggtgtgaggtgcgaaactgtcttccgacagatttgtaaatattacg aggaagttgatgtaatacggaagaggtccactggatttatgtgaatgaagaatcaaaagattgtaaaatgtttagatatgatgagctacaggg tcaaaggtgatttgatacacgattttcgagcagaaatgctgacttttcgaaatctcattgttgtttaatcaatcacgggatgtacgaaagggatct tggttttggattttgaaaatcaaaatattacaggaaaatataatgcaaaactagtacagactgtgaaaatgtttctaaccttgatttctgctccgt ccaactgtgaaattacattgtgtgtcaatttcaaaaacggtacgtgatttttttagttctggttttttaagtgaactttatgtatatgagctctgaaaaca ggaaaataagggaaaattaataaggtagtcagaatgaaatattgcaattcgaacataagcatttagtttgaaacaacccgtatttcccttattag ttttgtagcttctagtttgtcatgcactgattttccgacagaccggctatactctgtgggaatttccgcaaaaattaaatttaaaattaatagatgag atgtggtatgtagttttaaaaaagtcgatggattcagaaaatgctcagaaaaatccgcgcattaatttccaaaactatcacattttcagaaaagta tcaaacatcatatttttggagtccaatactacttcttcatttcttttttttttcttttccactagttttacaataaaatatattgttttgtcctaatgaa gcacatttcattttgtaatgttttttaactttctactgtaggatattctattccgtaatcgtacaaatcttctttctctcccaaatttaggctgcgccctgt ttcaaagctctgctaatagtacgcaaaacaaatgtattcgctaactcttcgctcatttcggtataagtgtcacttggagatctcttcgtctctcgcaa cccgtatttgtattgtttatcttccaaaatggtagtcgactgctcatatgaattgaattactagcgggatatgaaagagacatgagatttataaaa agtaactgaatatttcaacttttgaaattgaacttgtatcattttcgaaactaaaatggaaaaacaggaacgatattacttcattttccacttaaag atggagtagcaaaatttgggtgattgttttagaatcaaaattgatcctaaatacctattgagcaacttgaaaatgtctcaaaaattattgtatta ggttagtcattctcaaaagaaaacgggcaacccttcaagtattaaatcatttttgagcttgaaaagagagaacattgttcattaaaattcatgttt gggctcctaaatctacaaaaaatatcacatttatattttcggcaattctgatttcctgtaatcgacaatttcagcgattgccgaaatcgtcgaaaa -continued gtcgattaccgaacggcaattgctgcatgctatgtatcacaccgtttcagcgttgtgtatcgtatttgttcaaagataattttcttgtaaatctcgat gttattgactactgcagctaatacatttgaattcccattaattcctttaatttgataagtgtgacttggttcccgttgcccaccatcttttgttcctttcc tcctatcttcaaatcaaacgcatctggaatctatttttttcattgttgtctgtctaccgatgccaacgatctgacctttcttaattggtattcgcgctca ttttgacattgtgtcaacttcaactatttgcgcgggtttacctgcaaaaaagtaaacaagaaaaatggagatgaaatgaagaatttccaatag aaatttgttgttgaaaactctctgaaccatgagaccgtccaagacgttaacatcaaatcttttcaattcagaaacgtttcctcttttttctccttttgtg acacgttcctccgttcttttttggagagtcactatattttttaatacgattttgctttacaatttctttttttaaacttttattgattttgtgcttcttattt tccattttcataaaaagtattccaga

T05E11.3

SEQ ID NO: 73 gtcgcgaaaggtttgaattcccaactggaaaaactgagattaagaaatggaggtatattgcctgattgagatgagaaaccggtttatgagac ggataaacaagtaagtttgctgagtaacgatcacaaatttcacaaattctcaagacaagtgagatgattaatttctataaggattaatttagatg atccgaacattacttgagtgactgttataatagaaagactgaaaaatcgtcttttaaattaacatattccatattgctggatccggcaaacaaaa acaatgttccaggacactcactccacgtgttctgagctgtcgtctcggtcgttgattggctgattccgcctctgtttgcaactagtaacgcgcc gcagtttgcagttttcagtgaaggacaacgtgtttgcaagagacgcagacactgtgcggcacttgcaaattggggcgggacttttagggac acgtcgagaaggggtgagcccggcgaaagaaagcaaacaagcggagagaaaaggggagtaattgaccgttggaaagacacctcatt ccatttattctcggtcgttaggaagagacggcgatgagattccttttggtgggcttcgtcgcccttctggctgtttcaggtatgtcttttttattgatt ttcagagcttagtgagctttaaatagaaaccgtagttttgaaattgtaaaaaaaattttttaagcttaaatgtacgctgaaaatattaaaactgtgt tcacagaataaaaaacattaggctttattttttcattctgtgcatacacgccacgcagttttgaattcacgttttattcccaacaatcatcacttttcag ZK632.6 (cnx-1)

SEQ ID NO: 74 tctgcggttctgaaaatattaaaaccaatgatggaaaagaatttattcgggataaggattttttgacaaacggacatatggcatatcctaatgtga gcagaggagctgtggtcggagcaaccgaccgcaccggctcacttctgctgtgattcggctcggcgccacgaaaagagtaagagagacg tgacgacggcaatagatgaatcgaaatctatggatgcaagaaacctcttttcaaatcattcgaacggttagaattgtgcaaacacggcgacg cacaaacgcacatatcgtggggacacgtgaacgatggccgacttgagaagaggaagaataacagacggcgggagagacgaggaaag ggcacaaaactgagatgatggtggtcgcaggcgctgagcgtgatctcttctgttctatttcagacaccacgggattgtattcaacaacattttg ttgtttctactgatcggatgggatgattgtaattaaccactatttatgtttctcacgaattgtgacactaaatgtgaaaaccaatagaaaacataat cgtatttcttcaaatctgatattaaacgggtagttctaattatgaaaatattgccccacgacgaagaattaatattaataatatttcttattttttcacct gcacagacactatagttatcgatgatcccagttttatttggtctaaaaataaaatttgaacttctgagggattgttgagcgacattgatatggaag aagcgctatcgataaaaatttctatcgttccatgacaaccaatcacatgttcaaatgactgaatgccaaagaaaacctcgaaagcgaaccgg tttttcttccggtgaccgtttagattttataaaatcttttagttagctgaaaatgaaatttattgcagctccgtgagaaaaataatcagatatacgca gaaatgactgagggacgatacgaaaatgcgaagaatctgccttgcaagaggacagatgtcggtactcaacacgtacccaacacagtctcc tataggattgacaatttatcttcagagcagaccggaataatattaacaacaaaagctaaacttaaaaaccgaaacgaaagcaattcaaactt aaaatgaaaactaaaataaaaagcaaaaaccgaatgctgaaaaaaaaattgtctaccgtacacctacagtaagattctgcatatttgcgtgac agtgtttgcacatgtttattcgaaaaatgtcattgttttttttttcgttttttacttttttcgccaatcatttagctttaccctagattttcattcttattttg ttttccaaatcaatcaataaacaataaattttgtgaaaatttacctgcaaacctccattaaaatttgcaaacccggcaaactgtcacagagagaatgaa aaattgattgaaaataataaaactgcttggccagtttgaaccgattttaacaattaagcttaattttttttgaagtatttgcatacacaccatgcagtt ttttttttaaagttttaccgtaaatccctactgagctaataaattaaaaaatttcgattaaaacaagcatttatcacgagttctaaactgatatgagac atatttaatttattccgattcacttcaactgatgaaaacttttgttcaaattctcaaatatatttcaatcgtatcacatttttttttcggcagctgcagcga attttttcctttcatgagccatgggcaacggcttaattacaccaacagccgttgtcggtgtttggatgtattgccctaaatgaccgcccgtacgtt gtcctctccatgcaacgacgctgaatattcttctgctctcacactcgtatactagttgtggttgaggcgcctcgatggacagcatgagagaga gtgtatcctataataagacgtagacagacgcgctctagcaaattctttaccgcagcactccacagcgttcgtcagtccgccttgtttcacgttg -continued tcgattgcagacacaatgcccctcattttctattcacttctcattgtattctatctgtatgtgcatagtaacttgttttacagcgagtaatctcaaaaa tcgatatattttttccttttcataatattgttctgttaccttggtaccctcattattattttttgaatttaggtaacc Y38A10A.5 (crt-1)

SEQ ID NO: 75 aagtgatgtttttggcaattggaaaagctagactaggaatgaggataaattatgacatcattaggacttgtaatttagaaattacacggaggcaa accgtaatgcgttttttttaaaataatattttcttaattttttccttttaatttctgctcaagtttgtttgttggcaaaataaattatttaaaacttctcaaa actatttaaataggttttttgaaaggatgtgaaattccttatggaatttttagatgatcttcaatttgaaaactgttggcagagtatcgccagtgaaaaat ttttctaaacaaaataactcaaaaaaaatcagatctttcaaagttgtcagtagaagttttttggtaaattgccaaatgttccaaaaatgtggacgttt tgaaaatgttgagcatttcagatttaagctactgcaatcttcaaataaaaatatttgaaacatagctagaatatatgaatcgcaaaaagagttttg gtaaattggtatattttttcacaactgtggtattggtctcattcagttatacatctttattcttaactttgatataccgtactctaaataaactttcctatta caaccacacttttaaatttcatatgttttcactcttcagaggtcaaaaattggaagaaattattaacgaaaaaaataaaaaattagaaattaattatt atgttttatgttcaatttacgtttcaattttttcgtatttgaaacttggcaatttaccaaagctttcactataaattttttttacttttttctacaaaattttta gtgtgttttactacgttatcctgtcatttttagactataataagtgagtacagtattgttttcatttagttcatatttctatgttctattataattgtctgta tctgatattcgatttttttgaatgaacatgagttttaaagtatatcaaagttaaaatacggatgtatagctaaaggaggcagtaacacatatttgaaaactt tgatttcatgttctcttccttcttttcccacggcgttatgtttgaccacagaagcatctattttttggaatcaatataattttttttcggtgcttttagcaaat aatataaagtttgggaactacctctaatgttcattttcattttttgatattctcccttgacatatcaaaatatttcgagcagtatgcatttccttatcatttt tcaactgtatttcctgattttagcttttcatattaatcaagtaggttcatggtttcaataaaattgtgggttaattatagatctgcctaatcttcaagcca atgccttctacggagtattgccagtgtggatttagtttgaaaagtattctaataaaatactccaaaattttaagttagttttggcaaattgccaacat ttggacttttttgagctatttccagcattgccacaggaactgtcagaatgtttgaatacaaacagttgaaaatataaaaattgtagaaaattgtttta ggtctactttcaaaattttttataggttttattataactaaaattattatgactaattttttcaccataaaaaattaattgcaaataaaaaatttcaaaaatg ttttgaaacgttttactatttttatttggacatttaagcactaacgtgttcaaagctgaaatttcaaaacgtcataactttgctgaaacttgacttgggc agctaaattttcggagagatcataactaacagtcttctatcggatattcaacatgagaaccccaaacctacgggccccttcaaagatttccctt gtgaatgggcaattttaaataatctctccatttacgatatttcaccttcaaataaacaatgaattattctagattacttgttgtcattcagtcaagata ttctcaagtattccaagttctccattgtttaatgattttgctccaattctatccaatttcccttttgttcgctgctttagtcccgccaccacccctgtgc aaagagataacgtgtgagtgaatctaatagccagaatctggaaatatatatatgtttagaatcacaaaaggaaaatgtgcaggcggggagat caaaatcgaaactgtatttgtgtggaacaatgcaactattgagagaaacatgaagcatatggactacgagttgagtaggcttcaaaagtattc aggaatctcaaccaacgagttttgcccagaaaattaccaagaaaccagtgtaagtttcattttatttttttggatttagttagatttttttaaataatcaa aaaccgatttcttgccgatgtcatactgtagacactgtgagaagtaggactacctcaatattgataagtgcctacctatgtgcctagaaggca ggtgtggcttgcattgaacttaacagtagacgtaggtctcttgaagttttgcttccaggcaggcaggtaggcatttgaataatttaaagctatag taaggagtacgtaaattacaatatcatttcgtgataaatttcaggcaagatcgaaatcattttgcaatgctctacacctttccttatattacgtca acttgtgatcgtgtcagacttttttgttcgaaatgcagtttcctggagttcagaggtctaaaaatattcctgaaaaaattataattctagatgttcag gtgaaccgagcccgagtagcatgcgaatgtgaaaaaattgtggaaatgacgcgtggctaacgaggtacttctcgtcgccgatctttctcttg accaggaccgaataaatatttgaaaatgcacttattgtttgttctcaatgccgaattgtttacaatgtaccttttggtaaagaggaactcgtttgta ctggccagctaataaaatattcacattattcttcatactatgttttcatatagaatttatcaatttttataattagatgataacgagtgctgtactcctg gagtccaccaggacttgataagagaattgaagcaccacttttataatgagcagtactaaatttcgaatctggaaatgatatttcagaaacaatcc aggaaacaccagaaaaatatcaccactttgaaaaatatgtgcatttattcaattatgctcaaatttcagctttggctcacgagtgatacggtcaa ccacaatttctccagagtacgcaatttacgcaaacaccaaacgatggcgccaaagcgccattcaaattttattcatccgtttcagccttttca gtcttcttgtctctcattttcgccattttcattgttttatttacacaaacggtcgttaaaatgtagtttccatctttttccgatggttcatcatttttgtc atgcgtcttttgtgaaactggttttgcaaaacgaagcaaaaaatggataactgtgtcaagggcgattttcgattcgtcatgtccacataaacgcg ataatgtgttttatcgttggtttcattcagaaattggttgataaatacattctactacattctggctgtgtgatccaattttttaaatccgaaagtctag aaatttagtgcaaaataagcatggaaagttctaaaccccttaaagaatactgatctcagctgtttctgttcttttcaatcagattcccaattgcgat -continued aatatcaaaaagccctctgctggactgctgtccacccgcaagggcattatttccttatcccaaaatgctctccgtctgcatctcttcaactcact cactctctcgctctcttcgcagtgcgaggccgacacgcaacgtggcctctcatcagacacgctccgcctattctcaatgtgtggcgaccgcc gattggccagtcgctgacgtggaccaatagatacgcggcacctcgagccgtgtcagccacgcaagacacacgtcgacttactccattgtc gtagcagacgagctcagttcaacatcatcagtttcagttttgctcttgttcggtttcatttctagtctttcttctctgaaattctcgaattttattctttg gtatattctcattcaatttatctcttcttttccgattcatatgtttaattgttatatttacttttttaatttcagattcaacttggtgtcgttttatcgaaa aacgaa hsp-3

SEQ ID NO: 76 ttcactccttgtctgcaacaaacgaataatagaatcaatagatggcaaaaatttgaaaacagcgtacagtcaagataagggtaatgtatgttttt gtcgtcaacctctaaacgtcaaactgaaaacttaaagggcggcggttggttaaatggcgggcgtgtagtactaaaaacaaaggtttgagta agtgcgccccattgataacaaggatctgaagaagtcttcttcggataatggaggtcagttctgatgggaaaatcgagaaatcgagttttttttat ttgattgcaagctaatcacatttaaaacgcttacatgggaaagttggcgtttgaaaatcgaatgtaatatacattttttttgattttctgattacttttga gctagcattttaccatttatatgaaaaataaaaaactaagttgcgatttggatgtggtcaattacccatttataaaactgaaaagtatgtttatttca gttcaaaaacattagaattttagaacccttctagctaattcgacccttctccaagccatgcaataacctttgatgaatcttatctcaaccaattcac attgcagagattcttatctccagcataacgtatctccaatcgctttctccccatcgtccaacacagccgctattatcggcaaagtactacgtg tctcgagtccgatcctgacctacttttatgtgtactttagttcaattgcgtctggttggatttgaatttgttgattcccaaataggagagattctgg ataatttcttcgaaagcgttacaaaatgcgcagaattttgtgtattttaaaacagttgattttagttttttggtttaaatatctagtgtatctgcttttag caacaaaaaatgattctaaaactcgtttctttctaaatcatgtcaccacttatacttggccttttccgattttctcttctctctttctatagctctttct tactctcacctgccgtttccataacagtgctctctaaatttggtataaaacacgcagcgcaaccgcaacgcaacctagtaactgacgtgtccca cggacaccctccactcacgacactctcgcacacaaacgcgcacacagggccacacgcggcgctcgccgattggccgaatgactctgcg tctctgcgcgctgcacacggtgagccttcgctgtgctgacgttgccttgtcctatcgtcctaggccacgtcgacgattcggcagttcgttcctt cgctctctccctctcgatgcgctcgtcgatccgtcagtttgctctcccttcaccactcccatcggttgacggtaccatttcggcctacagtcgac cttgagcattcgggcggtctatcgggagagacgacctacaaacagaagcagtcctaggttttcctgcattccatttctctcaccgactggcct tgtttcggttctttcttatctctttcttctcagcaattcaacaagtcgtttcatattttaggcctaataataattttttatttttacaggaaaataaatcaa acacaaagt xbp-1

SEQ ID NO: 77 gccatttggtttgacaccacacttcacaaaaccaaagtcacaaatcatagaagttgagggaaatctttctattcgatggctttcagatctagtctt aaatagcgacaatatttgttcaaaaagaaacagaatcgttcgaaattctgatatttatcttaaatcaaagcgttatttggcttttttttttaaagatct ctattaacagaaacaccacgatgacgcgtgagtttataacttacaattggcaacaagaatagtgaataaaactgacaaggctacacttgacg ggcagaccatctcggaagacgacgaaacggacagaatgatctagaagagtctcgtctgcgggatttcgactcagcgtcgtcatcccttcc ggaacctccatatcaaatagcaccgtttctcgcttctccgcctcccaggcactattatgagctgttgtgtgtgtgcaagctcacatcatacaa gaaatctcgaattcccactaataatagacaatgagactgatgtttttgattgagttgagatcgtttgattagtcagaatagacggaaattggatgg accaacagaaaagagaggaacgcgaatcgaaaaatataactgtggaaatcggcaaaaaaaagaatgataacaaaagggaaagcg cgtggcatattcttccaacaaaatatgtgttttttggcgaccgactgtgcaactctctcatcatttatattctacacaaaataattcggaatatcc aaaaacatgcataaagtcgcggaaatgttacgaatgtcaatccgaaaacagaattgtgagtttacatgaatatatactcaaatctacttgaata atgctgaaatgtgtattccaatacacttttttaatctcacaaaattcagtaaataatctcacactggagagtcaaagagttctacagctaaatttct catttacgaatcaaattagagttttaaagcgttccttcgtattaatatcagtgtaaaaaataattaagacaaaaaatatttcaaaaaaccagaaa aagcgaaaaaatgaaaaaaaaaaaaagaatgacaaaaacaaagcgaaacttttttctcagactacggtagatcttgttgtgtgcagcgtgtttg cacagattgtcgaccgtacccggaactttttttatttgaaatattttcaaaaaaatatattttctctttccaaattattcacattttttcgatattttaatcgt ttcttcatggttttgctgtttggaaaaagacgttcatcacagggtaagatttataattgtttaattctcagcaattaatttccatgagcagcgaacg actaattgtcaaaattgagcgtgtttttatattgattctgtctctgtgctattccatctttcctgcctaaaatgtatggcttttctcgttacatttctccaat -continued actttccaaagagacgcagacataaacgaatgtttgccctattgcgaaagaagtaaatgaatcacccttccttttcccttttttccactattttttat tttttattttttgaagcaacatcggcgacc cdc-48.1

SEQ ID NO: 78 tccattaatctatttgtttaatttattctaattctcgatcgggaataaataatttggaaattattcaacttattaaattcatagatctgggaaactatcaa gaatcaaaatcttaagactattctcctctcgtctcgtttcacatctcttcgttctccgtctatcgatcgggtgatgctgcaaatcatttttatcgatct acaaagtgctgcatttactaacggcatatcgtttcgagacccaaacgctgatgtgcgttattgcaaataacagttattttttccaaaccagcatta cattacagtccactttttttccttttcatattttcatcctggacccagctacatacattaccgcaaacgtgcaaacggtagattttatttactagttcct tttttccgaaaaatttcaaaaaattgtaaactgcgtttccgttttcaaagaactttttttgaagtttcaacgcttttcatcgcaaatatttacaaatacgt ctcgttatttagaaattttaaaattttttgaacagtgaaaatccttttcaaacttcgcgctaaaattataaagcaaccgcgccctaacgtcagaatc accaaacacttttttgcgtacacttgttgaaaacacgcttctatatgcgtggatgatgacaattttcaaatctgtgtcgtttttagaaataatttcgtg aactttttttaaaatctcaattttcttttatagtttcgttcccactatcattttggacactcattcttcttattttaggtcttaaattgtacata cdc-48.3

SEQ ID NO: 79 atattcaattcattccaaaaacgattttttttaaagtttttttcaccagacacactttatttctctcaattttcaacagacacgatagttctgtccaacct ccattcgatttgtgtagtccttttccggcattcgtacttcaagctcatacaacgtgtcgtctgtttcatttcgatgagccatcataaacgcacgtct gtaaatgtgttcattatttcatgtcataaattatttgcaatatataccgttcgtttctttgttgaaccgatcgtttgatatactccaaatcttctggagtc aattgatgacgaacatttggtcctgaatggattccaattcttatttctattattaatttattatctccaccattgataactggcttttcattctgatctttct ttctcttcttttcatcagtattatcaacttttcttgccggttttgcttttttctggtgattttttgttttttctccaattgtgggcattgggtagtaagtagatg tggcgaactgttttttgttggtaagtaggtgcaatagctgatgaggatctgatcccattctttcaataggaaatttcagatgcttgtctgaaatattcaa ataattattttgttagttcggatgtttcgataagatattattcagatgcaaaattttttattctgcccgaaaactacggtactgtactataattttctcgc gaaaatcacaaaatattgcatccaaataacatccaatacgccttcaaatttatgaaaaattacggtagcttatgagtaggttttggcacatgtac attcgtgtgaacgactgtggttgtttcatgcttttgacttcttgcttgacttctgaaataaaaaaaactttcataagatgctttgttcattcaacaa aagccgtttaccttgcttcttgatactttctctggaacgtgtgcactagtcttctgatgagttggctccacagtatcgttgagcaaagttttcgag taatgcttcacatttagttcttctgattcaacacttgtcgattgacttgttggctgactgaatcatagaataattgataatctgaatatattaaaaagt taactcacgtttcgtcgaaatgtgcaactcgattgtgatgaatcgatcgttccaatggatgctctttcttcagtatcgctgatttggactttgagttt ttgttttttactatgactacagcccattcttgaatctttctctcttattgcacacgatacgatttcctggtattttgtcggcggaagaatatatgagtaa aatcagaaatgaatctttttttatctaaagttttttattcgaagaaagaatcttcgcgaaacatgtttctgtcacagtttatctgaactacaaatctta ggttcacgaacttacttacttgcttcgttaattaaaaaaaaattatattcttttgctttcgtttgcatgcaatttccaaaactataactcctattttcag cdc-48.2

SEQ ID NO: 80 gcaaatgtgaatggaaccaagaagagaacgagcaaaaatgccaccgggaaactcattatatcattctggaaacaattatacttcaaaaaat ggaagcaaaatataaaacaggagttgtgaatagagaaaacgacgctttatatcatcagttttggcattgaaatgaatcaataacataaattga gcgagaaaagagaaacagcaaaatagtgaaaaacgaatgattgaccgagagaacggggggaaggttggaattttgtaaacaaacgag ggaaacatcatgttgaaaacatatatatacacattttttatttaatgcgtcggaatattcagaaaatcgttcagatcatcgataatttttattgataaa agaccaaaaatccagtttacatgaggaaaacaatacactgtgaatttaaagaaaattaaatattccaaaaaaattttaatttaatttgtaatttgg gaaactgaaacaataaaacactatcgaaaacttaaaaaaaaaacatggattgaagctcaaaaaaactgttttaatgtttcgttttgtagaacttta gattttgtaaagcgggagacaccacgaatccgcaagaagtttcttccagaagcagattcgctgaaaaaaatgaagttgtcttaaacctgat gcttttttttgataattttttatacattatgtggtttcctggttggccattttgttaaaatcattatttcctgtaataaaagtcaggcgttctcagttatttc cagatatcggattcctaaaatagctgaactccaaaaaacggtcaagtctctgaacaccaaacgcgctccttcgaacaaaaaagcagcgcgt acgtttaacgaacagttttttcttctagaaattgttttctcattgcgcaatgcattgctcattataaataattatgttttaaacagttgctgggaggtttt cgctatctcagtcgttgttaaacaattaccagagtgtgttatcgtatttatctttgccgtataatatcttttccatatttatgcgattgcggaaattac cactgactctgcggaaactgcggaaatttaccactgaaatatcactcatatcgtacgtttctttgaattcgtctccttgttattcaaattatgtcttc -continued gttttttgaacgagatatttacctctagctttctagatcgtcacatcacttaggttcgccttgaacttctgttccgctaaagacggctggttcacatat attttttaacaatgtaattattacttatgacccgaataaaacggtagaacgctttgtgaaattattcgaaagcaaatgcgccccaaggagagagt gtgaatgagaggctgcgttttgtcatcatgtgagaggcagcattgggggtgttctgtagagaacttagtctacgtgtctcatctttccatatttcttaat tttgttctattggctctttttgcatctcttctttgattcgattctttaactgaattagatcagaaattatacttgaagttttatcttgaaaacctactgtag aaaagtttgtccgtgttctactttcttattagactttcgcgtttcggccttttcctatgttctaccccatcttccgttcttttttattattccaagattttta cagagaagtcgtttaacc ufd-1

SEQ ID NO: 81 ccgggctcgaacaagacatggacgagccattcgatatgtgatcatctgttatcacaaaaatgatcaattttcttcataatttatcaaagtttctgtt ttccttccatttcatctgatgaattcctactttcttgttccttttcactaacttattattataattataattattcataatgttctttctttcccatcatc atatccatccttctatacatttttgtttccatttgttgttgaaattttatatgctatttcatttttgtcgtcctttttttccgttcttcatttttattgactt ctcttcatgatttctggcattcagctcgataattcatttatacccgttctttctagtgttttttcgcgttgtttgtgacggttaaattcttccctctacat ctttgcgcgtttccacacaaaaatctgtacacgacattcggttttctcgttgttccatttcttttttgttcaacggagcgcgtttgtcgttgcaggaatcgg ttttaatatcatcatccattcacgcattctcttttcatgttgttcattgtgttttcttcaattttgtcaagtttccttcacacgtgcattttagtaatt tctttctataataaattgcagtttgttaaatatttaaatgatcaatgagctctcttttcttggttggctcatcctctttgtattttttgaattatagttgaa gaaaacgttaataacttttcagaaaaccaaaaataaaa npl-4

SEQ ID NO: 82 atatagaaaaacggtctcttaatttcaaaaaaactaaatcaaataatgtgatagactctctcaattgaaatagataaaattgagagagaccgtg gctattacatttgtaaattaattttcttaaactctacttctatctccagtgagccatactcgtgaattgatcgcattgaattcttctcttcaatatcacct tgtccaataattacatcgtctcgtgagcacatcttctattaaacaaaattagcactaggctagttctcttctaaagtgagaaatgagaagaaatgt gagttgtagagacgtgtataataaaatccataaaaattaaaaatattgtgagttcttctgagattacgtgaaggccgaataagaggtgacggt gataatcacaagaatttaaaaataattttttccatagaacgaatatataattgcgtaaatggtcgtggttgctcagaatctcgagagactgtggca aattgtcgaagttttggcattttgccaaaatttggtaaattgccaaatcatcgaaaatgtatattttcaaagtgatttcgagcagttttggaaacttttt actataatatttgagcacttgagaaaccgatttcaactatttccataccgtggaaaaattatgttttaagttttggcattctgccaaagttttgacatt ttgccaaaatttggtaaattgccaattagttcaaggtgtgtacttttaaagtgattttgaacagttttggaaactattactgtgatattttagcacttta ggaactgattttaactatttcaatactgtataataattctttcgacaacattctcatcgggccacatgcgatcacggaagaatctgaaattaaaag ataaatagaaaacaatttgagattattaaatattacctctcggtgagatctggaaaagcttgatcgtagagagtcaaaatttccggcacattttgt tcgtcaaccatgcgggaaaagtagaccaggtagtcggcgacctcatttggaactccatcctcatcggctgaagctgttaaaaattaagaaat gagataagtttgtgttgttaacaagcacctaaataactaccataaatatgtttatagaattactctattgattgattatcaattttctttttgaaaagat ttcacaatgcacgatcattgatcctctgatactcaacttctctctcgggcttttaaatgattaacttcttatgaactcttatgaacacctttcattttatt atttctttcaaatgaataaagctgtgattcatttaatctgagatttgaggatattcgacaccgaaaaacactgaaaatgacaaagtagtcatttt catatacaatgagggagttctgagaattggcattgattcttcactgtaacagtatttggaaaatttggttttctgaattttatgtattttgctcatgg aatgttaatctgcagtttttatgcaaaattatttcagaccaaattctccaaatgtctgtttgccgaattaaaataaatcggttaatcaaaaaggac cgagtcttcagtcttttcgaactgtttcaaattttaacatttttcaactcattttactcttattcatcaattctgaaaaatagcattctgtgaacttacaa gaaaaggtgttggtgcgacgacgatcagagtgatcttcagtggataaatcgaattccacgcgtcgagacattactgaaagaaggttttatat tgatattatttaaatgtcaaactaaattcgaaaaggtacgctaaaattaagagaaaacatttttttaattgtaaatttgatgaaaggaattggaaa atgtgatggaaaaagaaaattgcaagcgttgcatgggatttcgcaagagtgccgcacggttttttgtacgcatttgctcgtcattcatgttg tctaggcagttttgatgacatttttttattctaaaaacaaaatgttttatttcatttgctgtttaatgtttgaatatgtatggaaactaatttgatacccttt ccgctgcattattttttgcaaaatctcaaaattatatatcttcaattcactacctagaaggcatatcttcctgcatttaaaaatctattttatttcagat Nuclear Oxidative Stress Toxicity ugt-1
SEQ ID NO: 83
agatcaatggcactgaaaacgctcatttaaatgcaaaagatcgtgtcccgtaaaaattttctgtataattccgtgattattttcactcgggaatcg ctcgcccactatgggggagtctacgcaaggacaacgcaaggacaaggacaacattctaatggaatggaaacgattgcccgactgcacca attctagttcaagtgaacaatgataacttttgtattctgtattccttcacgtctcccagcgagcgtaataaattattattattatataaaaggagagt tttgatcagataaatttattatcgttgaatatccactttctctgtttctcgtttcattctctaaacgacgtatggataatacatatgatgaaggtctaaa aacttcaaagaaatgtctcctagttttgcaaatttccaccgaaaaaaaatttggtcggttctcggaccatttatgtattgtattttatttggcttatgtt ttactcaggaaagtaaataacttttgctaaatgtacataaaatcagcaatgttttcaaaaatgttttgaggtaatccggcttctatgtgatatattaa ttcaatcctaactgataagataattataaatttaaaacttactgctacctccaacttctggaacagcataagaattggttggtggaatggtaacat atcttggctgcccatatccatgacgtggtggtaatttgattctatagactgcccgttttctctaattgattcagttatcaaattccacgcatcatcg gaatatttctacaaaacattgaattaaaaacttgaaaaattaattatggaccaacttcaaatgttttcagatcttcaagggaagtaatttcaaagttt tcaatttcattaaaaaccgaaaaaattgaagcgagaatcgtaagaactgcaaaaacaatgagcagaatagtagcgaatagaaaatttgtgtg cttcattttttgttttcagtttcagacaggtgtctatattttatacttttcaacacaatagatattaattattttagagagaaaaaaacaggaaacagct acatagtgtgaagtgaaaatagaaatatgaaaaatgaaataacaatgactttgacgaattttatccctcttaccctaaattttcaataaaatcaaa atacaacaaaagctccaaactctaaaattactaaattgtattttgtaccaaaactagcttcccgacattgataagtaacgcactggcacaaact ctaatttttagtgaacacaaaaacagtaatctgcaaaactttctttctcgtattctctgtttctctacataccgtacttaatatttcactatcttatctct ctgtgtctcttgccgaccaaaaaactaatggtggatcgctatataaagaaatgttaggtaaggagttgaatgtcagttatttctgtaaaaactag aagtttctaaa ugt-13
SEQ ID NO: 84
attattatgttcctatttctttttatcaaatcaaatgcagttttaaaattttggacttttctgagaacgtacagcaataaataaaaatctaaaaccaatca cattcaaaaggtcggagcaagttcggagctccgggattcaaggtcacaataatgaaattgttttttttattgcttgacattgatcgaaattaatttg ttattttttgcaaaatcgaaatgaatattttttgaattagaaatgttttttacaaaattttgaaccgccataaaaaatgttgaaaagttaaagttttatta cgaaattcgtacatttgaaaaccttttgggtctacatgttcaaaatcgcccgaaccgttagtcttcctttaaagtcagttatgactgtgttctgtgtc tcctcgactctgttttctgaattgtcatcacaccaaaagaccaatctttagatctttgtatttcttttcattacttgctatcaaattagccatgaaaaac atatgtcatcatattactcactcaaaatactacaaactacactgacgaggttaccgtttgatcttatcatctcttaaattagtcggggtatataaga agaacaaatcgagtacattgtttcaagaaaaattccca hsp-17
SEQ ID NO: 85
gattattttcttatgctaaactggcagacagcagatcttttatatctgcacaaggggcggtgggatttatagaaacttaagtttactacgcctgc cgcctaatccgtgaaaccttatttttatattttccgcctcccgaaacagttgatacgtgaaaaagcacggaagagaaaaaagcttcttttggac ttgattaatctgttggtcatgagaaagcgtgacacaaggtaggttacggtagcaattgcgtaattaatcggatcagtctatgcgcatttctgaaa cattggggatttcaaatctagtttatcaaacagatacaaatcacattgacatctcgtggaaacagtctgtaaagtaccgcaaattttacaattttt gatattattgtcgttaaacaagttccatttcaaattttttattgaatacggtaaaaaaacaagagaggcagctggttgaagtgagtcactcttgttg agttttcgttactggaaacctgaatgaagatagttttaactttagcattacgcctcattattttcctatttcctttttactattttacttgtatttttaaa ctttgtttagcacattgagcacataaaaccaaatgttataaatatccttatcatcaacccatcggtttcttttaacttttttcttctcgaatttcaatga cccggaaaaccaccacatcatatgaaaatcgaatctaaaaatttgcagatacgcatctgtcctgctgcgctctttttttattttgaatgttttttttct gcaaacgttgggaacagtcatccaatccttcaaccgttcgtctcgttttgaatgacaaacgttctctttccgtcctctgtttgagtatatttacattg ctaattcaaaaaaaatagtatagaataataatgatacttagagatagttctggcataaagtttaaacttgaatgaaatcatcaatgccattaataa ctgtgtcactgcattagtttatcagcaagtgtgccagcaaaaaaaacgtttcgagacgattcgatacattcctgaaaaacttcgataaaggg aagtatccaaacaaccacacccaactttcatcattgactcgctgttttgcttttattttttgttaatcttccttacaattagttttaaagtttaaaacaaa tattacatgttagaaagaactgtattttggtcagtttgttcgaataatttcgaaatctaaaaccttttcttttttgatgattcgtcggagtagatgtttct -continued cgaaggaggtaaaaaaaaccgtgggcgattcttgtttgcattgaggataatagagcagtagtagaaaagcagggagtgtcaactcagtttt gtcttcttcttcccctatttctgtcttactttcgttttgtttctttgaaataattagattttcagaaactattataaa cdr-5

SEQ ID NO: 86 aggaaatttatccaaatgattttactatttgagaatgtattatgcggtaacttttttgaaataaactaatcgtgacactcaaaaacttagaatctattt taaaagaatagataattccagttttttgatatccgggaatttatgatttttttggaagaacgcaagaaatcgatacatttgggtacgcataataggta ctcttgcacttggatcaaattcctagagaacgattagatgctttagacgcagaaacaaaaaaatgtgaccgatacaaaatcgaccacaatctc aagaaaataagtgcgcaacacaatccgaggtcaatctagacatttatgctcttcctgcgagacaaaaatgcattgtattttttcattcagattc attcaggtgtcttgaagagatatcaaatcacatgtgacaaaattttgatcgaaaaataagttgcatcataataaaatcatcttatgatcttcctata taatcttt cttcaatttcggaaactacgattcgaatatatgttttattttaggcgaa rnp-2

SEQ ID NO: 87 aaccttagggtaaagtttatttatttttttttcttt acgatagggttatccaggctttctaagccgtaaataaacttccatttt aaattttaaaatatttt aaagctcaagcttatagtatagggaacaaagcttt ctgatagtttagaactaacaaagagcttatgttctacaaaaacagggacgttttt atttata gggggggaggtgtaaggattctaaccgtctctacacttctcccacttcccttttccccagtgatagaaggctaagagtgtatagggattaatg ctttt atttacaggatcaccggccagaaagtcagtcacgccatggatcaaccttcgctcttctccgaatacagctctgcaattgatccatccg tgcacagtgccaaacgctccttacgcgttcgatccctgagataattgcaataattcccacacactcgatttattccaagcctctaaacttcctgg ctaccgtaaccctgtgtgtgtgtgcgcacacttgtgtgcgcgcaccttgtttacgtcttctggacctttctgcggaggaatccagggctccgcc ctgccaccgcagaggggtatataagacgtggattctatcactccagatcttctcttacttttctgttccccttt acttgttcccttt gtctcatttctta cttgtacccattccattggggttattaattcataataaaatctattccttagcacataccttgttctgttgtagtatgggatgcaacaacttcggttgtc ataatgataattgagggg aacacttaaacaattaccggtatacgcttaaacatttactatatgttcattcaatcaatcacatatcgacacaacaat taacacaatccacaagttttt gcgcaatactccttcttctgttcctttgtgattcgtggatccgcacagaagccacgtcctgcccagagatggca gctgtaattttt atgaattttt attatcaaattcgaattcccgtcattttt tgttcataatcctatattttcaaagatctagctcaaaattgcgtgaaatt ccatgtttgcggacttttggcgctacagtaacccggattattttt gaaaatcgagatggagctctgaaaatatgggagaaaaggtagaaaatc atggaaaactcgaatttggcattgaattttt taaagaaaaaataaaatctgaaatttaaaaaattgaaaatttcacccaaagtttcaagcaaaatt atcgaacaaaaatatcgattttt atccgttttgtaatatcaaattcgaattcccctt cattttt tgccccaaccagagatctagctaaaaatcgcgt gagattcggtgtttgcgtacttttggcgctacagtaatccggtaattttt ctgaaaattaagctatttagagctcaaaattttcggtttcgggcaaa aaatggcagggaactcgaaaattttt aataaattttt aaaataaagtgcaggaaaaaagttacgaacgccccaaaacttactcaatattatcgt gacatgacggagtggtctgagcactttt caaattcattcgggtggaaatttggaatactcatggcaaaattggtgccgaagagcacataaaga gcagtaataatcagaaagaatcgcattctggaagcttctgacctgaaaatgctccagtggggagattttatactggaaaatttttaagtatttag ataattaattgttcgtatttcggaactgtgtttt atcaaaaagcactgtgttttgtgctcttaattctgtaatagtagatttttttccctaaaaattagag ttttt cattatcaaactttgatttttt tcatgattttttt ctaaacatgcggttcaacaattccatgaactcaaaacaagccgaaatttgaagtaaattct gtgaaaatgatatttttt ctaatatt attcaataaatctatttt cttgtcctatatttggagcatttcaattgaagtttgctccatttt ctgcccgcggc ctagaaacctccgtggccgaacaacaagcgcgctctactgcactcttttt atttt cgtattttcaatttaatttcaataattttt atcggttttcttcga tttttt cgcacttccccccagtatttttt caatttttccgataaaaatacaaattttccagctaaca dnj-13

SEQ ID NO: 88 ttttatacgaaaaatactttaaaatcagaggaaaatactttgggaccggtgaaaagcatggaggttcgcacaaacttgtttaggaaaacaga aatatgtctccgtggcaggaccatactgtgcgccgttgatgtccctt tgatacagtactcttcgcattattt attttttt cggcgcgcctaggggt tttcgagcgcagagttcaggaggccttctggattatggatagaggcttgatttttaaaattgtttaattcaatacagttttt attaaagtttttt ctaaa aatcttt tctaaaaataatatctgattgctgtttt atacacgagaacaaaactaatttcatggaaacaattttttt ctcttt atttt ctcttcgaataatttaa attttaacaattcaggttttaaataatcaatttttaaataagcaagtgaatttt aagcataacttttcttcctagtgtacgtaaatcattctttccaacaa acatatttttt cgtgacgaaacttcgccttccagaatattctttttt cagaaaataaataccaaaaagcacaatttcttatctcttgctcattcttttcttt tgtatcgtgctcatgctttt attcattcctcatttttt atcttgcgaaaccaatgtatttttcaataaaaaaaaacgagtgatgcatgtgcgctccaccgg -continued ccgacggaagatcgaacatgcactgcgcttcgcgagtaaatagaacgctctggaaagttccgcactcttctctctcatgattcggcgcactc tctcttccatttctccgtgtttcctcttctgatgttgacccatatttattctgccgggtgtattcttttatctatctgttgcttcatttattccgttaacc tgttactggtaatatttcaaaaattcatatgatttcttttcagattactttccaca dnj-25

SEQ ID NO: 89 aactaaacattgaaatttctgcacttcttttattgtaatgatgcttctgtgtctgacttggcattttcaaaaataatggaatggtggagaattgacag cgcagaccattgttaagactatgactgtgcagtttatttgcacagcactgtctggcacactctcttcatatcacatggactctctcttgctcaccc tttgacacggattaggttagaggcataccagtgggagtcagagtgctcagaaaagtagttgccatcgtggtaagagttctgaaaagcatcg aaggttttttagggaccaaggaaatatgaatggagcatgtaaaaatacttgtaaaactgtaaaaaataactcagcccaaaactgagggaacc gtactttctgaaagaaatatgtatgaataccgatgttttaggttcaatcaaacaatttattcggattttttcacgaaatattacagagagtgtgacgt tacataataatgttcactgtttgacgcagtcacgagcttccaaacaattttatattatcgagacgcaaagattcacaattttcgcgccagaatag cacaacctggtctcgacatgacaagttttagttaaatgcgaaaagatgtgcgcctttaaagagtactgtaacttcgaattttttcttgttgcggaat ttgtgaattttcatcgctttctcattgtatttcgaatgaaaaattggcttttttgacaaacttagacacaaaaataatgctcattaaattttaacaaatc gaggaaaaaaatattgtgaaatgtgaaaaattccgcagaaatgagacgctttccggtggcaacttttcccacaattttttcactgatagaatgta aattttttgaattaatatcacttttcagaagttttttatacattattttctccttataaagtttgtgtgaatcacattttcggccgaaaaaaccggttttccat ggaatgcatgcttccgatgcttttcgcttttattggcggatggttacgcaacctcaccgatttttatctctattttccgcacttttcttctctatttccaa aattttcagcctagtttattttttgaaattttcagcaaaataattaattttcctcacaaaactggcgaaagggcttttcgtttctctgccgtctctcttttcg cacgctctataagcaagtgtccgtgaagcgcacttgcacccgtttattttcacaacacgttttcagataatttttagctattttttcattgattttcagta gttttttacagctattataatggtatttttttagtaatttccagtataaatccg pme-1

SEQ ID NO: 90 tttctctgcaaaaaattggagattttttcagtctctttcaactaatgtaaatacgctctcttgtgactaagcgcgcgcgtttgaaccagaggacaa ttttttttcctcagcgctagtagcccctgaaagagttattcatacttgaaaaaagaaacttttctatagatttctgcatgaaaaatcaatcctcagcg cttcttctcttgcttttcctgattgtaatgaaattttagagttttaaattgtaaaaaaaaactaaacaagttcttttttgaagggaaaattcgttttaa atgcttaaaatgcttcaaaaaaaaacaaataaaaaaaattgtttctgtgcatacaccgtcacgacaaaatgcagacttgccattggtctcgcc gcgaaaaacatgtttcttttgaaagattgtcttaatttttttgatttcaatcatgatttcaatcagaattttgcgatcttcagcatttttatctattttaa agctttataaattaaaaattaaattttaaaaatcttccagattgtcatacgggtcccgg tag-124

SEQ ID NO: 91 aaattattatataattttcaaaattactggttgatgaggttagattagtgataccttggaagtggtctatgtaataacaattttgcacaaaaggag atgagatttgatatggaagattggcaacacaaacgtcaaagaatggccattccattttcattacatctcctccattaacttgtaatttgttttgtag aggtctgaaatatatttattttaaattcgaaaatatttttcaaaaaatacgtacgttcccataactctttttcttgacttcagcaatcattctaggatcga tttcacatgcaattacagttttttgccacctccagcattttaaccgtcaagtttcctgttcctggtccgacttcaagcactgtatcggtggctttaag agctgatttctcaacgattgcattcacaactccaggattttttgagaatatgttgtcctttgtcggtgttaaatggaagtgctataaaatcaatgttat gaatagaaattttgcaaaaataacatacattgaacatttccagttgatgatcctgctttcgtcttttttaactttactcgttttttcccatttttgagtttttt aaatctgaaaatgaacgaaaaataatagtatttctgaaaataggaaaataatgaaaagaaataaaggtagaatgatttgtccacgtgaagtac aaaacgtgggactaaaaaacaattctagtccgcgcgtcgtgtactcctctcagacaaacagaagttgcacaattttttgaaatcgatccctttt aatcactttttcctattcttctagcgtttaattattttctattgattttatttacaca pme-5

SEQ ID NO: 92 aaaaaaaccggctggtttgctgaacggcaattgctgttcatccctatacctgcctacctaccgccaattcagataatgtggtgaaaaatttcac gaaaaaaagagcaaaagaaactataattttaaaaccggagtttgaaaccgtcatcgtcgttgtcattaataccattatcattattgacatcagg aatcacgccattttgctccgttatcatacacatcgtcatcatcatcatcgtcgtcaacacccatcaaaaaaaatgtataaaaggtttcactcaaa aagagggttttatcattttatcaagacttaaaaaatgtcctcgtagtttgactatgatatcattttttccattatcaccatgtttgcgttttcctttttccaaa

```
catttcttttgcacggcgatgatgcttggcattttgcactcgtgaaagtttcagcttgccagtgcgccgccgcgttgtccatggcaatgcggca
tttgtattcaacggcagaaaattgagagatttgtttctctcgcgtacctcgcatgttttgattttcgacctcggttgtccctcaaacaaagagaa
tcgtttgtcgccctcaccgcgcacgcatatacggaaaaatgctacaatttcaaggcgtgatagagatcagctctcccgctgatttctatcgatt
ccaatagagatttattcacctcatacggcggcattagtttgggcggtgttttttggtgtttgttgtgtccaaaatacgaaaacgaaaaccttcat
ttcagcttagtttctaaaattgattttcttttatataattttttcaataatgctgaatgcacgtgctcgccggctgccttttgcaatgagactatgca
aacgcgcccgaatgcaaacgctgctggtggaccctctcggacataaaattatatttcttatttttcgaatctgttttctttcatattttcgaaaa
aaaatgacaatattatttgatgaaaaaactacgaaaattggcaaaaccaaaaacaaaaccaaggaaggatttctggcttccctcataaattga
aataaaagagtttaccgaactaggccattttggctcggccatatctggggtagatttacggcgcgttgcttgtcgcgtcgcggctcgagttta
gttgtaaaactaaatgtatttgtccgtgtggagtatacaactttgccacgcgttgtccagcaggagatttgcaatagagcaagaaaaattcaat
gaggaaggccgaccccgtgaaaattcgcagaaaagtaatgaaatcgaaacagaaaactccgagaggactacacggccgaggattttttc
ctcgtccgctcttttgttaggccattttttgaattggtaaacggagttttctagtccccgaaaatataatttagaccaaccagcgagcacgtgctg
ccattgtcggaccaaaaaaaaacgccaaaaaaccgtgtatttttttttcgtttttttgatccaaatgctcatttcgtcaaaactgatgcctactttg
gctgcctacctacgcctacctacctacgtgcctacatatcgcctattctttgcattttggcgtccagtacttcacttttccacagaatagataaaaa
agtgtattttgacaaaaaaatttatttgacctcggcgcatttgatctcgagaaaacgtggcgattttttgtttttaccagttccaaactacatgtaact
ttgccacgtctgccagatttgcgttccaacatgtcaaaatttggaaaaaaaaaccgttgtttaccgaatgacacacaaacacttttcccccatctc
attgccctcttaatctttgcaaggtttcacaacattttgagaattctgctaaaccgtctgcgtctctcattcctccaccctattgtcacggttttgcta
tctgtttctctcgttttttcgtggtttttctcttttatgaccttgcgtgtatttgccaactatttttgtttgtgggcatttttttgggaaaagttt
gatttctggatgatttgaatattcgtgtattttataagcttttcctaacttttctactttcgttcattctgttgtttcagccgtaatccgaacagc
```
air-2
                                                         SEQ ID NO: 93
```
tatttcttgtgattcgcttcgattttctgaaaaagatttaattgaatattaaaactacaaagaggttaaaaatgatttccgattttctcgattcaaatt
tagagaattccagattttagctcaattgttgtgaaaacaattttttagcttttgagaattaacttttctgccaaaaaaattacctggaggagccaatt
acaattagctccaagtgtttcaatacagtatttgagagctccatttggtccaagtccaagtcgatccattacatcattcacagtgatcatttcctaa
actttagtattttaaatgaaaatatgaccttaagtattaaaataacattgatagatgatctgtaccacgtttcataattattgtcctatattcattgga
ataaaatacttacagtgatatttacatcaggtgcgtatgccattgtgtcattagcaggatcaagattgatagtgagaaatggtcgtttggtttgtg
agaaaatgtccgttaatcctgcacaaaatgtagatttccagctccaggagctccaattacaagaactccgtacatagtccaatgagtactga
aattttctagttgaatcttaattttctacggattgttttgataggaaaacatttaagaagaacaaaaatatataaatacaatttaatttaatttaaaaca
aacaaaaaagcaggataaacgggcctggcacagggccaagtacgcatttacaccgtacatgacgacatattgcggaccattgcattttgc
cgcgttaattttttatttaaacggcttgcatttctccttactatccagctgacaatttttagtttctttagaattatttgcaatcaaaactcgttttttgta
aacatatttactcaggtaatgtgttgatttctcacttttttttgaaatcaaagcagaattagtcctatttttattctacataaatatctaaatgtattcaat
taaaaattgggccattgaacttctaattaattcaatttataaaattatcgtgatgttttcttttagttaatttgtccttaatcgtgccgtctattttatttc
ttcataaaaaaacttttcagttccgac
```
mlh-1
                                                     SEQ ID NO: 94
```
caccagcatcaggagccaacatcagtgccgacaccatcgtcgcgaaacatgcaaagctgtggagtcgaaagcactcaacagccggacc
gtaaacaggtgagcatacagtactcggaggaagaaggctccgaatattttaccgatgagcttgacgatgttgatgatgagattgatgatgct
gctgctgcagcccgtgcggctgagaatattcgtattccggcgtgtctattacagacggctgctcaaaatctgaggaagaggatgagtacg
atgtaagacactcattgggttacccattttctcttggttggccgagaaaaattatttactatgctccgatatttgttgatcgaaattttccaaaaaa
agagctgtaggaaattgagattgataaaattaattttttatgcattttttcgccaccacctgatgtcatggtttacaaaaaaccaaacagttaaatttt
aattagatacaattttgaaaaaaaaagtgttttgtacatttagaactaatccataagcgacgtgcatttcaatgaaattgtttattttttatttggcg
tatttctacgattttggacaaacttgtttgaaacaagacaacaattttcgaaatatcgtagcatcgtttgaacttatcatatttattttttaaaaatttct
ttccgccaagaaaatgggtaaccagcgtcgtcgaaaggctatgatcattaattttttataggtcatggagacgtatctttaattaatactctatat
actggtacgacgggtaagatacattaagttgtacaaaaattacagttttcctcctttattttctccaaaaaaccttttgtctagaaacatctcaacat
```

-continued tatttagttaatttttttttagttttttcaaagtttataatttcaaaaaattattttttctgcttttttcggttttttcttcatgttcaaaacttcttcctctctc gtcatttttgtataatgcatcgcggcgatataaatttgcattttatctggttatggcttcatcatttttttttcaaacgaattttgggaaaaaagaatgcta tagtcattttaattacatccctcatatttgtggcgtactgtttcctttccctgctatcccgattgatgtttttaaaggcacaccgacgagaattttcgatta aaattgtaaattagagtaaaatctatgacttgtcaatcgaaaatcttgtcggcgctcttaggaactccataaaaattgaaacaaaaattattttaaa aattaccaattttttccaggtggccgctgcgtggtcgacaaaaatcgacgtggacacgcgcctcgaacaagatcaaatggagggtgtcgat gaggcggaatgggacaaataggcgctactggaccatttcatattattttcagtcaagtagtgtacaatgaacacaattttctcacggttctgtaa aaatgttttttctattgaaatgtttgattttcgcccccatcaccaatccatcaccacctctccctctctcgcttttatttgtctcatgctttattcatca ttttttatgattattattatgagtattattactattgtatagtctccaatttcgtgattttggttttctagaaaattgcgcccgctcgcccgcccccacg acttaccacctcccctgaattttttgtgctcccatcgcctagtcgaatttattcttttgtattttgtgtgtccactttctctctcggtcgatgtgtttt aacatccatattttctgccccgcctcgtccccctctcaatcgcccgctccccgcccgcctttacactgtgttcgatgaaataaacagtaga gaattgtaaaactatgtgcgtgagaatttggaaaattttagttttttgtgatatcggaagcttttaggggaatttgaattattttaaaaattgttc aaagataaattagctccgaaattggaaatcgtagtggaacatttgaatttccgcagccagacatgtggcattgcggttaccgtacccgcaat tgtgatgaattttcaaaaatcggtgatcttctggattttcgctgtcaagcttgagtttaagggtctcctcactgatctatgtccattttgcggcagg aattcttttttttttagtttcattcggatatctctaaaatatcaagaaaaatcgataatttcacttttcctgaaaactttcatattttcagaattttcacta msh-2

SEQ ID NO: 95 tttcatagatttttttaataatcagtctgctcactgataaacacgtcgattgccgcagtatcttggagaagagaactgaacttcattgtttgaaacct agaaaatagtgaaaattagttagaaagagaaggagacggagaatgaaaaagggaaaatcgcgcgcgatggaagaaatttgaaaaaaga ctttacttttgatattttcgaaattttttaaaataattatgtttagagttaaaattgcaaggaaaaatgaaacaaaaattagtttaaaaataaaaacc accgtatctcttccctgcgaaaccaattcaccgtattattgtatgtgcctttaatcttaacagtaagcataacatgtgattttcgccttctttttatta aaatctaaattattacagaacttttaaataattttgattatattctttgtttaatttttaatcatttaaattcaatttagaaatgctaaaaatcccaaaacaa tgagacactatttccctgcaggaccattttacagaaatactgtatgcacctttaatttcttttcaaaagtaagcggcctttctgtcgaatcatttttc gttgatgaactctttttttcttcacttttactctatattatcacaaaaattcgaattttttcagcgaaaaaatcgaaa msh-4

SEQ ID NO: 96 agaatgtctggtctccgaatcgtcaactcccttgcatattcttagctccaggacagctcggtgtagctgcaatttgcaacggaggaggagaa gccacagcagtgctcatcaaaaaactgtaatatgaacctcttgcctaaatgttttctggtcttctattcatcattccttgattcacttttacaacaaa tttcgattacgtatttataaatagttaaggttcttgtcacataaatgtttattctcaaatggtgcatacgtgttattgattgggaaatgaattaaggtta atatgtacattatcaggaatggttttgagccatctcaaaagagatatactggaaaaatcggaaaagcattttctctttgagatatatcattcattca cgtcttcaaggcaaaacatataaggggagatcgtatacaaataatcacagggaagaattggtggatgataaaatgatcccataaaccattatt agttgagagatcaagttggggaatgagaatattaagggggaagaatttaaccgggaagcaaacatagagcgatttaattttttccgggat ttgctttgctaggcggttccaggtggcgaggttggctctgaggaatcctttgtttgtttcgccaacagatctgagcatgtaggggtatcttgga gttacagctttcttcaccgacgatgacacatttgggtagtggaagtttccagttatgatgttgtggtaggtgcgaaggatctgcaagacccgc ctatattgcactgacttcaaattggcttgggccaaacgatcctcgtatgaagaatactttatgttgcagcgttggaagacgagcctggtgaag aaatgagatgaatcaataaaggctatgaacgggtaactcaataaagtatcttcctggactgggatgattccgagaaaacaatcacaaacgat acggtaatgaataggaatccattgatttcattttatctgtaatttcagtgtctgacaagagatcgtcgtttcggaattattacaggcccaaatatgg ctggaaagtcaacatatctgaaacaagctgcccaactagcaatcatggcataggtaggatgcttcattccagcaaactatgcttcgttgccaa gtaacctaaaagttttgatttgctattttctatcgtcgaattaatttcagttttttaatcgtatcttctccag ahi-14

SEQ ID NO: 97 gatggtactgagaagaagaccgatttcgatgctccaacaacacttgcttaattattcacggagatgtcataattacagctttggttttcattatttg tttggttattatttatatcacaaatttcgctaatcggcgagacccctctattgcttttctctcctatctcgttttttgttaacccagtttcttttgaatgaac ccttgttatgacgattttatggtttttccaacggtaattcaataaatgatattatatgtggaaatcttgaatctgatttgatcgatttagtctcgaaacg -continued ttcatgaaggcaacaaacaaacaaccgttgattaaattagtttttgaatttcgcgcacctaatattccagaggagcgggcttgcattatcttttt
acacgaatttcttatttacagtatgcactattctttctcctctcccattaatttcttgtcaatcccatcccttttgtag msh-5

SEQ ID NO: 98 gcgagccgtttttttgagaccctgaaattcggaatttcttttatttatattttaaattcatttaaatataaaaatagagcacaaacctcatcaaatg
tgctcactagaaaattacacgtcctgcatttttcgttttttgatggtgacttcttttgtgacgtggcaccaattaatacagcaagcaggagcagtat
ccggctcatttttcaccctgaaaaatggaaaaaattggatttttatgtagctttaagacacgacaaaccgttattttagagaaattacacgcagaa
taagcgaatgagcgcggccgaatgcactgcaaattgtctacgttgtccagtttctcggccctgtgagcggagaaaagagagggagaaaa
gaaaaatgaacaaatattggctttgaccgggattactagcaaaagaggtgactgatggaagagggaacaattaaatattagaaaaattcga
aaaagttaattattttcgctggaaatcaccttaatttggggagtttcgaaagaaattttgataaaaatagaattatccactttttatttcgtgaaaaa
aacaacaatttcgactgaaaatccagctttaattcgagaaataacaaatatttatttatttaattaaattaaattaaattaaagaaaataattgaatta
ctgtagtgatcgttgcgggacccgatgaaccgaaatcggtatgcgccttgtagttacggtaagaaaaacgggcggtgtcgagaatttaattt
aaattgcatttccaaaacaattttcctcgtttgaaaataaattttacgagttttggttagtttaaatgctaaaaacttgatttaatttaataaaacgta
cctaaaaattcagtttcgtagcagaaaacacgaaaatttcagtttttagtaaaattttcggaatttctattttcaagtcttgtttatagttactttttatg
gtgttcaatcaactttttgaagtttaaaatgtttaaaacgtttaaaattacttttacaagaaccgaaaaaaaccgaaaatatttcaattttttagtttttca
gcaacctttctcttaaatcagaaataattttatgaaattttggttcaa tag-63

SEQ ID NO: 99 cgagaaacatcaaccatcgaagagcagcttccttggccagagtgtcgtctgataggtcgatgtagtcgagcaggcacacgactgctctgc
acagttctccgttgtaaaagtagaaaaagcagagtttcgcgggaatactcgcgaaaatctctcgatctttgctccgacactccatcgcctcctt
tcgtagagtttgccacgtgatgaacattttgcatgcggttcgttgatacttcgcaagtccttgaaagtattcggacgaggcgtagtatgaggtg
attcgagccaatttgctcagcgagttcatgtcaatcggtccattgacgccgaattcggcgataaaaagctcggaaatctcctgttgcaactcg
gcagtttgttcggcaaacccgatcaccgtgcagctcacattttttgcgtagctcatcagtttttcgatgtgctgcttgtcaactgacttgtttgtga
tcttcatgaaagtttatctagaaaaattaaaattaaactgttttaatggaattaacattattacatacataaaaagcaagttttttgattgattttcatta
aaaatcgaggaaaaattgaaatgaaagggtttcaacgcacgttatcttctaaaaaatttaaaaaattttcttctagatgatacgcttcacatac
gcgacgcgtaacattggagcaacgttgtcacttttttcttaaaaatctcttataagagttggcacggtgccagatccggaattccaccagatctt
gaattaaaataagttttttgcaagttttagcaagttgaagcaagttttttttattgattttcaccggaaatcgaggaaaattgaaatgaaacgattt
tcgaggcaaaaataaaaaatttccctccgatttgaagtccgtgaatgcgcgtgcggtgcaactgcgtacaaaacaccaaactttacgacag
tgcggtaaattctacttttcaaagtttgagccccaaaattcgtttaattttgtttaaaacttttcttgtttattgaattatttacatttttttcagtcgac polq-1

SEQ ID NO: 100 ttgaccaagatactttgaaatcatccgcggatcatacacaattagtacaacgtttgacatttctcctgaaaaatggaatttcagttctaaaaacac
aaaaataaagttagaaattgttaaaaacaaaaaagtttatttgaattcgccgaagagcgcgccaaaacatgtgacatttctcggccgtgaaaa
ctaggccaccgcggccacaaacaaattttagtttttcttcgctgaaaaaaaacatgtttttcagtctgaaatcagagtttttagtatgaaacaag him-6

SEQ ID NO: 101 ccctaaatatattcacaatatctcatatttctagatatgcagtttcttcttctggaactacacatcgttggccattatgcttcgcccatttggtaatga
tttggatacttgcgttgcaccttgggtcttctatctaactcatccggttttcggaagaaagttgttcagagaatatttattttttaggcctgactcatg
ataataaagtttcgatttattttctataagtccgcagagattgaaaagtggcaaatttgattttgcttattccataaaagttatctctacttaattaattt
tatcatgtttatgcaattttcaaagtaatgttggtgcgccaaaaaattctacttaagcttgaaaatttgagatgaaactctaaattgtatgcagttat
tttggtaatacagctttcaaaacacagaacttgcatcttttgatcatttctaacaatgtagccttcacctaatttttagttcccagaagttaactcaga
cggataatgagcgttttaaattttttgaattctggttttgccgccaatacttaacaagagcacacgctatctcgaggaaaacaactacctgaaaa
ggggcgtagtcatttagttcacacttctctgtgcgttttttttaaataatgttagtttccaaaaattttttagagacccgaagaactcgggggatgtcc
aattggggggattaccaactcgggggacacggttttaaaattatttttcttgttaattctcgctctattgagaaaaatacagttttaaaaccgtgc
ggcagttgcagaaatgggcgtattgcaagccacggttctgtgggcggggccaatcccccgagttggtaatccccccaattgggcatcccc

```
cgagttcttcgggtctcaattttttagaattgtttaaaaataataatgccaacccaaagcacaaaatccctgcctcttaagtgacagtcttcattctc cgagttttgaattccaggcgtgtgtgacgactcattcaaattattgttttttgtttttttttcagattctcactcaattttgaaattttctgcgtttcaaaag gttttttcggaatattttttaattctaaagcttcaaaaactgaattaaaagaattttctcctaaaaagtcgccgaagaaacgcagagaaaatcggc aaaaggcggcaaacattttattttcaaattttatccgctttcccttgtgtttatctttattttccctcaatttgcttaaccgaaacgtctgttttcagaat ataa
``` xpa-1

SEQ ID NO: 102

```
ggacgtgcggcgaattgcaccaattggtgcatgttcaaaaaggaacggagaagagccaccctgtgaccactcgagcactaatttgaatga atcaacctccccaagtagtaacatactaaccgagaatagtttgaagtctgggggtataaacaagaatggagatagcaaaactaacgcccg agagtaagtaaatacttatatggtgagcctaagtctcgcgtcgatttattgttttctgttcagaacacaacgtgcatatctagaaattttcgatgat tcatgcaaaaatgttttcaaataatttttcaaaaactgaagaaagtttgagaaataatataaatttaggctttccttcagataaatttaaatataaaa aatcatatatattttcaagatgcgagaaaaatatggaagcggccagcagagatacgctatagcgctaaacaatgtgtgcgattcacaagagc ttctgaaagataaaaattgtgactacgattcaataattgattcaaagtttgataagtcaatcgatttcaagtgaaaagaaagagcttgagaacat gatgagtagcaggtgtagaaaacgcatcgacgcgattttttgtttgtttggcgccactaaacacacagacattcggtcatacactcttccaaa tatagtcaatatacagtgtgttcgagtgagagagaatggaacatgtcgaaatatagtgtctgaagacgagacactggattattttgacgggaa agcgtgttccttccggttgcaggatgctggtgcagcaaagtgtcaaaatcgatgggaacagggaaggaccccaaggataattgaaagatg agcgaggagaaagagcgactgaatgagttattacgagcggcagatagccggaatagctggcctattttacattgcggtcgtcgcttttg cggaacgggtcgaacggttttcaatgcaattagacgattcgtcatcttttgacatttttagatacaaaaaatacttatcaataaaaaagttttta gaaaaacttaaaatatcgaatttatctttagaaaatgaattaaagaagatgaaaaataaaatgaaaatctaaaacagattccataccgtagttc acacaaagggacatttatagttctcaaatttgtgtcccgccgcgaaatcaaaacaaaagaaagttagtccgtgtactccactcggacaacatt gtttcgcaacacttttttctgcgaacattaaaaaatataaatttgttcaacttccatttttaatgttatcaaatgtttcaatttttcttaattttatgat attttcagctgaaattttgtttcgattagatcacaaactttttttgatgtttaattgaaattttagagatgtattagaaagttttttaatcttcaaacaa aaaacattttttgtcaaatcgagacctcaaaataatttatctttcaatacaatttagtttccttgcttttaacgttcaaatcttgatcatttcttttttttt gtttataaacgattgtttcagataa
``` nth-1

SEQ ID NO: 103

```
actgggtcgacgagaagttttggaagtgagaatttactaaaaaaagaattaaaattagaataattctgtagacatccacaaatcacctgttttt cagtcgatgaaaacttgaaagtttataatcgtctactttatcctccttcttttcaaagtcaattagaacaccatcagctcctgaacatcgatttttat atatcgatcactgggaaagaatctgaaatcactgatataatagagacattgcattgttgacataccttgtcagtcgaactcgaatcaacgatct gatcttcattttttgtgttagttggttagtcgttagtagattataaaattcggtaataaatttatagtggtagaaattaatgagaattatatccacgaatc cgcgtgtactgcggaaatattcattttatatttataaaaaatgttacaagtgagatcaaatttttttttaatgtatcatagaagagaagcgccaaat caatagaatgctgcacattttaccgcatccaatcgttccattttctgaatttgaaataattattcatagctccataacggttgagtaacgtgaatga taattctgttttaaattattaagactaattcccctatttgaattccctccaaaataagaactgcaagactagcgatttgatttgagcaatttgcatcg cctactttccaaccaatcaaattaagtgtgcgaagttcgaagtcgcctacctaccatatacttcccatcgggtctcttaacaatcattggcttga acgaaacttctctacaaactctcgttggtggcgacagaaaccgtcttgtcatttgccacgtagcaatagatccgccaatgcttcaggaatctg atttgatttcagtgcttctgatggaatacttccaaagcatcgatgaaatgcctgtgggactccatcaatgtcttcgaattggaacttccatagaca acatggttgttctctgaatttttaaaaaaatgattatgattaatgattgagtataagttcctgagccagttgggcaacctacattccaagagaagg atcgcactcctttccaaatgtgatccttggaagtatggactttgtgtcaaggattgctcgagcatccagattccgtggtagaagatatcgattgt tccaaaaatcatcgagaaccactagaatctctctgatcctagacctctcattatatgaatttacgatagaagttgtccgaaatctggcattttctc cccaatccatcggttttgtttcaatttgggtgaattttttagaaacgtctcacctgaatcaagaggatgtgatgaagatcttaaatctctgcagttca ccttcataacatacgtacatcagtggagacctacttccagggtctctgaaccatcgatcaggaatatgaattgttaaactgaacacgtgggtta ctgtagttatatttatatttctcacttaacaacaggaatcggtatctgtttgatagggttgaagtgtattccatctcgaaaatgaatcggaacatgg
```

-continued aagaattgtttcctggctagagatccacaaaagttcgagacgttgtcaccggtaatccgatctccgagaagaacaatctgtaagaggtctcat ctgggagaagcttatttcagtagttaccttctgttcagactctgcgattccttgactataatagtcgatcccttcaagattctgatgaattgcatcc gaaaatgcttctttaacaacttcgtgcaaatgaaaacgtaattcgttttgatcatcatactgaaacttcggaaagattttaagtattaccccgatcc aaatgtttcgaattaaagttataaatacggtaccggtttcgacacgattttgtcaaactcgaggaaactacagtagtccttaaaggcgcatac taatagcgcaaaatctcaaccttcgcttaccaacttacccgcacaccttcctttctctgcgaatcaataataaaattcgaaatcggcgtcatcatt ctataaccagtacaatgaataatcaaactaaatagaaaggcagcttgaaacatttctttaatcttctcgcaacgaaatgtgctccggctctcca ggcttatcagtgttagaagagaagagaaggataaaacaacaataaaaacagttttcatttgtctcgtttcttgcttcttcccccacgatctgctg atctgaaaatgcattctttcagt sir-2.2

SEQ ID NO: 104 caagtggtatgccaactcatttgagagatctaaacatcgaagcccatcctctacttcgacagcccgtagaagttgtgtagcacattttgaacat gtgagcctgtacaaaagccataatacttctcaactactatcatcgtcatctctccgtcaccaatgatctctactcaaaacggttatggacggtttt tttgcataaggattcaactagccctacacgattgctttgatctctgtacattttgcgtttaatatggatatttgcttttaatggattttcgatcttcta cttttattgttgattttctggttttgtgggggttgtgtacaaattttgttatttgttgtcggtaaccacgggtaccatatatgtgaatcgtttatcatc gtattaaatcatgtatacatgcattgtacagagttttgaatataataaatgaacatgacgtcatttgcacctactttgtgcttttgaactttcactgtt tcagatattttttatttatgaaaaaggtatctatgaacaagcttttcaatacattataactttgttgtatctggtctgatcctcaatattttgagtcttc aaaagaaacaattataaattgcaatacatctcaacactgttttatggcgtctcaaattttgaaaaaaaaattattttataaaaattgatttgcagc agacatgttgaaaacggtgcttttcttttaaattatttttgttgtgataatgtaattaactacaactttacataaattgaactgaatatacgggtcattc attttacaaaccttatctattctatcaataccatgacttttttcgcgaaaagtcagccgacatgacatgactcttatctcttttttttttgttaattcttt ttttgttgcgacaaattagtgtcaaaaaacgtgaacccattcgatcacataaacattttgaacttcaagaaaatcacacaatcgataaatgatgaag tatggtaagtcaaaattttctaatattccaactgattaatagttagtgtgtttgagttttacttttttcaaattaatgtttacattaaaacaactataacaa tcctcaattgaaatattgtacacgaaataaaaatcaaaacatatgtatgaacatatttctcttatcttttgtattctgtcaaaggggtctaattttttg accattttttgtcagttagaaccaaataaaatcatgccgcatgtctgtgaaaaatcaccttattctttctctttgagattgataaaaacgttctgta ggttttccaaaatgttaactaaaaaatcaaatttaagccgtcggtatagtattacaggctaggtataggatgctcggataatattaattttaaaaat tcgaaaatgcatcatacataaaacttttaatacaaaatatagatgttttcttttatttatttattaatataacgtatctatataattttcaattaagcaa taaatattttgaagatttgaggataaaactaagcaaattctaaaactgcaatgttcaatgaaattgcgttattcagtgttacctataaagattttca aaacgttactctcttattcttctcccattcacgtgttgcactttctgccagccgccttctcggagaaactaggaaatatctgtgactttctctagcc actctctactctctcgtcagtgcaaatagagcgcgaatgctttaaaatgacgcatcaatcactctgtcggtcatttgattttacacttttcactgat agcttaaagctcggaagcggaactatagtgaaacattttataaattacgatttagattttttgaattctgtatcatgctgcctaatttttaataatttg aatattttaggc exo-3

SEQ ID NO: 105 tgcccagagagccgtcgaccaattcaacggagtcgatttcaacggaagagctctacgcgtcaacttggctcaaaacagaaacaactaattt tcatatcggtactttgttacttgtttgatctttaatgatctcaataataataaacccatgaaatcgttatcataaatatatgctctatttttttatttcg aatcttcatttggggtcaatctgatggcaagcgttgaggctagaagcttgaaggaacggcttcggttcgagcaagttttgaatcctgggctatg cgcagcccaatgtgagcttacaactgaaaattcaagtttcaacactcttcgcggtcttattttggactaattcctcatattttcagcttgaaatgga aaaaatctgtcgaaatcgatgctattcgaggggcggggccaaaacgcaaccctggcacggttttacgcaactgccgcacgttttctccaa ggcagggtgagcggaaaaattaaaccgtcataaatttctgctacggcctaaaatcgtcatgtctggaatcttctctgtttacggttagtttttta ataatttatttttaagtattaaacaatcggaaactggttaaaatagccaataaaactcgatattgtcctgaaattttgggattttcggaaaaatcga attcgcgaagttttccctaatattttcatttgaaaaggcaattttaagtgtttagattcaaatttggttgcgaaatatttaaatcaattaaaattttcctttt ttttagttggaaacgctccattccagaccaccgaggaggagcttggaaacttcttcagcagcatcggacaaatcaacaacgtcaggtaact ctcccagccagcccgagcttcatgatttctaacgcaatatctcttttcagaatcgtctgtgatcgcgaaaccggacgtccacgtggattcgcctt catcgagttcgccgaggaaggatccgcacagagagccgtcgagcagatgaatggagccgagttcaatggaagaccactccgcgtcaac -continued ctcgccaacaaataagttgatcttcatatcgggttttttgttacttttttgctcttcactgatctcattattaataacaatccaatgaaactatcgattta attatttaattcaatttcaactattctctaactaatctgttcaacattcggggaagtttctctatttgtcatccttccatccgccgacctgattcaacttt cttcttccccagctgctccgttcaagagcctactcgactactaacctgttgctgaaa ung-1

SEQ ID NO: 106 tccggcaaatcggcacatttccggaattgaaaatttccggcgaatcggcaaattgccggaattgaaaattttctgcgaatcggaaaatagtg ggaaattgaaaattccggcgaatcggcaagtttgccggagtcgtaaatttctggcaactcagcaaattggaggaataaaacatttgcagac cggaaattgtcgcccacccctgttttgcactacgctttgacaagtgtgaatttattcgcttttttttatttgcctgaattttgccgataaagaagatttc cggcaaagtggaaaattgccggaatttaaaaatttccggcaaatcggcaaaatgcccaatttgccgcccacgcctgcttcacaaattgatta attgcagcctcttccgtagctgaacctctggaagaagccactacaacgagtgtgccagagccaacagagtttcaattgtcacgggacattta tagcactgtaaagccgactgatgaggctcatagcccgccgattcaagcccaaccgaagaaaaaagccacgccaagacggaagaaagc agatgacgtggaaactgtagtagctgacggaacagcgacgatcccgaagccgaagagaaaaaggccgccgaggaagaagcctgagc cgaagccgaatatcgttttgaaacaacgccgaatcctccgacagaaaagcttcgcagccaacaacaatttccagcagttccagtttcaaaat cagcctggtagttggacctacaacaatggattcggcaatggatatgggtacggcggtggaaccactggatacatggataatcttgttggca gagggtttgacacggttctcagcagcctggatttcagaatcaaggtacattttttaaaaggaattgagaaaaatgtgccaaaaaattttaaag gtggactacgctttgtggggaaattgctttaaaatacgcctatggtaccacaatgaccgaatatcatgattaaaaaattcaaaaattttttctaaa ttttatatgattttttgaaaattggaaaaatcacagttttccctaattcctatttgaattaccgccaattgaatttgttcgatggggcgcgcttgcac gttttttaaatttatttattttattttttgttattttccaccgattttttaatgttttcggtgtattttgctcgaattttagagaaaaagtcaaaataaatgc aaattttcgattaaaaagtgcgcttacaggcgtaaatcagtgaaattaattaattcaggttcgaaatcgtttaaaagcgttacttttcatttttacgcct gtaagcgtgcttttaatcgaaaatttgcatttatgttgattttttctctaaaattcgagcaaaaatacaccgaaaacattaaaaatcggtggaaaa taacaaaaataaaataaatttaaaaacgtgcaagcgcgcccccatcgaacaaattcaattggcggtaattcaaataggaattaggggga aaactgtgatttttcaattttcaaaaaatcatataaaatttataaatttttttttgaatttttttatcatgaaattcggtcattgtggtaccataggcatgt tttaaagcaattccccactagcgctaccccacctttaaaggaattgtgaaaattgtgaaaaaaaaatcaaaatttcgaaaaaaaagcgcta attttaactaaaatctctaattttggccacttttccgtgctgcagcgtccgaaagtgcacttttttttgaattattattcttattattatacattaaaaacc cccgtactcctccaataacgccaatattatcgaccatctggacgtgaccgcgtgcaaccacggcctagctgccgccaccccattcaaacga gacatttcggcgggagagtccttttttttcgataattcggattttttttgtctgtttcaagtaattttcgccataaaaattaccattttcttcttcggtgcc atttctaatgattttccagtgcgttttgagtctgaaagtttgaaaataagagttttgcacaaaaatgtgtgagaaaagttcaagaaaatcgtcga aaaattcaataaatttaattttaaaatttaaaaaaaaattaatttttttaaaaatcaattctgtgcatacaccgccacgcaaagtgcacacaattac ctaccgtagtcaatgcgaaattaaatgattttttatcgattttcttcattttcaggttacgaattcaccggtttgcctgcaaataactcgaataatttcc cattttttgtgatttaattttttcaaatatccttatctatgccctcaggtttattttatctcatttccactcgtgtttttttgaataaaaattcttttttttttct tctagatttccgtttatttcaga mrt-2

SEQ ID NO: 107 atttttcgaatatttttgtctgaaagtttcacgtgatgtcagagtgtctcatttcggcttgatctacgtagatctacgaaaatgcgggagttgagac gcagagttttcaactgatttcgcatggttaagaacgtgctgacgtcacattttgtgggcaaaaaatgcccgcgttttgtagatcaaaccgtaa tgggacagcctggcaccacgtgaaattccagaaaaaatgtctgaacctactgtagttcacaatttaaaggcgcataccaaaaaattatagcg ggaattaaattttatttaataattttttcagttacagagcaattaaaaaattcaatttcatcaaaattttatagaccaattttctcgctttatagctgag ctccgcgagccaaaataggaaggggagcacgaaaaaaaaacagaaaaatgagctcgacagagcccatagcctcaagcgctaacgaac caaaaaatgcacacacacacaggaggcggagtcgtggaaatttcgaaaaaaaaaacaagattttcttctctctcggctcaaatttgaatgcg gagcaagaatattacgggaacaaaaaattctgagaatgcgtactgcacaacatatttgacgcgcaaaatatctcgttgcgaaaagcaaacta cagtgattcttttaaatgacatttgtagtgtcgatttacgggatctcgattttcgaaatgaattcatttatcattgatcgagcccgtaaatcgacaca cgcactacagtagtaatttaaagggttactgtagttttgttttcgctacgagatattttgtgcgtcaaatatgttgcccaatacgcattctcaggatt -continued

```
ttttgttagcgtaataaaataacagaaaacacagaaaaaggcatgaaatttaatttgaaataccgcgctgagttttctaggccacgtgtcgtgt
actcccgtggacaagcggttttttgccttattttctgaagtacaaattctcaagtacaagtaaaaaagtacaaattttaccaaatttgaggaaaa
gaactagcatgacaaaaatagaattagaaaaattctagagaaaaactacggatttctggcttccctcataaaatgaaatggaagagtttgccg
aactaggccattttggctcagccatatctggagtagatttacggcgcgttccgtgtcgcggctcgattttagttgtaaaactaaatgaatttgtc
cgtgtggagtacacgactttaccacgcgttgtccggcaggcgattgtcaatggagcgcgaaaaattcaatgcaccagatttgacgcgcaaa
atttgaattttcaagttgtaaatccctttttttcttcccattgtcccatcaaatatccttcttcaaaaaaaccccctgcgtctctcaggccatatctgcgg
tagatttacggcgcgttgcgtgtcgcgtcgcggctcgattttagttgtctggcgggcgattatcaatgaagcgcgaataaatcaatgaggaa
ggccagaaccccgtgaagatccaagaaaagttttctaggccacgttccgtgtactccacgtggaaaatgtcctttccggcaggagattgtca
atggagcgcgaaaaattcaatgcaccagatttgaccacgcgtcgtgtactccacgtggaaaatgtggacactagggatctactaaatgcct
ggaaaatcgtaaaaatctcgaaacttcctaaagaaaaaaaagcaaatacacaaaaacgcattgatgtatgaacaaattgccctccccgtct
cccaccaaaaactcccaaaaattgctctttttttcatgtttatatgggggaccgcgggatttcataatagctccgtggtccgctcagctcatccg
gagccaaaaagagcacacacacacacgcacacataaaagttgtaaactagtttcgagcaaaaatgatacgacggatgagtgtgtcacgca
atcagtgagcttctctcgctttcgaaagaaaaatcttttttcgcaaaaagaaaaagtacttttacactggccacagtgtaaaataagggtgaaaa
gatcgaaaatcggaggtttcaaatttgaatttccgcgcaaatgagagggacgaggtgcgatggcctacaaaactccgcaggtgtactcctc
tcggaaaacggtgcgagaattaatttttttaatttatatttaattttcagcgattttctcagttttccggttaaaatttaaatttttttcaggaaaa
``` rae-1

SEQ ID NO: 108

```
aaactgcaatttcgtaaacgattgaaaattgagaaagatcaggtatctgaacaaaaacttgtacatttgaaatctcaacttcatttattccaggat
acctacaaatatgaatcctatgtgcttcaatgaattctacaggaaaatattcaataaatgaccaaatcgaaaaactttatttatgatcccaattatg
ttttctttgattatgctacaaattcaagaatcggcaaataatgggaaaatacgattttttttcacaatcaatatatactgcttgatctctctgttagaa
tttcctccaaaatctgaactgtatgaccaaaaatcaattttttttgaaaatgcatttgtcccaatatttcctttctaccattctgctttgatctttttttaacc
ttttttattcgaataaaaatatattccgaattaaatacaattaatgtgtttccaccaactttacacataaaaattcattttctgatgtaaagatttttttctaa
catacatgcattaacttatttctggagaaatatttctctggtttaaaaaaaaaaacttctatttagttatgattttttccttttcacaacgtgaaaagttg
caaaacttctgcgaacgacgccacttctccacggtgttgtttctccggaacattttttcccagtgggacgccacgcgcaactgcgctctactg
ccaattttcaaaaacggaattcttttcgctgaaattttcttttaatttttctttcgttttttcaacgttttttcattctctaaacttaaataatcgaaatatttcga
aatgattaatgaagaaaggtaggcgttataatatttataatcaaaatttctcaatatcatgttagatattcatttttggcgaatattcaacaattgaaa
atcaaaataccattatttatcgactggcgttatttttattgtttcagaaaagctgaaataaagcgaatgttggaaaaatgccgtaaaacggaaaa
ccgacagaaattttggcgatggttgcccaattttcagttgaacagctggcagactcctgttgtcattggtgttgcagctgtttctgctgcaattat
ctatcactattttttcctaattacccttattcctattgttcaattttttcttcatcctgattttgtgatctacctcatgtaataattttctcttcttctttatt
attttctgcgctctgtactttcttaaaactgtataaattaaaattgcaga
``` rad-23

SEQ ID NO: 109

```
cccacacagccagaagattttttatgggcggcagacattttcttaaatccaataatgttttaatttgataaaatcgaagataaaagttcacgataa
acacaagtgaagttaaaaaataaaaataaaacattcaaaaagaaataaacgcattctccgtaaatcgacacaatgacaattctggcaggtc
tcgccacgaagagtgttcaaatcatgtgcgcctttaagacgccaagccatttctcttctgtttttttaccacttattttgttcttcaaaatggtttttttt
gttttgttctttttattaataatcaaatgtttgttttattttatacatatatactgcttgttttgcattaatatcaatctgttatcgatatttatttcttttttc
tttcaatacatgactctattcgtaacatttcacaattttttgcagg
``` brc-1

SEQ ID NO: 110

```
gaacgtccgacatgatgagatgcaataacctgaaaatgaggcactttatgataagaaaatgcggtaaaacatgcgaaatatggcaccataa
accgtgagcaggacaaagaacaaacacttggaaagaaaagaaaatagaaagaaaaaaggaaaactggagaaaacaaactcaataa
cacaacgcgagaaatacaatttcgtttcgttttttcttctatttattagatttctcacaatttgttaccagtaaagtcacgttctatatttcaaactactc
ctaaaattcggtttgaacagttctctgataaacgaatttcgaagaacgatcagaaacaaatctacggttgtgtgtgatcaatggggtcaaac
ggtggacgaaaggggacggcggagagaggaaaaagtgagagaaaataaataaaattgaccttcgagtgcagagttttgctggtattttgg
```

-continued tcagaattgattatgaaaatctgaaaattaccgccgggaaagttgaaaatttgacgtggaaacgtttaaaaaaataagatgagaaagttagta ctgtagatgtcgtcggatcaagtgcacagtacgcaagcaccgttacgaaaaattgcactaattgctcaattaaatttttttaaaaaattaattttta tagtgtgttttgtgttttttttctgctttttaatgattttaaaggcttgattatgttttttctcaaaatttgaataatcaataacattaattaattact ttattaaaaaaccacatttggcattttaataaagcaagttatcgcgacaaacggcaaaaatgtctcttttataaaaattgttttttttgagttaagagaa gatgtggagttttttgaactacattagttttctaaaaattttatcatctagattttgaggaaaaaagcagattatatatctttaatcttggttttaaaattt ttttaaaaagcagaatattaaagtaaaatattataaaaagaaaaattcgtgtttgcaaaatttgtttgaacggaaccttgcaaaaatgatatttagc agctaaactaactgaaaactactgcataaagctttcccaaaaagagctaccatccagaaaatgttttttttttcaaagccgaaaaagaagaaa aaaagatagaaaaccgaaaaagcagcatcgttttcgcgcactcttttcttcttttttttcttttcttttttctaaaaaaaaatattctccgtagcttgaagtc tcaggatttccaaagggaatttccttgatagaatatggaaaaacaagagagtcatcagagaagggagaggaaaagcggggatgctggcg aagaccgggggcaccgactgaaatataggcaccggcggggaggcggggcgctctctcctctccgctttactccgccccgattgtcagtg gagcaggtttgcaatgagtgttctctgatgcccctcagcgcgggagttttgaaatcaaatattttgtatttaacctactttattgattttcaatta aaatgaaatgttatttgtttaaaatttaatttcag brc-2
SEQ ID NO: 111 tgtaggtctaaaaatatttgtttgagaataaatattcgaaatcaatctaacgtttttccaatctacaggtggcacgacacgctcacaaccaataa gtttcttgccacgctcgtcgattttttttgtagaattcccatttctgagagtgtttcttcgctttctgcttgctctggaacttctgaaataactttcccgcg attatttggatttctatatattttcaaactacttacctattttcgttttccaaagtctcgaattgtgtacttgtcgacgttggttccagatttgagcattat gaagaattccaattttaaaatcacaaactggctcaaaatctatacgctcgaatagagaattgtgtgatgtaagagcctgaaaattatatttgattt tctttccatctttttttattttcgggaataataaaacattcaaaagggctgagatctatctattttttcacatgcgacccatttctatttcacgtgaagc acatgattctgaagggcaatggaaatgaaaacccggaaaaacaaaatctttcagtttaaattgtatcaaaacaagttttttctagattacaaatgt acctgaatagtgatccatgaattgggacagaccacatcgaaataacatttcacacgtggcaatgagccattttgaagtttggctgaaattaa atttatgtcgagaaattaaaaaaaatcagagcgtcatcatgagaaaataggaaaggtttagactgtaaaatcaggttttcatggcgggaatga cattaaaatggtgataaggtgattattttatcaaaagaatttttgaatgattgcacctaaaatcgagtgcttttcttttaatttgattatcaaaagaa aatacccaagaaatggaaatgaaaatttaagagatgaaaggaaaaagcgacccggaaaaacatcaagctgggaagaaatctcaactag ttagaccaaagcttcgaactctgcgagcatgtatttttttttcctcactttctccttttcttctctatttctctagatctttattactgcgggggcaaaaa gagtaagagatagaaaagaatgacgcaaaaaatacacggatttaatatttgctttgcttttttattcagagaggaaaggtcaattgggggtttc ccctcgttttatgaatgaaaaccgcacataaatataattatttccacagttttaaacggcagaaacggttcgtgttataatttgtgagataattgat tttgcattacgaaattagaagaaaaggcgaaatcaatcaaattagtgtcgcaattttttttctcaaaaaggaaataatgcaattacgctccaccg gacagtaaaattctcagtttatttgaaaaacaaaaatttaattttttcccttttttttcaattgaaatctcaaatttctgaactcaaaatgaaattttcaga ctttaccagaatattgtgacatcgaccg rad-50
SEQ ID NO: 112 atcgcagaaatgtgaaatcataaaatccatagtgagattgagttgtttattattttatgaaatgagataatcagttggataactactgct cacgccgtattcgatctatcattcgattctccgattctggaacatcaaattttaatcatagggagagaggttcgggtacttgagaaaa aaatgtcgtgttttcgagaggttttgaaaagtcagttgttaactggttcggtcaacatgtagagattgtagagaaatatgagaacttag agaattgacgtatgaagagaaaaaagtgggaaaggggagccgctgttgttttcgaaagaagaaaataagacagaaaaaatcgg agaggaacataacaacaagttaagttgacttttgaactgaaatttgtcaatattgaaaaaaggaacagtgagaaatatcgatttcc acgtcgctcgattctatgaaaagaaattatgcacacacaagcttcacagtgagcatgctgaatgattgagcaaatacatgagaga ataagagaggaatgagatgaaaagaagcgttcaaatcaaaagaaaccagacaaaatggcgatttttttacgggaatatgaaccta ctgattggcagtggacagctggaagaataagaagatactgaaggaaggttgaagttgaagcttggaagacagatgatgagaga gaggaaaacctgttttctttttgattacgatcggacgaaatgagaaggaagtaagtgttttcacacgtaggtgggcattgagatcttt gaaggtgcattcgacaggttaataatcattctaaataccaggtgacaatggaggatacttttaaacagtaaatatattggaataaaa

```
cataaaagttagtcttactcagaatttctaaaatttcagccttctggaacgaaaggtaaaatcataataataatacaagtggggctgtt agtagccctaaatacaagtaaaatgaccgaacacagccgttaaagaatgttgcagaaaattgcgaaatatttccttactcttaagaa caacattcgatgtgacgcaatatgatgcatttccttagacaaaaacgttcagttcaaaataaacaacaataaaaccgtttgtacgatt tctagaatacgagtttatcagttgttcggaaaatatcttatcaatcgtttgactgatgttttttaaccatgtgagaatttgaaaaaaatt catgattgccaaaaattaaaataaacaggaagcttttaccgagttttcgtgattttcagaatgaagaaattaatatgaagctcaaaatc aaaagcagagggaaagaaaaaatcgaatcttctttcggttaaacaacacgcgcttgcggaacttcggagcatcgtatttttgttt tgcgctctatttttgaatcggaaactgttttttttgtcagttttcgaaattgtttttttttctgttttttttacttcatgcaagagtttaactttacgca aaaattaattaaaaatacgcagaaggcccacttttacacaggaattaattgaaaatactcaggaatttcacttttacttagtccttttttcca gagtttccaacggaatcaatatattaatttaatttcgcaacattttctttgaataaacctatttgcaaatgagaatgtttcagatatttgct tatcgaagcctgggaattgctt
```

Y47D3A.29
SEQ ID NO: 113

```
Gcgtaaaattggtttctataaaattcttgacaaaactcattccgaacggctgaaaatattgattgaactgaattcacattattcattaaaaaaaatagg ttagcctgttatgtagagaaatttagtgaataaaaaactgaatatgtatttatttaatagatttctcggcacacaggaattaggaataactcccaa aaaatagatatttggcaggagggccgaacagctgtgttttccgtgacgtcatacaggtcaatggacacaggatgtagtcatattacgggaac acacaattctgagaatgcgcactggggcatttgatttgacgcgcaatatctcttagcgaaaactatttacagtaagaatttaaattctaccgtag cgggctcaattttcgaaaatatattttcttatcgaattttgagagcagttttcagttttccatgcttgatttattattttatctttaaataaatttttttt cattgaaaaacggaaaaacaccgggagaaattgatctggtgagaaaattataatatttctgctgttttcctgttgacaactttagaaatgtcaatt aaacaactatattttaaaataatcatttattttttttaattacgtcaactagaaaacattaacttttttgcgaaaattcacttctaccacactcatcatccc gaaaacagcgaggtctcatgaaattgcaagcgcgctctactgcaaggaaaggcagcgcgcgaagcaaattttcaaacaatttttttgaacgt tttaccgcatttctcactttctcgcttaattttgctatgttttttgcgatttttttgtaatttttcttcgttttttcag
``` cku-80
SEQ ID NO: 114

```
tcactaaacaaaaaacatatatttgtaaaataccattttttcttttcatcaacagcttcaaaactatctgaagtgctggattttcgttcagctccgtcg atcagctcgaagtcttgctcctgttctggagtatcgctcattctggaaagatttaaatacaaccgaggaaccagaagagcgcatgaaaatata gagcgtgtaatttaacgtcagttattgacagagaaaatagaattacgaaagaccaaatcgggcaacgaggaaaacgtttaacacaaacaca acactgaaaataagcaagaaaaggaggaagttatcggaaaaccgaagaactttcaacttcggaaagaaccgtttaatttatgtttaaaatca aacaaaaaattcccgaaacatcccttttaaactttgattttcacgaaaaacaacgaatgaccgaaaaatgtgatcaatctctgagagtgtgcac ttttgcgtgacggtgaactgtccgcgtgcaccagattcgacgcgcaaaataatcggcgcgaggttcgaacgaacgttcgtgaatttgtggg agcggttttaatgtttaaaaatcagttttggtttattttatttgaaaaaaaaaacgataaaagctatattccagcagtatctaaaatgatcttctttta atattctaattttaatgttttaaaattcattttcgctgcagcaaaaagttggtgtttgcgtacaaaacccgcgccagtcttgaaaaacgcacgcat tatttattcacatgtttcgcaatatttccatatgaacttctcaacatcaccaatttaaattaagttacagga
``` him-10
SEQ ID NO: 115

```
cttgtttcatactaaaaactctgatttcagactgaaaaacatgttttttcagcgaagaaaactaaaatttgtttgtggccgcggtggcctagttttc acggccgagaaatgtcacatgttttggcgcgctcttcggcgaattcaaataaactttttttgtttttaacaatttctaactttattttttgtgttttttagaa ctgaaattccatttttcaggagaa
``` polq-1
SEQ ID NO: 116

```
ttctcctgaaaaatggaatttcagttctaaaaacacaaaaataaagttagaaattgttaaaaacaaaaaagtttatttgaattcgccgaagagcg cgccaaaacatgtgacattctcggccgtgaaaactaggccaccgcggcccacaaacaaattttagttttcttcgctgaaaaaaacatgtttttc agtctgaaatcagagttttttagtatgaaacaag
``` lin-35
SEQ ID NO: 117

```
ctcttcttttactaatccatcaagcgacttttcacggagtaatctgaattaataatatttatcagtgcatatctctgaaaactaacttgacgacaaat gcttcgacatcaaaatccggctttgtgacgtccaaaacactagacattttacattcaatactgaaaaattaaagaaaattcaggaaaactcgag
```

-continued

```
aatgaaaaaaaacagatttgagacaccatcaatacaaagggaacgaaatttgggggaaatgctggttgccgaaaaaataagtagaaggta
agatgtgttcaactggaacatacatttttctgaattgcaaactcgatttctctcacattcacaatttttaatcacatttaatgcttcagttttagaaagtt
ctgaagtatcctcttcttcctattcagtttctcaaaatcgatggtgtctccaggacgtgcacaaatgcgctctattgcgaattgtggaacatcatt
gcgcgcgcgactagaaaaaaatgagcgcgttcttgaaaattattttgctttctctaattttaaacgatttcgattacattttatctgaactttcttgg
gtttaatcgaataaaaaacacaaaaatattcttcagactggtaaaaacttcttcaat
```

Xenobiotic Toxicity Genes cyp-13A6

SEQ ID NO: 118

```
gtctagtttcaaaaaaaattaaattaaattaaattgtgtaatatgtggcattatttatatactttttgtcgatcatctgttaagttagttttagtcttatc
ttcttgtcgcacaaaacattatggtttgtgtttaatagaacaagaaagtgggtgacaagaatcgtatgatttggagaaacccagcaatcaaga
agatttgtttcaaaattcgtagtctggatactttagaatgtattctcaattttcgaataaagtttagaggatgttttttcaaacttttatcaattttgaa
aactatctgatggttttataattattacagtcacatatttgtagcttgtgaatctaaacctattatgtatattctcgtttaaaaaaattaattgccgaaa
aaaagcaaaaattttaatcttacgaaaaaagtttttttttggatttatcagcttcagtgctcattttcatccctaactttctttcaagaaattttaga
tatgaagaacaattttaaaattctagatcaaccaaatctctgaaacaaaactagttttctattgtttctacatattgatatttttttaaactccattatc
attttaatttttaaaagttttctaactaccatctgctctccatcacctctttatgttttttgcatttgagcagtgaaaagtttgaagaatattggtaca
acttttataccttccaaaaagtgcttgccccattctctatgttctcttatcagtacactatatctcaacagtcgacacatttgtgtggaaagtgttg
tttgtgtctgactgttgtttctaccaccgatactatttataaggtggtctaccgaaaaacatcaatacgtttcttttttattcctgaaaataaaaac
``` cyp-13A7

SEQ ID NO: 119

```
gtttttattttcaggaataaaaaagaaacgtattgatgttttcggtagaccaccttataaatagtatcggtggtagaaacaacagtcagacaca
aacaacacttttccacacaaatgtgtcgactgttgagatatagtgtactgataagagaacatagagaatggggcaagcacttttttggaaggta
taaaagttgtaccaatattcttcaaacttttcactgctcaaatgcaaaaacataaagaggtgatggagagcagatggtagttagaaaacttttt
aaaaaattaaaaatgataatggagtttaaaaaaaatatcaatatgtagaaacaatagaaaactagttttgtttcagagatttggttgatctagaat
tttaaaattgttcttcatatctaaaatttcttgaaagaaagttagggatgaaaatgagcactgaagctgataaatccaaaaaaaaaacttttttttcg
taagattaaaattttttgcttttttcggcaattaattttttttaaaacgagaatatacataataggtttagattcacaagctacaaatatgtgactgtaa
taattataaaaccatcagatagttttcaaaaattgataaaagtttgaaaaaacatcctctaaactttattcgaaaattgagaatacattctaaagtat
ccagactacgaattttgaaacaaaatcttcttgattgctgggtttctccaaatcatacgattcttgtcacccactttcttgttctattaaacacaaac
cataatgttttgtgcgacaagaagataagactaaaaactaacttaacagatgatcgacaaaaaagtatataaataatgccacatattacacaat
ttaatttaatttaattttttttgaaactagac
``` cyp-13A11

SEQ ID NO: 120

```
gaatcttcgatgttcattgtgaattttgtatcactgccttgcctttattcacttcaggaattttatgttttacttgtaatctcaataaaaatgaactttcaa
attaataataacaaactaattttctagttttacatcagatatctgctgagcttctgctcctcttccgtcaaaattaaatcaaattggctgagcagcg
gcccagtcaactagcgaagttaggacataggttttctttttttttttgttgaaatgggcaaattgccggaattgaaatttctggcaaattggcaaa
ttgccggaattgaacatttgcccaaatctgcaaattgccggaattgaaatttctggcaaatgggcaaatcgccagaattgaaatttccgccaa
attgtgattttgcacttttttctggaaatttcagaatttcaatttcaatcggcaaatttgtacgcatcctatttttgaaaagtaagcaaattctatgaaaa
tatctaaagaaaacgggaaaaaaactcaaaaagacactgttttagtgtttccgttttataaaaatgcctctaaacatttccgacaaatttgatg
atccggcaaacgacacaccggcaatttgccgacgaaaaaagttgccaaacggcaattgttactggatcttatagtgatcaaattttggaaaa
ctcaagtacagtcagaaaagcagtcagaacccagggtctattaaaacatcttttacacattgaaaagttacatatacttgaaaaaggagaca
tagagaaaaactcagatactgtctctgacaattttttctgctttgtgccactgaatggtaaacaagctgaaaggtataaaaactattgcaattttg
acagaatggtatttgaaatcaagg
```

-continued cyp-14A3

SEQ ID NO: 121 atgtaaccccaataatttttttttgttgcattttactacttatatccgtttccatttttaattttatgttgtcacgttttgtctaaatagtgtaatcttct
tgtactaattattccaattattttaacccgtaagcgataaatgaaacaacacttttggtttttatttgctaattttaaataaattgtcatcaattctgaaa
ataataaattttaaaaaaataccgaagaggcaaacaagacattttggaaattctgatccggataaatattccgttagatttttattagactcgaaatt
gcctgaaaccccgattttataacgaaacctcttgaaaacttctcaaaaaagagaagttaccaaactttaccaaatttggtctcccatcgacctt
caatgtacctaactctagttgaatacgcaagataattaattgctacaaccaaaattaaacgcggtttcaaaaaaatattgttttcagccgctgc
aacattgacaagtgggaaaaatttcaaattttaactaattttaggtcattttttgagccgccataacttttttgagaagttttcaagatatttattttg
aagttcggagttttcagacaacttcgagtcaaataaaaatatttttaagtcgacgacaccacctcggagataatctttaaaaaaatcttttcaga
aatgcaaaaattccaataagtgtcaaaactcccgagtagcgcttaagcagtggcacgtctgtatttatgtattttgtttttttttttactttattatttt
gtgctttattactgttttttttttaaatttatttgtttcatgaaatttttaggactaacgtgaaactcaacataaaaaagctagaaaagtttcgcgtactg
tattctattttctttgattttattaatgtaatacatcacttttatatcttgagtgactaaactcttgttaagtgtgtttcaataatgttttgatttttga
ctttacttatacgtgctttgtagttttagtgacattagtgaccgaaagtgagacgataacaaattgggagcggtatataagtgaactacgaaacttct
aaaaaaaacaaaggctgtttcaca cyp14A5

SEQ ID NO: 122 tgtgggaaaagttggaggttttttgcacattttaggtgagcgaatatcccgttgaaattatagaaattaccgattgccggacagttttggaaattg
tcaaatccatctattttttcgaaaaattaatagaaaactacattggttttcagtatttgataagtctacgagacaaaaatgtctacgagacaaatgta
cacaaattatcaaatttacacttccggcaattctgattttcggaaattgtccattccggcaatttttgcaaaatttgaaatttataaaaataattctct
acctgcctgcctacaggcatgccgcaactaaccttgaaaactttaaaagaaactccgaatttcttaaaattttaagtcggctggaaacttagaa
atctcttgccaagataaaaaacatcgagaacatcgtaatcaattttatttgatttgatacgttcacaaagtgaaattccaatattgaaaatcaaatt
caattaatcaattaagagttcagtgagtcgtccttgaaatgtaccaatttcacttgagcgctcagaatttcgttcaaaatcatcaatttctcgtcca
aaaatcgatgaaattttgcgagtaggtacaagtttgtgctgaaattaatttattggttgtatggatattttttttttaatttaagaattaaaaatttacc
atgaaaatatagtatgaaatattacaactatcagggtaaaccaagcaacgcgagatccagtcaaactgtacacgactaaactttaaatagca
atactaatctaaaaagcaaatattttctttaagtagaagcaaggcagaagtttgacattttttccgaccagttgaattgtgattctatatacatctg
gttcactcgaatttcagacaaacaactccacattcctcaatttctgtgatagaacaataacttattttcttcacatttctctttcaattatgcattttcat
tctttaagtgtctttttttaaaatttgacaccatttgcccgcgactcgttgtccggaggtttcctcttacctcggagaaattccgctaaatctaccat
gcatgagtctcaccacgtggacaacgagttactgtaacttgtgtcaatttacgggccgctatcctttttttaaatgatatgtaccaattgatacaa
agaaatacttgttttgttatcaaaatagagtataaaatataaatgaaataattcaaaaattattctcaattgggccagatacaataggatagtggg
gaagttcaaggatgatattgtgtcagacaaggagcaaaaatgcattaggccagttttttacagaattcattccaagtacagaattttttcaaacatt
ccattaggaaatggtgaagaaaaccaatacatttcaacttccaaattttttgaaatggatttaaagcttccctataaaatttgtttatgaaaataattt
taacgatttcatttacaatcaccacattttttagaattctcagcacaggttgaattgttcagtaccttttttcaacatctagttcacctacatatgagtt
cttaattttaattacgttttttgaaaagtaaatatgttatttggcaagtccattcaaacaaaagacgtcgaccacttataatcaaaaagtacacttgc
ggcagacatctcgatacttgttttctctgcctgttgtcactgatcttatcgatatgtaatattgtgaaatgttgcgcagtgttgaaaaataagatata
aaattaggaaagaattgtataaaaatcagacaaaactattctgtccaacaaagatcatt cyp-25A4

SEQ ID NO: 123 gatgagatgcaataaccctgaaaatgaggcactttatgataagaaaatgcggtaaaacatgcgaaatatggcaccataaaccgtgagcagg
acaaagaacaaacacttggaaaagaaaagaaaatagaagaaaaaaggaaaactggagaaaacaaactcaataacacaacgcgaga
aatacaatttcgtttcgttttttcttctatttattagatttctcacaatttgttaccagtaaagtcacgttctatatttcaaactactcctaaaattcggtt
tgaacagttctctgataaacgaatttcgaagaacgatcagaaaacaaatctacggttgtgtgtgatcaatggggtcaaacggtggacgaaag
gggacggcggagagaggaaaaagtgagagaaaataaataaaattgaccttcgagtgcagagttttgctggtattttggtcagaattgattat
gaaaatctgaaaattaccgccgggaaagttgaaaatttgacgtgaaacgtttaaaaaaataagatgagaaagttagtactgtagatgtcgtc
ggatcaagtgcacagtacgcaagcaccgttacgaaaaaattgcactaattgctcaattaaatttttttaaaaaaattaattttttatagtgtgttttgtgtt -continued ttttttctgctttttttaatgattttttaaaggcttgattatgtttttttctcaaaatttgaataatcaataacattaattaattactttattaaaaaaccaca tttggcattttaataaagcaagttatcgcgacaaacggcaaaaatgtctctttttataaaaattgttttttttttgagttaagagaagatgtggagttttttt gaactacattagttttctaaaaattttatcatctagattttgaggaaaaaagcagattatatatctttaatcttggttttaaaatttttttaaaaagcaga atattaaagtaaaatattataaaaagaaaaattcgtgtttgcaaaatttgtttgaacggaaccttgcaaaaatgatatttagcagctaaactaact gaaaactactgcataaagctttcccaaaaagagctaccatccagaaaatgtttttttttttcaaagccgaaaagaagaaaaaagatagaaaa ccgaaaaagcagcatcgttttcgcgcactctttcttctttttttctttctttttctaaaaaaaaatattctccgtagcttgaagtctcaggatttccaaa gggaatttccttgatagaatatggaaaaacaagagagtcatcagagaagggagaggaaaagcggggatgctggcgaagaccgggggc accgactgaaatataggcaccggcggggaggcggggcgctctctcctctccgctttactccgccccgattgtcagtggagcaggtttgca atgagtgttctctgatgcccctcagcgcgggagttttgaaatcaaatattttgtatttttaacctactttattgattttttcaattaaaatgaaatgttat ttgtttaaaatttaatttcag cyp-29A2

SEQ ID NO: 124 accatgtacccaatttctccagatgtctcaaaaagtccttcttcttgttaatatagctcgcctcctcaaattttgatcttccaattcctctccgccca atatattctagtccgtgtcttaccccttgacaaaaatgagcttttctcagattccgactaattccaaaaaaaattccctacgttttgaataattgtcgc tttgtatttttttttctcgttttcatacgggtgttcatcattcattttactttttttaaaaattttcctctcgttctcttttgaacgtcccatttttattgcaa tcgttcattgtctagggtctatccttctaatcattcttcttctcagaaatatcacaaaccgtctgtgttgcattcaaattttttaagtaaaaataataaacta aagaaccacaatgaaggtctaagttggcaaaattgaaaagccgaaagctttcccggaataatagtaattactggagtgcatcccgaactgtct aaaagtagagaaaagattaagtggatatatattttttatatttttaatatagtaatctgtttgaactgttatacaaaccgaaatcgtgttagtttgga caaagttttgcatcaaattttttttgagttttagatcgaactattgtgttttttaatgtaccagtcaatatttggcattcacaagcggtatagccaaatgt acccagagttgatcagatagcgttttttcttcactgtgttccgttgttatcaaataaattatgcaaaaactgcgaaaatttgagttcaaacattaaaa aaaatcatatttttctaggttattgcgagttttttagcaagaacaactaatgttttcatgtttaaacaaaaaaactgagtgagtgagaaaaaatctca tgtatgccatgggatcaagccatatattttccatagactaaaattatttagagatggaaaattgaaaacaggagacgggttactgtaggaagat ttttttaagactattgcaaatacataaatcttttgaatatattttacttcttcgaccgccgctttgaaacagtgcgttactgtgaacgttgaaaacca aacatttgaactcttcacctcacttgtccatttgttaattgtctagccaactgtagccacctttgatcaggtagaccttttccaatctgcgtctctca ttctctcaaattcacttagccatgttttgtacggacatcatttctgatacattaactacgataatagttgtgcacgctgtggtcatttgattaacttttttt tcctgttgcagcagttcgcgagtatataacctgtctttaactgataaatcgtttgcattggtcgtttgaaggaaacaacaatacgctttccaaaaa cyp-31A1

SEQ ID NO: 125 tacagttacaattgaaataaatggaaatctctcttattttttacattgaaatttcttgctggtcacttcttccaatccaccgtagttaaccgactgggt ggtctactaccgtttctggttttctctgcactctcttcggagagagtgcagacaaaattctccgcgttcgcagtcctggttctgtttcgagacgt tgacgtcgcccgacaccactcctacaactgttcggacagcgtctgcaattttcgattagtaatatagtttggttgtgaatataatataaattgtg aaaaattgcattgagaattaggaaaagagcatgtgagaagaggaggggaatttttagaataactgagaatataatttagagaaacacgatta cttcgcatcaattcagaatatcttttaaaatctgagaaattttggttaaaaaataacacagggcgcttagtttgtggttttctcaattctgtttaattttt aaaacagtaattcttatttcgataaactaaaatgaatatgaaattttcttacgattaaaaaaatgcatgaaaccagatataacaaattgaaggaaa actgaaaaacttcagaaagtgtttttttctgaaaataaaagcagaaaattcgaagctcgcgcaaagaacgtaaacgcgctccattgctaact catttgaacattagttttttttcattgggctttcaatcttgtaagtgatgtttaggcatctaaaagttttataaattgacaaaatccagcttaaaagatg ctatcaaaaactaacttttcagaatatttatttggctaatgtttgacccatacgttttttgccgaaaagaatttcaaaaatgaaaagtatcttgaaat gcatcaaaatccgggaatattgccgatggtcagttttcagcatttctaaattgagagactgaaatgggaatttatttattttttattcatctgctttttt atttcatgaatatccgcatctgaaatcagcttttttttttcaggaaaattgattgaaagaagacaataacagctcgttgttcaacatctcgattcttcc atatgaatcgatgaatggaaaaaccgtggcatttggtaaagttttggctggaaccgaagttgtctcccgcatcgccttcaataaatcaaacac gaagggttccaaggcttgcgtcatcaccgactgtggagaagttatctgaaaggttttatcatagattttcaattttttggtttattattatttctttct ttttgttccgataagtccatatatgaaatttgtccagttttttatgaaaataaacatttatttttatttaatatttttttattcatcatatgc cyp-31A3
SEQ ID NO: 126
tctgaaaaacgttgatttaaaattttataaaaaatttgaagcaaaaatgaaagagaaaactaaaaaaaaagtaaatgtactgaagtgattggca
gattaataataatttatcgataaaaccattttttaaaaaacttcatcagttttttgtgagtgtcagcaaagaagaagaagattcacgatcaaaaattc
gttgagcctatatgaaatagttgcgctggttttttcgacgggggggatcaaatacgtcaaataggtcaaatagacgaagcattcataaaaagtac
aatattcattgaaaaatagttttggatttgttttttttgttttcttcatttttttgttgaaaaaataatggtaattaaaagttttttaataattatttaaatca
agattgaaatatcagaaaacgacaaaaattcgttcgagaactttctcaagactaccgtactctttaaagacgcatgacgattttcacatgggtctcac
cacgacttgtctgaaatttgaatgttcgttcaaaaacttttttttttgcgattttcaaaaccaaagcttaacaaacaattttcctcaagttttcaacgct
ttttgctcgttttttttcgctcaaataaattatttcagaaggttttgca cyp-33B1
SEQ ID NO: 127
tatattcaaaaaaatatattttttttgtaaatgttcttgacaaggtgtcaggaaatcagaataaacattcaacaggtgtttatgtttttttttgtatcattcta
aaaatcctaacccgtgcctgattttcataaaactaaaacactaaatgttgtcaatctgtgaccctggagcctagaataagttttccaaaatctgat
tattaaaaacacaacaacagatttttaaatagatttgagcacaagtcatgcattgagcataagccacaaatgaaataacgagagtgaattttttag
agtctaattgaattgcattagcttttctaaaaactttttttttcggctcaaaatcatttccacaaaaaaaacagttttaaaataataagagttggccttc
agagcggttttgtgtttaacaaattataattcttattgtcagctcgattacgtttttttttcagtatcttcgttttgcttttttgttttttagttactcgcca
cgagagagggttttccctccaaattttcgcaaaaactagcacaaattatatgtatgtaccggaactaacctataatacttccgggttcatgccaaattc
taatttctaaatccccagacagacacgctctcaacttcctccctctttttgtttatgaatgaatttagtttgtgacaatcagctaaaagtcgtgatttt
gaaaagttcaagaaatcgtcaagctcgtgaccacgaaaaagttctagtcacaatacatcatagactagaaagcatttctcgatcaactagttg
acagcttttgtgaataaagattgagaattcgagttgttttcgaaccatgattacatggcttaacaataatacatgcagctcattgagtctatacaa
acacaaaatacgggtctgcgtctaattatttcctacaatattttttgttattattcacaaaaaaacgggagatagtcgacagctctcaaccggttgaa
gagttgtgtcgtgaagaaacaatataaaaacattgaaaagtaataactgataacaacagttctcaaacaatattatagtgatcaa cyp-33E1
SEQ ID NO: 128
agcaaataaaataattttatggttttttcatttgaaaaaaaagttattaaccttccggcgcaaatgaataaaataataaaaatgattaagttattgca
cggcccaattcatcgttgctatacttattgactacagaatatttttacttctatcaacaatgcaagtttgaaaatttccataaataagatttttcttatc
actaccttttttgcttattttcatttttaatttcgtggtctctgctctcccttttctgacctgctgacagtttgaatcgtcttcaaactaaatactcggtatgt
ttgcctaaatctcttgtaagagagtagtctctcattcagagaatttcactcttgttgttagaacaaacttcactggcgtgtattttgggaaaataga
ttatatatatttaagagattaatacgatttctaatttagttgtccatcaaattgaattttttttgtgtcgttttttctgaataaacatctgaaattgattcacc
atttttcaga cyp34A6
SEQ ID NO: 129
ttattaatattattgtatttctgaatgtaccgtattgtatttctacatattgaatcaataaaattgttttgtacaataattctttggctgagactggtcgga
caaattcaatgcaagcctgcaaacttattagactctaatagaaaattttctcaaattggaacaattattctataattccttgccggttttgcagaaa
aaatgtttttttaagaattaaaaattttaattatgttccaattaaacctacatcaatgctctagaattctccaaaacatcaaaaaaatttgttgacaag
attggaaaatctgaaatatttttaattttttaatatcaaaccccccttcaaatgctacacaacttaaaaataaaaacaaaagtgtggtcaacaactt
tcaaagcgtagaacacgcattttgtgttgtgtgtcttatttcttttctacctcttatctatcgtctcattcgcgcgcttttcaattttgggggtaggctg
agttagtataagaaaagttaataaaaaatattagtttctaattttcgagtttctaatctagcagtattttaaaata cyp-34A9
SEQ ID NO: 130
atctttaataattaaatgaataattaattgggagaaacatgtacataaataaaatttccattaaacaatgttcatttgtttaagctggcacagacca
caaaagctgaaaccacaaagttttttaaaccttgttcttttcttaaattttgtagtttcttatcttatcactcgtgtttcttgtcctccaaataattgtgaa
aattgtagttaatgtgtcaaaaaagtcacatataagaagacgaacaacttgattttttgttgacttcatttgaaaaaaaatagaaaac cyp-34A10
SEQ ID NO: 131
tactgaattttgcaaaaatgaggagtataggaaaactcgctcagaaaatcgaaaaaaaattagttccgtttttgtaacactcagactttacaacta
ccaattagaaaaaataataatacactaaaagagaagaatagaaatcagaagaagtcagtatcatgggagctcatgagttaattgcctgaaat

```
gcgtattcccagaaataaaaatgcggtttcttagctctgagatctgaagtgtaagactgccaatagattccatgagattcgttgtgacaaggg gttctgaaaaaggaatcgcgcaaatttatttattgcacagttgtagatgataaagtttcttcagatttgaataattttaaaagcttctaaaaatta tcttgcagctaattgtccaaaaattattaaacatttgaatattttctttgcttccaacaggttttatggaaattattaacaactgtaaaacgttaacgt agaataaagtaaatcgatcttgaaaacccaaaagaaccggccctatattttggcaggtggaaattttgaatgaaatttaataatatagctcctg aacttttaaacgatgatattagatgttgaatgatcaatttccttgtagtcataaccatacggttttgaaacatcataatttttatcgaaatcacttgta aatccccgggtacagctataaccaaccctattcgacaatttcaatttcggatattgtaaaaaaaattttaaaggtggtgtagtcgaatttttttt attgctttattaggttcaaaattgtctgaaaaaaaccgaatttcataatgaaacttcttgaaaacttctcaaaaaagttatgacggctcaaaaaa tgacctaaaattagttaaaatttgaaatttgaccgacttgtcaatgacgcagctgctggaaacaattttttttttgaaattaccgtccaatttgggtat ttaagttaattatctcgcgttttcaacttcattataaagcttataaacagcgagaattttaaattttttttaccaaatctcgccgtccatcgaattcaaa atacataaatggtgttgaaaacgcaaaatacataattacatgctatactcacaatttgacggtgatttcaaaaaaaaattgtttccagccgctgc gacattgacaagtcggtcaaatttcaaatttaaacgaattttagaccatttttttgagccgtcataactttttttttgttgagaagttttcaagaaattc attatgaaattcggcttttcagacactttttagtctaataaagcaatcaaaaaattcgacttcaccacctttaacttagcaattgccaaaattttta ttgcagtacatataaaattagaaacacacaatgtctcaaacctggaattactaggaattttaagaaaatgactgaaaaaacaaactatgccaa ggacaaatttaatgttttttttcaaagtatagcatgtcgaaaatactgtttttgataattaaactgtttaatactactaatttttcacattctcatacgact atgaaaataagtgtaggaaatgtaacctgtgtgatgaacattctactttgccttatcaaattggaaaacctcgtataaaatggtcaacaaaaa atgaaactgatttaacttctgatc cyp-35A1
```
SEQ ID NO: 132
```
aagttcacaatttattcattcatccatgtaaactgtatattttgaatttgtgttgtaaagaatttatcttcgaataaaatgttttaaaggttttaaattg tattctggtgagattgcttaaatagagtccttcggcgataaaaatgctaaaaattatatgaaaaaaactatacaaagaatatgtctcgaagtgttt cattccagatcaaagtcgaaaattagcttagaaaaaggatcttcgtcaaaaccctgatttaacaccaagacgaataggaaaaataaagtaa tttaaaataaaataaattacaagtgcgctccattgtaaaaacgctagaatttgcaaaaactgaacaatatttgattttcgactggaaaaaaaactt gttggtaaattgcatgaacagttttaaaatgtcattaagaaaactgatgccaattttggttgttttctctcgtttaggaaattaaaattccctcttatt tttttagcatgaaccgtcaacgatttctggtcagataaaatatggttattatagtgtgtagtttttgagtttaaaccaatgtttcgaaattttatcagt aaacagaaactacggtttgctgtatataagttaattccgatagcaaaagtagaaatccaaa
``` cyp-35A2
```
SEQ ID NO: 133
cttctgtaataaaaaaaattgaaatgtttagtgaggagagtgatagaaaataaaaaaagccgagactaaacatttccctgtgctgccctgttt ataaacgtttcaaaggaaaattctgaaccctgtaacaactgtcgtcgaccttcgaatagctcaaaaacatttggtctgcttgtggatcgcacgtt tgtttcacaaaattcattgtgatttgtcgtttgagatatatcccttctatcaatcaacatgttgatgccggaacttttaatcccaagaaatctgttaca caaagatcggaaaataccttaattgcttacaacttttattaatagtcgatagatacacttgcttttgacttgccagaaatttaagtatgatgcttat caaataattacattgattacaattattaaataattgaataattgctaactacaactaaaaaattattcgaacttttttgtaaaactaagaatcagtcc gcggatgaatggtaatattgttcaaattcgtctagaaaaaaaaccaaaaaaataattaaaaaatgagaaactgcgcaaaatatatatatttaaa atgaaacacaacgaggcggctctcgttaaccagcattgtgcaaataacccaaaaactctgttcacgccaaagtgctgaaaagagaaaaga ggctggcgtgaagccgacaggtataggtcctgaaaccgcgccccactggttactcgaatttgcgaatcattcttctttttttttttcaaagcaa cttccctttattaatttcagattattgaacattcaattttttttgttgtaaaaatcaattgttttctccgaatagttaagaaaatgtatgttttgaaaa ttatctgttcttgggaaataatagagttctgcaaacaaacttactatcagtcgattcgcctaattcgacccttctatcaaaaacgttgtgctgaatgt ataaattgtgaattttgagtgaaaataactgataagagctttttatcagtcaactgacagtgtgcatgttttgtataaaaacagtccactgatttc gaaaaatcaaatcagaat
``` cyp-35A3
```
SEQ ID NO: 134
ctttgtaaattattttcaattaatttatttgcacatgtgaactattagaaaagaaaagtttacttttatatttggtgctatattggtgataaatctatgc aattggtaataaatcggaaatacgtttattttctgcaattgaatataataaaaggtaaataaatgatgagtgcgagaaatttgagttccataattgt
```

-continued acaagccagggagttttgaaaaataacagaaccggtacctatttctcttttttataacatataacatctgaaaccgacatgttaaataaaaattttt gagaaagaaagttgttaattctcgttaatttgcgatatgtctataataaacctcgtagcatttctatcgactaaaaatttgttataatcagaaaaaa ccatcgaagttttcaagtcaaatttcaaaatactcttcacatcaaaacttgcaaaattaaactcacagactggaaaaggaaattcgaaaatgtct gaagaataacggttttggaaaccgagctgtactttttttccaggaagatcgttcacaaacaaaatcaaatagccataaattgaaatacttgcaca acttaaaaaatacgagaacattgaagaaatatcgatgttcttcaatacacataaaatgttgttgtcatattgtttccatgagcaaatggctgaaat ctgggcaataataatatttgataaatgtccattactcacttggtatagcaactttatgaactaaagaaattataaaagaattgataattataaatgc aagacatcggggtcgaaacctaacgaatgatcgaaaatttggaaatttcaatgatatgactttttgtattgctagtagaaacatggaaacagc gaaaatattcgggaaaacggtatttttgagaatgtgctattagagccataatggactgaacgatagcccaatttgtaattagaatcttacgattta catttctgaaaatttatagatattaactttaaaacatatatgaatggatcttacaatccattaattacaatcaatacaataacattgttcatattaatta aaaataaagtaatgctcattaataaagacatcaaatgattaattttttaaaatgtgacatgatttatgtctcaaataatgtgtcttgttgtgattccatg aacggcagtaaaatataaaaacgatactatttgtagaagcaaaaaccatcaataaagttatttcaaagtcaatatgacttgttgctaagttctga aaagtctgaaatacttgcatagcttaaaagcgtaaaagtgaattactatgcataagtctgtgggcgaaatgcatgtgacaacatttgcacctgt ttggttttaatagcctccaaatttaagactatgaaaattcattctgcggtccttcctgaacaatggcacgtccaaacgtctacaacatttgaatat ttatatttaatacaaaagtagaccataaaaatagaattaacatttttttgatcgacaatttccaaaaaataacaaaaactgagattgttccaaattt tttttccaaaagttatataaaattttaaaaaaatttcaaaactttttactatgatatatttacagccccccccccccacaaaaataacggatttcatcg ctttgaattttaataaaattttcaatgaaaatttatggaatagacacgggaccaggcggaagtcttgatacttttggtactgtgtaccaaccaaa aattgcagatacaaaagaataaaaacattttttttaaattttttattcaattttccgtatttttgaaccacacttaaataaactctatttgaagcaca gtcttatttccgtgttttcatcagagaccacagttccttatccttgcgttatcaattttcattacatctttacatcaaatcttttgtggcaaatgtacaaa atgtacattttgaagtaaatatacccgataagaattagttatcggtcaagagactgtttgattgctttatataaaatcagatatttcaattttaattctc aaatcgaa cyp-35A4

SEQ ID NO: 135 ttgtcttatattttattaaaatcggggcgaagccctgattttaaatccatattgttttttttgtcttccactatccctacaaataggaaagagaatgtgt tctttctgatgaagtaaaaacggcgcagccagccgacagccgaaattttcacgattttcggctggtagcgccagccgaaaaattaaaagaa gtcggctggcggcgccagccgacagccgaaccagcttttttgtcggctggtagctttaaatttttttccagttttttacagaaaattcgtccagtt cttacagaaaattcgcgtttctatgtttaaatttgataacatttgcagtaacggagactgctgacccggctgtttcccatgagaaaagagagag agagagagaggggggagacagtgagatatacggcagagacatagacaggggagacaccattagagatcgtctcctatagagtgctgccg gcaggggcgttgtggacctgtgggaagaaggggggagacaaccgcacactgtgcggttgtaaatgcggaataatccatttaaaactaa ggaaaatagtggtctaatgcttaacagtgagccgcctagataaaacaaaaaaaagtcggctggctgcgccagccgacagccgaaattttc actattttcggctggtgccaccagccgacagccgaaaaattgaagtcaatcggctgtcggcgccagccgacagccgaaaaatcagcca gccgctcagccctggtggggtggcgatgtgttggcagccaacccttcaacgaactgtatctcccgcctgtatctcccttcaaagtgagatcc tgtaacagtaattagagaccatatttacagccagcctacatgcatcactggagactctgtggagagggaggaggcaagagaaaggggag gcaagaggggcgggcgggcactgctgaaccttgaaagcgccgtagctccgctcacaattggaattgaaaaatgaaagtatatatttga agtcaacgttaaaaggagaatatgatagcatttgaaattttggaaattggtgaagaatgaaaaaaaaagcctctggagcaaggcttgaagct cacaacttcaggaacggggctcgaggaactcatggccaaaaactttttatttgtctcgcttctcatagcaaaaataataagatttaaaacataa aattgattatccaacaaaaactggtccaggaaaagagggaaactgaaaattcgaggtcaaaaattaaataaactaaaattgtgaaaatgg tcgtagagagctgtgctttcagctggcattcggaatttatgcacttattacgaatttaacataaaatcccatttgatagtggaaaaatttttcatttt ccagcaaaaacgtcattttttgagaaaatgcagcaatttgcgatttctgaagttatttttaacttttttgaaaaaaaaaaatatttttgaagagaaa atttcctgaaaaatacgttttcaaaaaatttacctcaaaaagtgccaaactgaccgacttatgacgaaaaccatcaaaaatcgctaatttgc acaccaaaaaaagggggggggggaaatgcaattttcgatttcacactaaagagcccacttctatagcaattttgagtttcactcaaaat atctcggctcaatgagctccaatctttctgaaaacaagaatacagaggtggggcaagcttttgaagagacagcaaaaaactgcatcaaaat ccatccacccaccgtcaagttacacgcgcgttttcatttaccacttttgtcggattttgaagcttaatatctcggctcctgtaaatcgaaatcggc

```
tgaaaattcacaagaaaacttacttcactacgatcctcctgtcattaaattttcgtgagcttagaccgaaaactgacaaaacgccaaactttgct aacgctcgccactgacgccaagccttcagacacgctttcactaaatacagtctattttccgtgttttcatcagagaccacagttttaaaataat gcgttttcaatttatttgatgtgatttatacattttcccatcagaaatgctgtgctaaatgtattcaatgtgtctttttgagtgaaaccactcttaattat cagtcaacagataatgttgctttgtataaaaaggattcatcgaatttgaaattttcaatcaaa
``` cyp-35A5
SEQ ID NO: 136

```
ggccaaaaatagtaaaacttgatcgttttctgccattgaaaactgcgttactatcatgcttggttttggggcgctggtatagaatatgtgctca aggaagtgccggatatcagaaaactgatagttttgatcaaaagttgtgtatgcctgtctttctgtctgtctgttgacactccctccgagaggca gccagagcctcagagtgacaaatgcgaacggcagacggaatggaggaaaaggatgagcggtgctaataacagtacacagtttgacgaa aatccaagtttattgagcagggcagctttaagctgggaataaacaaggcaaaaacgtagagaatatttagggaattgggcacgaagatcag caacgagcagccatggcgttggagaacgaagaaaagaagtgaagaatggctacattttaggccagaattaatatgagcaagggaataa acagcgcgcgctacgacactccgatgtgtacaatggcgcgcgcttgcatccttggcggcaaattcaaatgagaattatttaatttaattaattt aaatggtggaatgattattaaagaacgaacaaacggaattgtgtgagtaaattaccggcggatgattatcgctggattgtgggcaattcttgc cgataattataatccgcaaagttggggcggaggacctctactgaggccaagtcacaacactgtctaccgtctgtctattctatatctagaagat gtcaacattcagtggttatttttagtaataaaagtgtaaaacaaaacaattcagatctgcaaagctgaaaagtgatgaaaattgatatcttcaat tataatttatagtacttttttaataattactctaattacaccccactgctttactttgaaatctcatatctcgctccattctgaagtagtcaactagaaa cggtaaaaaatccatagaaaattgttttccaggtgacaattttaaataaaaatggggtgcaatagtaatagagcaattatgctaattttgtgaa actgtagtttcaatactttaaactctatctgtacgttgttctctattgaaaaatacataccagatcagttatcaatttcatttctcatatgtcaatcgct attaattttactgataagaacacgctgtgtcagttgtgtcagttgtagttgcaacgagaaatacaatttcttttgggtttcttcttaagtttctcggc ttgaataatgggaaaactaattaacagttgactaaattatttaattttattatcccgcccttaaaaagttacccaaaaagatttagtgaagttatgtc gttctaatataatacttcgaacaacttgtgtcagttgtagtcagttgttaaaatctaaatttggtgataagatagtcgtatcactagttctgcaacgt tattatttaaatagccggagattgacaaaaatattcattcataatttttaaaaa
``` cyp-35B3
SEQ ID NO: 137

```
tctttaatgataatttatgggatctgtatttctctttctgtcaataaaaattgaaaatgattttttacattctcaatattttctaaatcatgtttcgtgaagct gaagagtaaaattcgacatttagaaggtttcgttagaaaaatgaaaagtgtagtgccagaggggactttatctaaaacaggcctgaaggttc gacccgcgttacagttccagtctaaagtaataacactaattcaaaataatatatacgaaaaaaaaacacttgaatattatttgattttaaagattt tcaattttgaaattatcaaatttccttgaatttgggaattttttgaagaagtttcagatgcaggtttgaaatcctagaatgtgcaagtatgaaaactg aaacaaaatgtatttatacgactttttggtcactgccaaacttataatcggtcaaaactatgtttgcacaaatttctaacattaaaaataaacgatt ttaatttttttttgaaaattatgcctgtatacatttcagcattataagagcgttttaagcgattccctactgatgatactgtagcattctaaaattattg tagcttaatagctatctaatttgtaaaattaaatttaaaaaaataaatttgaagtggatctattagaaccttcatacaatatttcctactcttttaaattt gaaattttctgagtcagtgctagtgatagatagaatacatccattccgtagttatctacgctttcctcttggaatcaacacatcaaaactcaaagt acgcctttattaaagaaccgtgctttgtagttttaaattacttgcttccattgtttgtagcctttccttataaaagatagcaggttctgtttaactatctc aatttcaaa
``` cyp-35C1
SEQ ID NO: 138

```
attttttgaactaaataatatttcaaattgcacccgcaaatatcgtcacttttataccgataaacaaataaagtttagtgatgacttatgataagaac ctctttgagtctatatgtacgtgaaacaaacgttaaagaataacggctttacgtgttagtcattcataaaatttcataagttgatctggaaatttgtg ttatggacgttacgccattatttctcgtcactcaacgtctcgtcaatggtaattgtttttcagagacggtgaatcatgtttcagttgatgattttagg aaacgcatgccatgttgagacaccataataatttaaattttttgtgggtacctttttattgggattttctaacattttcagtcagaacttttagtagaatttt tttatagatcttttttttttcagcttaaaattagtgttctaattactgtttaaaaaatgaaaactgaaacgtttgatgattttgttttaaaaaattttcaat ttttttcgatatgttttttattgattgtaagatcaactcttttaaagtttacttttcattttttgttaataaataagaaaattttaccgactttttagaaat ttaatttattgaaaaactgataaacgtcttgttttgatcaattttccaataaagaatacttttagcgttagtcacaacatatactcaaatgtgtcaaaaaa
```

-continued caatgtttcgaacagttttattgttttttttagcttcatcccgaacaactaaaaattgacttttcccgataacttaagacgaataagtttaaaatttgaaat ctagttattttttcacgatttttgacttttgttctgtccgcgccgaatctgaaacttgaacactaattcaatgtacacataagaatagacaagtagtga atatgcccattatcacacagactacatactttgactgttccaagcgtcgcaagcgtcgcaagtgtagcattttgagtcagtgataacaatgtaa gaaagtatataaagaacatgcatttgttcatttctattgcaaaaca cyp-35D1

SEQ ID NO: 139 tgattccaaatgataattggctagtcttaaaacattttatattttagggaattcgaaatcaaaactatgcacgtcatatcaaaatcaattttttgttcaa tattaatgttatttattcatttgacagctatcaataattatatttattaaaatagctgatagaactatttagggcattcacaaacatttcagaatgtttcc gaaagttcgcaacagcggattcgccacaatgcttcctcataacccatttgtaacaccatttttcaattgtaaacatgcttgtcaaaaatgcagta tcattgggttgcaaaacataactcgggcatttgtatttaaatatattgaagttagaagaacggagctttgacaaacaggcaatgaatggagttt gtttcaaataaatgaaatcacatccaacaaaaaccaactctgtgtatcaatcgcctcttggcaaacatttatcggagaaactctgaaacgggta ctatttctagtttagttttggtatatttcacaactgaacaccttcacactgtttacttatttccactatatcagcattatttctcgagttccgataatcgt ccaacattctatgagctttatctccaaactggctatatcgtaaatgcttgaaaaaataaaaaggatcatagcaatccgactcattagcaggtgtt gtgggaatattatcaagaaatgcgttgtaattctccgtagtattttctgttttagcttttcacaaatgtttcttatagtatccgaaaagcatgtctttc catcttctaattgatcactgatatcatcaatctgaaaatatattagattgatttttgctgagaagaacctcaaaaccaactatgaaaaaatcatttagt ttgatgcagccgtcacggtagtttaacaaatgtgtacaagcaacttggacacaaggacgagggtcattgatgtagtaagattgcaaaaaag gaactcagaacagtaagaaagccaaagttaaaagcattgttgtcctgaaaaatccttattagtgtgtgataaaaataaatttcacaagttggac agttattatttcacaaaataaaatattattttgttgtgtgtactttacaattgacgaaaagatcaaaccgacgcaaaaatgatcaatataatccgttc atatttgtttggtaaagcattttttctgctaatcaaaaactgttggtgcaaaataatcgcacgttttttcgttttttttttaattttttggtctcaaaattaca taaattttcggaaacatttctaacgctgaaaaaaacatttaattgtgtgaagtgtagccgtgaaaatgtgttaggtgttgctaccctcttatcttca atcttatcatgttttgtctcctttataaagaattgccggtgaacttgaagttcagatgtataactgtttctatc vem-1

SEQ ID NO: 140 tcccttgttatttgattttttaagatttgcccttatgtcagtgtcttctgcatgagtacatgcatatttgcatattattagaatgttatgtataaaagaaa aagagagccacctcttaacgataatccaatttcttgttacgcagaaacgcctcgttttcctgtggacttttcgatatcttcaacatgctgctattatc actcccatgacccgtttcctatctgttttttatttcgattactacacatctgctagaaacacacgtcacgtgtgatttgtactcaccgttttctcctttc atacttttttagcctacaaaccacgaattgctttgtgacttgactcaattttctcccgaaacttttttttcgtcctcaattcccactacccatttcttgctt ctccctgttgcaatattttcaatttcccatccaaaaacggcccgagcacgggttttcttttccttttttgtaggttcacttcttcttttttcttcttcgtttct atttttttacacaatcattgttcacctttgggcaccccagtgaaacatttgtttgataaaaattgtgtgttccacggcactaaccacaaaatctttgc tacaaatactactcgtattgtttgtgatgactgtggtgaaagtaagaagaatcgagagacattaggggacaaatataaaatagaaacgataag gcgacgaaaacgcacattcttctcgatttccgaccgtcaatcgctgagtgaataattgttgacggcaactgggaaaatctgtgagaaaataat gtaccatgttttcgaatttctaaaattagagataatttcttccgttttctcttttacatcttgttttcttcattttacaacaaatccttcttctttctcttaccg ctttgtgcacttgcactgtaaatgacggcaacttacggacctagcgttcgacgaacacagtcaaggacgctcacacatcgtcgacgggttc acctgctctgttgcagtgattttttgatgttttttattggtgactagttttttgacttttttacaaa dhs-23

SEQ ID NO: 141 atttgaggactgggatgtcattaggactgaaattattctaaattagataatatattttaaggtaaaacgtctgtttaaattatttgtataagcaacaa aaaataaacgaaaactaaaattctacctgaagttcaggtcctgaacaataacataaaaaatttgggaaaacacgaaaaaatcaaacttaaaaa attaattaaaaaattaaagattaaaattaaagattaaataatctctagaacatagatctctaaaacacttcccgtagcggttcatttttgttcgagtc tgactggcgttttctatgggaaacagaaaacaacacgctgtttgctcagtttcgagaattttggaattcacagacttattttgttttgccgtatatg atcttaatcatagacatataatatttatgacaatgctttgctataattctgtgtggtgagcgttcgcagaaggttctgcacaattcttttcaatgaaaa aaaaaagaaaattataagaacttattagaaaattataagatgtagaaagttattcataaagttagtattcccaagaaaaatcataaagaaagg ttttttttcaaggtttttttcagattttggcgttgttcaacttgtattgcaatcattattattgcgatcattagtaatttaatataatttgctccagagca tttgtaagcaatgaaatccaattttccctctgtggtgtttggtttagaaacttttgcaatttcgtcttgatgtgccgcggcatgccgcaaaaatcata -continued ggggatttgatttcccagtagttgaagttggcagagttaactataaggatgacctaaaacaagttttaggctacttgttatagacatggacttcg atttctaatttggacagcatccgctacagtgaaagtctgcgcgattgatttcaaactctctaaaatcgaacgagttttcaattttttttttcaatttgat gcctaatttagtgaacacggtaattatagtttcttgtatataaaacccgtttaactccttaaattactgtttacgtttcgtgttgtaataaacgatctct tgatcttcattcaactatgctggcacaaaaatagacacaattcgaagaggcgcagagggagtaacagacacaaaaaatgttaggacgtctg cgatctcgccggtaagaaacactgaaaatactctctgcgtagtcacgaaagctacaaactttaatgtattcaaccaaataatgttaactgtata aaaagaaacaaagaaaaaaagtataaaaagaaactttaaaccaaaactaatcatcagattcaatatcttctatctgtttgacattctatttctgt aagctcgaaaat sodh-2
SEQ ID NO: 142 agtagagtcaatatcttgaaatgtttagaattctcgcgtatctcacatgttgaggtgagatatttgtaatgaatagtttcatagtctttggccaaaat atgattatacgttaaagcaaattttgatgttacgccgtttgaagaaatgtttttagcatgtttaacagagattcagactaaatttattctacacagttt ctgaagggatattttttgccagagtcaattttcttgtaaaccagtgagccttaggtacatagaaaattttgaaaaatatccaagaataaaatttttt ctgcatgccttattctgggcttatttttgcggttttcaattcaatttttatcgtatttcaaaaaattaaattagaacaaatgcatattcattttttacatcctt ttctaattggtaattataatttcaaaaatcttctttgcttatcatttgtaacaacaactacaaaaactgtactcgtagttttatctaaccgtattctttga ccgcatcctccttttgaccattcaagtaaaaagatgacaatcgccgtctacatattgccacgtgacgcaaattacttataaaaccattcgtata aatatttcattgatttcttgaattcaaaaagc ugt-16
SEQ ID NO: 143 cccgaattttttttatcgcagaaaaccaagatggaataaataaatggataatctaattaaaaattgtaatttactatttggaatcaaaaataaataaa caaatcttataatatgtcagcaataaaaataataaaagaacaattgaaagttcaatgtgttgtcaagaaatccattaaagtatcgtcatcaacgg ggtcatcaatttccatgttgttgttattgtcttccataacatctatttccatgaagtcttagagtactgacaatagtttatttagtaaattaattttttgag aaagtttcttgacacattgctttgagactttgattaaatcacaaatgactcactattatcataatttctatccaaaatgttgatttcatttcaatttcca ttgaatcagctattccattacatccatcagttggtttacaaaatgggaccagtggcctcaatatctgtattttcttccttttttgtgaaaatcgtacttt tgaaaatactaatggattctcgttctgatcgaaatgaggaaactgtgctgttttctaagaacacttgagacgtggattttctttgttgttcttaaata cgaaaatcaaatttactgacaaaatatctaaaacttacaatcacttcgttgctgtagggataatcacaaaaaatttgacatgattttctggttttcatt ctgaaaaactgggagcattttaatttgaaaaaaacgaaccgtagtctgccccaattgatttgttggtaaaggaagtgaattaaagcgacaagg aatacatttatctgttgaaagtgaatgcatttttctggaaagacggaataaattgaaattaaaacaatattcagttaaagggaaactgaattatcc caaacccgggttatttcaaaacggaatctacatcttactttaattctgattgtcagccctataacaactatttcatctattcaaaaagatacaaaaa taaaccaattaacattacttcgtagatacctcatcacatgaccaccctctcaagttgatataattaacttttctaaattgaccaaaagtgtttgctaat gtgtatagggtatagtaaataggaaggagttcggaagttcgatgagagtaaatatcttttgtgaaatatctattggaaattagcggaaaaaaga taaattttctcctgaagtgcacaactaataacgaatatcttaatgtggaaataaatcaaatcaaatcaatatacatcccaatcatgacatccaag aaccccacaaaaatatgttcctaaaaactaactgataattaatttgaatgtttccaacagaaccttgctcgcttttttgcacatttttccactttgtttc gctctacacgcttgtattttttaattaattatattttttcggcctcaataaaaaattaaaattccagattgaacacatttaatgtcagaatataattaca gtacctttttatgacaaaacatatttcggtataatctcagatttccacttcttgtttcatggcccaagttttttctcaatgctcacttgtaacggaaaat ggagtcagtgaagctgttcaattctagataatatgatgctatcaaaggtcttaaaatttagataaaatgatgaaaatgacgacattaaagtgtag ccttactgaaaaaccaattattgaactttaagaaaaaaaacattttggaaaataaaggtaattcattttttcgtacacctaaaatttgaaaaaccg aaatttcagtgagaacgtcttcaactgcatcaaaaaaattgtgaagaaaatcgaattgaaaagagaggctaaattggcttcatatctttaattta gccgattatacacgtcgggccagtctttttttaaatgactgtcatggaggacttgatttcaagattggaagtgatgaactacaaaaaatatcaaa caattttttaactgcataaaaacggttttttctccgggatcaaagatgttttcggtatcaagtcacattcatggttcattaaaacatactatttttctagt cttaaaatgtaatctgtataattttatgttgttgattgaactcataatatgacaggattttttttgtgatttctgtaatgaagtacagtcttacacgaaa actagagtaatacaagtcataaattttattcgtctttttttcccgtagtcctttcaataatgtatgaaaagcatttacaaactacaactcttttcaaaaac tagagttcttatcatacaaaccacacattttttgcagctctatataaaccaactgataatgaggttttgtctactctcattactcaatt ugt-63

SEQ ID NO: 144 gtgaataccacaactgaatgtctcgaatatggagccaatgattcggaaatctatgaggaaatggcatcgatttgcaagtatattgtacgggatt
cgagagctcacggggactcggttccagagtgattttttgttgttcgccaattttatgattgtttcttgttgttaagttttctaaaaaataaattctttgat
tttaataaatttcgaaaattcaaatattatggggacgccagggaatcagggtgcaaaggcgctctaacgccaaatgacaaccgagcattg
ggtctcgttaggaaatggcggcaaacgagacatttaaattttttattacgggaacacaaaattctaataatgcgtattgcacaatatatcttacg
cgctaagtatctcgtagcgaaaactacagtaatttttaatgactacgcttgtgtcgatttacgagctcgattttagagatgaatttattttcgaata
gtgtcagcgatatttcgctttaatttcgaatcgagcccgtaaatcgacacaaacgctacagtagtcatttaaagaaattactgtagttttcgctac
gagatattttgtgcgtcaaatatgatgcgcaatacgcagtctcagaactttgtgttcccataataaaaagtgagagttttcatgcgcccttggag
cgctactgcacctcaatttcaaaaaacgcattttctgcgtccccataatacaccgggattttctttctcttcgtctgaaaaacaatcaatcatca
ttaaaatcatcatctatcaccaatacagaatccatagatcaaacagatcaaaaaaccaacttgaacgcttgcaggcaactacgataaaaatat
attttgtagtgtagtcatcatatcaatcatctagctataataatgcctgccgtataaatacaaaacacgatgatgatcttttgcgaaa gst-5

SEQ ID NO: 145 attagagaacttttcgagaagtctaccgttgtagttttcgaaatagtaatttatttagtgacgtttataaaggtttacatgatttggtttggaaatttttt
aggagtttattcataaaaacaaagtaaccatggacattccagaagtctatagtacacgcgatcctaccgtacccttcagtatttctatcagattg
atagctttcggtagtcaggtacagcctaaaaaattcctgcttgccttttttgcctacatgtctgcctaccttcagtcataatgcctacataatgattt
ttccaattgaaacttgcagacagaaattcaaatggcaaaagaaacaaacaccgaaacattaatcacatttcttttcatatcagttttcctgtcaa
agcacatttctggagtctgtgtgtatttttttgtgtcttatgtgatcggtgttgtgaaatttgtagttgatgttgataacatactttttttttgaaacaaa
aagtgattgattaggcttgaattcagagatatgttcgtgatactttgcgattctcgagccaaaaacacggtatccggtctcgacacgacaacttt
ttcgcaaaatacaagctgatgtgcgccttgaaagagtactgtaatttcaacctttcgttgttgcggaattttcatagtttctcgttcaaaatatatgt
atttattaaacaaaaaactaaaacaaaacaattgagaacacataaattgtgaaaaatcaatgagaccacagcaaaaaattttgtatctacagta
ctctttaaaggcgcacatccgttcttattttcagcaaaaatgtcgcttcgagaccgggtaccgtatttttttttgtgcaaaactttaggtctaggta
atattaaaaaaaaattccacaaaactagaatctagagctttccattaaatttttgatgacatttgaaaattcatgatgattttttttccaacaatttcg
aaatatccctcttttcacctggtccactgaattctcttccgaaagaccaccacaatttcagggctccgcccatttcgtggtttgtagccttcccg
accctacgttttgatgacaattgtgagagaagtgagaggttcagacacaaaaagcgacgtggtcgaatgagtataaatagagagtgaagtt
tccaatttccctcacaattgtttgtttgcaatccactttccaaaaaaacacaacttcaatcaaaatcatt

T16G1.6

SEQ ID NO: 146

Gctaaactttcgtattcgactgataatgagaacgtggaggagtatcgtgaggttctcactgaaaaagctgaacgtctcatggaagacttaaa
gcgatggcacttgtacagtaaagatgtgacaaaggatttagaaacggcggaaaagttgactttatgataagaataccgataaaattatgaaat
ttctcgaaacttttgaattgtgaagcaacttcttaataaagtaactcattgactttaattttttaaaccacggcttagagaaaattaaaaatcaaaca
ctgcagcttttttgatgcgaaaattcattgatatggaacaaacctcaaatttgataaataatacaataatttgtcaagaaatcacaaaaacgttctt
ttgaaatgcaagttataagacatacgcaagatgttatgtcggtggctggttttaactataaaatacgaaacaattgacctcctgacacaaaattt
ccgagcttgatttgtctgatatcatttgtgctttggaattattgtttcatgtgcataaaatctacactgtgttcattcacgataagaagaatttcagac
agaaaccacaggaggttcatcgatataaaatgctaatcatttgatttaaagaaccatactcttttttactctcgtcgttaagaa Cell Division Toxicity Genes mei-1

SEQ ID NO: 147 cagctatcccgaattctcgagcgacatccgtcatctgaaagagatactaatgtcatgtgaagtggtattaaaaatatagtaagcacggtagaa
acattaacttataaaattgagatttctgataaataaaattttttccgggagttctgtaaaacttcttacggttttaacttgataattccatagggtttaaa
atttcctttttgtttcttgagtttcttctcggaatttgaacaaaaataacgcgtttaatctcgaatcagtacaatgatggactacacggcagttttaaa
aaaccaattaataataataatcctaaaaaatgagaagaatatttaagaaaatgtaaaagttttccgcggaattccgctaaaattcgaaaattgaa

```
agtgttcaaattgcaagcgattgtgcattcagacgtgacagtgtctggggtgtattgcgtactcgacattttaactgacgacacttgtacttttgc gccatacttccggagctccagctccgcggagccctgagcaattatttttttacttttatgaaaagctttctatagatatcttttaagaagttacact ataattgtgcaaatcaaactggctccggacaacacaaatttcgtctatacctttatgatctttttttgttaaacaagtgaaacaattatttccttttca aactgctcttgtttcttctctttattaatcaattttttttttttgctttgtgtaaattaattgtttgtcgcggatgagctaattctgagtttgaccagcag aaatctgttttctgaaaaatcaataactcgccgcttaattttggttttattcaagtgatatgcaattagaaggttctaatcatttatatctcgctgaaa gatctcagatttcaagccttttgctaaggatttaattcctaaaacttttttttgacctatcatttttgtgtgatctaccgctgtaaatacttgttgttttgc ggctaaactctttcaatgtttccaacaagtgagccaatatcaagtaaaaaagaaaaatcgttttctattcaacatttatttctgtaaataatatta aattcatcttcacggtacaatcttcttctcccatctaataaagtccacgcacactccgttccgtcgtttccctattcgttatcattcatcatcttgcca ttttcttctccgccaaatcccattgtcttatactaaatttcatcctctcgtctgtagaagtgtatattattgaaaaattaaagtatattttcagg
``` mei-2

SEQ ID NO: 148

```
cgcttcattttccaacaaaccaagtactggagccatttactataagaactaaattaaatattaaatatatcgtttcaagaattcattggaatgagg caaaagtaaatacttaggattaaaaaatccagctttatattaaaaactttaaaggcgcatatgagatgttattcgggtcccgcagcgctcatgc ggggtacgatagtacttcaaagaattacgcgggaatttcttttatgcgggaaaacggttttttcttgtttactagttccttctcttcgtctaattttgat atcttgtgtttttttccaattataaaatgtttgtctcttcttaaatttgaaattttgaaattttcag
``` mel-26

SEQ ID NO: 149

```
ctctccttcttttcatattctgtgtccacttctcactcattgaatcatacatctctatgttttctcatagtcatcatatattgtcagctgcagaaatctcat cattttccaaacgaaaagctcttaagagaaatgcttgttttctgtggggtacagcgaatggcttctgtgggaatgcagtttgtgaatgtaaata gattgttatgcagtcttgcaaatgtgtcggaggccaaaagtagagtagacatatttgaaatttatagctttgagtgtccttagtctattttgatattt catttctgctttcctcagtctctcattccagctgcaaaaaataaaaataagaaaaaaacacgaatcccgtccattcgccattcaacatagatcata ttcctcagatttttgcagaatatgtaattttgctgaatgctcgctctattgtccttcattggttatcaatcttttttgcattaatagctttaatttttgatgt tttcgaaagattagggaaaaattttttaatgtgtcttttgtgacttgagattatatgctacactgaaaaaattggtcgcataacatttcagagttcaa agtgtttttctttcgattgtgtaagcggcaaaattctactttatcatgcattttttgtttcaatcaaaaatttgatgtgatttgtacatggcgtcggtttg gtactagttgtccacttcctcagccatgaaaagtgtgagtaagtgataacgtttattatcttttttgaattcattctatgtttaagctacacgtatttaa ctagctgactcatttccaccaaatatgccaaaagacctccgagattttttttttgaagataaatttcgatttcgcagaaaaaaaaacatataagtgat gtgggggtgtgtcgccttcttcagctttccatagtgaaagtttcgtaaaaacaagcttgctatttcattttttccccgttctaataccttgtcgccca gaaaaaatatttatatgatctttttcaactcttttttttgtaaaaatggccaaagattagctaatatttgtataccatcaaagttctgccaaaatctcgtt gaaacatccatcgtagaacactcattgggttccatcaatacattttttgtgtaacatcagtcgattgttatcattcgtatatgcatggtcatctcaac cgcccttacgacgtcttcaaccatttctcttctaactctctttctctcaatttcacttctcactactctagtctattcaattctttgaaaaggcaaaaa aaaatgcataaaaagatgaagaagacattcaacagacgggtgtcttcctttattttattcaaatcaaaacaaatggcgaccttcttattcttctctt ttgcccgatgattcattttctttttccattaattttgttatctattgctgaataacccgctttactgaatgtgtggactggcatttgccacgttgcatttt ggaaaagagccgatgtagttcttccgggtatatgtattcacagaacgattcataagatcagacatatagacataaaattcagcgcattctgcct tgtggtttgtcaactacttccgtctttttctgcatattcatttcccgcttctgctgtcttgttcatgaactcttgaactttgcactttgccctctttttaag tttctctcgattgatgcagcagcagcagactgtcattcatatttgtctagtgatttcgtaggttcaaacaacttattaagcggtttcacctaaatttt cgcatcccaaaataaaagttcaattgcgaactagaagtacccagaagcgaaattttttgcttcaaaaatacggtacccggttttcaacaaaat cgttttcaagtgacatgagcgattttccttttatgaaaatttctaattcaaaaataaatatttgaaataccttttttagattattatatttattcttggta ttttctctattcccactaaaatagactgatacgagaacagttcttgtttgcgcaaactcacattttctctctctatctctccgtctcttcttccgtatct ctctgacggtcccatactctctcactcatcgtcagacaccaccacttatcgatctattttcgacgagtgagcggctgttcgtcgcatgttttttttat aacttgattcgatcaatttcatcatatcttcttcacttatttgaatttccgttttgaacatcattttttccgtcggaaagttgaagcatttgtttgattttctc ggtggaagattagatttcaaaactttcgaaatttaacaatagaaaaagagaaaaagtgtagttattaggaaatattttagacaattttgttggca attaattgaaattaatttcttcttttctacatattttaaaaatgtatcttttttttctatttatatttccttttccggggatgagcgacaattattttcggcagctc
```

-continued

```
tacaaaatgactgcttgagataaaatttctacttaaaatttattgtcgaaagatagaaaaatgttgcctcaaactgtaattttgtcgagttgcccaa
aataattgtcgcacacctcagattttttttctattattttttaaataattaaaattacagtggaa
``` cul-3

SEQ ID NO: 150

```
tattttgacttttgaattttggaggttttcaagaataggcaaacgttttggcatcttttttgaaaaaatctgattttttggtagattctatccactttctaa
aaattctacatgctctgaacaaagtggaaaatacactgaaaatttcagatcgaagtttcaggtgtttgaatttgtgtaatagtctgaaaaatctga
atataagctttcaaatgagacatctcgaagaaaatgaatttgtgaaaaaatccaattttttttctaattcgagcacaaaatgatgtcggtctatcac
acctccttgttgttaggtgaataattgttaaattcttaatctttatgatataacaaagataggcttctaactacgtcacgcctacatattcaatgaaat
tttgtagtgctactactatttgtgcaagccggaatatgaatgtcctttcatttttttttcgtcccaaaagtatataaaatatctcacgatatactcagag
attgggcaacaaagttcaggagaacttttgatgcacaccggaaataaaagggcttcactgctttttttgttgaattcatattggttttggcggga
aatattgaatcattattgactttttgaaacaggaatagacagtattttttcgtacggaaattcgataatttccgaaaatgttcggttgcctccctcg
cccccctttgaaattacaggagactaaaattcgaagaatgcgtattacgaaacgtatacgcgcaaaatatctcatagcgaaaactacagtaatt
ttttaaattactactgtagcgcttgtgtcgatttatgggctcgattaaaattgagcaaaaaatttagaaaatactatgcaggcgcggaggaaaat
aaaatatcgatatcactattcggaaacaaattcatttcaaaaatcgagcacgtaaatcgacacaagcgctacagtagcaattttttaaaaaaatt
actgtagttttcgctacgagatattttgcgcgtcaaatttgctgcgcaatacgcattctcagaattttgcgttaccgtaatatacacggtgaagaa
cacgagccaccaggagtacggtagccctgactttaattgcaaaaaaagagaaaacagtgaaaaaaatctgtatataattgctattatttttaaa
tttcgcaaaaaaaattagaaatgaccacattaattttgaattcctgcgcgaatgaattctattttttgcgtattcctgcaatatttattggattttctctt
agcctaaagcctaaaacgcagaaatttcgaataataaattgaccattttttgaattattggtgcaaaattgagaaaaattgtgaaaaattatacc
atttttttgaacaattacgctcagcttactaattgtaagattactcagatttatggcaaaacacgattttttacgccttcaaaaaatcctagcttttggc
aaaacttacaggaaattaaaaaattcagaataaaaagtaataagatccaggaagccatgactcgaatcattgtagttgaactgtatgaatgatt
tgatcccagcttcttccgccaccctaaacaccccataatttccgttttccgcttgaataggaaatgttgtatatttctgtactccttcctgaagtatt
aaaactcgttttcgtttattaaactgtttcttttttcagatcactcaacttcctcttctcaacgtcaacttcgactcggctaattataattttatttattt
ttctgattttttttaaaattcttgttttttctcaaatttccaatttcaacatcatcttattttcaaataaaaatatttattttgcgactttctattaatttga
aacagcgaatattgttaatttattaagtaaatttaatcattttagatcgttttcaaccgattttcgagggctttccacaaattttgtacttttaaataaatta
aagtttattctaccgaaaacactatttatttttccacgtggacaccgccaattttctctgaaaattctaaaattctggttgaaaattaattttttaaagcttcct
cacgagaaaagcgccaacgcacgaggagcgcgccagcaaacccgcattgacgcagtctcggtgcacttctgaactccaaaacacactg
ttcccgttcgatttttctcgcattttttcatagttttttttcgaaattgaagctttaaaggtgttttagacttgattcgaagtgaaatattgattgattgag
ccggaaaataggcaaaagttctggaaaaacgcgcgaaattaaaattccagtgactttcgagataatgatattgattttttccgagtaattaagt
tgatatccagctatttattttttgcgtgacattctaattaccggattttcaaagttttttcgaaaaaaaaacaaagcaaaatcgatttatttcgaattac
tcgcgacttctcaactttgaagctgaaaatagttagttttgtttttttctgttatcagtgcgcgctttttctgcaataataacattccgcagtacgattttt
ttcaaatttttttgcttttcgagaacggaaaatcaagtttatttcagtgtgcacgaaaaacgagcgagattctgacttgaccagttcgttcggaatc
gactcatttttggag
```

Cell Cycle Toxicity Genes cki-1

SEQ ID NO: 151

```
gatctgttctttccgaaaagaagtagttaacaggtgcggcttcactgggtggtctcattttttcattttaacctgttaatttattccggcttcacctcta
atccttaatgacattaacatcttcctaatgtgtctaagctttcccacggaaagctaatttcctctctcttatttttctcattaccgttctggttgagctt
catcttataccgtgaatggtttcataattacgtgctacataatttgttatgctggtcgaggctcaacgtttcgaacatctggctctttttccttcagct
aaccacaccactcttcgttacaatcccttctgcgcacacatatcctatctaccagccggacagatgctcgtttctcggtgcaaaacgttgaga
gttgagatcgagcagccggttggtagttcttaatgacaaattgccaagacttttctgaattattttaggatttaaaacttttctaaagtattacgat
agttcataatttctttcttttttaaaaattggctcttttttgtaatgtatggtatctaactaaaactaggcctcatttccataactattctttaaattgagtt
```

```
gagctcaaagagttagacagaactggtgtgaatcatagaacccacctgtgttttctttgaaaaatgtcggtcacttagtcgtctctctgt
ctgttcctttcctaatcacaagtaacaacacacagtcttctttcacatatattatttgttgaccaatcgtagggtcaactatctagtactcgagacc
gcctatttgaacagagctcctcactgtcaccaaatgtaccgtattgctttccggctgttattgttgttatcactgcttcttcttcctatcatgttaccc
atccaactatacacctagactagtcatcttattgatatacattcctcccatccaacacaacggtattctatttatttatccaattagtcatagtcgta
ccaccatccagcacgaaggtgcctctttagtaaagagtagaagaagaaccggatgggaaatgttttttgttacaaaaatgacacatattgta
gtggacagaaggagtgagacagacatgagcaagccaatttgttttataatttctcttctagaaaaaaatacatttttccatacttcactagtcaaa
acctttcacctttctaatacatctcgtaaaccataatcttgatagttctgagcatttcaatacgaaagcttctcactgtctagatctctgactgagtg
ccctcatcaaaagtgcaatctgtcatctgtttcctcataatcacggagcactaattttttctctctgcgtctctataatcagatatctctcgtcactaa
gaactttccgaaatgtttatgcttctcatctgaccacttcggttccgcacaaaaaagtacggcattccaaaagaaatctgatccccctccgttca
ttcgtggtccgagtcggtgccaccagtcgttgcgcattgaatatttgtttggtccgttcccttcttctccgactgctgacctcgggcactttgat
gaccgggccaccacctcagtacccctctattacaccctctttgcctccgcgcatatgactccaccccttctcgtggaaggcgtgtatctcccc
tcttttccgctattcctcgatggatatatattcaaatgtatgtgtgttcctgacggagagggcgtctcgcttgagagcatcgtcacatcttttacaa
ttttacttatgattttacttcatcttcttcttcttactgcgattttgatatgcattcttatgtaaactattattattccaggtttcctcactcttttcaa
cki-2
                                                                                  SEQ ID NO: 152
taggttaacactgataaatcttgcagaactgttttattttattaaatgagacattaccgatctaaataaatttacaatcccatcaaactttctccttat
cctccagaatcccatcattttcatcggcacttcttcaaaagtttaaatgtgagtgaccgcccgtctcgctctactaatcgtatatgcaaattttcttt
gatatcatagaacctgtcatacttctccaagtatatgaaagacaattaaaactactgagagaaagaagtagttcgcgataaaaaagtacatat
aatacacctttttcacctagaagagatgctttcaacttctactttttctggtcatatgtaaatagttgggttttttgacagtttgacaggtttacggcagt
caagacgacaaaaatggttatcaaaaggagctggcatacagccaataccaccagttctgatcttttttacgattatcaaattgtacatgggggg
ttaagttgaattttagtttcatttttttcaaaagtttaaactcgaaaaataactgaattgaaatatagtgaagttggcaatataccaagggtagaaaa
tcagacgagtgattttatttctagacaatcttaaattgctcaaattgtggtcttttctatatttgaacttttaaatgcagcaatttgtgaaacatacaat
tgaaacaaatttcctcaaaaactgccaccagctgaggtatcatgaagccttctgttcacacatgttgccacctaatcggtcacttatcctaatta
acattcttccactaaattgtccctagtcaccccacttgaacgatatacacaccaactgttctcgttcactaatacacttcttccggagggattc
aactggttatattctgcagttgtcggcaggtgtgtggtagacggtgacgtaatattgcacagggtgtcggggaatgattatgaagtcgagatg
cgcaacagctggtaattgaagccacgagagaaaatggaaaagactatgatgagggcacaaggatagaaaaattgactgggagtgacca
aacaggcgaggtcacaatgaaattggtgaaaatggaaaccctaaaagtaactttagattttagaaaatagttggacgattttcgttttcaaagt
tcaaagcatgcattattatcatctgaagatgcacgatttgacttgtgtgactgatatctcgtcgcgatcttaccgtaacctacagtacttccatatt
aactaaagttggttcgcttcgagacatcgggaacgtgagttatgtatttggcattattcgtcattttatattctagaaagatttacattctgtcaagt
tggaatatttttcttagccgtgcaatagaacttttgttgaatttctcagagtacaattttatgaccgccgatttcctctcgataagcattacgttatt
tacctatggttttcaactatttaatgagatttatcaggacctcccgtagttttatcttctatttttactcaaattttgagctcaaaaataacaggaaag
atttaatcgaaaaaacatatttctgaaatccaagagcaatcgcgcgctattgataatctggtttgccgcatttctcgcggcaacaacaaagag
tttgaatcgaaacgcctttttatttgaaaaaaacctttttgttttaaaatttagtctatacgtgaatctaacacacacaaactgttcactaatttctct
ttgttcgtctttttaccatttcatttcgaaactcgctgtcgtctcgtttctctcaccactcttcacacttttgccgcctaatcgatcgatcttgccgcg
gcgcactcacatttttctcttattttcttaccggcaaaaaatgtacgttttaccgcacttttcgcttacattactatttcaaattctcttatcaaattatt
tcagaaacgaagtaacacaa
pcn-1
                                                                                  SEQ ID NO: 153
catgaagaaacagtggccgtattgggaaaaatgaacgattttcggcgggaataattatttttttatgttttctatgcgttttcgggtgttttcgg
gttgctaagcgattggttgccttttgaatcactagtcttggtttttgttgttctgtgaatgaataattggttttcgaggttttttgtcaaacatgcct
aaaaaataaattatgacgttttagttgatttgtttgttcttaaacgtctgaaaataaggtttaaatctaatttattaattataaaattcgtcaaaataag
ttgcgcgtcaaattatatgtattgtacgcagtgtcaaactccaggcctcagttttcatgaatttaccagcgatttttgttataaattttttttattgaaat
```

-continued ttaaaattttttattttttcaaccaatttgcctcgaaaattcgttatttccccattaaaaaccgcttttctaaagtgttgcgcgtcaaataaaatgcctgg tacgcaatgcacggagaatgcgcaaaggacgactgctggcgcacttttttgaatgcggtaaattgaggcgcgaagtttcattcgaaaacgc gcgcgaaacttcattcatcgcactttctccgttcatttcgtcctattttttgtggttttttcgcgattttttcgcttttctgagtgaaaaataattttcctt cgttttttcaatgaaaatccgcggaaaacccatttttttcccgtgaaaatccgcattttttcgctgtatttcataattttttattcagatctcccgtcaaa smo-1
SEQ ID NO: 154 ttgctgttcttaattgatttcataaatatgtataaagcattaaatttgaatatatttttaataaagaaaaatcgatattcacattagagcgcgcttgca atttcacgatgagacctgacgataccgcgcgaattaaatcgatcgcttttttggcctaaaatgctcattaacaattgttttttgtagttttttagcttaaa attatattttaaaatccagtttgccttgttacatattggaaaacggtattttttagagttttttcctcaaaaaccaagcgaaaaccttgaattttgttccg aaaacttgttcaaaacatttttttcgttgaaaactcaaataattcaccaatttatctattttaggccgaaatctcttattttttcagtccaaaaagcacc aaatttggtcaaaaacctgtccaaaatctaccgtaccctcgtgttgctcgtgaaatgcggtgcattgtgtgcaaacaccgcggcgtgaacatg cacactctgcaacgcgggaaatcatttcgaaaaggttttttaggcgcgtattgcccgattttttcggctcatttcgtgtgttttcatttattttttgccttc tttctccggtcgcgatgcgtttaattaagttttgcttctaaaatttcgtcaatttcgctgaaaaaccacgtagaaaacttgataggaactggatatcc taaaaaaaaggattttccttgagaaaaatgggtttttttttctgaatttcgcagtgatattcttgaaattctcagcgcagcgctccccagacaatcga tattcctaattttttcaagcatcttgtggctcagccagctgttctgtaattatcgattttatttgttacagcgtctatataaataccctagaaagtcatca ttctgcactcttaatacctttcactcgtgtgagttgcattctccatagcaactctacctctctccttctatctcttttttctcttttcaaatctaatttcgttt cagagactcccgctataaacg rnf-1
SEQ ID NO: 155 ttcgctttaactcctccagaagttgacggtccgccagtgcctccactagtcgtcgggagtttatggttcagtttcgccttttttcatgtcctccggc ttcataatcgtatcatttaggcgtttgtgttttttacgttccattatttataagattctaaacgagaaactcttaagattttccggaaaataatgataaa aacggttgtgaaattgaatgagaataaaaaaacgaaacaagcacgagtgaggcaggtgcgctccaatgcgaatttctttgcgcggatgttt aaatggttatttttttatgggaatcgacaagtcacatgctacgctagagagagttttacattttacagtcttttttggaatttaataatatatatattatc ataaaatcgaataaaaattgtttcgaataatgaatagctttgttttttcgtcttgacttctgaaataattttaaatttgagaaaaatttgtgtcgcaata tataattattaatattattaataatgtaattttttttataataaactgatttatattttaaaaacaaaaaaggaatgacaattcagtttagttttatgaaaaa ctttgaaaagacaaaaataattacagtaaacgcgctccgctagactccccaaatttgtttttgttttccaggcttgtgtccaggcaaattccagct ttcttttttgtttcagaatttctaggtatttatctccgtgaaa Apoptosis Toxicity Genes egl-1
SEQ ID NO: 156 gaaaacttcgattcttatggttaaaacgagccttgttagtaaaaattattgagtgaataaataaattagatcaagtattttcacttctgccaaaattc aactaaatagaaatggttggaattaagttacaagctaccagtttacaaaacaataattgacaggtaatcggagtgaagacagttttttgcctttg ataattttacattcacatttaattttacattcacataaaaaaagaatcacacatttttttcaattgacaagttttgataaagtggaagacatcggag atatgacccgtcaaagttgctcagcagggtgcaaaactaaaagaggaaatactgtgaaacatttttgacaatttagagaaatacacagcgaa agaatgaaatctaaaaaagcgtattaactttaactagataaacatactaacttattgaggtaaatctgagcagatcctcttcctattcccaatattt acccaattagtcttctgattgcgcacctgcatatcttaagtactcaaatacaacacacatcttgagaaatgatgactccacactcagaatgcaat tcacactattagaagccatgtgcaatatgaaaacaagcttatcctgaagctgcaaacccatttacctcatcaattatttgcgatgtgccgacctg ttgcatggcttccgacactgtaaggggataatctgtttgtcggcacgcttcaaccgattaattggcgtgtgaaacgatactaatccagtcgatt ctcgactaactgtaaacactttgatgctaaccgacgtgccggctaatatactctctgtgttacgtcagaatcctttaaatatgcaaatatggataa ggtggaatgatctcaagaggtgtgattgggtcaaattggattacgtaattcttaagtgggctaaaggtatactgtaactggggtgcaatttatgt gggaagtgcggcgaagttatattgggttttatagattctataacttgttacattgattttgaatagatttcaatttcagaaaagtgggaaaactg tatttacattttgaaagaaatttaatgcaacagaaaatagtgattggctggaaaagtgcccctatgttataaaacttttttgttgaagctttgaaattttt -continued cacaaattattcaactgaagtctcacacgtcgaaaaatggccaaacaaattttaaaaaatagaggcctgatcatagtttctgccatttcatggc
cgtctgtgacgtcacatgaggttttcgactatttggcttccagggttttacctgttttaatttcaaaattatatattcttcagtaaatctctgaaagt
cacagtcgtttcagcgaactttcaaggccgcgtgtgacgtcacactcttgcaaagaaagctgcacgtggtgtcaggttgtcccataacggttt
gctctacgaaaaatgcgggaattttttcatcaaaaaatgtgacgtcagcacgttcttaaccatgcgaaatcagttgagaagtctgcgtctaagt
tcccgcgttttttgtagatcacaacggaatgggacattctgacaccatgtgaagctggccttgagatagttttgtagattcaaaatattttaatgt
ccaatatttgttttcaaaacattcgttaaaatgtgcagaatatgttaaactgaaggttcctaggttaaaacttcaagctaaagctttccggctcag
ttctcaggttcaggtctgtaatctttctgtaagcttgtaatcttgttagttcctcagacagacttagctgctaaatttatttcatgtctaatattcactt
caagagctatgagtttgtcttcataaagttttggctcccatataggaactttggaacatcatttgatcccgtttcgaaaacgttcgaaaattgtt
ttgtttctttatttaaacccgacagttcaaattctttatcttgatcaaaccctttttttcatctgtccattcctcggccttaacctaatttatacagtttcg
caataacctcccccgtgcttgctccagtaccagctgttgcgtcacgacttcttattttcaaaactcaaatcttgcatcacacctcatcaattaatc
atcctcatcaagcctgcaaacttataccccttctctagacccctctcctgacatttgacactcctgtggtagaggggtgtggccttgcctggg
cggggcgtgcaatgagaagctgtgcacgcacaccattcattcacacccaaaacattcacaccgattagtcgtattctaacttctctttcaattc
agttgatatgctggtaagtctagaaattatttattttgatctacatacctgtccaatattgttcgtctcccctcccctcctgagaaacaattttt
gtttttgtctgctcgcctcaccctcaacctctctctctctggatgtgttcgtggtgtagaaacaaaacagattttgtttttttgttttttgtttcttgttt
tagaacttgtatcctagtaattgttagacatctccctactatctttcccctatataaaccccttcaaaaccttactaatttccag cep-1

SEQ ID NO: 157
aacagaactcacccgtttctagaacaacgtttgctatcaactccaccccgaaagaatccaggtggttcgtctgacattatgctgcaattttatg
agaatattcagacgcaacaacaacgtgacaaacgacgagataaaaatctatcaaggctgaaacaatgacaaaaaagaaatcccgacaaa
tgaaaatggcgcctaaaacaaactttttaaaggacgtcgggtttcattcacagatgggtctcggaacgaaatcatggagtacggtatcacac
acttgaatttgaaagtgaacttctttatttgtttctcttgcaagtttaaacttaagttttaatttttctgcttgtttctcaataaaataaaaatattacttg
atttgtagcgcaga ced-3

SEQ ID NO: 158
ttctgcgtgaaatgtgatgtttctacagtaacccgtacaaccaaggcatcgaacttcacgacatttacgaattcaaatttgaattgcaaactttt
aattttatcgattttctttcttttgagctttatcaatagctctaagcgattattcaacagaatttcacttttttacgcctaaatgattgaaaatttgataa
aatatcaataatttacggttatcctcttcgtaatcttcgctttcttcccagagtagtgaaaatatcgacttttgatagaaactggattttttaacttcc
ctgttcgaaaaactattttccttaaatgagatctgaaataaggtgataaattaataaattaagtgtatttctgaggaaatttgactgttttagcaca
attaatcttgttcagaaaaaaagtccagttttctagattttttccgtcttattgtcgaattaatatccctattatcacttttcatgctcatcctcgagcg
gcagcgtctcaaagaattgtgagagcaaacgcgctccattgacctccacactcagccgccaaaaacaaacgttcgaacattcgtgtgttgt
gcctccttttccgttatcttgcagtcatcttttgtcgttttttctttgttcttttgttgaacgtgttgctaagcaattattacatcaattgaagaaaagg
ctcgccgatttattgttgccagaaagattctgagattctcgaagtcgattttataatatttaaccttggttttgcattgtttcgtttaaaaaaccact
gtttatgtgaaaaacgattagtttactaataaaactacttttaaaccttttacctttacctcaccgctccgtgttcatggctcatagatttcgatactc
aaatccaaaaataaatttacgagggcaattaatgtgaaacaaaaacaatcctaagatttccacatgtttgacctctccggcaccttcttccttag
ccccaccactccatcacctctttggcggtgttcttcgaaacccacttaggaaagcagtgtgtatctcatttggtatgctcttttcgattttatagct
ctttgtcgcaatttcaatgcttttaaacaatccaaatcgcattatatttgtgcatggaggcaaatgacggggttggaatcttagatgagatcagga
gctttcagggtaaacgcccggttcattttgtaccacatttcatcattttcctgtcgtccttggtatcctcaacttgtcccggttttgttttcggtacac
tcttccgtgatgccacctgctccgtctcaattatcgtttagaaatgtgaactgtccagatgggtgactcatattgctgctgctacaatccactttct
tttctcatcggcatgcttacgagcccatcataaactttttttccgcgaaatttgcaataaaccggccaaaaactttctccaaattgttacgcaata
tatacaatccataagaatatcttctcaatgtttatgatttcttcgcagcacttctcttcgtgtgctaacatcttattttttataatatttccgctaaaattc
cgattttgagtattaatttatcgtaaaattatcataatagcaccgaaaactacaaaaaatggtaaagtcttttaaatcggctcgacattatcgtatt
aaggaatcacaaaattctgagaatgcgtactgcgcaacatatttgacgcgcaaaatatccgtagcgaaaactacagtaattctttaaatgact -continued

```
actgtagcgcttgtgtcgatttacgggctcaattttttgaaaataatttttttttttcgattttgacaacccgtaaatcgtcacaagcgctacggtagt
catttaaaggattactgtagttctagctacgagatattttgcgcgccaaatatgatgcgtaatacgcattctctgaattttgtgtttccgtaataattt
cacaagattttggcattcctctttaaaggcgcacggatttattccaatgggtctcggcacgcaaaaagtttgatagacttttaaattctccttgca
tttttaattcaattactaaaatttcgtgaattttctgttaaaattttaaaatcagttttctaatattttccaggctgacaaacagaaacaaaaacaca
acaaacattttaaaaatcagttttcaaattaaaaataacgatttctcattgaaaattgtgttttatgtttgcgaaaataaaagagaactgattcaaaa
caattttaacaaaaaaaaccccaaaattcgccagaaatcaagataaaaaattcaagagggtcaaaattttccgatttactgactttcaccttttt
ttttcgtagttcagtgcagttgttggagtttttgacgaaaactaggaaaaaatcgataaaaattactcaaatcgagctgaattttgaggacaat
gtttaaaaaaaaacactattttttccaataatttcactcattttcagactaaatcgaaaatcaaatcgtactctgactacgggtcagtagagaggtc
aaccatcagccgaag
``` mev-1
SEQ ID NO: 159
```
aaattcgaggaattttagatttcatcttgaaatttgcaatggaaaaaataattattcaaagaaaatcacagaaaatgcaacaaaaaaacaaaa
aaagaacaaaaaacaagtcgaaaagtgcgcccgggtcgtttgctgacgcatctcttcaaacgagacgcgctgctggcgcacttctcgtgc
cctgtgcgtgcatttccgcaacaaaattcaacacttgttttgaaacgcaccgccctgtttctttttttcaattttgataagaaaatcagcattgtttca
gg
``` ced-13
SEQ ID NO: 160
```
tagaaacatgtttcccgtaagtgacctatccagtgaaacaaaaacatgtttctgtccgccttccttccatcggtggaggtgcatgctagattgc
ctcctaaactctaatacctaaaattttaataatttattgacaacatacagtttcaccgataaccgacactcttattttttctgatcctgactattctgtt
cattatttcagctcctatcatagaacgatctttccagatcttggacaagtcacagttacaggtaattttttcaacaggtgtttgtataatgtcttagtt
tctgtaaaattgttttatcatgtaaaatatttcagattattcgagggcagaaaaacgtgatattactattggagaggaattgacaaagttgtgtgat
aaatttaattttgag
``` bmk-1
SEQ ID NO: 161
```
cgagtttcttgtgagaaccaaaaactattcctctgcaagaaaaaatttattaatccggcataaaatactttttattacaataggaacttcacagtc
gcttcctccgacgctttgagcggtacatcgatgcttatcaccatgctgattgttacctttcttacccgtttgactttctgcaattttttaactgcaaag
atgtttaatgcagatactcgaaagaaacgaaaaaatgataaaaaagtgaaaaaccccaaaaataaatttgaaaactccgcgtaagcttgctc
gatcgctgcgagaccattgcataccgtactacttcttaaaggcgcacacatcaaatctagctgtttcgtgacaggacccagcaatgttcagc
cgcgaagttttgaatcgccattttttttttaatttctagaatgtttatagttttgctttcgatgagatttttaagcattatgaggaacaaatttttttaaaaa
ctttagaagttttaaaatttaattttgcgattatgctttgctttcgcgtgtcctttccgttgttcctcgctccaaatatcacagtaattaaccactact
tatgtagttatcacgtttctaaaaatataaattcattttatttctctattgattcggtttgttgctcttcttgtctcaatcttgtgctactgccgaataccc
tgctaatttttcgttttcagtcattcgattcacttgggttgttgtttaaaatggtaagattttttgcaggttactttctttcccatgaggtaaatgcatttat
tgcgggtgcgctctatcgcacgacgccgcgaatcattgtatttcaaattgattttcctgttgcacttttattagttacaattttttattagttattttttagt
tggattcgaca
``` rad-51
SEQ ID NO: 162
```
gaaaaccctaaaatgaacaaaattttttgtcattaaataacaacgcttcggttaacgcttgaaattgatattcggaaaataaaaagcctgattttgt
tcgatttctgaaatatatttcatgcttacccgttttaattgcgaacaattctaaatttgaaatataattttcaatcaacgaaaaacaattttcaagat
aaaaaattattatataaatttaagctaagtattaataaattaataagtaatagtattcaaaaatcatagaatcttgcaagaaaaaatgttttaaagat
ttaatagttcgagtgattgaaaaacgaatagtactttaaaaaataatgctttaaggcagaaaagtgatataaaaattaagctcaaagggcaaa
agataaggttaatgtccagttttggttttaaaatggttcggacacaatgtacatagtagacatttgggtgtcctcttccttctcttttccccattgcg
tccactgaccctccttgctgtatgtctgcgcatcgtcttttttctacactttttcctttttcctgcccgttcctatcggtgcctttcacacacgcgag
cggcagtggacgagacgggagggcgaggtgttgaacaagagtacagcaagtgcgcgccatcgaaaaagcggaaaaaaaatttcaaa
tggcgctactttgaaaattgagaattctgtatttactgccagttttacttgcatttaaatttccatgttttctattctaaaacgaaaatctatctaagaa
aacccttaataaaaaacctataaatcataaattgtgattcttaaattcgaaaatatgttcgttcaacttgacgcctagaaatatgtggacttaatcct
```

-continued

```
gttataaatcagtagttgacgacaaaaatagtagagcagcaaaagcagttctaacttgtgaaaaacatgaaagttcttgttttcgtcaagcgaa cgggggctcgaggaaggacttggcacgtgtctctaggccatgttttctcaatttttgttgctctagagaaagcttttgctattgattatgggaca atcttggggatatgaaggtaacattttaaaaataagtttaggtaaatgtgtagcataattttgaaaaaaaagctccactgttaaaaatgccgat tttagggattgcgaaacgttcactatgtacacataaatggctatataatttgaatttgcattcaataaatcttttccttccaattgtatgttttaactta aaaataattaattaaaattatctcaggagtcaaaa
```

The invention is a nucleic acid comprising a nucleic acid having a sequence as in one of SEQ ID NO: 1 through SEQ ID NO: 162 which is an inducible promoter and is operably linked, or fused, to a reporter gene. In one aspect, the reporter gene comprises a gene encoding a fluorescent protein.

The invention is a isolated nucleic acid comprising a nucleic acid having a sequence 95%, 96%, 97%, 98%, or 99% or more identical to the sequence as in one of SEQ ID NO: 1 through SEQ ID NO: 162 which is an inducible promoter and is operably linked or fused to a reporter gene. In one aspect, the reporter gene comprises a gene encoding a fluorescent protein.

The invention is a nucleic acid comprising a fragment of a nucleic acid having a sequence as in one of SEQ ID NO: 1 through SEQ ID NO: 162 wherein said fragment is 50, 100, 200, 300, 400, or 500 or more nucleotides in length which is an inducible promoter and is operably linked or fused to a reporter gene wherein the nucleic acid fragment is capable of promoting transcription of the reporter gene as described herein. In one aspect, the reporter gene comprises a gene encoding a fluorescent protein.

The invention is a nucleic acid comprising a fragment of a nucleic acid having a sequence at least 95%, 96%, 97%, 98%, or 99% identical to a sequence as in one of SEQ ID NO: 1 through SEQ ID NO: 162 wherein said fragment is 50, 100, 200, 300, 400, or 500 or more nucleotides in length which is an inducible promoter and is operably linked or fused to a reporter gene wherein the nucleic acid fragment is capable of promoting transcription of the reporter gene as described herein. In one aspect, the reporter gene comprises a gene encoding a fluorescent protein.

The invention is a transgene comprising a nucleic acid having a sequence as in one of SEQ ID NO: 1 through SEQ ID NO: 162 which is an inducible promoter and is operably linked or fused to a reporter gene. In one aspect, the reporter gene comprises a gene encoding a fluorescent protein.

The invention is a transgene comprising a nucleic acid having a sequence at least 95%, 96%, 97%, 98%, or 99% identical to a sequence as in one of SEQ ID NO: 1 through SEQ ID NO: 162 which is an inducible promoter and is operably linked or fused to a reporter gene. In one aspect, the reporter gene comprises a gene encoding a fluorescent protein.

The invention is a transgene comprising a fragment of a nucleic acid having a sequence as in one of SEQ ID NO: 1 through SEQ ID NO: 162 wherein said fragment is 50, 100, 200, 300, 400, or 500 or more nucleotides in length which is an inducible promoter is and operably linked or fused to a reporter gene wherein the nucleic acid fragment is capable of promoting transcription of the reporter gene as described herein. In one aspect, the reporter gene comprises a gene encoding a fluorescent protein.

The invention is a transgene comprising a fragment of a nucleic acid having a sequence at least 95%, 96%, 97%, 98%, or 99% identical to a sequence as in one of SEQ ID NO: 1 through SEQ ID NO: 162 wherein said fragment is 50, 100, 200, 300, 400, or 500 or more nucleotides in length which is an inducible promoter and is operably linked, or fused, to a reporter gene wherein the nucleic acid fragment is capable of promoting transcription of the reporter gene as described herein. In one aspect, the reporter gene comprises a gene encoding a fluorescent protein.

The invention is a construct comprising a nucleic acid having a sequence as in one of SEQ ID NO: 1 through SEQ ID NO: 162 which is an inducible promoter and is operably linked or fused to a reporter gene. In one aspect, the reporter gene comprises a gene encoding a fluorescent protein.

The invention is a construct comprising a nucleic acid having a sequence at least 95%, 96%, 97%, 98%, or 99% or more identical to a sequence as in one of SEQ ID NO: 1 through SEQ ID NO: 162 which is an inducible promoter and is operably linked, or fused, to a reporter gene. In one aspect, the reporter gene comprises a gene encoding a fluorescent protein.

The invention is a construct comprising a fragment of a nucleic acid having a sequence as in one of SEQ ID NO: 1 through SEQ ID NO: 162 wherein said fragment is 50, 100, 200, 300, 400, or 500 or more nucleotides in length which is an inducible promoter and is operably linked, or fused, to a reporter gene wherein the nucleic acid fragment is capable of promoting transcription of the reporter gene as described herein. In one aspect, the reporter gene comprises a gene encoding a fluorescent protein.

The invention is a construct comprising a fragment of a nucleic acid having a sequence at least 95%, 96%, 97%, 98%, or 99% identical to a sequence as in one of SEQ ID NO: 1 through SEQ ID NO: 162 wherein said fragment is 50, 100, 200, 300, 400, or 500 or more nucleotides in length which is an inducible promoter and is operably linked, or fused, to a reporter gene wherein the nucleic acid fragment is capable of promoting transcription of the reporter gene as described herein. In one aspect, the reporter gene comprises a gene encoding a fluorescent protein.

The invention is a transgenic organism comprising transgene which is a nucleic acid having a sequence as in one of SEQ ID NO: 1 through SEQ ID NO: 162 which is an inducible promoter and is operably linked, or fused, to a reporter gene wherein said nucleic acid is capable of promoting transcription of the reporter gene as described herein. In one aspect, the reporter gene comprises a gene encoding a fluorescent protein.

The invention is a transgenic organism comprising transgene which is a nucleic acid having a sequence at least 95%, 96%, 97%, 98%, or 99% identical to a sequence as in one of SEQ ID NO: 1 through SEQ ID NO: 162 which is an inducible promoter and is operably linked, or fused, to a reporter gene wherein said nucleic acid is capable of promoting transcription of the reporter gene as described herein. In one aspect, the reporter gene comprises a gene encoding a fluorescent protein.

The invention is a transgenic organism having a transgene which is a fragment of a nucleic acid having a sequence as in one of SEQ ID NO: 1 through SEQ ID NO: 162 wherein said fragment is 50, 100, 200, 300, 400, or 500 or more nucleotides in length which is an inducible promoter and is operably linked, or fused, to a reporter gene wherein the nucleic acid fragment is capable of promoting transcription of the reporter gene as described herein. In one aspect, the reporter gene comprises a gene encoding a fluorescent protein.

The invention is a transgenic organism having a transgene which is a fragment of a nucleic acid having a sequence at least 95%, 96%, 97%, 98%, or 99% identical to a sequence as in one of SEQ ID NO: 1 through SEQ ID NO: 162 wherein said fragment is 50, 100, 200, 300, 400, or 500 or more nucleotides in length which is an inducible promoter and is operably linked, or fused, to a reporter gene wherein the nucleic acid fragment is capable of promoting transcription of the reporter gene as described herein. In one aspect, the reporter gene comprises a gene encoding a fluorescent protein.

Inducible promoters for use in the nucleic acids, transgenes, constructs and transgenic organisms of the invention are typically chosen from those present in the host organism and are involved in promoting expression of its cognate gene in response to stimuli or an agent. Examples of stimuli or agents include, but are not limited to, stimuli or agents that cause oxidative stress, stimuli or agents that are genotoxic, stimuli or agents that cause xenobiotic stress.

Exemplary inducible promoters, constructs comprising the inducible promoters, transgenes comprising the inducible promoters, and transgenic organisms comprising the inducible promoters of the invention are described in more detail below.

The invention is a nucleic acid, transgenic organisms, transgene, or construct comprising a promoter of a gene involved in oxidative stress response fused, or operably, linked to a reporter gene where the oxidative stress response gene is from a pathway of cytoplasmic oxidative stress, mitochondrial oxidative stress, peroxisomal oxidative stress, endoplasmic reticulum oxidative stress, or nuclear oxidative stress (Zhong, M. et al. PLoS Genet 6, e1000848 (2010)). In a related aspect, the invention is a nucleic acid, transgenic organisms, transgene, or construct comprising a promoter of a gene involved in oxidative stress response fused, or operably, linked to a reporter gene where the oxidative stress response gene is from a pathway of cytoplasmic oxidative stress induced by juglone or other quinones or phenazine; mitochondrial oxidative stress induced by paraquat, mitomycin C, antimycin A, or maesanin; peroxisomal oxidative stress induced by aminotriazole or antimycin A; endoplasmic reticulum oxidative stress induced by tunicamycin, menadione or plumbagin; or nuclear oxidative stress induced by belomycin.

The invention is a nucleic acid from a gene involved in oxidative stress whose promoter is used in the transgenic organism, transgene, construct, or nucleic acid of the invention and is chosen from those involved in cytoplasmic oxidative stress that can involve pathways such as heat shock, phase I and phase II xenobiotic response, or proteasome. In one aspect, the gene is hsp-16.41, hsp-16.2, hsp-16.1, hsp-16.11, hsp-16.48, hsp-16.49, sod-1, gcs-1, hpo-15, dhs-18, gst-14, gst-32, W06H8.2, cyp-34A9, or ugt-41, where the promoter for the gene is fused, or operably linked, to a reporter gene.

The invention is a nucleic acid from a gene involved in oxidative stress response whose promoter is used in the transgenic organism, transgene, construct, or nucleic acid of the invention and is chosen from those involved in mitochondrial oxidative stress that can involve pathways such as heat shock or electron transport. In one aspect, the gene is hsp-6, hps-60, mtl-2, mtl-1, cdr-1, sod-3, eat-3, cyp-14A4, cyp-33C8, glrx-10, F56D5.3, B0222.9, F17A9.4, C35B1.5, or gst-4, where the promoter for the gene is fused, or operably linked, to a reporter gene.

The invention is a nucleic acid from a gene involved in oxidative stress whose promoter is used in the transgenic organism, transgene, construct, or isolated nucleic acid of the invention and is chosen from those involved in peroxisomal oxidative stress that can involve pathways such as heat shock or oxidative metabolism. In one aspect, the gene is hps-1, ctl-1, ctl-2, ctl-3, W01B11.6, F10D7.3, prx-1, prx-5, duox-2, prdx-2, pxn-2, mlt-7, ZK550.6, C28H8.11, or C35B1.5, where the promoter for the gene is fused, or operably linked, to a reporter gene.

The invention is a nucleic acid from a gene involved in oxidative stress whose promoter is used in the transgenic organism, transgene, construct, or nucleic acid of the invention and is chosen from those involved in the specification of apoptosis as in endoplasmic reticulum oxidative stress that can involve pathways such as heat shock, ERAD, or disulfide exchange. In one aspect, the gene is hsp-4, dnj-27, dnj-7, Y41C4A.11, arf-1.1, lips-11, srp-7, gale-1, ckb-2, fipr-24, arl-7, F07A11.2, C04F12.1, hke-4.1, or F22E5.6, where the promoter for the gene is fused, or operably linked, to a reporter gene.

The invention is a nucleic acid from a gene involved in oxidative stress whose promoter is used in the transgenic organism, transgene, construct, or nucleic acid of the invention and is chosen from those involved in nuclear oxidative stress that can involve pathways such as heat shock or oxidative base damage. In one aspect, the gene is ugt-1, hsp-17, cdr-5, dnj-15, dnj-25, pme-1, pme-2, pme-5, air-2, mlh-1, mlh-2, polq-1, him-6, xpa-1, nth-1, or cep-1, where the promoter for the gene is fused, or operably linked, to a reporter gene.

A promoter region for an oxidative stress response gene (hsp-16.41) has the following DNA sequence (SEQ ID NO:1) and activates transcription of its cognate gene (or a reporter gene fused or operably linked thereto) in response to or by e.g., heat shock. In one embodiment, the invention is an isolated promoter reporter construct nucleic acid comprising SEQ ID NO:1 operably linked or fused to a reporter gene. Preferably the reporter gene is one that encodes a fluorescent protein or a luminescent protein. Preferably, the reporter gene encodes a fluorescent protein comprising a GFP or RFP. In a related embodiment, the invention is a C. elegans line or strain having the promoter reporter construct stably integrated into the C. elegans genome at a single site or using a single copy insertion technology. In one aspect, this C. elegans line or strain has a constitutive reporter gene stably integrated into its genome in addition to the above construct wherein said constitutive reporter is detectably different than the reporter of promoter reporter construct (e.g., different fluorescent protein). Preferably, the constitutive reporter comprises a GFP.

A promoter region for an oxidative stress response gene (hsp-16.2) has the following DNA sequence (SEQ ID NO:2) and activates transcription of its cognate gene (or a reporter gene fused, or operably linked thereto) in response to or by e.g., heat shock. In one embodiment, the invention is an isolated promoter reporter construct nucleic acid comprising SEQ ID NO:2 operably linked or fused to a reporter gene. Preferably the reporter gene is one that encodes a fluorescent protein or a luminescent protein. Preferably, the reporter gene encodes a fluorescent protein comprising a GFP or RFP. In a related embodiment, the invention is a *C. elegans* line or strain having the promoter reporter construct stably integrated into the *C. elegans* genome at a single site or using a single copy insertion technology. In one aspect, this *C. elegans* line or strain has a constitutive reporter gene stably integrated into its genome in addition to the above construct wherein said constitutive reporter is detectably different than the reporter of promoter reporter construct (e.g., different fluorescent protein). Preferably, the constitutive reporter comprises a GFP.

A promoter region for an oxidative stress response gene (mtl-2) has the following DNA sequence (SEQ ID NO:27) and activates transcription of its cognate gene (or a reporter gene fused or operably linked thereto) in response to or by e.g., heavy metal ion toxicity like cadmium. In one embodiment, the invention is an isolated promoter reporter construct nucleic acid comprising SEQ ID NO:27 operably linked, or fused, to a reporter gene. Preferably the reporter gene is one that encodes a fluorescent protein or a luminescent protein. Preferably, the reporter gene encodes a fluorescent protein comprising a GFP or RFP. In a related embodiment, the invention is a *C. elegans* line or strain having the promoter reporter construct stably integrated into the *C. elegans* genome at a single site or using a single copy insertion technology. In one aspect, this *C. elegans* line or strain has a constitutive reporter gene stably integrated into its genome in addition to the above construct wherein said constitutive reporter is detectably different than the reporter of promoter reporter construct (e.g., different fluorescent protein). Preferably, the constitutive reporter comprises a GFP.

A promoter region for an oxidative stress response gene (ugt-1) has the following DNA sequence (SEQ ID NO:83) and activates transcription of its cognate gene (or a reporter gene fused or operably linked thereto) in response to or by e.g., heavy metal ion toxicity like cadmium. In one embodiment, the invention is an isolated promoter reporter construct nucleic acid comprising SEQ ID NO:83 operably linked, or fused, to a reporter gene. Preferably the reporter gene is one that encodes a fluorescent protein or a luminescent protein. Preferably, the reporter gene encodes a fluorescent protein comprising a GFP or RFP. In a related embodiment, the invention is a *C. elegans* line or strain having the promoter reporter construct stably integrated into the *C. elegans* genome at a single site or using a single copy insertion technology. In one aspect, this *C. elegans* line or strain has a constitutive reporter gene stably integrated into its genome in addition to the above construct wherein said constitutive reporter is detectably different than the reporter of promoter reporter construct (e.g., different fluorescent protein). Preferably, the constitutive reporter comprises a GFP A promoter region for an oxidative stress response gene (hsp-60) has the following DNA sequence (SEQ ID NO:26) and activates transcription of its cognate gene (or a reporter gene fused, or operably linked, thereto) in response to mitochondrial stress by e.g., paraquat. In one embodiment, the invention is an isolated promoter reporter construct nucleic acid comprising SEQ ID NO:26 operably linked, or fused, to a reporter gene. Preferably the reporter gene is one that encodes a fluorescent protein or a luminescent protein. Preferably, the reporter gene is encodes a fluorescent protein comprising a GFP or RFP. In a related embodiment, the invention is a *C. elegans* line or strain having the promoter reporter construct stably integrated into the *C. elegans* genome at a single site or using a single copy insertion technology. In one aspect, this *C. elegans* line or strain has a constitutive reporter gene stably integrated into its genome in addition to the above construct wherein said constitutive reporter is detectably different than the reporter of promoter reporter construct (e.g., different fluorescent protein). Preferably, the constitutive reporter comprises a GFP.

A promoter region for an oxidative stress response gene (hsp-6) has the following DNA sequence (SEQ ID NO:25) and activates transcription of its cognate gene (or a reporter gene fused, or operably linked, thereto) in response to mitochondrial stress by e.g., paraquat exposure. In one embodiment, the invention is an isolated promoter reporter construct nucleic acid comprising SEQ ID NO:25 operably linked, or fused, to a reporter gene. Preferably the reporter gene is one that encodes a fluorescent protein or a luminescent protein. Preferably, the reporter gene encodes a fluorescent protein comprising a GFP or RFP. In a related embodiment, the invention is a *C. elegans* line or strain having the promoter reporter construct stably integrated into the *C. elegans* genome at a single site or using a single copy insertion technology. In one aspect, this *C. elegans* line or strain has a constitutive reporter gene stably integrated into its genome in addition to the above construct wherein said constitutive reporter is detectably different than the reporter of promoter reporter construct (e.g., different fluorescent protein). Preferably, the constitutive reporter comprises a GFP.

A promoter region for an oxidative stress response gene (hsp-4) has the following DNA sequence (SEQ ID NO:55) and activates transcription of its cognate gene (or a reporter gene fused, or operably linked, thereto) in response to endoplasmic reticulum stress by e.g., exposure to tunicamycin. In one embodiment, the invention is an isolated promoter reporter construct nucleic acid comprising SEQ ID NO:55 operably linked, or fused, to a reporter gene. Preferably the reporter gene is one that encodes a fluorescent protein or a luminescent protein. Preferably, the reporter gene encodes a fluorescent protein comprising a GFP or RFP. In a related embodiment, the invention is a *C. elegans* line or strain having the promoter reporter construct stably integrated into the *C. elegans* genome at a single site or using a single copy insertion technology. In one aspect, this *C. elegans* line or strain has a constitutive reporter gene stably integrated into its genome in addition to the above construct wherein said constitutive reporter is detectably different than the reporter of promoter reporter construct (e.g., different fluorescent protein). Preferably, the constitutive reporter comprises a GFP.

In another aspect, the invention is an isolated nucleic acid or fragment thereof having 50, 100, 200, 300, 400, or 500 or more nucleotides, which is a promoter for a gene induced by heat shock, heavy metal ion toxicity, mitochondrial oxidative stress, or endoplasmic reticulum oxidative stress which is fused, or operably linked, to a reporter gene. In a specific aspect, the heavy metal ion stress is induced by cadmium or arsenic. In another specific aspect, the mitochondrial stress is induced by paraquat. In yet another specific the endoplasmic reticulum stress is induced by tunicamycin.

In another aspect, the invention is an isolated nucleic acid or fragment thereof having 50, 100, 200, 300, 400, or 500 or more nucleotides, which is a promoter for a gene chosen from hsp-16.41, hsp-16.2, mtl-2, ugt-1, hsp-60, hsp-6, and hsp-4 which is fused, or operably linked, to a reporter gene.

Apoptosis pathway genes: Apoptosis activation is important for understanding toxicology and in the creation of drugs to battle cancer. A compound that activates apoptosis leads to cell death is advantageous for combating cancer.

However, activation of cell death would be a detrimental property for apoptosis occurs by either the intrinsic (DNA damage and unfolded protein response) or extrinsic (Ras/MAPK signaling) pathways. Cell death is initiated by activation of the caspase pathway. Caspases activate pathways leading cell corpse engulfment and DNA fragmentation. Thus, the invention relates to transgenic organisms and in particular, nematode strains for monitoring apoptotic gene activation. An apoptotic gene's promoter is used to drive expression of a reporter gene. In one specific aspect the reporter gene is one that expresses a fluorescent protein. Preferred fluorescent proteins are a protein comprising RFP or GFP.

Examples of genes involved in apoptosis whose promoter regions can be used in the transgenic animals, transgenes, constructs, or nucleic acids of the invention are chosen from those involved in the specification of apoptosis as in cep-1, lin-35, jnk-1, pmk-1, mpk-1, ces-2, ces-1, atl-1, atm-1, brc-1, dnj-11, chk-1, cki-1, rad-52, cki-2, dpl-1, ceh-20, efl-1, hlh-2, or daf-16; those involved in the execution of apoptosis as in cps-6, crn-1, crn-2, crn-3, crn-4, crn-5, crn-6, cyn-13, nuc-1, bec-1, ced-1, ced-10, ced-12, ced-2, ced-5, ced-6, ced-7fnta-1, gdi-1, or ggtb-1; or those involved in the core of apoptosis as in drp-1, egl-1, ced-9, ced-4, or ced-3 wherein said promoter is operably linked, or fused, to a reporter gene.

In another aspect, the invention is a nucleic acid or fragment thereof having 50, 100, 200, 300, 400, or 500 or more nucleotides, which is a promoter for a gene induced in apoptosis which is fused, or operably linked, to a reporter gene. In a specific aspect, the gene induced in apoptosis is in the extrinsic pathway. In a specific aspect, the gene induced in apoptosis is in the intrinsic pathway. In another specific aspect, the gene induced in intrinsic apoptosis pathway is a DNA damage gene or unfolded protein response gene). In yet another specific the gene induced in extrinsic apoptosis pathway is a RAS/MAPK pathway gene.

In another aspect, the invention is an isolated nucleic acid or fragment thereof having 50, 100, 200, 300, 400, or 500 or more nucleotides, which is a promoter for a gene chosen from cep-1, lin-35, jnk-1, pmk-1, mpk-1, ces-2, ces-1, atl-1, atm-1, brc-1, dnj-11, chk-1, cki-1, rad-52, cki-2, dpl-1, ceh-20, efl-1, hlh-2, daf-16, cps-6, crn-1, crn-2, crn-3, crn-4, crn-5, crn-6, cyn-13, nuc-1, bec-1, ced-1, ced-10, ced-12, ced-2, ced-5, ced-6, ced-7, fnta-1, gdi-1, ggtb-1, drp-1, egl-1, ced-9, ced-4, or ced-3 which is fused, or operably linked, to a reporter gene.

In another aspect, the invention is an isolated nucleic acid or fragment thereof having 50, 100, 200, 300, 400, or 500 or more nucleotides, or a nucleotide 95%, 96%, 97%, 98%, or 99% identical thereto, which is a promoter for a gene chosen from cep-1, lin-35, jnk-1, pmk-1, mpk-1, ces-2, ces-1, atl-1, atm-1, brc-1, dnj-11, chk-1, cki-1, rad-52, cki-2, dpl-1, ceh-20, efl-1, hlh-2, daf-16, cps-6, crn-1, crn-2, crn-3, crn-4, crn-5, crn-6, cyn-13, nuc-1, bec-1, ced-1, ced-10, ced-12, ced-2, ced-5, ced-6, ced-7, fnta-1, gdi-1, ggtb-1, drp-1, egl-1, ced-9, ced-4, or ced-3 which is fused, or operably linked, to a reporter gene.

Genotoxin or Carcinogen Pathway Genes

Genotoxins are compounds that cause DNA damage. Carcinogens are compounds that cause genotoxicity or other procancerous activity such as, stopping cell cycle arrest, stopping cell-cell inhibition signalling, stopping apoptosis induction, etc. The arrays or panels of the invention can include 1 or more representative transgenic organisms, or populations thereof, having a promoter from a genotoxin or carcinogen response pathway gene operably linked, or fused, to a reporter protein.

From the Gene Ontology database, there are 162 genes involved in the *C. elegans* response to DNA damage stimulus (GO:0006974) (Ashburner et al. Nat. Genet 25, 25-29 (2000)) This group was compared to a meta-study cataloging the genes highly expressed after carcinogen exposure (Waters et al. Mutat Res (2010)). 24 genes were identified pathway-specific genes (carcinogen and/or genotoxin responsive genes). In particular, the genes identified corresponded to enyzmes base excision repair, nucleotide excision repair, mismatch repair, recombination controlled repair. Additional genes for inclusion in panels related to carcinogenicity include, but are not limited to, those involved in cell cycle control and apoptosis. To reveal which sections of the promoter contain transcriptional control sequences, data from two sources, 1) the Model Organism ENCyclopedia Of DNA Elements (modENCODE) project, and 2) related species alignments are compared and optimal sequence regions are selected. Once identified, the promoters for these carcinogen and genotoxicity pathway genes can be used to generate the promoter reporter transgenes, constructs, isolated nucleic acids, or transgenic organisms of the invention using genetic engineering technology, such as those described herein.

In one aspect, the invention is an isolated nucleic acid or fragment thereof having 50, 100, 200, 300, 400, or 500 or more nucleotides of a promoter for a carcinogen pathway or genotoxin pathway gene which is fused, or operably linked to a reporter gene. A carcinogen pathway gene is a gene whose expression is altered (e.g., induced) in a cell, tissue or an organism upon exposure to a carcinogen or genotoxin. In another aspect, the invention is an isolated nucleic acid or fragment thereof which is a promoter for a gene induced in base excision repair, nucleotide excision repair, mismatch repair, recombination controlled repair, cell cycle control or apoptosis which is fused, or operably linked, to a reporter gene. In a specific aspect, the promoter for a gene induced in base excision repair is promoter for exo-3, nth-1, pme-1, or ung-1. In a specific aspect, the promoter for a gene induced in nucleotide excision repair is the promoter of xpa-1, mrt-2, ercc-1, or rad-23. In a specific aspect, the promoter for a gene induced in mismatch repair is the promoter for mlh-1, msh-4, msh-5, or msh-6. In a specific aspect, the promoter for a gene induced in recombination controlled repair is the promoter of brc-1, brc-2, rad-50, or cku-70. In a specific aspect, the promoter for a gene induced in cell-cycle control is the promoter for lin-35, mei-1, cki-1, or cki-2. In a specific aspect, the promoter for a gene induced in apoptosis is the promoter for cep-1, ced-3, ced-9, or ced-13.

In another aspect, the invention is an isolated nucleic acid or fragment thereof having 50, 100, 200, 300, 400, or 500 or more nucleotides, which is a promoter for a gene encoding a protein in a DNA damage response pathway that is induced by irradiation with UV or X-ray exposure which is fused, or operably linked, to a reporter gene.

In another aspect, the invention is an isolated nucleic acid or fragment thereof having 50, 100, 200, 300, 400, or 500 or more nucleotides, which is a promoter for a gene encoding a protein in a DNA damage response pathway that is induced N-ethyl-N-nitrosurea which is fused, or operably linked, to a reporter gene.

In another aspect, the invention is an isolated nucleic acid or fragment thereof having 50, 100, 200, 300, 400, or 500 or more nucleotides, which is a promoter for a gene encoding a protein in spindle formation that is induced by taxane which is fused, or operably linked, to a reporter gene.

In another aspect, the invention is an isolated nucleic acid or fragment thereof having 50, 100, 200, 300, 400, or 500 or more nucleotides, which is a promoter for a gene encoding a protein involved in regulating cell division or checkpoint control which is fused, or operably linked, to a reporter gene.

Endocrine Pathway and/or Xenobiotic Metabolism Genes

In one embodiment, the transgene, transgenic organism, or promoter reporter construct of the invention has a promoter or fragment thereof having 50, 100, 200, 300, 400, or 500 or more nucleotides, derived or obtained from a CYP P450 gene, ABC transporter gene, SDR/Redox gene, GST gene, or a Sol. Transporter gene, which is fused, or operably linked, to a reporter gene.

Examples of CYP P450 genes include, but are not limited to, the following C. elegans genes: cyp-13A1, cyp-13A2, cyp-13A3, cyp-13A4, cyp-13A5, cyp-13A6, cyp-13A7, cyp-13A8, cyp-13A10, cyp-13A11, cyp-13A12, cyp-13B2, cyp-14A1, cyp-14A2, cyp-14A3, cyp-14A4, cyp-14A5, cyp-23A1, cyp-25A1, cyp-25A2, cyp-25A3, cyp-25A4, cyp-25A5, cyp-25A6, cyp-29A2, cyp-29A3, cyp-29A4, cyp-31A2, cyp-31A3, cyp-32A1, cyp-32B1, cyp-33A1, cyp-33B1, cyp-33C1, cyp-33C2, cyp-33C3, cyp-33C4, cyp-33C5, cyp-33C6, cyp-33C7, cyp-33C8, cyp-33C9, cyp-33C11, cyp-33C12, cyp-33D1, cyp-33D3, cyp-33E1, cyp-33E2, cyp-33E3, cyp-34A1, cyp-34A2, cyp-34A3, cyp-34A4, cyp-34A5, cyp-34A6, cyp-34A7, cyp-34A8, cyp-34A10, cyp-35A1, cyp-35A2, cyp-35A3, cyp-35A4, cyp-35A5, cyp-35B1, cyp-35B2, cyp-35B3, cyp-35C1, cyp-35D1, cyp-36A1, cyp-37A1, cyp-37B1, cyp-42A1, cyp-43A1, cyp-44A1, dpr-1, coq-6, fmo-1, fmo-2, fmo-3, fmo-4, fmo-5, pah-1, tbh-1, C01H6.4, C46H11.2, F30B5.4, R07B7.4, R07B7.5, T19B4.1, Y47D3A.22, and Y71G12B.4.

Examples of ABC transporter genes include, but are not limited to, the following C. elegans genes: abce-1, abcf-1, abcf-2, abcf-3, abch-1, pgp-1, pgp-2, pgp-3, pgp-4, pgp-5, pgp-7, pgp-8, pgp-9, abt-1, abt-2, abt-3, abt-4, abt-5, abt-6, abtm-1, cft-1, haf-1, haf-2, haf-3, haf-4, haf-6, haf-7, haf-8, hmt-1, mrp-2, mrp-3, mrp-4, mrp-6, mrp-7, mrp-8, pgp-10, pgp-11, pgp-12, pgp-13, pgp-14, pmp-1, pmp-2, pmp-3, pmp-4, wht-1, wht-2, wht-3, wht-4, wht-5, wht-6, wht-8, and wht-9.

Examples of SDR/Redox genes include, but are not limited to, the following C. elegans genes: dhs-1, dhs-2, dhs-3, dhs-4, dhs-6, dhs-7, dhs-8, dhs-9, dhs-11, dhs-12, dhs-13, dhs-14, dhs-15, dhs-16, dhs-17, dhs-17, dhs-18, dhs-19, dhs-20, dhs-22, dhs-23, dhs-24, dhs-25, dhs-26, dhs-28, dhs-29, dhs-30, dhs-31, ard-1, fasn-1, maoc-1, qdpr-1, sdz-8, C01G12.5, C06E4.3, C06E4.4, C06E4.6, C27D8.4, C30G12.2, C33E10.10, C41A3.1, C55A6.3, C55A6.4, C55A6.6, C55A6.7, D1054.8, DC2.5, E04F6.15, F02C12.2, F12E12.11, F20G2.1, F20G2.2, F25D1.5, F26D2.15, F28H7.2, F32A5.8, F54F3.4, F55E10.6, F59E11.2, H04M03.3, K10H10.6, R05D8.7, R05D8.9, R119.3, T01G6.1, T01G6.10, T25G12.2, W03F9.9, Y47G6A.21, Y47G6A.22, ZK697.14, ZK829.1, Y47G6A.21, Y47G6A.22, ZK697.14, ZK829.1, hsd-1, hsd-2, hsd-3, and C32D5.12.

Examples of GST genes include, but are not limited to, the following C. elegans genes: gst-1, gst-2, gst-3, gst-4, gst-5, gst-6, gst-8, gst-9, gst-10, gst-12, gst-13, gst-14, gst-15, gst-16, gst-18, gst-19, gst-20, gst-21, gst-23, gst-24, gst-25, gst-26, gst-27, gst-28, gst-29, gst-30, gst-31, gst-33, gst-34, gst-35, gst-37, gst-38, gst-39, gst-40, gst-41, gst-43, K10F12.4, K10F12.4, R11A8.5, W1008.4, Y45G12C.3, Y53G8B.1, Y53G8B.1, F55A11.6, F55A11.6, F56A4.4, gstk-1, and gstk-2.

Examples of Sol. Transporter genes include, but are not limited to, the following C. elegans genes: vit-1, vit-2, vit-3, vit-4, vit-5, vit-6, egg-1, egg-2, irp-1, irp-2, lbp-1, lbp-2, lbp-3, lbp-4, lbp-5, lbp-6, lbp-7, lbp-8, lbp-9, nrf-5, cit-1.2, C06G1.1, C05C9.1, F10D11.6, T19C3.5, ZC513.1, ZC513.2, C31H1.1, T10B5.10, D1007.16, C55C3.1, F14D12.1b, F46H5.2a, and ZK616.8.

Specific Panels of Representative Transgenic Organisms or Populations of Representative Organisms In one embodiment, the invention is a panel or array of transgenic organisms as described herein. The panel or array in one aspect is provided in a multiwell plate wherein at least 2 or more (or 3 or more, 4 or more, etc. as described in more detail below) has a transgenic organism or population of transgenic representative organisms representative of one-type of response gene e.g., having a distinct transgene that is distinguishable by the identity of the gene from which the promoter of the transgene was obtained or derived.

Panels or arrays of the invention include 2 or more representative transgenic organisms or populations of representative transgenic organisms. Panels or arrays can include 3 or representative transgenic organisms or populations of representative transgenic organisms. Panels or arrays can include 4 or more representative transgenic organisms or populations of representative transgenic organisms. Panels or arrays can include 5 or more representative transgenic organisms or populations of representative transgenic organisms. Panels or arrays can include 6 or more representative transgenic organisms or populations of representative transgenic organisms. Preferably, the panel or array has a control organism or control population of organisms.

Panels or arrays can include from 2 to 384 representative transgenic organisms or populations of representative transgenic organisms. Panels or arrays can include from 2 to 96 representative transgenic organisms or populations of representative transgenic organisms. Panels or arrays can include from 2 to 48 representative transgenic organisms or populations of representative transgenic organisms. Panels or arrays can include from 2 to 24 representative transgenic organisms or populations of representative transgenic organisms. Panels or arrays can include from 2 to 12 representative transgenic organisms or populations of representative transgenic organisms. Panels or arrays can include from 2 to 6 representative transgenic organisms or populations of representative transgenic organisms. Preferably, the panel or array has a control organism or control population of organisms.

Panels or arrays can include from 3 to 384 representative transgenic organisms or populations of representative transgenic organisms. Panels or arrays can include from 3 to 96 representative transgenic organisms or populations of representative transgenic organisms. Panels or arrays can include from 3 to 48 representative transgenic organisms or populations of representative transgenic organisms. Panels or arrays can include from 3 to 24 representative transgenic organisms or populations of representative transgenic organisms. Panels or arrays can include from 3 to 12 representative transgenic organisms or populations of representative transgenic organisms. Panels or arrays can include from 3 to 6 representative transgenic organisms or populations of representative transgenic organisms. Preferably, the panel or array has a control organism or control population of organisms.

Panels or arrays can include from 4 to 384 representative transgenic organisms or populations of representative transgenic organisms. Panels or arrays can include from 4 to 96 representative transgenic organisms or populations of representative transgenic organisms. Panels or arrays can include from 4 to 48 representative transgenic organisms or populations of representative transgenic organisms. Panels or arrays can include from 4 to 24 representative transgenic organisms or populations of representative transgenic organisms. Panels or arrays can include from 4 to 12 representative transgenic organisms or populations of representative transgenic organisms. Panels or arrays can include from 4 to 6 representative transgenic organisms or populations of representative transgenic organisms. Preferably, the panel or array has a control organism or control population of organisms.

Panels or arrays can include from 5 to 384 representative transgenic organisms or populations of representative transgenic organisms. Panels or arrays can include from 5 to 96 representative transgenic organisms or populations of representative transgenic organisms. Panels or arrays can include from 5 to 48 representative transgenic organisms or populations of representative transgenic organisms. Panels or arrays can include from 5 to 24 representative transgenic organisms or populations of representative transgenic organisms. Panels or arrays can include from 5 to 12 representative transgenic organisms or populations of representative transgenic organisms. Panels or arrays can include from 4 to 6 representative transgenic organisms or populations of representative transgenic organisms. Preferably, the panel or array has a control organism or control population of organisms.

Selected Agents

A "selected agent" refers to a chemical, object, or external stimuli that is contacted with or exposed to the transgenic biosensor organism. The selected agent can be given or exposed to the transgenic organism. In one aspect, the selected agent is dosed in a range at concentrations below a lethal dose and at or above levels where a therapeutic effect is expected to be observed. Such ranges can be determined in dose finding studies. Acute assays can be conducted using the compositions and methods of the invention and can range from about 2 hours to about 24 hours, more preferably from about 2 hours to about 18 hours and more preferably from about 2 hours to about 10 hours.

Typically, chemicals are given to the animal or organism in the range of 1 picomolar to 10 millimolar. In other aspects, the organism are exposed to an agent like a physical object e.g., in their growth medium, lining the vesicle or microwell plate or as a gas.

In one aspect, the selected agent is a chemical. In one aspect, the selected agent is a drug candidate or an agent which is a component of a formulation for a drug product. In one aspect, the selected agent is water. In one aspect, the water is a drinking water. In one aspect, the water is wastewater. In one aspect, the selected agent is a food product or liquid or an additive of either. In a specific aspect, the food product, liquid, or additive of either is intended for human or animal consumption.

Methods for Creating Transgenic Organisms

The transgenic organisms of the invention and for use in the methods of the invention can be produced by any technique. Preferably, the transgenic organisms of the invention have single copy inserts of the desired transgene at defined genomic loci and are stable. The transgenic organisms of the invention have a response element (e.g., promoter) reporter gene construct stably inserted into the host organism's genome.

In one specific aspect, the transgene is an inducible promoter reporter gene construct. The optimal promoter and gene-intron sequences of target genes are identified from publicly or privately available databases. For example, one such public database is found at www.wormbase.org. Gateway-compatible PCR primer sets are created for both the promoter and gene intron regions. PCR reactions are gel purified and cloned into a targeting vector (e.g., a MosSCI targeting vector) containing the desired reporter gene (e.g., tag-RFP, RFP, his-RFP, mCherry, or his-mCherry). Desired construction is verified by PCR and/or restriction enzyme digestion.

MosSCI integration (Frokjaer-Jensen, C. et al., 2008 Nat Genet, 40(11), 1375-83). Plasmid DNA mixtures are injected into MosSCI targeting strains. These strains have a Mos1 element at a specific genomic site on chromosome II and contain the unc-119(ed3) mutation, which is used for positive selection of the transgene. The injection mixes for MosSCI transgenesis contain three types of vectors: 1) the gateway reporter construct containing the unc 119(+) positive selection marker gene and sequences for homologous recombination into the *C. elegans* chromosome, 2) a transposase-producing plasmid, and 3) three plasmids acting as markers for tracking the presence of extrachromosomal arrays. Three injected animals are placed on each plate and transferred to 25° C. for 8 days.

After the 8 days at 25° C., the worms are screened for MosSCI events. Candidate insertion strains are homozygosed by clonally picking 8 Unc-119(+) animals that do not carry mCherry (RFP) arrays to individual plates. MosSCI typically produces one integrated transgene from ten injected animals. Thus, the 25 injections/construct are expected to yield 3-4 independent lines.

Desired insertions are verified by PCR with one primer annealing within the insertion and a second primer in reverse annealing outside the insertion. Outcrossing (2×) of the candidate lines confirms their chromosomal integration by observation of Mendelian segregation of the integration locus.

Validation of reporter construction. Candidate lines are imaged by confocal microscopy to record basal expression profiles. Animals are anesthetized on agarose pads on glass slides with glass coverslips. Laser confocal imaging is performed on a Pascal LMS system. Each worm is imaged with a fixed set of laser intensity settings and the level of RFP expression is quantified with NIH ImageJ.

Kits

The invention relates to a kit having one or more biosensor nematodes and materials for use thereof.

Thus, the kit of the invention has:

One or more transgenic biosensor nematode cultures and reagents necessary to reconstitute healthy populations;

Incubation buffer for delivering agent;

A control nematode culture that is similar to the transgenic biosensor nematode culture but does not have the inducible promoter reporter transgene; and A vesicle or reaction plate for containing and cultureing one or more transgenic biosensor nematode cultures and the control nematode culture.

The reagents necessary to reconstitute healthy populations include a medium. In one aspect, the medium is M9, S-media, or CeMM.

The incubation buffer allows for delivery of the selected agent to the transgenic biosensor nematode culture substantially affecting the nematodes in a negative manner (the incubation buffer minus selected agent desirably does not kill the nematodes). In one aspect, the incubation buffer contains DMSO. In a more specific aspect, the incubation buffer has about 2% DMSO. In another aspect, the incubation buffer has acetone. In a specific aspect, the incubation buffer has about 5% acetone. In another aspect, the incubation buffer has methanol. In a more specific aspect, the incubation buffer has 2% methanol. In some aspect, the incubation buffer comprises 2 components which are a solvent for the selected agent and a buffer. The solvent for the selected agent in is chosen from a solvent comprising DMSO, DMFO, acetone, or methanol. In one aspect, the buffer contains detergent. One detergent for use in the incubation buffer is 0.01% triton x-100. The incubation buffers for use in the kits have capacity to increase uptake of the selected agent compounds.

The vesicle or reaction plate for containing one or more biosensor nematode cultures is of sufficient height, size and depth to contain each transgenic biosenor nematode population separate while allowing for the additional of appropriate reagents for growth and exposure to selected agent. Additionally, the vesicle or plate desirably does not interfere with reporter assay.

Typically, the vesicle or each well in a plate has a number of organisms sufficient to yield an adequate signal of the reporter gene. In one aspect, each vesicle or well has 10 or more organisms. In another aspect each vesicle or well has 50 or more organisms. In another aspect, each vesicle or well has 100 or more organisms. In another aspect, each vesicle or well has from 10 to 1000 organisms. In another aspect, each vesicle or well has from 50 to 1000 organisms. In another aspect, each vesicle or well has from 100 to 1000 organisms. In another aspect, each vesicle or well has from 300 to 1000 organisms. In another aspect, each vesicle or well has from 300 to 800 organisms.

Generally, the nomenclature and the laboratory procedures utilized in the invention include molecular, biochemical, microbiological and recombinant DNA techniques. These techniques are explained in the literature. See, for example, Molecular Cloning: A laboratory Manual Sambrook et al., (1989); Current Protocols in Molecular Biology Volumes I-III Ausubel, R. M., ed. (1994); Ausubel et al., Current Protocols in Molecular Biology, John Wiley and Sons, Baltimore, Md. (1989); Perbal, A Practical Guide to Molecular Cloning, John Wiley & Sons, New York (1988); Watson et al., Recombinant DNA, Scientific American Books, New York; Birren et al. (eds) Genome Analysis: A Laboratory Manual Series, Vols. 1-4, Cold Spring Harbor Laboratory Press, New York (1998); Cell Biology: A Laboratory Handbook, Volumes I-III Cellis, J. E., ed. (1994); Oligonucleotide Synthesis Gait, M. J., ed. (1984); Nucleic Acid Hybridization Hames, B. D., and Higgins S. J., eds. (1985); Transcription and Translation Hames, B. D., and Higgins S. J., Eds. (1984); Animal Cell Culture Freshney, R. I., ed. (1986); Immobilized Cells and Enzymes IRL Press, (1986); A Practical Guide to Molecular Cloning Perbal, B., (1984) and "Methods in Enzymology Vol. 1-317, Academic Press; "PCR Protocols: A Guide To Methods And Applications", Academic Press, San Diego, Calif. (1990); Marshak et al., Strategies for Protein Purification and Characterization—A Laboratory Course Manual" CSHL Press (1996); all of which are incorporated by reference as if fully set forth herein.

Reagents useful in applying such techniques, such as restriction enzymes, coding sequences, fluorescent proteins and the like, are widely known in the art and commercially available from such vendors as New England BioLabs, Boehringer Mannheim, Amersham, Promega Biotec, U.S. Biochemicals, New England Nuclear, Life Technologies, Roche and a number of other sources.

References are provided throughout this document. The procedures therein are believed to be well known in the art. All the information contained in these references is incorporated herein by reference.

EXAMPLES

The examples below describe the construction and use of representative compositions for detecting and screening for response to exposure of whole organisms to selected agents e.g., a chemical or toxin. In these examples, the use of panels of transgenic nematodes as biosensors of toxicity pathway activation is described. The panels are composed of promoters of toxin-responsive genes fused to genes encoding reporter proteins. The promoter-reporter fusion construct is inserted into the nematode genome as a single copy gene insertion (e.g., using single copy or site specific insertion transgenesis techniques) at a defined genomic locus. The result is a set of transgenic nematodes strains or lines where each type of transgenic animal functions as a biosensor for a specific toxin (e.g., a representative transgenic organism). Toxins can be typed e.g., for their class of toxicity by observing which subset of strains show reporter activation.

The unique use of single copy insertion allows direct comparison between strains, where intensity of toxin response is de novo normalized between strains. This allows easier determination of the primary mode of toxicity (or other gene expression effects) when analyzing novel compounds. The transgenic strains Or lines can be configured into panel sets (or arrays). It is contemplated that the arrays can be configured to be specific to various types of responses (e.g., toxicity), such as heavy metal, oxidative stress, endocrine disruption, xenobiotic, carcinogenic, genotoxic, neurotoxic, hepatatoxic, nephratoxic, immunotoxic, and others.

Figure 5:
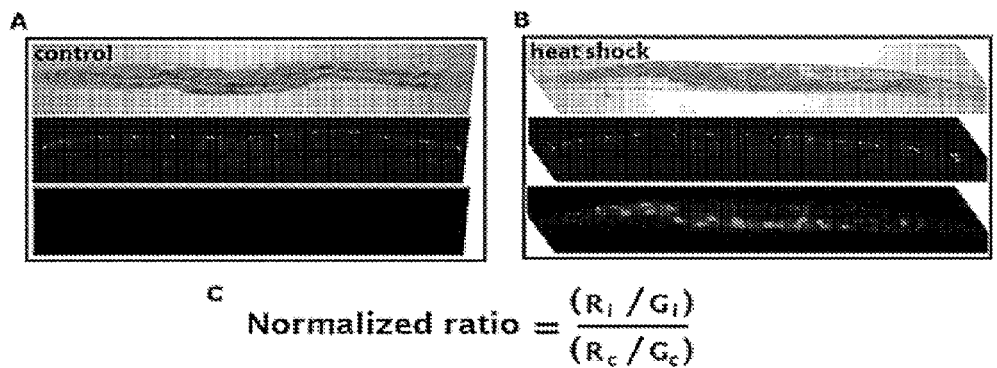
FIG. 5 shows the results of the dual reporter configuration for population normalization. A) Uninduced vs. B) induced (30° C., 1 hr) nematodes (hsp-16::hRFP, unc-47::GFP) were imaged in green and red channels. Panel A is the control worms (top panel is a photograph of the worm, the middle panel is the GFP expression, and the bottom panel is the RFP expression). Panel B is the heat shock treated animal (top panel is a photograph of the worm, the middle panel is the GFP expression, and the bottom panel is the RFP expression). Expression of fluorescent protein shows up as lighter shaded areas in the images. The images show significant induction of RFP in the heat shock treated animals. Panel C shows the equation used for normalization using values in the control animals where $R_t$ is the value measured for RFP fluorescence in the induced animal, $G_t$ is the value from GFP fluorescence in the induced animal, $R_c$ is the value for RFP fluorescence in the control animal and $G_c$ is the value of GFP fluorescence in the control animal.

Example 1: Studies in *C. elegans* Having a Hsp-16 Promoter-Red Fluorescent Protein Transgene The results described herein demonstrate remarkable responses of the whole organism biosensor to toxic insults (such as: heat shock, cadmium, arsenic, etc). For instance, a protein homeostasis reporter was created by fusing heat shock protein to a nuclear localized red fluorescent protein (hsp-16.42::hRFP)(the materials and methods for the construction of the transgenic organism are described in more detail in the examples below). Exposure to heat toxicity generates induction of nuclear localization. This heat shock gene reporter was screened for gene induction capacity using a heat-shock protocol. The hsp-16::hRFP construct is exposed to a 1 hr incubation at 30 C. Gene induction was screened 4 to 24 hrs after heat shock. Significant red fluorescence is observed in the nuclei of heat-shocked worm relative to control (FIG. 5).

Figure 3:
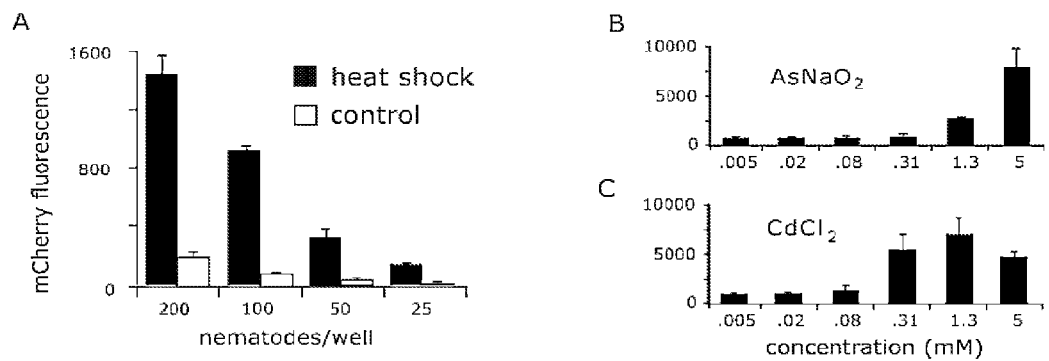
FIG. 3 shows the fluorescence plate-reader sensitivity and toxin response. A) 2-fold dilutions starting with 200 worms per well, assayed in duplicate, were exposed to heat shock (34° C. for 1 hour) and allowed to recover for 16 hr 15 C. B) Arsenic and C) cadmium responses: 24 hr exposure, ~600 worms per well, assayed in triplicate.

Toxin sensitivity of hsp-16 was confirmed with exposure to heavy metals and metalloids. To develop a rapid screen for the hsp-16::hRFP expression, a fluorescent plate reader assay was developed. To test the sensitivity of this assay, a titrating concentration of nematodes were exposed to heat shock. The worms were transferred to a 96 well plate and red fluorescence was quantified. Good sensitivity for a red fluorescence signal occurs at concentrations of 50 or more worms (FIG. 3A). Next, the toxin dosage sensitivity was measured. The Phsp-16::hRFP reporter shows higher sensitivity to cadmium chloride relative to sodium bis-arsenite (FIG. 3B vs. FIG. 3C). The $EC_{50}$ for cadmium occurs near 0.2 mM while arsenic sensitivity is near 1.5 mM. Thus, the Phsp-16::hRFP reporter shows greater sensitivity to cadmium.

Example 2: Control Reporter

Figure 4:
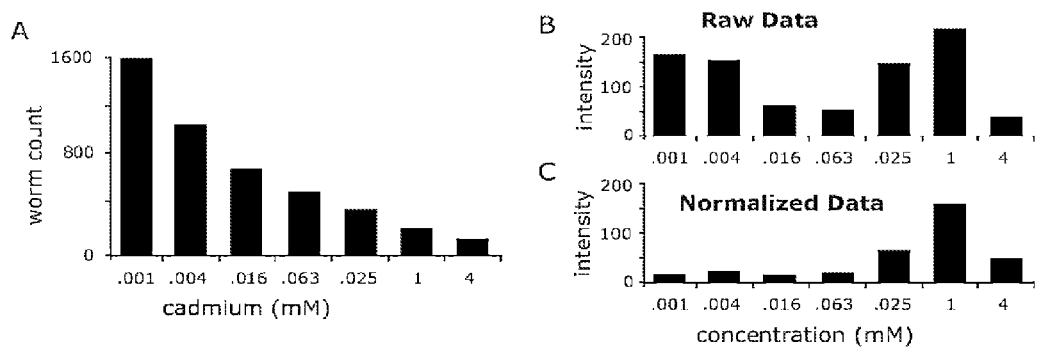
FIG. 4 shows the population effects of chronic toxin exposure. A) Chronic exposure was assayed for effect on population size during 72 hr exposure to cadmium at various concentrations. B) Raw data profiles show bimodal response in fluorescence intensity over the titration range tested. C) Population-normalized response curves show single-mode effect of cadmium on fluorescence intensity.

Advantageously, the transgenic animals described in these examples can have a control reporter (e.g., constitutively expressed). Exposure to some selected agents or toxins can lead to shortened life-span, lower brood sizes or other effects that need to be controlled. The problem becomes most pronounced in chronic assays. For instance, exposure to cadmium for 72 hrs leads to significant population effects (FIG. 4). Thus, it was determined a control for population mass differences between assay wells is desirable. Introduction of a second constitutively expressed reporter gene can be used to control for various population differences.

To create a population control in the fluorescence reader assays, the hsp-16::hRFP was crossed into a line containing a constitutively-expressed neuronal marker (unc-47::GFP). Expression of the control reporter remains constant, while the inducible reporter responds to heat shock (FIG. 5). The use of a constitutive-expressed reporter allows normalization of induction reporter responses—a toxin's effect on population dynamics is controlled.

Example 3: COPAS Cytometry

Figure 6:
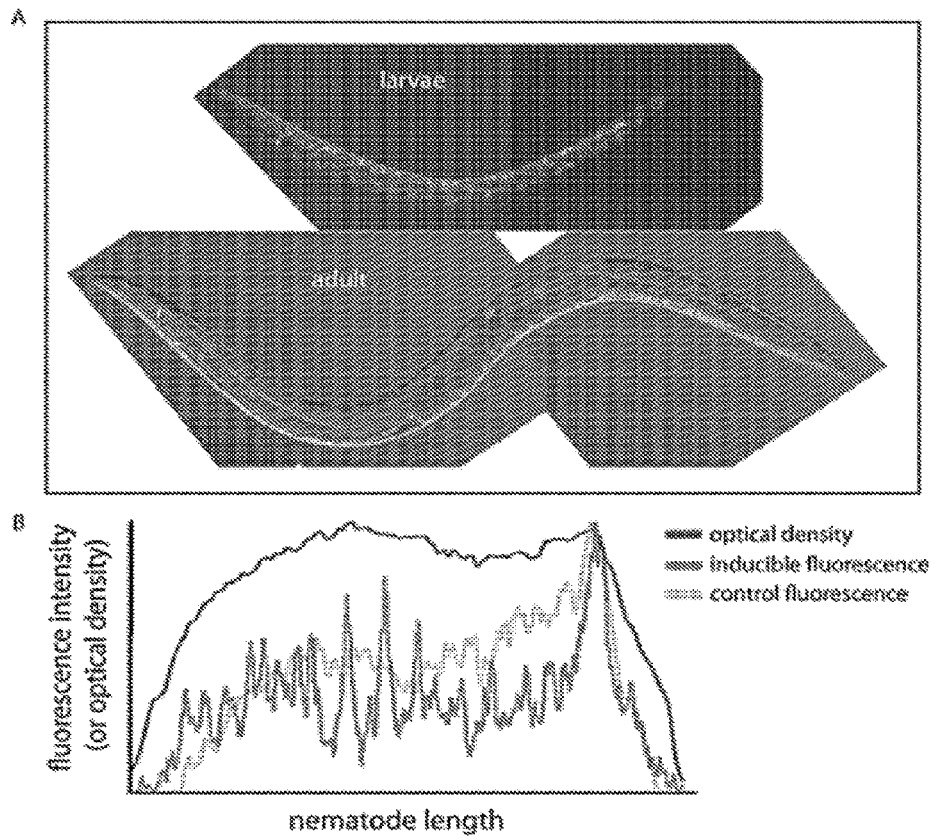
FIG. 6 shows the NIEHS findings with hsp-16::hRFP induction in unc-47::GFP background. A) Confirmation of heat shock responsiveness in the larvae and adults nematodes. B) Representative COPAS biosorting profile showing nematode size-dependent effects on observe fluorescence. The lighter shaded areas in the images indicated fluorescence of GFP or RFP.

The fluorescent expression patterns of individual nematodes was rapidly quantifiable using flow cytometry. The hsp-16::hRFP construct in unc-47::GFP background was sent subjected to COPAS biosorting analysis. Induction of the red fluorescence was observed (FIG. 6A) and COPAS biosorting generated size-dependent profiles for red and green fluorescence expression (FIG. 6B). As expected, the levels of fluorescence increase proportionally with nematode age.

Example 4: Gene Selection and Transgene Construct Construction

The genes chosen for an oxidative stress response panel were the following oxidative response genes (hsp-16.41, hsp16.2, hsp-6 and hsp-60, hsp-4, mlt-2, and ugt-1). To choose the oxidative-response gene promoters, a combination of modENCODE's TF-GFP ChIP-seq data and multi-z 6-species alignment was used to find the extent of conserved genomic regions containing TF sites in front of the oxidative-response gene's start codon. Promoter-reporter fusion constructs were designed for Gibson reaction cloning using APE plasmid editor (biologylabs.utah.edu/jorgensen/wayned/ape). In general, regions ranging from 300 to 4,000 bp upstream of start codon were chosen for promoter selection.

Example 5: Nematode Transgenesis

To make transgenic nematodes, the MosSCI transgenesis procedure was used. Briefly, using the custom transgenesis platform provided by Knudra Transgenics (www.knudra.com/product/custom-transgenics), promoters are positioned in front of a red fluorescent protein fused to histone H2B. The gene is cloned into a vector pNU142, which contains left and right homologous recombination arms of the Mos1 locus (2094 bp and 1825 bp, respectively). The pNU142 plasmid (Amp$^r$) contains CBunc-119 gene obtained from the *C. Briggsae* genome for use as a positive-selection marker. The resulting construct is inserted as a single copy into the Mos1 ttTi5605 site in *C. elegans* strain COP66, which is homozygous for ttTi5605 and oxIs12 (unc-47::GFP) alleles. Strains obtained with the MosSCI transgenesis procedure are verified by PCR for single copy insertion at Mos1 locus. Verification oligos for insertion at Mos1 site are forward SEQ ID NO:163 (GATTCCATGATGGTAGCAAACTC) and reverse SEQ ID NO:164 (CAGATGATGAGCCAAGAAGAGTT), which gives a 325 bp product specific to strains homozygous for insertion at Mos1 loci. The resulting nematode is a two-color worm acting as in vivo transcriptional reporter of gene activation. For the results herein, the 7 types of two-color worms used are hsp-4, hsp-6, hsp-60, hsp-16.2, hsp-16.41, mtl-2, and ugt-1.

Example 7: Nematode Preparation

Two-color worms are grown to high density (0.5 ml worm pellet/plate) using Perfect-GROW HB101 plates (www.knudra.com/product/perfect-grow). Worms are recovered from the plate and cleaned by sucrose sedimentation. Animals are distributed on 5 cm NGM plates (seeded with HB101, (www.knudra.com/product/perfect-seed) at densities of 200 adult animals per plate. For heat shock, plates are exposed to 34° C. for 1.5 hr, and then allowed to recover at for 4 hrs at room temperature. For cadmium exposure, fresh seeded NGM plates are pre-incubated for 24 hrs with 700 ul of 10 mM $CdCl_2$. Cleaned nematodes were added at 200 adult animals per plate and incubated for 15 hrs at room temperature.

Example 8: Plate Reader Assay

Each strain is transferred with 1 ml of M9 into a 2 ml deep 96 well plate. Plate is allowed to stand for 5 minutes to settle worms. Excess M9 is siphoned off and a repeat wash/siphon step is performed. Settled worms are transferred (about 200 ul) to a black 96-well read plate (Corning, Inc. #3651). The plate is read in a fluorescence plate reader (Biotek, Inc., Synergy 4, with optical cubes for GFP detection at ex. 485/20, em. 528/20 and RFP detection at ex. 575/15, em. 620/15 with reading set as endpoint from bottom well at sensitivity of 50). Reads are normalized as RFP/GFP ratio, which adjust for population differences between wells. Fluorescence intensity readings of the reporters in the panel are calculated as ratio of induced RFP/GFP ratio divided by control RFP/GFP ratio.

In conclusion, the oxidative response panel demonstrates the inventive system is feasible for use in testing the effects of external stimuli on gene expression at the whole organism level. As shown herein, the exemplary toxicogenomics studies is remarkably sensitive and selective for detection of oxidative stress toxicity. Furthermore, a simple 7 gene panel can differentiate between different types of oxidative stress e.g., heat shock and metal exposure. The inventive system has advantages over cell culture methods because it is easier to use, less costly to implement, and is believed results more translatable to more complex animal studies like mammalian studies. Importantly, the inventive system is a whole organism approach, which detects cellular response in a native context. The ease of assay implementation makes the system ideal for high-throughput applications. With respect to a specific implementation, toxicogenomics is very valuable in drug discovery. With this invention, pharmaceutical companies will decrease their financial exposure because better toxicology capture at the front end of drug development translates to lower frequency of drugs failing in clinical trials due to unwanted side-effect toxicity.

Those skilled in the art will appreciate that the concepts, specific embodiments, and Examples disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A population of transgenic *C. elegans* comprising: a first population of transgenic *C. elegans* organisms each further comprising:
   a first inducible reporter gene comprising a first inducible promoter from a response pathway gene operably coupled to a reporter gene encoding a first fluorescent or luminescent protein;
   and a first constitutively expressed reporter gene comprising a first constitutive promoter operably coupled to a reporter gene encoding a second fluorescent or luminescent protein,
   wherein said first fluorescent or luminescent protein is detectably different from said second fluorescent or luminescent protein,
   wherein said first inducible reporter gene and said first constitutively expressed reporter gene are stably integrated into the genome,
   wherein said first constitutively expressed reporter gene is present in an amount of 1 to 50 copies,
   wherein expression of said first constitutively expressed reporter gene normalizes the expression of said first inducible reporter gene, thereby the expression of the first inducible reporter gene can be detected at expression levels of at least four fold above background levels of expression, and
   wherein the first population of transgenic *C. elegans* organisms comprises at least 2 transgenic *C. elegans* organisms.

2. The population of transgenic *C. elegans* of claim 1, wherein the first inducible reporter gene comprises the first inducible promoter from a response pathway gene operably coupled to a reporter gene encoding a first fluorescent protein.

3. The population of transgenic *C. elegans* of claim 1, wherein the first fluorescent protein is selected from the group consisting of: GFP, RFP, and CFP.

4. The population of transgenic *C. elegans* of claim 1, further comprising a control population of *C. elegans* wherein said control population does not express an inducible promoter reporter transgene.

5. The population of transgenic *C. elegans* of claim 1, wherein the first inducible gene is present as a single copy in the genome of each *C. elegans* organism.

6. The population of transgenic *C. elegans* of claim 1, wherein the response pathway gene is selected from the group consisting of: an oxidative stress pathway gene, a genotoxin response pathway gene, a carcinogen pathway gene, and xenobiotic pathway gene.

7. The population of transgenic *C. elegans* of claim 1 wherein the response pathway gene is selected from the group consisting of dr-1, gcs-1, ugt-1, gst-38, hsp-60, hsp-16.41, mtl-2, hsp-16.2, gst-4, ugt-13, hsp-3, hsp-6, hsp-4, hsp-1, skn-1, dnj-13, daf-21, Hsp-17, cyp-13A7, cyp-14A3, cyp-35A2, zyg-12, ZK742.4, ZK742.3, fkb-1, fkb-2, fkb-3, fkb-4, fkb-5, fkb-6, fkb-7, fkb-8, fmo-1, fmo-2, fmo-3, fmo-4, fmo-5, ftn-1, ftn-2, fzy-1, gen-1, glp-1, gsr-1, gst-1, gst-23, gst-25, gst-41, H01G02.2, haf-6, syp-2, T05A12.4, T05G5.3, T06E6.2, T07F12.4, Hsp-12.2, T05E11.3, Cnx-1, Crt-1, cyp-35A1, cyp-35C1, cyp-35A3, pqe-1, cyp-37B1, cyp-35B2, cyp-35B1, cyp-22A1 (daf-9), cyp-14A5, cyp-35B3, cyp-34A6, daf-16, exo-3, nth-1, pme-1, ung-1, xpa-1, mrt-2, ercc-1, ZK697.8, ZK287.5, haf-7, hda-1, hda-10, hda-11, hda-2, hda-3, hda-4, hda-5, hda-6, hdac-1, hif-1, him-1, him-14, him-3, him-4, him-6, hmg-3, hmg-4, hmg-5, hpr-17, hpr-9, hrdl-1, hsf-1, hsp-1, hsp-16.48, tbb-4, tnc-2, top-3, tor-2, trx-2, xpf-1, xpg-1, rad-23, mlh-1, msh-2, msh-4, msh-5, msh-6, brc-1, brc-2, rad-50, cku-70, lin-35, mei-1, cki-1, cki-2, cep-1, ced-3, ced-9, ced-13, vem-1, dhs-23, sodh-2, dnj-19, Xbp-1, hsp-16.49, hsp-2, htp-1, htp-3, hus-1, imb-3, ire-1, irk-1, K07C5.2, K07C5.4, K08F4.1, K11G12.5, kin-18, lagr-1, let-2, let-92, lig-1, lig-4, lim-4, lin-12, lin-44, lin-49, lrk-1, lst-3, M18.5, vps-41, W01A11.1, W02C12.1, W03G1.5, W06H8.2, Hipr-1, cdc-48.1, cdc-48.3, Ubq-1, Ubq-2, Gst-10, Gst-13, f25d1.5, fil-1, k10h10.6, hsp-70, f44e5.4, f44e5.5, hsp-16.11, hsp-16.1, nurf-1, aip-1, y43f8b.2, Dod-17, Dod-24, C55A6.7, F56D5.3, cyp-13A11, cyp-13A6, cyp-25A4, mac-1, mboa-2, mdf-1, mdf-2, mec-14, med-1, mel-28, misc-1, mnat-1, mre-11, mrp-1, mrp-2, mrp-3, mrp-4, mrp-5, mrp-6, mrp-7, mrp-8, mspn-1, mus-1, mut-2, mxl-1, mxl-2, mxl-3, ndx-1, Y55B1AL.2, Y56A3A.33, Y66D12A.15, Y66D12A.15, Y73C8C.10, cyp-29A2, cyp-31A1, cyp-31A3, cyp-33B1, cyp-33E1, cyp-34A10, cyp-34A9, cyp-35A4, cyp-35D1, abl-1, abu-1, acr-14, acr-22, agt-1, ahr-1, air-2, ama-1, apa-2, apn-1, apn-1, aps-2, arf-1, asp-5, atf-5, atgr-7, ndx-4, nft-1, nhr-6, nol-5, npl-4.2, nuc-1, odc-1, paa-1, pas-4, pat-10, pcn-1, pdi-1, pdi-2, pdi-3, pdr-1, pek-1, pgp-1, pgp-10, pgp-2, phi-37, phi-44, phi-9, pink-1, pme-2, pme-3, T08D2.4, T08D2.7, T08H10.1, T10B5.8, T13A10.2, atl-1, atm-1, B0222.9, B0432.2, B0495.2, B0563.7, brd-1, C01G5.5, C06A1.6, C06H2.3, C07D8.6, C08H9.3, C09D4.3, C11E4.2, C25A1.5, C30G7.5, C35C5.2, C35D10.2, C35D10.6, C37A2.4, C37C3.6a, C44H4.4, C56G3.2, catp-6, cbn-1, F17A9.5, F18A1.5, F19G12.2, F23C8.9, F36A4.15, F43D2.1, F43G6.5, F44B9.8, F45E12.3, F49E12.6, F52B5.2, F52C12.1, F53C11.5, F53F1.2, F53F1.3, F53F10.2, F55B11.1, F57B10.5, F57B10.6, F58F9.1, F59A2.3, F59F4.1, fan-1, fdps-1, figl-1, trxr-1, tut-1, uba-1, ubc-1, ubc-20, ccch-1, cct-1, cct-2, cct-3, cct-4, cct-5, cct-6, cct-7, cct-8, cdc-14, cdc-48.2, cdk-7, ced-4, cel-1, cft-1, chk-1, chk-2, chn-1, cku-80, cle-1, clk-2, clpp-1, cmd-1, cnb-1, col-135, pme-4, pme-5, pmrt-5, pms-2, png-1, polh-1, polk-1, prx-6, ptl-1, R02D3.3, R03D7.2, R05D11.6, R05F9.10, R09H10.3, R10E4.9, R13D11.4, R151.6, rab-1, rab-7, srp-2, ssc-1, sti-1, sulp-7, sut-1, sut-2, wrn-1, xpc-1, Y110A7A.4, Y38F1A.5, Y38H8A.3, cps-6, crb-1, crn-1, crn-2, crn-3, crn-4, crn-5, crn-6, crp-1, csb-1, ctl-2, ctl-3, cul-1, cul-2, cul-4, cul-5, cyh-1, cyn-1, cyn-10, cyn-11, cyn-12, cyn-13, cyn-14, cyn-15, cyn-16, rad-51, rad-54, rbx-1, rbx-2, rcf-3, rcq-5, rec-8, rev-1, rfc-1, rfc-4, rfl-1, rme-8, rnf-121, rnh-1.0, rpa-1, rpa-2, rpn-10, rps-19, rps-26, T23G5.6, T26A5.5, T27E9.1, tag-353, tars-1, tbb-2, Y73F8A.24, ymel-1, ZC168.4, ZC395.10, ZC443.1, cyn-17, cyn-2, cyn-3, cyn-4, cyn-5, cyn-6, cyn-7, cyn-8, cyn-9, cyp-13A12, cyp-13A4, cyp-14A2, cyp-33C1, cyp-33C2, cyp-33C9, cyp-33E2, cyp-42A1, cyp14A2, cyp33C9, cyp34A6, D1081.8, D2023.4, daf-1, daf-14, daf-3, rpt-3, rpt-4, rpt-5, rpt-6, rtel-1, san-1, scav-1, scav-2, scav-3, scav-4, scav-5, scc-3, sdz-8, sec-22, sep-1, set-25, set-26, set-8, set-9, unc-11, unc-26, unc-57, uri-1, usp-14, vps-4, T15B7.2, T16H12.4, ugt-62, Y39G8B.1, Y39G8B.2, daf-5, daf-7, daf-8, dbl-1, ddb-1, dhs-22, djr-1.1, dna-2, dog-1, drh-3, drp-1, dut-1, E01A2.1, eft-2, egl-1, eif-2, emb-9, epg-2, eps-8, exo-1, F09E5.2, F14F9.5, F15E6.6, F16A11.2, F17A9.4, sft-4, sgg-1, sin-3, sir-2.1, sir-2.2, sir-2.3, sir-2.4, skr-15, slt-1, slx-1, smf-1, smk-1, sod-1, sod-2, sod-3, sod-4, sod-5, spas-1, ugt-61, Y43E12A.1, Y43F8C.13, Y48G1BL.2, Y50D7A.1, Y50D7A.2, Y54E10A.3, ufd-1, ugt-22, ugt-52, ZK1128.4, ZK1290.5, and Y39H10A.7.

8. The population of transgenic *C. elegans* of claim 1, wherein the first population further comprises a selected agent.

* * * * *